United States Patent
Hastings

(10) Patent No.: US 10,525,076 B2
(45) Date of Patent: Jan. 7, 2020

(54) ANTISENSE COMPOUNDS TARGETING GENES ASSOCIATED WITH CYSTIC FIBROSIS

(71) Applicant: Rosalind Franklin University of Medicine and Science, North Chicago, IL (US)

(72) Inventor: Michelle L. Hastings, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 15/835,698

(22) Filed: Dec. 8, 2017

(65) Prior Publication Data

US 2018/0117073 A1 May 3, 2018

Related U.S. Application Data

(63) Continuation-in-part of application No. 15/045,999, filed on Feb. 17, 2016, now Pat. No. 9,840,709.

(60) Provisional application No. 62/118,794, filed on Feb. 20, 2015.

(51) Int. Cl.
*A61K 31/712* (2006.01)
*C12N 15/113* (2010.01)

(52) U.S. Cl.
CPC ........ *A61K 31/712* (2013.01); *C12N 15/1138* (2013.01); *A01K 2267/0306* (2013.01); *C12N 2310/11* (2013.01); *C12N 2310/321* (2013.01); *C12N 2310/3233* (2013.01); *C12N 2320/33* (2013.01)

(58) Field of Classification Search
CPC .............. A61K 31/712; C12N 15/1138; C12N 2310/11; A01K 2207/05
See application file for complete search history.

(56) References Cited

U.S. PATENT DOCUMENTS

| | | | |
|---|---|---|---|
| 9,976,143 B2 | 5/2018 | Krainer et al. | |
| 2004/0096844 A1* | 5/2004 | Accola ................. | C12Q 1/6883 435/6.12 |
| 2004/0096871 A1* | 5/2004 | Accola ................. | C12Q 1/6883 435/6.1 |
| 2005/0048544 A1 | 3/2005 | Gardner et al. | |
| 2005/0186588 A1 | 8/2005 | Lyamichev et al. | |
| 2006/0147938 A1* | 7/2006 | Accola ................. | C12Q 1/6883 435/6.12 |
| 2006/0252722 A1 | 11/2006 | Lollo et al. | |
| 2008/0221317 A1 | 9/2008 | Khvorova et al. | |
| 2012/0094846 A1 | 4/2012 | Hantash | |
| 2013/0203055 A1* | 8/2013 | Aurich-Costa ...... | C12Q 1/6841 435/6.11 |

FOREIGN PATENT DOCUMENTS

| | | | | |
|---|---|---|---|---|
| WO | 96/06190 A2 | 2/1996 | | |
| WO | 01/73002 A2 | 10/2001 | | |
| WO | WO-2005006951 A2 * | 1/2005 | ........... | C12Q 1/6883 |
| WO | 2008/102057 A1 | 8/2008 | | |
| WO | 2014/045283 A1 | 3/2014 | | |

OTHER PUBLICATIONS

Friedman, K.J., et al., "Correction of Aberrant Splicing of the Cystic Fibrosis Transmembrane Conductance Regulator (CFTR) Gene by Antisense Oligonucleotides", Journal of Biological Chemistry, Dec. 17, 1999, vol. 274(51), pp. 36193-36199.
Igreja, Susana, et al., "Correction of a Cystic Fibrosis Splicing Mutation by Antisense Oligonucleotides" Human Mutation, Nov. 10, 2015, pp. 1-7.
Qiao, W., et al, "Charge-Neutral Morpholino Microarrays for Nucleic Acid Analysis", Anal. Biochem., Mar. 15, 2013, vol. 434(2), pp. 207-214, doi:10.1016/j.ab.2012.12.001, Epub Dec. 12, 2012.
Sazani, P., et al., "Therapeutic Potential of Antisense Oligonucleotides as Modulators of Alternative Splicing", Journal of Clinical Investigation, Aug. 1, 2003, vol. 112(4), pp. 481-486.
Tsui, L-C., "The Spectrum of Cystic Fibrosis Mutations", Trends in Genetics, Nov. 1, 1992, vol. 8(11), pp. 392-398.
PCT International Search Report and Written Opinion, European Patent Office—International Searching Authority, dated Jun. 20, 2016, pp. 1-14.
Crooke et al., "Pharmacokinetic properties of several novel oligonucleotide analogs in mice." J. Pharmacol. Exp. Ther., 277(2):923-37 (May 1996).
Kabanov et al., "A new class of antivirals: antisense oligonucleotides combined with a hydrophobic substituent effectively inhibit influenza virus reproduction and synthesis of virus-specific proteins in MDCK cells" FEBS Lett, 259:327-330 (Jan. 1990).
Letsinger et al., "Cholesteryl-conjugated oligonucleotides: synthesis, properties, and activity as inhibitors of replication of human immunodeficiency virus in cell culture." Proc. Natl. Acad. Sci. USA, 86(17):6553-6556 (Sep. 1989).
Manoharan et al., "Cholic acid-oligonucleotide conjugates for antisense applications" Bioorganic & Medicinal Chemistry Letters, 4(8):1053-1060 (Apr. 1994).
Manoharan et al., "Chemical modifications to improve uptake and bioavailability of antisense oligonucleotides." Ann. N.Y. Acad. Sci., 660:306-309 (Oct. 1992).

(Continued)

*Primary Examiner* — Brian Whiteman
(74) *Attorney, Agent, or Firm* — McDonnell Boehnen Hulbert & Berghoff LLP

(57) ABSTRACT

The present disclosure relates generally to compounds comprising oligonucleotides complementary to a cystic fibrosis transmembrane conductance regulator (CFTR) RNA transcript. Certain such compounds are useful for hybridizing to a CFTR RNA transcript, including but not limited to a CFTR RNA transcript in a cell. In certain embodiments, such hybridization results in modulation of splicing of the CFTR transcript. In certain embodiments, such compounds are used to treat one or more symptoms associated with Cystic Fibrosis.

30 Claims, 41 Drawing Sheets

Specification includes a Sequence Listing.

(56) References Cited

OTHER PUBLICATIONS

Manoharan et al., "Introduction of a lipophilic thioether tether in the minor groove of nucleic acids for antisense applications" Bioorganic & Medicinal Chemistry Letters, 3(12):2765-2770 (Dec. 1993).

Manoharan et al., "Lipidic nucleic acids" Tetrahedron Letters, 36(21):3651-54 (May 1995).

Manoharan et al., "Oligonucleotide Conjugates: Alteration of the Pharmacokinetic Properties of Antisense Agents" Nucleosides & Nucleotides, 14(Issue 3-5): 969-973 (1995).

Mishra et al., "Improved leishmanicidal effect of phosphorotioate antisense oligonucleotides by LDL-mediated delivery." Biochim. Biophys. Acta, 1264(2):229-237 (Nov. 1995).

Oberhauser et al., "Effective incorporation of 2'-O-methyl-oligoribonucleotides into liposomes and enhanced cell association through modification with thiocholesterol." Nucl. Acids Res., 20(3):533-538 (Feb. 1992).

Saison-Behmoaras et al., "Short modified antisense oligonucleotides directed against Ha-ras point mutation induce selective cleavage of the mRNA and inhibit T24 cells proliferation." EMBO J., 10(5):1111-18 (May 1991).

Shea et al., "Synthesis, hybridization properties and antiviral activity of lipid-oligodeoxynucleotide conjugates." Nucl. Acids Res., 18(13):3777-83 (Jul. 1990).

Svinarchuk et al., "Inhibition of HIV proliferation in MT-4 cells by antisense oligonucleotide conjugated to lipophilic groups" Biochimie, 75(1-2):49-54 (1993).

The International Search Report and Written Opinion for International Application No. PCT/US2016/018275 from the European Patent Office—International Searching Authority; dated Jun. 20, 2016, pp. 1-14.

Kim & Krainer, "Allele-Specific Inhibition of Nonsense-Mediated mRNA Decay in Cystic Fibrosis" Poster No. 804, Abstract Submitted. The 32nd Annual North American Cystic Fibrosis Conference, Denver, Colorado, Oct. 18-20, 2018, Pediatric Pulmonology vol. 53, Issue S2, Sep. 2018, one page.

Martinovich et al., "Rescue of CFTR Function Impaired by Mutations in Exon 15 in Children with Cystic Fibrosis" Poster No. 205, Abstract Submitted. The 32nd Annual North American Cystic Fibrosis Conference, Denver, Colorado, Oct. 18-20, 2018, Pediatric Pulmonology vol. 53, Issue S2, Sep. 2018, p. 224.

* cited by examiner

FIG. 4

>human CFTR intron 1, exon 2, intron 2 region (SEQ ID NO: 131)
ATATGCCAGAAAAGTTGAATAGTAGTTGAATAGATCAGATTCCAATCAGATTCCAAATCTGTATGGAGACCAAATCAAGTGAATATCTGTT
CCTCCTCTCTTTATTTTAGCTGGACCAGACCAATTTTGAGGAAAGGATACAGACAGCCGCCCTGGAATTGTC
AGACATATACCAAATCCCTTGTTGATTCTGCTGACAATCTATCTGAAAAATTGGAAAGGTATGTTCAT
GTACATTGTTTAGTTGAAGAGAGAAATTCATATTATTAATTATTTAGAGAAGAGAAAGCAAACATATTAT
AAGTTTAATTCTTATATTTA

FIG. 5

>human CFTR intron 3, exon 4, intron 4 region (SEQ ID NO: 132)
TCTCCCTCTAAAGATGAAAAGTCTTGTGTTGAAATTCTCAGGGTATTTGAAATAAATGAAATTTAA
TTTCTCGTTTTCCCCTTTTGTAGGAAGTCACCAAGCCAGTACAGCCTCTTACTGGAAGAATCATA
GCTTCCTATGACCCGGATAACAAGGAGAACGCTCTATCCGGATTTATCTAGGCATAGCTTATGCCTTC
TCTTTATTGTGAGGACACTGCTCCTACACCCAGCCATTTTGCCTTCATCACATTGAATGCAGATGAG
AATAGCTATGTTTAGTTTGATTTATAAGAAGTAATACTTCCTTGCACAGGCCCCATGGCACATATATTC
TGTATCGTACATGTTTTAATGTCATAAATTAGGTAGTGAGCTGGTACAAGTAAGGATAAATGCTGAAAT

FIG. 6

>human CFTR intron 4, exon 5, intron 5 region (SEQ ID NO: 133)
CCTTTACTTAATAATGAATGCAATAATAACTGAATTAGTCATATATTATAATTTTACTTATAATATATTTGTA
TTTTGTTTGTTGAATTATCTAACTTTCCATTTTCTTTTAGACTTTAAGCTGTCAAGCCGTGTTCTAG
ATAAATAAGTATTGGACAACTTGTGTAGTCTCCTTTCCAACAACCTGAACAAATTTGATGAAGTATGTAC
CTATTGATTTAATCTTTTAGGCACTATTGTTATAAATTATACAACTGGAAAGGCGGAGTTTCCTGGGTC
AGATAATAGTAATTAGTGGT

FIG. 7

>human CFTR intron 6, exon 7, intron 7 region (SEQ ID NO: 134)
TTGAATAAAAGAAATATGACTTAAAACCTGAGCAGTTCTTAATAGATAATTGACTTGTTTTACTATT
AGATTGATTGATTGATTGATTACAGAGATCAGAGAGCTGGGAAGATCAGTGAAAGACTTGT
GATTACCTCAGAAATGATTGAAAATATCCAATCTGTTAAGGCATCTGCTGGGAAGAAGCAATGAAAA
ATGATTGAAAACTTAAGACAGTAAGTTGTTCCAATAATTTCAATATTGTTAGTAATTCTGTCCTTAATTT
TTTAAAAATATGTTTATCAT

FIG. 8

>human CFTR intron 8, exon 9, intron 9 region (SEQ ID NO: 135)
ATTATTAAAATTCATATATAAGATAGCACAATGAGTATAAAGTAGATGTAATAATGCATTAATGCT
ATTCTGATTCTATAATATGTTTTTGCTCTCTTTTATAAATAGGATTTCTTACAAAGCAAGAATATAAGA
CATTGGAATATAACTTAACGACTACAGAAGTAGTGATGATGAGAATGAACAGCCTTCTGGGAGGGTCAG
AATTTTAAAAAATTGTTTGCTCTAAACACCTAACTGTTTCTTCTTTGTGAATATGGATTTCATCCTAA
TGGCGAATAAAATTAGAAATG

FIG. 9

>human CFTR intron 9, exon 10, intron 10 region (SEQ ID NO: 136)
GCATCTATTGAAAATATCTGACAAACTCATCTTTTATTTTGATGTGTGTGTGTGTGTGTTTT
TTAACAGGGATTTGGGAATTATTTGAGAAGCAAACAATAACAATAGAAAACTTCTAATGGT
GATGACAGCCTCTTCTTCAGTAATTCTCACTTCTGTCCTGAAAGATATTAATTTCAAGA
TAGAAAGAGGACAGTTGTTGGCGGTTGCTGGATCCACTGGAGCAGGCAAGGTAGTTCTTTTGTTCTTCAC
TATTAAGAACTTAATTTGGTGTCCATGTCTCTTTTTTTTCTAGTTTGTAGTGCTGGAAGGTATTTTTGG
AGAAATTCTT

FIG. 10

>human CFTR intron 10, exon 11, intron 11 region (SEQ ID NO: 137)
CAAATAAGAATATACACTTCTGCTTAGGATGATAATTGGAGGCAAGTGAATCCTGAGCGTGATTTGATAA
TGACCTAATAATGATGGGTTTTATTTCCAG**ACTTCACTTCTAATGGTTGATTATGGGAGAACTGGAGCCTT
CAGAGGTAAAATTAAGCACAGTGGAAGAATTCATTCTGTTCTCAGTTTTCCTGATTATGCCTGGCAC
CATTAAAGAAAATATCATCTTTGGTGTTTCCTATGATGAATATAGATACAGAAGCGTCATCAAAGCATGC
CAACTAGAAGAG**GTAAGAACTATGTGAAAACTTTTTGATTATGCATATGAACCCTTCACACTACCCAAA
TTATATATTTGGCTCCATATTCAATCGGTTAGTCTACACATATATTTATGTTTCCTCTATGGGTAAGCTACT

FIG. 11

>human CFTR intron 12, exon 13, intron 13 region (SEQ ID NO: 138)
CATGTAGTGAACTGTTGAAGGCAAATCATCTACACTAGATGACCAGGAAATAGAGAGGAAATGTAATTTA
ATTTCCATTTTCTTTTTAGACCAGTATACAAAGATGCTGATTTGTATTTATTAGACTCTCCTTTTGGATA
CCTAGATGTTTTAACAGAAAAAGAATATTTGAAAGTATGTTCTTTGAATACCTTACTTATAATGCTCA
TGCTAAATAAAAGAAAGACAGACTGTCCC

FIG. 12

>human CFTR intron 14, exon 15, intron 15 region (SEQ ID NO: 139)
GATTCAAGTAAGTAATACTATTCTTTTATTTCATATATTAAAAATAAAACCACAATGGTGCATGAAACTGTA
CTGTCTTATTGTAATAGCCATAATTCTTTTATTCAG**GAGTGCTTTTTGATGATATGGAGAGCATACCAG
CAGTGACTACATGGAACACATACCTTCGATATATTACTGTCCACAAGAGCTTAATTTTGTGCTAATTTG
GTGCTTAGTAATTTTTCTGGCAGAG**GTAAGAAGTGTTCTATTGTAAGTATTACTGGATTAAAGTTAAAT
TAAGATAGTTTGGGGATGTA

FIG. 13

>human CFTR intron 15, exon 16, intron 16 region (SEQ ID NO: 140)
GTGATGTGAATTTAGATGTGGGCATGGGAGGAATAGGTGAAGATGTTAGAAAAATCAACTGTCTT
GTTCCATTCCAGGTGGCTGCTTCTTTGTTGTTGCTGCTGGCTCCTCCTTGGAAAGTGAGTATTCCATGTCCTAT
TGTGTAGATTGTGTTTTATTTCTGTTGATTAAATATTGTA

FIG. 14

>human CFTR intron 19, exon 20, intron 20 region (SEQ ID NO: 141)
TTTCAGGTACAAGATATTATGAAATTACATTTTGTGTTTATTGTTATTTGCAATGTTTTCTATGGAAATAT
TTCACAGGCAGGAGTCCAATTTTCACTCATCTTGTTACAAGCTTAAAAGGACTATGGACACTTCGTGCCT
TCGGACGGCAGCCTTACTTTGAAACTCTGTTCCACAAGCTCTGAATTTACATACTGCCAACTGGTTCTT
GTACCTGTCAACACTGCGCTGGTTCCAAATGAGAATAGAAATGATTTTTGTCATCTTCTTCATTGCTGTT
ACCTTCATTTCCATTTTAACAACAGGTACTATGAACTCATTAACTTTAGCTAAGCATTTAAGTAAAAAAT
TTTCAATGAATAAAATGCTGCATTCTATAGGTTATCAATTTTGATATCTTTAGAGTTTAGTAATTAACA

FIG. 15

>human CFTR intron 21, exon 22, intron 22 region (SEQ ID NO: 142)
TAACCAAGTGACAAGTAGCAAGTGTTGCATTTTACAAGTTATTTTTAGGAAGCATCAAACTAATTGTGA
AATTGTCTGCCATTCTTAAAAACAAAATGTTGTTATTTTTATTTCAGATGCGATCTGTGAGCCGAGTCT
TTAAGTTCATTGACATGCCAACAGAAGTAAACCTACCAAGTCAACCAATACAAGAATGGCCAACT
CTCGAAAGTTATATGATTATTGAGAATTCACACGTGAAAGATGACATCTGCCCTCAGGGCCAAATG
ACTGTCAAAGATCTCACAGACAAATACACAGAAGGTGAAATGCCATATTAGAGAACATTCCTTCTCAA
TAAGTCCTGGCCAGAGGTGAGATTTGAACACTGCTTGTTGTTCAGTAAGTGAATCCC
AGTAGCCTGAAGCAATGTGTTAGCAGAATCTATTATTATTGTAACATTATTATTGTGAAATTTAATTTGCAGAGTCCTGAACCTAT
ACACACATGTTTATTATATGGAGTCATTATTTTTAATATGAAATTTAATTTGCAGAGTCCTGAACCTAT
ATAAATGGGTTTATTTTAAATGTGATTGTACTTGCAGAATA

FIG. 16

>human CFTR intron 22, exon 23, intron 23 region (SEQ ID NO: 143)
TTCCAATGGTTTTTATTGAATACTGAATTATGTTTATGGCATGGTACCTATATGTCACAGAAGT
GATCCCATCACTTTTACCTTTATAGGTGGCCTCTTGGGAAGAACTGGATCAGGAAGAGTACTTTGTTAT
CAGCTTTTTGAGACTACTGAACACTGAAGGAGAATCCAGATCGATGGTGTGTCTTGGATTCAATAAC
TTTGCAACAGTGGAGGAAAGCCTTTGGAGTGATACCACAGGTGAGCAAAAGGACTTAGCACAGAAAAAGG
CAACTAAATTATATTTTTACTGCTATTTGATACTTGTACTCAAGAAATTCATATTACTCTGCAAATAT
ATTTGTTATG

FIG. 17

>human CFTR intron 23, exon 24, intron 24 region (SEQ ID NO: 144)
GGGTGTTTCTTATTTTAAAATAATTTTTCTACTTGAAATATTTTACAATAAGGGAAAATAAAAA
GTTATTAAGTTATTCATACTTTCTTCTTCTTTTTTGCTATAGAAGTATTTATTTTTCTGAA
CATTTAGAAAAACTTGGATCCCTATGAACAGTGGAGTGATCAAGAAATATGAAGTTGCAGATGAGT
AAGGCTGCTAACTGAAATGATTTGAAAGGGTAACTCATACCAACAACAAATGGCTGATATAGCTGACAT
CATTCTACACACTTTGTGTGCATGTATGTGTGCACAACTTTAAAATGGAGTACCCTAACATACCTGGA
GCAACAGGTA

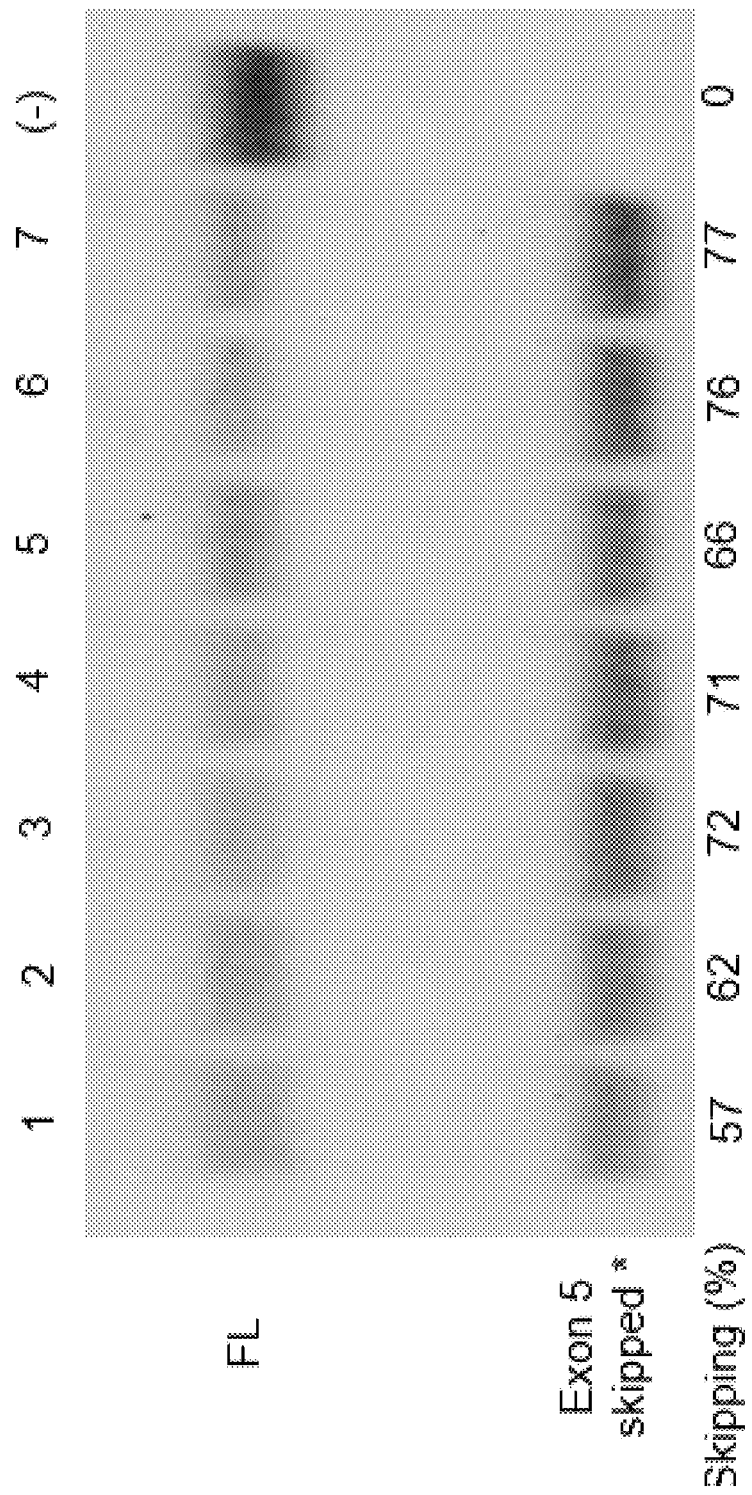

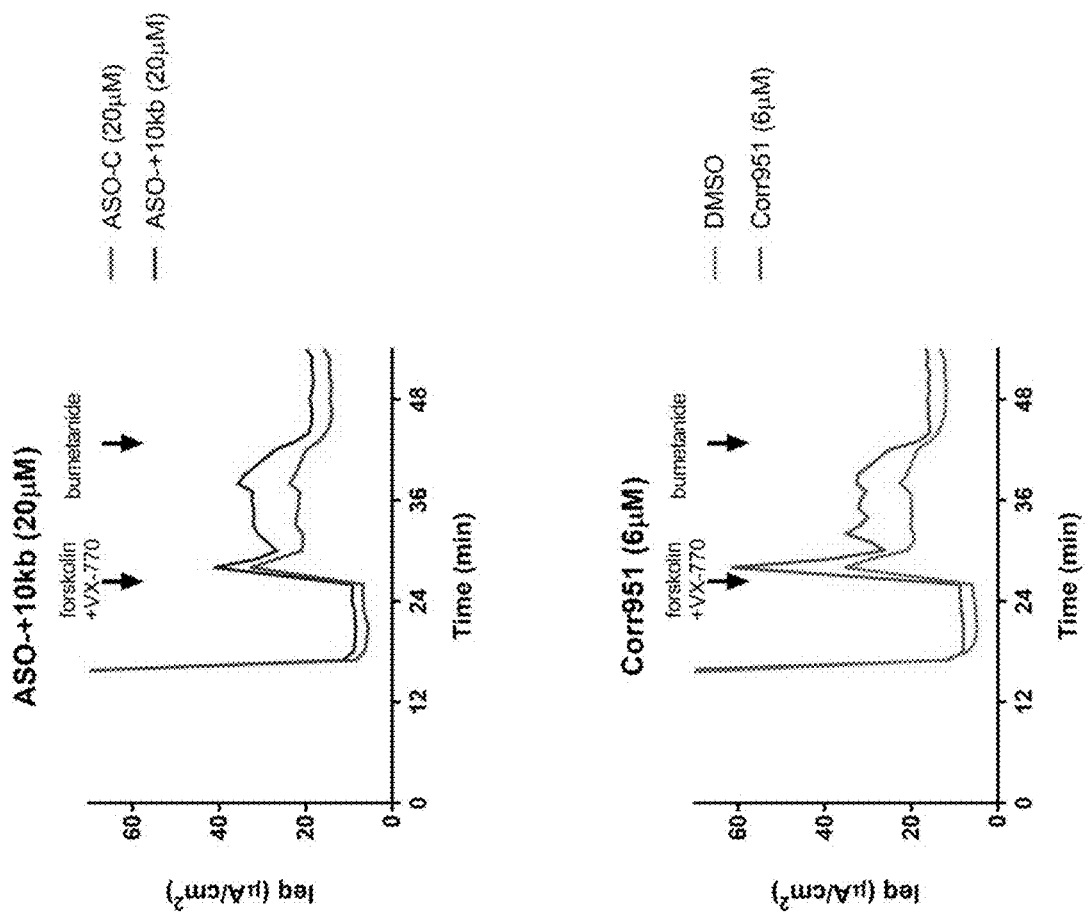

SEQUENCE LISTING

```
<160> NUMBER OF SEQ ID NOS: 151

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
ggtccagcta aaagagaaga gggca                                               25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
ctttcctcaa aattggtgtg gtcca                                               25

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
tatgtctgac aactccaagt ggtgt                                               25

<210> SEQ ID NO 4
<211> LENGTH: 25
<212> TYPE: DNA
<213> ORGANISM: Artificial Sequence
<220> FEATURE:
```

<223> OTHER INFORMATION: Synthetic oligonucleotide

<400> SEQUENCE: 4
ctagtttttc agacaagtgg tcagc                                          25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
ttcctagcaa gacaggctgg acagc                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
ataggatgct atgattcttc ctagc                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
ataagcctat gccaaggtaa atggc                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
tgtcctgaca atgaagagaa ggcat                                          25

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9
aatgcgatga aggccaaaaa tagct                                          25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
tagctgttct catctgcatt ccaat                                          25

```
<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
catcttccaa aaagtattac cttct                                              25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
ttgttcaggt tgttggaaag aagac                                              25

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
atcaagaacg cggcttgaca acttt                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
cacgagtctt tcattgatct ttgca                                              25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
ctgattccca acaatatgcc ttaac                                              25

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
caatcatttt ctccatcgct gattc                                              25

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 17
attatgtcaa cttactctct caagt                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
gcctgtggtc attaagttat actcc                                              25

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
ctcctcccaa aatgctgtta cattt                                              25

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 20
tatttagaaa tctcacctcc tccca                                              25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21
ctttctccag taattcccca aatcc                                              25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
gtcaccattg ctttgttgta ctttc                                              25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 23
ctgaaactga cattgttctc atcac                                              25

<210> SEQ ID NO 24
<211> LENGTH: 25

```
<212> TYPE: DNA
<213> ORGANISM: Artificial Sequence
<220> FEATURE:
<223> OTHER INFORMATION: Synthetic oligonucleotide

<400> SEQUENCE: 24
aggatttccc acaaggcaga gatga                                      25

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
atagccaaca tctctccttt ctcta                                      25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
ctttcctgat ccagtagatc cagta                                      25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
ctttcctgat ccagtagatc cagta                                      25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
tccagttctc ccaaaatcaa catca                                      25

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
tgtgcttaat aattccctct gaagc                                      25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
```
attgagagca gaatgaaact cttcc                                          25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
gatattttct tgatagtac ccggc                                           25

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 32
acactcttat atctgtactc atcat                                          25

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
ctgctgtagt tggcaagctt tgaca                                          25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
cataaatatg cttacctgct gtagt                                          25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
gggaatctaa taggtacaaa tcagc                                          25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
caaatcagca tctttatata ctgct                                          25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
actcagtcat agaacatacc tttca                                              25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
aacaaacata cttacctcaa ccaga                                              25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
cctgcctgta aatcatccca tagga                                              25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
caaggtgggt gaaaattgga ctcct                                              25

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 41
cgaagtgtcc agagtccttt taagc                                              25

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
cagagtttca aagtaagtct ggcgt                                              25

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
ttggcagtgt gcaaattcag agctt                                              25

```
<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
ctattctcat ttggaaccag cgcaa                                        25

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45
agaggacaaa tatcatgtct attct                                        25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
atggagatga aggtaacaac aatga                                        25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
aacttaaaca ctctgctcac agatc                                        25

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 48
ctaaaacgtc agatgatcct tctct                                        25

<210> SEQ ID NO 49
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 49
tatcactttt cttcacatgc tcatt                                        25

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 50
accatttcgc ctccagaggg ccaga                                              25

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
catccatgta tttcacagta aggtc                                              25

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 52
atgttctcta atacggcatt tccat                                              25

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 53
cctctgtcca ggacttattg aaaaa                                              25

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 54
gtaatgctga aatctcaccc tctgt                                              25

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
aattccatga gacaccatca atctc                                              25

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 56
gtactttttc ctgatccagt tcttc                                              25

<210> SEQ ID NO 57

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 57 cattttttgtg ctcacctgtg ttatc                                    25

<210> SEQ ID NO 58
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 58
catctttcca ttttccattg ggatc                                     25

<210> SEQ ID NO 59
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 59
ctcatctgca actttccata tttct                                     25

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 60
tatttgtcat ccttacctca tctgc                                     25

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 61
atcctttcct caaaattggt ctggt                                     25

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 62
gtatatgtct gacaattcca ggcgc                                     25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
```
cagatagatt gtcagcagaa tcaac                                              25

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 64
gtacatgaac atacctttcc aattt                                              25

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 65
gaggctgtac tgctttggtg acttc                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66
gaagctatga ttcttcccag taaga                                              25

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 67
gtgtaggagc agtgtcctca caata                                              25

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 68
aatgtgatga aggccaaaaa tggct                                              25

<210> SEQ ID NO 69
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 69
gctattctca tctgcattcc aatgt                                              25

<210> SEQ ID NO 70
<211> LENGTH: 25
<212> TYPE: DNA

```
<213> ORGANISM: Artificial Sequence
<220> FEATURE:
<223> OTHER INFORMATION: Synthetic oligonucleotide

<400> SEQUENCE: 70
cctgtgcaag gaagtattac cttct                                          25

<210> SEQ ID NO 71
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 71
ctagaacacg gcttgacagc tttaa                                          25

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 72
tggaaaggag actaacaagt tgtcc                                          25

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 73
actgatcttc ccagctctct gatct                                          25

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 74
atttctgagg taatcacaag tcttt                                          25

<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 75
agtatgcctt aacagattgg atatt                                          25

<210> SEQ ID NO 76
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 76 atttttcca ttgcttcttc ccagc                                           25
```

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 77
attggaacaa cttactgtct taagt                                              25

<210> SEQ ID NO 78
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 78
tccatcacta cttctgtagt cgtta                                              25

<210> SEQ ID NO 79
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 79
ctcctcccag aaggctgtta cattc                                              25

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 80
ttaaaaattc tgacctcctc ccaga                                              25

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 81
ggctgtcatc accattagaa gtttt                                              25

<210> SEQ ID NO 82
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 82
aattactgaa gaagaggctg tcatc                                              25

<210> SEQ ID NO 83
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 83
taatatcttt caggacagga gtacc                                          25

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 84
gatccagcaa ccgccaacaa ctgtc                                          25

<210> SEQ ID NO 85
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 85
agaacaaaag aactaccttg cctgc                                          25

<210> SEQ ID NO 86
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 86
ctcccataat caccattaga agtga                                          25

<210> SEQ ID NO 87
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 87
attttaccct ctgaaggctc cagtt                                          25

<210> SEQ ID NO 88
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 88
acagaatgaa attcttccac tgtgc                                          25

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 89
gtgccaggca taatccagga aaact                                          25

<210> SEQ ID NO 90
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 90
atgctttgat gacgcttctg tatct                                          25

<210> SEQ ID NO 91
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 91
ttttcacata gtttcttacc tcttc                                          25

<210> SEQ ID NO 92
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 92
tctaggtatc caaaaggaga gtcta                                          25

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 93
ggtattcaaa gaacatacct ttcaa                                          25

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 94
acaatagaac attcttacct ctgcc                                          25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 95
tcgttatttg gcagccaaag ttact                                          25

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 96
gagccacagc acaaccaaag aagca 25

<210> SEQ ID NO 97
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 97
tccaaggagc cacagcac 18

<210> SEQ ID NO 98
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 98
ttccaaggag ccacagca 18

<210> SEQ ID NO 99
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 99
ttccaaggag ccacagcaca accaa 25

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 100
aacagaaata aaacacaatc tacac 25

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 101
tttccaagga gccacagcac aacca 25

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 102
acaatctaca caataggaca tggaa 25

<210> SEQ ID NO 103
<211> LENGTH: 25

```
<212> TYPE: DNA
<213> ORGANISM: Artificial Sequence
<220> FEATURE:
<223> OTHER INFORMATION: Synthetic oligonucleotide

<400> SEQUENCE: 103
cacaatctac acaataggac atgga                                              25

<210> SEQ ID NO 104
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 104
acacaatcta cacaatagga catgg                                              25

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 105 gactttttt ctaacatctt cacct                                               25

<210> SEQ ID NO 106
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 106
atggaacaac acacagttga ttttt                                              25

<210> SEQ ID NO 107
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 107
atcgaacaag acacagttga ttttt                                              25

<210> SEQ ID NO 108
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 108
gagtggaaca agacacagtt gattt                                              25

<210> SEQ ID NO 109
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 109
```
cacaatctac acaataagac atgga                                              25

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 110
caagatgagt gaaaattgga ctcct                                              25

<210> SEQ ID NO 111
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 111
cgaaggcacg aagtgtccat agtcc                                              25

<210> SEQ ID NO 112
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 112
aacagagttt caaagtaagg ctgcc                                              25

<210> SEQ ID NO 113
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 113
agttggcagt atgtaaattc agagc                                              25

<210> SEQ ID NO 114
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 114
ttctattctc atttggaacc agcgc                                              25

<210> SEQ ID NO 115
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 115
ggtaacagca atgaagaaga tgaca                                              25

<210> SEQ ID NO 116
<211> LENGTH: 25
<212> TYPE: DNA
<213> ORGANISM: Artificial Sequence

```
<220> FEATURE:
<223> OTHER INFORMATION: Synthetic oligonucleotide

<400> SEQUENCE: 116
atgtcaatga acttaaagac tcggc                                    25

<210> SEQ ID NO 117
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 117
ggccagatgt catctttctt cacgt                                    25

<210> SEQ ID NO 118
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 118
atctttgaca gtcatttggc cccct                                    25

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 119
ccaccttctg tgtattttgc tgtga                                    25

<210> SEQ ID NO 120
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 120
tctctaatat ggcatttcca ccttc                                    25

<210> SEQ ID NO 121
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 121
ccaggactta ttgagaagga aatgt                                    25

<210> SEQ ID NO 122
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 122
aagcagtgtt caaatctcac cctct                                    25
```

<210> SEQ ID NO 123
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 123
atccagttct tcccaagagg cccac    25

<210> SEQ ID NO 124
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 124
agctgataac aaagtactct tccct    25

<210> SEQ ID NO 125
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 125
aagttattga atcccaagac acacc    25

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 126
ctaagtcctt ttgctcacct gtggt    25

<210> SEQ ID NO 127
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 127
gatcactcca ctgttcatag ggatc    25

<210> SEQ ID NO 128
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 128
ctcatctgca actttccata tttct    25

<210> SEQ ID NO 129
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 129
atttcagtta gcagccttac ctcat                                           25

<210> SEQ ID NO 130
<211> LENGTH: 250188
<212> TYPE: DNA
<213> ORGANISM: Homo sapiens

<400> SEQUENCE: 130
tgaatgagag gtgccccatc aactggactt ctcctgagtg ttgaaaaggt aagagggttt     60
tgcttcttta ttcactcctt tcttactatt tgcattgtaa tataactctc ttgggactca    120
agggaacaaa ccatacagtg tcttttgcta aatgccaaaa atcaagaagc cagttgaagt    180
tttcagttca aattatttca caagtgttac acagtagaaa acctttatgg tggctcacgc    240
ctgtaatccc aacactttgg gaggccgagg tgggtggatc atgaggtcag gagtttaaga    300
ccagcctggc caagatggtg aaaccccgtc tctacaaaaa atacaaaaat tagccaggcg    360
tggtggcggg cacctgtaat ctcaactact ggggaggctg aagtagggaa ttgcttgaac    420
ctaggaggca gagattgcag cgacctgaga tcgcgccact gcactctagc ctgggcgaca    480
gaccgagact ccatctccaa aaaaaaaaa aagaaaaga aaagaaaaga aaagaaaaa       540
aaaagaaaaa acaacaacaa aaaaaaacca aaacaaaaaa ccttttttttt ttttgtctc    600
agtttgaggt ctcttgttac aaatttaaag aaaattaatt ttacaatttc ctattctcaa    660
tgattttgat ttactgatat tttaccctac aacaatatag tgaaaagtg tggtcatggg     720
attggttaga cctaattcag gactaccaat actagatgtg aggctatagg caggtgtgtt    780
aaagattctt tggaatctta ttttactcaa gagtaaaaag tatgtgtagt aataattatt    840
tcataagtat attgagagca ttaaatgggg aataacaacc atataaaagg cttagcatat    900
tagagactta atacaaatca atttcttgca ttttgcttat cctggatata tcgtgggttt    960
gcttcatatt ggaaaacaag acagcaacaa agatccatgt ttcattcttc agtgacttaa   1020
aatattagtt gttctggcca ggtgtagtgg ctcacacctg taatcccagc acttcaggat   1080
gctgaggtag gatgattgct ggagcccagg agtttgggac cagactgggc aacaaagtga   1140
ggccctgtat ctacaaaaaa taaaaatcgt agccaggcat ggtggtgtgc acctgtgatc   1200
ccagatacac gagaggctga agcaggaaga ttgcttgacc ttagaaggtt gaagctatag   1260
tgagccttgt ttatgccact gcattccatg tattagttgt tctacaaata aaaatatttt   1320
actttcaaaa catgttttac taaaagtttt tcagtaagga tgtaaaaact attaatggtc   1380
aactttgact acttccaaaa tgcttttttt gagtgaaatg ttacacctct tgttagttc   1440
attgcaataa tacttaaata tttaaaattg aaagtcagta atggtaaata tagaagaatt   1500
agaggataaa atgagtggag atatggaaag gtacagattg aatataatta tttaagtaaa   1560
atcctttcct agagaaaata gaaaatagaa ctttgaggtt gaatctcttt taatgtaatg   1620
ttttttctcga atccaagtgt ttttacacta tacaatagga gtagaaattt gtcaccactc   1680
tgtggccaaa ctcactttt ctttcttttt ttattttac attaaaaaaa aattttactt    1740
taagttccag gatacatgtg caggatgtgc aggtttgtta cataggtaaa tgttttattt   1800
taaatttaat ttaacacttt ttatttttaa gtcatacaac tctcatagcc agtagttaat   1860
attaccttgc aagtttggta tggttgatga attgcatcct gttaataatt gctacagatt   1920
tttgaataat tgcagaccag tttgatggtc ctgggttggc ataagtacat gaagatttac   1980

```
tttttcctgt gagctttctt gggatgaaga aatttagtgt tttttttttaa ttttttaagaa    2040 atatttatta tttttttacat gatttatttc ccactgaaaa ataaatccca ccgggcataa    2100
agtgtatttt tttaagtcac agagtaaccc aacttgaagc tagtttttca gacttaggca    2160
gttcatgctg taagcccgag atctcatggt caccccttgca agagaaatat ctaattgaaa    2220
aaaaatatga agagtattaa ttttgatagt gctaaaatga cataaaggga tctcactggg    2280
cttgagatat taagtattaa aattgttaaa ggtttaaatt gttagtaact tgttattgca    2340
tagaaaatgt gccaaatgtc agtaaataaa aaaactttt ttaaaataaa aatttacaga    2400
aaaattatga cgatactaca aagaggttct gtacaacccc ctcccagttt ctcttactat    2460
taacatctta aattagtatg ttacatttgt cacaattagt gaaccaatat tgatacatta    2520
gtactaacta aagtcagtgt tccttttact ggagaatggt gttagaaact aaggtctggg    2580
cactgtggta tggtggttgc tattgagatg ttgttatttt taggttcttt ctcagctgac    2640
agagcaaaga aatatatgtg tgtatattaa cctatgtgta cacatacatc tatgattatt    2700
tcgatatgta acatctgtat ctttattaag ctaaatatga gttcatatgg tgtcttcaat    2760
tctaatcaat tactgtatag attattctag cctcttcctc ttgcttatct gtaacttcct    2820
atttcaaacc gtgaaaaatc tgtcttccac cacctactat ctgcttacct aatttctcat    2880
ttccagttta tgtatacagt ggcttcagaa ttattacata tagccctgtg ggatacaact    2940
ttgtcaacta gagtggtgct tatgtaagtt cttctatctt tagttttact gactctactc    3000
attttcaaag ttgcttagtc cagaacattt cactcatact cctcctagtg aagttgtttc    3060
atatgttagt aacacagatt cttttttttgc agtctgcatt ccattttagg gttccctcct    3120
ctccaatctc ctaaattatt atttttttaaa ttcatataca tcaaggttta ttctttgtgc    3180
tgtaaagttc tataggtttt gacaaataca aagtgtcatg tacccatcat tacaatgtca    3240
tacagaatcg tttcactgcc ctaaaaatat cccttgtcct ttgcctattc aacccttccc    3300 ctccttttccc aaactcctgg caaccactga tctgtttatc gtggagctgt gtctcttcca    3360
gaatgcatat aattgaaatc atacaatatg tagactttttc accctggctt attttgttag    3420
caatatgcat ttaacattca tccatgtcct tatgtggctt gtagttcatt actttttact    3480
gctgggtagt attctatcat agaaatgtac cacagtttgt ttatccattc gctgattgaa    3540
gtatatcaat ataccttgga acatgactgc tagatagtat agtaagacta tatttagctt    3600
tgcaagaaac tgccaaactg tattttaaag tggctgtacc attgtgccac cagcaactcc    3660
tgccagtgat ccagtattgt cagttttttg gatttagcc attctaaaag gtgagtgatg    3720
gtatctcatt gtcgttttaa tttgtaatac tctaatgaca aatgatggtg gatttcttt    3780 catatgtttg tttcccattt gtatatcttc tttagtatgt gtctgttcgg atgttttgct    3840 tactttttttt aaactggggtt gattgttttc tttttctttt tcttttttttc ttttgagacg    3900 gagtctcgct ctttagccag gctggagtgc agtggcgcca tctcggctca ctgcaagctc    3960
tgccttccgg gttcaagtga ttttcgtacc tcagcctccc gagtagctgg gactacaggc    4020
gcccgccacc acacctggct aattttttttg tatttttggt ggagacgagg tttcaccatg    4080
tcggtcaggc tggtcttaaa ctcctgacca tagatgatct gcctgtcttg gcctcccaaa    4140
gctaggatta caggctagga ttgcaagtag gataggcgtg agccactatg cccggctgat    4200
tgttttctta ttgttgagtt ttatattcct ttattttgga atggagtaaa taagcacaat    4260
aaaactggtt gagaagataa tcattttaaa aaatcataat gaattatatg atacacattc    4320 tattattttca tgagaaaaat catggaagag tcagttcaat attcagtgaa tcattaatgt    4380
```

```
gaggatgtaa aatttgatac acacacaatt tattgagcac ttatcctatg tcaatcagtg   4440
cgctaaattt ttttctttta tattaactca tttaattccc actacagccc tgtgtaatgg   4500
aagctgttct tcccaccatt ttataaatga tgaaaccttn gatcacactc agtggaagag   4560
ttctaaagcc ctatgtggtg ctgtctgata gaaaatatat tttaaaatga gatgatctaa   4620
ggtatgttta cctacagagc taaaggaaag tatgtcttaa atttaataat gagtgattat   4680
agaaacagat tacaggaaat agtccatctt tcttgaatta tccaaagtgt tacaagcctc   4740
aaattcattg ttgtttgtat gagaacacat ttaggtgatc ggatacaagt atatagtttt   4800
tcccagatgt ttatttcaca tcaacttttt tttcatcttt actttcttca aggcaagtag   4860
gatagaatgt aataatcaaa taggttttc ccccaccca ttttagagca gtaaataatt   4920
ccaagaggca tttgctttgt tattggataa gtaattaaca aaaagaattc ctaaagacaa   4980
ttagaatcat gaccatactg ggtcttgaaa acatagcagt gcaatcacag ccaatggctg   5040
gcttggtggc tggcgatgag cctgcagcat gggactgggt gttccaccac ggcttggctg   5100
ttgtccaggg agctttcagt cgctggggtt cccacagtgc caagcacgag gcaggtgcag   5160
aaaggataaa ggtttctgtt ccccattagt gttgagggca tgcaggtcgt ctgacatgag   5220
gggcatgaga agtgaagttc ctgctttgct ttgggtaagg aatctgcatt gacagggct   5280 taagaacctg ctcttatacc tcacatgtct tagcctggcc tttgagatga gtagggagtt   5340
tgagtgggag tttgagtttc ctcttagaga aacagaactg agtgaggcac tttcattttt   5400
tagtttccta gtaccttttg ttaaggaaaa aaaagccaaa atgagtgtta aaaatttaaa   5460
atttttagat tttaaatttg catttaaaaa attaatgctt ttttttttag atggagtttt   5520
gctcctgttg cccaggctgg agtgcaatgg cgtgatcttg gctcactgca acctctgcct   5580
cccaggttca gcgattctc ctgcctcagc ctcctgagta gctgggatta caggcgcccg   5640
ccaccacacc cagctaattt ttgtattttt agtagagacg aggtttcacc atgttggcca   5700
ggctggtttc gaactcctga cctcaggtga tccacctgcc tcggcctccc aaagtgctgg   5760
gattacaggc gtgagccact gcgcccagcc aaaattaatg ctcttaacat gtaaaaagta   5820
aagtgcagtg gaactttggc acttatgcaa gataatacaa cttaaaagat ttataagaat   5880
attaactgct aatgaacagt agagggatct aattaacatt gaaagttaca tgaagaaagt   5940
gtttgtcttc tattcccaac agggcatctt tgtaactata atgactcttg agaagatttt   6000
gttttcagtc ttaaaacagg aatggggaa aaatgtaggc ctgggtaagt acaaaaaagg   6060
gaaatcgaag gagactaggg agttactgta gattttgcag gactgaggaa agtcagaata   6120
aatacaagag acaatgatgc tggtaatttt ctttgggctc agagaagtaa tgctttgctt   6180
tgtcagagtt gtagtaaaat ttagatctaa gaagctcgtt ggaagttgta gcagaatcct   6240
gtcttgttta ctatgtccac tgcctggcac agagatggaa cactataagc tttccaaaaa   6300
catttgtgga atggaatcag aaagtcactt tactttccaa gatgcaattc tttattttga   6360
aacataaata tttaaaaagt ttataaattt ttgacataat tatgacatac atccttccag   6420
gcttttttca atgcttatgc aaacatgtat atgtgacctg taggtctcct tttacccagt   6480
ttttggagta caaataaggt cacatctctt cttaacttta aatgtttaaa acattgaagt   6540
tagcaagaag cccagaaact ttttctaaag aacttttttct accccctaatt gtccaagaac   6600 tccaagttt cttggttcaa agaggtaatt tctgtttcta aacactagaa aaaggagaat   6660
atgaaggatc tgactagtcc attgtcacat gccccacccc attttctgct gcaagagcct   6720
```

```
ctgtcaccac agcattgtgt cactgatgaa aataggtcct cccacagagt cagatgcatc    6780
ccagtctatt gctactatta tcaccctgtt ggaacagatc cctgcacagg tcacagcagt    6840
tcctggaaga tgaaactcat tctcccagcc ttaatatcag ccaggaatac tttattcttg    6900
gacttccaaa gttgctatag tagttttcaa agcccaccta gcacctaagg atgggtgagt    6960
aaagacaagc ttccagtttc agctgcagaa acaagaaccc atctcccacc acatagtagg    7020
tgttggcatt aaacttctct cttatgatgt aatgtgttct ccttgggatc tttggtattt    7080
ctgtttgcat acttcatttg gggtcatctc aacacaccaa acagattcta actacactga    7140
atctcaaaag aaatagaagt agtctttgtc aagccacaga aaagagcttg ttcttctttc    7200
ttctcctcct agacacctgc atacttttca ttcctctaat gaagagggtc cattcaataa    7260
attcagaaga aatgaagaaa aaatacaag tctagtttgt gataagtcct tgttttcacc     7320
taaacagaga agcaagaaca taaattatat aaggcacctt ctcttaatta aataaacaaa    7380
agagttctat gtggtctagt tacacagaga tcacagtgat taactactca gctctggagc    7440
cagacaactg ggtttgttca gattctggca ctctttcttg aatttgggca tggcatttga    7500
ccttctgtac ctcagtttct tcatttgtaa attgggatgt taataataaa atgtactaac    7560
tttatagggt ctttcctgag gcacataatg taatttaaac aacaaacaag tatacataac    7620
agacattttt ttcttacaaa gacggtacca tactaaactt aatttgcttt ttttgaaaaa    7680 ttatatttt aggtaaaact ttgtaagtta attttttggg gtgaaaaaca tgatacaaat      7740
ttatcaattt gattttgctt cattagcatg atatactttg ttctagaaag tacttaggca    7800
attttcatac atgtctttaa atataatttt tgcacatgta aataagagtt ccaaagtatt    7860
ttgccatcac ttcatcagtg ttgcctctca acagcctttg aagcgaggag atgccagtca    7920
ctgtctcaga cacaaggatg caggctgtgg aggccagtga gccatagtca ctgaactggg    7980
aattggctgt ccttttgacc atacagatta atcactgtag tttcaccaat cacattgaac    8040
ttgaagatca ataaatgacc ctaaaacaat gagatttcat agactctttc tatatagtgg    8100
aagttaaagc aaatcagaaa ggagtcccta aacctgtgaa ttcttgaatt ttagttttcc    8160
aggtcaacaa gccttcttta agtgacttca tgtcccgtcc ttggttttg atcatagact     8220 ggtataagaa atgaccataa aataaatgtt tttgagaaaa ttatagctga aaatactgtc    8280
catgatacca ctcagtgata taagtctcta aacagcaaac tcttccatga atggggtgga    8340
gggaagatgg ttttttctttc caggtgaact tacatattgc cttttctcag atatcagatt   8400
atgagaataa tacaatggac tgggctttga cagccaagac tttcagaatt gctgttagtg    8460
cccatgtgca ataaaatttt tctatcatgt ctctcttatt atttcaaatg ccctgtttta    8520
ctgttttgat tactaattat ctatttagag ggaaacagtt ataaataaat aattcactgt    8580
tctacttact gtgcacccct gcctttctaa atataactct tctatgtagc atgtaaatta    8640
ccacagaact catctcagaa aaagatcac tactttcttt tttagaattc aaatttataa     8700
tatctaattc tataggtggc atctggcctt tagcatgata tcaccaatga aaatttaatc    8760
tgtgttatga attcccttgt ttctagaaaa gcttcagcag gaaaatgaga agagaaccca    8820
taaaaaccat aaaacatttc atgaatggta gctttagaaa atcttacagg atttggtagc    8880
ttttacattt atgacaaagt gatatttttg atgttgttca taattatttc agttcattag    8940
cagcattaat aagctcccgt tttgtacagc ttgaagatct ttaagacttc cttaatgaga    9000
aactaccttt aagctacgga agacccatca gggtgccaaa ttccatctgg acacagttac    9060
aaatacacca ctgttgatga gctgaaaatt agagcaacca aacaacagag ctttaaaatg    9120
```

```
ttatttcaat gcaaagggac attttcacca tagaaaaata gaagtttgcc tctaaataaa   9180
aatgatttta caattgcaag agtacttgat ttacccettt acatttagtt caaataccaa   9240
aaatttctta aggaatgaga aattccaatg ttcctgagaa ttctgatagc ttttagagag   9300
ttcagttttc tgtagcattc cattttgcaa tcctatacaa atttctaatt tataaccagt   9360
ggtatgtaat gataatttct aatatttatt aagtgtttat tgggttctaa gtgctttacg   9420
tctgatatat gtatcacatt taatttattt catccagtgg ttcttaactg gggacaactt   9480
tgtacctctc tccccaacat atttggcaat ctctggagat agtcctggat ctccagatct   9540
atctgtcaca acctaggatg tatgtggtcc tacgagcatc cagtgaatag aagctagaga   9600
tactgctgaa cattccacag tacaagggca acccccacat caaagaatta tccacaccca   9660
aatgtcagta gtactgaggt agagagaccc taacttaatc tgttcaacaa tcctatgagg   9720 tgatttttt tttttttttg agataaggtc ttactctgtc acctaaactg gagtgcagtg   9780
gcatgatcac agctcactgc agcctcgatc tcccaggctc aagccatcca cctgcctcag   9840
cctcccaagt agctgagatc agaagcatgc accaccacac ctggctattt tttttatttt   9900
tttgtagaga caaggtctta ctgtgttgcc caggctgatc tcaaactcct gagctcaagc   9960
aatcctcctg cctcagcttc tcaaagttct gggattacag gcatgagcca tggcacctga  10020
ccaaggtgag tgtatttaac ctcattttca ggcaaggaaa caaagacag aaaagttaag  10080 tagcttactt aaggtcacag agctaagtgt ggtgccagga ttgaaaacct agttctttat  10140
tgctttagca caagctattt ccactatact ctgtcatgtt cagagaatgt tgatgtccat  10200
cagtggattc taaattttga aggatggaga tactgcctta ttctgtacat ctgctttagc  10260
acccaagctc ttgcttggtg aaaaattaat agtaaacatt catcttttga gcatcttcaa  10320
atatcccctt tagaatgaca ttcaattatt aggtcagtaa ccccaagaga aaacggttgt  10380
ttgagtgtat atactgtatt acaaaataag gggtgaattc aaaggaaaac ataagatgca  10440
attcgtgcct ccaaggaggt gtagggaag aggggttatg aatgtatgta aatagaagtt  10500
ggtgtgcgtg tgtgtttata aacagaattg tcagaccaaa cattattttg gaagcagtaa  10560
aagtaaacta gaatctggcc tagtcatgtc ccaggacacc tctttcaagt cctgaaacat  10620
ctttgtaaga ctgtaatgtg tgtttacatc ctaggtaatc actgtggccc actgttgaag  10680
agctgtggct gttcttaccc ttctagctta gataaactta taagcacaac cagactacat  10740
atatgaagct gaagagacct tgtcttttt taacgagctt ttcttcccga taggagtgac  10800
tatttctttt cttcttccac attttcaggt tttagtgtac ttgtgattgc tacccactta  10860
tcactattaa agtctactca ggagagaatc tgagaaacac tctcaaatta agttgaacat  10920
gatggataag taaagtattg tgaaagttca ctctcatgat ttctaatggt gaaacctggc  10980
agggtgacta atctttgacg agaaggttat cacttataat ctttcatata ttgagatcat  11040
ttgtaagaag cacccagcac attgctgaac acaaagtagg tattaaataa atgttggctt  11100 cctttctcc tactcatcct cgctcttctt tttaatatac ctttaaaatg atgccacaga  11160
aatggccacc caatcttcta tatttaaggt cagttcttgc attaggaaat tctataggg  11220 aagtatgtga agtatgtgta gtcagtcatt aaatgcttgg gctctggcca cagattgttt  11280
aggtttaaat cccagtttcc tctttattta ttaattgtgc aacttgcttg ggaaaacatg  11340
aaacttgttt ttcctcaggt tcattatctg taatatatag tgaatgaaga agtttcctgt  11400
cccatgaagg tgttgtaaag attaaaaaag gcaaattagg ctgtgtattt gtcataataa  11460
```

```
ttggcatata tggtaagtga ccaacaacca taaggtatta taaaattgtt ataaaatgat    11520
atgagctatc attgagcagc atgaaagaag agcttcactg tttcacctac tatcaccctg    11580
gcccattaat ctctttcctg ttcctgacat ttcagagata cgtttaggat ttcaatcatg    11640
accttaagcc acatttgaac aattttctgg tggataagtc ctcattccca cattatgtat    11700
gtacctagat gcaaatcctg aatatcatgt cgcaattagt gcatctggac atgcttgcta    11760
actgtgttaa agctctgaat aatggtaaag ttttatttct accaaaacaa atttgggctg    11820
taatgtttta tgataaaaat ctgtggtctt cctatgtaca tgtgtgtgta catgcttaaa    11880
atgcaatgtt atagttaaat gtaattcatt aaaagtatgt aactccagtg gctacttagt    11940
ttggctactt ggtttgtaga tttctgcttt cctgtttcat tgttaaacag gtctagaagt    12000
tattatttca tgaaactaat gtgaggaaaa agactatgtt gatatataag tgacattata    12060
taaatacatg agggatgatt tgattagaag cagtattaca cagtgatagg agtaatggtt    12120
tagaactaga ctcaggtttg aatcttagct ctatcattat aggcatttac ttaacttttc    12180
ttgtttgctt aactgaaaac tgaagataat aacacctatt tacatggttg ttataagggt    12240
tatatgaata atgtctggca aatagtaaga actcaagtaa ctgtttcact ctttccagaa    12300
ggagattggc tgaaaaatat ttggagtctc ctccagccat attccttggt cagcttctat    12360
gatcctcttt ggagcttaat tcttaatccc tttattttca cttgcttgtt gataacaaag    12420
aagaactaat tattaattta tttcaaaatg catgtattat atttgatggg ccacactaac    12480
agttataaac caaacaacag attgggaatg gggaagtgga tgtggtgagt tcaatcacat    12540
gtctgggaaa agtcaatagt gaagacagag tctcacaatt ttttgtcata atggagagat    12600
gaaaacacag gtagaggatt tcaaacaaca gagtggatgg tgagttaaaa atgctgaaat    12660
tctttcctgg tgtctaactt aatgcaatgt ggtttatctc tttgctcttt tctctactat    12720
tcaaatttag gataataaag attaaatgtt tctaaatctt actttacaat atcaagaaaa    12780
aaaggtatgc ttttgcccac ggaagggcaa agcagagcta tgaaaacctg ctgaacacat    12840 tcttttatttt caacacaggt tcttgtcttt ccatcatgaa atgcacattt tatttgtact    12900
gtatttgggt gaccacaagt caacaacaag ataattcaca agacccttgc cttagatgtg    12960
tcggcaataa agtaatcagg ccaaaatttt tactttcctt tgaattttc aattcaaaca    13020 caatgtatgc ttgcttttac acagtagggt tcagggatta gagggttggc tctttaaaaa    13080
ccgtcagaga cacaggcaat cctacacaaa attctcagaa ggaaggcgcc tacgcctggg    13140
aatgcccaga tgcccctcag agagttgaag atggcgtttc tctgagtcag gtcaaagtta    13200
acacattacc ttcgcttcaa agactgcttg gcttcctttc ggtggattag tcaagatgtt    13260
ttgctgactg agactaggaa atctatagga gggcgggtta gtttacattg ttccttgtca    13320
ttatcgctaa aacactccaa agccttcctt aaaaatgcgc actgggctaa aaaggataga    13380
caaggaacac atcctgggcc ggtaattacg caaagcatta tctcctctta cctccttgca    13440
gatttttttt tctctttcag tacgtgtcct aagatttctg tgccacccctt ggagttcact    13500 cacctaaacc tgaaactaat aaagcttggt tctttttctcc gacacgcaaa ggaagcgcta    13560
aggtaaatgc atcagaccca cactgccgcg gaacttttcg gctctctaag gctgtatttt    13620
gatatacgaa aggcacattt tccttccctt ttcaaaatgc accttgcaaa cgtaacagga    13680
acccgactag gatcatcggg aaaaggagga ggaggaggaa ggcaggctcc ggggaagctg    13740
gtggcagcgt gtcctgggtc tggcggaccc tgacgcgaag gagggtctag gaagctctcc    13800
ggggagccgg ttctcccgcc ggtggcttct tctgtcctcc agcgttgcca actggaccta    13860
```

```
aagagaggcc gcgactgtcg cccacctgcg ggatgggcct ggtgctgggc ggtaaggaca    13920
cggacctgga aggagcgcgc gcgagggagg gaggctggga gtcagaatcg ggaaagggag    13980
gtgcggggcg gcgagggagc gaaggaggag aggaggaagg agcgggaggg gtgctggcgg    14040
gggtgcgtag tgggtggaga aagccgctag agcaaatttg gggccggacc aggcagcact    14100
cggcttttaa cctgggcagt gaaggcgggg gaaagagcaa aaggaagggg tggtgtgcgg    14160
agtaggggtg ggtgggggga attggaagca aatgacatca cagcaggtca gagaaaaagg    14220
gttgagcggc aggcacccag agtagtaggt ctttggcatt aggagcttga gcccagacgg    14280
ccctagcagg gaccccagcg cccgagagac catgcagagg tcgcctctgg aaaaggccag    14340
cgttgtctcc aaactttttt tcaggtgaga aggtggccaa ccgagcttcg gaaagacacg    14400
tgcccacgaa agaggagggc gtgtgtatgg gttgggtttg gggtaaagga ataagcagtt    14460
tttaaaaaga tgcgctatca ttcattgttt tgaaagaaaa tgtgggtatt gtagaataaa    14520
acagaaagca ttaagaagag atggaagaat gaactgaagc tgattgaata gagagccaca    14580
tctacttgca actgaaaagt tagaatctca agactcaagt acgctactat gcacttgttt    14640
tatttcattt ttctaagaaa ctaaaaatac ttgttaataa gtacctaagt atggtttatt    14700
ggttttcccc cttcatgcct tggacacttg attgtcttct tggcacatac aggtgccatg    14760
cctgcatata gtaagtgctc agaaaacatt tcttgactga attcagccaa caaaaatttt    14820
ggggtaggta gaaaatatat gcttaaagta tttattgtta tgagactgga tatatctagt    14880
atttgtcaca ggtaaatgat tcttcaaaaa ttgaaagcaa atttgttgaa atatttattt    14940
tgaaaaaagt tacttcacaa gctataaatt ttaaaagcca taggaataga taccgaagtt    15000
atatccaact gacatttaat aaattgtatt catagcctaa tgtgatgagc cacagaagct    15060
tgcaaacttt aatgagattt tttaaaatag catctaagtt cggaatctta ggcaaagtgt    15120
tgttagatgt agcacttcat atttgaagtg ttctttggat attgcatcta ctttgttcct    15180
gttattatac tggtgtgaat gaatgaatag gtactgctct ctcttgggac attacttgac    15240
acataattac ccaatgaata agcatactga ggtatcaaaa aagtcaaata tgttataaat    15300
agctcatata tgtgtgtagg ggggaaggaa tttagctttc acatctctct tatgtttagt    15360
tctctgcatg tgcagttaat cctggaactc cggtgctaag gagagactgt tggcccttga    15420
aggagagctc ctccctgtgg atgagagaga aggactttac tctttggaat tatctttttg    15480
tgttgatgtt atccaccttt tgttactcca cctataaaat cggcttatct attgatctgt    15540
tttcctagtc cttataaagt caaaatgtta attggcataa attatagact ttttttagca    15600
gagaactttg aggaacctaa atgccaacca gtctaaaaat gcagttttca gaagaatgaa    15660
tatttcatgg atagttctaa atactaatga actttaaaat agcttactat tgatctgtca    15720
aagtgggttt ttatataatt ttcttttttac aaatcacctg acacatttaa tataggttaa    15780
aaaatgctat caggctggtt tgcaaagaaa atgtattaca aaggctgcta agtgtgttaa    15840
gagcatactc atttctgttc tccaaaatat ttcataaggt gctttaagaa taggtatgtt    15900
tttaaaagtt aagttcctac tatttatagg aactgacaat cacctaaaat accaatgatt    15960
acaaacttcc ttctggcctt ctggactgca attctaaaag tgtaaaaaac atattttctg    16020
cattaagtta ggcagtattg cttagttttc aaagtggtag gctttggagt cagattattt    16080
tgattcagat cctacatcta ctgtttagta gctctgttgc ctgaggcagg tcccttaaca    16140
tctctgtgtg tgacttgacc tttaaaattt ggagactgtc ataggggtta atcccttgag    16200
```

```
aaaatgaatg tgaaaagtta gcctaatgtt aactgctatt attatggatt accatatttt    16260
cacattcatc acagtacatg caccttgtta atataagatg ctcaattcat ctttgagtat    16320
aattttgtga ctctcaatct ggatatgcaa tgagtgggcc tgtatgagaa tttaatttat    16380
gaaaaattgt gtttcacatg gccttaccag atatacagga aacacgtcac atgtttctat    16440
tgtatgttgt taaatgcctt agaatttaac tttctgaata ggatcccttc agtttgagag    16500
tcataaaaga gtaaaattat tatggtatga gttatagatt gtattgaata tctctttata    16560
tgtctaggtt ttgtcattgg aaaaccaaaa agtttggaaa aaaaatctaa gttatttctt    16620
actttcttaa ttttgtgtgg atttcacatc aagtataaaa tttgaagaac atctgaacta    16680
tcataatcca tatatatata taaaataaac ataatctaag agagaatttc accatgaaaa    16740
attcaggtag ttcatgacta tcagagcaaa caagtacatt aaattgaaac ttttatgaaa    16800
ataacattta tgaaatagga agctatttt  aaactagaag tgatatatta gcatataatt    16860
tataattcat atacaagtgg gattgattta taaatggtca ccaacagaga ttgtgctatt    16920
taatttggga aaattttta  aatttacatt ttctcacaac ttttaaggta gttattcagt    16980
ttgttcctct ctgtctcttc tctcatgccc tgaatttttc atatttcgtt tagttgtaag    17040
agtgtatatc aaaccgtgtg tcacatgaca taacttgaat tttcgtcgtg atatctgtgc    17100
tatgtctagg tctatactga ggaactgtgg gaaccccaca gaatccaagt atacagtgcc    17160
actgatttct tacaagggat gtggggtctc ctgtaaactc tgcagttagt ctcaagtaag    17220
accaaagagt aaaatattgt taggatctaa ggtggaaatt cagcaaagaa tcacatagtc    17280
taagtctcga gtttaacagt aagataattt gagatacttt tgtaattatt aaacacaaag    17340
taatgagaga ttttaaaaca aacaaataca cctgaattta tatatcagaa taggtatggt    17400
ggttcaaaat agctatctaa taaaaaccac actcctattc taaacatttg cctttgatca    17460
aaataatttt gggtctctta ttatgaaatt gcctttctaa ataatacata aatttcttct    17520
cataagtata tattagccac attatttat  tgttattgtt ttatattcat agcttgcttt    17580
agattaaaaa ttatattacc cagactggtc tcttggactt gcttccaagt gacttttgac    17640
tgtatcacaa aatcaaattc actctgaaaa tataaagatt tttcatcata atttcctttg    17700
ttaacagcca agtgctacct aattttaggt gttttcatta aaaaaaaatg cattgcaaac    17760
tttaaagaca attcttttgt ttgtttgttt ttaaaagaca gagtctcact ctgttgccca    17820
ggctagagtg cagtgacaca atcataactc actgcaacct ccacctcctg ggctcaagtg    17880
agccttccat cttgcctcac gagtagctgg gtcttcaggt gtacaggtgt gtaccaccat    17940
gcctggctaa ctttttttt  ttttaagtta tatagagaca gtatctcact atgttgccca    18000
ggctgctctt ggagctcctg gcctcaagtt atcctcccac tcagtctccc aaagtgctgg    18060
gattacaggc gtaagccacc tcaccctgtc agcctaaaga cagtgcttaa tgaagagaaa    18120
tataagtgct ttgagcaatg gaagtataat taaaattata ctatgaaaga tttataaaga    18180
tgaccatttt gaatgggacc acacttattt ggttatataa attatgatac actattaaaa    18240
attcatcatg atgattttgt atttacattt tatttacatg tttgcaattt gtgaggaaag    18300
ctaaaattat ggctaagcca taaatatttt tgcagtttgt tgagggtgtt tgtaaaagtg    18360
ttgccaagga agaccagttg gctacccaaa caagggttta gtctaggtct gatcaataca    18420
tacacattat ctcaggtttg tctatcagaa aaacccttagg ttatccaaat caaaataaaa    18480
tagatgcata aaacaaaggc caatatgtgt tgaacaatta tattgtgata tacaactgcc    18540
aagcattccc gattaccatg actccattta gtcagtccat gggcaaatgc catcaatgag    18600
```

```
gacagcccag ggtttccata ttctctcttg gctttacatc ctataggaat tggaggggcc    18660
cacctctggg ataggagccc ttctgtcttg aacaatgttg tctgaacact aacaaatgtt    18720
gactttctac accagtccct caatagtctt ttctatttat ccttttgctg accatgtttt    18780
gttattacac agttgagatt tttcagctgg aatctgtgt taattttgta ttaattttga     18840
ttagcttaac tctcagagtt ctaaaagtac ctcctgtacc tgatatatga caaaaattat    18900
aattacattt atttatatat aaaatatctt tgtatatgta aaatatcttt gtatatataa    18960
ttatataatt gtttcttta attttgcaaa ttttaaaaag ttctcctttg ttttgaagtt     19020
tattcctata gttttttata tgctagttaa attattaatc acttgattca agtaatattc    19080
ttatatactt ataaggaata gtgtagtttt aatatttaat tccttgctaa agagagaagt    19140
ggaatctatt tttcttagct acttcatcaa tattttatgt ttgatgtgac agtcaaaata    19200
tccctcagag ctaactgtta cactagggaa atcacggttt tccagttttc catttatgtg    19260
ttatgggagg gagtggaact tagtgtaata atattcaata cataaatgtt aacacttgtt    19320
taaaggtcct tgagtgagta ctgctataaa atgcattatt attgctagtg tcatttcaca    19380
agagcctata atttcagtgt gatagagcta caatataagt atagtattgc aaaaccatca    19440
ggaagggtgt taactattta gcatgcagtt atgtgttggt tgtcaaaacg ttaaaaacat    19500
ctctgactca gcagcaattt tggcaatttt gatcctgagg catctgtgta gggcatcttc    19560
ctggagaaaa acctctgaga tgcaatgagg tcaaaggggg aaaacagact atgataaaga    19620
tcaagttgtt tggagatctt gtagaaagat taatttacaa atatgtcaag tgcattatca    19680
tggaggaaaa cattgctatt tctgttggtt ctcttcagag ctctagaatc aatttaccac    19740
atagttgttt cagtgtgaaa ttagcattac agagtggctt tacggcttta ctgtagggca    19800
ttgtgtcagc aaagagctta ggcttctttt agcaagaagc ttgtaaaaat ttaatttact    19860
cttagattgc ttgatgtaga gaattacatt cctacagagc tctgaaaaat cttttttcag    19920 agttttcac agctgtattc aagttgcaag gcttgtcaac tttgctattt ttctgtgcag     19980
ctctgttaac ttattattat cttttgacat aaattatgat tccaaattgt aaagctctgg    20040
atgtcagggc cttttctaat ttgtttagta tgatattcag accatttcaa gactcttccg    20100
tggaacaatt taataaagat tttttgtga tgttaatgag ttcatggtga tcaaccctag     20160
agacctgtgt ctattgtaga tcgatgacat tcaacagtcc tgcagtgctg gcatcatttt    20220
gataaaaagg ggtcaaagca agtgggactg tgggcagatt tttaatgctt agaacaatta    20280
ttccatcgaa gttttcttgt gtcccttctg ccttagcctt tgtaggatag catgcttgct    20340
aatttcttgc tcatggggta aggaaatgaa gattttgct aggtccgtag gattattagg      20400
actactcagg cctgaagcta tgcctggata tagccagaaa actctcccat agcttgctcc    20460
aaggagctga gatacagcag tacttccttt gtaggtcatg attctgggta acctggaaga    20520
tgacctcatt catattctgt attctatgtg agacgttaag aaggtagagg tggccaagaa    20580
ggaaattgtt gctgcctttta tggaacaaat tatctgaaac ccagctttct cgagggcttc   20640
attgaagtac tcaactgggg cacttaaccc agtctaaggc tggtcaagga aggcttgctg    20700
ggggaagtgt cttttgtatt cacacctaaa ggaggttatt caattagaat tatccaaaga    20760
gggtagggat gggctaggaa aaatttaaac aggtagtgtg gaggactgac aggataagta    20820
agcatggcac cttcaaaata tcctgagaag ttccctatga cgggaacata aaatatgtga    20880
cagagatttg tgggagatgg gtctggaaac tctagcaggg gccagatcgt aagggggctt    20940
```

```
tgtaggctttt gtaggctttg tttgggcttt atcatactgg aagtgaaaag ccatggcttt    21000
taaacaggag agggacataa tcagttcata tactgttgca gttttgtaaa agaaaagatg    21060
agctgaaaga gtggccatgg tggaggtggg tggggtgggg gggaggggc ggggagagag    21120 agagagagag agagatttga aagcattta ggaggtaaaa tcaactggtt tggtaatcaa    21180
ttagtagttg aaggtgaagg aaagagaaga gttaaggata acatctatat ttgttgattt    21240
ggataataga ggggacagtg gtgctgctta ttgaatgaga aaatttaatc ggagaagaag    21300
gcatggagca ggagtgcaga cctatgtgac tctacttctc tcaaaaccag aaacggaaat    21360
gatgtatatg gctcagggtt aggtaatatg gttatttgaa aatgtattaa agtgatttag    21420
agcttagtct taggtaagag atataagatg tctgaggtga cagttttata aatatgtaga    21480
gtgcccactt gtttggcctt attgtggcat agtgtgacct gagagtgtta ggaagaagca    21540
gctgagttct agggacagta ctggttaaat tctacttaga aattatactt agaactctcc    21600
tatataacct gctaactgat gtctgaacct cctgataact tcactccttt aggcagtgct    21660
tttcacatca cgggacacaa catatgagag atcatagaaa ttcaatgtgg tatgaaaatc    21720
tgcttgggac ttcagatatt gtctccagtg attaataaa aataggagct cacctactat    21780
gatgaggttt ctgtgtgtgt taaaagaagg ttttcattac ttttgaaaag gttatgtatc    21840
cttgttttat gttaaaactt tgagctttgt taaatatgca gagttctctt tcttagcatg    21900
gactacagag gtgcaactac ctcctacctg acttcacatc tactcccaaa tgcctagtga    21960
aggcttaata atttcaaaaa gggactctag aatttcattt gataccagtc agacaaatgt    22020
gtgaaaatta agcataatag gcagaatccc aggggtactg acagctgtat taagaggtga    22080
ttcaagggct aaaccttaga gtccagcatt ggttatgggt gtgacaagaa aatgaagcct    22140
atgttggctg ggattagcaa ccacagttct agaggaagca aggtggagaa actatatagg    22200
gggctccctt tgtacgtttt atttatttta aacatctcta taaactctag aaattaaaac    22260
aacaatacca acacaaaagc atcactttt cgaccaaaga ccattgctat acttttttgt    22320
gtaaagggct agatagtaaa tattttcagc tttgtgggcc acataagtct ctgcaataga    22380
caatatgcaa acaaataagc atggctgtgt ttcaattaaa ctttattatg aacattaaaa    22440
tttgaatttc ataaacttt tacatgttgc aaaatattct ttatttaaat tctattgcaa    22500
tatgctttaa aagatacagt ttttagtctt tcttagttta aaataaaatc tagaaaaaat    22560
tttaagtctt ctataacttt ttttcggtaa ctgaataatt ttaaaagtaa gtgaaacatt    22620
tagacatgca aaatggactt ttcagaagaa gaaaatggta gcttaacagt tattagatta    22680
ttgtccagaa taatttttga cttataagtc tctgttgacc atttcattgc ctctttttt    22740 ggaatatgca tcttttaatg tgtccttcaa ggcaaaggct ctatcttatc tatcttgtgt    22800
cttgcatttt cccagggcaa tgttttcac aattttttta aaaacaata ctgtaatcaa    22860 ttttcaaata aaattttcca tgggaccgca gtgtatacaa atagcagtga caataaaaga    22920
taataactct cccataaata caagaaaca gttaacctag tgctctaaag taaaggctac    22980
agtgattttg tataacattt atatgtaatt ttcttgatcc tacatggttg tgttttcac    23040 agtgttatgt ttctgaaatc gagatgcctt ttataattga tgtcaaaaga aacttgtcag    23100
ccacaaggcc caggaataag ttgtaatatg ggaacttagc aatacataaa ggtatatata    23160
ctcctgtgac ctcagctgaa ttatttgcat tggttgcatc ccacaaggtt gactcttaaa    23220
taaatttagt ttgttgcttg aaatttcttg ggataaatta ctttgtgatg tagttttgaa    23280
aaaaaaacag gtaatattta gtctgaagtt tgtctgacat actaagcaat gtaattaaag    23340
```

```
tagaagtcgc ctaagctcag cactttatta tgccttgaaa ttatactgcc tgtcctacag    23400
gtgaaggtgt tatgaatgca gtttgtcact gtaactctat tcatagctct gaaaggctga    23460
gagtgactca gaagaatatt tttgctctga atatgaagaa cgcttagact aaaactttaa    23520
ttacgatgct gaagaagaaa gtggtaggtg attgcatgaa taagtatgta atattgttaa    23580
tttctaaaaa ctgtgtatag ttaatgtagt gcttcttttt ggaaaggcta ttgttaaatt    23640
gatggtaaat tctataacca atatcacctt aaagcaagta cgcatgataa agtattataa    23700
aaccatgata atatcatatg tggcttatta ttgttccctg agtgttgtac aactctgtta    23760
tgctgtgatg aaacctcatg caaacaggta tgtcaaagat atgatgggct gttaactgag    23820
cttggcccac atatggtgta gtgacatgct cactaatgca gtgcagagat aaccaataac    23880
agatcataac aggtttaaat atgtgcaagg agatgtcagc agaagctttc ctacatagtg    23940
aatactaaac aagcctgaca gcccaggatc atgttcggat caatctagtg tgctaaaatt    24000
aacatatagt cctacatttg agaatgtgtg attttcttgg ttcctgtcta taaataata    24060 ttttaaaata catacatttc aaatcagaag ttggtgaatt cactgaaata tttctagaga    24120
acactaggta ttggggctca tagtgtgaaa accactgact taattcttcc cccatcttgg    24180
ttgttcctga tcttcccttg tgtccccatt ccagccattt gtatccttag aaaatgatct    24240
catattctac ttcatctttta tcttcattgt caactgtcag gtagcaatat atgatggaag    24300
aagcatgtac tttggaatca gacagacctg gctggaatcc taactctgtc acttattaac    24360
aatgtgatct taggcaattt acttaatctc tctgaacctc agctactctc gtcagtacaa    24420
tgagttatcc ttatctttac atggcacagt attattatga tatcaaaaat tcattgagta    24480
tttactctgc atattagtca aggttctcca gagaagtaga accaatgata cacacacaca    24540
cacacacaca cacacacaca cacacacaca caatttatta taaggaattg acttacatga    24600
ttatgatggc taacaagtcc aaaatctgca gtatgggtca gctggcagga aacccaggag    24660
agtcaatgtt ccagtttgag tctgaaggca gtctgttggg gaatttcgtc cttctctggg    24720
aggccagcct ttttgttcta tacaggcctt caaccgattg gatgaagttc acctttatta    24780
gtgagggcaa tctgctttaa ccaaagttta ctgatttaaa tgttaatctc atccaaaaac    24840
acccacccag ttgacacata aaattaacca tcactctctg taagcacttt ctatgcatta    24900
agtgatagca aataatgcca gacatagggc gtctttaata aatggtaagc actgttatca    24960
gcaacaacag gattattata attagcacct tttcatcttt ctgtctgggc tctgagaaag    25020
tacctctctt ctctaaattt atccctcctt tcctatgaat tagacccagt gctttctctg    25080
aattatgaag gtcacactcc tacaaatgcc ccttcccaat tgcacatctg tcggctttct    25140
ttgccattga cttttatctc tagcttttaa atttacaggc atatgtcagt taacaatggg    25200
aatgcgttct gggtaatatg tccttaggca attttatcgt tgtgagaata ctatagagta    25260
tacctacaca agcctagatg tcgtatagcc tactacacac ctaggcaata tgacatagtc    25320
ttttgcttct aggctacaaa cctgtacggc ttgttactat actgaatact gcaggcagtt    25380
gtgacacagt ggtatttgca tatcggaaca tgtctaaaca cagaaaaggt gcactaaaaa    25440
tactatgtag tgatctcatg ggaccaccat tgtatatgca gtctgctgta gactgaaatg    25500
tcatgcagtg cataactgta tcttaaatac tcaaagtatc acctttgttt gtttgtcccc    25560
ttgtgtgcat catcctaacg tggaatttct ctgttgatta gggccagcgt attagtttgc    25620
tagggctacc ataacaaaat accacaaatt tggtggctta aataacagga atttattatc    25680
```

```
ttatggtttt gaagactaga agtacaagat caaggtgttg gcaggttttt cttctaaggg   25740
ccatgaggaa gagtctattc catgcctttc ccctaccttc tggtggtttg ctagaaatcc   25800
ttggcattcc ttgacttaca gaggcatcac cctgatctct gttttcatct tcacatggca   25860
ttctccctgt gagcctgtct ctgtgtccaa acttctttac tattaatata aggacaccag   25920
tcatattgga ttagggtcta ctttagtgac ctcattggaa tgttattacc tctgtaaaga   25980
tcctatctct aaataaggtc acatccttag gtaccggggg ttaggactca aacatacctt   26040
tttttgggga aacacaattc aacctataac aattgataac actctttagg agcagaatgc   26100
gatatggaag taatttgaga ccataaagta tatacatgta gggagttaat ctatgaaacc   26160
tattgaaagc catatatacc tcatgtatag tggtccataa atagcatgga gacattgcag   26220
aggatgttaa gtgatatgat acaggaacaa tccaagaagg tcataagaaa aaggaccttt   26280
tgctcttgag aggactgaag aatgactttc catttatgaa attttggtac atgtccacta   26340
aaaataggat gaaggccaaa cttaggaaga atattttgat aatggagaag gttgcatata   26400
aaaacatttt attgaggaca attaaataat gttggctgga agtttagga tgatcatctt   26460
taggactcag aaaaagagaa gaaacattat taaagaattg ccctgaaca agtataggca   26520
ccctcacatt tgcattgcat ttactataga attgaaaaat gttttgacct ttttttttg   26580
gcttttaata tatttgacca agagtaacag ctaagcaata cctatttgca atcagtgtca   26640
tcatgtgggc tccaaacata tcatgtttgt gtaattaatt gattgaccca ttaatttgtt   26700
caatttctgc tctgttccag gcactgaaca acatgatgga gataaaagat aaatattaca   26760
cctgccttgt cctcaagaag ttagtcttct gagggaaaga aattagcaaa caaattgtaa   26820
tctcagttat gtgccatgtt ccatgctggg cacaggggat acagtagttt aaaaaaaaca   26880
caagatctat aaggtgtttc ttcttgtgga ccttacagtc tagggtgctt ggaaacatgg   26940
ggcgttggca gacaagtaaa tacacatttt gtggtaaagg ctcaggtaga agaagtacag   27000
gatagaatag agcacaccat ggggaattaa tctagacttc agagaggctc acacatacat   27060
aatttatgtg tgactatttc aatgcatttg aggtttcttg gaaatagagg ttaggttta   27120
ttttaaggaa gttaccattt tttttttcag tgtgatgtgg ttgaaccaaa gaatgccatg   27180
cccagtgatg gtaataggat aatcttttta aaaattaaga gccacctaat aaatcaatag   27240
tttcattcag cgggagctcc tgcagagttc aaaaagaaga gaatctggca cagcgtttcc   27300
tttaaagttc attttcctag agtgtgaatg gaagcaagag attataacat tttgaggtca   27360
aaaaaattct gaaatgccta taaaaattat tttctccaaa ttatcatcat ttgtgctttt   27420
aatgacctga ttgcaaagat gaacattttg aattcttaaa ttgcttatta ggattggtta   27480
atgaatcaat tatctattac tgtatgtttt gctattggaa aaaatagcaa cttaagtgtt   27540
ttgcagacct ttacttaggt atatgttgct tttatgaaaa aaagatgta aatattaagt   27600
aaagggatt taaagcaagg cttttgaggt agagtcttat taattccttg gtaaaccttg   27660
agccaattgt tgtctatgtt ctctgcctct gtcttgctcc ttccttctgg gattcactgt   27720
gggaatgcgg gattgttaat ctggggatgc tgtccaatcc tgcctctctc aagctttgct   27780
attgatctcc ctcccagtga taataaagct tgaagaaaat gaaagtagcg ttagtattgg   27840
tcctcaaact caagaacagg atgaaactta aatcttgagt catacaattg tgtctacata   27900
ctgctcccca aaaagagaag taagaagat gctaactttc ccttttaatt tgcagtactt   27960
agcaatttgt tttcttgagg gttaagtaat aacagtggaa gaaaaaggg ttaaaatgcc   28020
accaagaacc caattccatg tttagtttga agtgggaaa tcagctgcca ctgggaagtc   28080
```

```
tgaatccaat gccatgatgt tctttgaatc cttctgagaa ataatcatgt gtagccataa    28140
catacctgta taacagagca gagaacataa acaaatgaag gtgaagggaa gattaagaca    28200
gaagagaaaa attccagaat cgactgatca tttttatctg tttagatgat ttcaggcaga    28260
atcctagaga ccaactttat cacaactgaa ttttaaaaat caccagcttt gtcattgtga    28320
tgcagcatca gtttcagtat tatccttgga gtattaattc ttaatcatct tcatcttaga    28380
acatttttga ggtcacttct agtctctatt tcaccagtga agaaacaaaa atccccaaac    28440
tatatcaggt ggaattacac agtatttttt ttttaattt ggggaaagtc gattcaaggc     28500
agtaacttgc aagctagtgt tagaaaggat ttaataaata gtggtttttc tgtacacata    28560
gtgagaggtc attacatcat ttggttgttg aaagtcataa ggatgtctag catgcgcttt    28620
gcctgtagtg gttcatgcca ggcagattcc tgactcctat aacccagagc ttatcagagc    28680
atttatgtcc ccaaagagaa atgtcacctc catctttcaa taaacacttt agcaaagaaa    28740
aatcaagtac tttaattcca aatcttgagt taattccaga ataacaatga tggctcggaa    28800
aaatatgggt atttctgtca aaggacagag aaacctagta gagagtattt actttgggtc    28860
ctagtgatgg tatctgaaca agctaggtga acaaagagcc tcaataaggg attttgaggt    28920
ctagaaaaag agaggaaata ccaaataaat ggaataatta taaaataaat accagcaaag    28980
ttaaatcaat atatcatgtg ggagatatcc ttatatcact catgtgattt ctattttgtt    29040
cctatattag gccaaggaga ggtggaactt gttttccttt ttccctctca gctacgaatg    29100
gacatactta aaactgtttc tctgcttctg ttctctaaaa tgtgattgtc taacagtaac    29160
cgtgatgacg ttttgacagt tgcacaagtt tctttcttta agctttaaaa atgccagcca    29220
gtaacccagt ggcatttcta ctataaaatc ttaaggccaa tccatttccc cttttcctta    29280
ttttcttggt ttcaaatata ttttattgc caatggaaat aaaaatccta aattagagag      29340
caatggcatc ccttgtcttg tgaataaaga gctcctaaat gtgaacttat acaggatgca    29400
gcaatttata gggtagttaa tcattcttct ttctagccag ttgttccagc tacagttttg    29460
tggctcttgt tagtggcttc attcccagat agaataaaaa tcaaaccaaa atcctggaaa    29520
ggcactctga ggatgcttct ctaaagtaga tgggcatcaa ctataaatca caatgctttg    29580
tttcctctgt tatgtttcaa gatgggtggg attttttttg tagcattact tattattgcc    29640
tctcaagtgc ttgagtcttt gaaatccaag tcatgtgagt gaattagata cagctgttag    29700
aagtggcctt tcaatgccaa tggtacacat tccttggttt ctttacgata ctattgctct    29760
tacaactttt atctgaagtc ataaattcat agttgtccca gaagttaagt tccttgcttc    29820
tagaggacag aaaacaaaca atttacacaa ctcatggtgc atgtcaccag tccttagatc    29880
tcatgaaata tgcatgaaat cttaaatcac ttgctgtagc cacccagcca ttgacatatt    29940
tgaaagactt tagtgtatca aagtcactat aatgaaaatt ttgatttcac cagttctagg    30000
agtgaaaaat caaatgttta gtaaaacttt ctaaaattaa cactgacagt tgatttctgt    30060
atactgttgt tcttaataat agctttattg agatataatt catattcaaa acaacttacc    30120
catttaaagc atacaatcca atgatttttt agtatcttca aagagttgcc tatcaccata    30180
accaatttta gaacactttc atcactgtaa aaagaaactc cattcctatt agcagtcatt    30240
ccttattcca aatccccctg ctcgccctag acaactacaa atgtactttc catctctata    30300
gatttgcctg ttctggaaat tttatgtaaa tagaacaaag tgttcttttg tgactggctt    30360
atttcactta gcatttttt tcaaagattc atccctgttg tagcgtgtat cagtgcatca    30420
```

```
ttcttttttta ttttttttaga gacagggcct tgctctgttg cccaggttgg aatgtgcagt    30480
ggcatgatca tgggtcacta tagctttgaa gtcataggcg aaagcggtcc tcccacctca    30540
gtctcccgag tagctgagac tacaggcttg caccacatga ctgtctaatt tataatttc    30600
tttagagaca gggtcttgtt atgttgtcta ggctgctctc aaactccagg gctcaagtgg    30660
tcctcctccc acagcatcct aaagtgctgg gattataggt gtgagccaca gcacctggct    30720
tgcatcattc ttttattgt tgaataatat cccacttgta agaatatgta ttttatttat    30780
cctttcccca gttaatagat atttcgattg ttcctaattc ttgtctatta taaataatgg    30840
tgctatgaac atttgtgtac aagtttttgt gcagacatcc attttccttt cttttgggca    30900
tatacctacg agtgtaatgg atgggccata tagtaacttt atgtttaata ttttgaggat    30960
ttttcaaact gttttccaaa gtggctgcat cattttaaat tccttccacc attgtgtgag    31020
tgtttcaatt tctccacata tttgcaacac ttactattat ctactcttaa aaattacagc    31080
catcctactg ggcatgaagt ggtatttcat tgtgagtttt ttttttcttt ttcttttttt    31140
cttttttgc taatgtttgt ggattttctt ttcattttct tgatggtgtc ctttgaagca    31200
caaaagtatt taattttgat aatttccaat ttatttttg ttattgctgt ttgtgcttct    31260
ggtgttgtat ctaagtgtat gctactttaa aaaattagtt gtaatatggc aaattggata    31320
catgtgtagg ctttggtgtc acaatcctaa ttttaaaatt ctgactctgc ccttgacaaa    31380
ttaactaatt aagcttcctt agcctcagtt tctcaactgt aagttggaga tattaccaag    31440
acctacctct tgaattgttg tggggatcag atgaaataat gtatgtgaaa tatttagaat    31500
tatgcaagtc tgtggtaatg aatactaatg ttagctatca ttattgttat aatcccaata    31560
ataaattctg gtgctttgaa aattaaacca aagccaagca gttgatatga agaagcatgt    31620
aataatgtac agacataatg ctttatagac aacattgaat ttggctctca tgaacatcag    31680
gaatagtggt catggtagtt attatctcca gcaggaactg tagctgagag atcttcagag    31740
cttttttccaa ggcgatatca ctgggaaata atagagacaa ggttacaagc tagggctgtg    31800
ttttcttctt aaaatcttta gttcagttttt tttcaataac agatttgtag taggcatcag    31860
gtgactgggg attcgtattc ttcaagttga aatattaccct tgttgagaaa gaaaccatgt    31920
gtgagacaac catgttgaga agaaaaagt gattttatag aaaattaata ttgatagtga    31980
gcattatatg aaaatcatga agttagaaca tatttggcca gaaaatttac attaatagtt    32040
acccatagca attaatgcat tataattaca catacctttt ctttaatgaa aaagaattct    32100
ttccttccaa agttatgcat gctattgtta aacattagag aatatagaga agcaaaaag    32160
aaaatatctt tttgatatt tccttaacat acgtctgttc ctaataatgt ttatagtta    32220
gaagcattgc atgaaatggg tagatcaatt ttctatttaa tgtttggatt cattaggtac    32280
gaagttagca aattaatttc cattagggtg cctgtatggt tgtaaatcct ggacctgcag    32340
aagattttc agtattggtt tgtagtcttt tgtttagcag caaataatta gttctccaga    32400
gcttctgaaa ttaattgacc actttaatgg tgtttaccta cctagagaaa gaaaagaac    32460
ttctccaagt cccttggtaa aattaagcct catgaacaat taactcaaat atacacaagg    32520
cttgtcttta gcgagcatat actccctaaa gttgattaag ctgaccaagt gattactgct    32580
tataaattca ccattttatg gagaagaagc aaacactgct aaataccttg tggaatcaga    32640
ggagggaaa ttagtaactt gaccccaata ctgcgatttt aaattgaatt cttgaagcct    32700
acaagtttta cacaggactt tagagagctg gatagtatca ctttgtcaag tcctacttt    32760
actatgattc tttgagaaaa atacatctga ctaaataact ctgaatctaa attggataaa    32820
```

```
ataaatgtga cattcaaaat gttatttatg attttagaaa aatatcctta tagacactag   32880
atgagtttta gtctcaaatc aatcctccct atcatagtca cttatcaaaa taactaaagc   32940
aaagtggtag agctgtgctc tagaagtttg ggatttatga tcacaatctt ttccaatgag   33000
tccctctttt cctctgcctg tcttcaacat ttgttttttt ttttttttgg ttaggactat   33060
ccagattgtg tggcctattt caaactcatg gcaaatacat tggatgatca gaaattttct   33120
aatgtatttg aatttgtcta cacaaactag agtaattgct attaattcct caagtgttaa   33180
ttatttcatg caaaaaggaa aaaggctatt agtctttaag tgtattagta tgtcaatatt   33240
tgggagaagt gtcatgcaat tagtggtttg aatttcctat tttattttat tgcattttat   33300
tttatttgcc tagtcaaata aaagtaatg ttaaatacat ggaagcatga ttgttttcta   33360
cactaaaaat cattttgact tgaaaagatc tgatatccat gaccttcatc tgaagttttg   33420
gcagatgaaa atgtcagatg cgtcttttgg attaataaaa ggcaaaagtc agatcgaaaa   33480
atgagtataa gctttaatta tatgacttta ggaggatatg ttatgaaaat caaagcttta   33540
atagtgatta taattggcaa gttctttttt tataaggaat tacaagtcac tctatacaaa   33600
aattggaatt tttgtcctaa gaatgaaat ttactatagt ttcatctgtg tgtgtgtgtg   33660
tgtgtgtgtg tgtgtgtgtt taaaaaatca agtgataggg cttttcctca ataaaatctg   33720
aaatctctta tagttaagtg aacagaacag tgtatctagg atgctagact ttttttttcaa   33780 agttagttta aaacttatac atagtaaaat ctgtatgcct tagggatctc tgtttgctat   33840
cccatagtga atgattaatt agtttctgtt agaaatagtc agaactaggc tgggtgtggt   33900
ggtggctcat gcctgtaatt ccaggacttt gggaggccaa ggcaggagga tctcttaagc   33960
ccaggaattt gcaaccagct tgggcaggct ggtgagatcc tatctctaca aaaacaaaca   34020
aacaaacaaa ggacaataag aaagaaagaa atagccagag ctttgaacaa aatttctaag   34080
tagaccaatg taaagtctg tcgtcaatat gtagtggcta tgaatggagg ttatgaatga   34140
aagagaagga taagatgaac tagaggtgag aggggaagac agcaggccca agtgaaaggc   34200
agagccgagt ttattgcttt ttggttattc caggtgtgtc tgctttgtct catgaaacac   34260
ctggatgatc actgatttct agtggaagaa atgctgaaaa gtccttactg tgcatttaaa   34320
cattctaggt ttaatatact cagggttttt caaagaaag ggtggctgga gtttgcact   34380 aactaatatt tcataaagtg tctaagtata gatgtctggt tttttttttgt atttctaaga   34440 ctggcttgag gtaggcatgg agaattcttc gatgggacat aatttttcttc ctttctttt   34500 tttttttttt tttttttttt gagacggagt tttgctcttg ttgcccaggc tggagtgcaa   34560
tggcacaatc tcggctcact gcaacctccg cctcccaggt tcaagcaatt ctcccacctc   34620
agcctcccgc gtagctggga ttacaggcat gtgcccccat gcctggctaa ttttttttgt   34680 attttagta gagatggggt ttctccatgt tggtcaggct ggtctcgaac tccttacctc   34740
aggtgatcca cccacctcgg cctcccaaag tgctgggatt acaggcgtga gccaccgcgc   34800
ctggcctgat gggacatatt tttcattcaa ttttattgat ttaacctcac aaaataaaat   34860
atttccttaa gatgactctg tggtcattgt tgggcagcat aagcttaatg gatttagtt   34920 atcataattt accttaaacc caatttgtat ttcaggatat aaatagaggt ttattgtagt   34980
gaatcttcca ggaaatacta agtgatacta ataattatag atggtgaact taagtctta   35040 tattactgaa tttgttggt ttgatgatgc taggctatgg cattcttgct aatcaaaacg   35100
atgtgtcatg gtgtaacata acttattaaa atgggcacag ataacacagg aagcttttta   35160
```

```
taaaagcagc tcacaaattg tgttactttg aactgaactg gccatttatg ggaaaggtca    35220
ctgggttgta aataaggacc aaaagagtta cgtttatatt ttttaaaaga gattgaggag    35280
atttattttt acatttcttg aaaatgcctt attttggtat ggtattgaca gatagtgaaa    35340
ttctgctcat ttgtaaatat agtgtcatat tttaataatt tcaaacatat tgaaaatgca    35400
gaatttatta atagtgggag cacattttcc tttttactaa atgttctaca ggttcttttc    35460
tttccatcca cacacagtgc cattaccctc attctaagcc tttcaaacat ctggcagtaa    35520
gtgatctgct gcacttagct ctttccagct gagctgattt ttaaattttc agaaaatttg    35580
tgagctaatt gttaaacatg gccattatta aaattaaat tatttcaact tataattaaa     35640
taaattatat taaacaaaa gtattaaaaa ctcaaaagtt ggctgggcgc actggctcac     35700
gtctgtaatc ccagcacttt gggagaccga ggcaggtgga ttgcctgaag tcaggggttc    35760
gagaccaacc tgaccaacat ggagaaaccc tgtctctact aaaaatataa aaaatagcc     35820
gggcatggtg gtgcatgcct gtaatcccag ctactcagga ggctgaggca ggagaattgc    35880
ttgaacccag gaggtggagg ttgtggtgag ctgagattgc gccattgcgc tccagcctgg    35940
gcaacaagag tgaaactctg tctcaaaaaa aaaaaaaaa aaaaaaaga aacaaaaaaa     36000
aaaaaaaac aaaagcaaa caaacaaaaa aacaaaatt atcacttcct aattattttg      36060
cattttacta ttatctatgc tattaacgtt atttgccttc attgtatttg aaaggtggac    36120
tatattctat tgcactttca ttgtactata ttctaatatg caactgtgta tcccttccca    36180
actctgtgtt caatgacttt atatttggtt gctttaaaat gatgacgatg agagtattta    36240
tatcatagaa attggcaaat gccgtaagtc agttttttgtt tttgttttttg ttttccggag   36300
agggggattgt taaatatttg cctgcatgca acaccactac atgcagtctg ctatcttttg   36360
ttcttcctgc tttcaggctc ctctcccagc tgtctgtcta gcacaaccca gcataccaaa    36420
ttttcttaaa tagggaaagt tgaacatggt aaaagaatga atgaagtcaa agaatgtgg     36480
aaagacctag gctttgccat ttagtaaagt ttagcatctc taagcctcca tctctttatc    36540
aataaaattg agcaatgatc ccttttagtt ctacccatttt aagaagattt tcaaatgaaa   36600
accacaacct gctcatgttt atgaaggcac tttggaaagc gctaaataca cgggtttta     36660
ttagtagtaa acacttactt caccttttttc acttcttgac tttagtttac aagggctcat   36720
aatctaaatt atatcataaa ttgctgtccc agatttttttt acagcctaat tgccacctgt   36780
atgttcgact ttccttctgt tctttatgtt agatactggg atagtatgca ccaggtgggt    36840
gtgccatcac tttctcagat gatgtccact gaagaccttg catgatcatg gcattcattt    36900
tcctgctgta ttcagactgg cctcaactat tttctttatt gctctccagg aaaaattaca    36960
aatgaatcag actgggcaat gaagggtaaa cctaattatc gctctttgtt aaagacagct    37020
cttgttaaaa tgcggatatt gcaaattaat ggaaaaaata tgacatagta aaccatactc    37080
acttattaat atcttagtaa ggaataattg atgaagttac ttaaccttag agccctaatt    37140
cagttaagtt ttaatgaagg acaagttgta gagatatcga gaacccaggg caggtgccta    37200
ctgaagaagt tccagaccaa ggaagtataa agaaggacct gggtgggagc agtgagattg    37260
gatatgaggg ccactggcaa agttttgccc cagaacagtg tcaaaatgtt tgcatttggc    37320
atagcccttt ctcttttttgt tctgaatggc tttgctagaa tatctttttct ataatgaatt   37380
tatcctgctt ctcagatatt gctaaagcac tcccttttga attttggtgc tttaacatgc    37440
attttgatac attaccaaat aaggtctgaa tgacacaaat tttagaactc tccagagaaa    37500
agaaagatgc tgagggaaaa agcataggtt tgggactcac taaatcccag ttcaattcct    37560
```

```
ttctttaata aatatattca attttacctg agaaagctct cgtgctctcg aattttattt    37620
agaaatttct ctttgtacat gattgatttc acaatccttc ttctgcctcc tcttctactt    37680
tcttctttct agattttcct atctttatga agattattct gccttatcct caacagttag    37740
aaacaatatt tttgaaaatc actacggtat cctgcatagt gatttcccat gccaacttta    37800
ctaatttcca ttataaatta ttatttattg atgcctagag ggcagatgag tgtagctgct    37860
atggagtgag gagacaaaac ataagaaagt tatgatccta ccctcaggta atgattcaga    37920
catgataatt aagtcaacaa attgatagaa actaatcact aactctctgg ctatagtcat    37980
tctttcaatg aatagctcat tactgagtat gcatgctaca gtaacaaaat tatataaggc    38040
tgttgattaa atgttgatta agtgcatgtc ttattcagag tttttttata tttgaaatgg    38100
aagaggctgg acttcagtaa tttgctataa actgctagta tatgattatt tgggggcagt    38160
tattttttaa agaataattt aaatatggaa tgtttagcag tttgttttt ccctgggaaa    38220 aaccatacta ttattccctc ccaatcccct tgacaaagtg acagtcacat tagttcagag    38280
atattgatgt tttatacagg tgtagcctgt aagagatgaa gcctggtatt tatagaaatt    38340
gacttatttt attctcatat ttacatgtgc ataattttcc atatgccaga aaagttgaat    38400
agtatcagat tccaaatctg tatggagacc aaatcaagtg aatatctgtt cctcctctct    38460
ttattttagc tggaccagac caattttgag gaaaggatac agacagcgcc tggaattgtc    38520
agacatatac caaatccctt ctgttgattc tgctgacaat ctatctgaaa aattggaaag    38580
gtatgttcat gtacattgtt tagttgaaga gagaaattca tattattaat tatttagaga    38640
agagaaagca aacatattat aagtttaatt cttatattta aaaataggag ccaagtatgg    38700
tggctaatgc ctgtaatccc aactatttgg gaggccaaga tgagaggatt gcttgagacc    38760
aggagtttga taccagcctg ggcaacatag caagatgtta tctctacaca aaataaaaaa    38820
gttagctggg aatggtagtg catgcttgta ttcccagcta ctcaggaggc tgaagcagga    38880
gggttacttg agcccaggag tttgaggttg cagtgagcta tgattgtgcc actgcactcc    38940
agcttgggtg acacagcaaa accctctctc tctaaaaaaa aaaaaaaaaa ggaacatctc    39000
attttcacac tgaaatgttg actgaaatca ttaaacaata aaatcataaa agaaaaataa    39060
tcagtttcct aagaaatgat ttttttttcct gaaaaataca catttggttt cagagaattt    39120
gtcttattag agaccatgag atggattttg tgaaaactaa agtaacacca ttatgaagta    39180
aatcgtgtat atttgctttc aaaacccttta tatttgaata caaatgtact ccctgggaag    39240
tcttaaggta atggctactg gttatcaaac aaatgtaaaa attgtatatt tttgagtacc    39300
tgttacatgc caggtagaat atctcctctc agccactctg agtggaaagc atcattatct    39360
ctattttaca gaaaagcaaa ctgaggctca gagagataat atactttgcc agttaatgaa    39420
tgatggagcc atgattccag ctgaggtctg tattgccttg ctctctagga atggtagtcc    39480
cccccataaa gaatctctca gtttcctttc caatcaaaag gttaggatcc ttttgattgc    39540
cagtgacaga aacccaattt actagcttaa gtaaataaaa ggaacgaatt tattggctca    39600
tgaagcctga actatgtgaa gacctaggtg gagaactggc cttaggaact caatgggacc    39660
aaggactcaa atgccacctg gtggcatttg ccttatgctg gttttatttt ctcagaccgg    39720
accagctttc tacataaagt gggtccctgg ttagaactct ttgctcctat cttaaggac    39780 cacgaaagaa ggagcccttt gtccttggct aaatgtgaaa aatcccagag actcttgagt    39840
catagtgctt acccttggg ccactcatag tctagaatga actaggctga gtctcgtgcc    39900
```

```
aacagcacag gcctgatgcc agataaaagg gtgagtgaag ggggataaaa aataagacat    39960
agctactaaa ttattgcacc aaagtaaaaa cattgagttg acttgcaatt tgtttctttt    40020
aattaaattc atttccttt tttggcattt tgaaggcaaa gtaagatatt aaactttatt    40080
tttattgatt ttattcaaag aattaagcta gtgggagtag cagattcaca cttctaagat    40140
caagggccag cttctattat tgaacacttg gtgtgtgcaa atgccatgag gtagggatac    40200
tttgttttgt tttttatttt ttattgggtt cgatctcttt tgtttatgat gtatccccaa    40260
gtgcctagaa tagggcctgg catatggtat atactcaata aatatttgtt gaatgaatcc    40320
atgatggaat gtgaaatggc tagcattaca tagaaacctg tagcattgct ggagagataa    40380
aatatataaa cataatccat tgcaggtata ttgacaagtt caaaataata taatgggtat    40440
tgaatatcta aatgtttgtt gttgttgttg ctgttgtttt tgagacagag tcttgctctg    40500
ttgcccaggc tggagtgtaa tggtgcaatt ttggctcact gcaaacttcg tctcctgggt    40560
tcaagtgatt ctcctgcctc agcctctcga gtagctgggt ttacaggcac tcgccacaat    40620
gcctggctaa ttttttgtatt ttagtagatg tggagtttcg ccatgttggc caggctggtc    40680
ttgaactcct gacctcaagt gatctgccca ccttggcctc ccaaaatgct gggattatag    40740
gtgtgagcca ctatgcccag cttttaatat ctaagtttta attggatgct gagggaatga    40800
ttaatcagag tagggctggg ttaattgaaa aatgtgatac atttgtattt atggccagat    40860
agagaacatg aatctgaatt tgcagaatta tctggcttaa cattttttc tttccagttt    40920 tcactgtatc ccccatgttg attcaattta aaaaatatac ctattttact tcaattcaac    40980
aatgctatgc cagtacaaac ccatacgttc tattattttt gttttgtttt gttttgtat    41040 ctccaccctg ttacttcttt tcttataaaa ttggtatttg aaatttattg aaatatttg    41100 gaagagtgac ataccatttt tggtactttg tacctctgca cccttgggaa gtgaccctgg    41160
cttcacattt cataactgcc ttgtgaccat ggccctcaag tggttgccag atggttgaag    41220
aacattaacc tatctggctc aattttgtga ccatggattg aatcctctac ataactgcag    41280
tgtgcaaacc acacatccgt tccaagattg tagtcaggat atgaactttt taagaataaa    41340
acttcttccc ttctgatctg ggcctggtat gtggtcctac tagaaccaca tcacctactc    41400
ttggtgctaa caatttgtgg caccaagttg ttcaagtttc acccattaaa gaaattcccc    41460
gaccttgcct tctcctcagg taactacccc attctatttt ttctttcata gctaacattc    41520
tctgctctcc tggtctctct acttcacttt catttacatc tcagctcctg aagtatggtt    41580
tccaccatgt tcctaaaact acattgccca gggtcactag agacctctta tgaaatataa    41640
caacaccttt ctacattact tccgtgtgga ccactttttc acattgaacc cattttgttg    41700
gtttatgtac acaccccttc cttggctttc ccatctgatc catttctcct ttgatggaga    41760
aggtgagtct gctccatatt tagcttctta ctctgagtaa ccaaatgtta tggatgggag    41820
gttagctctg tgtgtgagag aaaggtggag aagcatgtgg ggagggaaat agatgggaaa    41880
aggtaattag gctttataga agggctctca ttagcaagct tctaggggat gccaagatcc    41940
atgcttagag attgccaggc ttgtcttcaa atctcagctg tgtattactc ctttatgttt    42000
tttgtttgtt tgtgttgttt gtttttgaga cagagtctcg ctgtgtcacc caggctggag    42060
tgtagtggtg tgatctcagc tcactgcaaa ctctgcctcc tgggttcaag cgaatctcag    42120
tctcctgagt agctgggact acaggcatgc accaccaggc ctggctaatt tttgtagaga    42180
cggggttttg ctatgctggc caggctggtc ttgaactcct gacctcaagt gatctgcccg    42240
ccttggcctc ccaaagtgtt gggattagtg gcgtgagcca ctgccccggc ctattactcc    42300
```

```
tttagagtga tttagagcca tgtttactta tggtaacttg acagtaatgg gaataaccac   42360
tgatgaaacg taaagccttt gtctaattgt ttacctagtt cttccttgtg gttcatgaaa   42420
tttttcatct ctgtacagtt tgaaaattaa gatgataata tttagagata ttttattcct   42480
ttgtgaagag aaaaaaggct ttcattaaca gaaatcagtg gcataacctt aataaataca   42540
atcagctggt gttcctatag tatttaaaag aaaacagaaa gtttactaga tttcagccag   42600
ttttcagact atttaatgtc tattcttact ataatagaaa atatataatt tgatcttgtt   42660 ctcattttc aaagaccttt aatacatgat tttagtagtt gaaaatgaag tttaatgata   42720
gtttatgcct ctacttttaa aaacaaagtc taacagattt ttctcatgtt aaatcacaga   42780
aaaagccacc tgacatttta acttgttttt gatttgacag tgaaatctta taaatctgcc   42840
acagttctaa accaataaag atcaaggtat aagggaaaaa tgtagaatgt ttgtgtgttt   42900
attttttcca ccttgttcta agcacagcaa tgagcattcg taaaagcctt actttatttg   42960
tccacccttt tcattgtttt ttagaagccc aacacttttc tttaacacat acaatgtggc   43020
cttttcatga aatcaattcc ctgcacagtg atatatggca gagcattgaa ttctgccaaa   43080
tatctggctg agtgttttggt gttgtatggt ctccatgaga ttttgtctct ataatacttg   43140
ggttaatctc cttggatata cttgtgtgaa tcaaactatg ttaagggaaa taggacaact   43200
aaaatatttg cacatgcaac ttattggtcc cactttttat tcttttgcag agaatgggat   43260
agagagctgg cttcaaagaa aaatcctaaa ctcattaatg cccttcggcg atgttttttc   43320
tggagattta tgttctatgg aatctttta tatttagggg taaggatctc atttgtacat   43380
tcattatgta tcacataact atattcattt ttgtgattat gaaaagacta cgaaatctgg   43440
tgaataggtg taaaaatata aaggatgaat ccaactccaa acactaagaa accacctaaa   43500
actctagtaa ggataagtaa aaatcctttg gaactaaaat gtcctggaac acgggtggca   43560
atttacaatc tcaatgggct cagcaaaata aattgcttgc ttaaaaaatt atttttctgtt  43620 atgattccaa atcacattat cttactagta catgagatta ctggtgcctt tattttgctg   43680
tattcaacag gagagtgtca ggagacaatg tcagcagaat taggtcaaat gcagctaatt   43740
acatatatga atgtttgtaa tattttgaaa tcatatctgc atggtgaatt gtttcaaaga   43800
aaaacactaa aaatttaaag tatagcagct ttaaatacta aataataat actaaaaatt   43860 taaagttctc ttgcaatata ttttcttaat atcttacatc tcatcagtgt gaaaagttgc   43920
acacctgaaa atccaggctt tgtggtgttt aagtgccttg tatgttcccc agttgctgtc   43980
caatgtgact ctgattatt attttctaca tcatgaaagc attatttgaa tccttggttg   44040
taacctataa aaggagacag attcaagact tgtttaatct tcttgttaaa gctgtgcaca   44100
atatttgctt tggggcgttt acttatcata tggattgact tgtgtttata ttggtcttta   44160
tgcctcaggg agttaaacag tgtctcccag agaaatgcca tttgtgttac attgcttgaa   44220
aaatttcagt tcatacaccc ccatgaaaaa tacatttaaa acttatctta acaaagatga   44280
gtacacttag gcccagaatg ttctctaatg ctcttgataa tttcctagaa gaaattttc   44340 tgactttga aataatagat ccataatata tattcttatg gaaatctgaa accattggg   44400 catttggggg taaaaagtat tttattagta aatttaaatg aggtagctgg ataattaaat   44460
tactttaaag ttacctttga gatgattttt ctcaatcaga gcaccaccca gagctttgag   44520
aaacaatttt attcacagct tctgattcta tttgatgtaa ttttagaaa ataagttttg   44580 ctggttgctt tgaatcaggg tatggagtac agttcactct gatcctatca tataaatcat   44640
```

```
gtaagtatat aacattttca ataagtgatt gttggattga agtgaatgat atttcaagta    44700
attgttatgt catggccaag atttcagtga aactcaaaat ttctcctggt tgtgttctcc    44760
attgcatgct gcttctattg attaacctaa gcactactga gtagaagctg aagaggggt    44820 ctaattagaa ggccccttc tatgctctgc ttggcttgta aaataattta tttctctaga    44880
tcccaccaac atagtagttt catgtatgca aaaacaccca cctaaatgtc aaagtttgta    44940
tgatacatgg acatatctat agaatttttt ttggtctggt gcatgccaaa aaataaacat    45000
gatatagaag aatttaatat ttattgagta cctaatctgt tccagttcaa tatgaaggtc    45060
tttatgcaga ttatttact taattttcct agtaactcca tggagcaaaa attatctcta    45120
atttatataa caggaagttg agcgtgaggc aaattaagta actttcccaa agttacacat    45180
atggtaagtt tgagagatat cccagtctct ttagctccaa agcctttgac cctttcacca    45240
taccagatta tgattgctat taatatataa ttataattat aatgattgta tttaggtact    45300
caacagaatg gtgactctag taaccagcct tggttctgct gagcttctct gcgtcttctc    45360
aggagacaca ggctacagag cttgaaggct gaggattctt ccagggtcac ttcagggca    45420 aatctgaaac tttcttcagg acaggaatca acgagatctt ctcacttact tatacctggg    45480
ggaggaactg tatgaaatcc acccaagaac cagtcatgct aagggccaaa cctatagaca    45540 aaaaaggga taggagaatg gagtatgtat ggagaaagac taaattgttc ttaaacttct    45600
caagcttaaa aatatcccag caaaagagat cgtaaaagcc cttcatggcg tattaattat    45660
ccatgcatgg gggtgagtgg aaaggtactc ctgagcccga ggctacagct ttggaactag    45720
cagcaccttt gaaggggaaa gcgtgtttcc atcatctcaa ctcctactga taaccaatgg    45780
aatattggtg agtaaaggat cctgggggaa gaagcagctg aaatgtgtag gtgagaaggc    45840
agagagaaga atatttatat tgggaatggc acaagtgtga tgaggctgca ggttttcac    45900 ccttgtcata gagaaaaaac cacgctgaca ccatgcagtt ttaaatagtg agaaatttgc    45960
aaattgttag atcttaaata atttagataa acatagtggc catttagatt attgcagttt    46020
tttcaggata tctgatctct tgatttcatt ctttttgtct cttataagaa taaaggggg    46080 ggagaaaatt tagccattat agtatttctc tacattttct ctgtcctttt acataactta    46140
caccagtgcc ttcctattta tggtattatt tatgggtatt tcttcttttc tttcactgag    46200
caaggataaa tgagccaggg attcttgaaa ctactgtaac acttctctta gaaatagatg    46260
gtcatacttt cagaatctct acacattctt agtccctcta aacaatgata gttgtggcat    46320
aaaaatattt gcttggtttc aggactgata gagaaaagta ctataaaatt tgctgttaac    46380
tgtgaaaggt taaaaaaaag gaggtgccat catgaaggag ctaatctttc tgaagtactg    46440
ctgtagtttt aaatattatt agctatgact tctcaccatt aactatgcac ttgcttttc    46500 ttcatctgac tcagcagcca gatagatgca acattgtctt taacatttaa gactcctagc    46560
aagtccgggc acggggctc acacctgtaa tcccagcact tgggaggcc gaggtgggca    46620 aatcacaagg tcaggagttt gagaccagcc tggccaatat ggtgaaaccc tgtctctact    46680
aaaagtacaa aaatcagcca ggtgtggtgg cgtggtggcg ggcacctgtg gtcccagcta    46740
cttgggaggc tgaggcagga gaatagcttg aacctgggag gcagaggttg cagtgagctg    46800
agatcgcacc actgcactcc agcctgggtg acagagcgag actccatctc aaaaaaaaaa    46860 aaaaaaaaa agactcctag catgaagag aaactggctg ttgaaaacct gaatgtgaga    46920
gtcagtcaag gatagtttga gggaagccaa gtagaggaag ctctcacaag cagattggtg    46980
agagaatatg attatacaat gcatttatta tgataagaaa ttcacaagca ttcattcaaa    47040
```

```
atactcttga ttcctaggca gctctgggca tatttccacc aacaaattga ggcatatgtc    47100
agtgcagcct aggtcagact acctttttc attaaacctc acaaaattaa aggacataca    47160
ggagaagtcc tggtactcat gttgcagact acagtctata tggcaaagga ggatctctgt    47220
cccttatgtt tggatgaaaa cattgggtag gcatttgaat acaagcctac tgctaatatg    47280
gggctaaggt cttttggcccc ctaaaggttt gctgaaatat tactgacagg aggcagattg    47340
ataagaggaa aagcacataa atgtatttga catgtataca tgggagcctt caggatgaag    47400
acctaccctc tcagtgcagt atggaagctt gtataccatc ttgaggttac agaaagaatg    47460
ggggtttgga tctttgtaaa acaggtttca gtggcaagac aggttatgag aaggagaaag    47520
gaagagactt gggtagcaaa gggggtcttg ttttgtaggt aaatcgttgg cagcccacag    47580
agaaaataga tggagaatgt ttcttttcag accttggcag gtgtcagatt ctcagttaat    47640
ctctcctaga tttgaaaaaa aaaaaaaagg tctagaaagg gagagcctgg ctgcactaac    47700
acattttcta cagatgcaaa tttctcccac aaaatacagc tttgcaggtc cacttctatc    47760
tgctgggcct gtggcaacca tttcaaaata tgtgaatgaa atatatgtgg gggtaaacta    47820 ttttatta cttccctaaa gaagggatgg tgttctctcg ggaattctgt gcatagagag    47880
cctgtggctt aggcactttg atttatgtat atctcttcct gtgattggct atctagggac    47940
tgctatctcc agcaaatctt ctaaatgtct gccatgtaga attcctttct catctttctg    48000
tctcaccccc ttatctagct gcttctctaa ccctagagtg acactgcact ccccacaatc    48060
tcctatgtcc tgaatatttt accccatcct aaactccatc tctaacacag atgcactttc    48120
ttgtgctgcc tactgcattg tacatcttcc ccttagttcc catgatgcaa ctctgcccta    48180
ccccagaaaa tgtaatttaa ttggtctggg ataaaacctg ggacactatc attcttgaaa    48240
tattccccaa gcgattctaa ttatatagcc aaagttgaga actatttgta gacaggcatc    48300
agcatgatca cttaatgatt tgacttttgc tagatctaag gtgaggaaat tggagagtgg    48360
tatccatagg aagaactgtt tagtttaatt tttttttat ttttcttct aaaaaaaaat    48420 ccaacaacga gatacatgtg cggaacatgc aggtttgtta cataggtata atgtgccatg    48480
gtagtttgtt gcacctattg acccatcctc taagttccct cccctactcc ttacttccca    48540
acaggccctg gtgtatgttg ttcccctctc tgggtccacc tgttctcaat gttcaactcc    48600
cttttacgag tgagaacaca tggtgtttga ttttctgttc ctgtgttaat ttgctgagga    48660
tgatagtttc cagcttcatc cacgtccctg caaaggacat gatctcattc cttttttatgg    48720 ctgcatagta ttccatgatg tatatgtacc acatttctt tatccagtct gtcattgatg    48780
ggcatttggg ttggttccat gtctttgcta ttgtaaatag ttctgcagta aacatatatg    48840
tccatgtgtc tttatagtag aatgatttat attactttgg gtatataccc agtaatgaga    48900
ttgctgggtc aaatggcatt tctggttcta gatacttgag gaatcgccac actgtcttcc    48960
acaatggttg aactaattta cactcccact aacagtgtaa aagcgttcct atttctccac    49020
agcctcacca gcatctattg tttcctaaca ttttaataac tgctattctg actggcatga    49080
gatggtatct cattgtggtt ttgatttgca tttatctgat gatcagtgat gctgagattt    49140
ttaaaatatg tttgttggcc atgtaaatgt cttttgtgaa gtgtctgttc atatcctttg    49200
cccaccttaa tagggttttt tttttcttgt gaatttgttt aagtgccttg taaattctgg    49260
aaattagatc tttgtcagat ggatagattg caaaaatttt ctcccatttt gtaggttgcc    49320
tgttcactct gatgataggt tcttttgctg tgcagaagct ctttagttta attagatcca    49380
```

```
atttgtcaat tttggctttt tttgcaattg cttttggcat tttcctcgtg aagtctttgc    49440
ccgtgcctat gtcctgaatg gtattgcgta ggttttcttc tagggttttt atagttttgg    49500
gttttacatt taagtcttta atacatcttg agttaatttt tgtataaggt ataaggaagg    49560
ggtccagttt cagttttatg cataatggct aggcagtttt cccaccacca tttactgaat    49620
aggagatctt ttcctcattg cttgttttg tcagatttgt cgaagatcag atggttgtag    49680
atgtgtggtg ttatttctga ggtctctgtt ctgcaccatt ggtctatatg tctgttatcg    49740
taccagtccc atgctgtttt ggttaccgta gccttgtagt atattttgaa gtctggtagc    49800
gtgatgcctc cagctttgtt cttttttgctt aggattgtct tggctatatg gagtcttctt    49860
tgattccata tgaaatttaa ataattttt ttttattctg tgaagaatgt caatggtagt    49920
ttgatgggaa tagcattgaa attataaatt actttgggca gtatagccat gttcacaata    49980
ttgattcttt ctatccgtaa ggacgacact ttttccattt gtttgtgttc tctcttattt    50040
ccttgagcag tggtttgtag ttctccttaa agaggtcttt cacatccttt gttagctgtg    50100
ttcctaggta ttttgttctc tttgtagtga ttgtgaatgg gaattcattc ttgatttgcc    50160
tctctgctgc ctgttgttgg tgtaaacaaa attcatttct tgttcttatt tgtgaaattt    50220
tggaaccaaa tctattttca aattagaaat tgcttgtgat aatggttttg caacttagac    50280
tggatatgag acgatgagat attagttctt tcattccttt gtaggaatat ggtgcatctt    50340
gcattatttt agctaactag tgtccttaa tgactaatga atatgacatg gtgaaacaaa    50400
gtaaaatata tatgatgcac taagtatgca ttgtttccaa aggttcagca ttttttttt    50460 gttaactctg ctgggatctg ctttatgcac tgataacata acttatttta tgatcttaag    50520
caaataaaaa cacttatctg gacctcagtt tccttaactg tacaactgag ggaaactgta    50580
tagtatagct atagtacagt ataccatctt taccgtcact tccatctttt aaattatgtg    50640
tatataagat agggcctaga taaatggtat ttatcttaaa ttacagtgat actagcttat    50700
aacttaattt gctaggtcat gttgaactga taacaatgtg tgaactgatg agcaactgag    50760
aagtaaccag gttgtgttat aacagtttgt ttttgattta gggttatcag tgagggtggc    50820
ggtggggagg ggactttgga gtctaactgt ctagttcaaa tattagtttt tgtttattt    50880 tatttttaat ttttgtgggt acatagtaga tgtatatatt tatggggtac atgtgatgtt    50940
ttcatatagg catgcaatgt gaaataagca catcatagag aatggggtat ccatcccctc    51000
aaacacttat cttttgagtt accaacaatc caatgacact ctttaagtta tcaaatcaca    51060
gttttgccag ctactagcca tgtgattttg ggtaggttac ttaaattctc ttcatctcaa    51120
tttcattatt gtaaagtgga gataatgata gcacattttt tcttttctt ttttctttta    51180 ttttttatta ttatacttta agttgtgtga tacatgtgca gaatgtgcag gtttgttaca    51240
taggtatcaa caactctata aaacatgttc tatccaggaa aagaaactat catcagagtg    51300
aacaggcaac ttacggaatg gggagaaaatg tttgcaatct agatggcgat tgcaatggcg    51360
gttcgctgca tccatcagcc catcatctac attaggtatt tctcctaatg ctatccctcc    51420
ccttgctccc caccccctca caggcccctg tgtgtgatgt tccctccct gtgtccatgt    51480 gttctcattg ttcaactccc acttatgagt gagaacatgt ggtgtttggt tttctgttct    51540
tgtgttagtt tgctgagaat gatggtttcc agcttcatcc atgttcctgc aaggacatga    51600
actcatcctt ttttatggct gtatagtatt ccatggtata tatgtgccac attttctta    51660 tccagtctat cattggtgga catttgggtt ggttccaagt ctttgctatt gtgaacgctg    51720
cagcaatgaa catacataag catatgtctt tctagtcaaa taagttataa tcctttgggt    51780
```

-continued

```
atgtacccag taatgggatt gctgggtcaa atggtatttc tggttctaga ttcttgagga   51840
atcgccacac tgtcttccac aatggttgaa ttaatttaca ctcccaccaa cagtgtagaa   51900
gcattcctat ttctccacat ccgctccagc atctgttgtt tcctgacttt ttaatgatca   51960
ccattctaac tggtgtgaga tggtatctca ttgtggtttt gatttgcatt tctctaatga   52020
ctagtgatga tgagcttctt ttcatgtttg ttggctgcat aaatgtcttc ttttgagaag   52080
tgtctgttca tatcctttcc ccactttttg atggggttgt ttttttcctg taaatttgtt   52140
taagttcctt gtagattttg gatattagcc ctttgtcagg tggatagatt gcaaacattt   52200
tctcccattc tgtaagttgc ctgttcactc tgatgatagt ttcttttgct ggatagaaca   52260
tgttttatag agttgttgtg agaattaaat gcattaagca catagaatag attctggtac   52320
atagcaagtg ctctctctat atatggaact ctatatgtag ttggtgcaaa agtaattgtg   52380
gttttcacca ttgaaagtaa tggcaaagac catcattacc ttttcaccaa tttaaatata   52440
tggaaggaat atatatataa aacctatata tatatgtcac atatatgtct ctaacccatt   52500
attataatat ataatacaat atatattata attataattg tatataacat atgttatata   52560
ataatatagt aatatttatt ctaaataaat atataatact ataaataata taataattta   52620
tatatatgat tataatatat aataggctat attatatatt attaacatat acatatgtgt   52680
atatatatgt ctttcataga cttaaatata tagagcaata ataggttaga aaatagcaaa   52740
catgtatata taaacatata tacatataga aaacatatat aaaaacatat atatatatat   52800
atatatgtgt gttttctgcc tttcattttt agagacaggg tctcatcatg ttgcccaggc   52860
tggtctcaaa ctcctgggct caagtgatcc tactgctttg gactcccgaa gtgctgggat   52920
ttcagacatg agacactgca cccagtccag tccctgtctt tttaaataga ctctctacct   52980
aagtgcacaa atactcatta tttacattta gttatttctg tatatatgct ataagcaaat   53040
cttgtagcac cagtttgatt tttataaggc acaagaatat attttactaa tgctttaaaa   53100
tggcagctag attctagtat tactttagaa attaaaatta atattttaac acatctttca   53160
ttattgtgtt atctgaacca aacctattat tgctgctatt tcagcaaatc caggggcttt   53220
ttcttataaa atatgaagaa tatagcttag atttctagtg aagatgttac cagtaataat   53280
taataaaatc agtaagcact aaaaggaaaa taccaaaact aaagcatttt gaattagtca   53340
ttgaatctaa aagaaaggta gattttttttc tgagattctg ttctaggtgt ggtatatgtg   53400
tattttttgca aaaactataa acaattgtgg caaaatgaag gaaatattta aaaacaaacc   53460
tcttaattct tcagtggatt aagcgtgaat atgtttttat tttctatgat gaatatgaaa   53520
aaattcattt ccttagcaat ttgtatgagc ccaaaaacta ttgtcagact ctgctgtatc   53580
aaaatagaca aaaaattgac actcactttt accctgccaa aagcaaaatc ttaaactttt   53640
gctttagtat ataagccagc attcattgta tcctatgatg ggttctgagt gtaggtgtat   53700
ttgctttctt ccattttttg tatgcatgtt ttctttttat ttattattgt aagttgtatg   53760
aaatttttat ccaatttttt attttcttct gattaataat cagaataatc agataattac   53820
tggtaaattt gatgttaatc cttccagctt tttcccatgg gaattatac ttaataaagg   53880
ggagaagtca tcattacata atgtgcatat taatctgctt ctccctttaa tgtgttgtga   53940
atgcctttcc atgtcattag atgttttttct acctagttac tttcatgaat catatggctg   54000
taccatgatt tatttaatca gttcctcatc attgagtatg taaattgcct ccatttttt    54060
attactataa aaggtccttc agtacacacc cctttaaaag ctgactctta gaaggtgttc   54120
```

```
ttgactctct acctaagtgt aaaaatacaa ataaattgct ttccagaaaa ggtgcactac    54180
tattttactt tcctgatact aaactatgaa aattcagtcc taacaataga tatttaaata    54240
aagttttaaa aatgccaagt gaaaaagagc atattattat tttcatttgc attacttttg    54300
gttcctggtg agtttaatct gttttttgtat attaattatg catttatatt tcttttttgtg   54360 tgtgtgaatt gcctttcatg ttctttgtgt gttttttattt tgttgtattt gtctctttct    54420
tgatatatga gagaatattt tccctagcct gtcaattgcc ttgtaatttt gtttctagtg    54480 agttttttttt tttttttta caattaaaag ctttaatttt tgaaaatttt gctggcaaat    54540
ctatatatct ttttctttgt tttctgcttt gacattattc ttttataaag gcccatgcca    54600
cccaaatatt atgtaagcat gcatctatgt ttttattact tcatcttttta catttaaata    54660 tctactctat ttagaattca ttgtgatgca tgtatgaggt agaaatctaa tttcaaaaag    54720
atgagtatcc agtttgtcca tcatttattg catgatctct ttctccactg aattaaaatg    54780 ccgtattttta taatatatta aagtattaca tgtgcttgga catgttcctg acttttgag    54840 ataaatcagt ctatttcttt gtcatgtcac atattttatt ggctttatga tttaatatcc    54900
agtaatgtaa accctctgac acattattct tattcctcaa atgttttga tgagttttct    54960 tccaaatgaa atttataatc attttattca ttgattcaac aaatatttgt tgaatggata    55020
ttctgtgctt ggtattgtgc atggtattag gattgttgca aaaattgaga ctgacagtcc    55080
ctactcttac ggtgctaaaa attcacttcc aaaaaaatct ttaaatgttg atgaagattg    55140
cactaatctt ataaaataac ttggagggga atgtaatctt tgcaacatta agttcttcat    55200
tttagaaagt tttaagactc tccatttatt tgagactttt aaaatatgtc ccaataatgt    55260
tttgtgagat gtatattttta agatatatat cttattgcta ttacattgta tcttttgtta    55320
tattgttact atgaatggga tactcattta attagatgtc attttggta tatagaaatc    55380 tattttctta gcatagtcat ttttttaaacc tcgatctatt aaattcttga ttcatttaca    55440
tttgttacac aatcatattc tatgctgata atacttcttg cttctttcca atatttgtac    55500
ctcgatcatt tttcttgttg agttgtatta gctagaagtt ctagaaaaat gttaaatggt    55560
agtaatagct agtattctgt ttttttcctga ctctaaatgt aatgcatcta gacttttata    55620
attatggcat tgattgtaac attttgagga agaaatcctt tttcaggtta ataatgtatc    55680
tttatattca agtttattaa gaacatttat tggaaacata ttgaaatttt atcagattcc    55740
ttttcagttg ttactgagat aatcataggt tcttctgtat tcttttaatt aatttctcaa    55800
aattaaactg tcctattatt cttggaataa cgacatataa agtactgtat atttaaaaga    55860
agttaaaatg ataatggtga ttttattaag tgacctcaca caatagaaaa cagtgtagcc    55920
ttagaagttt tccaagtgac cattctactt agaaacaacc ctgctttggg atcagaactg    55980
taatttttaa agtaaagttt tctgggtttta attcatttag tgtaattaca agcatgagtt    56040
caggttctta ttttttttcac ctgaacttttc cttcatggtt tgaatatcta gaaaaagcag    56100
actttcctat ctctagacta aacatttgat cctatcttag gtatgcatta caattttta    56160 accataaatg gttaaagaat ttagactcat ctacaataac tttgaagctc tggtcttgaa    56220
gaacatgtga gaaatgagat ataactccta gaagatatag gagacatttt tagtcttcca    56280
aattttccct gggaggctga tctaaattga gtcacaaaat tgttcccacc aggaatgcaa    56340
tcacttgagc tgttttctaa tctgagcccc tctacccaga tgatcttctg aactcatact    56400
gttcagactt tcatccttct gagtagaaaa cagccatagt catggcagga tgagggctag    56460
gacaattacc caaggaattc ttggcctctg ccatgggact ctgcagactc agatcatata    56520
```

```
atcagagatg ttagcactgg aggggacatc acaattagct ttctccacct cttagtttat   56580
cagtgaggaa aactgtccag agcgcggaag agactaaaat aacacagcca atgtaggtaa   56640
tgtgctggat aagaatttgg aattcacgat tttgaattca gtgtttattt caccatcacg   56700
ctggcttaca cgttggtatc aggcttcttc tattattgaa gtgagccatt aagtgaattc   56760
catcttgatt tgtgtctgat acagagtaat aaactatttt attaaatatc caaataatta   56820
tacattcctc cttcttacat gcaagcctaa gtttgcttgt actatttcat gtggtagcaa   56880
atcaggacgc ttcttgtgtc tctgaaaata ctctgagtaa tggagtacag tcagctttct   56940
tgtaccaaga atatagggac tatgtttctc ccagtcattc tggggataat ttttgtgaag   57000
gattgcactt cataggttaa gctaggtatc agttaccagt gttttttcca aataaaaaaa   57060
aaatcaggtg atatctgtaa atggttccat tgtaaatatt aaagaacatg atgcttaaaa   57120
cagattaggg aaaactatag aaggggtggg gtttcggagt gctaattttg tccttgaatg   57180
gtaacagctc catgtggtgg tgaggtttat gttggtttgc tgtttgcaga tgatcttatt   57240
attagaattt ttcataccga aaataaactg cattttagtt tgtaaacatg cccttccaga   57300
gtaatgctac cagttctttg tgaaatagct actgttgttc aaaggatgac tatgtcctct   57360
tcggttgagg aaagatgaca acaaactcag taatgacatg taaaataggt attacaaacc   57420
aggtatggtg gcatgagcct gtaatcccag ctacttgaga ggctaaagca ggaggatctg   57480
ttgatctatg gatttgaggc tgtagtgtgt tgtgatggca cctatgaata gcccttgcac   57540
tccagcccaa gcaacaaagc aagactgtct ctgaattttt gttttgtttt gttttttgtt   57600
tttttttttt tgagacagag tcttgctctg tcacccaggc tgaagtgcag tggcgcgatc   57660
tccactcact gcaagctccg cctcctgggt tcacgccatt ctcctgcctc agcctcccga   57720
gtagctagga ctacaggcgc ccgcctccac gcccagctaa attttttgta tttttagtag   57780
agacgaggtt tcactgtgtt agccaggacg gtcttgatct cctgaccttg tgatcctcct   57840
gcctcggcct cccaaagtgc tgggattaca ggcgtgagcc accgcgcccg gcccctgtct   57900
ctgaattttt taaaaaggca ttccactcaa attaatacac attttaattg tgttttgttg   57960
taaattacaa ctgaataaaa attcagcaaa taagtctgtt gtggtaggga aaagtctatt   58020
gtgatctgga aaatataatg gagaaatcca gtggaagaga ttttatttca cattactcaa   58080
aataaaaaaa tcttatacaa gtctttacac ttgtaacttg aaaaattctg tgctaaaatt   58140
tagcttggtt gctaaaatat ttctctttt ttctcagaag cttcttttta gcatcctata   58200
gacacaagtt acttttaaa atatttgcat acttgctttg caatgtattg tttatcagta   58260
gttctatatt ctttgagata gtctatccag tctttctgta tttatcgtat gtctgtatag   58320
atatatatta gcagataaat gagttctgaa aggggagaaa tgtgattatg ctaatcatga   58380
tataaagaat tgactttata agcagtgttc acaggtcata cctttcccgt tactgtctta   58440
cagtgaacaa gaaatgatgc tttgtctggt atgcatggta aataatgccc cttgctctct   58500
gcttcatgat cacatgtgat acttctaaca tagatagcac atgtaaatcc agtggccttg   58560
actgcaactc aagagagcat tttggccaag tacaaaccca ctagtcatga aaaaaaaaa   58620 aaaaccaaat caaagtaaat tgatggtatt gacatttgtc tatgaaaaac aacataatat   58680
agaacaattc tggggtaaaa tattgatcta aaataatttt aaggattaaa tattgccatt   58740
gtaagcatac tatgagcaat tatgtttgta atgcagatat atttataatt ttaaatccaa   58800
gatttacctt aattgtacat tttcctaatt taaaaaagtt attttgaaaa aaaaatcctc   58860
```

```
gaatctagag aaaggttggc aaatacatat ggaactttgt aaaaaacatc cagggcagca    58920
ctttcactga ttgcagtagc ttaggagtga aaaacaacac aactgctcca atgtatggca    58980
atgggcaaat atcccgattt attcacaggg tggcatgtta ggcagtgctt agaataaatg    59040
agttggttat acaagtatca atagggataa atgtgaaaaa cacagtgtta agttttaaa     59100 aagttgtaaa aagcacagta ggatgttatt tatataaaat ttaaaaacct caaaaaccat    59160
tcttctttga tatatattct aaagatgaac atatatgtaa tagaagtaca aaacatacat    59220
aaaataatat acactatgca gtcatttgtg tacttacttt tcaaaaatat ttcagtagat    59280
atagcaaaca gttaacatgt aatatttgga taggaggttg gcaattttct ttttagcacc    59340
tgcctgtctg ctatcattca aactcacatt taaaatgtgg ctatgtgaga tgagagaact    59400
ataatattcc aggtttgtga ttagtttgga acttttttaa aagtttgaat gtggtctgag    59460
agatagtttg ttataatttc tgttctttta catttgctga ggagagcttt acttccaact    59520
atgtggtcaa ttttggaata ggtgtggtgt ggtgctgaaa aaaatgtata ttctgttgat    59580
ttggggtgga gagttctgta gatgtctatt aggtctgctt ggtgcagagc tgagttcaat    59640
tcctgggtat ccttgttgac tttctgtctc gttgatctgt ctaatgttga cagtggggtg    59700
ttaaagtctc ccattattaa tgtgtgggag tctaagtctc tttgtaggtc actcaggact    59760
tgctttatga atctgggtgc tcctgtattg ggtgcataaa tatttaggat agttagctcc    59820
tcttgttgaa ttgatcccct taccattatg taatggcctt ctttgtctct tttgatcttt    59880
gttggtttaa agtctgtttt atcagagact aggattgcaa cccctgcctt tttttgtttt    59940
ccattggctt ggtagatctt cctccatcct tttattttga gcctatgtgt gtctctgcac    60000
gtgagatggg tttcctgaat acagcacact gatgggtctt gactctttat ccaatttgcc    60060
agtctgtgtc ttttaattgg agcatttagt ccatttatat ttaaagttaa tattgttatg    60120
tgtgaatttg atcctgtcat tatgatgtta gctggtgatt ttgctcatta gttgatgcag    60180
tttcttccta gtctcgatgg tctttacatt ttggcatgat tttgcagtgg ctggtactgg    60240
ttgttccttt ccaggtttag cgcttccttc aggagctctt ttagggcagg cctggtggtg    60300
acaaaatctc tcagcatttg cttgtctata agtatttta tttctccttc acttatgaag     60360
cttagtttgg ctggatatct ctcagaccac agtgcaatca aactagaact caggattaag    60420
aatctcactc aaagccgctc aactacatgg aaactgaaca acctgctcct gaatgactac    60480
tgggtacata acgaaatgaa gacagaaata aagatgttct ttgaaaccaa cgagaacaaa    60540
gacaccacat accagaatct ctgggatgca ttcaaagcag tgtgtagagg gaaatttata    60600
gcactaaatg cctacaagag aaagcaggaa agatccaaaa ttgacaccct aacatcacaa    60660
ttaaaagaac tagaaaagca agagcaaaca cattcaaaag ctagcagaag gcaagaaata    60720
actaaaatca gagcagaact gaaggaaata gagacacaaa aaacccttca aaaatcaat     60780 gaatccagga gctggttttt tgaaaggatc aacaaaattg atagaccgct agcaagacta    60840
ataaagaaaa aagagagaa gaatcaaata gacacaataa aaaatgataa agggatatc       60900 accaccaatc ccacagaaat acaaactacc atcagagaat actacaaaca cctctacgca    60960
aataaactag aaaatctaga agaaatggat acattcctcg acacatacac tctcccaaga    61020
ctaaaccagg aagaagttga atctctgaat agaccaataa caggctctga aattgtggca    61080
ataatcaata gtttaccaac caaaaagagt ccaggaccag atggattcac agccgaattc    61140
taccagaggt acaaggagga actggtacca ttccttctga aactattcca atcaatagaa    61200 aagagggaa tcctccctaa ctcattttat gaggccagca tcattctgat accaaagccg     61260
```

```
ggcagagaca caaccaaaaa agagaatttt agaccaatat ccttgatgaa cattgatgca   61320
aaaatcctca ataaaatact ggcaaaccga atccagcagc acatcaaaaa gcttatccac   61380
catgatcaag tgggcttcat ccctgggatg caaggctggt tcaatatacg caaatcaata   61440
aatgtaatcc agcatataaa cagagccaaa gacaaaaacc acatgattat ctcaatagat   61500
gcagaaaaag cctttgacaa aattcaacaa cccttcatgc taaaaactct caataaatta   61560
ggtattgatg ggacgtattt caaaataata agagctatct atgacaaacc cacagccaat   61620
atcatactga atgggcaaaa actggaagca ttccctttga aaactggcac aagacaggga   61680
tgccctctct caccgctcct attcaacata gtgttggaag ttctggccag gcaatcagg    61740 caggagaagg aaataaaggg tattcaatta ggaaagagg  aagtcaaatt gtccctgttt   61800
gcagacgaca tgattgttta tctagaaaac cccatcgtct cagcccaaaa tctccttaag   61860
ctgataagca acttcagcaa agtctcagga tacaaaatca atgtacaaaa atcacaagca   61920
ttcttataca ccaacaacag acaaacagag agccaaatca tgagtgaact cccattcaca   61980
attgcttcaa agagaataaa atacctagga atccaactta caagggatgt gaaggacctc   62040
ttcaaggaga actacaaacc actgctcaag gaaataaaag aggacacaaa caatggaag    62100 aacattccat gctcatgggt aggaagaatc aatatcgtga aaatggccat actgcccaag   62160
gtaatttaca gattcaatgc catccccatc aagctaccaa tgactttctt catagaattg   62220
gaaaaaacta ctttaaagtt catatggaac caaaaaagag cccgcatcgc caagtcaatc   62280
gtaagccaaa agaacaaagc tggaggcatc acgctacctg acttcaaact atactacaag   62340
gctacagtaa ccaaaacagc atggtactgg taccaaaaca gagatataga tcaatggaac   62400
agaacagagc cctcagaaat aacgccgcat atctacaact atctgatctt tgacaaacct   62460
gagaaaaaca agcaatgggg aaaggattcc ctatttaata aatggtgctg gaaaactgg    62520 ctagccatat gtagaaagct gaaactggat cccttcctta cccttatac aaaaatcaat    62580 tcaagatgga ttaaagattt aaacgttaga cctaaaacca taaaaaccct agaagaaaac   62640
ctaggtatta ccattcagga cataggcgtg ggcaaggact tcatgtccaa acaccaaaa    62700 gcaatggcaa caaaagccaa aattgacaaa tgggatctaa ttaaactaaa gagcttctgc   62760
aaagcaaaag aaactaccat cagagtgaac aggcaaccta caacatggga gaaatttc    62820 gcaacctact catctgacaa agggctaata tccagaatct acaatgaact caaacaaatt   62880
tacaagaaaa aaacaaacaa ccccatcaaa aagtgggcga aggacatgaa cagacactac   62940 tcaaagaag acatttatgc agccaaaaaa cacatgaaga atgctcatc atcactggcc    63000 atcagagaaa tgcaaatcaa aaccactatg agatatcatc tcacaccagt tagaatggca   63060
atcattaaaa agtcaggaaa caacaggtgc tggagaggat gtggagaaat aggaacactt   63120
ttacactgtt ggtgggactg taaactagtt caaccattgt ggaagtcagt gtggcgattc   63180
ctcagggatc tagaactaga ataccatttt gacccagcca tcccattact gggtatatac   63240
ccaaaggact ataaatcatg ctgctataaa gacacatgca cacgtatgtt tattgcggca   63300
ctattcacaa taggaaagac ttggaaccaa cccaaatgtc caacaatgat agactggatt   63360
aagaaaatgt ggcacatata caccatggaa tactatacag ccataaaaaa tgatgagttc   63420
atgtcctttg tagagacatg gatgaaattg gaaaccatca ttctcagtaa actatcgcaa   63480
gaacaaaaaa ccaaacaccg catattctca ctcataggtg ggaattgaac aatgagatca   63540
catggacaca ggaaggggaa tatcacactc tggggactgt ggtggggtcg ggggaggggg   63600
```

```
gagggatagc attgggagat atacctaatg ctagatgaca cgttagtggg tgcagcgcac    63660
cagcatggca catgtataca tatgtaacta acctgcacaa tgtgcacatg taccctaaaa    63720
cttagagtat aaaaaaaaaa aaaaaaaaag tttgaatgtt ttcttgcatt cagagccttg    63780
gttgacatag ttaattaaaa ataaaacatt gtatataaag cacagaatga gcagctacac    63840
aaagctgctc aatcaatgac agctctatat gggttagggt ttcttgtggg gatgacattg    63900
atgtagaaag catggtcatc tattgagaat gatggggctg gaggtattgg atacttgagg    63960
tttagaaaat acattgtaga aaatggacaa aaaccccctca aattaaggga tgaggcagaa    64020
taatgcttgg caataccagg ggtaggctgc agtctttctt ggaaatatat attttaaatg    64080
gaaccaatta tcatagcatc atttcctctc agggttaccc tctgatccct attttactaa    64140
atcgttataa acaaaatga  ggaattatgt gtccttccct tttgaagcca atgtaacaag    64200
atgggtaaga attagacctc ctgagttcaa atccctggga ttcagatcta ttcctgtata    64260
ttcaggagaa gtggtaataa attcgatgga caatttggtt tagtagtcga ttgaggaccc    64320
tgatgaggta tatttgggaa aacataactt ccgctctctc tcattgactc acgggccttt    64380
gaggagtcca ggagtcattg gaatctggcc tgaggttgag gctgctggca aaactccttc    64440
cccaaagtcc attcctattg ctgactgaga agggactagc attggaagtg gctgatttta    64500
aataccgcta gtgctggtgt gctcctccct cccattccca gctctgcttt gtgtagttgc    64560
cttgagaagc taagttcatt ctgaaaataa tgccattgca caaacactt  ttgaaagttc    64620 tagtttgaaa ttacatcagg tcacttggtc tgtgtggcct cagtttcttc atctgccatg    64680
tgaaaataat aatgcctact ctgtagcaaa gaaagtctct atagtaaaca aaaaaaaagc    64740
ctactctgat actgaaagtt gttatgaaaa ataaaaaagg gaaatgcttt agaaactgtt    64800
aagtgctatg tagatgttac taattaacaa accatttcag aaactatact ttttatttta    64860
tggccactat tcactgttta acttaaaata cctcatatgt aaacttgtct cccactgttg    64920
ctataacaaa tcccaagtct tatttcaaag taccaagata ttgaaaatag tgctaagagt    64980
ttcacatatg gtatgacccct ctatataaac tcatttttaag tctcctctaa agatgaaaag    65040
tcttgtgttg aaattctcag ggtatttttat gagaaataaa tgaaatttaa tttctctgtt    65100 tttcccctttt tgtaggaagt caccaaagca gtacagcctc tcttactggg aagaatcata    65160
gcttcctatg acccggataa caaggaggaa cgctctatcg cgatttatct aggcataggc    65220
ttatgccttc tctttattgt gaggacactg ctcctacacc cagccatttt tggccttcat    65280
cacattggaa tgcagatgag aatagctatg tttagtttga tttataagaa ggtaatactt    65340
ccttgcacag gccccatggc acatatattc tgtatcgtac atgttttaat gtcataaatt    65400
aggtagtgag ctggtacaag taagggataa atgctgaaat taatttaata tgcctattaa    65460
ataaatggca ggaataatta atgctcttaa ttatccttga taatttaatt gacttaaact    65520
gataattatt gagtatcttc tgtaaactgc ctctgttgta gttttttttt tctcctaatc    65580
atgttatcat ttttttggaa tccatggttt cctgttaaga tgactcacac agcctacata    65640
aaagtaattg acaaaatatc atcttatagt aaaatgccac atatctttat gttcagcaag    65700
aagagtataa tatatgattg ttaatgataa cccaaacaac aaaagatttc accttaactg    65760
gttgtcataa gtagtagtat ccaccgcctt attttgagtt ggatttttat catcctatga    65820
gccctacaaa tttaaagttt ttggaacagc acgtgcattg aacccataag aacctactct    65880
gcttttctgc atgtattgtc cagacaagag accaaattgc cgaggcatca tttaggtgaa    65940
ttctaattaa catttagcta ccttacaacc acaattcaag gttgtttcaa aggcatgtgc    66000
```

```
ttgcatcatc ctgattcact accatgtgtt actaacttgg atctgcaaag tcattataaa    66060
aagctgtttt gatggactta tttggatatt gctttaccct tcttctctct tttcttttat    66120
caatgtaaaa acattatatg ttaaatactt ggcttttaag agcatagatc tgaaatctgc    66180
ctctagcaaa taacccataa cacttctaag atatacctgc aaggtcaatt gtgttgtaaa    66240
accttgataa ccatacttta ttgttcaaaa aagccttttta tgaaggcaga agttaaaaaa    66300
aaaaaacaaa aaaaacagag tccacagtta tcacctcagc tacaatctca tcagttcaca    66360
agtaccagca aaacatgtga taagtcaaca aatgttttat ttcaatctga acattttacg    66420
taagtgaaga ctttgttaga tatcatttgg aatgtggaat ctacacagtt ggcatatcag    66480
agaaggttga attcagttta ataaatgttt atagaaagtg cttgttatca taatgataat    66540
agctcaggat gtgcatgaca agcttttaag cgattgggta cactatctca tttgatcttc    66600
tgcacaacta ttaatggtag gtactattat ccctatctta tggataagta aactaagatt    66660
taaaaagtac agaacatggt gtgaacactg cttcaaaatt tctaaaatag gtaaatcacg    66720
atctctaaac tggagggttg tccaaccact agggacaata gagtactgat atttagtggt    66780
cagactgtaa tgcgggaaga dacaggcatg ggctaaacgg gtgtagagat caaataaggg    66840
gcaggttagt ttgtaaacat gtccatatgt aacatttagc acaaatacag gatataggtg    66900 cttttcagacc cagctgcatt gataaaaagt taggtggtat tgtatctgtc ttccttttctc    66960 aatgttgcat atctgtgttc ttgcccagtt tgcttcatct ctctagccac acttattggc    67020
ctacaatggc atcatcacca aagaaggcaa tcccatctcc gtgtggcttt ggtttgctcc    67080
ctaaagtaaa ccttgtgttt acttttccca ggtctcatgc tttcccatat ctgacctgtt    67140
ttgtcctcat ggccaggata tgtgggacct ttcctacaat gttccaaagt ttgtaataga    67200
gctcttctct gctttgttcc aaattctgca acatttact ttaaataatg aatttaaata    67260
caaacaaact tgagctttgc ctatactttt caagaatgca gagataacta aattaataaa    67320
aatattcatt gagtccttac tgtgcacaca gctctatgtt aagccttgtg cagaactcaa    67380
agtcactcga gattaagcct gttactaagt tatgtgcaat ttagctcagt ggatttcccc    67440
cacttcatat tgctctgata atgttttgga attaactgcc ttgattcctt cttttctctg    67500
cttgtctata cactatttat tattctacac catctcaaat tctaactcct caagaaaatc    67560
cttccagatg atttttctaa ccaggagttt taacttcctt ttaactaccc tattactttc    67620
tacttcctta actcatctat catattatat ttagttattt atatactagg tcgccttgaa    67680
gaagggattg tgttttcata aatcttaata atccctgagg catcaagtac agtgatttgc    67740
atttactaaa tgctcaacaa atatgtgagg gattcacttg aaactaatat tagataattc    67800
ccagtcaaag tgatctaata gcaaatcaat tcttcagttt tataggcaaa gtatgactct    67860
ggttttccat aatcataatt aatttgtcaa ctttataatt ttaattaagt aaatttaatt    67920
ggtagataaa taagtagata aaaaataatt tacctgctta actacgtttc atatagcatt    67980
gcattttcct ttgtaaaatt taagaatttt gtattaataa acttttttac aaaagtatta    68040
attattcagt tattcatcat atactttat tgacttaaaa gtaattttat tcaaagagt    68100 tagtatagga ctacatgaaa aattcaaggc caaggcttaa tttcaaattt cactgccttt    68160
ggctctatct tttaaaacaa aacaaaaaac tcccgcacaa tatcaatggg tatttaagta    68220
taatatcatt ctcattgtga gggagaaaaaa taattatttc tgcctagatg ctgggaaata    68280
aaacaactag aagcatgcca gtataatatt gactgttgaa agaaacattt atgaacctga    68340
```

```
gaagatagta agctagatga atagaatata attttcatta cctttactta ataatgaatg    68400
cataataact gaattagtca tattataatt ttacttataa tatatttgta ttttgtttgt    68460
tgaaattatc taactttcca ttttttcttt agactttaaa gctgtcaagc cgtgttctag    68520
ataaaataag tattggacaa cttgttagtc tcctttccaa caacctgaac aaatttgatg    68580
aagtatgtac ctattgattt aatcttttag gcactattgt tataaattat acaactggaa    68640
aggcggagtt ttcctgggtc agataatagt aattagtggt taagtcttgc tcagctctag    68700
cttccctatt ctggaaacta agaaaggtca attgtatagc agagcaccat tctggggtct    68760
ggtagaacca cccaactcaa aggcaccttg gcctgttgtt aataagattt ttcaaaactt    68820
aattcttatc agaccttgct tcttttttaaa actttaaatc tgttatgtac tttggccaga    68880 tatgataccct gagcaattct tgttctgggt tgtcttatgt gaaaaataaa ttcaaggtcc    68940
ttgggacaga taatgtgttt tatttatctt tgcatatcca ttacttaaaa cagcattgga    69000
cccacagctg gtacaaaatt aattactgtt gaattgagca atatttatt ctaaatgtct    69060 ctgtcaaatg acagagtgtg gttgtgtgga ttaagtccct ggagagagtt ctttgttctc    69120
tcatgttcta tgctgtggtt cttgcttat gcaaaaagaa gtaagttact taaaacctgg    69180
acatgatact taagatgtcc aatcttgatt ccactgaata aaaatatgct taaaaatgca    69240
ctgacttgaa atttgttttt tgggaaaacc gattctatgt gtagaatgtt taagcacatt    69300
gctatgtgct ccatgtaatg attacctaga ttttagtgtg ctcagaacca cgaagtgttt    69360
gatcatataa gctcctttta cttgctttct ttcatatatg attgttagtt tctaggggtg    69420
gaagatacaa tgacacctgt ttttgctgtg cttttatttt ccaggacttt gcattggcac    69480
atttcgtgtg gatcgctcct ttgcaagtgg cactcctcat ggggctaatc tgggagttgt    69540
tacaggcgtc tgccttctgt ggacttggtt tcctgatagt ccttgcccct tttcaggctg    69600
ggctagggag aatgatgatg aagtacaggt agcaacctat tttcataact tgaaagtttt    69660
aaaaattatg ttttcaaaaa gcccacttta gtaaaaccag gactgctcta tgcatagaac    69720
agtgatcttc agtgtcatta aattttttt ttttttttt ttttgagaca gagtctagat    69780
ctgtcaccca ggctggagtg cagtggcacg atcttggctc actgcactgc aacttctgcc    69840
tcccaggctc aagcaattct cctgcctcag cctccggagt agctgggatt agaggcgcat    69900
gccaccacac ccagctaatt tttgtatttt agtagagaca gggtttcacc aggttgccca    69960
ggctggtctc gaatgcctga cctcaggtga tccgcccacc tcggcctccc aaagtactga    70020
tattacaggc atgagctacc gcgcccggcc taaaaaatac ttttaagat ggtgtaaata    70080 ttactttctg tatcaatggt acatttttta cttgtcagtc tctagaattt ctttataaat    70140
atgttgattc agttcatttt tgtagattat aaaacaggta aaaaggata aaacatttat    70200 gtgaattaaa gggaataccct aattttttgtg tagagtttat tagcttttac tactctggtt    70260
tatggatcat cacaccagag ccttagttac tttgtgttac agaataacta atatgagtga    70320
atgaatgact tacacaagtc actgcttagg ataaggggct tgagtttgtc agctagagta    70380
tgacagaaag tatctaagtt ttggagtcaa atagcacttt gtttgaatcc cagattgcat    70440
gcttactagt tatgtgacct tagtcaagcc acttcacctc actgagtctt tgcttttttc    70500
atctctaaaa tagagatacc caccgctcat aggctgtcat aagggataga gatagcatat    70560
ggaatgagtc tgtacagcgt ctggcacata ggaggcattt accaaacagt agttattatt    70620
tttgttacca tctatttgat aataaaataa tgcccatctg ttgaataaaa gaaatatgac    70680
ttaaaacctt gagcagttct taatagataa tttgacttgt ttttactatt agattgattg    70740
```

```
attgattgat tgattgattt acagagatca gagagctggg aagatcagtg aaagacttgt    70800
gattacctca gaaatgattg aaaatatcca atctgttaag gcatactgct gggaagaagc    70860
aatggaaaaa atgattgaaa acttaagaca gtaagttgtt ccataatttt caatattgtt    70920
agtaattctg tccttaattt tttaaaaata tgtttatcat ggtagacttc cacctcatat    70980
ttgatgtttg tgacaatcaa atgattgcat ttaagttctg tcaatattca tgcattagtt    71040
gcacaaattc actttcatgg gctgtagttt tatgtagttg gtccagggtg ttattttatg    71100
ctgcaagtat attatactga tacgttatta aagaatttcc tacatatgtt cactgctgct    71160
caatacattt atttcgttaa aacaattatc aagatactga aggctgattg gtaactcaca    71220
tggaactggg agagtataca attctgaacc aaatagatga ttctctatta ttatatctta    71280
atttatgtgt tatggtatat taaacatgaa aaaaattgta tttggttaga atatgtttgc    71340
tcttccttaa ctcgggaatg acatagggta atattcacag attgggttcc tataaatcct    71400
ccacttgaag tgaagtcagt tcaagtaatg aaagctacct cctgagatag aatcagtact    71460
tggcacctat ctctagtgtt cttttcacctc atataacctt tcactgatta gtaaagatta    71520
tatccaacaa agaaagtaca gcacagactg agatatgatt actgagataa atttgggcaa    71580
aatataaact acagcatttc tgtagcaatg agaccatttt tcttcagttg agctccatgt    71640
tctacaaact tcaatcaaaa aaggttctag gagactcagt gaaagttgat acactgttca    71700
aggaacaaat aatttcagca catgggaatt tcacagggaa aaatatacta aaaagagagg    71760
taccattttg gatggtgtca atatgggtta tgaggaattc aggctgctga gtccagtgta    71820
caatggaaac tgagctgcag gtgtgtgatt gtaacaacaa aagaaatgct gaaatattaa    71880
gtcctttgcc atgtaaatag aaaaagagta tttatttccc aaacattatt gctcacctgt    71940
ttttgttatg ccttttcaaga taaatccagg aaaggaattg catttctttt ccagaaaaca    72000
agttcttggg ggaattgttc aattggtaga tgttgttttt ctcattaaca agtgagtgct    72060
ccatcacact tgctgagtgc tccatcacac ttgctctctg cattactcct ctgcctgcaa    72120
acacatatat agcaagggtg atgacaagga tatcagaggg tctggttttc tcaaactcat    72180
gataaactca tggctgggtc attcttggtg ctgattttac tttgtttttt gttgttattg    72240
ttccctcttc ctcaaaagat gaaatctatc cctcttactt ggaatttctc tttgatatat    72300
agcgaatgtt tggttgtaac ctgtataatc tggcatgaaa ttgtcactcg aaaaggctag    72360
aagtgttgac ataaatatgg gacagcaaga gttgctccta ctcaagagag caaatataat    72420
gttctggaag agattggcag aattcacatc aaaggagtga ttacttcagc ctgggccact    72480
gttgtactgg tcaaaaggct gtgcaaagct ctctgaaaat ccactctttt attgctcttt    72540
agtaataaag tcactttcaa ttttaaaaat aacaaactga tatatttta tgactcataa    72600 aatgttagca attatattat ggagaatcta ctttctgggt gattcttaca aatgttcttg    72660
gatctatttt tttttcttat agtacctatt cttcccattt ttctcagctc tagttaatat    72720
atttcaacaa cagttcaaca aatttaacat ttttataaaa agtgtttcct atcattttat    72780
aaataccagc ctagtccatg ttattccttt tcttgttgag gagaaaggac acacattgta    72840
aattcaaata tagacctcta ctgtgctatt taatcttggt aacaactcca caaggagat    72900 gacatgtttt ccttctatag aggtagattc tgtaaagtta gagggaagag tgacttgctt    72960
aagatggcat aagctgtaac tggcagaacc aggattcaaa gccaggtggg atgccaaaat    73020
cataatctgt cttcagtgtc aagttactga aattggtaaa cattagacct aaatagacgg    73080
```

| | |
|---|---|
| aattgcaatc cgggttgggc acattaaact ccattttctt catcaatgtg ctcagattac | 73140 |
| attttacttt tcaggctaaa aatggaaaaa aagagtccct cttagttctg cacttgagaa | 73200 |
| tgagaatagc ttttctgaat tatacaagga agaagaacta atgcccaaat gccaggtacc | 73260 |
| cacatgcact atgccatggc acagctgttg ccccctttca ccagagccct ctctctgtat | 73320 |
| cctggttgac ctttccttgg gcaagagctg ggtggggagg atcacaagtg actccaattt | 73380 |
| ggatggcttc gggaagactg ggaccgagct gaaggcagtg ttgtcctctg cactccctgt | 73440 |
| tttctgtctg ctggagcact gaagcctcac atatgtatta aaaaataat ttccatttgc | 73500 |
| atttcagact agaagattga acgtatagtg taatgtgatt gcaaataatt atattgaaat | 73560 |
| gagacagaga ggatgtagta tctactgtca taattttttca aaacccacct gcaacttgaa | 73620 |
| ttaaaagaac cacttgggtt ttttttttttg tttcaaacgc aaatcctgga aacctactga | 73680 |
| gactcattca gtcagtatct ctaagaggca agcttgagac tgtatattta aaaagcatct | 73740 |
| caggtgattt ttacacatgc taaggcttaa gaaccacttc tctgtagctt atatgttatt | 73800 |
| ttcaatgttc ctcaaagcca agttagaatt tccaaagtgt taagaatcca ttagacaatc | 73860 |
| acagaattgt ctttttcctt tataaatctt gcaatgttgt tctcatttcc atacttaatt | 73920 |
| acttaaaaca ccaaccaacc aacaagcaaa aaatgattag tctaactaat attacaagtt | 73980 |
| aataatgaag taaaggttta aaaataatgt cataataatg ttaataacaa attattaatt | 74040 |
| ataatttaaa aataatattt ataatttaaa aataatattt acaagtacta caagcaaaac | 74100 |
| actggtactt tcattgttat cttttcatat aaggtaactg aggcccagag agattaaata | 74160 |
| acatgcccaa ggtcacacag gtcatatgat gtggagccag gttaaaaata taggcagaaa | 74220 |
| gactctagag accatgctca gatcttccat tccaagatcc ctgatatttg aaaaataaaa | 74280 |
| taacatcctg aattttattg ttattgtttt ttatagaaca gaactgaaac tgactcggaa | 74340 |
| ggcagcctat gtgagatact tcaatagctc agccttcttc ttctcagggt tctttgtggt | 74400 |
| gtttttatct gtgcttccct atgcactaat caaaggaatc atcctccgga aaatattcac | 74460 |
| caccatctca ttctgcattg ttctgcgcat ggcggtcact cggcaatttc cctgggctgt | 74520 |
| acaaacatgg tatgactctc ttggagcaat aaacaaaata caggtaatgt accataatgc | 74580 |
| tgcattatat actatgattt aaataatcag tcaatagatc agttctaatg aactttgcaa | 74640 |
| aaatgtgcga aaagatagaa aaagaaattt ccttcactag gaagttataa aagttgccag | 74700 |
| ctaatactag gaatgttcac cttaaacttt tcctagcatt tctctggaca gtatgatgga | 74760 |
| tgagagtggc atttatgcc aaattacctt aaaatcccaa taatactgat gtagctagca | 74820 |
| gctttgagaa attctaaagt tttcaagtga taagactcaa tttatacaaa gctaattgga | 74880 |
| taaacttgta tatgattaag aagcaaataa atacttatta tgcttttttg ctgtttattt | 74940 |
| aaatatttaa cccagaaaat aagtcactgt gacagaaata aaaatgagag agaagggtga | 75000 |
| gccactctta ggtagttctg gcattattta atctaggcca gaggttgcaa atggtgtccc | 75060 |
| atagaactaa ttttggctcc tagacctgtc ttatttaacc tttcatttaa aaaatttgta | 75120 |
| ttggttgcca gcaattaaaa attgggagat gtctcacaca cacacacaca taaacacaca | 75180 |
| cactcatgtg tgcagcctct tttgaagaat tggaataact agtcaactgc gtcctccttt | 75240 |
| tccacaagct gtgacagctc cctgctcaca gagcacctgc cctctcctgt tcatcatgct | 75300 |
| ctcttctcag tcccattcct tcattatatc acctatttgg tcctgagact aagtgagttt | 75360 |
| gagatctgtg atttagacaa agtggtgaat ctagctctga atcatagtaa gtagctctgg | 75420 |
| gaatcatctt gtcttctgtt agcccattga gagagaaata gagagagaga gagagagaaa | 75480 |

```
gaaagaagaa gaaacagatc tggggagagt cactgaatgg gagcatagag acagagaaac    75540
agatctagaa aaccaaactg ggagaaaatg agagaaacca aaagagaggt agagaggagc    75600
agagaagaaa atgaagaagc aaggcaagga ccaggctttt tcattatttc ttatggccaa    75660
gacttcagta tgcgtggact taattcttcc ttatgctcct accttcccta gggaaactga    75720
tttggagtct ctaatagagc ccttctttta gaatcacagt ttgatgcctt aaaactagtt    75780
atataccttc acatgcttcc ttaacccaca gaagtgatgc taatgaggcc cttaataagg    75840
agcgtgctat taagatgaag acattcattt tttttctccg tccaatgttg gattaaggca    75900
cattagtggg taattcaggg ttgctttgta aattcatcac taaggttagc atgtaatagt    75960
acaaggaaga atcagttgta tgttaaatct aatgtataaa aagttttata aaatatcata    76020
tgtttagaga gtatatttca aatatgatga atcctagtgc ttggcaaatt aactttagaa    76080
cactaataaa attattttat taagaaataa ttactatttc attattaaaa ttcatatata    76140
agatgtagca caatgagagt ataaagtaga tgtaataatg cattaatgct attctgattc    76200
tataatatgt ttttgctctc ttttataaat aggatttctt acaaaagcaa gaatataaga    76260
cattggaata taacttaacg actacagaag tagtgatgga gaatgtaaca gccttctggg    76320
aggaggtcag aattttttaaa aaattgtttg ctctaaacac ctaactgttt tcttctttgt    76380
gaatatggat ttcatcctaa tggcgaataa aattagaatg atgatataac tggtagaact    76440
ggaaggagga tcactcactt attttctaga ttaagaagta gaggaatggc caggtgctca    76500
tggttgtaat cccagcactt tgggagacca aggcgggtgg atcacctgag gtcaggagtt    76560
caagaccagc ctggccaaca tggtaaaacc cggtctctac taaaaataca aaaaattaac    76620
tgggcatggt ggcagatgct gtagtcccag ctgctcggga ggctgaggca ggagaatcac    76680
ttgaacctgg gaggcggagg ttgcagtgag ctaagatcac gccactgcac tccagcctgg    76740
gcaacaaggc gagactctgt ctgaaaaaga aaaaaaaata aaaataaaaa taaaagaag    76800 tggaggaata ttaaatgcaa tataaaagct tttttttattt ttaagtcata caatttgttt    76860
cacataacag atcaggaaat aatacagaga tcataagttt tggagctggg tttgaatcct    76920
ggctctgcca tttactttct gtgtaatcta agtcaagtta ctgaactttg tgggccctct    76980
ggctctccat gtgtaaaatg gagaatatta atatttaccct tgcaagtttg ttgtgaagac    77040
tgaaggagag aatttaggta aaacattcat cagagtacca tgcacacagt tgttcctcaa    77100
taaacattag cttctctgat tgcaagttcc agtctaaagt gctttatata taccagccaa    77160
taaaaggatg cgagagagat ataccagtgt attgttttct accattttaa acctatttc    77220 atccactgtt acaaattcta tcatactgct ccacataaaa aatattatca atgatttta    77280 gtctctgaag tgcaatattt gattattgag cacacctgtt gaagttttag tttcttctca    77340
cttacatggg ttgtgtaaag gtaggaggta taaaaccagt gtcctaggtc taaatctttc    77400
ttaatgtcat actttggatt cattgatata agtaacttga gcaccagcgc ttcattttac    77460
ttcatttttt aaagatatag taagagtaat tcccatctgc ctagcaaaat tgttttgtag    77520
aaaagtttgt ggatcagatt tattttactt tgatttagg aatttcaagt gtcttcgtcg    77580
gcatgaagga aaaatatgca gtttgacatt ttctactact ttcaggtcat tatttttccta   77640 ctctggtgca aaaaccctca attcctgtct cactccatct aatcaaatag gtagcatgct    77700
tgagccctta ctatgtgcca ggcactagga taagcacttt atatgttttg tcccaattaa    77760
ttctcacagc atttctatga cctaaataaa attaatattt tcatttcacc aataataaaa    77820
```

```
tggaggcttc aaaaagttta gggacttggc tcagctcaca caactggcaa ggactgaaaa    77880
tggattttag tcccaaatgt cataggctag agccctttca ctaaactgtt gtcttccatc    77940
tggtggcatc ctcttcctcc agtctttgtc acctaaactc tgggcacccc ttgatggcat    78000
ttacttatga tggtgatgct tgttaaactt cctgtttgcg acttcaacgt ccatataaat    78060
gagtcttcca atactgtact tagaacttat attttgtagt gacttcttta aaagctttct    78120
ctcttagtca tatcctgagt tttgttagca cctggactta ccttactttg gaaatgttgc    78180
actctgaaat ctcttctca gcttggaatt tcctaatctt ccaactgttt gagtctttta    78240
attctacatt tactgccttt ccatttcatc aggattccta gtctctttaa ttcttccttt    78300
tgaactcctc ctgatttaac ctctgcttat tcgaagaaca ataatttat tctctcagct    78360 gcactctcaa ttccctttc cttttggtga ttttcttt tcctacagaa cacttacttt    78420
atcagttttg gagaaggaag tgctatctgg gtaacagtag tgctatctgt tgactctagt    78480
caactgtaag ttttatacat ttattgttta aaccttatat gggtctataa tccttcttgg    78540
gaaatccttt catttgtctt taatttcctt taccatttcc ctaaaggcta ttccagattt    78600
ttatcacatt cacaaaattc ccgtcttttc tcaggatctg ttcaccccca gtagatagcc    78660
ttgtctccca caatacatgg agaaaataga ggccaccgtc atatttgaat gtttccaact    78720
tctctcttca cctttggaat tatcttttc ttcttttgtg tctaagagaa agatgtatac    78780
ttcttcttac ccttgtctga actactctat tttgcttcat cttctcagaa caggggacca    78840
gcaattattc ttcctccaga agcttcaaca tcttttgtca actgactcct tctcatgttt    78900
aaatattttc aagttaaaca atttctttcc tgactttcgc tcacgcaacc tcatgcccaa    78960
aaccttatca ctcttcttcc ctttgctgtc aaggctgttc tcacttcttc acttttttgtg    79020 gacttctccc cactacaaca tagattctgc tatcaccaat ctattaaaac tgttatactc    79080
ttgtggaatt tatcatttaa tttagcttca gtgaaccgtt cttccagat tattttggcc    79140 tcagaccatg acttctaagt ctgccgtgct tgccacttaa gtgatgatgg gccagtgggt    79200
ccccacctag gcctctgtgt tagtctgttt tcatgttgct gataaagaca tacccaagaa    79260
tgggcaattt acagaagaaa gggggtttgag ggactcacag ttccatgtga ctggggaggc    79320
ctcacaatca tggtggatga tgaaaggcat gtctcacatg gaggcagata agagcataga    79380
acttgtgcag ggaaacttcc ctttattaaa ccaccaggtc ttgtgagact tcttcactat    79440
cacgagaata ggatgggcaa gaccctcccc catgattcaa ttatctccca ctgggtccct    79500
cccacaacac atgggaatta tgggagctat aattcaagat gagatttggg tgaggacata    79560
gccaaaccat atcagcctcc ttctggcttt ttatgttctc cgtgggtgac ctctctcagg    79620
ctcaagtgat aaccaatgtg ctgatgactc tcaaatgcgc atctctggct tcagtttctt    79680
ccttgaactt catacatatg tttccaaatt tcctgcgtgt acctcaaggt tcttgttcat    79740
cacttcccaa gcttcataaa cgcactcatt ttagtgtatt ctctgtctcc tttgatagca    79800
tccctgagag gcaagtccct ggtgagttat atacaactcc tcccttgctc caaacctgag    79860
agtaagtaac attcctatta acatattagg aagctgaggc ttagacagtt taagtaactc    79920
aagcatggtt acacaactag ctagggcaga gctaaaatgt caggctaggc ttctgtgact    79980
ccaaagccct ttctcactta gcatatcatc acttattttt tttttaatc acatatatga    80040 ttttttttc tttaagagat agaatcttgc tctatcacgt gggctggagt gcagtggcac    80100
aatcatagct cactgtaacc ttgaacttgg gctcaagtga tcctcctgcc ttagcctact    80160
gagtagctag ggctacagac acacaccacc atgcctagct aatttttattt tatttttattt    80220
```

```
tattttttga gacagagtct cactctgtca cccaggctgg agtgcagtgg tgcgatcttg  80280
gctcactgga acctctgctg cccgggttca agcgattctc ctgcctcagc ctcctgagta  80340
gctgggatta caggtgcctg ccactgtgcc cagctaattt ttgtattttt agtagagacg  80400
gggtttcacc atcttggcca ggcttgtctt gaactcctga cctcgtgatc cactcgcctc  80460
ggcctcccaa agtgctggga ttacaggtgt gagccaccac gcctggccac ctacctaatt  80520
tttaattttt ttgtagagac agggtctcac tacgttgccc aggctggtct tgaactcctg  80580
ttctcaaaca atcctcctgc ctcggacacc ccaagtgcag ggattacagg catgagtcat  80640
tgcagctgac ctgtatatat gatttttagt atatgtaaat atacatattt attaaatgta  80700
aatataaata taaatgtgtg gagtgatatc cattgaaatg ttaaacatag ttctcagtgg  80760
tacaactaca ggtgatttct cttttcttat ttctggtttt ctgtgttttc caaatttctt  80820
gaaatgtgtc ttctgtaatc agaaataaaa gttattagta acaacagtct tccactggta  80880
caagtgctta ttggataaaa gtcccacttc taagcatgat actcacaact tttaggttaa  80940
tagcctttgt caccttgcca tatacatctg atccagccac tcacaccatt cctgagatat  81000
attttgttcc tttgtgccta aatcattgtg catgcagatc catcttcctg gaacacctat  81060
aaccatttct tagtcctgtg aaatcctact tacatccttc atagcctagc atgtatgtca  81120
tttatttggt caagggtgag ttggttgttc tcttgaatgt actgccatat gacgtggtgt  81180
gatttcaatt gtagcaccaa gctcattgca atattaattc gtttgtcatt ctcccatgta  81240
ggatgtttga agtagtttct aacacagaga ttatactcaa taaatattta ttagataaat  81300
aaatgaataa gggaataaca aatgcctttg tctcatttta aaatactttc attgttagct  81360
acccatataa taaaaaacta aaagcagtag ttttcaagca tgattgttta tgtatgcctt  81420
aaaagaattt tgaaaaccta tgtacccctg acacacttt aagttaactt ataaattttt  81480
caacatagtt ttaagtggtg gcaaatgatg tagtttcttg tgtattttaa actgcttaag  81540
tatgctatac atggatttct tcaaaaccct gaagctgcag tttcagtgca ttcaatttat  81600
ggaaaagaaa ttaatttata aaattggttc ttattgtcaa gtcaatcagc taaatataac  81660
ttgctttctg tcaggaaaag tctgacttta aaatacagat aagtaataac tattattaat  81720
taattaaatt attaaaatta aaataattaa ataatttgtt aattaaaatg ccttattccc  81780
ctacttattt ctgcaatttg actctaagaa tagataggac atgtagattg ccttaggttt  81840
gaaatctggg tgaaataaga tactgcctcc ttcagtattt ctgcctttgc ttttatggga  81900
gcctctttca agaaaaagtc attctctcat ggtccctttg tttgagtccc agaggttttc  81960
ctactccaga aagtgcaacg tagtgagact agtactatac tcccttgcat ggtaagtgag  82020
aaggctgtct gtataaaatg agggaaggac tcatgagagg gaagtaggtc aggagaaatg  82080
ataggttctc aggcaggtta atttttaggaa agagtgaata gagtccctta aaacaaggtg  82140
catctgcttc ctcctgatca atctttagga ctgtttactt tgatttgaag accactatgc  82200
taaagcttcc cacgggggca atagtgaggc aaggaattttt taaaagggaa ttacttcttc  82260
gtagctactt ttgtgaaatg aattcatttg aattatctgg caatctcttc atatttatat  82320
tcaacaataa ttacttaaag aaatgctttg agcttctcag aggagggtgc taccagtgtg  82380
atggagtaga attcagattt gggtagtgac tttaaagctg tgtgacttta gtcatttaac  82440
tgctgagtca cagtctacag ctttgaaaga ggaggattat aaaatctatc tcatgttaat  82500
gctgaagatt aaataatagt gtttatgtac cccgcttata ggaagagagg gtgtgtgtgt  82560
```

```
gtgtgtgtgt gtgtgtgtgt gtatgtgtat gtatacatgt atgtattcag tctttactga    82620
aattaaaaaa tctttaactt gataatgggc aaatatctta gttttagatc atgtcctcta    82680
gaaaccgtat gctatataat tatgtactat aaagtaataa tgtatacagt gtaatggatc    82740
atgggccatg tgcttttcaa actaattgta cataaaacaa gcatctattg aaaatatctg    82800
acaaactcat cttttatttt tgatgtgtgt gtgtgtgtgt gtgtgttttt ttaacaggga    82860
tttggggaat tatttgagaa agcaaaacaa aacaataaca atagaaaaac ttctaatggt    82920
gatgacagcc tcttcttcag taatttctca cttcttggta ctcctgtcct gaaagatatt    82980
aatttcaaga tagaaagagg acagttgttg gcggttgctg gatccactgg agcaggcaag    83040
gtagttcttt tgttcttcac tattaagaac ttaatttggt gtccatgtct ctttttttt    83100 ctagtttgta gtgctggaag gtattttttgg agaaattctt acatgagcat taggagaatg    83160
tatgggtgta gtgtcttgta aatagaaat tgttccactg ataatttact ctagtttttt    83220
atttcctcat attattttca gtggctttt cttccacatc tttatatttt gcaccacatt    83280
caacactgta tcttgcacat ggcgagcatt caataacttt attgaataaa caaatcatcc    83340
attttatcca ttcttaacca gaacagacat tttttcagag ctggtccagg aaaatcatga    83400 cttacattt gccttagtaa ccacataaac aaaaggtctc cattttttgtt aacattacaa    83460 ttttcagaat agatttagat ttgcttatga tatattataa ggaaaaatta tttagtggga    83520 tagtttttttg aggaaataca taggaatgtt aatttattca gtggtcatcc tcttctccat    83580
atcccaccct aagaacaact taacctggca tatttggaga tacatctgaa aaaatagtag    83640
attagaaaga aaaacagca aaaggaccaa aactttattg tcaggagaag actttgtagt    83700
gatcttcaag aatataaccc attgtgtaga taatggtaaa aacttgctct cttttaacta    83760
ttgaggaaat aaatttaaag acatgaaaga atcaaattag agatgagaaa gagctttcta    83820
gtattagaat gggctaaagg gcaataggta tttgcttcag aagtctataa aatggttcct    83880
tgttcccatt tgattgtcat tttagctgtg gtactttgta gaaatgtgag aaaaagttta    83940
gtggtctctt gaagcttttc aaaatacttt ctagaattat accgaataat ctaagacaaa    84000
cagaaaaaga aagagaggaa ggaagaaaga aggaaatgag gaagaaagga agtaggagga    84060
aggaaggaag gaaagaagga aggaagtaag agggaagcag tgctgctgct gtaggtaaaa    84120
atgttaatga aaatagaaat taagaaagac tcctgaaagg caattattta tcaatatcta    84180
agatgaggag aaccatattt tgaagaattg aatatgagac ttgggaaaca aaatgccaca    84240
aaaaatttcc actcaataaa tttggtgtca ggctgggtgc agtggctcac acttgtaatc    84300
ctagcacttt tggaggcaga ggcaggtgaa ttgcttgagt ccaggagttt gagaccagcg    84360
tgggcaacat ggcaaacccc acctctacaa aaaacacaaa caaagaaaaa tagctgggtg    84420
tggtggtgtg tgcctgtagt cccagctact gggaggctg aggtgggagg atcacctgag    84480
cctgagaagt ggaggctgca gtgagccatg attgcaccac tgtaccctag cctaggtgat    84540
aggctcaaaa aaaaaaaaaa ttggtgtttg caatgctaat aatacaattt ggttgtttct    84600
ctctccagtt gttttcctac atacgaaaca gcttttaaaa caaaatagct ggaattgtgc    84660 atttttctt acaaaaacat ttctcttctt aaaatgttat tattttttctt ttatatcttg    84720 tatattatta ctagcagtgt tcactattaa aaaattatac tataggaggg gctgatacta    84780
aataagttag caatggtcta aacaaggatg tttatttatg aaaaggtagt aattgtgttt    84840
catagaattt ttaaaattaa ttctgcgtat gtcttcaaga tcaattctat gatagatgtg    84900
caaaaatagc tttggaatta caaattccaa gacttactgg caattaaatt tcaggcagtt    84960
```

```
ttattaaaat tgatgagcag ataattactg gctgacagtg cagttatagc ttatgaaaag    85020
cagctatgaa ggcagagtta gaggaaggca gtggtcccct gggaatattt aaacacttct    85080
gagaaacgga gtttactaac tcaatctagg aggctgcctt ttagtagtat taggaatgga    85140
acactttata gttttttttg gacaaaagat ctagctaaaa tataagattg aataattgaa    85200
aatattaaca ttttaagtta aatcttaccc actcaataca atttggtaat ttgtatcaga    85260
agcttaaaag ataacctaat agttcttcta cttctataac ttacccaaat atgtttgcag    85320
agatcttatg taaagctctt cattataaca ctgctttcag gagccaaaaa ttgggtgggg    85380
gagccccata aatgttgaat aatagggggtt tgattagata aattttggtg tagttctata    85440
atggcgtgtt attcagccaa taaaaggttt gttaaagaat gactgtgacg gatgtatatg    85500
atatactctt aagtgaataa agagttacaa aatgttatgt acaagttaca aaatgtatgt    85560
acattatgat ccattttttca taaaatcata tgtatgtata tatgtgtgtc tggaaggata    85620
aatttatcaa gttgttatct ctgaaatttt gggtatattt tatatttcta gattttctgt    85680
tactttgtta ctttactgat aaagtaataa cgttgttgac ttttgtcact ctcccctatt    85740
aataatcatc taggctgcaa aaggatcatg tcttctttat ttttatattc caaggactgt    85800
caacaagtgc ctagcacttg acaggtatat tatagaaatt taactgaata tctttaggaa    85860 atagatttt gtttgtagtt gttctagtct acattaaatg tcttgcgctt atgaaacttc    85920
cttgaattat tttagtgaag caatattagt atagaatttt gcatcactgg atgcccttga    85980
ctgaaagctg gcttatggca tctcaccagt gtgtggggag tttcagtcct tctgttgtct    86040
gcatcacagc tgaagcagtg ctgttgctga caattcctga caccaccttg tctctattat    86100
tgatcattgc ctcactatgg tactgagttt tagcttattc ttgtaataac tgggactcat    86160
atgtatagaa taagctatta gctcacgttt ttgcttgctt tttatacaga atacatgtct    86220
gcaaatagtt ttatcaatat tttggaattt tgggagatat gaagttaaaa acatcattga    86280
atatatatat atacacacac acatatatat atgacactat acatgattta ttttatttaa    86340
tttttaaaat tttattcttt ttagagatta ggtcttactc tgtcacccag gctgaacttc    86400
agtggtgtga tcatagctca ctgtaacctt gaactcctgg gctcaattga cctttccgct    86460
tcagcctccc aaagtgctgg gtttataggc atgagccact gtgtctggtc caatatgcat    86520
atatatattt ttaacctgga ttatcagagc tatattgtgt ttaggtttat aaagctgtac    86580
tatgtgaaaa tatcacttct aggtttaatt ttgtacaaag gaattttata tagaaatgag    86640
gtaattcaga tttttttccca tgtaataaga attgtaaaat ttactgaaac aaacatcaaa    86700
aagatatctg ttacatgacc ttcctttctt ttgaatatat ttcaggtgat attatttatt    86760
aaaatttaaa aatgaaaatt aaaatatata aaaagttgaa aattattcct ttctttactg    86820
tctctcatct gtccattttc cattctcctg cattccctca tccaaccaag gtagccaatc    86880
caggtaactt ttttttagtat cttcccagag atgtttctct ctatatatat aatcaatata    86940 catttttttat tattccccac ctctcttttt atgtaacaat atgcagagtt ttgcttcttg    87000
cttttcccac tatcttggac aactttccat attcaaagca cagaggactt gcacatatgt    87060
tcagactgct gaatatttct gtctctcccc tgccattcat atgttgaaat cctaattccc    87120
aaggtgatgg tattgcaggg tggggccttt gggaggtgat tagtccatga gggtgaagtc    87180
tttagtaaat gagattagtg tctttataaa agaaacctta gagagaccct cacacccttag    87240 agagaccctc accccttcct gccatgtgag aacacagcag gaagacagct ggctatccag    87300
```

```
gattcaggag tctcttagca gacccaaatc tgctggcacc ttgatcttgg acttcccagc    87360
ctccagaact gtgagaaata aattcctgtt gtttataagc cacacagttc atggtatttt    87420
gttatagcag cctgaacaag gacacacaca cacacacaca cacatgcaca cacatttaaa    87480
tagatgcata gtattctatc atatggatgg atattctatg atataatgaa tcactattga    87540
ttgacatttg ggttgtttcc aatattttgt taacacaaag aacaacacta caaataactt    87600
tatatacata tcatttagca catctgcaat tgtatcagta ggcttcctat aagtggtcaa    87660
gcatttgtgt acttgtgatt ttggtagatg ttgtcaaatg tccttccctg aaatttgtac    87720
caattcgtac tcatgccata cactctaaat agagtgctga tttccccaca gcattactaa    87780
cagatgatat tatctaattt aaaaagtttc tcatcttata gggaaaatag tatgtcaatg    87840
tattcttaac ttgcatttct tttattataa gtagtgtaaa atatcatttc aacttataca    87900
caggaggaat ttctctctat ataaagtgat cctagaatca taatgaaaaa tatcaccaac    87960
tcattaggaa aatgtacaaa ggattgaata gatatctcat caaaaataaa aatataagtg    88020
gcctttaaac attgaaaggt aacatttgaa caaagacttg caggaggtga gggattaggg    88080
aatgcagact ctgggaagag tcttccaagt agcaggtgaa gcaagtgcaa agctttcaga    88140
tgggactgac tatacctgtc tggtttgaag aacagtaagg aggtcactga ggctggcata    88200
gagtaagaca gggagggtag aatactgtca gagaagtaat cggcggtgga ggtaggggt    88260 aaaccataaa gtgctcgtaa agactaaggc ttatttctct gggtgagatt agaggccact    88320
ggagagtttt aaacagaagt aacagggcca ctttggctaa tgtttttagg ctattctgta    88380
gggagacaag ggaggaagca aggagatgag ttaggagtct attgtgccag ttcaggcaag    88440
tgatgatggt ggcttgatcc aggtagtagt ggaagtagta tagtaggaag tgatcagatt    88500
caggacatgc tttgaaggaa gatccaatag gattaatgga taagttgaac aatggcatat    88560
gagaaaagtc acagaggagt caaagatgat tccaagcttt ctggactgag taactggaag    88620
gataaatgtg ccgtttacta gaaagataat gggagaaaca ggttttggat ggagcttggt    88680
ttgggaatat taagtttgaa atgcctattt gacatccaaa tagagatgtt agttggatgt    88740
acaagtctag tttcaaggaa gaggggggctg gtagtgtgaa gatggggctg gataagattc    88800
taaaggaaag aggggttgata agaagagaaa ggggtgtagg ggttagccta agggcattct    88860
aagtattaga ggttaaggag gtgggtgaag aaaacccaat aaaataaaag tctgagaaga    88920
caaagctagt gaatgaatgt ggtatcccgg aacccaactg atgtcaagca gaagggtgtt    88980
atcaactagg tcaaatgctc attcatcaag taagatgaaa ctgttataat taaccggtgt    89040
cttctgaaat acggagataa ctcgtgactt aatgaaagca atagtagaga aggtcaaact    89100
tgaccagaat gaaattagaa agaataagag gaaagaaaag accaaataca gacaaccatt    89160
gatgccttat tcttttgata tactcctgga gtccacttgc taatacaatt gacccttaaa    89220
caatacaggc ttgaactgca tgggtccact tatttgtgaa ttttttttca gttaatacat    89280
tggaaaattt ttgggggtttt ttgacaattt gaaaaaactc acaaactgtc tagcctagaa    89340
ataccgagaa aattaagaaa aagtaagata tgccatgaat gcataaaata tatgtagaca    89400
ctagcctatt ttatcatttg ctactataaa atatacacaa tctattataa aaagttaaaa    89460
tttatcaaaa cttaacacac actaacacct accctacctg gcaccattca cagtaaagag    89520
aaatgtaaat aaacataaaa atgtagtatt aaaccataat ggcataaaac taattgtagt    89580
acatatggta ctactgtaat aatttggaag ccacttcctg ttgctattac ggtaagctca    89640
agcattgtgg atagccattt aaaacaccac gtgatgctaa tcatctccgt gtgagcagtt    89700
```

```
ctctctccag taaattgcat attgcagtaa aaagtgatct ctagtggttc tcgcatattt  89760
ttcatcatgt ttagtgcaat gccataaacc ttgaataaca tcaagcaatc catacaaagt  89820
gccactagtg atgcacggaa aagttgtaac agtacaagaa aaaagttgag ttgcttggta  89880
tttaccatat attgaggtct gcagctacag ttgcctgcaa tttcgagata aatgaaccca  89940
gtataaagac tgttgtaaca aaagaaaaga aaatgtgaaa ccatcagtgc agctatgcca  90000
gcaggtgtga agtcttgcac tttttgcaaa atacaaaata tgaaatatgt gttaattgac  90060
tgtttatgtt atctgtaagg tttccactca acaataggct attagtagtt aagttttgt   90120 ggagtcaaaa attatacgtg gattttgac  tatacagtgg gttggcaccc ctaaccttca  90180
tgttgataaa gggtcaatgg tatattattt aatttttttg tatttatatt cataaataag  90240
attaaatcta tatttccaag taatctctat aagattttgt tattaatatt actattattt  90300
ttgagacaga gtcttactgt caccaggctg gagcacagtg gtgcgatctc ggctcactgc  90360
aacctctgcc tcccgggctc aagcaattct cctgcctcac cctcccaagt agctgggact  90420
acaggcacgc acaaccacac tcagctaatt tttgtatttt tagtagagac ggggtttcac  90480
catgttggcc aggatggtat tgatctcttg acctcatgat ctgcctgcct cggcctccca  90540
aagtgttggg attacaggca tgagccactg tgcacagcca ttaatattat tgttacccaa  90600 taaaaaaat  ttggaaactt gtcttctttt cccctgattc tgtttaaata gcactggagt  90660
tacctgtttt gaattttttt tccaagcggt cccttatgag ttttctctat gttttatttg  90720
tttcatttct tttttttttt ttttttttt tttgagacg  gagtctcgct ctgtcgccca  90780
ggctggagtg cagtggcggg atctcggctc actgcaagct ccgcctcccg ggttcacgcc  90840
attctcctgc ctcagcctcc caagtagctg ggactacagg cgcccgccac tacgcccggc  90900
taattttttg tatttttagt agagacgggg tttcaccgtt ttagccggga tggtctcgat  90960
ctcctgacct cgtgatccgc ccgcctcggc ctcccaaagt gctgggatta caggcgtgag  91020
ccaccgcgcc cggcctgttt catttcttat atcgtatttt tgcaactcct ttattgatac  91080
ttttcttcct gattaggttt ctactaaaac caaacaagct ttccatgaat tagcttttag  91140
atttacttat tagtttaact gttctgttgt attgtaactc attaatttat aattttatct  91200
ttattaatta ttctattttt cttcgctttt ttgttgtttt tctagttttt gagttagatg  91260
tttgacgctt ttttaaaaag ctgtgcattt tcctctgggt aatactttag ctgtatatta  91320
tgtattctga tatatagtgt ttccattaca ttgttttcta gaaatctgt  agctttgatt  91380 tatatttgtt tcctctttga cctaagatat cctaagggaa aatttaacat tttccagaaa  91440
gaaaacaaat tttctttgtt ttccaagaat gttgttcaaa ttatttctac tgcttggaat  91500
ttttatcatt tttgtgtatc cagtaaatag tcaatatttg tacttgctct ctgaccacat  91560
aaaagaatat attcgtgtag tttctattaa tagattagag ttcaattcag atattaaatg  91620
tacatcatta ttcatgatat ttaggtcttc tacatcttca cttatctttt ttctacttgc  91680
tttgccatta acagataaag ttgaattaaa ggcttctact acatacattt ctccctgtta  91740
ttccttatag gttctgtaat ttttgcttca agaatattgc ttttaaatt  taatatatag  91800 atacttataa ttacactcta gcattataaa gagcctttc  ttttcattg  aatgtatttg  91860 ggcctgcata tgtctaacat gaaaattata gtccttttt  tgtttctttg tttgtattta  91920
cagttttaag ttccatttc  aacctttatg cactctttgc tttaggtgtg tctcttttag  91980
ttagcataaa gttaggtttg tctttaattt cacctgaagt cttttcctct taatagatgg  92040
```

```
gttaagccaa ctgaaaaata aaactgactt atatactttt atttcaagta tgtcctccac    92100
aaatattttt tgaatagatt agcttatata ctttggaatt tgttaaaaaa agatttttat    92160
aaaaaataat tgtggtgaaa tgtacataac ataaaattta tcattttgac catttttaag    92220
ggcatagctc tgtggcataa agtatactca catagttgtg caactatcac ctccttttga    92280

тттттттта ctaattttgt aaatttgttt catctgagct gtcttattat gtttgtttt    92340 atgtttttct ttcctttatt atgaagtcac tgtattgtct gtaggctata tgtatctgtg    92400
agtgtgtgtg tatatgtgtg tattatggtt tttaaaaaag tctatatttg ttttccagtg    92460
gctatactta atactaataa ctttatgtta aatttttcat tctatgtgac tctagttcac    92520
taatatgagc tctgataaaa tcagtgcttt ttcgaggtta ggagatcaag accatcctgg    92580
ctaacacagt gaaactccgt ctctactaaa aatacaaaaa attagccaga cgtgatggcg    92640
ggtgcccgta gtcccagcta ctcgggaggc tgaggcagga aatggcgtg aacccaggag     92700 gcagaacttg cagtgagccg agatcgcgcc actgcactct agcctgggtg acagagtgag    92760
actctgtctc taaataaata aataaataaa taaataaata aataaaatca gtgctttttc    92820
ttcctctgct acctcctttc cttctactca gttttagtca gtagtattat cttttttcag    92880
atttatcttt gtattgttaa atctgcttat gcttctatta ctttatttat tagctttaaa    92940
tgataccttt tgactttcag cttttcttaa taaagcaatc agcaaatttc ctttacactc    93000
cacacttata ccccatttcc tttgtttgtt tatttggttt ttacttctaa cttttcttat    93060
tgtcaggaca tataacatat ttaaactttg tttttcaact cgaattctgc cattagtttt    93120
aatttttgtt cacagttata taaatctttg ttcactgata gtccttttgt actatcatct    93180
cttaaatgac tttatactcc aagaaaggct catgggaaca atattacctg aatatgtctc    93240
tattacttaa tctgtaccta ataatgtaa ggtaatctac tttgtaggat ttctgtgaag     93300
attaaataaa ttaatatagt taaagcacat agaacagcac tcgacacaga gtgagcactt    93360
ggcaactgtt agctgttact aacctttccc attcttcctc caaacctatt ccaactatct    93420
gaatcatgtg ccccttctct gtgaacctct atcataatac ttgtcacact gtattgtaat    93480
tgtctctttt actttccctt gtatcttttg tgcatagcag agtacctgaa acaggaagta    93540

ttttaaatat tttgaatcaa atgagttaat agaatcttta caaataagaa tatacatttc    93600
tgcttaggat gataattgga ggcaagtgaa tcctgagcgt gatttgataa tgacctaata    93660
atgatgggtt ttatttccag acttcacttc taatggtgat tatgggagaa ctggagcctt    93720
cagagggtaa aattaagcac agtggaagaa tttcattctg ttctcagttt tcctggatta    93780
tgcctggcac cattaaagaa aatatcatct ttggtgtttc ctatgatgaa tatagataca    93840
gaagcgtcat caaagcatgc caactagaag aggtaagaaa ctatgtgaaa actttttgat    93900
tatgcatatg aaccttcac actacccaaa ttatatattt ggctccatat tcaatcggtt     93960
agtctacata tatttatgtt tcctctatgg gtaagctact gtgaatggat cattaataa     94020 aacacatgac ctatgcttta agaagcttgc aaacacatga aataaatgca atttatttt    94080 taaataatgg gttcatttga tcacaataaa tgcattttat gaaatggtga aattttgtt    94140 cactcattag tgagacaaac gtcctcaatg ttatttata tggcatgcat ataagtgata    94200
tgtggtatct ttttaaaaga taccacaaaa tatgcatctt taaaaatata ctccaaaaat    94260 tattaagatt атттттaataa тттттaataat actatagcct aatggaatga gcattgatct   94320
gccagcagag aattagaggg gtaaaattgt gaagatattg tatccctggc tttgaacaaa    94380
taccatataa cttctagtga ctgcaattct ttgatgcaga ggcaaaatga agatgatgtc    94440
```

-continued

```
attactcatt tcacaacaat attggagaat gagctaatta tctgaaaatt acatgaagta    94500
ttccaagaga aaccagtata tggatcttgt gctgttcact atgtaaattg tgtgatggtc    94560
ggttcagtag ttattgctgt aaatgttagg gcagggaata tgttactatg aagtttattg    94620
acagtatact ccaaatagtg tttgtgattc aaaagcaata tctttgatag ttggcatttg    94680
caattccttt atataatctt ttatgaaaaa aattgcagag aaagtaaaat gtagcttaaa    94740
atacagtatc caaaaaaatg gaaaagggca aaccgtggat tagatagaaa tggcaattct    94800
tataaaaagg gttgcatgct tacatgaatg gctttccatg tatatactca gtcattcaac    94860 agttttttt ttagagcccc attcttattt tttatacact ttgagagcat aatgaaaaga    94920
aaagctacct gcaaaagttt tggacttacc tcaaagagga tatacttcat tcctcaaaag    94980
gccttcttcc aggaatagta tttcataacc tggaggttgg aaaaatctgg atttgttaca    95040
aaaaaatctg agtgtttcta gcggacacag atatttgtct aggaggggac taggttgtag    95100
cagtggtagt gccttacaag ataaatcatg ggctttattt acttacgagt ggaaaagttg    95160
cggaaggtgc cttacagact tttttttgc gttaagtatg tgttttccca taggaattaa    95220
tttataaatg gtggtttgat ttcctcaagt caacctttaa aagtatattt agccaaaata    95280
tagcttaaat atattactag taataaattt agtactgtgg gtctctcatt ctcaaaatga    95340
gcatttacta atttctgaac actgtgctag gtcctgggaa taccaaattg aataagacat    95400
agtctatttt tctgaagggt ttatagcaga gtcccctgtg ttaataatga aggagtgtgt    95460
ggtatgtgaa tcatatatca atagggttgt taaaaataat gaaaaaagga gaagaggaag    95520
aacatctttt ttttttctga ttgcacgggc agccttaaaa ttattttga agtgtacaat    95580 tcagtgtttt tttagcatat tcacagggtt gtattatcat caccatattt ttggcctctt    95640
gaaaagaaat cctgtgccta ttagcatcca attaccgttc ctttgtagct aagtctcccc    95700
cattccagct ttaaacaatc acccatctac tttctgtctc tataaatttg tctcttttgg    95760
acatttcaca taaatgaaat aatataatag ggttttttgt gcctaaataa gcttctaaag    95820
aagaataagg taaggaatca tcattcagca aatatttatt aagacttgct ttattttata    95880
cagtgtacta ggagctggag atgaaaatat gtgtagaaca tgaatcatat acttcgggaa    95940
tttgtggact agtgggaaag attgacatat caataacaaa tcgaattagt gatgtaatag    96000
aggcattttt acaggagtaa aatgaggtag catggactct atctgggtct gaataatgtg    96060
aggagtaacc tccttacaca aagaggcaca aggctaatgt cctctgatgg aatgattcac    96120
catgcaattc taagggtgac aagaatgaaa gttagggcct tgaagaaata ttttgattaa    96180
gagctgccaa taaagtagag taaagattag attgatgtga agaagtggga gattaatgag    96240
taaatggtca ctggcttgtt gagaagatta aatgagatgt acatgtaatg tacctaacac    96300
aacgtcttgt acaaagtagc cattcagtag agactagctt gtattatctc cctttgaggt    96360
aaagaaaact gttagaaata gtatttctac tactgatagt atttcttcta cttatgcctc    96420
cctttgaggt gaagaatact gttagaaaac atgacatagg agaaataccc ctgagagaca    96480
gttcttatta gtgactactg tgcagaaaag atggaggttg gtgtaattaa ggagaaggaa    96540
agccatgaag ccaaagtatt atgaaaaagc atcaatatga attttcatgt tgacaaagtg    96600
gtataaaaga taattataaa gatggtcact tataaatacg gtagttctgt gtgacacaat    96660
ttacagaagt tggtatatcg tgtggaagaa aacagcataa gatcctgaag gtttgaactg    96720
tgggcacatt ggctccatgc tcaggaaatg gcaatggggt tgggaagtga ttccactta    96780
```

```
tgtcccttc   agacacataa   aaattacttg   tgtgagtatc   ttatgccaga   cactattcac   96840
tgtgtagtga   gcatggtggg   tatgaaatga   caactttatt   gtctttcctg   tcaaagaact   96900
tgtaggctgg   ttgggggaaa   gagaccattt   caatatgaag   tgctgagcta   gaggtaccct   96960
tagggcacta   cagaagccta   gctgatggct   tttagcctgg   ctagacagtt   caggatctct   97020
aaaagcaggt   gccttgaagg   ctgagtcaaa   tacaaaaatg   tattttggac   agaggaaatt   97080
gtatgaacag   aaacacagaa   catgaaacta   cttggttggt   gcagggtatc   atcagcatag   97140
aaccagacag   aaccagagtg   taaataagcc   agaaggccat   gtcatggagg   ccttgtatac   97200
cagtctcagg   aatttggttg   tggagagctt   tcatcagggg   aatgatgtaa   tcagcttgga   97260
aatgtagata   tatcactgac   tgtgatagtg   aggagcagaa   ttaaggtgga   cgtgattaga   97320
agctttgtga   atagcagaaa   gaacatagat   tttgaaagct   ggcagacgta   ggttactgaa   97380
gaaagttact   taaccttgct   atgtctttag   ttttatcctc   tgcaatatgg   ggataatact   97440
gcctattttg   tagagtcttg   tggattcttc   tggcatatat   aatagaaaat   aaaacagcta   97500
ttattattat   tgttgatggt   actatttgct   atatctgact   acaaggagaa   agactaatag   97560
gaaaccattt   caggaatcca   gatatggtca   tgatggacag   gaagagacaa   gagttacata   97620
gaggaattct   gggaagataa   gaaatgtcat   ttttatgtac   tgtttgcatc   catcagacaa   97680
ggcatcagga   aaaatgatcc   ttcaggaaag   agtgattttt   tttcttcaag   aaattagaag   97740
aggggagaaa   ttggtttaag   attaaggact   ccatgcataa   gagaaactgg   gagggaagac   97800
aggtagaaat   gctatggggt   taggaaggaa   gaatgcagag   gtggattact   agaattgag    97860
acatctgatc   aagacagagg   gatcacagct   tttgctaaca   aagtactagt   ggaggatgcc   97920
actaggtgag   gtttaataaa   taattgttga   caataagttc   catttaaaaa   ataaacaatt   97980
tatgcttctt   ctttgcctaa   gtgtcaaata   aacattcag   attttatttt   caagtatcc    98040
ctgagtccct   gttcccttt    ttgtcctgct   gacttttgga   actgatttag   gcttccttag   98100
tcatctcata   atagaaaaaa   tcagccaggt   atttcctaca   tttcttgtat   tttaaaaaaa   98160
tgtaatggat   gtaatgaatt   ttaagcaaat   gtaatgaata   caataagtaa   cttagtatat   98220
gctgttttct   tctctatgct   gaatgtttca   tacatgttat   tttctataca   actacatggt   98280
caattccttg   aaaatatcaa   ctccaaaatc   tttattttgg   tatactccac   gtagcacatt   98340
gagagagttt   taaactcttg   ttggatgact   gttttcaaaag   tgtttgaag   taggcatgtc   98400
agttgcaaaa   agtttgctca   gcaaatgttg   ttctgtctca   cagtctcaga   cattgagcag   98460
atgattacat   gacagcacgt   gattgctggg   agtaacagac   aaaagtaact   gaaagtgctc   98520
ggttatcttg   acagtcaaaa   tcaaaagtgt   cccctattt    cagtgaccta   agagtttctt   98580
tttgtgtttt   tggtattgtt   gttaaataag   tgttctcacc   tttgaaaagg   tcaataagaa   98640
ttcaatacag   tataatgtct   gtgtgccaaa   tgaaggtgcc   ccttattttt   aagtgtggag   98700
gagttttgat   cataagaact   tgaaatacct   acagaatcct   tgatggttaa   gcagctggtg   98760
ccagcacaag   aatccctcaa   tatgttctct   atgaagcccc   gatcaccaaa   tgcaaacatt   98820
catgattcag   tatattttca   tcttgactgc   caaagttgat   ctgtttctta   atatattaca   98880
tctagacttg   gaactggaga   tgagaacaga   atattatctt   cctcattttt   gtgttttgt    98940
tcaactctaa   tgtctgcaaa   gcacttgcgt   atgtaatgat   gctcagtgtc   ataggagcag   99000
gcaggtaagt   gtaaatttgt   ctggatagga   gaaagcatgc   acaacatatt   tcacatagtt   99060
ttctgatttc   agtttgtttt   tgcaaattat   tcactcagtg   agatagctta   aagacgttat   99120
cacagggaaa   ggcatggaga   tagttctgtg   ttgatagaaa   acttgtaatg   tacagccatg   99180
```

```
agtgagaagt caggttcaga ttcttcacct tcagtcctcc tctttcataa acagctccat   99240
gtcctatttt acatatccta ctttaaaacg agattataga agaatgaatt tctaggcaaa   99300
gtgacactta ttttaaaata ctattacgta tccctgtgcc cattaactta tcctaccatt   99360
tttcttcccc tgtgtccaaa ccacctttag aatctcctaa atatttgtag ctattgtaaa   99420
cagcactgga gactttgcta gtttaaaagg agaaatcaac gcaattaagc cctagttaat   99480
ttacttatcc cttatgagat tataattgta ttttgttatt aaaaggggga cagagtacac   99540
tgttctcttg ccttttttaat ttccagacta ccacttctcc tgcacttgac aataccgcag   99600
tctaccacgt agtcccatgg ctgacaggag gagaattcta ggcaggccag tgtttgagta   99660
gtgagtaatt ggactgtctt tacccagcaa ctcactgttt tgtaaatgta cctgagtttg   99720
gagaagtaat tggcttttat aaggggtgcg gggtggaggg ttggggtggg gagagtgaga   99780
aggaggtcag agctttagga tatataattg gtctccacaa agttgttgtg atacttttgg   99840
aaccacgtaa tggtcttcat taactaagtg tctgtcatga cagccattac atatgcatta   99900
taataaaaat ttatttacag tgtaagttga agaaggtaaa atctggatgt agtttctaaa   99960
ctctgcttgg cagttttcat atttaagcca ctagaagaaa aaaattggga gggaagctga  100020
gaagaattta ctgaaagaaa aaaatacttg ggagggaaat tggcaagaag tatgaaaaag  100080
cttgggaggg aagtaagcaa ataaatgagt taatgactgt tctggaaaat aaactctatc  100140
atgcagatat cacatgactg attaaatttg aatttgacct cctgctttcc aggtctggta  100200
aaaactaacc tgtaagaact tgaaacttag cctttgaatg gtcaatccac cactgtagga  100260
gaatttatga atgttcagtt gagagaactg aaaataaaga agtaccatag gaattaacat  100320
ttgcattcag tagccaagat ataatggaca tctgaaacag gtatttgagg ccaggcgtgg  100380
tgtctcatgc ctgtaataat agcactttgg gaggccgagg tgggtggatc acaggaggcc  100440
aggagttcaa gaccagccta ctaaaacaca cacacacaca cacacacaca cacacacaca  100500
cactagccag gcgtggtggt gcacgtttgt agtccaagct acttgggagg ctgaggcatg  100560
agaatagctt gaacccagaa ggcggaggtt gctgtgagct gagattgcgc cactgcactc  100620
tagcctgggt gacagagtga gactctgtct caaaaataaa ataaaacata tatttgaaac  100680
acattgaatt atgtccctta aacaagaata aacatcacta aatgactgta ccttgaacta  100740
cctgtaattt tctcctgata ggtaattaag cttcaaagta ctgacactta tttactgtaa  100800
tatgaagcaa taacttaaaa aaaaaaaaaa actattgaac cagaaccaaa caggaatgcc  100860
atagcatttt gtaaactaaa ctgctatttc atttcatttg agccctggaa cttgaaaata  100920
aatgctagct aacatctgtg aacagaacat acccatcagt actgtgctaa gcacctttca  100980
tgaactggtc attaaatcct cactttccat ttatttagtg acaacttcac ccagagtttg  101040
cagtcaaagt gaaaatgtgc tgaattccaa aagtgtgagc taggttttag aagttaatca  101100
caattctgga acaaattact agcttaacaa atgagagttc ttatgtctct aaaaccaaaa  101160
tagccctaag tctgtccctc ccagtaagat ttgggccagt caatggaaca gtaatataca  101220
aatataatta cagctgtcta ggagcaaact atccctatgaa tagataataa aattaagaca  101280
cttaagccat gttttcatat taaaacacaa agtaaaaaat cattgttttc caaagataaa  101340
agccatactg tatcatgaca tatatatgcc cgatgtttcg accctcttga agaattgaga  101400
ttctcgactc tacactctta gcgttttcta tattgaacag atgtttaatt taaggaggtc  101460
aagagaaatc ttacacttat ttttttaatgg taccttagac atagaaggaa cctcagaaat  101520
```

```
ctctggctga atatttccat ctgcagatga tcatgtcatt aggcttctga ctctatagcc   101580
atagaaaaat attcatgaag acctttcagg aagggaatgt tggtatttct aaaaattgag   101640
tacaagtatt ctctagacaa aacagctctt gaaatggcag attgtattcc cattattata   101700
tttcagaatc aagacattaa tacctacttt ttatttacca ggtttagtta tccttgaatt   101760
agattttata aattaaagaa atagatttca ataaatattt gttgagttcc tagtatggaa   101820
acatcgtgtt tggcaccagg gatgttgcct gcaagtataa caggagttcg tatttgtaat   101880
gagtttatga tttacagata tttgggggc aaagatatca ttcggtaaat acttatgagt   101940
gcaaactttg aactagggac tgggccaaac tctaggaaca tatttgatga cagagacaca   102000
atccctgtcc tcaaggagct ttcattctag tagagaagat gaaaaccagt acagtttggt   102060
aagttagatg atattggtta atgtagggtt cttatgtaag tctagagaag tagcatttaa   102120
tctgttctta gaaggtcagg aaagatttcc ctggaggaag tgacatttaa gctgagagag   102180
gatggataaa caggagtcat ctgagtgaac aacaggaga acattccaga aagagaacaa   102240
aatgtacgag gcctgatgcc aagagagaac attcattgca ttggggaact atagtcactt   102300
ctgtgtggct gggatgtaga atgaaatgag cctggaccca agagagcact ttgccctttg   102360
gggaagctgt aggtattaca gtaaggttgg agtctgaaaa gaaagggggta tattgtgaga   102420 tctgaattgg gagaggacag ttatatccag acctttatat gctccagtaa aagactgaa    102480 ctttacactg ggggccatgg gactcactga atggcattaa atttgagagt ggtcatatga   102540
ccagatttgc attttacaaa gattgtcatt gactgcaaca tgaagtatgg agtattggag   102600
gagcggtaag gctggtggca gggagataat ttaggaggct ttaggtgagg gatgataatg   102660
acttgccagg taggaaggag taaatttctt ctcagtggat aattagaaga ttgaatggat   102720
ggacttggtc actatttggt atagaagggg aaaaagatg tcaagatga tgccaatttt     102780 taaaaataat ttaacattta ttttttaaata ttttttcagc cttattaagg tataatggac   102840
aacaattgta ggtatatgtc atttacaaca tgatgttttg atttatgtat acattgtgaa   102900
atgactgcca tagtcaagct cattaacata tccatcactc acataattaa cattttgtgt   102960
gtatgcagtg agaacatcag gctctactct cttagcaatt ttcaagtata gattacattt   103020
gttaccaact atagtggcca cactatacaa tagagctcca ggacttattc atcctgccta   103080
actaaaactt tgtactcttt gaccaacatc ttcccattcg tctctcctcc ccatgccaag   103140
tttccatctt ggtcagttgg gtggatagta gtactatctg ccgaggcagg ttggtagggt   103200
gaaaacaatg tgttcccttt tggaaatgct gaggtgacca gggaacttcc aagggaatct   103260
gtctggatct agagcttaga agagatgttt gggctggaaa cagacatcag gtattcttca   103320
gtatatgggt tgtaaatgaa gtcacaggag tgggtgatat caccaatggt gagtgtagta   103380
taagaagact ggactgagga cagatttcca aggaatttca atacttaaga ggtacgcaga   103440
gaaaagaggg gctgtgaagg acaccaagga ggagactaag agccaggagg gaaaactttc   103500
aagagagtat tgcattatgg aagggaagaa gagagaacat tttaaatgat acgcaatgct   103560
caataatggt atccgctttg gagaggccaa gtaagattcc taagtaccca ttggatcaag   103620
gtccttaatc ttacaaaaac ttatgcaaat caataataaa gagatgataa cccgataatc   103680
aaaaatagac aaggcatata agaagaaat gaattaaaaa tattcaaagc attcaacata    103740
tacaaatgcg ctcaatctga tatataatga aagaaaagta aattaaaaca acaatgggca   103800
tgactaaata acagtatgag ggagcctgag gagaaggagc atttgaaatt tcagtacaga   103860
agagaaaagg ggtgacttat agaaaaagga gacagaaacc atagaacatg tttggaggat   103920
```

```
aagactcaaa caggtagtgg ggaccctttt ctagagtagg atgaaaacag gtaatgtgtg  103980
tggatgcaaa tatgaggtag gatgtaatgg gaagttgagc gaattcatat ttagtcattc  104040
attcaaaaat acttaattga gttactgctg tgtggcaagc atcattctac aaacagaggg  104100
cacagtgata agcaagccag tttgtactct cgtgtaactt acattctact ttgagaagac  104160
agattataaa taggttaaaa agtcaataat atgatgtttc agcatcaaca ataaaaaatt  104220
agggtgatat atagagtgcc agggaaagtg ctttcatgga cctcttcatt ctctcctctc  104280
ctggtgtcat aagctactcc ttcatccatg ctgccatttc tcttggttta cggttccagt  104340
atagtactca tcacattatt actatagagc catccacctt atgaaggtga aggtgtccat  104400
ctccttactt aaaaaaaaaa aaaacaaaca aaaaacaaa aaacccgaaa acaaaaaaa  104460 gaggcagaaa gacagaaggt cctccactaa cttttcacgtg ccatgtaacc agcgaaatcc  104520
aattatttta cagcattcta gctatagaag agtttgggaa gcgtagtgct tagtgttcta  104580
gcctttgtag cacaggaaag ggcctggaag gaaaggaatt gtgtcttccg cagttgcttt  104640
tctttatggg gaagtgctat agcccaaaca atattttagg aattttcatc tattgtcaat  104700
atgcaaactg gaaggggata atgaaaatgt tgtggttaga agtttatgaa atattgttat  104760
tcacatttta aagtaaaaag agggaatgtt taagagactt gtttaagatc acatgtctca  104820
taattggtgg gaccagcaat acaatccaaa tctaactact tatctttttg ctatgcccta  104880
ttagtgttca tattagaaaa gaaattctat ctcagacact aatgatttgt tctttggaca  104940
ccaatgactt taagttaaaa cttcatacta gttaatttaa ttatggtgta gcagtattat  105000
taaactatca agactataaa ttttctattt gtaaaggaga ttatgatacc aaagattagt  105060
gaactaatga tattgagaat tctatgacat aattttgaaa atatttgca ggatatttat  105120 ttttgtgtaa atgatgcttt caagctacca taatcctaag taagtgtata tttgggaaaa  105180
ccacctattc taacacactt gaaatttaaa taagtcagga aattttttc cagatcttct  105240 cccaaattat cttcatcttt ttcctctccc cttgggaaag aatctcttca tgcctcataa  105300
tatcaaattt aaactatgga agtccaggtg gtggacagtc agcaaagggg aagatgagaa  105360
gcttgtgtta taaagccagc tcttgtcaga ataaggatct ggtaggaact tcagaagtga  105420
tgggtaggta agtatgaagg ccaggtccta agatctaaat tacaaagcag aagacttact  105480
taccagggag ctgaaaaaca tgttaggaaa tccagagcag gaacagatttt caagatagca  105540 caataatata gcagtgaagt actgagaaaa gagtttttt cacggggttgg atttattcta  105600 gcatttttagg cagcatttgg gcatttctaa gtggtcagac ttagaggaga tagttaagga  105660
attagcagct gctaaatgcc aattcttaga ccagttgaat caaaatcatc taaaaagctt  105720
tcagaaacca gacttttaa gggccatttg agagactctc aaatctggaa tccagaaatc  105780
tatagctaga tgagtttaag gtagagccag aataagaaaa ataaaatagt ttgtttgttt  105840
caggtatctt ttccaatatt atttccgaac ctaccccaaa caccttaaat cactgcattc  105900
tatagccatt cttttaaaaa tgcttgagtt attagttttc aaaacaaat acaaatctgc  105960 acacatacag aaataaacat taaagagaca taaagatatt aaacagagtt acatatactt  106020
acaacttcat acatatatat tatatataaa actgaatatt aagtgtttga tattagtgac  106080
aaaatctgta acatccatta tattagtgct ttttgtactt tttgttgggt gtagtaaaaa  106140
ttgcattcga atttgagttt tctgctatat atttggtcag ttcctatcag tgaaggaaaa  106200
accttttttt attattttat tgttttttta tttttttgaga cggagtcctg ctctgttgtc  106260
```

```
caggctggag tgcagtggca tgatcttggc tcactccaac ctctgcctcc cgggttcaag    106320
cgattctcct gcctcagcct cctgagtagc tgggactaca ggcacctgcc accaggtcca    106380
gctaattttt gtattttag tagaaatggg gttttgccat gttggccaag ttggtctgga     106440
actcctgacc tcaggtgatc tgcctggctt ggcctcccaa agtgctggaa ttacaggtgt    106500
aagtcaccac gcctggcccc tttttatttt ttaagctgat tgaagattct tagttctcat    106560
gctttctagt ggtgattaat ctttagccaa tatttctata tacagttatt agtaatcatg    106620
tttgacttag gtcaacaaac aatctttcct aaaaaaacag aaccccaatt ttaatttctg    106680
aattatttag tatctatttt ctgctgtgga agttgaatta tgttgataga tatcatacag    106740
ggccatgtaa cactctcaga tacacgttca catgtatagt agctgtatac aaaaatgtta    106800
cttcattctc tctctcttta taatactctt ggctctctta cgttctctca cacactctac    106860
tcttcccttc ctctgttctt tctacttgtt ccctctgctc ctaccacact tattccccc    106920 ttgtccattt tccttgtgca taaagcacaa gtgcttagta attatcaaat attaataaca    106980
atgacactaa ccacccaatg atttagtgtt aatgacatgc tttattgaat ggcattacct    107040
ctaaagttca tgtttccttt acccaaccaa gcttcttacc ctcctcccct accacaagca    107100
tctatattgt caaggttgtt ataaagagta ataagccagc cattaaaaaa gggtttatgg    107160
tattttccta tctacaaagt cacaggaagc tcaaatgtac tcagtaaata ttgcaaaatt    107220
acacaggacc attaaatgta acactccacc ctttctctct ctctctctct ctcttgctct    107280
ctctctctct ttctgtcaat atagcaacac cctatatcat tgccctttgt atgtgcaaat    107340
cagagttaat aagctttata ttagcaatta ctccttaaca acttctggtt tgtttggtcc    107400
agttgaataa tgtaagcact taaaaaaatg aaattataaa catttatgtg aaaagtgcat    107460
atatcacatt ggatatgttg ttatgcactc cttaataata aagtaagtta atctttattg    107520
cacacttatt ataatattac tttgaccctc tctagtactc tttatctaag tattctcaag    107580
tgctttacaa tctcaaacag acccaatgtg ttgtatacac agaatccttt gaagctgaca    107640
tttgcctttc tgaccagctt gttgtaaagg aaatcagcca aaaacaagt atctagatga     107700 gtagctcaaa cattagtaca catagtaatc acaggtcaaa atgcagatag attaccctgt    107760
ccaaattctc ctgagtaaga gtaggtgaaa cattttttaaa taagctcccc aggtgattct   107820
gaaattggtc caaggaccac atattaagaa ctaatgatcc aaacaatttg acttttatt     107880 gtagattaaa ccatgctgag aaaattatta aaaattgaaa tggcagtgga ggatggtttg    107940
aaagaaaggt ttttcagggc cctttcaaca ataaaattaa ttgaacacaa tattaaaact    108000
ctatatttga tttaagacta aggttttcat tgttttttaaa tctcagtaat ttttatgtaa   108060
caggtcaatt catacccagc atcttaattc caatgaatga tttcccacaa caattttgt     108120 ggataactcc aagggaactc gaaggaagtt gtagtatgaa caaagagaag tagaatttgt    108180
ccctgtgtgt aaggcttctc tgataagcag cacaggctct catactgctt tttaaaaaa    108240 ttatgatagc atcaagtgga attaatttt tttagattat actttcatgg aagggaagat     108300
ctactgtgaa ggctggaaaa ccaacacccct taagataaat atattaccag atttgagcgc    108360
tcttagtaat cagcaaagat aaatgtttaa cagtgcatac aaaatgaagt gttttatgtt    108420
aaatcaaata gagaaagcca aacactaata atgtggttac aaatgaacaa taaattaggt    108480
aatcagaaca ggtacagaca ttaatagcag gatattggta ttattaatgt attttgtttt    108540
aaaataatga acttaattac aattctcctc atcctacccc actattttat tttattccag    108600
attcagcagc ttcatattat gtctctgaaa cacttattat taaagttatc caaatgtaca    108660
```

```
catttctctt tatataaatg tttcagtcca gaaaaggagg ccaaatacat tagctcagaa   108720
catcaaatct tctcagatgt gggaatcttt tattttcaca cttttaaagg taatctgtat   108780
ttctagcgtc tattatagac agaaaacttt catatgacaa cattcctatt ttcttaactg   108840
ccttgatagg ggcgaagaca aattctaagt aggactttt accccattct tcttaccatc   108900
attctttcac aaaacccca gctttagaca atcgctatta tgaatttgac atgtactatt   108960
ccaatccatt cccataaatt tacacccata tatacatata gttatctatg aacaatattt   109020
agtagctttt ttgtgtgtgg ctttaaaatt tacataaatt gtataatttg tgcacattct   109080
tctttaattt gccttcttgg ctacggttat cttttgaga tctagctatg ctgctggtat   109140
gtagaattct atttcattct ttttcattg ttgttttgta cccataacgt gtcacatttt   109200
atttatacct tctgttcctg atggacattt agattcttcc aggattttac tcaatactgc   109260
aatgaaaatc tttgaatttt tctcttttgc acatattcaa gagactttc tgacatatat   109320 atctataggt gaattgtgta gtcatatgat acatacacac attttaaatt tcactagata   109380
ctgccaattt gcccttgaa atagccatac aatttatagt accaccagcc acttatgaaa   109440
gttcccattt cctcaaatct ttgaaagttc ttattataaa cagacatatt aattcttgcc   109500
attctgattt gtaaatcaga atctctattg ttctacctct agttctaatt tggaattccc   109560
caattacttg taagatgcta tatattttca tgtttgttag tcattctgat ttcatatcct   109620
ttaccaatta tcttttggt aagttattgt ggtggccatg agatgtgcct tacagaggcc   109680
ttgctagagg gaatgtgatt gaatgagagc cccagatgct gtgtattaaa atcctgcact   109740
gagtttgtct caagatttct tgcacgtgaa tgaatgagta cagctgggat actaaagcag   109800
atgtgtattt gggagatatg agacttcttt agtggctgat ttttggctca taaatgactt   109860
tgccaaacct tccttagact gctcagtgtt ctaacatctt ccatccagcc ttctacccct   109920 cttttccttta ctaggggatt gaatttacat tgaggtctca tagccttctc tgcctctctc   109980
cttatttcct tttatacaaa tatttcccct aataaatcca tgcacattta ataccatttt   110040
gctatttgca acctgcaggt cctggactaa cacagttcta tacattgcat taccattctc   110100
tagagtggga tcttttgttg tagagagttt taaaattttt atgtagtcac ttttatccat   110160
attttctttt atggtttata tttttgtgtc ttctctttaa cacatctttt ctagcagaat   110220 tcataaaatat attattctat attgccaaaa gtttgaaagt tgcaatcatt agaattaatt   110280
tttgtatatt gtgtaagtta agaatctaat tttattgttt ttcattggaa agccatttgt   110340
cccaagataa ttttttagta gtccctcctt cccctattgt cattctgaca tattttttct   110400
aggttccgat ctatgcatgt gtttctttat ggaagagttg gccctttgta tctttgagtt   110460
tcaaatccat ggattcaatc aaccacagat agaaaatatt tagaaaagcg tcagaattga   110520
acatgtacat acattttgct tgtcattatt ccctaaacaa tatagtataa caactattta   110580
tgtaggattt acattgtatt aggtattgta agtaatctag agatgattta aagtatacag   110640
gaagatgtgc atatgttaca tgcaaatact accccattta tataagggtc ttgagcattc   110700
atggattttg gtatccacag agagtcctgg aaccaattcc ccacagatgc caaggcacaa   110760
ctgtatttat tctatcatct acttgtttaa tctcacatca gtatctactt ttgaaataac   110820 aataaccttta ttatttaact ttttttatta cttaggatta gagaatttcc tctggtgagg   110880
catcatagtg tctcaagctg gccataaaga caagtgaggg ctaggatcgg taagactggg   110940
cagaggaaga tacaacagat ctcctatgca tgaagcaaaa gtgcagctca gaagccagct   111000
```

```
ctttcattaa gttgtcctct ataccctcac tagattgtaa gctcttgaaa tgagaggcta  111060
taccttaatt gtctctgtta tctaaaatac ttccactcac tgcttggaac atattgcctg  111120
caataattaa gcttgccctg gctcccaaag catagagcaa atcacactcc tccccttgcc  111180
tttgagaagc tcacagtctt cgaaggtaga gatatgtgaa cagataagaa aatggatgac  111240
aggagaacag aaacgcatga ctgtcagaga agtcattgga gactttacag aggaaattaa  111300
atttttattg atcttgaaag agtttgccag atgaagtaga ggacaggcat tttagacaaa  111360
gggaacagga aatgtgaaaa cacaaagtga tggaagtcat ggtgagtttg agaactata   111420
aaacttcaat gtggctgaag ggtaaggtgg atatagagga gtgctgggag gtgaggctga  111480
agaaataagc taggaaatgt ctttttatgc catttttttaa agtttggact ttattctgaa  111540
gttcacatgg atccaatatt ttttgttttg tgttgtttta gcagaagcg tgacatgatc   111600
agcttgaatg atgaacaact tgaattgttt aaagtggatc acacagtcta ctgttttaca  111660
gttattcttt gaccaagata ttctttatta actgaggaaa aaaagggctt tcctgaattt  111720
tgcagtcatg ggatatatga taagcattct tgatttatca tcttcaatcc tgttacataa  111780
cataataacc attgttatta cctttagcaa tgctttcctc agtattatct aatggcctat  111840
aaaatgtgac tttcatttgc aaatacagta catctaacaa gaacttacca cagctgctat  111900
gcaaaatacc aatacaattg acccttggac aatgtggggg ttaggggtgc tgattcccca  111960
tgcagttgaa catgttacat aacataatac ataaccattg ttattatgta acaggattga  112020
aaatgataaa tctttggaaa gtggggcaaa tgaattctta tgaattccat atcttccaca  112080
tgtgttttac tttttttgata agaagtagta acctagttca gaaagaaaat aatcatcccc  112140
ttttacttat gcaggatacc aagtctatct tagcaccata atagtgaatg ataggaatca  112200
agctctatga atacattcac atgtacatat atatggctat ataggacaca tgcatgcaca  112260
tatacatata tacacttgca tatatgtgta tatacatgta catatatgca tgtatattca  112320
attgtatatg tgtatatagc caagttattg tacagttgac cttttgaacaa cacgggtttg  112380
aactatgcag gtccacttac acgtattttt tttttccgtt tctgacaccc ctaaggcaac  112440
aaggccaact cctccccttg ctcttcctcc tcagctgact caacatgaaa actatgagga  112500
cgaagacctt tatgaagatt caccctccact taatgaatag tacatacatt tcttttttccc  112560
catggttttc ttaataacat tttctttttct ctagcttgct ttattgtaat aatatagtat  112620
ataatacata taacatacca agtatgtgtt aattgactgc ttatgttatc agtaaggctt  112680
ctggtcaaca gtagactatt gctagttaag tttctggtag ttacaagtta tatgtgggtg  112740
ttcgactgca tggggagtca gcaccccaac cctcatgttg tccaagggcg ttgtccaagg   112800
gtcagttgta attggtattt tggatagcag ctgtggtaaa ttctggttag atgtactata  112860
tttataaatg aaactcacat tttataggcc attaaatatt attgaggaga gcatttctaa  112920
gggtaaaatc ttgtctaatg cttgaaacat cttcattttc ctgtcagttt agatcttttt  112980
gaagtaattc tgaaaatctc tcttttaagc taaatttaac acaaccaaat agccaaatat  113040
ttaagttcca ctaatgaaga tatctaaatt tctgttaaaa atttaagata tatgttaaac  113100
ccttctaata taactcttct ctcagtcaaa cttttttttt taacagttgc tttgcttctt  113160
ctttcaaagt catacttcaa caaagttgct attgaatatg tctgactaaa catgttagct  113220
atatgataag atggctggat aagagataaa tatagaaaat gtagcttttt ttctacttgc  113280
aataaccctt taggaattaa aatggaaaac taataacact ttgattcata atagtagcaa  113340
accgtaaaat attttagacat aaatctacta agaaatttat aagacatata tggagaaaat  113400
```

```
tcaattgaat aaaccgttat tgaagtatat aaaataagat ctggatgaat agaaagatca   113460
taatttttaa taaaattttg catcttaaaa agtgaaccct ctccaaatat atgcacattt   113520
aataaaatta taaatacatc ccaatgaggt tggttttgaa attttgttaa ttggaactta   113580
aatttcacct aagaagaaaa aataaagaat agttaagagt gcatgctttg tagacaaatt   113640
gccttagtta gaatcctggc tctatcatct attagctatg ttatctttgg gataacattc   113700
atcttttctt atagatatgc ttaaaacagt gcctgacata tagtaagcac aaatatccat   113760
tagctattct tcttattatt tatgttatta gtattgttaa tatttgttat tatatggaag   113820
actaaatgac caaagagagt caagaaattt atgaataaga tttatgcgtt gttagatatt   113880
agagccatta aaaaaaaaaa aaccaaagtg ccaaaaaacc tagcacagtg ttaatacagg   113940
aataaaaaaa tggatcagag gaaccaaaca gaaaagccag aaatggatct taggaaacat   114000
gagaatatga tatatgatag atgctaaatg aattcagtat aaaaatatta atgtaataaa   114060
tcatgcttgc tattcaagta aaagaaaatg aggttagatt catgtctcat accaaatata   114120
accataaatt ataccttgat taaattttt aattaaaaag caataatatt tgaaaagaaa   114180
tataggatac tcaatgtata acctgaaggt tgggtagtac ttttcaacaa atataggaat   114240
ttttcacttg aaatactaga agaaaaaaag atagcaaaca aatacaggaa ttccaatttc   114300
aagcagatat aatgatttca tgaaatgtta actgtgcaca tgatagatgg tctatggata   114360
gtgcaaaaga aaagagaaa agaaaaaatg ttttttaaca tatgcagcaa aaaaggtttt   114420
taacatctat tacatacaaa taaaaatgaa tgtataacac agacttcaat aaaaaatagc   114480
atttcacagg agaacaattc agatggccag tatttacaat ttcataggta ttaaggaaaa   114540
tacaaattaa aatggcaaat tagcaaaaat tgaggtgtga ttatattaat atctgttggt   114600
ggtggtgatt atgggaaaa gggtactttc aaaacttgct aatataaata taattctttt   114660
ggttgttttg taaaggaacc tgacaatatc tttttaaaaat aaagaaaacg catacttttg   114720
acctagccat cccattcatg agggtatgtc ttagaaaaat aagatcacaa aatcatagag   114780
atttatgtgc aatgatatta ttggtaggtc attttttatga ggagggtgt ggatagtaaa   114840 tgccagggta aatcacatag catctaataa acgtatttat gaactacaaa agcttacact   114900
ttcagtctag tctagtccag actgcaaata aatgtgagca agtgaattca agcacagaag   114960
tgcttgaagg caggtttcat aaatctactt tcttacagta tcctgatatt gacttatcga   115020
gacagttact gtggggttga ttattaaaat atttatgtat ctaggtattt ttcattcagt   115080
agtatgttat tcaattagca acaagtgtgg ggatttaaag atattcttgt ttgtttttac   115140
tgctgaaaca tattctagtg gaaatttcga ataaacgatt agtcatccta aaagcaagat   115200
acattttctc agaaaagaca aggtaaagaa cttgtatatc ctccctcaat tcgtttataa   115260
ggtaataaga tgaataaaaa tatcatagta caatttagca ttgtaaaata aaattaattg   115320
gtcatctcta gtgtggtcgt gcttggaagg tgaaagaagc caagatcttg tctgggaata   115380
tcatgtctac cttgacctca cccttaagaa tcctagcctt tagtttaaaa tcacatggct   115440
acatacatac caacttcaac aatagtacat ctggcaaggt catgcaaacc tgggacttga   115500
gcttctgatt ctaagtccag tgcttttttgt gtacatcatc tcttgtacat accttatgat   115560
gatatgctaa taaaagctac gtgatcaggc cttaaaaatc tgcttttttt ttgtaatggt   115620
agaatggggc atattatcac atcaggtaaa cactctattc aaggataaat ggaaatgaat   115680
gtcatatata gatcattgat aaaatatctca ttacaaaatt atgagagtta ccaatgtttg   115740
```

```
agtgtatatt atgggccagc cctttatatt aaattacttc aaattttttac aactgttaaa   115800 ggaagatatt attataccca ttttatagat ggacaagtta gggccagaaa agacttcctc   115860
aaagctgtta gtccagtaat ggagacaggg ctagaaaaca ggtcattttg ctctttgact   115920
aatgttacta ctcatgtttt gtattttgtt taaagttta ttttattttg ctttatttat   115980 ttttttgagac aagatcttac tctgtcaccc aggctggagt gcaatggagt gatcacggtt   116040
cattgcagcc ttgacctcct gggctcaagc gatcctccca cctctcaatc tccagagtag   116100
ctaggactac tacaggtgtg tgccaccata cctggctaaa ttttgcattt tttgtgggga   116160
cagggtttca ctatgttgcc caggctggtc ttgaactcct gggctccagc gattcacctg   116220
ccttgacctc ccaaagtgcc agtatcacag gcttgagcca ccatgtccag ccaagtttta   116280
ttttagaatt aaaaaaaatt ccacttggat tgttacattt tatctcattg ctttatattt   116340
atagaattac tttataaatg ccactttctt aattttcata gttagcactc tttatgaaac   116400
ataaactatt atttgaccca ggtttttgtt agaggaattg agtcagagag ctgttaagta   116460
actgagattt cacaataagc cagacagacc agggttcaaa ttctgggtct cacattatcc   116520
aattcaatat tccagctttg ttacttattg agcaaccact acaagcacag tttacatgac   116580
atctgatagc tctcaaaatg aattttacaa acataattca gatttcaact cagcagtgac   116640
tcaggagaaa ggacacttgg atgcatttct ttatggcatt tttcccaggg tacacgcaac   116700
ctggaagatc tcccaagtat gggggaaggt ttcaccctga ggaatcccat tccctctaat   116760
ctgggacaag ggggaggaga gtactgtctc ttatcagcca tctccccagg gaggcctggg   116820
ccctcctgga atgcatacca tggcttactg actcaaagtg ttgaaaagac caggcattgg   116880
gacacacaac actactctta aaataaaaaa agaatcagag tagcttgtgg ttataattga   116940
aatggacaga gtaacatggt accaagaaac tattagcaat tccttcccta aatccctcat   117000
tttcttaaag cattttctcc ttttcctcaa caagctttaa gttggatttg aagaatgata   117060
agactaaaag gagggctgtt tctggtcttt ggaggaattt gatattccat tcgatctgag   117120
tgtgcaaagc ctgagttcac atgaactctt ctgatctctt tctctaatat ttttttcacct   117180 tattcatatg ggaaagaagg aggggaatac tttagttcca ttctccctcc tcctatttcc   117240
ttgacttgtt taaaatataa atgttataga cacctaagat agaaatttga ctgaaacagc   117300
ctcttaatta ttgtcttaaa aaattggtat aatgaaattg catttgtagt ctttggacat   117360
ttaaatccag aagggatatt ttcttttttct tttttaaaaa tttaattcaa tagttttttgg   117420 gctacaggtg gttttttggtt acatggataa gtgcttagt ggtgatttct gagatttttga   117480 tatacccatc acctgagcag tgtgcactgt acccaatatg tagtctttta tccccccccc   117540
gctccaccct tcctttatcg tccccaaagc acattatata attattatgc ctttgcagcc   117600
tcattggtta gctcccactt gtaagtgaga acatgcgata tttggttttc cattcctgag   117660
ttacttcatt tagaataaat tgtctctagc tccattcaag ttgctgcaaa ggccattatt   117720
tcattccgtt ttttggctga atagtattcc atagtgtata tatgccacat tttctttatc   117780
cacttgttga ttgataggca tttaggttgg acccatattt tcgcaattat gaattgtact   117840
gctgtaaaca tgagtgtgct tttttttttt ccatataatg acttctttc ctttgggtag   117900 atacccagca gtgggactgc tggatcgaat ggtagttctc cttttagttc tttaaggaat   117960
ctccatactg ttttccacag tggttgtact agtttacaac cccaccagca gtgtaaaact   118020
gttccatttt cagcacatcc atgccaacat ctattatttt ttgacttttt aattgtggct   118080
attcttgcag gagtaagatg gtatctcatt gtggttttaa tttgcatttc cctgataatc   118140
```

```
agtgatgttg agcattttt  cctgtgtttg ttatttgttt gtatatcttg agaattatct 118200
attctgtcct ttgcccactt tttgatggaa ttatttgttt tttttttcttg ctgatttgtt 118260
tgagttcctt gtagatcctg gatactagtc ctttatcgga tgcatagttt atgaatattc 118320
tttcccactc tgtaggttgt ctgtttacca tgctaattat ttattttgct gtgcaaaagc 118380
ttttcagttt aattatttcc catctattta tttttgtttc tgttttattt gcttttggga 118440
tcttagtcat gaacttttta cctaaaccaa tgactataag agttttttcca atgttatctt 118500
ctagaatgct tatgttttct ggtcttagat ttaagtcttt gattcatctt gagttaattt 118560
ttgtataagg tgagcattga ggatccagtt tcattcttct acgtgtggct tgccagtttt 118620
cccagcacca tttattagat agggtatcct gtccccactt tatgttttg  tatgctttgt 118680
caaagatcag ttgactttaa gtatttggct ttatttctgg gttctctatt ctgttccatt 118740
gtctacttgc ctatttgtgt accagtacca ggctgtttta gtaactatag ccttgtagta 118800
taatttgaag tcgggtaata tgatgcctcc agatttgttc tttttgctta gtattccttt 118860
agctatgtgg gctctttttt agttccctat gaatttttagg atttttttct agttctgtga 118920
agaattatga tgatattttg atgggaattg tattgaattt gtagattgct tttggcagta 118980
tggtcatttt catagtattg attctaccca tccatgagca tgggatgtgt ttccatttgt 119040
ttgtgtcacc tgtgatttct ttgagcagca ttttgtagtt ttccttgtag agatcttaa  119100
cctccttggt taagtatatt ttcatgtatt ttagtttttt tttttttgttt gttttgtttt 119160
gttttgtttt gtttttgcag ctgttgtaaa agggattgag ttcttgattt gattctcagc 119220
ttggttgttg tcagcaggga catttttctaa agtatagact gtagttcctt atcttctatc 119280
tgtttcttac tgtcccttc  agtattcttg tcctttttttc ccgctattat cttttttgacc 119340
ttttaatata tagatatcta cttctacttc tgacaatttt tgcttctcca attttctttc 119400
tttttctcct ctgcacacat ttatttattt tcttctatgt acttcttttat ttttaactta 119460
atatttgatt aacttccctt ccctgtctct tttccttctt tccataaatc ttcattaatt 119520
gcctgcactg agctaggatt ctatactctc taaatcaata atctattttc tatagtcaac 119580
tgtgttataa tcgtactgtc aagataacta cttatttta  atacttaaaa atattttgaa 119640
attttaacca atttaattaa tacaatgttg agttcaaatt tgaaaaaaac aatggaaaac 119700
tgtaataatt ctagcaacct cctgcttttt aataatgtat tagaaaattt gcctcttttt 119760
caaaagccta cagtgaatct attcatacaa ggcaaaagca aaccattctc ttcattctct 119820
ttttttctcc aaaagattta agtgtttttt gtttgttttgt tttgttttgt ttttagata  119880
ttgagtcttg ctctgtcatc caggctgcag tgcagtggtg tgatcatagc tcgctatagc 119940
ctcgaattcc tgggttcaag caatcctcct ccctcaccct cctgagtagc tgggctaca  120000
ggtgcatgct accatgccca gctaatttaa aaggaaaaaa attgtgtaga gatgggtctt 120060
gctatgttgc ccaggctggt ctcaaacttc caatctcaag catttctccc acccagcatc 120120
ctgaagtgct gagattataa gtgagccact atgcccaacc agatttagtt tttaaaaga  120180
gaatacgatt tgaaaaagga aaatgtgag  gcaggagaga agaaatacac acacgagctg 120240
ttttgtaatt gctgtaaaac tgaaatcttc agcctcacta aaggagcact tgcatgaaca 120300
cctctaaatt accttattac cttctaaatt aggtgtgaag tctaacttct aaattatgag 120360
tgaaatccac tgcaattctt gttatttgga tggaatccta ggtatgtggt ccagttcatg 120420
agttgaacaa aagcatgctc atttaggcca ggtagaaaga aataaagacc tatgttttac 120480
```

```
atgtctcata accactgaag gtccttctca taagcagtgc ttatgggtat taacgacctc   120540
tctatatttt acttctccag tgcctaagta gccgagtcca ctgagtcctg ctacatctcc   120600
tccaacatgt cagcattttt ttcacaggcc ttttgttact ctagatcaga aatgttgata   120660
gcaacagttc cttgagggca gcagctagca tgatgccagc caacaggaac caccaaatgg   120720
ttcttaatat aaattactac ttattaatct atttactttg tgcatttgga gttttgcatg   120780
taaagtccta tttatgtcca tatggtagat aaatggaaca aatgaataac agaagtaacc   120840
attttgatac tttagatata gataatattg gattatttct ggattgtgaa agaagaagga   120900
agaagcatat ggaagagaag ttttagtaga ggggaggaag gaggaggtgg aaacgaatgt   120960
acaaggatgg gaggagaaaa gggagagaga ctttttttt tttaaggcga gagtttacta   121020
cctatctaac tcttcgcatt cttgaagtct cagaccaaat cccatcggtt tgaaagcctc   121080
tagggtattc tatctattgt atacttctgt tatgtacaaa attaatttgc caattaattg   121140
tgaactgttt tataaactat cttaaaatgg ttagttaaat ctttgggata gtatttagct   121200
ttctccagga ttatgactta ccttctaaat tagacataca atgcctagga gtcaaggact   121260
attttgcata aattccagtc ttcttttaca atgcctagaa tgattgttac cacagaaata   121320
ttcattacct gggagaaagg atgacaggag gggcagaatg aatggagaga ggtcgtgaga   121380
atgaggtgct gaggatggac gaggaagaaa gctgttttag ttgggaggat aggtgacaga   121440
agcatggaaa ggaattgcct tggacccatg gaagcccagt gaagatactt agatcctgca   121500
ggggtgtgaa taatgttctt ttagtttctc ttcttaggag gtttgttcat tttgggagat   121560
ttcttttgaa aagagtgaac ttaaattgga gaaaagtaca ttttagtatg ttgataacat   121620
ttgaatttgt aaaatggacc tatggatgat ctacacatat ttatatacccc ataaatatac   121680
acatatttta attttggta ttttataatt attatttaat gatcattcat gacatttaa   121740
aaattacaga aaaatttaca tctaaaattt cagcaatgtt gtttttgacc aactaaataa   121800
attgcatttg aaataatgga gatgcaatgt tcaaaatttc aactgtggtt aaagcaatag   121860
tgtgatatat gattacatta aaggaagat gtgcctttca aattcagatt gagcatacta   121920
aaagtgactc tctaattttc tattttggt aataggacat ctccaagttt gcagagaaag   121980
acaatatagt tcttggagaa ggtggaatca cactgagtgg aggtcaacga gcaagaattt   122040
ctttagcaag gtgaataact aattattggt ctagcaagca tttgctgtaa atgtcattca   122100
tgtaaaaaaa ttacagacat ttctctattg ctttatattc tgtttctgga attgaaaaaa   122160
tcctgggggtt ttatggctag tgggttaaga atcacattta agaactataa ataatggtat   122220
agtatccaga tttggtagag attatggtta ctcagaatct gtgcccgtat cttggtgtca   122280
gtgtatttgt ttgcctcata gtatagtttta ctacaaatgg aaaactctag gattctgcat   122340
aatactggac agagaagatg taaatatctg ttagttccat catagaccct gccactccaa   122400
tgtacacacc agctttaggc ttcttggtat agataaacat acattttcaa aattttcat   122460
cataattttc ataacaaaat aggaaggcaa atgatgtcac ttggcttaaa atctataata   122520
tttaaaataa acaggacaaa tgcattaaca ttgttggggg aggaggtccc ttagtagaaa   122580
cactcttggt ccaagcattt taaagctgtc aaagagatgt aaatatagat aatgtatgtc   122640
aaggagagag ctttgtggtt aaactgtaac tttcagttta aacaattatt ggtgactctg   122700
atgtcaaatg tttctcaagc tttatctgaa caaaattctt ctcactttgt tgccaaagtc   122760
gttaacaaga aatcacattg actcattgat gttttggctc ctttccctta ctttctgttg   122820
cttcccaaaa gctgagacag gaaactaacc ctaactgagc acctgcaatt gcctggtagt   122880
```

-continued

```
attctagtca tgtgtgtact tttgtgtgta tgtaatcccc ttacagctct gcaaagtaag   122940
aattgttctc cctgctttac agaagagatc ataagataat tgaggctgtt agatgttaac   123000
ttgccaaaag ccatacagga aaatggtaga gtcacagttt gaaccaggtc cttttgattc   123060
tttacattaa accatgcttt gatcttggaa atacactgta aggcaataaa tcaatagata   123120
cggataattc acaggcttct aaataaatgg aagttgattg ttttatctg tgagccaaag    123180 taagacttat tctaagaatt ccacaaattt agataagata gagtatatgg cttctagaca   123240
tccaacatag aactgagttt gtgttatcag tttaagattt ggttttgctg taaggtgcac   123300
acactttgag gaactaaaaa taattgtctg ttcttattct gatcagaatg tgtaatgtgt   123360
tgtccagttt tggatgatga atttcttatt tctaatctca taagaaactt gtcatagatg   123420
tgagggagaa aattaagaac agagtgtggg gaagaaactg tgtacatttt gatgggatcc   123480
attatgtagc tcttgcatac tgtcttcaaa aataagttac actataaagg ttgttttaga   123540
cttttaaagt tttgccattg gttttttaaaa aaatttttaa attggcttta aaaatttctt   123600
aattgtgtgc tgaatacaat tttctttatt acagaagtac caacaattac atgtataaac   123660
agagaatcct atgtacttga gatataagta aggttactat caatcacacc tgaaaaattt   123720
aaatgttatg aagaaattat ctcatttcta ttaatatggg aactgtgtct tcatctttat   123780
tactgttcta aggtcaactc aatgtagatt ttacttgctt atggtttcat attttagcta   123840
aatagtaaaa taatatggat atacattttg ttgtgactta ctcatacttt ccttatttgg   123900
aacttttatg aatatgatat agagactgaa actacaagga acaaaatgca atatcaatta   123960
tacagttgtg gcagcactgc tatcaatttg ttgatagtgg ttaacactta gaaaaacatt   124020
ttaaaaataa tttcacataa gtaatgtaat ttattagctg tctctgacat tttacagttt   124080
ggaatagttt attttctttt tggtgtcctc accaaaaccc aacatcttca agggcaggaa   124140
ctgtataatt tttgccattg tattttgagc acatagcatg gtacttgcct ctaaatagat   124200
actattgtta aaatatttt taaggtaata ttttaaagtg tatgctatgg tacagttcag    124260
tttgtgactt ttgctagttt atgccactta cagttagcaa aatcacttca gcagttcttg   124320
gaatgttgtg aaaagtgata aaaatcttct gcaacttatt cctttattcc tcatttaaaa   124380
taatctacca tagtaaaaac atgtataaaa gtgctacttc tgcaccactt ttgagaatag   124440
tgttatttca gtgaatcgat gtggtgacca tattgtaatg catgtagtga actgtttaag   124500
gcaaatcatc tacactagat gaccaggaaa tagagaggaa atgtaattta atttccattt   124560 tcttttttaga gcagtataca aagatgctga tttgtattta ttagactctc cttttggata   124620
cctagatgtt ttaacagaaa aagaaatatt tgaaaggtat gttctttgaa taccttactt   124680
ataatgctca tgctaaaata aaagaaagac agactgtccc atcatagatt gcattttacc   124740
tcttgagaaa tatgttcacc attgttggta tggcagaatg tagcatggta ttaactcaaa   124800
tctgatctgc cctactgggc caggattcaa gattacttcc attaaaacct tttctcaccg   124860
cctcatgcta aaccagtttc tctcattgct atactgttat agcaattgct atctatgtag   124920
tttttgcagt atcattgcct tgtgatatat attactttaa ttattattat acttaacatt   124980
tttatttact ttttgtgtta gtattttatt ctgtcttctc cttagatagt aaccttctta   125040
agaaaatata tatgctaagt gttttactgg tttaatatgc ttagactact catctacctc   125100
aatacttcct tggagatctc ctcctcagtc acacagagct caggacttat atttccttgg   125160
aactcctgtt agggtccaat gtacatgaaa ttccctagac agacagacag tcagttatat   125220
```

```
ggcttgattt caaagtttca aaatgattta atggactatc aagtagttta ttaggagaac  125280
agttattata ctcttctaaa aataaagact ttaagcaata aagatgtata tgtatataaa  125340
atggctgggt tattcctaga agtacctttc ttagaattta gttaaattta atatccaaga  125400
tactatcttt tcaaccctga gattgtgaaa agtaacttct atcaatataa actttactac  125460
atttgtattg tgttagtgtg ttacagtata atctagaaca atgtgtcttt ctatatgata  125520
tatgacattt taatgcctaa aaaaactgat atgtcttaga tgattctagt caggatttac  125580
ttctagaata gattaaaatt ctatttgagg agagtcaaat taattatcga attctcagtt  125640
gttattattg ctgttttatt tttagtgaaa cagattagtc ttaatgtaaa cacttgagaa  125700
ataaattgat ggtcaaccta aaatgtaaaa aagaaattaa tagaaaattt aaagagcaac  125760
aaagctctga catttaaaag aaatgaagta caaatctcta gggaccttaa agatcatcta  125820
ataatttcct cattttctag ataaataaac tgagagaccc cgaggataaa tgatttgctc  125880
aaagtcaaat atctacttaa tataggaaat ttaatttcat tctcagtctg ttaacatgca  125940
acttttcaat atagcatgtt atttcatgct atcagaattc acaaggtacc aatttaatta  126000
ctacagagta cttatagaat catttaaaat ataataaaat tgtatgatag agattatatg  126060
caataaaaca ttaacaaaat gctaaaatac gagacatatt gcaataaagt atttataaaa  126120
ttgatattta tatgttttta tatcttaaag ctgtgtctgt aaactgatgg ctaacaaaac  126180
taggattttg gtcacttcta aaatggaaca tttaaagaaa gctgacaaaa tattaatttt  126240
gcatgaaggt agcagctatt tttatgggac attttcagaa ctccaaaatc tacagccaga  126300
ctttagctca aaactcatgg gatgtgattc tttcgaccaa tttagtgcag aaagaagaaa  126360
ttcaatccta actgagacct tacaccgttt ctcattagaa ggagatgctc ctgtctcctg  126420
gacagaaaca aaaaaacaat cttttaaaca gactggagag tttggggaaa aaggaagaa  126480 ttctattctc aatccaatca actctatacg aaaattttcc attgtgcaaa agactcccctt  126540 acaaatgaat ggcatcgaag aggattctga tgagccttta gagagaaggc tgtccttagt  126600
accagattct gagcagggag aggcgatact gcctcgcatc agcgtgatca gcactggccc  126660
cacgcttcag gcacgaagga ggcagtctgt cctgaacctg atgacacact cagttaacca  126720
aggtcagaac attcaccgaa agacaacagc atccacacga aaagtgtcac tggcccctca  126780
ggcaaacttg actgaactgg atatatattc aagaaggtta tctcaagaaa ctggcttgga  126840
aataagtgaa gaaattaacg aagaagactt aaaggtaggt atacatcgct tggggggtatt  126900 tcaccccaca gaatgcaatt gagtagaatg caatatgtag catgtaacaa aatttactaa  126960
aatcatagga ttaggataag gtgtatctta aaactcagaa agtatgaagt tcattaatta  127020
tacaagcaac gttaaaatgt aaaataacaa atgatttctt tttgcaatgg acatatctct  127080
tcccataaaa tgggaaagga tttagttttt ggtcctctac taagccagtg ataactgtga  127140
ctataagtta gaaagcattt gctttattac catcttgaac cctctgtggg aagaggtgca  127200
gtataaataa ctgtataaat aaatagtagc tttcattatt tatagctcgc aaaataatct  127260
gtatggaagt agcatatata aggtatataa acatttagcc tcttgatagg actaactcac  127320
attctggttt gtatatcagt cttgcctgaa tttagctagt gtgggctttt ttttatcttg  127380
tgagtttgct ttatacattg ggtttctgaa aagatttctt ttagagaatg tatataagct  127440
taacatgtac tagtgccaat cttcagacag aaatttgtt ctattaggtt ttaagaataa  127500
aagcatttta tttttaaaac aggaaataat ataaaaagga gagttttgt tgttttagta  127560 gaaaacttaa tgccttggat gaaatgagcc atgggcaggg ttgtaatgaa ttgatatgtt  127620
```

-continued

```
taatagtata gatcatttgt gaataatatg acctttgaca agacacaagc cattaacatc  127680
tgtaggcaga agtttccttc tttgtaaaat gagggaataa aatagatccc taaagtgtgt  127740
aattttagta tttctaaact ttatgaaggt ttcctaaatg ataattcatc tatatagtgt  127800
tttttgtgt gtttgtttgt ttgtttgttt gagatggagt ctcgctctgt cacctaggct  127860
ggagtgcaat ggtgcaacct cggctcactg caacctctgc ctcctgggtt caagctaatc  127920
tcctgcctca gcctcctgag tagctgagat tacaggcatg caccaccatg ccgagctaat  127980
ttttgtattt ttagtagaga agggtttca tcatgttgac caggctggtc ttgaactcct  128040
gaccttgtga tccacccacc tcagcctccc aaagtgctgg tattacaggc gtgtgccacc  128100
acgtccagcc tgagccactg cgcccagccc atctatatag tttaatatca atctaaatga  128160
atttctcagt cctgagccta aaaatttagt tgtaaagaat gatatccttg actaataata  128220
gtttctatta atggattgca tctagtgcta ggtggcatat atttagtccc cacaactacc  128280
ctggaaggta tttaaaattt ttcacatttg cagataagga aactaaagtt cagagttcgg  128340
caacatgctt gaattcaagc agctcctagg atgttaatgg tggaggttgg gttcaaatcc  128400
agatctgtct gactcaaaaa atgcatactc ctaaccagtg cactatatcc caattccata  128460
ggagcccttc tttgtgattc atagcacttt cccatgagtt ttgttgattt tgtgagaaac  128520
aaaactcttt ttcctttgga ctgtctggaa tctctctttt tcaaattttt gaatgtatt  128580
tctatgccaa aagacaaaga tttctagagg aatatgccta ggatgagaat tatgtaattt  128640
aaatcacagc tggaaagaga gaaagtccta agttactaag aaatgttcaa acacaaatga  128700
gctttcagtc tattggaaga cctttatagc tagaagtata ctgaactgta cttgtccatg  128760
gaccctgaa gaaacaggtt aaatcaaaga gagttctggg aaacttcatt tagatggtat  128820
cattcatttg ataaaaggta tgccactgtt aagcctttaa tggtaaaatt gtccaataat  128880
aatacagtta tataatcagt gatacatttt tagaattttg aaaaattacg atgtttctca  128940
tttttaataa agctgtgttg ctccagtaga cattattctg gctatagaat gacatcatac  129000
atggcattta taatgattta tatttgttaa aatacactta gattcaagta atactattct  129060
tttattttca tatattaaaa ataaaaccac aatggtggca tgaaactgta ctgtcttatt  129120
gtaatagcca taattctttt attcaggagt gctttttga tgatatggag agcataccag  129180
cagtgactac atggaacaca taccttcgat atattactgt ccacaagagc ttaattttgt  129240
tgctaatttg gtgcttagta attttttctgg cagaggtaag aatgttctat tgtaaagtat  129300
tactggattt aaagttaaat taagatagtt tggggatgta tacatatata tgcacacaca  129360
taaatatgta tatatacaca tgtatacatg tataagtatg catatataca cacatatatc  129420
actatatgta tatatgtata tattacatat atttgtgatt ttacagtata taatggtata  129480
gattcatata gttcttagct tctgaaaaat caacaagtag aaccactact gatattttat  129540
tatttcatat tacatataaa atatatttaa atacaaatat aagaagagtt tttaatagat  129600
ttttaataat aaaggttaag agattcgaaa gctcaaagta gaaggctttt atttggattg  129660
aaattaaaca attagaatca ctgttgatat tttattattt catattacat ataaaatata  129720
tttaaatata aagataagag ttttaatag attttataat aaatgttaag agattaaaaa  129780
actgaaaata gaaggctttt atttggattg aaattaaagg ccaggcatgg tggttcatgc  129840
ctgtaatccc agaattttag gagactgagt ggggaggatt gcttgagccc aggggtcaag  129900
accagcctgg gcaacacagt gagacaccgt atctacaaaa taattaaaaa attagctggg  129960
```

```
catggtggtg tgtgcctgta tgctaccatt aactaaggag gctgaggtgg gagaatcgct    130020
tgagcctggg aggtcaaggc tgccctgaac tgtgattgtg ccattgcatt ccagcctggg    130080
tgccagagag agaccctatc tctaaataaa taaataagta aataaataaa cagcaacaac    130140
aaaaacactc aaagcaaatc tgtactaaat tttgaattca ttctgagagg tgacagcatg    130200
ctggcagtcc tggcagccct cgctcactct cagggcctcc ttgaccttga cgcccactct    130260
ggctgtgcgt gaggagccct tcagccctcc cctgcactgt gggagcccct ttctgggctg    130320
gccaaggcca gagccggctc cctcagcttg cggggaggtg tggagggaga ggcgctgggg    130380 gaactgggc tgcgggtgcc ttgtgggcca gcgcgagttc tgggtgggtg tgggctgggc    130440
aggccccgca ctcggagcag ccggccggcc ccgcgagccc caggcagtga ggggcttagc    130500
acctgggcca gcagctgctg tactcgattt ctcactgggc cttagctgcc tccctgcggg    130560
gcagggctcg ggacctgcag cctgccatgc ctgagcctcc ccccaacctg ccgctgcagt    130620
gggctcctgc gtggcccaag cctcctgacg agcaccgccc cctgctccac ggcacccagt    130680
cccatagacc gcccaaggc tgaggagtgt gggtgcaggg cgcagggctg gcaggcagct    130740
ccacctgcag ccccagtgcg ggatccactg ggtgaagcca gctgggcttc tgagtctggt    130800
ggggacttgg aggatcttta tgtctagcta agggattgta aatacaccaa tcagcactct    130860
gtatctagct caaggtttgt aaacacacca atcagcaccc tgtgtctagc tcagggtttg    130920
tgaatgcacc aatcagcact ctgtatctag ttaatctggt ggagacttgg agaacctta    130980 tgtctagcta agggattgta aatataccaa tgtgcactct gtatctagct caaggtttgt    131040
aaatacacca atcagcactc tctgtctagc tcagggtttg taaatacacc aatggacact    131100
ttgtatctag ctaatctagt gaggaggtgg agaacttttg tgtctagctc agggattgta    131160
aacgcaccaa tcagcaccct gtcaaaacgg accaatcagc tctctgtaaa accaatctgc    131220
tgtctgtaaa atggaccaat cagcaggatg tgggtgggc cagataagag aataaaagca    131280
ggctgcctga ccagaagtg gcaacctgct ggggtctgta gaagctttgt tcttttgttc    131340
tttgcaataa attttgctac tgctcacttt ttgggtccgc attgcgtta tgagctgtga    131400 cactcactgg gaaggtctgc agcttcactc ctgaagccag cgagatcacg aacccaccag    131460
aagaaagaaa ctcctaacac atccgaacat cagaaggaac aaactcagga cacgcggcct    131520
ttaagaacta taacactcac tgcaagggtc cttggcttca ttctcgaagt cagtgagacc    131580
aagaacccac caattccgga cacaatttga ctgcagaaaa tggatgtcca ccctgtggt    131640 ttccctgggc cacattggaa gaagaaagga gttgtcttgg gccacacata aaatacactt    131700
actatagcag atgagctaaa gaaaagaaaa aagtccatgc gtaatctttg tgatatgtgc    131760
caccaccaat aagcaaaatt gttctcttat tcaaaggtt ggacacagct gctctagata    131820
ttttattatt aaatatgcag gcaattactg tttaaatgaa gatttcctca cagaatgaga    131880
ttaaaagtat atattagtgg cttagcattc atttagaca accatttag agattcaaat    131940 cacacacttg cttacagaaa ttttgttgtc ttcaatgtcc ccattgtggt ttctttacca    132000
agcctctact gttcttcaca tcaccaagtt aaaaaaaaaa aaggggcggg gggcagaat    132060 gaaaattgca tggtaggcca caagttcaga tcctcatcga cacaagaggt gcctgaagca    132120
gtggatgagg ctttctatg gatcatgagc agccacataa atgcttaaaa gggcctggca    132180
gggagcatca gtgggtgatg tggctgggag gctgaatgga gagcatttgt tcttcagtta    132240
tctatagaag gcagctgtca ctcagcacca gctaagggct tccccatgagg gaactgggga    132300 tcaggtttcc cagatctttt tatgtaacag gataagacag agatccagct tttttgggt    132360
```

```
aattatttcc tattttaaaa tacgggtagt tgattaaata aaaacaaacg aatgaacacc   132420
atatgggcac aacaaaacac atctgtggct tggattcagc ttgtgaatga ttactgcaga   132480
tatttattct agaggacacc cctgggtatg tcctaatata aaacctaaat ctaaactcaa   132540
gtcccatgct accttcagag aataaatgac ccagaaaaag aaccacctct cctaaggaag   132600
tataaatttg taaataactg agacccaaac ttacaactat acattttct tattgttggg    132660 ctgttgctaa cctcaattaa gaaggcttga tgatatttgt aaagtgtcat cactccacca   132720
tggtccagta acatctgatc actccaccat ggtccagtaa catctgaatg gtcaagaaat   132780
atctaaacgt atgtaccaaa aatttgtgta tactactgta ccaataaacc atttgtttcc   132840
atttgatctc tgagtgtggt aatacatgtt atttgccctg ctgttgtaaa taaacaaacc   132900
aaatggaggc ttgatgcaag atgcagtgta gcatagtgcc aactctggac tccgactact   132960
cagggtgtaa attctaactc tgttctatta acaccatgaa actgagcaag ttagttaaaa   133020
ctcgctgggc ccattttctc atttatacaa tggagatttt aatagtacag ctacataggc   133080
cattttgtgg tttaaaatac atcatgatta tgaaacactt aatgtagggc ttgctacata   133140
atgagcaagg tttgttgctg ttatcattaa tatccttaat tctcattatt ataaaacttg   133200
agatagtatg aggtgaacaa gttcataaca gcaatataat gaaaatttta ataattcctt   133260
ttatacttta acaaaaatac gagattgggt aatttattat ttttacatga gtaataaata   133320
ttgcattaaa atatatttaa aatttaccac attaatgtct gccagtcatg ccaaatgacc   133380
aacatgaatg tgaataaaac tcagtctgtg cccatttaat cttaaccaac cctttataat   133440
tgttaatgat ttgaacctct gccttgaaag atcacattac ttgattgtct tcaacttatc   133500
tgaatgtggt agtgatttct gtaaatttat aggacctttg tctcatgcag ctccatggag   133560
ttgaacttat gcacctttaa aatggtatat acttaattaa ttaagtgttg atctgcttca   133620
catgtgtata atattattag ctcactaaac caagaaaaca gtggtccttt agggaaagaa   133680
actaaattac aacagagaat ataaatacca tataaatatc tattatttat tgaactgtca   133740
caattattgc aaaaaattac cttttagtgg acaaaacaat tgatattgcc cttttctgga   133800
aaagaaataa tgtaatatat gatgaatagt tttggccagt atcctctaga ccttgccagt   133860
taactggctc tcaaaatttt gaataataaa aacttggtga tagtagaaaa atagtaattt   133920
tttaaaagta tgtgcacaat tatacaacta aacaattcat tcaccagtgt tcacaattct   133980
attgccttct ttgaatcaaa atttacatag ttttctttt agactaagct cctttatgat    134040
accagtgtgc ccatttctca ttaccattga aatgtctcat gagcatgtca cattctggta   134100
caactgctaa tccaggatga cagtttagtt cttttaaatc caattgagag ccttctactc   134160
atgaccagag aacctaaaga aaggttaaga tacatttatt ccttggtgta agtgatttgt   134220
ctatttttag ttttcctaag ggtcatattt caatttagat ttttttttat aggttaggta   134280
aaataggctt ccctttttgca atatgaaata tgtagtcttt taaaaaattt cttcaaagct   134340
attaaactga aaaaaaatta atttggtcta ttcagtttgt tagcacttac cattttggaa   134400
agagagtgac tctactttg tatttggtaa catttcccct actacagggc agtatctttt     134460
gtaagttctt agatattagc accaaataaa taggcaaaaa aaatctatta tgttaattct   134520 tagaaccct gcttggcagt gcatcattga ctagatggag aagaaatgaa aataatacat     134580
taggaagcag tttcctggtt ctttgaaaa caactagaga gtcttgttgt tgactggaat    134640
atctgaagat cctgtttaat gctttcattc tatgattgtt aagaatatgt catagaactg   134700
```

-continued

```
ctgtatcctg tttctttatg tcttcccttc tgtttgttga ttagaaatcc ctgagtggct    134760
ttacattatt agtacagtag atatgtagta tattcccata ataccactgc tgctattgac    134820
taatagtaat aattttaggg cagctttatg acagttggtt tatgttttag ggtgtcattt    134880
gacttgtgaa gcattgaaat ctgggtatta agcacactgt tttctatgtg gtatggaatg    134940
attcttaaag ccctgagaaa atggaaaata aaatatttt tccttttac cataatcacc      135000
tatgactgtc actctatcat aaactgcata aactttataa cctcaaaaca ttttggaaat    135060
gaaatgacag aacttgctta ctcaattgct tctatataca ccaaatattt ttttaaagta    135120
ttatgttaag tccttgaaaa tattttgttc tactcaatag aagcagttta ggttggtagt    135180
tctatgtgga aaccgtgagg aaataatttt atattatgat gactagacca gtctttgaac    135240
atcactttgg ttattgttcc attagtaaat attataatta tttctgagat ttactcacct    135300
tcaaagaatg ttggcaatgc cagcattatt aacactcctc tagttagaac aaagaggaaa    135360
tgtaataaca aaacataata atagccaaat aaagagtgac ttagaatgta caccttatc     135420
taggatcctg agtaattcga ttattcttag gaaatacact tttgtgctag aacaaagact    135480
tttgaaatag ctaatttctg ggtttctttt cattttgaat taacttgaat ttcaaggaaa    135540
caagggtagt ttttacagat acagtgcata gaagctctgt gtacaatgaa gaaaagtagg    135600
aaagtgagaa aaatgccatt agattttca tcgttatact atctgatatg tgaatttaac     135660
taaaacttat atacctcatt atagtacttc ctaatgtaat ttcttaattt aagtgttccc    135720
cataaggttt ttttttatat aaacttaagt actgttaaat atttaaggca aattcaggta    135780
taaaataaga cttgttgata tcttattcca agcatatttg tttctctcct atttatttt     135840
attctgtgtt catttccaaa attgttttac tcacaactgt tgtttttc tgtttcattc      135900
tgtggtaaag gtatcatttg gctaattgta taatttcagt gtcatttcta atattccaat    135960
tgtgatagta tcaacacaag attaaatttc tctacatggt ttatgagaat ggaatgccaa    136020
attgaaaatag aacagagcac agatgatcta aatataaaaa gaactacaaa atcacagtt    136080
gtttaaaaag gttttttgtt tgtttatata tggtgcagaa catttgttcc ttagccaaat    136140
gtttccacct tgagaaagct atagagattc tatgtagtcc tagtaccaat aatatgtttt    136200
aacctgaatg taccttatct ttattcataa actgtgactt tttacactgc tgaaactttt    136260
ttttttaaga caatctcact ctgtcgtcca gtctggagtg cagcagtggt gtgatcttgg    136320
ctcactgcaa cctctacctt ctgtgttcaa gcaattctgg tgcctcggcc acctgagtag    136380
ttgggatcac aggtgtacac caccaggcct ggctaatagt ttttgatatt tctagtagag    136440
atgagttttg ccacattggc caggctggcc tgaaactcct ggcctcaagt gatctgcctg    136500
ccttggcctc ccaaagtgtt ggtattacaa gtgtgagcca ctgtgcctgg cctgaaactc    136560
ataattcatt tccattaata ttaatctcac cttttccaat aattaattga tttcacaagt    136620
attagtcccc tataatcatt gaatggctaa taaaattatt tatagcaaac agattaatta    136680
tctgccagca gtctgagatt agtttcttta aaaaatgttt attatttaaa acattcagct    136740
gtgatcttgg ctttcttgtg aggttcaata gtttctattg agtaaaggag agaaatggca    136800
gagaatttac ttcagtgaaa tttgaattcc attaacttaa tgtggtctca tcacaaataa    136860
tagtacttag aacacctagt acagctgctg gacccaggaa cacaaagcaa aggaagatga    136920
aattgtgtgt accttgatat tggtacacac atcaaatggt gtgatgtgaa tttagatgtg    136980
ggcatgggag gaataggtga agatgttaga aaaaaaatca actgtgtctt gttccattcc    137040
aggtggctgc ttctttggtt gtgctgtggc tccttggaaa gtgagtattc catgtcctat    137100
```

```
tgtgtagatt gtgttttatt tctgttgatt aaatattgta atccactatg tttgtatgta  137160
ttgtaatcca ctttgtttca tttctcccaa gcattatggt agtggaaaga taaggttttt  137220
tgtttaaatg atgaccatta gttgggtgag gtgacacatt cctgtagtcc tagctcctcc  137280
acaggctgac gcaggaggat cacttgagcc caggagttca gggctgtagt gttgtatcat  137340
tgtgagtagc caccgcactc cagcctggac aatatagtga gatcctatat ctaaaataaa  137400
ataaaataaa atgaataaat tgtgagcatg tgcagctcct gcagtttcta aagaatatag  137460
ttctgttcag tttctgtgaa acacaataaa aatatttgaa ataacattac atatttaggg  137520
ttttcttcaa attttttaat ttaataaaga acaactcaat ctctatcaat agtgagaaaa  137580
catatctatt ttcttgcaat aatagtatga ttttgaggtt aagggtgcat gctcttctaa  137640
tgcaaaatat tgtatttatt tagactcaag tttagttcca tttacatgta ttggaaattc  137700
agtaagtaac tttggctgcc aaataacgat ttcctatttg ctttacagca ctcctcttca  137760
agacaaaggg aatagtactc atagtagaaa taacagctat gcagtgatta tcaccagcac  137820
cagttcgtat tatgtgtttt acatttacgt gggagtagcc gacactttgc ttgctatggg  137880
attcttcaga ggtctaccac tggtgcatac tctaatcaca gtgtcgaaaa ttttacacca  137940
caaaatgtta cattctgttc ttcaagcacc tatgtcaacc ctcaacacgt tgaaagcagg  138000
tactttacta ggtctaagaa atgaaactgc tgatccacca tcaatagggc ctgtggtttt  138060
gttggttttc taatggcagt gctggctttt gcacagaggc atgtgccctt tgttgaacct  138120
ccatttgact ggcatgcaca tgtctcagat attataggtt atcatatatt gttgctccta  138180
atatttctgt gttagataat tagagtagct tggtttgtaa gaatgtgatg ttggtgggac  138240
tgtagcagaa caagaaggcc cttatgggtc agtcatacct ctcttttcaa atatttggtc  138300
tagctctctt ctgggcatct tgttgccaat atatagtatt gctcaaaagg gcaggagatt  138360
tgaagtgatc aaggaaaata tattttttct attgattaag tcttttgatg gggtagaata  138420
atctaatttc atgtaactgc tcaaagttat atggtagggg gatcccaaat gtattttaaa  138480
actattttta tatcatcata tttgaagtaa tagaaagtca gagtagcaga ataaaggtac  138540
taaaaatttt aaaaactaat aaggtacttt gaaagaaatc aattatgttg attcctcatt  138600
aaacaaattt gcacttaaag actgaggtta ataaggattt ccccaagttt tttcatagca  138660
acctgtgagc actttctctg ttgaggcatt tatggtatga aaagatgagt aaggcacagt  138720
tcttgccctg gagaaggtca caggtgagag gaggagttga cacagaaaca tttgatataa  138780
agcaaggaat aaattccaag actaaaattt tcagaaatct aaaaaactca agataagaaa  138840
aacccattat attttctggg taacaaaatt tcagtgttat taacatgtag gaagatcttg  138900
atatttattc tgaagcccat gtgtgttgct gaaatattgc cgcatttgca tatactcatc  138960
accatcctct gttttggagc taagaatttt agactcaaga tgtctaatta agttgatcca  139020
ttgattttat ttttttatgga aatctgagac ccacagaagg caggggattt gcccacattt  139080
ctagaagagt cagacatgag cgatgaggca cagtggaaag aacatgagca ttgcctgagc  139140
tctgagttgg cgctataaga gcagtgatca tgggcaagtg actcttctga gccttggcct  139200
cctcacctgt taagtgaaga aaagaatatt tcagaagatc tttgtgagaa tgaaacaagg  139260
caatttactt gcctgctaca tagccaatgg gaaatcaata taagttcccc gtggttccct  139320
tctgtggggt tttgttccca cagagggtgc actggccatt ccacttcttc ttttccaagc  139380
tcctcattcc ctttaacgct gttcatagtt ggttccaaac catttgaaat ataataagca  139440
```

-continued

```
ccaggatggt ttttctttc caccaaagca aatttcattt tctaaacact gtttataaat 139500
atcaatggct atttttcaa tttttgatta tcatgaaaat atacaaatat gtttaattaa 139560
atatgctaaa gaatgtatta ataaatatgt attaaataat tcctacatat aaggccttt 139620 tgcttggggt atgggtgata caaaataaat gtggcatgaa cccactgacc tctagcaatt 139680
tataacctag aaaaagagtt atgatatgtt tataagttcc tgtgatataa gacatgcata 139740
tagtcattat aacagaggtg caaacaagat gtatcaagta tgtccagagg aggaagagat 139800
taatcccagc tggaggaaac actgatgctt tcttgcagca ggggcatttg agttgagaaa 139860
gggaggaaac atagattttg acaatgagag ctgaggggaa aggggtttca ggtgggagga 139920
accgcatgtg gaaagcaggg aggtaggaaa gtgtagagtg tgtttaaaga atagaccagt 139980
ttggctgaaa caggatattt gagcagagga agcttgtact aggtaggtgg gttgaggcca 140040
aattatgcaa ggcattaaat attaaactag gaattttgga ctttatcctg cagtttatgg 140100
ggggtaaatg ataagattca atatcacttt atttgtacag tattatgtta catttatct 140160 aattgtttgt ttaattcctg tctagacaat gaattcctca agggcaagga gcatggctta 140220
ttcacctcag taatttcagt gcctagcatt gtgcctggta caaagtggac acttgtatat 140280
aacctttttt aattgaagca acaagttgtc aaccttacaa atgtgaatcc gtgattcaga 140340
tgacaggttg aaatgtagat tgtctgcgaa gagggcagaa agagagtatg acaaaggagg 140400
acaagacagt ggggcaggca gggagagaga gcagccaggg tttcggtaga ggtatgtcaa 140460
aaaggtatgg aagtcagagg agaaggagac ccctatgtta tagaatacaa atggaaggga 140520
aatgatgaca acagtaagtt gtcattaaat gcaaggttgc aaaagtaaga ttgtaaagca 140580
ggatgagtac ccacctattc ctgacataat ttatagtaaa agctatttca gagaaattgg 140640
tcgttacttg aatcttacaa gaatctgaaa cttttaaaaa ggtttaaaag taaaagacaa 140700
taacttgaac acataattat ttagaatgtt tggaagaaaa caaaaatttc taagtctatc 140760
tgattctatt tgctaattct tatttgggtt ctgaatgcgt ctactgtgat ccaaacttag 140820
tattgaatat attgatatat ctttaaaaaa ttagtgtttt ttgaggaatt tgtcatcttg 140880
tatattatag gtgggattct taatagattc tccaaagata tagcaatttt ggatgacctt 140940
ctgcctctta ccatatttga cttcatccag gtatgtaaaa ataagtaccg ttaagtatgt 141000
ctgtattatt aaaaaaacaa taacaaaagc aaatgtgatt ttgttttcat tttttatttg 141060
attgagggtt gaagtcctgt ctattgcatt aattttgtaa ttatccaaag ccttcaaaat 141120
agacataagt ttagtaaatt caataataag tcagaactgc ttacctggcc caaacctgag 141180
gcaatcccac atttagatgt aatagctgtc tacttgggag tgatttgaga ggcacaaagg 141240
accatctttc ccaaaatcac tggccacaaa gtgtgacatt ttggcattgg catcactatt 141300
tgatggaagc caacctcccc ccaaaaggcc tgtattagaa tgaagatgga ttccctgggt 141360
gggttacact tgaaactagc ctcacccatg aacactttgg cacagattag ctagcccatt 141420
cccccacagt aaggaccata aggaagggac agaagcaaag ataagttta gaacaaaaga 141480 gaggggaaag aaaaaatcta gggttttatg agggctgtcc ctgagtgata gatgtgaata 141540
ggcctccagg gcaggctggc tcagaggctg actctttggg ttggggtgac tgattggtgg 141600
tgaggatgga gaagaaaagg ggagtggagg aggtgaaagt gaccttggga cattaggtct 141660
ccataagtga caggatttaa ggagtgttgt aagctgtggt tgttggacca ggtttaagca 141720
cagcttcctg agcttcctga ctggtttagg tcaagctcca gagagcaaat gccacagtct 141780
cagtgatctc cttggagaaa cagttggaat aggatgttgc ccatgttggg atgagtcatt 141840
```

```
gtccgctctt gctctttccc taccccctgca aaataataat actgtatttg attgaacata    141900
taaaacaaaa gaaggattat cacataagta tgtatatata accaacattg gcaggtgcag    141960
aaaaaccaga ctgtcagttt gcctcatctg aaatgattga cacaaacaaa tatatttact    142020
gtcccaagtg aactttggca ttttggatat ccttcagttg ttctgtttaa agatataact    142080
tagaagcagc tgatggaata tttaaatcca tgcgttgaat tcatgcattc aaagaaacat    142140
gtcctgagtc actaaatgct gacatttgtt tttcatgtta agagtgtaaa taactggtcc    142200
caaatataat attattacat cagataaaaa ctggaatgtg aacctcttaa cttgattgtg    142260
aaagtatttg ccaatggtgc ctcttgataa ttatttgagg ctcacttcag aactcctctg    142320
gaagggttaa ttttaaata gtcatttat aaattaacat ttttgacata tgtgatggct    142380
ctcaaatttt ttcttttatg ccagtttgaa tcatttctgc tcaattttt ttttaattg    142440 ggatggagtc tcactctgtt gcccaggctg gagtgcagtg atgcaatctt ggctgactgc    142500
aacctccacc tcctcggttc aagcgattct ctcgcatcag cctccagagt agctgggatt    142560
acaggcgcgc accaccatgc ctggataatt tttgtattat tactagagat ggggtttcac    142620
cacgttggcc aggctggtct tgaactcctg aactcctgac ctcaagtgat ccacctgcct    142680
cagcctctta aagagctgga attataggtg tgagccactg caccaggccc tgttcaactt    142740
ttaatgctaa gattcatttg ttgttgtttc acaagtgatt aggcagaggt cttttatatt    142800
aatttaccca ttttatttgt aagagagtct catattaagg aagcataata tatgacaatc    142860
caaatacagt acaaatttgg ttaattttga ttttgttaaa taattaatca cagggggtcct    142920 tcaaattgtg agctcctctg gttatactta tgttttacct ctggttatac ttaatttcaa    142980
acaaatgaaa tttcattcta ttcatgatat ttcagaagca gatctgttgc acaaaataaa    143040
gcatacctat aaattttctt ttttttaaaaa aaagtctctg ttcactctat tttctattat    143100
ttttctcttt ttaaaatttg aattttattg tggcaagtcc acttaacatg agatttaccc    143160
tcttaacaga tttttatgtg taaaatacaa tattgttcac catgggtaaa tgttgcacag    143220
cagatctctg gaacttattc atttttgcact actgaaattt tatacctgtt gattagtatc    143280
tccccatttc cctctctccc ctgtcctgtt acccatggtt ctgttctttg cttctttgag    143340
tttgagtatt ttgatacctc atgtaatctt cattctatt tctaactttg acaatgttct    143400
gacaaatttg ctttccggat tggagcactg tatagtgaaa attgaaaatc ttggttattt    143460
tctacagatt cccactattt taccttgagc agacacttat cttgaagggt ctcagatttg    143520
tcacttgtag aatgggggaat ataaacctga taatggtccc tttcagttct aaagttatat    143580
cagttgaaaa tacatgtgtc acttatggta acgggtagag aactggctca ctgaacagca    143640 tatgatatt ataaagtggt tttttttaat cctttctgca gacagttact ttatacttta    143700
ttcaaatgga ttattgtgaa gtacatgtta gcggactttg tacctttaa aaatgtatgt    143760 atttggtgta atgtagaaat atagaaattt attaagtatg atttatttca atgttaagca    143820
tgagaaaata tgctccgaaa ggttagatag cttgcctaaa tgacaagctt gtatttcaag    143880
cagaactttc tgaatcaaaa gactccaaga cgaatgccca gctttcaaaa actgtctaac    143940
caaaataaat cctaagattc accttcatac taaaattatt taaaaatagt ttatttttaaa    144000 ttaatattca cttaaaatgt atttatcatg caatacttta agtgtctgg gaaatgaaaa    144060 tatccaaaga tcaaagaaca ccatgttttc aaacttcaaa aatgttatca gtgacctaaa    144120
caatttttaa aattttcata gagcctatga aaaatgtact tgcaaatggc tactttctga    144180
```

```
ctaggaatag aatggggaga gtatttagtc caacaatgat agactggatt aagaaaatgt   144240
ggcacatata caccatggaa cactatgcag ccataaaaaa tgatgagttc atgtcctttg   144300
tagggacatg gatgaaattg gaaaacatca ttctcagtaa actatcgcaa gaacaaaaaa   144360
ccaaacaccg catattctca ctcataggtg ggaattgaac aatgagatca catggacaca   144420
ggaaggggaa tatcacactc tggggactgt tgtggggtgg ggggagggggg gagggatagc   144480 actgggagat atacctaatg ctagatgacg agttagtggg tgcagtgcac cagcatggca   144540
catgtataca tatgtaacta acctgcacaa tgtgcacatg taccctaaaa cttaaagtat   144600
aataaaaaaa ataaaaaaaa gtttgaggtg tttaaagtat gcaaaaaaaa aaaagaaat   144660 aaatcactga cacactttgt ccactttgca atgtgaaaat gtttactcac caacatgttt   144720
tctttgatct tacagttgtt attaattgtg attggagcta tagcagttgt cgcagtttta   144780
caaccctaca tctttgttgc aacagtgcca gtgatagtgg cttttattat gttgagagca   144840
tatttcctcc aaacctcaca gcaactcaaa caactggaat ctgaaggtat gacagtgaat   144900
gtgcgatact catcttgtaa aaaagctata agagctattt gagattcttt attgttaatc   144960
tacttaaaaa aaattctgct tttaaacttt tacatcatat aacaataatt tttttctaca   145020
tgcatgtgta tataaaagga aactatatta caaagtacac atggattttt ttcttaatt   145080 aatgaccatg tgacttcatt ttggttttaa aataggtata tagaatctta ccacagttgg   145140
tgtacaggac attcatttat aataaactta tatcagtcaa attaaacaag gatagtgctg   145200
ctattactaa aggtttctct gggttcccaa atgatacttg accaaatttg tccctttggc   145260
ttgttgtctt cagacaccct ttcttcatgt gttggagctg ccatttcgtg tgcccccaaa   145320
ctctacttga gctgttaggg aatcacattt tgcagtgaca gccttagtgt gggtgcattt   145380
tcaggcaata cttttcagt atatttctgc tttgtagatt attagctaaa tcaagtcaca   145440
taaacttcct taatttagat acttgaaaaa attgtcttaa aagaaaattt ttttagtaag   145500
aattaattta gaattagcca gaaaactccc agtggtagcc aagaaagagg aataaatatt   145560
ggtggtaatt ttttaagttc ccatctctgg tagccaagta aaaaagagg gtaactcatt   145620 aataaaataa caaatcatat ctattcaaag aatggcacca gtgtgaaaaa aagcttttta   145680
accaatgaca tttgtgatat gattattcta atttagtctt tttcaggtac aagatattat   145740
gaaattacat tttgtgttta tgttatttgc aatgttttct atggaaatat ttcacaggca   145800
ggagtccaat tttcactcat cttgttacaa gcttaaaagg actatggaca cttcgtgcct   145860
tcggacggca gccttacttt gaaactctgt tccacaaagc tctgaattta catactgcca   145920
actggttctt gtacctgtca acactgcgct ggttccaaat gagaatagaa atgattttg   145980 tcatcttctt cattgctgtt accttcattt ccattttaac aacaggtact atgaactcat   146040
taactttagc taagcattta agtaaaaaat tttcaatgaa taaaatgctg cattctatag   146100
gttatcaatt tttgatatct ttagagttta gtaattaaca aatttgttgg tttattattg   146160
aacaagtgat ttctttgaat ttccattgtt ttattgttaa acaataatt tccttgaaat   146220 cggatatata tatatatatg tatatatata tatatatata catatatata   146280
tatagtatta tccctgtttt cacagtttta aaaccgatg cacacagatt gtcagatagc   146340
aattctgtga ttgaagggga aatatgtcac ctcttcatac tcatattggt gaagggtcct   146400
agcttcaaaa ttaatagatt cctaaagagg ggaaatgaaa catccgcatt tacacacaca   146460
cacacacaca cacacacaga gttcctcttg tcggtaagtt ttgtttttt taaatctcta   146520 ctagataaaa tttgttatct aattgtgagt tttacacaaa gaaaaactgt cacagaaaag   146580
```

```
aaagacagtg tcacattttt caaaagaaaa agaagaaaag aaagtgccat gttttcaaa    146640 tacaaatgtt ctggattgat tttaggatct ttagtgaaaa acaaagtatt tcataataag    146700
taaaataaaa atctatgtag gtaaatttgt ttctctaatt taagaatttg aatttctgag    146760
tatttatgat aagtgttgaa ataacttctt atatgtgaca gtgaatactg gcagagcaaa    146820
tgccaaatca atgccaaatc tgtaggatca tttgattgta ggaacagaat tctactcaaa    146880
ccgaaagcag gcatttgctg gagttacaga aaggcctcat ggaacaccga gaaggtggtg    146940
ccattcgact cttaaagaag ctgcaacagg cacaagagag tcagctgcag ctcttcttct    147000
tgagtctata tctgtcctgg gtccattcct ttttgtggtt gcttcattcc tttctctctc    147060
tgaagactgg tttttctggt ctaccagggc tatgccacat tgactttatg tagtgtctcc    147120
attctggcct cctgaattta caggagagtt cctctgtaca aactcaaagt cctggagaga    147180
acagaaaaca gcttcctttt ggctcagggg tccaactgca gtctactctg ctgctatgag    147240
gatagtgggt tcaccaccct tgttgttctc tcagctaggg cagtgggaaa tgactctatg    147300
aaaggaatat acatgggcag gcaaatgtac taatcctcat cagtactgta atttaagca    147360 actttaaaaa attcttttaa gttatttgaa aataagatca aagaaggctg aattacataa    147420
atgaagattt gttaacaatt aattcaaacc aatataacac atgctataac atggttgagt    147480
gtgattgagt cttgatttat taggggcaat aatcaaaaca tttaacaatc attatagtac    147540
agaacttacc aatcaaatca gatgctcagc cggagtggat gttggccacc cagctattat    147600
tatccctggc tcaattggtc ttcagctgtg ttaacttgca aacattaatt aactatctaa    147660 gccctcatt ttcctcaagt gtaaatagac acaataatat tacctattcc ataggtgtgg    147720
ggtgaatagt aaatgtaata atttgtccaa aacacttagt atagtgcctg gtccatggta    147780
aatactaaat aaatgttatc tgacttatta ttaaaatttt atcttctcag cttaaccttc    147840
agaacagtaa tatattgggg tctagataaa tcttgcctat atgaaaataa tttaatacta    147900
catgcagata tatgctgtgt atattatgcc ttctgttaga ggaattgcag aaacaaaaat    147960
ttcaattaat aataagatga attatttctc ccaattgtag aatcttttga caattttatc    148020
atgcattaca gatgtaagaa ctcttgattg ggacttgata gtctaacttt ataataattt    148080
aagaacattc ctcttagaga atttctatgg ccataatact gaacacatga attttaatta    148140
gctgtcctct ttagccctaa aaaaaaaatt actgtaattt aacacttaag tgttgttctt    148200
cccaggtaca gtaatctttt tttttttttt tttttttttt tgcatagagg gtaatctttt    148260
ctctttccaa atggcagaac tgttagtttt ctgactgtcc ggtgaaattc taagtccact    148320
tacttcccaa tagcatgcaa ttagcaaagg tcctccttgc aaaggcacag aacacaccta    148380
aacatcttgc agatgctgtt tggacactct tcccctgctt ttggtctctt tgtaaagcag    148440
ctcatctgga tacaggatct ctttttcccca ttgcccattc taatatatgt taccgttatt    148500
acttatagaa taatagtaga agagacaaat atggtaccta cccattacca acaacacctc    148560
caataccagt aacatttttt aaaaagggca acactttcct aatattcaat cgctctttga    148620
tttaaaatcc tggttgaata cttactatat gcagagcatt attctattag tagatgctgt    148680
gatgaactga gatttaaaaa ttgttaaaat tagcataaaa ttgaaatgta aatttaatgt    148740
gatatgtgcc ctaggagaag tgtgaataaa gtcgttcaca gaagagagaa ataacatgag    148800
gttcatttac gtcttttgtg catctatagg agaaggagaa ggaagagttg gtattatcct    148860
gactttagcc atgaatatca tgagtacatt gcagtgggct gtaaactcca gcatagatgt    148920
```

```
ggatagcttg gtaagtctta tcatcttttt aactttatg aaaaaaattc agacaagtaa    148980
caaagtatga gtaatagcat gaggaagaac tatataccgt atattgagct taagaaataa    149040
aacattacag ataaattgag ggtcactgtg tatctgtcat taaatcctta tctcttcttt    149100
ccttctcata gatagccact atgaagatct aatactgcag tgagcattct ttcacctgtt    149160
tccttattca ggattttcta ggagaaatac ctaggggttg tattgctggg tcataggatt    149220
cacccatgct taactgagtg gtgccaaatt gtcctcaagt ctgttgtact gatatatatc    149280
cccatcaaga gagtacaaga attctcatag ctatgtatct tcaacaacac ttggtgtctg    149340
gtagatgtga agtgattact aaaaatatag ggaagctgca tacataatta ttggcttttg    149400
ctgttctctt acattaattt cttattcatg ttgattactc atttgtcacc tagttttttc    149460
ttccttaatt aaattgtagg aatttatgaa ttatggattg atcatcagct ctatacattt    149520
caaacataat ccctcagtca gtggcttggc ttatagagtc ttttgatgaa aagaagcttt    149580
taagtttaat aaagttcaat ttattgtctt ttcctttatg ttttgtgctt ttggtatctt    149640
gattaagaac tccttcctta tattgggttc tcaaatttag cagcataaca ttttcatact    149700
attatttaaa ttttttttcac attatttagt gatagcacct ttcttattcc taaagtgttt    149760
atcattgcct tctgtctttc tgcttgataa atattgccac acatttgtat actttattag    149820
tgtgtacaaa gaccacattt tagttgtgtt atttctcttg ttttggtttt ctagaatgca    149880
gagccattaa tattatagta atgcttatgt gctaatacca tatcagggc acaaatccca    149940 ttgcagcggg actgagaaat taaaggaaat gatgcacatt tactcatttt tgtttaaaaa    150000
atcaaatgca tatttttcaa tcagactata tggttggtct ggatagcttc atcattgaat    150060
ttttaaagta tttttgtact actgtattta aaattattca ttcaccactg cttttgtaga    150120
tggtttagaa acccaagtta ggaatgactg tgcaacacta ttattatact cttttaaaa    150180 ttatactttt tgcttaagtt tctttccttg ttctctgaga cagtgttcat gttcccaaac    150240
cacacacatt tattcagcta taaaatttgt atgatcaact cctgtcagaa caaacatcat    150300
tataaaaaat atctccagga aaagaaaac cctttaatg ctctcttctg gttcatgtgt    150360
cttcttattt tctttaagca ttttcataac ccattgagct gtaatttaat tggaacatga    150420
tttatactaa agttggttc tttaccttta actttttttt ttagtttgat cagctctctt    150480
tagcttctgt agttcggtct ttaattccat tccagtatgc ttttggagtt gggtctcata    150540
aatgtataga aatgtttctg ttgggaaaca gcaggagaat attaaataaa tattgtgctt    150600
acatctattt aattctttgc ccaacttct acaactttga ctttacattt aagctcctca    150660
tgcacttaca tgtttcttta cctaaaata tcttttcacc atgggtgtgt acaattcctt    150720
tgtccttgct gtattaattt tcttggttta catagtagcc tctacacatt gatgtcaaaa    150780
cctctgtttg gtgcatttct actctgcgtg ttcaatctcc atgaaagttt ctgtaaggta    150840
ttttcattcc tctagttttt cacatgtgca tcctggcttt gtgacctgtg ctttgatatc    150900
gtgcctttca tcttgtggca ttgaaggatc tttgcaagga cctattgtgt tataatacag    150960
tctatgaaaa atatcaatat ttgcatttga tcacatttaa aaaaatcaca ttcttttgtt    151020
tgaatatcaa agctaatatg tgagtgattt ccctgccaaa tagcacaagt agccttcct    151080 gggtgtttat gggcatttat ctggttaatg attcccatca tagtgctgtc acccatgcca    151140
ttgctaaact tatacagtaa cttttttgtt ttcacctcag catatgttga gagtaggaaa    151200
tagataggac tatgccctca aatttacgt ttatatgatg ttaatcctaa aggtccttgt    151260
gacttctgaa gtaaaaactc agtgttgtca tttacttac tgaattgtta gctgagttta    151320
```

```
gagttgagtt tacaatggag taaacaaggt gtttagtttg atgtatgctt ttagtctttc   151380
agaaaaaaat gtttatactt ggaaagaata gtttatttac ccatctggcc tagtttagac   151440
aaaaacacag agtcaaatgt caacagaatt ctgaagttat aaaaatgaca gtgtggcttt   151500
tttttttttt aaccttccac ctggtgctta tgcccaagtg cctagctttc tttagctctc   151560
aactaataaa ggtaatgttt agataacatt taacgttaag ttgcattgtg tttatgatca   151620
catatctcaa atattggtac acgaaactgt acaacaacct tttttattag attttcctac   151680
gaaattcctt attatattcc ctaagatagc ttttcccac cttcttcttc cttctccctt   151740
ctcaggtgct ccaataattc caacccctgc agccagtgac tttattatat cttttttaa   151800 aaatctaaaa aaaaaattg atgcaaccag gaagaatttt ctcatttctc tccaccagtt   151860
gtaccagcct actgcacctc tcctcatgca ccaccttctg cctgtgttct tgctcctata   151920
ttcaggagca agtaatatgc aatacctccc tctttgtggg atctttctca ttagcataaa   151980
aatactttcc cttgatctcc agctactacc ccatttcttt gacctacata tagcaaaata   152040
tttgagaaag gaccactttc catctttttcc tcaatctact tccattttt tctcaatcca   152100 ctttcatttc attgttctcc tcaacccatt cttttccacaa cctacttcat tttatttcca   152160
tcagccccat aactcaggat caacatcttg ccagagccaa tttccttgtc tcccttaaca   152220
gctccagcag tatttatgcc atggacaaat tattcttctt gtgatacttt ctctcttgct   152280
tccatgacac tactcccact tcattttctt tctacctctc tggctcttcc ttggtccctt   152340
ttcctggccc cttctctctt tcagatctct aaacatcagc tatatctcag ccctgttcta   152400
ctgacactct ctagctgtta ttttctaaac ccatgtttca gaaccatat cttgatgaat   152460 cttggaaggc cgaggcaggc gaattacttg aggtcgggag tttgagacca gcctggccaa   152520
cgtggtgaaa ccccatctct cctaaaaata caaaaattac ctggccgtgg tggcatgcac   152580
ccagctactt gagaggctga ggcacaagaa tcgcttgaac ctgggaggtg gaggtttcag   152640
tgagccgaga tcctgccact gcactccagc ctgagcaata gaggagactc cgtctcacac   152700
acacacacac acacacacac acaaagaaaa taaaccatct cttgatgaat cataaatttg   152760
tgtctctagt ttagacctct atcctgctct ctaaatgatg tatccaacta tcatcttgac   152820
accatcatat gttcataaaa cataattata gaatatcttt cagtaggctt gacattttaa   152880
ggcatgagtt tccgttcagt atctccttaa aatataccca gggtctcagg agactattca   152940
aacaggacaa agcttctatt ctacttacta atgtgtctgg ccctatttgg caggttggat   153000
aaaaagtcat ctgaacattg tcactttatg aataatatag tttaatagtt tgtgaatcac   153060
ccctgcaatt taaaaaatag taaaattatc agaatctaat ttaataattc ctattggaac   153120
accccatgtt aggggatttc cagttatttc aattgatatc tcaatgtttt aaagattgtt   153180
tatttctatt actaattcac tctttatttt aacataaatt gtggctatct atctctattc   153240
atttcaatta tatttctcat accattctat agatgggtg aaaagaaaag tgttaatttt   153300
ttaaaactcc atacctcaaa tactatatga atttatagtt gttattgcta aagcaattat   153360
cttacatctt ttcctccaaa acaaagttat gtgctggttt attttctttg tactcataag   153420
atgccttcca tttttagtaa cataagtctt gtctttctcc tattcttagc tacttaagca   153480
ttatgtagct taaataagca ctaaagattc ctatctgtat gaaaaaataa agattaaata   153540
aataagatct agaagggtg acaaggtgat gcttcaaaat gaaccatacc aagccatcta   153600
gcgattgata aattactcac actcataatc acattgttgg aaagaagcca ttgacaattc   153660
```

```
agtttgtttc acaactgtct atcacatagt gagcacaact aaaagactac ttttgtcttt  153720
ttactgcttg ttttgttgat caagtgactg attgtacaat gaccaacaag aagtctgatg  153780
tgtagagaaa aggggaacct ggcttttctg ccttactcct gatgcctaat tctgagcatg  153840
tgaatattat tctgtttctt taattctcca agtgaagcag cagataaacc atccttgttt  153900
ccattagctg tctaccctgt tcaactgtgt gtttctaata acataagaat aagaaagcca  153960
ccagggtgag cagggaaggc aatgagtctg caaggcttgt ggatagattt ctgttagtga  154020
ggctctagaa agttcttcca agattgatgc aatctgagaa gagttttctg tcaatacaaa  154080
ctccctgggt ttctcctttg tccttttact gcctgtgttt gttttgggtt ccagtaaaga  154140
tcaagtgact gattgtacca tgaccaacaa gaagcctgat gtgtggagaa aagggaacc   154200 tggcttttct gcattactcc taatgcctaa ttttcttgta ctgaaagtag ttttgctgt   154260 aagaatctga ggggaggagt catttcttca atttttttt ttggtctcct tttaatggtt   154320
tcttgatcat gtctatcctt attttctgt tttcacaaat ttttgtggta tattttcctc  154380
tcatgacctc tgtctcaaga cttctttcca tccatctctt ctcatttcat cctgtagagt  154440
gtctgtggta agagccctgc attctactct ggccttgcca tgtgtggcct tgggcaagtc  154500
ctagcctcct tgagggtctt atttttctca tttgtaaaat gaaacagttt gatgagaagt  154560
tttctaaggt tccttcaagc tttgacaatc tctctcttct ggatctttt cccatgaaaa   154620 atttcaactc ttgattagca tgtaggcagg gattattcca catccttata ggaatcacat  154680
ttctgctact gtccctgaat gctagagtcc attgattaag ttattcactg ctgcaattgt  154740
cagagctgat caaagaactc tgaaccagtg tgttactaga actaacaaag aaaatgccat  154800
tatgatgttc tagagtcttg aattagtaga agaggtttaa taagaaccct aagggattgc  154860
tagaatgtta aaaacaaaca aacaaaaaaa aaggttgaaa agtttagaaa attcactggt  154920
ctttgtgccc atcattttac ttccagggtt tagataatct cattttgca atgaaggaat    154980 ggattagatc acaagttctc atcctagtag cacatgcaga atctttataa aaacacagag  155040
tagccaggtg cggtggctca tgcctgtaat cccagcactt tgagagcctg ggcaggtgg   155100 atcacttgag aataggagtt gaagaccaag ctggtcaaca tggcaaaacc ctgtatctac  155160
taaaaattca aaaattagcc aggcatgatg gcacatgcct cccagctact ggggaggctg  155220
aggcaggaga atcgattgaa cccgggagat ggaggttgca gggagctgag atagctccac  155280
tgcactccag cctggtgaca gggtgagact ccatcacaaa caaacaaaa caaagaaag   155340 caaaaacaca gattactcag ggtccactaa gaccagtgaa gtcagttctc ttggtagggg  155400
gcagggtgac tgagcatgat gtttgtaatt ttaaaagtgc tccaggtgat tctagcgtgt  155460
atcaagcaag acttgtgaac cactgaacta catgctaaga ctcattttag ctctgatttt  155520
ctgtgagtca tagcagaggg ctcagcaaac ttttctata aatgctaaga tagtaaatat   155580
tttcagcttt gtgggctgta tcgtctttat gacaactcaa ctcagtcttt gtagagaaaa  155640
gcagctgtac ataatatgta aactaatggg agtagctaga tgtgtcctgt gggccatagt  155700
tttgctgact cctggtctat gtcatagaat ttccttttga attgatggac caccagcaaa  155760
tgatttttgt cctgtatcaa tcaatgatac atacataaat ctctacaaga catgtaaagg  155820
atgaggctta atgacagagt actttgggga agacataata ttgcaaaatt aagatgctta  155880
gagaaaaatc atattaaaat agtgaaaact gtgagaaggt attttgattt gttgttttgg  155940
attcctcttt ttgcaaattc ttttgaaata ttttcagtgg aagctacata gatccaattg  156000
tattcaccaa gctagattgt aattaagctc cagagtaagt aatagatttg atgagtgatg  156060
```

```
tccaacctttt tacatggaag agtaagtttg agtcttcctt tgcccattga cacacttagt  156120
accatgttta ccaaagttct tagttattga aatgggcacc agcatatttt gaaacgttgg  156180
tgttaacttg ggatatgcct tttgtcatgt tgcaaataga ttttgtttct gttttgtgaa  156240
gatcaccatc tctgtcactt ctgatagaaa aagtgacact gacttctcaa gtgatttgac  156300
acaggttaaa atatgtaaac catttctgta gagagcaagc tgtaataata tactaaaggg  156360
ctaggtttat agtataatat aaataactca tttatgctgt taataattta tagcaacatg  156420
gcatttgact gacttttttat gtgctctagt catgtaagta atagatgtgg aaacatagac  156480
cagagtttca agaacatgtt ttgggcagag tctgttttct tgctattatc tcttaagttt  156540
atgttcatgg cctaaagatt atgctaatgg atctgccttg gtcttgggtg tcaggtctgt  156600
gttagcgagt attgaaaagc atagtttttg cctactggga aggatttatg atttaaaagc  156660
cctaaatctc ccctttatg tacttcatac ttagaaaatt tttcctgtaa actgtgtgac  156720
ttttttacat tgtgccagtt ttctagatga ctctcgtcat atttatttct tgcaatcctt  156780
ctataactat cagttatgaa gtctctttat agtgttgcca gccaggtctc aggtgtgtga  156840
aatgtatttt ctattatgga ttttggggta tgatggcaca tagtttgggt gttaatgcct  156900
aatcttgatg tactggcttc tgaacaacca aaaggatgaa aggaaataga acaaatattt  156960
ttgtgaggga gaggagtctg gcttcttgac ttactctaga aaaagcctgt aagcctcctc  157020
ttccctcctt gtcacacaaa gtgacaaaga aaatcaagaa ttgttttctt cttggcttaa  157080
atgcatccct tataaagtaa ggctgagatc aggctgtgaa gctatctttt tgtcaagact  157140
gtcataattc caaaacactt tgttcttcta atgcttaggt tagtaacttt aaacattttt  157200
ataaagatag tgaggtccag ttttaaggat tgaccccttc tcaaggggct cagaagaggg  157260
tttggagaat aataaaatta aataatgaaa ccaataattt aaaccagatc atgatcctta  157320
agaaaaaatc ccatcaaatt tgggctaaac tctaatatac agaggtctgc acaacttatg  157380
tcaagtattc ttccccacaa atgaagaatg gggttcattg tgtcattggt tgggtctcat  157440
tttggcttca tcttctattt ctcaaagtct aagaaaagtg ctcctacgga agtgggtgtt  157500
ggctatcatg agactttgct gctggcaggc cagcttgctg ctctagacag agatatccct  157560
cgatcctcct tggacaactg ttttctgtgc acaggaagca gcaggctggg gttaaggagt  157620
ttgccaatcc agtcattctg ataattgctg aatatgaatt tctatccagc acaatctagg  157680
tagctacaat ggcacagtag ttttttatgta tcaggtgaaa atgtttaata ggcactctaa  157740
atgagagaaa aggttaagtg aggttaaaag ctcaatgaaa acaaatagat gagactaaaa  157800
atagttcaat aggttgtaac ttccatctca tccaaacagc aatgaatatt ttgaggctga  157860
ggcgctgagg ggtaaaattg cagcctggac tacttgctaa tgtagaccta cagcactgtc  157920
attcttactg cacagacact gctttctgca taggaggtag aataatgaat tcatttatta  157980
ttaacaaaga tttattaagt gactgcatgg tgctaaccac tagatgggga gggatgtttt  158040
gaactgtcca ttgtttgact ataacaagga acgctttgaa cgaggttact atcataggca  158100
gaatttgttt aacatgaagc ctatgagaca taagccacag gtcctctcac gtgcaggaac  158160
tcctttgaag gccctatact taattttata tgcatagttt ggatttggat tctttttttt  158220
ttaagagttc cccaaattac ttaagcttca ggctccacaa aacctggatc taccccctggt  158280 agcagctatg aatctttgac tatgaaatta agtgtacaag aaatatgact ttacttttc   158340 tgtgattgag tttattttct atttgagcac gcattccact gagtgaaaga aataatatca  158400
```

```
ttgaattcag agattttgct gggttctaag tggagtttac agaatgccat gatattagga   158460
attaaggagt gtgttgccct acatcatctt ttgtccgtgc tcactgtctc tgaggcactg   158520
atgttcctat gtgacctaga ggggcatggt ccaggtagat ggagtctgtc cttgttctca   158580
ctgtgagctc tcgcttgctg acccttcttc agtttcttcc atgcccctga ggggtaaaaa   158640
gattcaaatc tgaagctata tcaagccatc tgtgcataga cattccaagc aaccatgttc   158700
actctactgc tcccatgtca tgcaaggcac aggaagcttc actatggcat gagtattcc    158760
tgggctttgc cttggaattg aggcacgggc ctcctttgtt ctaaaattcc ccaaatctac   158820
ttgaggatag aaccaggatt tggttgcaag gcagaacttt tcttagagga cctggtatct   158880
aaaccctctt gttaccccca tttatggacc ccatttatgg ggtgaggaga gtgactgctt   158940
ctaatccatc ataattttg tctatggcta ctgttttgc atagacacta tgttttgagt     159000
ccttaggctt tggcttttgg cgcttaatgg ccaatattca catggctcaa aattttcaaa   159060
tgatccatat ctgacttgag tttcaaaagt cagtttttga aacttaaatg atcagaattg   159120
atttgttctg ctctggttct gatgtggcct ctccttccag aggtactgga ggtagaatat   159180
ccaaggtgga aagcccacga ctacaaggaa ttggttagta attcataatg ttagctgtcc   159240
acatctattc agtaatggca tttcagtggc tgcacaactg accatggtga aagtgtctgc   159300
acaagccact ttttcttcct gtcagaaaat gttctcaccc actgaattga atgactgtct   159360
gctcatatgc tgtgaatgag tgcccagtct taagattaaa tcacacgttc ttggctatgc   159420
atatttgggc atgctgtggg gagttataat aggctgtctt agagtcacat taagcagcta   159480
gacagacaat gagttggaaa gttacatttt ctaaatttga ttggtacatt ccatttgtca   159540
catttgacat tagaagttct ggattcaccc tctatggtga gcttcactaa tggagaatgt   159600
aatttgcaat gctcaaacac aagtcctaaa cagaaaacat tgtatgttac attccagtgc   159660
taccaaaata gtggttttga aagtccttat tttctaatac tactatgtgt aattttgagt   159720
catttagata gcaacagtta aatgttttat agattgtttg gaagtattaa atgtgaagg    159780
attttttgtta tatagtgtct ttcctatctt gcttaataaa atataagttt agaattgtgt   159840
atagaattaa catgcaaaaa tatcaagtct caactttata cagttaatct acatttgtgt   159900
atacccttca attatttcaa gagagggata ctattcttat gcaggataaa tacaataaga   159960
tattttaaat gaattttaac tacatctctg gcagtttcat ctcaatagta gttgtaattt   160020
tatctcccag accttattat agactagcag ctctctatga aaattagtga cagtgtgagt   160080
gtatttttaat tcaaagttaa tcaagaatga ctgagtcaag agttagctac ccctgaaagt   160140
aactcataat tcagaattta aaatattaca tgtggaacaa tcatgactat atgccttta    160200
ctttctctat cattatttag gttgtgggct ttgggtcctt ttcacatccg ttaacagtgg   160260
gcttgacttc aaaggattat tttcttgaat cttgaataat tgctgaagac aatttgaaga   160320
tattttcaag atgaaggaaa ctgaagcaca gaatcactag agtgaaaaaa gaacttcaca   160380
aacagtgcag gcttgatcaa tggcatggga aaacaggcaa tacagttaga attgctaaga   160440
tggaatttta acgttcaatt aaggatctat ctctaaactc ctctgcttta tccaccaatc   160500
attccatatt aaagatgaag aattgttccc atttcacctt ttgataagga aaatagaaa    160560
taacagaagc aaatacactt tgcccacat ttttttccaa aaagaataat ttttgaagtc     160620
taaacgtttg gtgtaaataa gatgatgtgt taatattgta aaggaaagct agttaagttt   160680
ttgactgaat aaagccagca tcaataatta ctagtaagac taaaaataag agcagtaaaa   160740
ttgtgtctaa tcagctacta atatctggga aggattgagc cacaggatca aagatggtat   160800
```

```
cttttaaaaa tagaagttga gtgaattcgg tcttcaaatt ctttcttttt attcatttat  160860
atttatttac tcattagtat attcattcct ttattcatgt attgttcaaa tatatattgg  160920
gtacttatta tatgccaagt tgtttttaaa atcacattcc aaattcccgt aagtcataat  160980
tattcagaga tgtatgtttt ttttaaaaaa aattgaacac ctttaaaaat tatcaagtcc  161040
ttttatttct gtatgcatta aagataaact ttactaaatg ttacatgaat agatttataa  161100
agcagataaa tatttaattt caaatataac cctatatgc aattatatttt tccttagcac  161160 taaaaatgaa tatttaagta atttatatta aaagtgtaat tatttaactg cagatgtatg  161220
ccaatgactt aaattgttta aagattatag caaagttgtt taaaattgtc taatcatgaa  161280
gagttcactt aaccacctgg ttgacacata aaattatagt tagttactaa ggtagttcga  161340
gagaaagaga agaatcttca gtagtggttt tgaggtgtgg tacattttat tataatatac  161400
cggttataca gcattgtgca gtgctgctca tagtagaaat aaattttctc tttgatgtca  161460
tctattccct tgtgtggctt acataactga gaattaggtg atcacaaaaa taaacaggcc  161520
tatacagagc ccatttatat aagtcctggt tatttctctt cagttaaact tttaattata  161580
tccaattatt tcctgttagt tcattgaaaa gcccgacaaa taaccaagtg acaaatagca  161640
agtgttgcat tttacaagtt attttttagg aagcatcaaa ctaattgtga aattgtctgc  161700
cattcttaaa aacaaaaatg ttgttatttt tatttcagat gcgatctgtg agccgagtct  161760
ttaagttcat tgacatgcca acagaaggta aacctaccaa gtcaaccaaa ccatacaaga  161820
atggccaact ctcgaaagtt atgattattg agaattcaca cgtgaagaaa gatgacatct  161880
ggccctcagg gggccaaatg actgtcaaag atctcacagc aaaatacaca gaaggtggaa  161940
atgccatatt agagaacatt tccttctcaa taagtcctgg ccagagggtg agatttgaac  162000
actgcttgct ttgttagact gtgttcagta agtgaatccc agtagcctga gcaatgtgt  162060 tagcagaatc tatttgtaac attattattg tacagtagaa tcaatattaa acacacatgt  162120
tttattatat ggagtcatta ttttttaatat gaaatttaat ttgcagagtc ctgaacctat  162180
ataatgggtt tattttaaat gtgattgtac ttgcagaata tctaattaat tgctaggtta  162240
ataactaaag aagccattaa ataaatcaaa attgtaacat gttttagatt tcccatcttg  162300
aaaatgtctt ccaaaaatat cttattgctg actccatcta ttgtcttaaa ttttatctaa  162360
gttccattct gccaaacaag tgatactttt tttctagctt ttttcagttt gtttgttttg  162420
tttttctttg aagttttaat tcagacatag attattttttt cccagttatt tactatattt  162480
attaagcatg agtaattgac attatttga aatccttctt atggatccca gcactgggct  162540
gaacacatag aaggaactta atatatactg attttctggaa ttgattcttg gagacaggga  162600
tggtcattat ccatatactt caggctccat aaacatattt cttaattgcc ttcaaatccc  162660
tattctggac tgctctataa atctagacaa gagtattata tattttgatt gatatttttt  162720
agataaaata aaagggagct gaaaactgaa ttgcaaactg aatttttaaaa ctttatctct  162780 ctgtggttaa ttgcaaacac agatacaaaa atatagagag agatacagtt agtaaagatg  162840
ttaggtcacc gttactaaca ctgacataga aacagttttg ctcatgagtt tcagaatata  162900
tgagtttgat tttgcccatg gatttagaa tatttgataa acatttaatg cattgtacaa  162960
attctgtgaa aacatatata taggatgtgc gaaaagtccc tgtgtatcat gtgaaatggc  163020
ttaaaacaga acaccatagg tattcatatc agtgaatacc ataggtagct gaaagtgttt  163080
tttcctgggg tcgccaagat gaatgccaaa agtgatatca ttattataaa caatagccag  163140
```

```
aataggttgg tataaacctg gtagaaagcc ttgataaatt gactttctct cctcctgaca 163200
tcctgccacc cctttgcttt gctgatgctc atttgtccac taaattaaac tcaagcaagc 163260
cctagtaaag taatagaatt tgtggagtcc tcattagtat aggaagtttc cctgatgtga 163320
gattagtaat tagagatgta gcaaaatgag aaagaagtaa tatgcttaga tatttcattt 163380
tctctgaacc tgtatataca aaataggcca tgcgtgttca gtaactattc actgcaaggc 163440
actctctagg tactttgggg gaattggaaa ttactcacat aaggctatgg attgtgccat 163500
ttgtcaaaag acaaaatgac aacaaattta gtttaaagac ctcagtcagc tttattttct 163560
attctagatt tggacagtcc ttcatttcac aaattggagt aagtgttcca ataagttgag 163620
caaaggagct tggctttata gacccaaaaa aagggccaaa ggaagcagaa acaaagaaca 163680
ataagagaat tggtcatttc aaagttactt ttcttgaaag gtggggacaa ggagacagaa 163740
taatagaaaa gtcactgatt ggttaacatt ggattaagaa ttaaaacaga ggaaacttta 163800
agattgaagt ttgaaactga cttgtttggg aaatcaggct gtcttctttc ttgatttctt 163860
agaaggccgg ataacaactg agtttgctt tggtgaacat gggtgactcc attttactt 163920 ttagtctggt ctgttgaggc ctcgtgagag agcttaatct aaaacaatga cttcctataa 163980
tttttgtttg acacatccaa agagggactc taatatttat tgagagctta tcatatctta 164040
agtactgttt aaacactttt atttgctatt acatttgatc ttattataac tctaaaggca 164100
gaaatgattg cttttatttt ccacaatgga ggaaactgag gttcaattaa gtgagtaagg 164160
aagcagggat cttaaaccca gataccattg ctcctctta aaggtggaag aacagaaaac 164220
atggggcagg ggaagagaga aagtttctgt cccaggacat gataatctaa aagggaaaac 164280
gtaagatcca ctgaaacctg aggcagattt attgtggcaa taacaaagct taagtttcac 164340
agaccttcat ttgcctgagc caactttgaa ggccatgtat ctaattttgt ttttataatt 164400
ctataatctt tattcttgaa aagagccctc cctccaaatt tacaagcttt gggcccccaa 164460
aatccttgaa atgcccttga ataagagata tccaggtaaa tgctatggga attcagagga 164520
ggaagcagtt agtatcagtt ggcggagagt taggctatta agagaaggtt ttatatagga 164580
agtggcattt agaatgaagc tttgagaact gagctgtgta tttgaacaag taaaggtggt 164640
gttgcagaat tttgctcctt agttctatta aaaacccggg ttcttgtcac atgatccgga 164700
aaatttaggc acacagatac attgaagcat gagtagagca ggattttatt gggcaaaaag 164760
gaaaaaaaga aaactcagca aatcgagatg gagtcttgct cacagattga atcccaggcc 164820
accacaaagg aactgaagag atcgggcttc tcccctgcat aaggtgcaaa ttccccatgg 164880
ctccacccac ttccccttag tgtgcatgtg gggctccagt ccacggtggg catgcccaga 164940
caagccttgg gcaggttccc tcatctgtgc aaaagcatct gatgtaaaca cttgaggggt 165000
ggttcggaga ttctctggga cccttttatt ttcttatctg cctaggcatt tggctgtctc 165060
agtgggtggg aaagggtgct ccaggcaaag ggcataacat gaggcaaagg gcatgcacag 165120
aaaacagtga ctggttcagt caggttgggg gatgccaaag gaagtaatgg gagacaagat 165180
tggagcaaga tagataagag attgtggatt ttttttcttt tttatctata taaatacaga 165240
gacagggtct cactatgttg cccaggctgg tctcaaactc ctggcctcaa gtgatcctcc 165300
cacctcatcc tcccaaagtg ctaggattac aggcatgagg cactgtgccc aacctccaat 165360
tttggatttt gagagctaaa gcaatatagt cgaaaactca gataatccag gtagattttg 165420
ctattaggtg ctatttggtt cctggtacag agctaaaacc cttggaattt cctaagtgat 165480
aagagctaca ggagcatctt ttgttatatg tttccccccc tagttcctga aatagctcta 165540
```

-continued

```
gagaaataca ggtgaataac atcctttgtt attcatatca agcccctatc aaccataccc    165600
cagtttctat ttatgaagtg gcttttggga agtccctaaa gacaggagtg gggaaaggct    165660
ggttgtcagg gggatgggtt gaaactttca tcttccccc ttgacctcca gggagggatg    165720
agtggctgaa aattgtgtaa aatcaacaat ggccagtgat ttaatcaacc atgcctatgt    165780
aatgaagcca cccgataagc cttaactgga acttttgga gagcctccag gctggtgaag    165840
acattgaggt gctcagaagg tggtattcca gagagagcac agaatctctg ttccccttcc    165900
cacattcatt ttgctatgca tctctcccat ctggctgttc ttgagaggta tccgtttata    165960
ataaactggt aacctagtaa gtaaactgtt accctgagtt ctgtgagcca ttctagcaaa    166020
ttatcaaacc taaagagttc atggatacgt gcaatttaca gatgcacagt cagaagcaca    166080
gatgacaatc tgggcttgcc attggcattt gaagtgtgtt gggaggcagt cttacagaa    166140
tgagccctta tcctgtgggg tctatgctaa taacagacag ttgtcagcat tgcttggtgt    166200
cgaaacccca cattgttggt gtcagaagta ttgtcagtag gatagggaaa acagtttgtt    166260
ttctttttt agtggtcttt ggtcatcttt aagagcaggg cttctcaaag tgtggtcctt    166320
gaaccagcat cacctgtacc acgtaagaac ttatgagaaa tgttcattct tgggccccaa    166380
caaagaatta aaaattctga gggtgtgaac ggggtctgag tttcagcaca acttcccgac    166440
catgctgatg cattcttgcc caagcatgaa agccctccct tgtttaagaa ggccattagg    166500
gccgggtgtg gtggctcatg cttgtaatcg agcactttga gaggacatag tgggaggatc    166560
acttgagccc tggagttcta gacaagcctg gcaacatgg caaaatgctg tctccacaaa    166620
aatcacaaaa attaggtggg cgtgtgttgt gtgcctatag gcccagctac ttaggagact    166680
gaggcaggag gatcgcttga gcccaggaga ttaaggctgc agcgagctgt gatggcacca    166740
ctacagcctg gatgacagag tgagacactg tctcaaaaaa aaaaagaaa aagaaaaaga    166800
aaaaagaaag gaaaatgaaa aagaacgcca ttaggtataa aggagcaatg gtaaagacc    166860
agttgcaaaa ggttagggaa tgggtggtta ctgaaataag aagctatgta gaacactagt    166920
gttggtggca ggaagtagaa agcaagagca ctgctctgtg ggggatggtc atagcaaatg    166980
caatatggag gcatttgcct ctgcactgag gagaaaacta tcttttccaa gataggagga    167040
aaggagataa gtggaattaa agagaacctt tgagcacaga gttgggaaac tgaaggtatt    167100
tgtgttgtgc tccctcaatc ttttaattca actataagct aaacccatga aacttgagta    167160
gtttcagtta tctgactttt ttcttctctt ttgatacagt gttggctatt ctgggtcttt    167220
tgcctctctt tatgtactta agaatcagtt tgccaatgta tgcaaaataa ctggctggga    167280
ttttgattgt gattggcttg aatctataga tggagttggg aaggactgac atcttgacaa    167340
tgttgaagct tccattcat cattatgaaa tatttctcca tttgtttgat tctttgattt    167400
cttttatcag aatttagttt tcctcatata gtctttaaa atattttgtt atattttgtt    167460
caagtatttt gttttgagg aatgccaatg taaatggtat tgtgatttta atttcaaatt    167520
ccaattttc attgctgtta tataggaaaa tgattttttt tgcatgttag ccttatatct    167580
ttcaactttg ctataatcaa ttattgatag tttcaaggat ttttttggtca attatttga    167640
atcttctaca tagattatca tcatctgaac ttagtttat ttcttccttc ccaatctgta    167700
tacctttatc tccttttctt atttcattag ctaggacttc cagtatgatg ttgaaagtag    167760
tggtgagagg ggatatcttg gtcttgttct tgatcttagt gggaaaactt caagtttctt    167820
atcattaagt atgattttag ctggagggtt tttgtagaag tttttttttt ttaagttgaa    167880
```

```
gaagtctcct tctatttta gtttgctgat ttttaaaaag aatcaggaat gggtgttaaa    167940
ttttgtgaaa tgcttttctg caactattga tttgagcact ttattttct tctttggctt    168000
gttgatgtga agtacattaa ttgattttg aatgctgaat caacctttg tacctgagat    168060
taatcccgtt tggttgtggt atataattat ttgtatacat gttgagttcg atttgctaat    168120
acttttgag aattttgca ttggtgttca tgaaaaata ttggtgtgta gttttttgtg       168180
acatctttat ctgcttatgg ttttaaggta atgctggcct catagcatga gttagggagt    168240
atttcctcta cttttacatt tgagaagaga ttgcagagaa ttagtaaaat tcctacttta    168300
aatattttgt ggaattcacc agtgaaccca tctggacctg gtgctttctg ttttggaagg    168360
tcattaatta tttaaaata gatataggcc tattcagatt acctatttt tctcatgcga       168420
gttttagcag attgtctttc aaggaattgg tctatttcat ttaggttatc aaatatgtca    168480
acgtagagtt attcatagta ttcttttatt atccttttaa tgtgcaaggg atctgtagtg    168540
atgtccctt ttttgtttta ttgatattag caatttgtgt cacatctttt attttgcttt     168600
gttagccagg ctagagatat ctctatttt gatgttttg atgaaccaac ttttgtttt       168660
attgattttc tctgttgatt tcgtgatttc aatttcatga ttttaaatt atgcttacat      168720
ttgatttaat ttgatcttct tttgctagtt atccaaggtg gaagcttata ttgttaagat    168780
cctttgcat tcttatgcat tcaatgatgt aaatttccct ctaagcactg cttttctgc      168840
atctcacaaa tattcatgag ttgtattttc atgttcattt agtttgaaat attttaaat     168900
ttctcttgat atttctcttt tgacccatgt gttacttaga agtgtgttgt ttaatcacca    168960
tttttaaaaa ttttctagct atctttctgt tattgatttc tagtttaatt ccattgtggt    169020
ctgagagcat atattgtata atttaattt ttataaaatt tgttaaggtg tgatttatgg     169080
cccagaatgt ggtctatctt ggtgaatgtt ccatgtaagc tttggaagac tgtgtattct    169140
gctatatttg aatgaggtag tctatagaca tcaattatgt ccagttgatt gatggtgctg    169200
ttgaattcaa ctatgtcctt actgattttc cacctgctag atctgtccat tctttgcaga    169260
gggacactga agtctccaac tctagtagtg aatattctat ttcttgttac agttttatca    169320
acttctgctt catgtctttt gatgctttgt tgctagaaac atacacatga agaattggta    169380
tgtcttttgg agcatgaccc atttatcctc atataatgcc cctcattatt tcctcgccct    169440
gatgtctgtt ctctctgaaa gaaatatagc ctctccaggt ctcttttggt tggtgttaaa    169500
atgacttaac tttctttatc ccccttactt ttagtttata tgtggttta aatttaaagt     169560
gggtttcttg tagacagcaa atagttcaga gttgttttc gatccacttt gacaatcttt     169620
gtcttttaat tggtatattt ggactattga tattttaagt gattattgat atagttagat    169680
aaacatctac tatatttatt actgttttct gtctgttaca ctacttgttc tttgtttata    169740
tttttattgt ctactctttt tctttccatt gtggttttaa tcgagcattt tatatgtttc    169800
cattttcttt tcttagcata gtaattcttc tttaaaaaaa catttttag tggttgcccc      169860
tagagtttgc aatatacatt tacaactaat ctaagtccat tttcaaataa tactaaataa    169920
tttcatgtgt agtgcaagta cctttaata ataaaacact cccagttcca ccttccagtc     169980
tcttgtatta tagctataat ttagttcact tacatatatg ggtataccta agtatataca    170040
ttatcatatt tatgattgaa tatattgatg aaattatttt gaaaaaactg ttatcgttaa    170100
atcaattaag agtaagaaaa atagttctaa ttttattata aaatgaaata ccttcattta    170160
ttcattctct aatacacttt cttctttat gtagatccaa gttctgacc tgtataattt       170220
tccttttctc tcttcagctt ctttgaacat ttcttaccag ccagacctac tgacaacaat    170280
```

```
tttcccaat ttttgtttgt ctgatagaga ctttatttct tcttgacttt tgaagaataa   170340
ttccacaggg cacagaactc tagattggtg atttcttccc ctcaaaccct taaatatttc   170400
attccactgc cttcttgctt gcattgtttc tgagaagtta gatataattc ttatctttgc   170460 cttttctatag gtaagatgtt ttttcctctg gcttctatca agattttttc tttatgaaca   170520
tgatatgcct ttcttttga acatgatatg cctttctttt tgaacatgat atgcctttgt   170580
gtcggatttt ttttggcatt attctgcttg gttttctctg agtttcttgg atatgtggta   170640
tggtatctga cactaatttg gaaaaattct cagtcattat tgcttcaaat atttcttctg   170700
ttcttttttt tcctttattc tccttctggt attcccatta catgtatgtt acagtttttg   170760
tagtcatccc gctgttttgg atattctgtt tttttcagtt ttttttttcct tcgcatttca   170820 gtgttggaag tttctattga catattctca acctcagaga ttctttcttc agctgtgttc   170880
agtctaccaa tgagtccatc aaaggcattt tacattttta ttacagaatt tttgacctat   170940 agaattttctt ttgattccat cttttgaatct ccatttctct tctgctttc atctgttctt   171000 gcatgttgcc tacttttttcc atgaaaacct ttagcttttt tttttttttct ttttgaggtg   171060 gagtctcact gttgcccagg ctggagtgca gtggtgtgat cttggctcac tgcaacctct   171120
gcctcctggg ttcaagtgat tctcctcctc agcctcccaa gtagctggga ttacaggtgc   171180
ctgccaccat gcctgagtaa ttttttgtatt tttagtagag atggggtttt atcatgttgg   171240
ccaggcgggt cttgaactcc taacctcaag tgatctgccc accttagcct cccaaattgc   171300
tgggattata ggtgtgagcc accatgcct gcctttagca tgttaatcat agttgtttta   171360
aattcctgat ctgttaattc caacatccct gtcatatctg actgtggttc tgatgcttgc   171420 tctgtgttttt caaatggtgt tttttttttt ttgcctttta gtaagccttg taattttta   171480 ttgaaaggtg gacatgatgt gctgggtaaa aggaactgta gtaaataggc ctttagtaat   171540
gtactggtag gtgtagcaga gggtgaggga agtattctgt agtcctatga ttaggtttta   171600
gtcttttagt gagcctgtgc gcctgcagct tggaagcact tgtgaagtgt ttttttcaccc   171660 cttttggtgg gacatagtga ctagtgtgag cgggagttga gtatttccct tcccctaggt   171720
cagttaggct ctgaaaaaac cctgataggt taggcatggt aaaatagtct cttttgaggg   171780
caggcattgt tataagaata gaatgctctg gggccaggtg cggtggctca cgcctgtaat   171840
ccccgcactt tgggaggcta aggcaggtgg atcacctgag gtcaggagtt cgagaccagc   171900
ctggccaaca tggtgaaacc ccgtctctac taaaaataca aaaatcagcc aggtgtggtg   171960
gcacacacct ataatcccag ctactcagga ggctgaggca ggagaactgc ttgaacccag   172020
taagtggagg ttacagtgac ccaagattgt gccactgcag tctagtctgg gtgacagagc   172080
aagactccgt ctcaaaaaaa aagaatgct ctggcatatt tgaaaatggt tacttttccc   172140
tttttttctc tgatcttcac tgtgagaacc tggtaagcat cctataggca aaattcataa   172200
aagtatagaa gtcggccagt gacttggacc cacttggaat tttcttgctc tcacatcatg   172260
cacactgaat ctccagcaat ttttcactta cagtttaggt tttcctaccc tactactggt   172320
tctctcagag gttctgcttt attggttct gttttgtaag ttgtgattct ctgtacctaa   172380
ctgcctgtct cccatttggg ggggcagtgg tttgccctgt gacctcactt ctctgacaga   172440
tctaagaaaa gttgtttatt tttcagtgtg ctctgctttt tacttgttac gatgaagcca   172500
accactttca gaatttctac aaaccagatc agaatctgga agtcctgttt ttttattttt   172560 tttatcccctt tgtttagcat gttacctatc ttaacacatt ttaaataagt gaatgcatag   172620
```

```
cttatatcta cttctaggtt atatgcttcc ttagaatagg aattgattct taaaatgtcg   172680
ttctgctcac gcctgtaatt ccagcacttt gggaggccaa ggcaggcgga tcacttgggg   172740
tcaggagttc aagaccagcc tggtcaacat ggtaaaaccc tgtgcctgca aaaaatacaa   172800
aaattagctg ggcatggtgg tggccatctg taatcccagc tactagggaa gctaaggcat   172860
gagaatcact tgaacctggg aggtggaggt tgcagtgagc tgagatcgcg ccactgcact   172920
ccagcctggg tgacaagagc aaaactccat ctcataaata aataaataaa taaataaata   172980
aataataaaa ataaaaaaat aaaataaaac aaaaatttta ttctgagcag tctctgaaga   173040
atataaattc tactgccttg cctttagaac ttataacagc atctcgcaaa ctatcacaag   173100
atgctccaaa catacttctt atgtgctgaa ttaagaagtc aactcaaatt tagtatacta   173160
gtaatatttt tggatatccc aaaacactgc cagctcagct ttaggctgcc cttcttgggg   173220
gggaaaaaag cagttgaaat ttaggactta agtgggcatc tcgtttaatt tttaatggat   173280
ttctatgttg ttggttatgg tgaagaggtg aaaagaataa atattctgtg cagaaaaatt   173340
attcagtctt catgtgaaaa cactttgtcc atagcaatta ctttatgaaa aagatgtggt   173400
attactttct ttgctcttaa ctgagacctt taatttaaag aacctatact ttacaagttt   173460 ttatttttcaa tgcatgaaaa atgtagcagc tatttcacaa cctttacttt taaaatccat   173520
ttttcttttt aatctcaaat agttttttct taaaaccttt tgactttttta tctaaattgt   173580 aatagccaga gcaccttccc acaactagaa tatctcatcc tttttgtctt ttcttttttcc   173640 tctcaaaatg cctactggga acttaatttg gagtcagatt cttcatgata aatctggact   173700
taatcaaaat tcctcatatg gtatattgta tatatcacag tactggatag tcctctgatt   173760
aaatagatat ttgatagtac tttaaggtct atactttttgg atgaacttaa ctgctttctc   173820
catttgtagt ctcttgaaaa tacagaaatt tcagaaataa tttataagaa tatcaaggat   173880
tcaaatcata tcagcacaaa cacctaaata cttgtttgct ttgttaaaca catatcccat   173940
tttctatctt gataaacatt ggtgtaaagt agttgaatca ttcagtgggt ataagcagca   174000
tattctcaat actatgtttc attaataatt aatagagata tatgaacaca taaaagattc   174060
aattataatc accttgtgga tctaaatttc agttgacttg tcatcttgat ttctggagac   174120
cacaaggtaa tgaaaaataa ttacaagagt cttccatctg ttgcagtatt aaaatggcga   174180 gtaagcacc ctgaaaggaa atgttctatt catggtacaa tgcaattaca gctagcacca   174240
aattcaacac tgtttaactt tcaacatatt attttgattt atcttgatcc aacattctca   174300
gggaggaggt gcattgaagt tattagaaaa cactgactta gatttagggt atgtcttaaa   174360
agcttatttg cgggaagtac tctagcctta ttcaacagat cactgagaag cctggaaaaa   174420
caaatcccgg aaactaatta ttatgtgcca gttatataaa caagaagact tgttgggta    174480 caaaccagtg attccttgcc tttgaaaaat gtgtcagata tcatgcatta ccagcagttc   174540
aatgatataa ggaaaccaga gtaatagcta aaacctttaa agctaaacca aagatttaca   174600
aattgcctct tcatccagtc tttcccaacc taaaaactga gttctctaaa aattttagta   174660
tttttttctg aagaaaaggg aacatggaca tttatctaat cctcattaga aatctgacta   174720
atgataacaa ggatttagac ctcaagcact tcttaccaaa attcttgata tgaccttata   174780
gcaaattact ttcacctgtt gaactttcct ttcttttatt cccctgtacc tcacctgcac   174840
tgggcatatt caagttgctt atacaacact ttactattgt gttagaaaaa tcatgacaca   174900
tgatgaatgt gtttgtgcaa catgagctga ttcataaatg aaaatgtgca ttgaaattcc   174960
acaatatttt aaaattagga gtttatctag caattgaaca aaattgatta aatccattat   175020
```

```
ttgttagatc agctaaatta cataagttca ttcatctgct cataaatcca tccattcttc    175080
catctggcta tcccttagtc aattcaaata aatatttatg gggcactttg ggtaagccag    175140
gtgctaagaa ttcaatgcaa aacaagatag actcccctgt ccttgttgaa cttatatttt    175200
tggtacaaac aaaagcaata atcaagaaaa aataaaaaaa gtactgattg tgattaataa    175260
tatgaagaaa ttcaacagag tattgtactt aacatttgat tgatctgatt ttctcagttg    175320
tctgagaaca aacatttgtg aaaatctcat tgtagagttc ttacgatgga taggggtca    175380 actgtgtcat tattgcttat cagcttatcc caaagaccta gtttattacc agattgcaaa    175440
tagtgttcaa taaattattc ttattaaggg ttgttatgta ctctaaaaca tttattgtgg    175500
tcccttcact ggttctggtt tacaaactta cttttctatg atgacatagt atagaaattg    175560
agagtgaata tttagaagtt catttttatt atatatttt  gaagtattga tatgtagtga    175620
attagaaatt taaaagaaa  acaaaactgt ccttcactac agattgaaaa gcattatact    175680
aaaagaccat ttgctcagtt atagtatata aaggccaaat gacttaaaaa caaattgtgt    175740
aaggagaagg aaacaaccat ttattcagtg ccactaactg tcagccagtt ttttcagtgg    175800
tcagttaatg actgcagtag tgttctacct tgctcaaagc accctcctca agttctggca    175860
tctaagctga catcagaaca cagagttggg gctctctgtg ggtcacctct agcacttgat    175920
ctcctcatgc agtgcatggt gctctcacgt ctatgctatg ttcttatggt ctttaggtaa    175980
caagaataat tttctttctt ttccttacta tacattttgc tttctgaaat tcccttctcg    176040
ccaatccagg tgaatgtcag aatgtgattt gacaactgtc caaagtactc attcactgag    176100
gagtggtaag gccttcgccc aacctgcctt ctctgggaat atactgctgc ctgaacatat    176160
cattgtttat tgccaggctt gaacttcacc aaattaattt attagggtca acatctaaat    176220
attagaacta tttcagatta atttttaagt cgtatccact ttgggtacta gatcaaattg    176280
caggtctctg cttctggctt gagcctatgt ttagagatga tgtgcatgaa gacactcttt    176340
gcttttcctt tatgcaaaat gggcattttc aatctttttg tcattagtaa aggtcagtga    176400
taaaggaagt ctgcatcagg ggtccaattc cttatggcca gtttctctat tctgttccaa    176460
ggttgtttgt ctccatatat caacattggt caggattgaa agtgtgcaac aaggtttgaa    176520
tgaataagtg aaaatcttcc actggtgaca ggataaaata ttccaatggt ttttattgaa    176580
gtacaatact gaattatgtt tatggcatgg tacctatatg tcacagaagt gatcccatca    176640
cttttacctt ataggtgggc ctcttgggaa gaactggatc agggaagagt actttgttat    176700
cagctttttt gagactactg aacactgaag gagaaatcca gatcgatggt gtgtcttggg    176760
attcaataac tttgcaacag tggaggaaag cctttggagt gataccacag gtgagcaaaa    176820
ggacttagcc agaaaaaagg caactaaatt atatttttta ctgctatttg atacttgtac    176880
tcaagaaatt catattactc tgcaaaatat atttgttatg cattgctgtc ttttttctcc    176940
agtgcagttt tctcataggc agaaaagatg tctctaaaag tttggaattc tcaaattctg    177000
gttattgaaa tgttcatagc tttgatagtg ttttcagaa  gaccaaattt acagtgggag    177060
ccttgggctt ttgttttttta acagctcttt tttgttcctg cttcagtggc ctgacctcca    177120
agttagcaat cgccaggttg agaaatgctt tgcgagacat aacagatgct cctgaaataa    177180
caaacacttg gaatcatgag gtagtggaat tgaaaataga aagtgtagtg attgttttt     177240 gttatttgga tgggatgaac aatgtcgatt tagtctgtaa ctattttttt ttaatgtcac    177300
tctgatttgg tcacaaagga tctctagtct cattgcctta gtatcattct acgaattaga    177360
```

```
atgtgttact gtgtaagagc acttcttgta tatgagagaa atagcaacag ttccagttta    177420
aagtgatata aatggaaacc aagaaatgtc tttactggga ccaaatctgg acagcattta    177480
ctgtattttt gctggtattt tctctagtct ttccgggtat attcacattt aatgatcact    177540
tttctccctt tgtgctaatg acactgaat ccattccact accatagttc ttgctaatac     177600
tactctactt tttacacaaa attaaaatgc caggagcacc tccaggtaga ctgactataa    177660
atctagactg aaaaaaaagc ttgtatttct taacagatta ccttgtggaa catttgctcc    177720
tttcaactaa tgaggcacta atattgtaa ctgctcaact ggtgctttta atttatttgt     177780
ctagactttg tcatgttgcc agaagcttta tcctggttgg agttttgaaa acagtattgt    177840
ttcttcagaa agaaaaaagg gattgtcaga tgatctaaaa ataaagaaac actggaaata    177900
caagtatccc aaggtgatag cattaggcaa gataaaaatg ttgaaaagcg aaaaagaact    177960
ggttgataga gaagtgttgt tattcagtag aacctaagtc ttgtggtccc attttttaatg   178020 aaaaatggtg aatttttggg tttttattgt tcttgttcac acaaatctgc ccattagaat    178080
aagccaagcc ctaaaaatta atttcagttt cactgggaat cctttagttt atctactatg    178140
tagtagagag gttttgtttt attgcatgtt tgacgtagga acgtatatat gcaagacatg    178200
gaggaaaacc aagtgggcca gagttttgaa aattctttat cttttctttc tgccaaagtg    178260
agtctcccaa gtttgtcttt tttttttcat ttccactctt ctatggtttc tagcattata    178320
taaaccaaac aaaaaaaata cgttcagaga ttccttcaga aatgctggat gatcttgata    178380
tcgatgcttt tcatatatgt gtttatgatg ctggtttctg gggctggctc tcagtatcac    178440
aaagatgtct gtaaacagaa tatgctattt cttctttgtg acaaattttg aacattatgt    178500
gaatgtccaa gaaagagcaa aagagggcaa acttctcata cattttttgat gtcgaaacca    178560 agagacgctt ttattttcct aactttttctt tgaaagttca aattaagtaa ttttatcctg    178620
tcctaaagtt taaaaagaaa aaaaaaagga agaaggaatt aaaaatccaa agaaaattat    178680
gtttgtttgc ttttctgttt ttttcttcct tccaactccg agactttgca agggcatagt    178740
tctgaagatc tctgacactg agacattaga gatctctgta tcaatggatc atttgttttc    178800
agacatatga aacaggaact ttgaacaaga aatttccccct cttttttctca tagtgatcct    178860 gagacatcag ctgtggaatc acaacacgtc attagttttg gcaggtcctt gcaggtgttt    178920
tgttttgttt tattaatgtt cttccctcct gtagctagac agcaatcttg gagaatctgc    178980
cagcttggaa gactattgtg taaatttcaa ggtggagcct cctttaattt gttctgtgtt    179040
acctgtgagc tgtgaggtca tgaagaggag acaatgaggc taatcatgag agccccattg    179100
gtttaggcaa ttagaacaac aagatctaaa atggtttatt agccttgaat tgtgttaagc    179160
acataattca taaaaacag aaaaaatatt tttaaatgta tgtctaaatc ttcagttaca    179220
agtttgaaag gtgacaaact attctgagga aatgattagg cctattcttg caacgagtct    179280
ttatgatctg aaaagaatct atgtccacac ataactccca cctcaaagat ggggcatctt    179340
ttgctctggg agatatcaaa tgcgaccaaa acaagtgttt gtagatttga atgatgattc    179400
agcagtgtag cagttctcac tcatttata ataattaaca acttaataat taattattaa     179460
actcctacat gcttaacatt ataagtatga taacttctgt ggttacataa aagatataca    179520
tagcacttgt ccttgatctg tcacagtgag gtcccaatcc aacctatgag cttcaaatga    179580
aaagttcaaa attacactca ttgtcataag tcagagatca aaggaagaaa ggatttaacc    179640
aaaatgataa attaaatata ggtgattaaa tatagtcatg gttcaaggca tgggccagtt    179700
agggagtgtg atgtgggtaa ttatgaaagg ccagctccca agccctgttg ttgctactcc    179760
```

```
cccacatcag tcatccttcc ttttttttcta cttctactgc agtgccttcc tcatctttc   179820 ccttgcatcc ctccattata tgagtcatac aaattagact tttcaaagca acattaacat   179880
tgtgtgaatt tggggttttt gactaatccc aacattccac ccccacattc cagtcccaca   179940
tgggatttgg agccttgttt ataaacctgg cacttctaat atatcttatc ttagagtaat   180000
ccttgtattt gtttaatttc cacttagcat tgtaaatact tgcaggtatc ctagttaaga   180060
aagcaaggtt taaacacaaa atcatcacca attaaagcag gctagataaa gaatgtaata   180120
gaaatgctag ataaaacaga ttttttctta ctaagttttc tgtcccttat agagtgcata   180180
acacaataac ttgcttgata agaattcaat gtacattgtt ttgtgctgaa tcactaaatg   180240
cttgatttct gtaacaagag attgtggttc catcagtatc tggattttag tctgtgtaat   180300
cttaggcaag ttatttgatt tctctgtgcc tctgttttct tgtctgtaaa atgagtataa   180360
tggtagtaac taattcattg tgttttgtg aggattaaat gagttaataa ctagtactcc    180420
tccctggcac atagtaagta caatatgctg tgctgtggtg gttgttatta tttttttatag 180480 ttccttgagc aaaagaaata atgtccccat cttagtataa tattggaggt atataccata   180540
gaagtgaaca aaagaatata gtttcacaaa gaaagtgata attaaggcgg ttcataaagg   180600
gtcataaagc ttgtagattt tagaaatgtg ggggcatgag gatgtggaga gggtattcca   180660
ggatgccaga cagggagatt atggatgagt actaagatga gaactagaaa aagctgaggg   180720
gcaaaaggtc agaggaggcc acaagttagg gagtattagg aaaagaagt taatacttga     180780 caagtgccaa catggcttca cgaggaatgg gttgggcctt tttgagtgag gaagaggctg   180840
gtgaaagggt ggtggaggac actgctgctg ctgatggcat ggggtgtagg tggcaggaga   180900
ggcagggaca tgagctagga aactctccag ctatgaagtg atgagtctgg agtaatataa   180960
ggacagtagg ggtggagtgc tgaacttaag ggaggagaga aaaataattg gtatggaagt   181020
aggtacaatg caattttatt atttctgagc ctaaaaatgt gaaattttg attatttggt    181080 cagaccaggg aagtattttc ttttatgcta tctctgaaaa tgtatacact aaaaagttgt    181140
agtataaaaa ggttgtaaag cattaagtaa ttttagagga aacaataatt tggatatttt   181200
acatgcaatc atttatatgc aaatatatgt aaatattaca aaattattct ctatttgtta   181260
caaaccttaa atattttga ctgaggaata ttttattcat ctaattatag ctactttgtt     181320
ctaactaata gatattcttg aaaacaaagc aacactttt tggagacaga gtcttgcact     181380
gtcacctaga cttgagtgtg ttaccttgaa ctccagggct ccagtgatcc tcccacctca   181440
gtctcttggg taggtggatt acaggcccac actaccatgc ccagctgtat tagtccatcc   181500
tttcattgct ataagaaat accggaaact gggtaattta taagaaaat aaatgtaact      181560 ggctcacggt tcttcaggct gtacgggaag catagcagca tctgcttctg aggaggcctc   181620
aggaagtttt caatcatggt ggaaggcaaa taagaagcag gcatgttaca cgacgaatca   181680
ggagcaagac aaagtgaggg aggaggtgcc acacactttg aaatgagcag atctcatgag   181740
aacagcgcca agaggatggt gctataccgt tcatgagaaa tccaccccca tgatccagtt   181800
acctcccacc aggccccgcc tccaacactg ggaattacaa ttcaacatga gatttgggca   181860
gagacacaga tccaaaccat accaccagct aataccaaaa aaaaaaaaaa atttttttt    181920 taagacatgg tcttactatg ttctacaggc tggtcttaaa ctcctggcct caagtgatcc   181980
tcccaccttg gcctcccaaa gcactgggaa ttcagacatg agtaacagtg cctggccaat   182040
acttattttt aaacattctc taccataaac ttaggatctt gatttgttca cattgaacag   182100
```

```
attttttatta tacagattga atttataaga aaatgttgca gacattgtca aaaagggacg   182160
tccaaaccac tgtgatattt ataagcattt gggccacatt ttgatagaac tatacacgga   182220
gtgtgtgtgt gtgtgtgtgt gtatatatat atacacacac acattattta tatatatgta   182280
tatatgtata tatatatatg tatttatata tatatgtgta tatgtatgta cacattattt   182340
acctacctac tgtgtgagtg tgtgcatata tacacgcaca cacacacaca caaatatata   182400
tatttccctt ctgagacaaa gccaaacagc actgtatgct taaagaaaaa cagtcacact   182460
tcccacttat gtaatttata ttacatccag tcaccacacc agccaaactg ctttattgtt   182520
ttttgtttga catccaatgc taaagcataa tgcctgttgc agtgaaatat acatgagcaa   182580
ccctgagaac tcaatatagc ctcacgtgtt gccactgagt tgagttgagg agtcaagctg   182640
tagcaaaaag gtttgtcacc gggtgagtaa tggtgctctt attttctct gggtctcaag    182700 aagtgctctt tatgacatat atggcattaa ataaatatca gatatttgca catcctaact   182760
ttcctattgg tgaagtttct taaaagagag ataaagggcc attgtgtgat tgatagtttc   182820
aggtatattt ttgctgcaca gtcagtccga gtgtaccacg tagggcaaac cacgtaactt   182880
ctcagggcct tgactgtttc atttgtaaac cagagaaaag gacttgggtg acctccaaag   182940
acctttcaaa tttggagatg agtttgtgga agttcaaac agtttagaaa acagaactaa    183000
gacacccact ggcaccctg gaagcaagag agtgccaggt actatttgta atacaggaat    183060
gaaataccta attgtatgaa attgaattct aactgaacca gtttgttcag ttaaatttt    183120 tttttcaatt agagtgctta cttcagtatc taacactaga cagtaaactg tagacaaaag   183180
acctacagaa tttctgaatg gtatcaaatt caccacactt aaaactttgg gatgtctaat   183240
ttcaaccaac agctttcttt cttcataatg ttgaatatat gtgtatctat tttagctaaa   183300
tttaatatat atcaatatac tttgatagat atttttatata aactattaga ctatagtatt   183360
atgagtaaaa gacccaccat ttcccaagca attataaaga acgatcaaaa ttttaatggg   183420
ttgttagtat tatttctttta aagattgtga tactgataaa tatttggcca cattttaata   183480
gaattataca tgggatgtgt gtgtgtgtgt gtgtgtgtgt atatgtgtgt gtgtatatat   183540
atatggcagt agagatatat atatctacac acatctagat atatatatac atgtatatct   183600
atatatacac acatatatct gtgtgtatat atacatatgt atatataccct acatacatat   183660 gtacatatac atacatgcat atatctgtac atatatatat agtgtgtgtg tgtgtatata   183720
tatatatata tatatatttt tttttcctg agccaaaaca aaatactagg ttgtaatagc    183780
tgttctttca gaaggaagaa aaacaacatg tgctgaactc tgagtttgat gttttttgtat  183840 tttacttcct attttcatat cagtccattt atttattcag gaagaattta ttgagcatat   183900
attatgaaca cagcttttgc taaggacagg gtatgcagca gttatggcct agtaggagat   183960
atggatgtta aaaacaaaat gctcacaaat gcacatataa tcttaatact cattgtaagc   184020
tatgaaagca gagtgtgagt attatgagac catatgttgg gagatttttat ttggtattga  184080 ggatcaggaa agatacccct gaggaagtga tatttaattt gaaacctaaa gaaagcagtt   184140
ggccatggga agaaggtagg gaatgagatt cccaagcaat aggaatccaa tgtgtgaaga   184200
agctgaggga gtgaaagaaa gctagtgtgg tggcaggaag aaagagaaga gaatgggaaa   184260
gggcactaaa tgagtcagag aagtaggagg ggctaaacca tgtagggtcg tgtaggccat   184320
cttaaaggcc tgagtgtagt ggaaaacctt tgaaggtttg ttaaaaggtc aatgaaatgt   184380
tctaatttct gttgtagtga attgcttttga ttgctgaatg cgaatggatg ggtagagatg  184440
caagagtgaa agggaagaaa tcaattagga ggctcttgcc ctgctccaga taggactgat   184500
```

```
aattaatttt atttgggaag atcagggaga aagataagtc atgaatgact cccaagtttc   184560
tggattgaag aaatgaaggt accatacact gagatgggaa agcctagggg tagagtagct   184620
ttgagaagaa aggtagcatt tccccatttc ataaaacatg gaagaacaaa gaggctggat   184680
tcctgtttgt agacatacct tccaggccag aactgcatta ctacaacatc tttgcaagcc   184740
acattgcctt tcataactct gtgtcagtgt tgatgccgta acatctttgg ccttcccct    184800 accatcctcc cgcagtcctc catgataatg ccattattcc gtttcaaatt gtgtgcttcc   184860
attggatgtg tgagtctcct tgaaagttat aatgaggctg tagcccatat gaaatgcttc   184920
aactcaggtc ctgcatagga agaggaagct aatctctcca ggaactgagc ctgtggctag   184980
agggatggat aattgtttaa ataaagaata tgctgctgag tactgatggg ctctttatgt   185040
acccatttgg ctgctgctgc ccaaccttta atctttcctg agctttaaat aggaaggaaa   185100
aaatggtcca caaaggattt gagccatttt gctgtggtga tgaggagcac gggtttagag   185160
acaaacactc ctgtgtttga attccagctc ctactatctc ctagctaagt gaccttggac   185220
aagtcactta ccttctccaa cctgctgttt cttcatgtac gtaataggat ttacctcatg   185280
aggttgacat gaagattgaa agaggtaaca tatagaatga gcctgtccca ggacatggtt   185340
catgataagt ctgccataaa tgggagctat gtgtcccacc cttttggagg agataactgt   185400
tctgtagcag gtaatatatt gtttgatact tggttaaccc ttacaattat catttcctgt   185460
tcttctcaat aatgctagaa accttttatt taaagaacca caatataaaa tgaaaaatat   185520
ataaaaaaag caaatgggaa aattctattg gcaaggcttt ttaactttat atactaaata   185580
aatccaattg cttaaataat gaactgactc aagttctcag cactgcttct tgtttaattc   185640
tctttagttt ttcagaattc tccaataatg acctttgtct actctcttca gtttattcag   185700
aaattacttt tatttacata gaagtttgga agtggataca caaacatatc cctcacatat   185760
cttatgatcc tatgagtcat atactcatct cttatattcc ctctgtaaag caatgtaggt   185820 accttcagg aaggtgattt ttatgtaggt tgagaaatat cagcatggag gtcctagctg    185880
acctctctag agagtttctg agacatttga caacaacttt ttctttaagt catcagttat   185940
gccccggggt atgaaatttc taacatgatc ctcagtaaac ttggctgcct tgctgaggat   186000
actctccatc tgcctgagag acacagacac cattaattgg gaattgactt gacttgtgtg   186060
gttccttgtg gaccagatgg ccactaaata ttctcatttc aaggcaattg gtaaaaacta   186120
cacttcaaga aatttcattc ttaattcccc ttagtggatg ttattaacca aaggcaaaag   186180
aaaaaaaggg taaaaaaaat attctaaatg ttaatatcaa aaatattatt ttcaattcac   186240
cccaggcaca gagaactaag tattattatt gctattgcac cggcattccc caatgagaca   186300
gtgattttct tttaagacat ttttaaataa tataggcaga attaagtaga cggtgatctg   186360
gtaagtagat gtttcagggt aacagctgtg caatgctcca tgcagggaat tagattgtca   186420
ttttattcct taccaggaac atacattcag ttaaacaatt atttgacttc tgctcttcca   186480
ctgatttcta agttgaggct ctctcttgtg cctgtctgat cagataagta gagttgtgcc   186540
ttggtttata tgatgagataa atgtgtattt gaataagcat aagttaaaga aattttaaaa   186600
tcccttagga agctaggctt atcagagaaa tccaaggaaa tacattaaca aactaggaat   186660
ttgttctaac aggttaatta taactcataa acttattggg ttttttttacc ttttaatttt   186720 atattacatt tgcttataat aaggaatatt gctaggaata aaattttta atattctaca   186780 attaacaatt atctcaattt ctttattcta aagacattgg gattagaaaa atgttcacaa   186840
```

```
gggactccaa atattgctgt agtatttgtt tcttaaaaga atgatacaaa gcagacatga   186900
taaaatatta aaatttgaga gaacttgatg gtaagtacat gggtgtttct tattttaaaa   186960 taattttttct acttgaaata ttttacaata caataaggga aaaataaaaa gttatttaag   187020
ttattcatac tttcttcttc tttcttttt tgctatagaa agtatttatt ttttctggaa    187080
catttagaaa aaacttggat ccctatgaac agtggagtga tcaagaaata tggaaagttg   187140
cagatgaggt aaggctgcta actgaaatga ttttgaaagg ggtaactcat accaacacaa   187200
atggctgata tagctgacat cattctacac actttgtgtg catgtatgtg tgtgcacaac   187260
tttaaaatgg agtaccctaa catacctgga gcaacaggta cttttgactg gacctacccc   187320
taactgaaat gatttttgaaa gaggtaactc ataccaacac aaatggttga tatggctaag   187380
atcattctac acactttgtg tgcatgtatt tctgtgcaca acttcaaaat ggagtaccct   187440
aaaatacctg gcgcgacaag tacttttgac tgagcctact tctctcctca ctggtatggc   187500
tccaaccatc aggccctatc ttggtccatt taggctgcta aaataaaata ccaaagactg   187560
agctgcttat aagcaatctt tggaggctga gaagtcaaag atcaaggtgc cagcaggttt   187620
gctgtctcgt gagagcatac ttcctggttc attgatggtg cttctcttgct gtgtcctcac   187680 ataatggaaa gggcaagacc tctctggtgt ctcttttaca atggcactaa tcccatcatg   187740
agggctttgt tctcatgacc taatcacctc ccacatgtcc tacattctaa tactatcacc   187800
ttgggggtta ggattttaac atatgaattt gaggaggtgg cggggggggac acaaatattt   187860 agaccatagc atttcactcc tgacctccaa agttcatgtc ttcttcacat gcaaaataca   187920
ttcattccat cccaatagcc cccaaagtct taacttgttc cagcatcaac ttacaaggct   187980
aaagtccaag gtttcatcta aatatcagct aaatcagcac aaacagctaa atcaggtaga   188040
gtgggactta aggtgtgatt cctctcttagg cagattgctc tccaactatg aaattgtgaa   188100
atcaaaccta ttatgtactt tcaaaataaa atggtgaaac aggcacaggc tagacagtcc   188160
catttcaaaa aagagaaata gaaaagaaaa aaggagtgac aggtctctat aagtctaaaa   188220
ctttaaggct tgagaataat ttgctttgct ttgcctccag gctcactggg gtggtgtctt   188280
acctctggac acactgggt ggaggctcta tcctcatgga tttgagtgtc tcattctttg    188340
tggcaggtct gtgctccaat cccacaccta tggctccctg agtgtgcaat tgcatgcctg   188400
gtggttctac tggtctggga ttgcataggt ggcccagcct tcatagctcc actgggcatt   188460
gccctaatgt gggctctatg tggtgacctc accctgggc ctctacctgg gccctgtgac    188520
tccctgggtt cttgaaatct aggtggaggc agccatcccc ctacagttgt gctgagtgta   188580
gtgcatgagt gctggggtct gctagagcta taccctagggt ggtggagatg tatggcaatg   188640
gagtatgggg agctgatatg gtttgggtgt gtcccccaccc aaatcttgtc ttgaattata   188700
atttccataa tctccatgtg ttgagggagg gacctggtga gaggtgactg gatcatgggc   188760
atggttttcc catgctgttc atgtgatagt gagtgagttc tcacgagatc caatggtttc   188820
ataaggcagt tttccctgct cttgcaccct cttttcttgcc tgtcaccatg taagacataa   188880
ctctttccct tccgccatga ttgtaagttt cctgaggcct tcccagccat gtggaactgt   188940
gagtcaatta aacctctttt ctttataaat tacccagtct ctttacagca atgtgaaaat   189000
gtgctaatac aggagcaaag actgcagtgt gaggtggcaa tgtgaagtct gcaatgtgag   189060
gtggcacggg gcagttgtag cccctccttt gaaatctttc ttccctaccc caggcctctg   189120
cactctgaac tatgatggga aaggcagctt ggaagatctc caaatggctt tggagtcatt   189180
cttccattgt cttggactat aaattctggc ttctgtttag gtggctgact aatatcccca   189240
```

```
ctgtctgaat gcatagcacc tagtttctgt tgagatggct agtccatagt aatttactta 189300
tcaaatttgg ccacacccctt tgtattctct cctgagcagg ctttctcatc tttcacaata 189360
tggataggct gagaattttc caaattttga agttctgctt ccctttttgat caataattcc 189420
attttaaagt catttctcat cttgaatttt actatgagca gtcaagagta actaagctgc 189480
tccttcaact ttgcttggat atttcctcag tcaaacattc aatttcattg ctttcaagtt 189540
ctgccttcca caaaacacta ggacacaaac agctcagcca agttctttga cattttataa 189600
gaaggatagc ttttcctcca ttgtccaata acatgttcct catttccatc tgaaaaccca 189660
tcagattggc ctttaccgtc catatttctg ggaacattct gctcatgacc acttaggtat 189720
tcggtaagaa gatagtagct ttctctatag ctctcctcct ctctggagcc ctcaccagaa 189780
tggcctttaa ttgtccattc acagcaatgt aggcttttc tagcatgtac ctgaaaactc 189840
ttccagcctc tactcattac cttgttccaa agctgcttcc acattgagta tttgttacag 189900
cagtacccag atcccagtac caatattctg tcttagtcca ttggggctac tacacgatgt 189960
cttataaaca acagtaaaat ttattttttca cagttgtgga ggctgggaag ttcaaaatct 190020
ggtgccagca gattttgtgt ctggtgaagg ccttcttcct cacagatggc tgtgttctca 190080
ctgtgttgtt acatggcaga agagtgggca ggctagctct ctgggatgtc ttttataagg 190140
gcagtaatcc aaatcatggg tttagggtag agccctcatg acctaaatca cctcccaaag 190200
gccccacctc ctaataccag catctttgaa gttaggattt caacatatga ctttggcagg 190260
gggacagaag ctttcagttt atagcaaacc ctataggtag cactactttg tccttttccta 190320
atcaatttgc gtcaatgaaa catgaattag aagagaccta ggcgactcca ctatactggg 190380
attattccca gtataaatta tcatctctcc acaccttctc atctactccc tatctgagtt 190440
ctgaagctct ccactacaag aaggaggctt tggtttgact tgatatactt ctctgggaaa 190500
caggtttagc ataaaacagt gatgctcatt ctagaacacc tgcaaatgac aatagttttc 190560
tttcgaagtc gccaggaatc gtctgccttt gggtatgtgg ctgtgagcac tgccgggcaa 190620
aatgccatat gacctagatg aggcatatgc catcctttga agccattagg acattatata 190680
ggaaatatat taactaaaat ggaataaaat tttctaaata acaccttatg tttatccaac 190740
aggtggttca ttatacttga gagcattata cagaggaatt tgatggggag gagagctgga 190800
gaaattctcg aaattctggg tttctttaac agaatactct agctataaac ttataatttt 190860
aaaaaataag cattatatta aagaaaaggg aacataaatt attttgtttt attaaactta 190920
agtccaaagg tctggattgt ggcagaatag gatcagggga cctaaaatgt tgagcctcaa 190980
aggtcttctt agagaacaac tgtattccac tattagcgct tttggtcctt ttagcccaat 191040
ttctgtttat cccaaatgtt cttccctttt ctgccttcct tcacagtgga ccctgccagg 191100
agctttgaaa tgcctgtgag tgttaaacac ttacccattg agtgcccaac cttaacatgc 191160
ccctaataaa atgtacttag attaaccgtt ttcattatca aagttccctt attacccaac 191220
aaacacaggc gctttaaaga aaacattaac taaattgcaa gtgacacatt ttaagatctt 191280
tgatatgact tcagagaatg cactatagga acacaatgca atgggaggga aacttgggag 191340
ggaagacatt agcctttata aaatctgcaa gtattgccaa atcaaaataa aatttacagg 191400
aaagcaggat cataaatata atctaaaatc ttagaacctg tggttatgat tttaaatact 191460
aatacaatgc aaaattttta cctgtttagg ttttttatttc atcagttcat atttaggtat 191520
atacttttac tgttctcctt ttttataatt taccattcac aaagatgatg atgttagtct 191580
```

-continued

```
aactttaatg tcatgagtgc tttgagtagt agtgctaagt ttttgttgag tagtagtgtg   191640
cttttttgat tagtagtgat aggttttga tgagtaagcc tgctagcagc atacaaacaa   191700
acaagcaagt atcagcctag agaagcagaa aaggcatttg ggtttcaaag tcacaaggcc   191760
taggctttag tctaatacag ctgataatac aatttgtcca aacaggacat ttttgggtgt   191820
gtcaaacact aaactggaca ggacattatg acaaaagtgc aaagcaggac tttccggggc   191880
aaaccaggat gtatgtcatc tcactgagtc ctctctttgt ccttgccatg actagtatct   191940
ctagaggtaa atgaacagag taatgacaaa tagccagaca cctgaatctt atcccaacag   192000
cacctcctac ataattcccc attatcccaa atggaaatta aaatatata cagtgataat   192060 tccaggccaa gaaatgcttt atttctagct tggacttggc ttccatgtcc agtgtagaat   192120
cttatccttg ctgatctgga ctgtatctca tgaagccatg acttgtacct agttactagc   192180
tggaaggctt agaacaaaag ctggtccaga gagcctcctt tttccttatt tcctgggtcc   192240
acacctttac catggcagtc tgcctatcat ttgatggagg aatttaaagc aagtccaagg   192300
gaagggaaga gagtttctaa aatctagaac ttggatagtt taatttacct atcccaaaac   192360
agcttaggcc cagacagctt ctctccaaga ttggtgccaa actgaaatta ccagctgtgt   192420
agaccaaaga gaatttcaaa agaaactgaa tcccaagaga aaaaaaaag acttctggca   192480 ttgtggccca ataaattggt aggattgttg tgacttttca agtttacatg taaaatgggc   192540
ccagcgcagt gcctggcaaa tatgggtact aagtaaaagt aactataatc atgttttttt   192600
aatctggact tcacttggtc atcctttaaa tggtgtctga cagaatccta gttcttgtct   192660
cactttactt agtttccctg ggaaatttca tgtgtccttt tggctttaat taatatctct   192720
attttgatga cctccattat ctgcctattc ccagagcttt ccacctgata tctcagcaca   192780
tgaaaagcac cttatgtcaa taagtgagtt ccttccctgc cccaccacat acctgtcctg   192840
tgttcctaat tccactgaat ggcatcccat cctccagttt cccaaggcca agacctggga   192900
ctcatctttc actctcaagt tcctccacgg gtacccacat gtcacatcct gtcaatgctg   192960
tccctgggga gtatctgaaa tatattcact tttcttcatt tccacctgac accactatta   193020
acacttgcac aaatttctga ggttcctggc tcatttccct cattgacccc caatagttca   193080
ttctgctctt tgcagctctg gtgatctttc caaacccccac atctgatcac ttgtttcttc   193140
ccttcatatg gctccttaat gccttctgga ctaagtccac actgcttaag gtggcttacc   193200
aggtccttca tgattttgtc tttgtttggc tttctacact cactgcccaa cttcccctta   193260
cttcccatga ttcagttata ctgaatttct tggttctct aaagcacatg tgctttctgt   193320
tctgcagagg ctttttgtt cacttgctat tctctacctg ggaaactccc ccagcccttc   193380
actgcctcct tctaccatct ttcaggcctc tccttacaca tcacttcttt ccaaaaatct   193440
gccttgacac tccaggtctc ggtttcctag gtgtacccta taactccacc cctttcatag   193500
catttctcac tctggctgga gatttacctt ttaacttgtc catgtccccc actggagtgg   193560
aagttcctgg aggtcaggga ttatatccta ttaattgttg tatttccagt gcctagagta   193620
gtcttgcata catggatggt attcaataaa tattggttga atgaataagg agttctttca   193680
tttcatatgt aatagatcat ggaaatagcc ttgtgattga tacacagcag gtattaccat   193740
cctcacttta gaatgaggac tcagagcctt gagatgtctg agggccttga ctgggacagc   193800 tgcagatgc aggagcagag ctgcatcacc cctgtgggct atctcagggt tgtctgtaat   193860
ctaagtacaa tgtctgttga ttttggactg aaggcttttt gggtaattgt ttgctttttc   193920
aatacttata aaatagtttc catccttact cattgatagt aaggttagtt attttagaaa   193980
```

```
acaagctaaa tagcagaaat agtggccttt taagttgaaa atttaccctg aaaaatctac   194040
agagtagcaa acagagtatc aaaaggagtt gactgtatct atttttataa ctgccactta   194100
tggattattc agtaaaacca caattcactt ttatgatttt ttttcatgtt tctctgtcac   194160
aagagcaaac tcttgctcca taataacatt ccagaataca gcaatagcaa aagtcaacat   194220
tttgaatcct ttacaaactc ttagacattt ttttttttt agtttaacat gttacaaaac    194280
aaaatttctt cttttttcac agcagtttgg gaagtacata ctatttatta gctcatcagc   194340
atgaagctgg aaaattcttt ttcctaaagt tctttatatc tacaaactgt tgatgttttc   194400
atttatttat ttttaatgct acgttgtaat gaaaatcatt ggaaaacttt agattctagt   194460
aattttgaag tcttcttagt ttggacagga ctgagctaaa gtttgtactt tttttaattt   194520
attgaaaaat ggtttctaat gatagtatta acaagattat attgggggca ggacgcagtg   194580
gctcacactt gtaatcctag cactttggga ggccgaggcg gttggatcac ctgaggtcag   194640
gagttcaaga ccagcctggc caacatgtag aaatcccctc tccactaaaa tacaaaaatt   194700
agctgggcat ggtggcaggc actgtaatcc cagctacttg ggaggctgag gcaggagaat   194760
tgtttgaacc tgggagtcgg aggttgcagt gagcccagat cgcaccactg cactccagcc   194820
tgggcaatag agcaagattc tgtctcaaaa aggaagaaag aaagattata ttggggatat   194880
atatgtgtgt gtgtgtgtgt gtgtgtatat acacacacat atatatatac atatatacat   194940
atatatacat atttaaagga taaggattc tgctgccaca gatcactaaa tcagatgatc    195000
tctagcaatt tcctgtttgt ttgtttttg cccatagtgc ttatctcttt gaacagtaat    195060
tttccactta ctatttttct cccctttgg accataattt cctttaaggc agagcctcct    195120
gttactcatc tttgaatctg ggtctgtca gagtacctag aatttaataa actctcatta    195180
agagccagtt gaaagaatat atgactaagc agtcatttac atccaaaaga tccgtaggag   195240
aattcttatc agcacatgtg attggtaaca ataactttgt acttttcaaa aacaattact   195300
aatctatctt gctttccatt atctcaccaa aacctattag catgtctggc agaaaataga   195360
tacttaataa atttcttaaa tgtttactga cttcaatttt aagttttatt aactatgttg   195420
acttttctct aatgaagatg attctaaaaa gcttttact atacttcaca gtgaataaaa    195480
cagtgagata ggaatattgc aaaatgtccc ctgtgttggt cagtcttagt gtcattcatt   195540
ttaaaaattc tgttctctaa atattgacag ttatatataa atttatgtaa ttgtttactt   195600
ctaataaaga atttcatctg gggaaaaaca tactttgctc agctctttgc cacaagtgca   195660
aagtctaaga cagtcaaata gctttcctag tacggcctta ggaacttagt atatgactgg   195720
tgtgaatcta gagggagcat actgcattct gaccaaaatc tccaccctgt tactatggcc   195780
atcactaact tcgcagtatt gcagtacttc ctgctagctt agttcccaag gcaacttgtg   195840
aaggaaaatt tttacaaagc tgttgtcaca caaaggtagt gtttcagttc ctgagcccat   195900
gtccttggag ttgcccaggc tccaataata ctaataatta ctgtacatta ggtacttacc   195960
atgtgccata ttctgtggga gccgctttcc acaaattatc tctggtaatc cttgtaacaa   196020 cccctttgaca tcaatattat tattttctcc attttttac atatgagata aatgagactt    196080
aaaataatgt gcctgatatc atcagcaaat gagctgagga gggcagattc aaagctgatt   196140
gtgtttgact ctagagctgc agtcttaagc cagacctttt cttgctggtt aatttttactg   196200 aaaaaaaaaa aaaaaaaaaa aaaccctcaa atactgctga ttgatctaaa gtactaacat   196260
ttctatcagt gttagggaaa ttttaatttt ataatttgat tttgtgagaa atttatagca   196320
```

```
tcttgaatac tcacatgcaa agtgatatgt cttagataac attttacaat ggcagagctt   196380
aagccagtgc tcagtcattc attcatcctc aagttttgat tcatttatca ttcatcaaaa   196440
ctctgttttg tttggccacc cacattctag gagctcagta catatttgat aaatgaatga   196500
attgttgagg ttgacagtta cccaggactg cattaggaa cacagagctg aagagcacgt    196560
ttttaccctc aagaagctta cagtctaacg agggaacttg cacaaatact actatcacta   196620
ggtgcctggt tgaatggctt aagagatgat cagggatatt cagaaggata tgtcaggctc    196680
agcaatggca tcacttgaga gcatcaaggt gtttagggaa ctacaagatg tttggttctg    196740
ctgggaataa gagtgaaggg ggctccattt ggatgcctca tacaccaggt gagagatctt    196800 agatttatt ccaccaggag gagaactacc ataggattta aaacagaaat gatatggtca     196860
aacctacatc ttaggaagat ccctggggtg tttgtatggt ggacttgcaa tttgactaat    196920
tgagatttgt aggatgattc ttaagagatg atgatgaccc agactgggat cactataata    196980
gagttggtaa ggaggagaat gatttaaaaa gtagttggaa gaattctagg gatggagata    197040
aacatttgaa aattattaac ttataggtgg tcatcaatac cctgaaaatg actgggatct    197100
cagaggagag tctggagagt tggaaatgac aaagactaat attcaagggg gcaggaagag    197160
ggagagttgt tcacacatga caataggaag aaatggccat agagtgtgtg gtttctctca    197220
agccaaggaa tagatgtttt aagaaaggaa aattcttgtg gtgggaagca gtagagatga    197280
cagatacaca ttaatttctt gagatttcta gatgactaaa tgggcagatg ttgaatgata    197340
gctaaaggag aacccagaaa caagggaggg attttgtttt tgttttttaa aaaagataga    197400
ccatagcagc ttcatagact gaaacaataa aaaagttgaa ggcacaaaga aagacacagg    197460
tcctctaact ccctgcccag tgcccttat tcatattctc agcacttgta tttctaagtt     197520
ttatgtttga gtcttcgggg atacatcaga gtagtccccc ttgtctaata aatgtgttta    197580
catttcctgc cataccagaa accctcca acttaatg aatttctaca aggtgagatt        197640
actttaatga gaaaccaacc aaggaaagga gtatcatctg caatatactt tcaaatgttt    197700
tttgcttgtt tgtttcttgt ccagctaaaa aaaaaaaaa aaaacaagcc attggtccta    197760
acacaacttt catattctac cccaatatca aagaggctta aaatctcctg gtcgtgtgat    197820
gggcacacag ttaattttt gtgaacaaac acagtgttat gggccatttc tgaatttatc     197880
tctgaaatca taagattctt tctgagccat tatctcattc tatattacag tcaggtggag    197940
cccatcttac ctcctcatac taaattctag acttctcaag ggcaggagac aatcatctgt    198000
atatctcttt ggccttcata cactcaggag tacttgccaa aaataaacat ttaatgcaca    198060
tttatttgaa taattgataa gatccaatac ttcaataact ttgtcatatt tttatagaat    198120
gggtttctat atctcatttg catttttcaaa ctttactttt actgtctagc tttaaaaaa    198180 aagcctttga ctctaataca gccctcatat tctaccccaa tatctaagag ctttatatc    198240 tcctagtgtt gtaccactat tttaactcca gtattttta cttcatagtt ttacctattt     198300
gttacagtta gttttatga attcaagaga tgaatagcaa ttttccatat gtaatttaaa     198360
aaaccccaca gttgactatt ttatgctatc ttttgtcctc agtcatgaca gagtagaaga    198420
tgggaggtag caccaaggat gatgtcatac ctccatcctt tatgctacat tctatcttct    198480
gtctacataa gatgtcatac tagagggcat atctgcaatg tatacatatt atcttttcca    198540
gcatgcattc agttgtgttg gaataattta tgtacacctt tataaacgct gagcctcaca    198600
agagccatgt gccacgtatt gttttcttac tactttttgg gatacctggc acgtaataga    198660
cactcattga aagtttccta atgaatgaag tacaaagata aaacaagtta tagactgatt    198720
```

```
cttttgagct gtcaaggttg taaatagact tttgctcaat caattcaaat ggtggcaggt    198780 agtggggta gagggattgg tatgaaaaac ataagctttc agaactcctg tgtttatttt    198840
tagaatgtca actgcttgag tgttttaac tctgtggtat ctgaactatc ttctctaact    198900
gcaggttggg ctcagatctg tgatagaaca gtttcctggg aagcttgact ttgtccttgt    198960 ggatggggc tgtgtcctaa gccatggcca caagcagttg atgtgcttgg ctagatctgt    199020
tctcagtaag gcgaagatct tgctgcttga tgaacccagt gctcatttgg atccagtgtg    199080
agtttcagat gttctgttac ttaatagcac agtgggaaca gaatcattat gcctgcttca    199140
tggtgacaca tatttctatt aggctgtcat gtctgcgtgt gggggtctcc cccaagatat    199200
gaaataattg cccagtggaa atgagcataa atgcatattt ccttgctaag agtcttgtgt    199260
tttcttccga agatagttt tagtttcata caaactcttc ccccttgtca acacatgatg    199320
aagcttttaa atacatgggc ctaatctgat ccttatgatt tgcctttgta tcccatttat    199380
accataagca tgtttatagc cccaaataaa gaagtactgg tgattctaca taatgaaaaa    199440
tgtactcatt tattaaagtt tctttgaaat atttgtcctg tttatttatg gatacttaga    199500 gtctaccccca tggttgaaaa gctgattgtg gctaacgcta tatcaacatt atgtgaaaag    199560
aacttaaaga aataagtaat ttaaagagat aatagaacaa tagacatatt atcaaggtaa    199620
atacagatca ttactgttct gtgatattat gtgtggtatt ttctttcttt tctagaacat    199680
accaaataat tagaagaact ctaaaacaag catttgctga ttgcacagta attctctgtg    199740
aacacaggat agaagcaatg ctggaatgcc aacaatttttt ggtgagtctt tataacttta    199800
cttaagatct cattgcccctt gtaattcttg ataacaatct cacatgtgat agttcctgca    199860
aattgcaaca atgtacaagt tcttttcaaa aatatgtatc atacagccat ccagctttac    199920
tcaaaatagc tgcacaagtt tttcactttg atctgagcca tgtggtgagg ttgaaatata    199980
gtaaatctaa aatggcagca tattactaag ttatgtttat aaataggata tatatacttt    200040
ttgagccctt tatttgggga ccaagtcata caaaatactc tactgtttaa gattttaaaa    200100
aaggtccctg tgattctttc aataactaaa tgtcccatgg atgtggtctg gacaggcct    200160 agttgtctta cagtctgatt tatggtatta atgacaaagt tgagaggcac atttcatttt    200220
tctagccatg atttgggttc aggtagtacc tttctcaacc acttctcac tgttcttaaa    200280 aaaactgtca catggccagg cacagtggct tacatctgta atcccaatac tttgggaggc    200340
tgaggtgggg ggattacttg aggccaggaa ttcaagacca gcccaggcaa catagtgagg    200400
ccccatctgt ctttattaaa acaaaacaaa actgtcacag cttctttcaa gtgatgttta    200460
caaattccct atggtttagt cacaaggaag ttctgaggat gatgtatcac gtcatttctg    200520
ttcaggcttt tgagcctcct ggaggtaaat ggtttcctta ctgaaggctt gttattacca    200580
tgattatcac taagcttgaa gtaacaaatt aggggggcag actcacaacc tcttgccctg    200640
ccatggacaa gttcaagaat ctaagtaaag tcctctattg tctgatcttg gatttgctca    200700
acctgaacaa gccaaggagg tgtattaaac tcaggcacat cctgaccaat ttggaattct    200760
taagcttcag atcactgtgg aagaggctca actcttatg gtgctgtaga cttacgctca    200820
ttttctaggt aatttataag ggacctaata ttttgttttc aaagcaactt cagttctact    200880
aaacctccct gaagaatctt ccagctgctg agtagaaaat cacaactaat ttcacagatg    200940
gtagaacctc cttagagcaa aaggacacag cagttaaatg tgcatacct gattgttcaa    201000 aatgcaaggc tctggacatt gcattctttg acttttattt tcctttgagc ctgtgccagt    201060
```

```
ttctgtccct gctctggtct gacctgcctt ctgtcccaga tctcactaac agccatttcc  201120
ctaggtcata gaagagaaca aagtgcggca gtacgattcc atccagaaac tgctgaacga  201180
gaggagcctc ttccggcaag ccatcagccc ctccgacagg gtgaagctct tccccaccg   201240
gaactcaagc aagtgcaagt ctaagcccca gattgctgct ctgaaagagg agacagaaga  201300
agaggtgcaa gatacaaggc tttagagagc agcataaatg ttgacatggg acatttgctc  201360
atggaattgg agctcgtggg acagtcacct catggaattg gagctcgtgg aacagttacc  201420
tctgcctcag aaaacaagga tgaattaagt tttttttttaa aaagaaaca tttggtaagg  201480
ggaattgagg acactgatat gggtcttgat aaatggcttc ctggcaatag tcaaattgtg  201540
tgaaaggtac ttcaaatcct tgaagattta ccacttgtgt tttgcaagcc agattttcct  201600
gaaaacccctt gccatgtgct agtaattgga aaggcagctc taaatgtcaa tcagcctagt  201660
tgatcagctt attgtctagt gaaactcgtt aatttgtagt gttggagaag aactgaaatc  201720
atacttctta gggttatgat taagtaatga taactggaaa cttcagcggt ttatataagc  201780
ttgtattcct ttttctctcc tctccccatg atgtttagaa acacaactat attgtttgct  201840
aagcattcca actatctcat ttccaagcaa gtattagaat accacaggaa ccacaagact  201900
gcacatcaaa atatgcccca ttcaacatct agtgagcagt caggaaagag aacttccaga  201960
tcctggaaat cagggttagt attgtccagg tctaccaaaa atctcaatat ttcagataat  202020
cacaatacat cccttacctg ggaaagggct gttataatct ttcacagggg acaggatggt  202080
tcccttgatg aagaagttga tatgcctttt cccaactcca gaaagtgaca agctcacaga  202140
cctttgaact agagtttagc tggaaaagta tgttagtgca aattgtcaca ggacagccct  202200
tctttccaca gaagctccag gtagagggtg tgtaagtaga taggccatgg gcactgtggg  202260
tagacacaca tgaagtccaa gcatttagat gtataggttg atggtggtat gttttcaggc  202320
tagatgtatg tacttcatgc tgtctacact aagagagaat gagagacaca ctgaagaagc  202380
accaatcatg aattagtttt atatgcttct gttttataat tttgtgaagc aaaattttt   202440
ctctaggaaa tatttatttt aataatgttt caaacatata taacaatgct gtattttaaa  202500
agaatgatta tgaattacat ttgtataaaa taatttttat atttgaaata ttgactttt   202560
atggcactag tatttctatg aaatattatg ttaaaactgg gacaggggag aacctagggt  202620
gatattaacc aggggccatg aatcaccttt tggtctggag ggaagccttg ggctgatgc   202680
agttgttgcc cacagctgta tgattcccag ccagcacagc ctcttagatg cagttctgaa  202740
gaagatggta ccaccagtct gactgtttcc atcaagggta cactgccttc tcaactccaa  202800
actgactctt aagaagactg cattatattt attactgtaa gaaaatatca cttgtcaata  202860
aaatccatac atttgtgtga aactttgttg ttttcagatg cgttcacttg tcatgtttca  202920
tcagtctctc actccaattt ctaagcttca tggaacatga aacacgaatc tgtcttttag  202980
atatagcctc ttttgagaat tcacatgaat tagaacacac attttttagtt atctgtttaa  203040
actatggtaa aatatacata acataaaatt ttccattttta accatttta agttcagttc   203100
agtgtcatta ggtacattca catggttgtg caaatatcac catcatcctt ccacagaatt  203160
tttttcttgc aaaactgaaa ctctttttac ccgttagtca ataatcccgc atttatcttt  203220
cctctaatgc ctggcaacca ccattttact ttctgtctct gattttgact actcgaagga  203280
cctaggagtg ggatcataca gtatttgtat ttttgtgctt attttcatcta gcataatgtc  203340
ttcaagcctc atccatgttg caacatgggt caatttttctt ccttcttaag gttgaataat  203400
attcattata gagtagtccc ccccttatcct tggggaatat gttccaagac ccccaatgga  203460
```

```
tgcctgaaat cactgatagc actgaacctg attactgtgt ttattcctat acatacacac   203520
atacatatga taacatttaa tttataaatt aagcacagta atagattaac aacaataatc   203580
ataaaataga acaattataa caatatatta tgacacgagc gatacaaatg tggtctctct   203640
ctttctcaaa atatctcatt atactgtgcc acaggtaact gaaaccacag agagcaaaac   203700
cttggatagg gggaccactc tataaatatg taccacattt ttcctcaccc attcatccat   203760
cactggctac ttggtttgct tccacttttt ggatatagtg aataatgctt ctataaatat   203820
gggtgtacaa atgtttcttc atgtccctgc tttcattact taggatatgt ttgaagttat   203880
ttttattttt aaatggaggc ttatagaaca caaaagattt atattctgca agtgtccatc   203940
tatttctttt aaagcttatt caaaaagtgg tagctatctc atagctcttg gtaagttaaa   204000
aatcttcatc aacgaaaata ctatttctgc gttggcacct gcatggattt tctttgtcca   204060
aatccctctt tttaattgat gaggcttctt tagttccttt ttttcttcct tgttgagctt   204120
cttcatgaaa tgtgcagttg ctagcatgtg gtggacggac tgcagatccc tactgaatgc   204180
caggccctcc ggccctgtgt tctctttctt ggagaggttt gttttcacac gtaacccaa    204240 gagggcagtc tcagagcgtg ttctagtcta gttctttttt taaaattact aaactttatt   204300 tttttaggg cagtttagg ttcccatcaa aattgaacaa aaagtatgga gagttcacat    204360
ataacttctc catacatgat agcctccccc attcaacatc ccacactaaa gtagtacatt   204420
tgttacaact gtgaaagcaa atagaatttc aagaccccaa gctcactatg ccaaagggca   204480
agttaagctt cagagctgaa ttactcaata ttgccttcct tttgttccct aacagccgta   204540
acttcacaat cttgtgtgat agcctcatcc ataaccagg ttcccacaat gatagaaggc    204600
cacatatctc cccaaatgac ctccctcaca attgtgccca aggaaaatcc ttgtgagacc   204660
ctatctttta ggatacatat ccctcctata aaatagccct aaaactgagt tatgttgaat   204720
ttcaccctga tgatgtcaat taccagcttg tcttcatagg cacaggacgc gggcaagacc   204780
agaaatcatc gtgctgtcta ccctgcaatg aacacataat tgacttttcc tttactccct   204840 cttttacct ataaaatttg gatttactga acactaacca aagcctcccc tgaatagaac    204900
catttgcctc actgcctacc ctctatcctc ttttccttct ccgtgtttgc actttactct   204960
ttaaatatta aagttcccaa accctctttg gaaaagcaca ggtcacagat gctcctctgg   205020
cttgtgttct tcctgggtgc atctgcaaac tttggctaaa caaacctcta tcgattaaga   205080 caccigcctc agtcactttt tccttaacac aaccaatgaa cctacattga cacattatta   205140
ttgcccaaac acaatagttt atattagggt tcattattgg tatttttacat ttcatgggtt  205200 tggacaaatg tgtaatgaca agttaactac cattacagta tcttacaggg tagtttcact   205260
gcccaaaaaa tactttgtgc tctgcatatt cattcccctt tctcccctaa cttttggcaa   205320
ccactgacct ttttattgtc tccatagttt tgcctttacc agaatgtcat ctactagaa    205380 ttacgcagta tgtggccttt tcagattggc ttctttcact tagtaaatatg catttaagtt  205440 tcctccgtat cttttcatgg cttgatagct catttctttt tagtgctgaa ttatattcta   205500
ttgtcagatg taccacagtt tattcattga cctactaaag gacatcttgg ttgcttcaac   205560
gttttggcaa ttttcaataa agctgctgaa acatctgtgt gtgggttttt gtgtaaatat   205620 aagtttttaat ttctttgggt aagtaccaag gagttcaatt gttggatcat atagtaaaag  205680
atgtttcgtt ttgtaagaaa ctgccaaaact gtcttcaaag tggctgtacc attttgcagt  205740
cccaccagta acgaatggga gttgtggttg ctccttatca ttgccagcat ttggtgtcct   205800
```

```
cggcgtttta gaatttggcc attctaatag ttttgtggtg gtatctcatt gttatttcaa    205860
tttgcatttc cctgatgaca tgatgtggag tatgttttca tatgcttatt tgccagctgt    205920 gtatctttt tggcaaggca tctgttaagg tctttggccc gtgttttgat caggttgtgt    205980
cttgttgttg agttccttta ctggatttct tttgttagca tggtataact ttatccatcc    206040
ctttattaat ctacctgggg ctttaaattt aactaggttt cttatagaca tcatgtaagt    206100 cttgctttt gattcactct cacaatcttt gttttttagc tcttgacatt taaaatgatt    206160
attgatataa ttggattaat atctaccata tttattcctg ttttctgttt gtttcctttg    206220
ttctttattc ctattttac tttccccatt tttttgcctt tttaaatttt attgagcatt    206280
ttacaggatt ctattttctc accttcttaa catagcaatt cttctttttt taaactttt    206340 tagtggttgc cctacagttt gcaataaaca tttacaagtg acctatgtgc ctttaaataa    206400
caatattcca tttcatatca gtgcaagtac cttaaattac aaatttctag cttctgtccc    206460
ttttaccatt tcaggtattc atttcattta tatattagct tatatatatc cctcacacttg    206520 attttttcctc atatgagatt ttcttctc tttcccattt aaaaaaataa aataaactat    206580
tatagccaca gacttctat ttttatttgt tttctgtatt gaagtcttga ttttgggct    206640 ttacttgtcc ctgtctatgc ccactcctat ctgacacaca ctttcttaat ttatttccta    206700
gttgtttcac tttgttatc ttcattatga ggaaaaaaag ccaaaacctg aaatgaatat    206760
gcttccttcc agtaaccagg gaccttccat ggttgggaaa ttgttaccta ttcgagtgaa    206820
aggctaataa aaccccccaag gtaaatattt tagtacttca ctaaagaaag aacctcaaat    206880
actatgtgga agacaatta aaatgaggtt taaagagctc aatataaaaa cctgtttgac    206940
ctgttaaaac aggtgtggac aatcacaatt ccctatttaa aaatacagtg aaaaaaccta    207000
caaatgcaag acaaatacat tggagcatga gaactccaaa ttgttaggtt aggaattaga    207060
agctgttccc agtgtgtaga gctaagagac ccaagtcatt gtcagttgac agggagccgg    207120
gactcaatac ctgtgtactt tctcagagaa aggagaggtc ttggcaaaat tttgggttta    207180
tccttaattc catacaatgg gaatattcaa ttgctctttta atcactcagt attgatagg    207240 acagggggca gagaaattct aggcagaaaa gggcgggacc ctggtgaaac cccaccctca    207300
atccgaaaaa cctgaaactg ccaccgaaag tgagaacttc tatccctgtt ttcccactcg    207360
aatgttgcct ttttctaaac tacccgtggc ctgctccacc cccatccttt gcctataaaa    207420
accccagact cagttggtag atgggactat aactggacat tggagagaag tggcttgact    207480
tcagagcgac agcttgacag catactttgg agaagaatct gagaggagaa ggcaagactt    207540
caggggaaga ttacctatct gccctgtccc ctgttcagct ctatttccca ctgaaagcca    207600
ctttcatcag caataaaatc cctcatttac catccttcaa ttcgttcatg tgacctcatt    207660
ttttctggac gccagacaag agcttggagg ccacgagtat ggatacaaaa ggctgtcaca    207720
ctggctgttt gcccttgctg gtggagggca gctgcctcac atgaaaaggc aaagagctca    207780
ctgagctgtt aacacttaag ccttccgcag acggcagagc tgaaagagca ctgcaacaca    207840
ccctctgggc ctcaggctct caggcactcc tacctggttg cgccgctggg cccgcacaga    207900
gtttgctact gccggcacct gaaagcggtt ggctggttcc tgcactcgct cgttctggtt    207960
cctgcactta ttcattcgca cgctccctcc cacaaggggt agacggggcg ggatgggtaa    208020
atgaggcacc cctgtctcaa gtcccgtgaa ggcgtcaggg aaataatctg cttcagtttc    208080
tctagttgta aaatggttaa gaacattatg aaggtggtc aacaactta taagtgaata    208140 tgctaatgct ggccttaatt ctaaaatgct acttggatca aaagttatga ttcagttcca    208200
```

```
atacatcttc tattcattga agtacagaat ctgtacacaa agtacaattg tatcttcaaa  208260
aactgccacc ttgtggagat ttggttttat tgttaagaca gccagtgcca acaacagaaa  208320
tgagtacaga gcctcacata ctaatgtaag tgaatctcaa agacatttta tctttaagcc  208380
attttgaaaa gtagaaatta agcctgaata gttttggggc acaaattgct ctttaactct  208440
cttctttccc attcacctt  gtcactgatg gaataataga aggagcaatc tttatcagca  208500
atggcagatg tgctgataaa tgaaaccaaa actgaattga caaatattga cacaaatact  208560
tatagaagca atttaaaaat ctaccttgca attaatcctt atgaaattta agtcataatt  208620
tactaaaaat tataatataa agaaataaac tttctctgtt ttattaaaag aaaggatcaa  208680
tacatttggc cacaattgat tggccataat ttttgtcaat gttctataag ctaattgaaa  208740
ataagactat tttaaatata attatctccc ttctcctttg cctttcatt  ggcagcaggt  208800 gccatgggct tattcatatt ctaaaagaga agttgtgtga gcaaatttgt catcataggc  208860
aatcctcttg taaggaaaaa attatgattt gatttttatt ttctcttatc tcctaattgg  208920
gtcagatact ccagtgtcct cgggagcca aaccaggagc cagtgtgtcc ttacacaaac  208980
acagcttcct tcctgcttgg agctcacacc aagcatttgc atttgaacca gcaatgttg   209040 acaggctatt gagccacaga agttaaacat tccaagtgag cctgagacga ccattacatt  209100
cttttacatt ttctggtcga ttaaaatttt aattgtttaa aatttcaaat agatacaaaa  209160
atagacatag agtataataa acttcacacc cctgtcactg aacttcaata gttatcagct  209220
cacagtcaat cttatttcat ctatgctccc tcatgcttcc ctcctatatt attttgtgca  209280
aatccaaaca gcatataact ttagctctat gtgtctctaa aagacacggc tttctctatc  209340
attctttttc ttttgaaact gatccatatt acctttacca gaactagaaa acagtcatc   209400 tttaatatcc tcaaatattc actccatgta taaacgtcat tgtcagtttt ttcccaaata  209460
taggtagtcc tcatgttgca cattaatatg gcactatgaa aatcaccatg caagataatt  209520
taaataatta atgggggaaa aattgttcca tgacctttaa aaatattaaa aatttaaaac  209580
tttcttactg ttggttataa acaatagga cacaaaaata gtgaaacatt tagtaagtaa   209640
tttaaaacat tagaaacact gagaattaaa atgtttcttt taaactactt atcaagagta  209700
gtttgagcaa tacttggttt cttttggtta tgtaacttgc aatatgaaga aagcatcttt  209760
tctatgcctg ggcaagttgt catactcctt tctaatttag gaccagcttc caacattgta  209820
tccttcgtga cttcaatgtt gtaaaatatc tccaagagtt tgtttaaggt aatgattttt  209880
gctgatgtca cctcctctgg ggcatctgac aggcattcct gctaggtcaa cctatagcag  209940
agggtggaag ggcccagaga tggcaagaga gaaaggggg  gaaccttta  gaggtgatta  210000 ggctatgagg gctctgcttt catgaatgga ttaatgccat tacggcagtg agttcattat  210060
aaaaggacaa gtttggcccc cttctctctc tttcttgctc tcttttggcc cttttgcctt  210120
ctgccatggg atgacacagc acaaaaaccc tcaccagatg ctgacccctt gatactggac  210180
ttcccagcct ccagaactgt aagccaacaa atgtgtgttc tttataaatt accccagctg  210240
tggcattctg ttatagcagt acaaaataga tcaagacaaa gggggattgc aggcaggaag  210300
ggagcccctg acctcttagt ttcactcatc tggaattag  ccactacaac acagagctgg  210360
ggcttgaggg gataagaaat gctattgacc tgcacttccc agggtgatag tacagttaca  210420
ggctgtaaac tcaagggaga gggaatgcca tcatcttggc cacatcagcc tggagtagag  210480
cttctatcac accaagttgg gggagggaag agggagcagc ttgtgactga agtgccataa  210540
```

```
acttttgttc ttactgagat tagtatattt tctggaataa acgctgctgc ttttgctgta    210600
tgtgcttagg gccatttcca gagactttaa atgattgata attgttacca gtaatggtta    210660
ttttgatggg tagttggtcc acagagctcc tcaccttgct gttctagaaa ttgtctttta    210720
gcttagtatt aattcctgaa tttttcagtt tttctgatct tttacctcca ggatgactct    210780
ttgaaacaac tctaaattat tgactgaaac ttttatgtat aattctcatt tgttcttca    210840 cacaatctct gtgaaggagg ttctaagaac taagaggctt agagagggta aggatcttcc    210900
cagaaattac acagcactcc cagatttgga acctttagaa agtttatata cttattggaa    210960
aacttagctc attttaatc agagggaagt cattttacag tgccccatac agggagtcag    211020
ataactactt cctagttagg ttttcctctc tatagagagt caaccagccc tgctgtactt    211080
tcccgtggga tctgaaactg cagaaatcta ctgagaaaaa cagaatgctc acagcaggat    211140
aaagctcatg ttttctagag ctactaagat tcaggcttat gcctctgtgt ttgattttt    211200 aatagtcttg ctaatgtcaa agtgattcta tcttacacac cccaaagtct gtaaaggtat    211260
aataacaagg ggtgagattg tcttaaatct gcagtttctt gatctgttta gtgggctact    211320
ataggttact gcaggacctc tcaaggtttc tagtatgcaa aggtgcattt tgactctgta    211380
agagtggaat atcatatgta atgtttctca attgatttgt ctacataacc gtattttctt    211440
gtgccattta tatcctgtgt tttggggaag gttggcctag aacatttatt ctaaaaggaa    211500
agggcatggg aaattcttac cattggcagt gtcggggagg aaaaaatgca tacttcttac    211560
ccatttagtt tattttgcta gtttacaaat taaattgaga taagacagat taataggaga    211620
aaatcaactt taattatgtg tgtatacatg ggagtcccac aaaaatgtaa gactcaagga    211680
agcagccaga tgattgagac ctatatatta tcctgagcta cagaaaggga taagggtttg    211740
gggcttttgc ggggttgtgg aggcaaattt tgggaaggcg aggagaggaa atgtatgatc    211800
aataaatgtt gccttgttgt gcagataaaa gtgtcttagg tgataaagat gtttccaaag    211860
agtagttctc ttcatggtac agatatttta ctcatgatca tttcctttat agatataaat    211920
ttcctttacg aaagggggaa ttttatttta tgtagttagt ggagaagtcg gtaaagagct    211980
tttcctgtat tggctgattc tcagttttt ttagctcaaa atgatcaata tgccgaagtg    212040
gcatgttctg aaatgacata ttctgaatcc tttcagctgg aatatatttg tatatcaaca    212100
gtgtttccat ctgtcagccc ttagggtctg cttatggaag atataagcac ctggatgacc    212160
atgacgaaaa tctggagatt tgagaaaac actggtgcaa ggctccatcc aaaatcaatt    212220
aaagaagaat cttggaagat ggggttaggt cactgatagc ttgaaaggca tcccaggtga    212280
ttctaatacg cagccagttg agaagcacgg atttttttat tgggtttttc aggctggctg    212340
aaagaactgc gatgctcagg aaaccagggg tgcctggcag gagtttgacc ggggagactg    212400
aagcctgtca acagggacaa gaacggtagg ctggtgcctg gcacctgagg gtacttcaga    212460
ggtgctcatt aaaaaagagg aggggacatc aagcagagaat tcttaatcag acattcaaca    212520
aattgagggt cgtctatgtg ttctaggtgc taagaactcg gcagcaaaca aggcaaagtt    212580
ctcagtgtca tggagtttac attctagtgg atgaggacaa aagtaagtaa atgttaaaaa    212640
tatatagcag atggtaacta aagagacaaa gcagagaatt aggttatttg ctgtaacatc    212700
atcaaaaagt cattagtatg gtggcaattg agcagaaaca tgaaggaagt gaggaagtca    212760
gctgtgtggg tgtcttgaac agtgtttgaa gcaaagggaa gagcaaatgt aaaggcagaa    212820
tcatggctgg gatgttggag gagcagcaag gaagtgctgt gaatcttggg gaaaagagg    212880 tttagatgat atgggcctct gtaagagccc tggcttttac tttaagtcat aagggaaaac    212940
```

```
ttcggagttt tgagtgaaga gtgatgtgat tggaggcaca ttatagcagg gtgactctga  213000
tgctgtactg acaccagact gaaaagtgta gagcatggaa gcagggagac cagttaggag  213060
tctattgtaa tagtcctggt gagagaccac agcggcttgg actaagatgg caactaaggt  213120
atatctgaga ggtggtcaga ctctgcattt atcttgggaa cagaagcatc cagatttgct  213180
gatgaattgt atatactgta ggagaaggag aggactcaag gatgatgtga agatttcag   213240 tctgaggagt tttaaggatg agactgggaa gaatgaagga gaagttggtg ggatgggaag  213300
gatttagggc attttagaca ttaagtttga gacatcttgg tggaatgaca agcaagcagt  213360
tgaatctgag tctgaagttc aggaaaaaga ttcagagtgg agacagaatt ataaaagtta  213420
tcaaaatgga gattgtattt aacacgagtg tgaactagat tcttgttact gcaccatca   213480 acatcacctg ggagcttgtt agaactgaag actctcagac cctacctcgg aactgctgag  213540
tcagtatcag gatattgtca cgatcccagg tgatctgtag gtactttaga gtttgaggat  213600
tcctagatta gatcatctag ggtatgaatg aatgtagaag agaaagactg agaacctgag  213660
acaatctatc tctggaggcc ttggaaaaga gctggagact gagatgatat aggaaagggg  213720
aatttagaga gaatagtgtt caaatccaag ttaagaatgt gtttcaagaa agagggagtt  213780
aaatgcgtag gtcaattaaa atgaggaatg ctagtttacc actggatata gaaatatgaa  213840
tgtcatttgt tacttctata agagcatttt aataggattc aagatattgg gaagagaaat  213900
gttagagact gaggatagac cttcatgagt tttttctaaa ggaaaggaga gaaagggag   213960 gtaagtggat gggaaactca aggcaggtaa aagttctggg cacggtggct catgtctata  214020
atcctagcac tttgggaggc ttgggagaat tgctagcacc caggaatttg agaccccatt  214080
tctacaaact gaaaaaaaaa ttagccaggc atgatggcat gtgcctgtgg tcccagctac  214140
tcaggaggct gtggtgggag gattgcttaa gccccggtgg ttgaggttgc agcaagctct  214200
gatcacgaca ctgcactcca gcctgggaaa tggagtgaga ccccatctca aaacacaaaa  214260
aaggtgagag aagtaacatc ctactggcat agtggatata tagataacaa attaaggggt  214320
ggggcatttg gtggagctgg gggtatgtgg aggccaaagc aactctgtct tggaggctaa  214380
ttcacaattt tgacttctga ttaaccccctt ttctgggaat gcctctaaga tttctatttt  214440
atctactgtt ccttgtgtaa gagcatgtac ttaccataaa tcctgccctt aatcaattgt  214500
tctatacatc ccttctgaag cacatatata tcctttccct atggtgtata agcccggggt  214560
atggaaagta agagtgtgga gatccagcat cttgtctcac tgccactgag atacagacat  214620
ggcttctgtt tttaagtctc tattaaatgt ttctttccaa gaaactggat acatcagcct  214680
cttccttcag cttcagcttc taagtttggg tatatccgcc cacagcagaa caggggagaa  214740
ttgagagtca ttccaggata ccctgaatag ttgagaggga aggaacgctt ggaacaagag  214800
aagggatcac ctttagtaag gaggatggaa agtcactcct agaagtagga gaaaaggtag  214860
cttggtagat gtgggatag aaaattgtaa gttttctttc aattgactca gttgttatca   214920
atgtaaaggg aagaatgtca ttaattaaga atgaggatgg gaaagaagct actggagatt  214980 taagggggaat aacatatgaa ctgtcactta agacagttcc cccaacgttt taaagccatg  215040
gcacacataa aaaatgagaa tatttgagtg acaactagga gggatttgg atccctggcc   215100 aagtttactg gggcaggagg caaatggctc agggggtctg gttgccattt gcccagatgg  215160
ctaaagaaag taatatcttc tggcatcctg gttctgtttg acacatgaat tggggagctc  215220
tgaaagaaga gatgggaatg aataaagcag acaggcagaa aggtagtcag atagcaggaa  215280
```

```
ataccttatg tgagtgaaat tcatgaattt gaagaggagc tggtgaggat ggtcatattt   215340
ttaaccactt cagctacaca ggtatagtaa tgcaataggg ggagaactgg atttaactaa   215400
gtttggggtt atgcctagca agtatgacag agaggggatg agggagttga ggagagatgc   215460
caagtgtaga ctaattatga tcatgtaata taaactaggt gagaagagat attaggacat   215520
ggaataggag gggaatattg gaaaggtagt ttggattctg aattttgtgg ggtttcactg   215580
tttttggaga taagagagag aaggagatga ctggagaata gaatgcttgc aattgatcac   215640
tgatgagatg caggtgatgg taatgacaaa gtcaggtgt tatatgggag tgggaagtgg   215700
aggcaccgtg gaggagaaga ggctgttgga ctgagaggtc atggtattgg aggagttatt   215760
tacattgata ttaaaatctc taagagtgat ggcaggaggg tgacagtgaa cctggaggta   215820
aaattcaaca attcatttgc ttcattgaac aaatgaagca aatttagtag caaattttgt   215880
tgtataaccc caacaaattg acatgactat gaaagaagg gccagtgtag tctggtggta    215940
gagtctgagg tcagaacttc agaaagggc atttgtcggg gagggagata caatgtgtgg    216000
aagtgacaat aaggagcaag gaggccatca tcctctacct ccatgtctgg ttatcaaaga    216060
tattggggga ggaaagcagc ctgcttgaga aggcctctgg aaaaactgtg ttccccaaag    216120
ggagccaggt tttcattagg accatgtggt gaaagaactg tttaaagatg caggaagttt    216180
tgctgagaag gttgtgactc tggagggcac aaggagatag tttggggaaa ttgagaaggt    216240
ttgagagatg agagcccatt gtgggatgtg tgaggtacta aggagatgag agctcaagtg    216300
ccaaggtctg gcttgaagag gcaggcttct tgttatgaaa actgctgctt tatggatact    216360
ggagagcaaa caactccaga tagcttcagt gttttctacc caagcaacta caggttatct    216420
aacatcactt ttcagagatc atgtttcttc tggagacaga aaataatttc cccataatcc    216480
agctgagaaa attgcttggc cttcccttaa ccttccttg aaactttccg taaaattatc     216540
gattccagaa atgagaaatg aaagagaatc ttgtttttgt ttgtttattc tgttttgttt    216600
tgttttgaga tggattctag ctctgttgcc caggctggag tgcagtggta tgatctcggc    216660
tcactgtaac ctccgcctcc tgggttcaag caattctcct gcctcagcct cccgagtagc    216720
tggtattaca ggtgtacacc actacgccca ggtaattttg tgttttagt agagacaggg     216780 tttcgccatg ttggccaggc tggtcttgaa gtcctgacct catgatccac ctgcctcagc    216840
ctcccaaagt tctgggttta caagcgtgag ccacagtgcc tggccaagaa tcttatctta    216900
atcctctgtc ttaagacaat ttatcctgga aaaatgatta tccattttct tcaagtctct    216960
ctccataaaa cctctttatg gaatctcctt ttgatttgaa ctttgatcca aatcataaac    217020
aatcctcatt ccctcttaat gttatgtatc acggatgtga gactgggtgt ataccggtgt    217080
atatgtgggg gaacagtggt gtcctgaatg ccctttagac ctgatcttta tgaatcacca    217140
tgatatttct atttcctatg acctgtgtga ttttggttg ttacttatct tgacaaatat     217200
tcttttcaaa aacattgcgc actgaaggac atctggaaaa ttccaggagt ctgtctaggt    217260
tctaattgag atgcaatttc ctaccttcat agccttttat tgggcaatgt tgttgacac     217320 ttgttttcca agttactgga ttactcattt cagagttcag ttacccagaa accacctact    217380
tctatgccta cataagaag caaacaagag gttttttgcaa taaagacaat cagtatctag    217440
gataagggct ggcatgtggg ctggtcccat ctttgctgtg aagctacggg gaggaggtag    217500 ggagggaga gtctggcttt ctcagtttgt tgagtaaccc cagcgggaca tcctgcctca    217560
catcctggca gttgaattag ctgggctttt caaggtcaca agaaggaatc ctatacccat    217620
cacctgcaat gataggagtt tattgttcaa atagtaggta ggaggggaag gatgggaaac    217680
```

```
ttcctcatca ctgttcaatt ccccctggtc ccagggcttc agagctggaa taacacacaa   217740
cagacttctt acctccaatc aaagggcagg caggtaattt gtcttctttt tgtttccctc   217800
acacaatgga gagtgcacaa ttgggtcggc ttttgatctc tcactataat gctctacaac   217860
tggacatggt taccaagtcg cttctgtgat ggtcagcttt tccagcatta ggagttttaa   217920
ctgaggcttc agggattcat accctgcccc tcgccctggg attttgtgcc agaatgaggg   217980
tctgagcatg tgtgcatttt tttgcgaaag gatatgatcc tgtttataaa ggggcctcaa   218040
tctttgcttc aattcactgt ggctagcgta acagatttat gttttactca tagctcgtga   218100
caatgcaggc agggatgagc ccatttgaat caccatcctc aaaaagaatc catatgctgg   218160
cagcgagtga ctcctcctgc agctggtcat gtatcagagt gttgtgtgag gtaatcccct   218220
cacttcctca cactgatttc tgatacctct ggtccttcca caagtcacag aaatgccccc   218280
atcttctggc tgtgtacacg tgctcataca ccaccctgc ctccatgaca gaatgtagaa   218340 aagtttctt gtgtggttct atagccaaat aagtccctt catgctattc aaatagggtt   218400
tcatagtgct gcactcagtt ctattttct tttaaaatga tcaaggttga ctaaatgaaa   218460
ggcatttcag gattttagt tcctagaaag cagatggttt atatatcaat ctcctactct   218520
ttagtagcaa agattctaca actgcacata caaacttcaa gaattccagg caatcctaaa   218580
ggttttcctg ggccaagcct ctgtgcagag gtatgttttt aaccatctcc aatgggattt   218640
tcagtatttt cagcattgac tcaactccag tcaacagcga tatcaaaaca agtgaacatc   218700
aagtctgaaa agaaagtctg aatactgtta tccaatcaca aaaagacgg gtgatgtgaa   218760 tgtgtgttgc tctttaaagt tggttatttt aagtcaaatc cactcacctt tcaatataat   218820
cagtaacctt catagcttgg ggctgcctgg gcttcagaca gcagagttag agaaaacaga   218880
acagtgattt gtgtgtttgg ctttggagca atgcaatatg cagttcaaat tcaacctcat   218940
ttcattaact ctgtaactga agtacctgat agcaactacc aaaactaaca tgtagaaaat   219000
aaactttatt tcacccaaga gttcagttca ctgacatcga aaggcttcag agatttggat   219060
cacatgaata taacatgaga gctttacaat ttttaaaaac aagtatgttt agaatagga   219120 tgaacactat tctgtcagca tcaagaatca tttctaattc ttgtagactc ttttccatga   219180
taagatcaat gtaatttgta acaaattacc cttgggttga gtccttggag aaagctggac   219240 tcattttaa aaagagaatg aaaattaatt tcaatcaaag gcacttaagg cttttattta   219300
tactttgcat ttgttttagg gaattttgt acgtttatca atagtccttt attacaatat   219360 tttatcctt gaggttaaaa aaacaaaaca aaaacaaaa caaaacaaaa aaacctggct   219420
gggcatggtg gctcacgtct gtaatcccag cactttggga ggccaaggca ggcagatctc   219480
ttgaggccag gagttcaaga cctgcctggc caacgtggtg aaaccccatc tctactaaaa   219540
atacaaaaca ttagctaggt gtggtggtgt tcgcctataa tcccagctac tcggaggctg   219600
aggcaggaga actgcttgaa cctaggaaac ggaggttgca gtgagctgag atcatgccac   219660
tgcactccag cctgggcaac agagccagac tctgtcttaa aaaggcaaa aaagctaata   219720 ttcagtaata cgtgcttaat acaaaccttaa aagttcccat ataaacctgg aatcaattct   219780
aggaaagaca cataaaatat ggtgattata ttttatttca ctctgctgtg ggagagggct   219840
gggataatgt ttaaattaaa acaaagtga caatacccct atgaaggaga ccaggtcaac   219900
ataaccggct ggcatcatgt ttatcttctc agcatttaaa acacacacac acacacacac   219960
acacacacac acacacacac acacacacac aaacttttg gctctacttc tgaccttggc   220020
```

```
ttttatattg gtgttcattt gttttttcaga ggggcttggt tcttttatt gaagatacat   220080 cctatttgtt ggaagaactt ccattaaatt atcttgtcag ttctcactaa attttctttt   220140
cacagctctt gctgtctggg ttataaaaac ccatggcaaa catgggaggc cccaaaggaa   220200
tgtgtgctgg gatcctcttg aaatattatt gccctggatc ctttgagctc tttgagtcca   220260
gaaagcagca tggagaagga gggcaaacct gcatagtttc tcagaatgga tgagttttc    220320 ttcagagtag ccatgtagag cagctcagga aatgactgct cttaagctga caggctggca   220380
gaatattaat aaatgcaaaa taagcaactg tcctgcaagt atttcttgga tgctgtttat   220440
acttgatttc tatccaatgc tctttagcac atcttctcag agtctagaaa gttgtctcct   220500
ttttccctca agccaaatgg gttactgctt tcaagctatt tttgctatga agacaacaat   220560
aacaaaacag ctatgccaaa ctacttctta ttttcaaaac cagtttgatt tcctctgaca   220620
aaccatcagg ccagtgtgac tttgcatcac tggattaggt tagtgtaggt gctgtggttt   220680
gaatgtgttc cctaaagctt attggaaact taatccccac tgcaacagca ctgagaagtg   220740
ggagctttaa cagctgagct gattaggtct tgagggctcc attccttgtt actgggttaa   220800
tgtcattata atgggagtaa gttaatcagc cagggagtga gttcctgata aaagatgag    220860 ttccccaatt cccctcttct cttctgcaac agacatgctc tcttgacctt ctgccttctc   220920
ccatgggatg actcagcaag aagacccttg ttaaatgtgt gccctcagc  cttggactta   220980 gcctgcagaa ctgtaagaaa taaatttctg ttctttacaa attcccact  ctcaggtatt   221040 ttgcttattt atagcagcac aaaatggact aagacagagt gtaactagat gtatgaggaa   221100
atgacctctc tctacatagg ctgtctatct ttggagtaca gctccaggtg gacagtggca   221160
ttgtttaggc ttgctaggag gacagctagg agtgaattaa aaaaatccat tttgcttcta   221220
aaactaaaag ggtcattta attaaaataa taccataaac ataatttata ttaaaaacaa   221280
agtcatatac aaattagaga aaaatacaaa gaaatgccat ttcctaggtt tgattcgggc   221340
atcttcattt ctaaaattaa ctattcctga gttctgctaa tgtgtcctgc cacaagtgta   221400
ggcataaaaa ggtgaaggaa ttaaactacc aggctctgaa tcaagggact tgtttaatag   221460
aattatgtat aatgaagaat cctactcgct ttgaattcaa cgtggaagtt attcctccca   221520
ccaaaagaag cagagaggga aggaacctcc cagaaaagtc caggcagaac ttacaagttt   221580
gagccatatg aaacaggtaa tatttgacca ttttttgctga agaaacatat caattccata   221640
ttgattgaca caatagaatc atcaacttct ataatgggag ctgtggcctt ttccacttt    221700 tcctttctcc tatatttgag cagaaattcc cagaagggag taaaacttgc tctacctata   221760
gaataggcaa gaaattgttt tctcttcctc catccttctg caatatcaaa aaatatcttt   221820
aagtattcaa gagacgtgaa cattattcct attctctcct gggattcagc catccagcct   221880
tctttacccc agtgggcctc aaagttctct ctctctcttt tttttttttt tttttttttt   221940
gagacagggt ctccatcatc caggctggaa tgcagtggtg caatcactgc aggctcaact   222000
tcccgggctt aggttattct cccacctcag cctcctgagt agctaggacc acaggtatgt   222060
gctgccacac taggcttttt tttttttttt ttttttgc    atttttagta gagatggggt   222120
tttgccatgt tgtccaggct ggtctcaaac tcctggactc aagggatcta cctgccttgg   222180
cctcgaaaag tgctgggatt acaggtgtga gccaccacgc tcagcccta aagttctctc   222240 ttaattaatc ctcctaagtt tgctggggca gagggagggt ggggcggata tgggagtact   222300
ttatatgtat aaaattttgc catagggtag gttttaattc tcagttctta tgttttcata   222360
atttcttgga gtaaagaact ccttcaggta ttgttcatga tatatatcta taacctcaac   222420
```

```
tgactatctc aattaagatt ttggtacaca atgagtgtag gccacataat cctcatccct 222480
tacggaatgc tgtttagtga gtgttatacc tgtctaggca tgtttcttgt tacacttatg 222540
taagttttaa ctttcttgaa ggctgtctca gaatatattc ctatggctca atgcctttta 222600
tgttcttggc ttcccgtcaa tagaggccat agcaatgtgt gcttgctcac ctcatctgct 222660
gttcaactga gcacacatta cctggcatgg ggaataact tcaaatttct tcagacaaag 222720
gtccaacagg ccagacaagc tcatggctag ttccttgacc tgaacaatct tgttatttac 222780
agaatctcca acattcaaaa tggaggaact tccagctcat gattaaactc tttagcattc 222840
tttcaacatt ggcaccatta tatatttcga ttaacagcat tttaaaaaga gatagtgtat 222900
tagcttcctg ggctgttgtg acaagggacc acaatctaga tagattaaaa agcagttatt 222960
ctctcacagt tttgaaagtt ctggaagtct gaaatcaaga tattagcaag gccatgctct 223020
ctctgaaggc tctagtgggg gattatttcc tgcttcttag cttctggtgg ttgctggtaa 223080
tctttggtgt tccttggctt gtaaatgtat cctttgaatc tctgcctcca tcacatggca 223140
ctctccttct gtgtggctga atttctctct tattatcctt aaggatacct tcatccattg 223200
tggcctcatg ttgatacgat taaatttgca aagaccctat ttccaagtaa ggccatattc 223260
acaagtttgg atagacatga atttggggca tactattcac ctccgtgcaa gtagtcttga 223320
agatttgctt ctaaatataa taaatccatt taaataaaac taaatgtgat tcaaataaat 223380
acttatacat aaataatcac cactatgtcc caagctccat cagctccatg tttatattta 223440
ttcatttgtt aatttaacaa atacagatta aaagtctatc atgtgttctg agcagtactg 223500
gggccaaaat aatgaaccag agggacaagg tccctgttta cgggatgttt atgttctagc 223560
tgggagagtg ataaacaagt ataatttcat ttgtgctctc aaagcaatat tgagaactga 223620
ccaagtgaca gtcactgaga atgaaaaagt gaaagagta aagtccatgt cttcatagaa 223680
cttacattct attggtaggg agataatgca taaatgagta gataagtaca caaacaaata 223740
acattagcta gtgataagtg ctatcaggaa ttaagaggca gggcaaatgg ttgcagggtc 223800
agagagcttt gtgtcttttc atctgagccc tgaaggaagc cagggaatga gtcttgtgaa 223860
tgtttgggtt tagtgttctg gtgggaggaa ctgcagatac aaagaccttg aagagagcaa 223920
gttcctggtg tatttgggaa gaacaggagg ccagtgaggc ctcttgatgt gaatcaggac 223980
agagaaaggg attgagtggt agcctggggc tcaaacatcc tggtaaacca tgacaagagc 224040
tgttactcca agtactatgg gaaagcaagc agagggtttt gagcaggaga gcaacatgaa 224100
tgtacttgaa ttttaaaggg agaccctctg gcgacggtgt gagtactgga ctgtagggga 224160
caatgggtgg agaaggggtc acgcttgggt gggattttga ctacagagcc tgtggtattc 224220
agagagtgga aagtgctatg aagtagacat ggcatgatgg agagggggt aggaaggaag 224280 gtcattcatt gggtagctag catgtagaga ggcttcaccg agaagacgat gttttcgctc 224340
atatgtgaat gactagaaat cgccagcctt gtgaagatct tggaagatat tttcaagtag 224400
aagcaaaaat tggaaaaaga aaattggaaa gctctagctg tggtgtgttg gagaaaagaa 224460
aggaggacag ttgaaaccta gtaagccaga agatgccctg taggagacaa aggaaaacag 224520
ggaggcaggg cagtgtcagg aaggcccctg tggtccttcc tggtactgtg aacttcctga 224580
gagtactaga agaaagagtc tctgtccata gcttgctggc gcctgctatt ttgtatggta 224640
taacattacc caatgtgaga ggaggaagtg atgaacgttc taaggtgcat agagttagag 224700
gatgtctctc tacaaatttt acaggtcaca atttaaaaat gtcgatggcc ttacacatag 224760
```

```
caaaataatt tctaggaatt tatcctacag aaacaaaatt acagatactt aaatttagag   224820
cataaatatt ttactgtggc cttgactaca atagcaaaag taaccaaaaa taaccagaaa   224880
cacctggaaa cagtccattg ttaagaaaac agatgaataa tttatggtgt atgtataagt   224940
ggacatgtat ttagctatta aaataatgtg tgggagctat atttgttgtt gacttagaaa   225000
aatgtccaca atttatattt caaatggtaa attgacctac ataaataata tgtaaataaa   225060
gtataataca caaatataa aattatttttt aaaaactcac catggtggct gggtgcagtg   225120
gctctcgcct ataatcccag cacattggga ggcaggcaga tcatttgagg tcaggagttc   225180
gagagcagtc tggccaacat ggtgaaaccc tgtctctact aaaaatgcaa aaattatccg   225240
ggcgtggtgg cgcaggcctg tagtcccacc tacttgggaa gctgaggcag gagaatcctt   225300
tgaacccggg agggcggagc ttgcagtaaa ctgagatctt gctactgcac tccagcctgg   225360
gagacagagc gagactccgt ctccaacaaa acaaaacaaa gcaaacaaa aaacaacaa     225420
aaacacccac cgtgaggtga tggaagtgtt ttaaatctta ttttgctgg tagtttcaca    225480
ggtgtacaca actgtcaaaa cacgtggaat tatactttaa ggaaaggcag ttccttgaac   225540
atagtttctc aaagttgaac aaatgttctg tatcttaaaa agtgtctgtc ttctatcatt   225600
ttggtgtgta cctacatttg gtaggtttc tatgagcaaa ggaagaaaat ataggaagat    225660
acagtggtta catagagatg ggtttggaga gaatggtacc taattttgta acctagagt    225720
gtccttagcc ccaaattcct gtccaaccaa aatatctcaa tgtgaagata cacctttgtt   225780
gtctactgag cagaggtagc taaacatttg gactggctaa gtaaggaaaa tacttcccat   225840
gtcacttctg aactttttgt acatgtgcga gttgggagaa ggtggcaagg acattctcca   225900
gcatggtggt agtcagctaa aattaaactt aagccagtga ttggaggatc aacaaaagga   225960
taattatcgt tttgcagtct atcatggaac atagtggaag aacaagatct ttgaggtcag   226020
aaatacctga attttaactc cagccttgtc ccttcctggt agaacaagtt ttgtgtggct   226080
ttggaaaatt aatctacatg gtctttattt tcctcaaatg caaacaataa ctcccatagt   226140
gttgtagtaa agattaaatc agatgaaacg gtcacagggc cttctatatt gtagaatgtc   226200
agtacttgat atcattatcc actgtggaag aaaagattgt aaatttctta ttctgaggat   226260
tagtgagttt aaagtgctta tttgcatggt tggcctaggt gttgttcttc aaaaaggact   226320
aattctagac tctgctacaa gcccactata caatattgtt gtgatctgat aagcttttaa   226380
aaattgaatc tgtaggccag gtgcagtggc tcacgcttgt aatcccagca ctttgggagg   226440
ccgaggtggg cggatcacga ggtcaggaaa ttgagaccat cctggctaac acggtgaaac   226500
cccatctcta ctaaaaaaga atacaaaaaa tttagctggg catagtggcg ggcgcctgta   226560
atcccagcta cttgggaggc tgaggcagag aattgcttga acccgggagg cggagcttgc   226620
agtgagcgga gatcgcaccg ctgcactcca gcctgggcga cagagagaga ctctggaaaa   226680
aaaaaaaaa aattgaatct gtaatgactt cagcatgctc tccaatatcc caatggaatc    226740
attatgttta gtcagattgc tcaaaatttt ctgagctctg ttgtgccaag tttaaggcag   226800
ccggaactct cttcccttgc agacagtgaa atttctctgg tgtgaaatga tgctcataga   226860
tgtttatatg atgctcatat tgggaggatg acttgcccca aatggcctgt caccccaaat   226920
ggttggtggt cttgtggtct attatccagg agacaccat tgctccctgt cacattggtg     226980
acaagcagaa gagattaggt tgtcctttga tttgttgata cacatgccac gctgtcagat   227040
gatatttgag attatgccct gagctcagag atgcatagcg tgaggatgac atgtgacggg   227100
tatctctgtg ccccattact gtggagcagc ctctgctgca agacctgacc tctctggcat   227160
```

```
ttacagaaga tcctccttat ccatggtttc gctttccata atttcagtaa tgtgagatca   227220 actgggtct gaaaataggt gagtataata caatgagaga gagagagaga gagagaacat    227280
taacatactt gttactaaag tatattgcta tacattttct attttattat tagtgttgtt   227340
aactcttact gtgcctgact tacaaactaa attttatcat aggtatgtat gtatagaaaa   227400
aacgtatata gggttcagta ctatattcca tttgaggcat ccattggggg tcttggaaca   227460
tatcctccac agctaaacag tgacttctgt accctctgtc agtgcagaat gaggtgcact   227520
gcattagcat cgtaggcctc ggtttctctt tacaacagac ttggtaggta gctttacgtt   227580
aatcactttg ggtccaagct atgcatctgg aaactgggga taagaatact atttccatat   227640
ctgtcaaaag gcagaggagt gaccacatgg tccttccaac tttaagtgtt attcacccca   227700 attttaatt tttctgcttt tctcttgcca aattctttct ggttgtcctg tcctttatag     227760
ataggacatc atcacctgaa attgagatat ggagaaccaa gctcagaatt ttatgttaga   227820
aactactatc cacgcacttc ctaatttta gagggacaga ataagggtga tttgcatgtt    227880
tgtctttact ctcctgacaa ctgagacagg aaaccaagga taggagctca tgcaggtaaa   227940
gaagaaacag gttcagatgt ggacatgaca actttgaagt cactgtctga catctacttc   228000
acagccaatt agatcaaatt tacaagccac cacacacata tatagtgcta gtaaatatca   228060
gcatataagt ggttaaacca tgggagtgga tgagatccct caggaaaatt gcattgagtt   228120
gaagaggagg tgtcaagcgt aaattgtgct tggatgtttg gggtgaacag aagaagacat   228180
tgcagtgaag aaggctgaga agcaccatca gagcagaaag accaacagca cttggtgtca   228240
tgggggccat ggaaggagaa agcctttatg ggggcaggag gagcctgatc agtaatgtcg   228300
aatagaacag acactatata atcgaaggct ttaacaacaa acatgaaaaa aggctcaaca   228360
tcactgatca ttagagaaat gggaatcaaa accacaatga tataccatct catgccagtc   228420
agaatggcga ttattaaaaa gtcaagagac agcagatgct ggtgaggctg tggagaaata   228480
gaaatgcttt tacactgttg gtgggaatgt aaattggttc aaccattgtg gaagacaatg   228540
tgacaatttc tcagagatct agaaccagaa ataccatttg acccagcaat cacattactg   228600
gatgtgtacc caaaggaata gaaatcattc tattatagag atacatgcac gtgtatgttc   228660
attgcagcgc tattcacaat agcaaagaca tagaatcaac ccaaatgccc atcaacgata   228720
gactggataa aatgtggtac acatacacca tggaatacta tgcagccata aaaggaatg     228780 cgataatgtc ctttgcaggg acatggatgg agctggaagc cattatcctc agcaaactaa   228840
tgcaggaaca gaaaaccaaa cgctgcatgt tctcacttat aagtgggagc tgaacaatgt   228900
gaactcatag actcagagag gggtaaaaca cactggggg cctgttgtgg gggtgggga     228960 taaagagagg gagagtatca ggaaaaacag ctaatgtgtg ctgggcttaa tacccaggtg   229020
gtgggttgat aggtgcagca aaccaccatg gcacactttt acctatgtaa caaacctgca   229080
catcctgcac atgtattcca gaaattaaat ttaaaaaaaa attgaaggca ttaaaaatta   229140
ccttttgctt ctgaagacca gacggtcatt ggtgatttta ggaagagcat tttcactaat   229200
agagtgggca tagagcacat tttagttgat taaagaataa aggagaggaa gacaagcctg   229260
gattagacaa tctggaaaga gatgtcagtt gttagaaggt gatccttttt gtctcttcac   229320
tggggctttt tgagtgacat gctggctcaa gggaaagatc cacagcaagg gaagatgaag   229380
gcaaccaagt agatcattga gggagcaaag tcctggagta attgtatagg tgaaagggaa   229440
aagtctcatc ttattatctt ttgtaataag aagtagttta gttcattttc tctaagaaga   229500
```

```
agctatgaag atgtgattag atgtgcaaga gattcgttga gataacactt gtaaaggata  229560
aagaagaaag tggggagact cttcagatct caggagaggt ctgacacctg tgaaggagag  229620
gggaagaaaa gaccaggtag gaaatgtgtc tagctgtaag acagttccaa gaaaggccta  229680
tggagtgaaa aaaaccttca tttaaagaag acacatgtcc cacagaaatg ggcgtggaaa  229740
tgtcccctcc attctcagtc aacaattggg agcagcatgc tggaagcctg gtcccaaagc  229800
agatgcagag ggggacccag agtgtagcag ctgaagtcag cagcaattac gcacgctctg  229860
gacatctgag cagtgcgctt tcatggtaaa accctgatat aactggctga tctggatgtg  229920
cagaaatgag aacaggaaga taagtgagtt cccaggtggg ggcctcattt attttgaag   229980 tatgaagtat taggattatt ctagctagaa tgggaataga gaatggaatt ggagaaactt  230040
gagtgatggg ttagaagagc agaaactgaa agaaggtagg actttgatct gcacaaggtc  230100
tcattgagaa tgggtcctgt aagggactgt gatgtgttgt ggcattaaca tggcatgact  230160
atgattttcc tctagaagga tgtagtaaga atagagaagg tagattttgt gacttatctc  230220
tttactgtta atgctactcc tggttccaag gctgccccag ttttataatt cttaagttat  230280
tagtaacttg tcctttattt gattaaacac acaaaaaaat acattgattg agccttatgt  230340
atgaagcaca ggaggagata taagaatgga tttctgccat ccaggagtgt gtacttaaca  230400
gcaataccta tgatgcaagg cagactacga caggtaatat aagagaggta gaaataaagc  230460
ctatggaact tcgaagagg aatagagtat ctgagtaggg aaaagagagg acagactcaa   230520
agactttatg gaggtggctt ggtttgggat tcataaagtg ggtataattg tgacagattt  230580
gttatctatg tctactattg tatggtagaa acctttcttc ttttaatct gcctttcaag   230640 gccttcatct aggctggatg gtgaccacct catgcccaga ttactaatga attgctcagt  230700
ccctctttaa atctactgtc tcatatattt gattacaaat acaactgggt aaattatgtt  230760
gttcatataa cctagaagtt ttggggccct ctccctgtt tctcaagcat aactgatgct    230820
acagtacttt gtcctttttg cacatttcca tgatgtctta ttgtactaat aagtgctctc  230880
tagactgtga tgaactagtt gagttataac cttgggtagg aaattacata agcttggtac  230940
atggtagtgt tagagcaagg tcttagttat ttgcttagtt ttctcacctg ccagtgagtt  231000
tgtaaatcac agtcaaggtc ttggtttgga gaggaaggga ggtagctctg ctgtattatt  231060
taatctgatt taccagtaaa gaagctaatg ttgaatgttg attcttcact tggataagac  231120
tccagttgtt tataatatgg aattgtaata tggaataata ttttcacacc tcagtaatcc  231180
ataatgagtt cctcttccac cttttccagtt acttgggata aaaactacct gaaattacaa  231240
gatatgcaaa atgttgtata atcagggcct ctatcttaaa aactgattta ctactatttc  231300
tgggaaatgt gcctatttta cactttggac cttattcact gttgttaaat ttttcagata  231360
aagctcaaca cagtccagca actagctatg cttagcctcc ttatcttcat ttttaatgcg  231420
acaccgtgaa ctccagtcaa gaaaacacat ttaagaccct ttacacttga ctgatgcacc  231480
tgaggctttg cagtgttatg cagaggtatc agtaaatatt taatagttgt gaatgaaatt  231540
aaagtcctgg aacccttgtc caactaaata ggcccctcca agagactgct ctgatgtcat  231600
ttactcacat agccagtgct tagatgcttc atgattagta attttttgtat cctttctgga  231660 ggttttttgc tctccatttg gtggtaaact ctggtaatga attttttcact ccaattttttg 231720 cctaggttgc tactattggt ctattagggt gccttttttc agacgaaaag acatcatctt  231780
ttaggaaacc ttgtcaaggt caacaaaaca tgaacttatt ttaataatcc ttttgtatta  231840 acagtatta cttttagaat tatgaagatg tgtttatcct tccaagcagc agtctgggtt   231900
```

```
gttgccactt gaaaaaaaaa tacggtctat tggagttgga gaataggcag gaaccttgat  231960
gtcataaagg aaaggaggta aatggacagt accttagtgt ggttaaggaa agggctgagg  232020
gaggtttagt ctctctcaga tgtggtagaa acttccatgt gagaacattt gccacctcag  232080
atgagaacac ttttccatt ctccataagt ctaactctaa gcttttttt tctttttttt    232140 ttttttgtac tttattttat tctttgagag gtggggaggt gagctgccct ttctttgact  232200
taaggttctt acttttttgg cttacaattc tcagagactc tggctgtctg catacagagg  232260
ccattcagag ctccatttca acaagcaatt gcatatttga tccaataatc ctccagcacg  232320
aggatttggc aatcctttca aaaacatttt ccaagtagtt cttaaaacca tcccttttca  232380
ttaggcaagt gccaggtgaa taaacatggc cctaaacact gtccaccctg ccttggcaag  232440
ggaacatcta aggcttgggt aattgatttc cccgtggttg caagaagttc ataacatt    232500 attcaatcat ctctcaagtt tgcttgtgat tgctaaatca tttgtgacat tggcctgacc  232560
tcttacattt agacttcctt attcttacct ataaaacaag ataaaaggat tacttgattg  232620
atgtctccaa atggccagtc tgtggaccac tgaagcacac tggctgcctc atgtccaagt  232680
tcaactgtga acttcctata acacaagcct taataactcc atcctcttcc tctccaactc  232740
ctctcttaga gacccttgta attaatttag gtaaatggcc agcgctcagg cctaaaatta  232800
ggatctgcca aaggaattta ccatgaagtt acacttgtaa tgaccctccc taaacctcca  232860
aatattctcc tcagaggtcg caagataatg aagtagtcac agccatgtgc tacagtcctg  232920
caccagctag acctgtaccc tcatacttcc actacttgac cctggtagat ctcatccaga  232980
atcaaagtct atcttttgct ccgagtagaa aaatatgaat gagtaagatt gtgctttctg  233040
gtccagatga tcatgactca aactacatgg ccatctggcc cctccatcta cagttagaag  233100
caccaccttg gcaataattg aaatgaactt tcaacaaatc tgctagagtc aagactgaat  233160
tatgcattgt tttataatat cattgccata tgaagaggga acaattgtg tgtggcctat    233220 gaaaaaggtg ttaccatccc tggattgcaa ttttttttgtt agtttttttt gagacagagt  233280
ctcactctgt aaccaggctg gagcgcagtg gcgtgatctc ggttcattgc aacctccgcc  233340
tcccaagatt aagcgattct cctacctcag cctcccaagc agctgggact acaggcgtgc  233400
accatcacac ctagctaatt tttgtatttt cagtagagac gggctttcgc catgttggcc  233460
aggatggttt cgatctcttg acctcgtgat ctgcccacct tggcctccca aagtgctggg  233520
attccaggca taagccactg tgcctggcct gttagggttt tgtttgttttt ttttttttgg  233580 catgacaact ttattgagat ataattcaca tacacatagg atatcataca atttgcccat  233640
ttaaagtata cagttcagtg gcttttagta tattcagttg tgcaactatc accactatca  233700
attttagaat cacctcaaga agaaaaccca ttcccttaa ctatcagccc ctgtcctttc    233760
tatctccccc agtcctaagc aacacttaat ctactttcta tctctgtata tttgtaaaat  233820
tttaaaaaag attgttcaat tggaagaatt tttaaaatat atccacaata atatagttta  233880
tatgtgttat atatcatttt cttaacatgt gttctctagc ttggatttct cccttttcta  233940
gatcattgat gtggagaaat agacactggg tcctgttctc tgccctccat ttgatctagt  234000
gcccacaact aaacacaatt ttctacaaaa ataaaggcag acaaatggg atagcataac    234060 tgacccttct gatatacttt ttttataaaa aagggggaaaa aaattatctt ctcaagttag  234120
gaactacaga attgacctgg aaaaagagtg ggcccaaaag aaagattcct aaagtatctc  234180
attagtgcca tgactagcag gcaacataag cagctcgatt agctcaccat atgattgaca  234240
```

```
ggagatggag aagatgttgg gggtggtggt ggtggtggta gaattggggg aagagttatt  234300
tatatttggg tgtggcatat gagtttcctc agagattctt gctttgggta ttaaaagtgt  234360 ttaatttta taaaaatttt caataaaaag gcaaatacct aagtgccctg aagaagtttg  234420
agacttagat accaattcaa aattcaagaa ttatgactgt tctagaagtc ttatgaaact  234480
tgtatacttc atctgtgtga tatttggcaa tgtgcatctt gactttggca tagataagtc  234540
actcacctga ggttttaaag caataacttt ttaatttagg gtagactctt ttttcagctt  234600
gttcatgagt gatagatact ctgggaaggt ggacactttt ctcagtcgaa gggaggtatt  234660
attcatatgg aattctatat aaatgtatat aaatggtgtc ccctaaagca taagtctgtt  234720
gatgagtctt taaagagact ataccggtta gattctacaa tatacaggtt gacaatatcc  234780
gatgggaaat gtggcttgat ttgaaattag aaggcagaca ttcaaatgac taatctcaag  234840 tctgcccca aggtactgta taattctatg attctgggct tcattttga aaagtctaaa  234900 gagatgatga agtacatctg tcaagaaagg catgagaaga aacaaaatga tccatcttgg  234960
ctgtgcaaat gctgtaatga atgggaagt tggtagatgt ggtcttaaca gggtgtaggc  235020
ttgtgctgaa ataaataaat aaataaataa atacaaacca caagactgac gtgactgccc  235080
agttgtgaac attgtatgaa ggtttagttg gcagagtaat gcttttcaag tatgttggat  235140
aaatattagg tttaaaggcc aagatactta taagtattta caggattaag tgaggtataa  235200
aataatattt agtgtctcaa aggatgggaa ggaagatagt gttgtggtca ttccacagag  235260
gaagttagaa ctgcacatcc aaaatttggt tcagatatca atgctaatga tgacacaaat  235320
acacacatac atatacacat acacctcaag atggtattaa caattttatt attcatataa  235380
tgaggtcttc tgagaaaaac aggccaggct cccaagcaag tctaaaaatg gattgagaga  235440
acagggaggg agaattgact tggggtttta tgtggtggag tagtgtggct ggagagagag  235500
ttgtcttgtg taagctgggg cttatttggt ttgaatttct caataatgca aaagttgagg  235560
catccaagca tctcatcagc ttctctagat gtggcttgag ttgccaggag gcaaattcaa  235620
ctgttagtgt tttgtgtcct aagacatctt gtctaatctg aggtaaaagc ttttccctat  235680
tttttagaag gtgtataatt ttggctcttc tgcttagctc taccatccat tttgagttga  235740
tttttatata tgttataaat taaggattgg agttttcttt tattggtatt tattgataat  235800
acaactgttt cagcatcatt tgttgtaaag attgttttc tccatggaac aacttttggca  235860 ctttataaaa aaaaataagc atgtgtgagt gggtctattt ttgaactcta ttctgttcca  235920
ggatctgtac atttgtcctt atgccagtac caccttatct taattaccgt agttttatag  235980
taagtatttt ctgttaatgc caattctaca actttatttt tttcaaaatt gttttggcta  236040
ttttatatcc ttcatatttc catataaatt ttaggttcag cttattattt tttataaaaa  236100
atcggaagtt ttttttgcaac ttctgcaaag gttatcaaaa accatcaaag gagattgctt  236160
tgaatctatg aattatttgg gggagaattg acatcttaaa aatattgatc cttctcatcc  236220
attgacatgg tacatctcca tgttttttag gttacagtgt acacatctta tatattttat  236280
taaagtaccc atagatattt cttaattttg atgctattat aaatatctta aattacagtt  236340
tgctagtatg tggaattaca atttattttt atatattgat cttgtatctt aggaccttac  236400
taacttattt attagtttta gttgcttact tttaggttcc ttaattttta taacatcaat  236460
cacatctgca aaaaagtttt actacttttt tcaccatgca aactttaatt ttctttatct  236520
tgtctattta tactagctag aatctcacgt acaatgatga ctagaggagg caaagtggt  236580 catctttgtc atatttctga tctcagggggc aaacataatg ttagctgtgt tcattttgtt  236640
```

```
tgttttttac agatgtactt ttcaagttaa gtgccttctc ttcctggtca gctgagagtt    236700
attttttaat cacaaatgaa tgttaaattt tgtcttatgt ttttctgcct gtattgaaat    236760
gatcatgtgt tttcctctcc tgtgtttcac ctttgtttta gaaagatatt ttcactagat    236820
aaagttttta ggtgacagt gttttcttc cagcacttaa gaaatacttg attttcttcc     236880
agcacttcag aaatatttga ttttcttctg cagaatacag tttatgataa atcagaagtc    236940 attcttcct gtaacatgcc tttttctctg gctacgttta agattttctc tttatcactt    237000
agtacttcct aattaaaaat ccatgcccca gcagtggtca gctagcattc taaagaggaa    237060
tgctgaggca gctaccacaa acacttctct aactttatta ttgattgaca ttacagcctt    237120
tgctaattag tgtaataaat gtcagaaatt agtaacttga cagtcagctt actggaagtt    237180
agaattacga tcttgttggt taaataagta ttcaaattct gtagcctggc taaagtatt    237240 tgaagacact cttgagagag actagaacat aagcatcaaa ggaacccaag caccttctgc    237300
aaggcagaag gggttcggtg ggtatgaaat gatggaggtg ggaaaggaag atcaaaaaag    237360
gggttgggta atgccaaaac ccaaatactg gggattatta aagacatgg ttcaagagag     237420 aagctaatcc atgggtgcag gccagtgtcc agagagagag accactgcaa gaggccctgt    237480
ctggatgttc aggacctctg agaatatatt gtttgctggc tgattgccca cttccacag     237540 ggccagttct atttctttgt ttttgccct cctattatcc acttactcca tgcaatgtga     237600
ccgcaagagt tctaaaagcc tacataatag acatgtaaat accggtggtg gtgacagagg    237660
tggtgagagt gagaaactca caatttaat tgagaggaac ttgaactgaa atgggttctt     237720
ggttaggcta ggacaccacc attatatcat gatgatcata ttttatagt tcttgtcaaa     237780 catatatctc ctatagtact tgtatatgat agtactaggt attggaagcc aaaataaatg    237840
agtaaagtat gaatagactt cgccttcaag cagctgacag ggtttggttg gtagtaaata    237900
tttggaacat ttttttccc cttaaagttc ctggactcag ctaggactag ccaaatgaaa    237960 tgtctctta ccaaaatgct catcttcagc ctgtgttgct tttttgcact cgtgtccact     238020
tttccggctt ttggcccatt tccttggctt tgttgctccc cacttcggtt ccagcaggtc    238080
cttggtcact acccccaca taacaacatg cacctggggg catcgcctga gcttaaaggc    238140
ccccattcct caattgtatc tgatcccttc cctctaacta aatgcaggat tctgattcca    238200
ttccctcagc atttgggcag gaaagaaat ctcaactatt tgagatgtgc ctgatgaatt    238260
acagaagcaa agaattctgg agttagaagt tatcttagtt ccaagttaaa aatccaggcc    238320
caggaaagtg tcacatggtc aatgacacaa atcactcacc ggcagaacag ggaggagttt    238380
cactacttca attctctatt taccatatca caaatatgt aagatatcac attctaataa     238440
tgtaattcag aaataagaga aggatagcgt agcaggaaca ccacaccttg cctctcaaat    238500
tacaccacac agaggctgca tattcacta gttccaattt cattactcac aaagccaatc     238560
ttgaaaatgc ccaggtaaag taaattgtca ggaagttctg aataataaac tcgtttgata    238620
aaaccaactc acaatgcttc ttccttaaaa atattttggt ggaaatatta ttatatttgg    238680
acataaatac cccctgaagg acttgttagg aagaaaatag atcattgttt aggtcccta    238740 gcacagaggt ctgaaagtca aataaacttg gtcaggctgt tttctcttcc taagagaat     238800 aaaaggcccc caatcaatgg gtggtcacca tagaaaaaat tcggctctaa gtcagagtga    238860
cttgaatatc tgtgtgctat ttttatttca gaaaaccaag aagacacacc aaaaaatccc    238920
gattaaaagg gaagaaatgt gtttaaagag cttgttgact tcttaaaaac aaaaattcct    238980
```

```
gcatagattt tggttaggat tgctttaaat ctgtagattt ggagattttc aaaaatatag    239040
tacattatta ttattattgt ttgagacaga gtctcgctct gttgcccagg ctggagtgca    239100
gtagcacgat ctcagttcac tgcagtctct gccttctggg ttcaagcaat tctcctgcct    239160
cagcctccca agtagctggg attacaggtg cccgccacca cacccagcta attttttgtat   239220 ttttcgtaaa gacagggttt caccatatca accaggctgg tctagaactc ctgacctcag    239280
ataatccacc cccctcagcc ttccaaagtg ctgggattac aggcatgagc cactgtgcat    239340
ggccaatata ttattattaa ccatagtcat catgatgtgc aatagatctc ttgaacttat    239400
ttctcccttc tgatttttt tttttttttg agacagggtc tggctttgtt gcctaggcta     239460
gagtgcagtg gcatgatctt ggctcacagc aacctccacc tcctgggctc aagccatcct    239520
cccaactcag cctcccaagt aactagtact acaggtgtac accaccacac ctggctactt    239580 tttttttgtat tttttgtaga gatggggttt tgccatgttg cccaggctgg cctcaaactc    239640
ctgagctcag gagattcacc tgcctcagcc tcccaaagtg ctaagattac aggtgtgagc    239700
caccatgcct agcctttaac tgaaattgtg tacccttgga gcaataccctt cccaatctcc    239760 tctccattct actctctact tctatgagtt catatttttt aaagattcta ccacgtaagt    239820
gagattatgt ggtatttgtc tttctgtgcc tgacttattt tgcttatcat aatgtcctcc    239880
aggttcatcc acgttgtcac aaatgacagg atttccttaa gactgaatag cattccattt    239940
tgtatgtatg ccatattttc tttatccact catctgttga tggacactga ggatgattcc    240000
atatcttgga agttgtaaat agtgctacag taaacatggg agtacagata atctctttga    240060
cacgctgacg tcatttcctt tggaaatagc cctaccagta gtatgattgc tggatcctat    240120
gttctatttt tctttttctt tttccttttt ttttaatttt ttattttttg agacagagtc    240180
tcgctctgtt gccaggctgg agtgcagtga tgcaatcttg gctcactgca acctctgcct    240240
cccaggttca acaattttc ctgcctcagc ctcctgagta gctgggatta caggtgcatg    240300
ccatcacacc cagctaatta ttgtattttt agtagatatg ggatttcacc atgttggcca    240360
ggatggtctt gatctcttga ccttgtggtc tgcctgcctc agcctcccaa agtgctgaga    240420
ttacaggcat gagccaccat gcccaaccta ttttttaattt ttaaaggaac ctctatactg    240480 tttttatttaa tggctgtact aatttacata cctaccaacg gtgtacaagg ggccactcta    240540
catcctctcc aacacttgtt acctttcatc ttttttcgata tgattattc taacaggtgt    240600 gaggtgacat atccttgtgg tttaatttg cattgccctg atgattcata tgttgagcat      240660
tttttcatat ccctgttgcc ttctcttgag aaatatctat tcaggtcttt tgcccactta    240720
attgggttgt tttcttgcca ttgagttgac tttttatata ttttggatat taatccttat    240780
cagctatgtg gtttgcaaaa atgttcttcc attctgtagg ttccttcttc actctgttga    240840
ttgtttcctt tgctgtgtga tgctttttaa tttaatgtaa tttaatctca cttgtctatt    240900 tttcataag aagagttgcc agtgctgttt accctggctg ctacataccc tgatccctga     240960
agaccgtttc ttgaaccatt ctgctctaaa gtaatcctcc ttccatgatc tttaccaagt    241020
gctttgtatt attaatacat cactatactg atttccttta tagaacatac acaatgaaaa    241080
attatcttgc tttgtttatt tactcactgt ctcagcccta ttaagatgga aaatgcctgg    241140
catgtcttaa tgctttattc ctagtcccta gcacgatatt actttaatga ataagtaagg    241200
tttgaagcca ctctgagtag atgtgaatat ttgaattagc ttaggagaaa tatattctcg    241260
atttccttaa attacaactg aaatgacttt tgtgatatgt atagctgatg cccttactat    241320
aaggtatcag gatatactgg aaaaacttgc aggattttt attttccat tgtgttttc       241380
```

```
tttctaggag gcagaaaaac cttctgaatt tttaccatga tgacattaaa gccagagatg 241440
ttaagtgtca ttgtagttag ctctgtggcc agaacctgag ctggcaactc ctgatatgag 241500
tgcttcacta tgaaagacag actagatatg gcaagtaact gcacattcct tctcagtgtg 241560
tttcccagtc ttctctttca aattaacact caatgggcat cctgatacac aactaaacat 241620
acatattcat ggtcaaatcc aggctaatag aggatatcta ttcactcatt tcctcctttg 241680
acacctgtag aatgttatct gaataaaatg attttgcaaa gggatgggat agaatttaga 241740
aagcatcgca ttacttcaga gagtgacttt tctttaatgg gtcttagttg ttaagaacag 241800
atgcctaaat aaggtgatgc ctaaagtgat gcctggggct agtcaactga atttaatgtt 241860
cactaaggat taactgctca caaaaactgt atttgtgaaa aattgacctt gtctatccaa 241920
attggctact tctaataact agcttttata gtctacttgt tttcttttt acataaacaa 241980 ctacaaaatg tattagtcta ttttggagaa actcttaaaa tagaatgaaa ttgaaaattg 242040
ctaaagtgtt atagttattt tcagttagat atttctatga attattttat acactcatgg 242100
tttaaaatcc aattttcata atatagttgc cagcatctgt gaattattac aatttgaaaa 242160
gatttggaat gccataactt tttaaaaatg ttctgctctg atctttattt cctttcttct 242220
aactctgggc ttagtttgtc cttgttttct ttttttttat tattattata ctttaagttc 242280
tgagatacat gtgcagaatg tgcaggtttg ttacatagtt atacacgtga catggtggtt 242340
tgctgcaccc atcaacccgt catctacatt aggtatttct cctaatgctc tctctaccct 242400 agcccccac ccaccgacag accctggtgt gtgatgttcc cttccctgtg tccatgtgtt 242460
ctcgtggttc aactcccact tatgagaaca tgcggtgttt ggttcctgtg ttagtttgct 242520
gagaatgatg gtttccaact ttatccatgt ccctgcaaag gacatgaact catccttttt 242580
tatggctgca tagtattcca cagtgtatat gtgccacatt tctttatcca gtttgtcact 242640
ggtgggcatt tggggtggtt ccaagccttt gctattgtga acagtactgc aataaacata 242700
cttgtgcatg cgtctttata gtagaatgat ttataatcct gtgggtatat acccagtaat 242760
gggattgctt ttctaatgtc ttgaggtatg acatttaggt tattttggat cttgtccctt 242820
ttttaatgta tattactata aacttccctc ataaaactgg tttgccgcac cccgtaaggt 242880
ttggtatggt gtttccattt ttgtctcaag acattttaaa tttgcctttt aattattca 242940 ttgatccatt ggtagttaag catgttaatt ttcatatatt attgaatttt ctgaaatttc 243000
ttattgattt ctaatttcat accataggtc agaaagata tttgatatga tttcaatctt 243060
cttaaagcta agtcttgttt tgtggcttaa taatgaccta tcctggagaa tgttctgtgt 243120
gtgcttgaga agaatatatt ctgctgttgg aagaaatgtt ctgtatatac ctatgtccat 243180
ttggtctaaa gtgtagttta agttcaatat ttccatatcg attggatgat ctgtccattg 243240
ttgaaagcgg gatattgaag tctcctactg ttattgtatt gctccaactt ctgatcctta 243300
aaatttgctt catatagaat accataaaaa gttctgagat attgattact tatttttatga 243360 atgtgtgagg caactaggaa ggctttactg cgttatctaa cactcatgga caacctgtag 243420 gttttttttaa ctacagagaa aacgtaatag aaaagatgtg ccaggcacag tggctcatgc 243480
ttgtaattaa tcccagcact ttgggaggcc gaagcaggtg gatcacttga ggtcaggagt 243540
ccaagaccag cctggccaac atggtgaaac cccgtctcta ctaaaaataa aaaattagct 243600
gagcgtggtg gtgcatgcct gcaatctcag ctacttggag gttgaggctg gagaatcgct 243660
tgaatctggg aggtggaggt tgcagtgagc tgatattgca ccactgcact ccagctgggt 243720
```

```
gacagagact ccatcttaaa aaaaaaaaaa aaaaaaaaaa aaagattaac ttgtctcatg   243780
ccacacagct aataaatggc agtgcttaat tcatccccaa ggctgtttac caccaaagac   243840
tatatgaccc ctcaatgcag cctccactta agtaatgcag ttaagaactg ccaacactag   243900
gtgccatgat agggtattga ctctcaaaga tatttgacca tgacccagtt atattttgtg   243960
tcacatatac atacattcct acatccacga tagaaacaaa agtctcacca acagttcttg   244020
tattgactgt gagacaataa aagatgactc tgacattttc taattttttaa tgctagttgt   244080 aactcactaa attgctataa tgacccactg gtattatacc tgtatttgaa agccgtgttc   244140
taaatgtcct ttttagacat cttgcagtct gccctcaatt acaaaaagtg catttgttga   244200
atgttactga cagtcacatg gatcaattac tacaagtcat cttaataatg tattccaaaa   244260
atggttttgt tttctcacct ctagtccttg agtacactaa tgggatcttt atcttcagaa   244320
aagctgctaa tataaaacac aatgccttat cactaacaaa tcaaattaga tataatctaa   244380
gcaggtgtat gtgagcagga aaaaaaccac attagagcca cctgaatcta gatatgatct   244440 atgatttga cagcattcag ttttgttctc aagatcagtg acataatctt tactacatat   244500
tgttattttt aaggtatgtg cagttttgta acagcaatac aatgcaggta tgtacacttc   244560
attgtaaata accattctgg cgaaaaaaag gctttcaatg actttggaca agtaaatgat   244620
tcttggtaca aaatcatact tcttttggtat ttatgaaaaa aaggaaggt gttttaactc   244680 tgagcaccca attcctggtg ctccatttaa gtatttaaga tgtttctaat tagggttgag   244740
tcttgttgtg aacagctagt gaaatactaa catgggaggg caagtttttat gagcattgat   244800 aaattgaaca caaattatct gttacagaga ctacaaagag ctatagataa aaagtacagc   244860
aaaatgattt catgaaatca atattttatt cagtgtcaaa gcatcttaac tgaattgtgt   244920 aagtaattt gtctgtaatt ttagaagtaa catttgtaga aatatcaat attatcagtt   244980 gtgctactag aaatattgaa ggagttaatt ctgaatttat tcatttatgc agttatctat   245040
atccacttag gtacaaaact tttgtaagaa agataacact tttattgcat tataatttca   245100
tattttacag gagtcataat gcaaacttat aagcataaat atatacatga tgctaccaaa   245160
tggcaatgta accactaaga gatttaaaac ataaaactag aatttaacaa gcaaaatact   245220
taatatggct tttaatggaa ataactgtt tagaaatgat ttgttattgc cccattctag   245280
tcattcccca tcaagtgaac ataaaattat gatctccatt taaaacggta caagttatct   245340
aagccaactt tgtacttttt tgctactttt ttgtagcatg tatgcagtat gatttctgga   245400
cttccttaaa tatacataca tatatacata tacagata tacagtacac agttctgttt   245460
taatacccct gaacatcttg attaaaacta ttacaatttt tctattataa aactacttga   245520
aaagttggca taacttcctg gtattgaagt tcaatcctac agaattaaaa aaaaagcaa   245580 caaaatgttg gttataaata cattctttac aaaaaaaaat tgaatagtgg tcccgcactc   245640
ataatttata ttacagtgaa aacatttttat caatttaaag gtatttgtat cttgttgtcc   245700
ttggtttctg tgtgaaatag aggaagttaa taatgagaat attgtaggca ggcctatttg   245760
ttaggttttt ctaggtgttc atttttgtgt aagttccaat tcacttcttt tgagttgttg   245820
ttgatttcta tttgccttgt attactgctg ctgctgcttc ttttggtgtt ctgggaacac   245880
tgggtgactt tacttctagg aacaggaaga aaagatttaa ctcttgaaac acccaactca   245940
gtctttgatt tactgttgct gcattcagta gtttgatggc tgctgagagg actgacctcc   246000
tgtaagagac aagaaaccac acaagttatt cacaaacttc tcctgttatg agccctaccc   246060
ctgcctcctc tttgagcaaa tgtacaggag tttctctcta aaactatagg ttctcgtgaa   246120
```

```
aaatcaaaag aaaatggaga ggagaagctg agtaattaat ttcctataga cttactgcat 246180
gattttcatt aatccatctg ctgttacaaa attcctaaat acaggagtca gtgaatcaag 246240
tgctaaggcg tcgatctcct taccaacaga aacttcacaa aattacaggc atgaggaaat 246300
caccaaattg gagtagtccc atttgtaggt agctctacaa actatgtcac cttgggtaaa 246360
tcacctaact tttctgcttt ctactttcaa gtcttaaaag tgaactatta ctcaataatc 246420
aaataatctg ggggcatata ggagaaaaca taagagaaac attccttccc tagcagaacc 246480
tacattcatc tatggttagg ccactcaaga tcttccatac ttggaagctg catgttctca 246540
tttctctaat gtttcagaaa tcctgtgatt acctggtcaa tgtctctcat tttgcccatg 246600
aagaatctga gagctggata ggtaagatga tttgcccaca gtgaacggag tggtgaagct 246660
gggacaagac ctcaggtctc ccaactttca ctcaaggtat tttccctata ttgcattaaa 246720
ttctgcaaac taacaaacat gacatgactc ctactaagtg acctactctg aatgcctctg 246780
aaggagttga ccttgataac ttctcctctt caaaagtaat aatgcaccca acagcaatat 246840
aaccattaca agaatttaaa acaaaactaa aatttaacag gaaaaatctg gcttcatctg 246900
gcagttgcgg cagttgcatt ctcctgggta tcgtcttata tgacattgga atcacctggg 246960
ggagctttaa tagtcattgg ctgggcccta ttaccagaga ttcatattta atagttctgg 247020
ggtgtggcat ggacatacga ttttaaaaaa tcttgcggcc aaagaacgcc tagcttaact 247080
cctcactatc cttttttctcc attgagcaat taaatcaagg gtccccaagc cacaggctgt 247140
ggaccagtcc atggcctatt aataactggg cagcacagca ggacgtgagc gggggcgagc 247200
cagtattacc acctgagctc cgcctcctgt cagatcagca gcattagatt ctcatagtag 247260
tacaaacccct cttgtgaatt gtgcaagtga ggggtctagg ttgcccagtc cttgcgagaa 247320
tctaatgcct aaagatctga gatggaacag tttcatccgg aaactaccca ggtccgtgga 247380
aaaattgtct tccacgaaac cagtctccag tgccaaaatg gctggggact gctgtcctaa 247440
atggtagcat ttttcttagc cctctataag tcacacattg ataatctttc ccttcagagt 247500
atttcaagct ctaagtattt cccaaagttc tttctttagc cctcatttat ctcctgcatt 247560
tccaccccac taattcacct atatgtctag ccacacttca aattcttctct aaaactgtat 247620
ttattgcatt tcttcaatac taatttctaa agccttccg cttggctcat tactggctaa 247680
tgctgctctc ccagtgaatt tagcaggaaa tcctcagtta tctttagcag ctgcctttct 247740
ctctctcctc accaacctaa tccaatgtta cccacaaaat gggcagagaa ttatggctgt 247800
gtttgtgtga ataggaaggt aaaggataag tcctcactaa ctggcatgtc actaaagttc 247860
ttttaaagtt tggctccaat ccccttaaa tcctattttt cctttacttc cctgttaaag 247920
tcctaattct ttaaagccca acacaacatg ttcattaaac taccccctaaa tcaccaaagt 247980
gaaatctctt ggggtcagat tttcagactc agctaatctt aagtggaaca gcaatgtaac 248040
tctaatatat acttggctag tggtttggga aaatataaaa acactgaaac aacaaatatg 248100
taatggagaa taagaggggg acaaatctgg ggtccaggcc acctgcattt acaggaaag 248160
gaaagagaag tctagactgc aagaagctag cttagaaagg caagagcttc ctgataaaac 248220
aaaaaacaga tgggctcggt tttaactacg tccgaggaag cctggaaaaa ggctgagcta 248280
catctggtga gggaacacat cctagtccat cctcgtcacc tccatgtgta cttgatggta 248340
tgttaagggc gaatctgctt agtatgttct gcttttgttt tgtaaagatg cttatgctgt 248400
caagttacca gaaagaaaat gagaagttac attgcttgtc atgagttgga tggtgatagt 248460
```

```
cacaactgta aaaacagtgc aggtaccagg atccaatctc atttttccta acaagaaatt   248520
actgttaagt ccgcaaaatg ggacttggtc atgggcctac taaggccaat tagaacttgt   248580
aatttggttt aaaacaccag caaatgcaac acatacgtag tattcagaaa acatgaaata   248640
tggcattata ataaggataa cagtagttg ctatacagaa tctggtggtg aggggagttg    248700
tttaattttg ccattattgt caaatctaca gagttaatta atgccatggc ccagaggaag   248760
gaaaggagac atacactgtt ctagtctgtt tctgtacctg caacatgatg gtgagggag    248820 tgtaccttca tggtctgagg caggaaatat ccacatgaaa taaagtactg agaagtaccc   248880
agaacaacta aaaacatgta gtttggtcag tccctggaag tgtgaggcta aatggaagg    248940 agttaggatg agaacatgga gaatcacttg ggcttagcgt gagccacagc aattcaaggc   249000
caggagtgca agaatagagc aggtgaccaa tgcacagcat cctgcctgaa aagtgctcct   249060
gacaccctgg aagtcaagcc taggggcag cggagtttag gagcaggaga gttacaggtg    249120
tttaatgctt cctgggctaa aacccccgaa ttatctgtat taaatgtata acgtttacta   249180
tccatattgc tgtgcatgtt aaactcaaaa actaatttgt gtagaaaggc actgacctaa   249240
agtaagtttt atttagcctt aaagaattgg taaatcagag caattcattc aatacacagc   249300
atctactaga agctaagaag atattgtaat tcctctagat gggaaagtta ggggcaggag   249360
gaaaagaaca acatgtaggg aaggtggcat tggggtgag tctttaaaga ggcacaggac    249420
tgtgacgaga gaaggttcta tgggaggag tacagaggga agtagtaaat tacatgtaaa    249480
aaaggaacat gtgaaaagct acatgaaggc atctcaatcc ctctaaagat atatttggaa   249540
agaaagaaat gggtggaaaa tgaagatgac agatcagggc tatgttttag aacagtgggt   249600
ctcaaccctg gatgcatgta agaatcacca gggacccttta aaaaacccat tgtccaggct   249660 tccccctcaga ctagagtcca ggccctgaag ttaaaaaaaa aaaaaaaaaa gaagcctcaa   249720
gtggatttca tcatgcaacc aaagatgtga acttgtcctt tcagaggatt agtttggatt   249780
tacataaaag gaaaacattt attaacattt gttcttcctg ttgatttaaa tatgtatatt   249840 tgttttttaat tcagaaggcc tgctaaatgc cacttgatta gtaaacccaa ttactctccc   249900
ttactgttag agcagtgagg agttatattg ttgcaaataa taaagataac ttactcattt   249960
ttgttttcca acagataatg atggttgcag ggcccctctt caatggaggc attgccagcc   250020
ttctggccat gaaggagaaa gtgatttcaa ctaacccagg aaactcttac ctctaaatgg   250080
agatacttcc tgataacaga agaaactggg catctaaccc agaaatacca gctgagtagg   250140
agaagagaaa aggcatcagc cagtcaaggt ttcagaaggc tgccaaca                 250188
```

<210> SEQ ID NO 131
<211> LENGTH: 300
<212> TYPE: DNA
<213> ORGANISM: Homo sapiens

<400> SEQUENCE: 131

```
atatgccaga aaagttgaat agtatcagat tccaaatctg tatggagacc aaatcaagtg    60
aatatctgtt cctcctctct ttattttagc tggaccagac caattttgag gaaaggatac   120
agacagcgcc tggaattgtc agacatatac caaatccctt ctgttgattc tgctgacaat   180
ctatctgaaa aattggaaag gtatgttcat gtacattgtt tagttgaaga gagaaattca   240
tattattaat tatttagaga agagaaagca aacatattat aagtttaatt cttatattta   300
```

<210> SEQ ID NO 132
<211> LENGTH: 420

<212> TYPE: DNA
<213> ORGANISM: Homo sapiens

<400> SEQUENCE: 132

```
tctcctctaa agatgaaaag tcttgtgttg aaattctcag ggtatttat gagaaataaa      60
tgaaatttaa tttctctgtt ttccccttt tgtaggaagt caccaaagca gtacagcctc     120
tcttactggg aagaatcata gcttcctatg acccggataa caaggaggaa cgctctatcg    180
cgatttatct aggcataggc ttatgccttc tctttattgt gaggacactg ctcctacacc    240
cagccatttt tggccttcat cacattggaa tgcagatgag aatagctatg tttagtttga    300
tttataagaa ggtaatactt ccttgcacag gccccatggc acatatattc tgtatcgtac    360
atgtttaat gtcataaatt aggtagtgag ctggtacaag taagggataa atgctgaaat     420
```

<210> SEQ ID NO 133
<211> LENGTH: 300
<212> TYPE: DNA
<213> ORGANISM: Homo sapiens

<400> SEQUENCE: 133

```
cctttactta ataatgaatg cataataact gaattagtca tattataatt ttacttataa     60
tatatttgta ttttgtttgt tgaaattatc taactttcca tttttctttt agactttaaa   120
gctgtcaagc cgtgttctag ataaaataag tattggacaa cttgttagtc tcctttccaa   180
caacctgaac aaatttgatg aagtatgtac ctattgattt aatcttttag gcactattgt    240
tataaattat acaactggaa aggcggagtt tccctgggtc agataatagt aattagtggt    300
```

<210> SEQ ID NO 134
<211> LENGTH: 300
<212> TYPE: DNA
<213> ORGANISM: Homo sapiens

<400> SEQUENCE: 134

```
ttgaataaaa gaaatatgac ttaaaacctt gagcagttct taatagataa tttgacttgt     60
ttttactatt agattgattg attgattgat tgattgattt acagagatca gagagctggg   120
aagatcagtg aaagacttgt gattacctca gaaatgattg aaaatatcca atctgttaag   180
gcatactgct gggaagaagc aatggaaaaa atgattgaaa acttaagaca gtaagttgtt    240
ccaataattt caatattgtt agtaattctg tccttaattt tttaaaaata tgtttatcat    300
```

<210> SEQ ID NO 135
<211> LENGTH: 300
<212> TYPE: DNA
<213> ORGANISM: Homo sapiens

<400> SEQUENCE: 135

```
attattaaaa ttcatatata agatgtagca caatgagagt ataaagtaga tgtaataatg     60
cattaatgct attctgattc tataatatgt ttttgctctc ttttataaat aggatttctt   120
acaaaagcaa gaatataaga cattggaata taacttaacg actacagaag tagtgatgga   180
gaatgtaaca gccttctggg aggaggtcag aattttaaaa aaattgtttg ctctaaacac    240
ctaactgttt tcttctttgt gaatatggat ttcatcctaa tggcgaataa aattagaatg    300
```

<210> SEQ ID NO 136
<211> LENGTH: 360
<212> TYPE: DNA
<213> ORGANISM: Homo sapiens

<400> SEQUENCE: 136

```
gcatctattg aaaatatctg acaaactcat cttttatttt tgatgtgtgt gtgtgtgtgt      60
gtgtgttttt ttaacaggga tttggggaat tatttgagaa agcaaaacaa aacaataaca     120
atagaaaaac ttctaatggt gatgacagcc tcttcttcag taatttctca cttcttggta     180
ctcctgtcct gaaagatatt aatttcaaga tagaaagagg acagttgttg gcggttgctg     240
gatccactgg agcaggcaag gtagttcttt tgttcttcac tattaagaac ttaatttggt     300
gtccatgtct ctttttttt ctagtttgta gtgctggaag gtattttggg agaaattctt     360
```

<210> SEQ ID NO 137
<211> LENGTH: 420
<212> TYPE: DNA
<213> ORGANISM: Homo sapiens

<400> SEQUENCE: 137

```
caaataagaa tatacacttc tgcttaggat gataattgga ggcaagtgaa tcctgagcgt      60
gatttgataa tgacctaata atgatgggtt ttatttccag acttcacttc taatggtgat     120
tatgggagaa ctggagcctt cagagggtaa aattaagcac agtggaagaa tttcattctg     180
ttctcagttt tcctggatta tgcctggcac cattaaagaa aatatcatct ttggtgtttc     240
ctatgatgaa tatagataca gaagcgtcat caaagcatgc caactagaag aggtaagaaa     300
ctatgtgaaa acttttttgat tatgcatatg aacccttcac actacccaaa ttatatattt     360
ggctccatat tcaatcggtt agtctacata tatttatgtt tcctctatgg gtaagctact     420
```

<210> SEQ ID NO 138
<211> LENGTH: 240
<212> TYPE: DNA
<213> ORGANISM: Homo sapiens

<400> SEQUENCE: 138

```
catgtagtga actgtttaag gcaaatcatc tacactagat gaccaggaaa tagagaggaa      60
atgtaattta atttccattt tcttttttaga gcagtataca aagatgctga tttgtattta     120
ttagactctc cttttggata cctagatgtt ttaacagaaa aagaaatatt tgaaaggtat     180
gttctttgaa taccttactt ataatgctca tgctaaaata aaagaaagac agactgtccc     240
```

<210> SEQ ID NO 139
<211> LENGTH: 300
<212> TYPE: DNA
<213> ORGANISM: Homo sapiens

<400> SEQUENCE: 139

```
gattcaagta atactattct tttattttca tatattaaaa ataaaaccac aatggtggca      60
tgaaactgta ctgtcttatt gtaatagcca taattctttt attcaggagt gctttttga     120
tgatatggag agcataccag cagtgactac atggaacaca taccttcgat atattactgt     180
ccacaagagc ttaattttg tgctaatttg gtgcttagta attttctgg cagaggtaag     240
aatgttctat tgtaaagtat tactggattt aaagttaaat taagatagtt tggggatgta     300
```

<210> SEQ ID NO 140
<211> LENGTH: 180
<212> TYPE: DNA
<213> ORGANISM: Homo sapiens

<400> SEQUENCE: 140

```
gtgatgtgaa tttagatgtg ggcatgggag gaataggtga agatgttaga aaaaaaatca      60
```

```
actgtgtctt gttccattcc aggtggctgc ttctttggtt gtgctgtggc tccttggaaa    120
gtgagtattc catgtcctat tgtgtagatt gtgttttatt tctgttgatt aaatattgta    180
```

<210> SEQ ID NO 141
<211> LENGTH: 420
<212> TYPE: DNA
<213> ORGANISM: Homo sapiens

<400> SEQUENCE: 141

```
tttcaggtac aagatattat gaaattacat tttgtgttta tgttatttgc aatgttttct     60
atggaaatat ttcacaggca ggagtccaat tttcactcat cttgttacaa gcttaaaagg    120
actatggaca cttcgtgcct tcggacggca gccttacttt gaaactctgt tccacaaagc    180
tctgaattta catactgcca actggttctt gtacctgtca acactgcgct ggttccaaat    240
gagaatagaa atgattttg tcatcttctt cattgctgtt accttcattt ccattttaac    300
aacaggtact atgaactcat taactttagc taagcattta agtaaaaaat tttcaatgaa    360
taaaatgctg cattctatag gttatcaatt tttgatatct ttagagttta gtaattaaca    420
```

<210> SEQ ID NO 142
<211> LENGTH: 600
<212> TYPE: DNA
<213> ORGANISM: Homo sapiens

<400> SEQUENCE: 142

```
taaccaagtg acaaatagca agtgttgcat tttacaagtt attttttagg aagcatcaaa     60
ctaattgtga aattgtctgc cattcttaaa aacaaaaatg ttgttatttt tatttcagat    120
gcgatctgtg agccgagtct ttaagttcat tgacatgcca acagaaggta aacctaccaa    180
gtcaaccaaa ccatacaaga atggccaact ctcgaaagtt atgattattg agaattcaca    240
cgtgaagaaa gatgacatct ggccctcagg gggccaaatg actgtcaaag atctcacagc    300
aaaatacaca gaaggtggaa atgccatatt agagaacatt tccttctcaa taagtcctgg    360
ccagagggtg agatttgaac actgcttgct ttgttagact gtgttcagta agtgaatccc    420
agtagcctga agcaatgtgt tagcagaatc tatttgtaac attattattg tacagtagaa    480
tcaatattaa acacacatgt tttattatat ggagtcatta tttttaatat gaaatttaat    540
ttgcagagtc ctgaacctat ataatgggtt tattttaaat gtgattgtac ttgcagaata    600
```

<210> SEQ ID NO 143
<211> LENGTH: 360
<212> TYPE: DNA
<213> ORGANISM: Homo sapiens

<400> SEQUENCE: 143

```
ttccaatggt ttttattgaa gtacaatact gaattatgtt tatggcatgg tacctatatg     60
tcacagaagt gatcccatca cttttacctt ataggtgggc ctcttgggaa gaactggatc    120
agggaagagt actttgttat cagcttttt gagactactg aacactgaag gagaaatcca    180
gatcgatggt gtgtcttggg attcaataac tttgcaacag tggaggaaag cctttggagt    240
gataccacag gtgagcaaaa ggacttagcc agaaaaaagg caactaaatt atatttttta    300
ctgctatttg atacttgtac tcaagaaatt catattactc tgcaaaatat atttgttatg    360
```

<210> SEQ ID NO 144
<211> LENGTH: 360
<212> TYPE: DNA

<213> ORGANISM: Homo sapiens

<400> SEQUENCE: 144

| | |
|---|---|
| gggtgtttct tattttaaaa taatttttct acttgaaata ttttacaata caataaggga | 60 |
| aaaataaaaa gttatttaag ttattcatac tttcttcttc ttttcttttt tgctatagaa | 120 |
| agtatttatt ttttctggaa catttagaaa aaacttggat ccctatgaac agtggagtga | 180 |
| tcaagaaata tggaaagttg cagatgaggt aaggctgcta actgaaatga ttttgaaagg | 240 |
| ggtaactcat accaacacaa atggctgata tagctgacat cattctacac actttgtgtg | 300 |
| catgtatgtg tgtgcacaac tttaaaatgg agtaccctaa catacctgga gcaacaggta | 360 |

<210> SEQ ID NO 145
<211> LENGTH: 6132
<212> TYPE: DNA
<213> ORGANISM: Homo sapiens

<400> SEQUENCE: 145

| | |
|---|---|
| aattggaagc aaatgacatc acagcaggtc agagaaaaag ggttgagcgg caggcaccca | 60 |
| gagtagtagg tctttggcat taggagcttg agcccagacg gccctagcag ggaccccagc | 120 |
| gcccgagaga ccatgcagag gtcgcctctg gaaaaggcca gcgttgtctc caaacttttt | 180 |
| ttcagctgga ccagaccaat tttgaggaaa ggatacagac agcgcctgga attgtcagac | 240 |
| atataccaaa tcccttctgt tgattctgct gacaatctat ctgaaaaatt ggaagagaa | 300 |
| tgggatagag agctggcttc aaagaaaaat cctaaactca ttaatgccct tcggcgatgt | 360 |
| ttttctgga gatttatgtt ctatggaatc tttttatatt taggggaagt caccaaagca | 420 |
| gtacagcctc tcttactggg aagaatcata gcttcctatg acccggataa caaggaggaa | 480 |
| cgctctatcg cgatttatct aggcataggc ttatgccttc tctttattgt gaggacactg | 540 |
| ctcctacacc cagccatttt tggccttcat cacattggaa tgcagatgag aatagctatg | 600 |
| tttagtttga tttataagaa gactttaaag ctgtcaagcc gtgttctaga taaataagt | 660 |
| attggacaac ttgttagtct cctttccaac aacctgaaca aatttgatga aggacttgca | 720 |
| ttggcacatt tcgtgtggat cgctcctttg caagtggcac tcctcatggg gctaatctgg | 780 |
| gagttgttac aggcgtctgc cttctgtgga cttggtttcc tgatagtcct tgcccttttt | 840 |
| caggctgggc tagggagaat gatgatgaag tacagagatc agagagctgg gaagatcagt | 900 |
| gaaagacttg tgattacctc agaaatgatt gaaaatatcc aatctgttaa ggcatactgc | 960 |
| tgggaagaag caatggaaaa aatgattgaa aacttaagac aaacagaact gaaactgact | 1020 |
| cggaaggcag cctatgtgag atacttcaat agctcagcct tcttcttctc agggttcttt | 1080 |
| gtggtgtttt tatctgtgct tccctatgca ctaatcaaag gaatcatcct ccggaaaata | 1140 |
| ttcaccacca tctcattctg cattgttctg cgcatggcgg tcactcggca atttcctgg | 1200 |
| gctgtacaaa catggtatga ctctcttgga gcaataaaca aaatacagga tttcttacaa | 1260 |
| aagcaagaat ataagacatt ggaatataac ttaacgacta cagaagtagt gatggagaat | 1320 |
| gtaacagcct ctgggaggag gggatttggg gaattatttg agaaagcaaa acaaaacaat | 1380 |
| aacaatagaa aaacttctaa tggtgatgac agcctcttct tcagtaattt ctcacttctt | 1440 |
| ggtactcctg tcctgaaaga tattaatttc aagatagaaa gaggacagtt gttggcggtt | 1500 |
| gctggatcca ctggagcagg caagacttca cttctaatgg tgattatggg agaactggag | 1560 |
| ccttcagagg gtaaaattaa gcacagtgga agaatttcat tctgttctca gttttcctgg | 1620 |
| attatgcctg gcaccattaa agaaaatatc atctttggtg tttcctatga tgaatataga | 1680 |

```
tacagaagcg tcatcaaagc atgccaacta gaagaggaca tctccaagtt tgcagagaaa    1740
gacaatatag ttcttggaga aggtggaatc acactgagtg gaggtcaacg agcaagaatt    1800
tctttagcaa gagcagtata caaagatgct gatttgtatt tattagactc tccttttgga    1860
tacctagatg ttttaacaga aaaagaaata tttgaaagct gtgtctgtaa actgatggct    1920
aacaaaacta ggattttggt cacttctaaa atggaacatt taaagaaagc tgacaaaata    1980
ttaattttgc atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagacctta caccgtttct cattagaagg atgctcct     2160 gtctcctgga cagaaacaaa aaaacaatct tttaaacaga ctggagagtt tggggaaaaa    2220
aggaagaatt ctattctcaa tccaatcaac tctatacgaa aattttccat tgtgcaaaag    2280
actcccttac aaatgaatgg catcgaagag gattctgatg agcctttaga gagaaggctg    2340
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgctt ttttgatgat    2640
atggagagca taccagcagt gactacatgg aacacatacc ttcgatatat tactgtccac    2700
aagagcttaa ttttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa atttttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc aattttcac tcatcttgtt    3300 acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt ctttaagttc attgacatgc aacagaagg taaacctacc    3660 aagtcaacca aaccatacaa gaatggccaa ctctcgaaag ttatgattat tgagaattca    3720
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga agagtactt gttatcagct    3900 tttttgagac tactgaacac tgaaggagaa atccagatcg atggtgtgtc ttgggattca    3960
ataactttgc aacagtggag gaaagccttt ggagtgatac cacagaaagt atttattttt    4020
```

```
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctgaat gccacaatt tttggtcata     4380
gaagagaaca aagtgcggca gtacgattcc atccagaaac tgctgaacga gaggagcctc    4440
ttccggcaag ccatcagccc ctccgacagg gtgaagctct tcccccaccg gaactcaagc    4500
aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg     4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt   4860
gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat aagtaatga taactggaaa cttcagcggt ttatataagc ttgtattcct     5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
ccctacctg ggaaagggct gttataatct ttcacagggg acaggatggt tcccttgatg     5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaatttttt ctctaggaaa    5700
tatttatttt aataatgttt caaacatata taacaatgct gtattttaaa agaatgatta    5760
tgaattacat ttgtataaaa taatttttat atttgaaata ttgactttttt atggcactag   5820
tatttctatg aaatattatg ttaaaactgg gacaggggag aacctagggt gatattaacc    5880
agggccatg aatcaccttt tggtctggag ggaagccttg gggctgatgc agttgttgcc     5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aaatccatac    6120
atttgtgtga aa                                                        6132
```

<210> SEQ ID NO 146
<211> LENGTH: 1480
<212> TYPE: PRT
<213> ORGANISM: Homo sapiens

<400> SEQUENCE: 146

-continued

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
    275                 280                 285

Arg Gln Thr Glu Leu Lys Leu Thr Arg Lys Ala Ala Tyr Val Arg Tyr
290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
    355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415
```

```
Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
        450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
```

835                 840                 845
Tyr Leu Arg Tyr Ile Thr Val His Lys Ser Leu Ile Phe Val Leu Ile
                850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
                915                 920                 925
Met Gly Phe Phe Arg Gly Leu Pro Leu Val His Thr Leu Ile Thr Val
                930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
Asp Phe Ile Gln Leu Leu Leu Ile Val Ile Gly Ala Ile Ala Val Val
                995                1000                1005
Ala Val Leu Gln Pro Tyr Ile Phe Val Ala Thr Val Pro Val Ile
                1010                1015                1020
Val Ala Phe Ile Met Leu Arg Ala Tyr Phe Leu Gln Thr Ser Gln
                1025                1030                1035
Gln Leu Lys Gln Leu Glu Ser Glu Gly Arg Ser Pro Ile Phe Thr
                1040                1045                1050
His Leu Val Thr Ser Leu Lys Gly Leu Trp Thr Leu Arg Ala Phe
                1055                1060                1065
Gly Arg Gln Pro Tyr Phe Glu Thr Leu Phe His Lys Ala Leu Asn
                1070                1075                1080
Leu His Thr Ala Asn Trp Phe Leu Tyr Leu Ser Thr Leu Arg Trp
                1085                1090                1095
Phe Gln Met Arg Ile Glu Met Ile Phe Val Ile Phe Phe Ile Ala
                1100                1105                1110
Val Thr Phe Ile Ser Ile Leu Thr Thr Gly Glu Gly Glu Gly Arg
                1115                1120                1125
Val Gly Ile Ile Leu Thr Leu Ala Met Asn Ile Met Ser Thr Leu
                1130                1135                1140
Gln Trp Ala Val Asn Ser Ser Ile Asp Val Asp Ser Leu Met Arg
                1145                1150                1155
Ser Val Ser Arg Val Phe Lys Phe Ile Asp Met Pro Thr Glu Gly
                1160                1165                1170
Lys Pro Thr Lys Ser Thr Lys Pro Tyr Lys Asn Gly Gln Leu Ser
                1175                1180                1185
Lys Val Met Ile Ile Glu Asn Ser His Val Lys Lys Asp Asp Ile
                1190                1195                1200
Trp Pro Ser Gly Gly Gln Met Thr Val Lys Asp Leu Thr Ala Lys
                1205                1210                1215
Tyr Thr Glu Gly Gly Asn Ala Ile Leu Glu Asn Ile Ser Phe Ser
                1220                1225                1230
Ile Ser Pro Gly Gln Arg Val Gly Leu Leu Gly Arg Thr Gly Ser
                1235                1240                1245

```
Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
    1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320

Leu Arg Ser Val Ile Glu Gln Phe Pro Gly Lys Leu Asp Phe Val
    1325                1330                1335

Leu Val Asp Gly Gly Cys Val Leu Ser His Gly His Lys Gln Leu
    1340                1345                1350

Met Cys Leu Ala Arg Ser Val Leu Ser Lys Ala Lys Ile Leu Leu
    1355                1360                1365

Leu Asp Glu Pro Ser Ala His Leu Asp Pro Val Thr Tyr Gln Ile
    1370                1375                1380

Ile Arg Arg Thr Leu Lys Gln Ala Phe Ala Asp Cys Thr Val Ile
    1385                1390                1395

Leu Cys Glu His Arg Ile Glu Ala Met Leu Glu Cys Gln Gln Phe
    1400                1405                1410

Leu Val Ile Glu Glu Asn Lys Val Arg Gln Tyr Asp Ser Ile Gln
    1415                1420                1425

Lys Leu Leu Asn Glu Arg Ser Leu Phe Arg Gln Ala Ile Ser Pro
    1430                1435                1440

Ser Asp Arg Val Lys Leu Phe Pro His Arg Asn Ser Ser Lys Cys
    1445                1450                1455

Lys Ser Lys Pro Gln Ile Ala Ala Leu Lys Glu Glu Thr Glu Glu
    1460                1465                1470

Glu Val Gln Asp Thr Arg Leu
    1475                1480

<210> SEQ ID NO 147
<211> LENGTH: 152082
<212> TYPE: DNA
<213> ORGANISM: Mus musculus

<400> SEQUENCE: 147
aattggaagc aaatgacatc acctcaggtc tgagtaaaag ggacgagcca aaagcattga      60
cctggtcctg gatatccaga tgtcgagtcc aacctgaatt tagccgaaca cagacctcat     120
tgcctcacgg agacatcatg cagaagtcgc ctttggagaa agccagcttt atctccaaac     180
tcttcttcag gtgagagggt actcagcgga tctttgcacg acacatgtg cctatgcagg      240 agaagggaat gaatatgggc agactttggg aaaacaggaa gagattttg ttgtgttttgt     300 tttgttttaa aaggtgtgtt gtcattcagt gctttaaagg aaataagcat ttttgtacaa     360
taaaatgaag ctgattgaat agagaacaaa atatacttgc aactgtgaat cagacttgca    420
acagccaaat atgctacgga gcaatagata tatattttt taatttcctg aaaaaagtta     480
tacttcataa gtgtacttaa tagaacattc ctaagattgg tctgttattt tctccaagaa    540
aagctgaccg caagtgcagt gcctgtgtaa taggtgctct gaaaacattt gttgactgaa    600
tttttttaaa agtccaggaa ttatattgta tttactttt gccgttgtaa tattgagtaa     660
```

```
gtctaacatg ctcatcacag ttacattatt ctttttaaaa atgagcaagt cagttaaaat    720
atctaacttt aaaaagaaat aatataagca atgcattaaa aaagtgagtt accatgggga    780
tatgaaacta gagttttagc cactgaagct atattcaatt gacaattagg acattgttct    840
cttatcctac attgtcaaaa aaccaaaccc tcaatctaat aggattttta aattagaatt    900
taagttggaa gacctaggca agaattaagc gctttgtatt tgaagtgctc cgtggagctt    960
cgtctgctct gatcctgtag tgtgaatgaa tgaaaagagc agcgctcatg ggtcctcagc   1020
tgactcaccc ccccccccc acacacacac caatgagtca gcacactgaa gtatcataag   1080
tgtcgaatat gttctcaacc tgccctatgc tgtgggtagg gggcaaggct cagccttagt   1140
cttcctgatg ttccttttc agccggtcta gagctcaagg ctgaggaaag acaagtgctt   1200
ctgcaggaga gctcccccg gtggttggga gagaaggaag ggctttcttc tttagaatga   1260
atatttgtgg tgccttttgt tacttcatct ataaatctag cttatcggtc tggatctatt   1320
ttcttattac ttacaaaatc agaatgtcac ttgacataca tgtgaggctt ttatgaaagc   1380
ctattgagga acctaaatgt caatgtgtct gtaaaggcaa gttttcagga gaatgaatat   1440
ctcttgtgtg gttttcccac taagtagtaa gaaacttcaa aattttttcac ttatcaaagt   1500 gtttcaaaaa tttcccgttt ttataaccca cctaataaat tgtagtgtgc tttacaaatg   1560
ttcttaggct gatttggaaa ggaaatgtat tataatggct gtgaaatttg ttaagaacat   1620
actcatttct gccctccaaa tgatttcata atcagttgct ttaagaatag gtgtgttttt   1680
aagagtttag ttcctactat ttataggaac tgacatttag ctaagtacta gtcagtgatt   1740
ataaacttcc ttctggactt taattttcaa agagtaaaac cctttctcc actggactag   1800 gcagtgccgc ctagtgacca gggcagtggg ccctggattc ccatggcctg gactcaggct   1860
gcagatctac tgcttagtag gcaagccctt tggtgtctct gcatgacttc agtgctacaa   1920
cttggagtct gtcagtgtga cacataatgt aatgggttag tctgttgagg aatatatgct   1980
gtgctttgag gacatgttag ctgcccttac tgttgtttac atgtttacat tcctcgaagt   2040
gctgggatcc tcactgtaaa ggacagtgag tttatttctg ctgggtgcac ttttgtgact   2100
atagcctgta tctatgccat ttgcttgaga agttagcata ggggatagat agcctcacgt   2160
agcatgggct tgttagatac ttagatgaaa gccatgctct tacatcagat ctccttcagt   2220
gccttagaat ttaacctatc ccatcaagct tagggttata aaagactcct aaaagctgac   2280
ttctatgtgt ctactattat ggtcttggtt ttggattata ttaattaaca ttttaattat   2340
ttagattatg ttactgagaa accaaaacaa gtttaataat aatttaagta cttttttattt   2400 ttttaagttt tcagtaagta aaaaaatgga aagacattgg aattggtcta acacagaaga   2460 taatttacc atgaaaattt caagtaattt tttttacttt catggaaaat aaatgcatta   2520
acttgaaggt gtaatgataa catttatgaa ataagttgtt tcaaaacaag tggtgatata   2580
tttatacaga atttatgatt gacatattag tggaatttaat tcctaaaaac ctttgatttg   2640
tagaaatgtt tgaactttac actttcatag agatttaaga aaaagatta tgcctaacgt   2700 gtacctgtta gtgtgtgtgt gtgtgtgtat gtgcgcgtat gcatgtttgt atgaccatag   2760
agtgcagtat aagctatcat ctcttgagtc atgtctctca ttggcctgaa tctcaccagt   2820
tatgttagac agacttgcca gtgaacccaa gggctttccc tgactctacc ttctcagcac   2880
tgggattaca atcttgtgtc actctgcccg ccttttcacc taggagcttg ggattgagct   2940
cggttcttca ttcatgtgaa gttcttctct gactgggtta tgaacagtcc caagaaattg   3000
ggtagcaaca tttccattct gtttgtgatc catattacag agattatact tgacaaaact   3060
```

```
taaggttatc caaatctgaa ggccactttt gatatactga ggatatggta tttagaaaac   3120
caagaattgc tgtcccttca gttgatggat gtcatacagt ggccacagct ccagatttca   3180
tttggctttt ctttaataga aatgggaaga agccacatct aggatggaga gaccctctgt   3240
ttggacagtg tacaagcact gcccgatact ggctctgtgc cagcaactta ggactccctt   3300
ctgtttattt tcttttcact gataatgttt ggttgttaca cagctcagaa atttcaactt   3360
gggatttatg ttaggttcat gtcagttttg tttagtttaa tcaacagttc taagagcacc   3420
tcttgtacag gacatgatga aatcatgatt ttgtgtatgt gcatatatat gtgtataata   3480
aatatctcta tacagtgaaa tttattttag ttgatatcac aattattaaa atttatttta   3540
aggttttata gcacattact acacaatata ttttgatagt caattcctca gagcagagga   3600
agctattatc ttaaaaataa cttcttcaac attttgtttg atatacgatg aaatactact   3660
cagtgcacac tgatatacaa gggaaatcaa ggcttttgt tttctttatg gaagtttgac    3720
ttaactgtga taattcctaa gtgttaaaac atgtttaaga ggtccacaaa taaatatcac   3780
cataaagtat gttattactg ttaatgccct ttcataggaa cctgtaattt cactgcggta   3840
gcactataga taagtatagg attgccaaac cataagggaa gggcggtaac catttagcat   3900
gcagtgagat attatttgtt gagactttaa aaacacatct gagtcagcag agtttgggcc   3960
gttttgattt gctcttcacc atgcatcttg tgcattccct cagagccaag tctgcaaagc   4020
agtgagtata agaggcgaaa actatgaaag aggtccactt atttggagat actaacagag   4080
ggatttcata aatacatttt tcatcatcag taagggaaac attttaatgg cttcccttca   4140
gctcttaaga atggaatgga tgcaccatgt agggttttct ttgtaaaatc agcattacaa   4200
agtggcctct tcatggactt gattgtcaga gaacttaggc ttttagcaag aatactctag   4260
tagttcagat gaggcttgtc aaaatgtcaa tttcagtata agccattaat tatcttttga   4320
cattaatgac tatttgaaat tgtaaactac ttttgtgttt agtattcaca tcatttcatg   4380
actccaggat tacatgatta taatacctgt ttcttgttga aattgtctca caatgctaaa   4440
catcatctat atgcagtata catacatact ctaccctcaa aataatggga caatcatttt   4500
gatacaatgg gtgagggaa acaactgttg acacattttt taatagagta agtattcctt    4560 cacatttttcc ttgtgatgtt tatcatataa actcttcaga aggcagtcta ctttatgact  4620
ccttgttcta gggcagtagt tctcaacctg tgtgtttcaa gggttaaatg acccttacac   4680
atgtgttgca tataagctat cctacatatc agctcttcac catacaatga ataacaatag   4740
aagaattaga ctcatgaagt agcaacaaaa attatcttat aatttggatt caccataaca   4800
tgagaaactg tattaaagag ttccagcaat agaaaggttg aggaccactg cgctagggta   4860
agggaatggt ttgagagattt ttgaagtctt tagcattgtt agacttctta gcttggaaga  4920
tattctcttg atatcataag attagctgtc ctccccaccc aagtcaaagg ggtatttccc   4980
cagtatttcc tgtaggtcat gatgactcag agcaatgttt ggagggcaat ttcattcact   5040 ccctttttcac caccaccgta ctccatgctt ggcattaagg tggtagaggc gctgccctct  5100
gaatgaatga ataccttaaa actgatgatc tcaagccaca gagatcccta tcccatactc   5160
atggctgtct agcaaggttt gatagagaag tgttgtatag gaactgcaag aacaagtgag   5220
agaacagcag tggttcagag aaggtctgga gtctgtcctg aaagcatgtg acagaacttg   5280
ggaggtagat ctggaaacta gcaagggcta gaccccctggg taccttatat atttcttagg  5340
gctttattgc actgctcatg aaatgaaagg tgggaaattt taagcaggca gagatgtgat   5400
```

```
tatttcaaga ttgttggcgt tttttttttt gtttttttgt tttttttgttt tttttaaaga    5460 ctgacagaag ggatagagaa agatgcctga aagatgtttg ggaagcaaaa taatcatatt    5520
tttaaattag aggtggaagg tgagagtgag gaaaaaataa gagggcttgg atgggtcagt    5580
ttgggtggta gaatggtagg tgatacatac tatgaagtgg ggtccttcta ttagaggcag    5640
aggcctggtg tgaggttaga tgcctatgca agactgcagt ctctaaaaga aagtgcaact    5700
ggcttgaggt gggttataca gtttgaatga attctttgtc ttgtcaatac tgttttttcaa   5760 caaataataa ttagtcagaa ctaatatttt atttggtagt gctaggcacc aaacccagac    5820
ccatgtctat attaaagcat tctcctacta aactgcaccc cagccccaag taattacttc    5880
ttagcagaga aattcctagc acttagttca gacagatttg ccaactaaca tttgcttttc    5940
tactccatta cacctgacat ttaatagtca ctgttttctt tacataaaaa tattggtctc    6000
tccctctctc tgtctctctg tctctctgtc tctgtctctg tctgtctgtc tgtctctctc    6060
tctctttctc tttctctctc tctctctctc tcacacacac acacacaatt aaaagccatc    6120
atggatcagt gtcagtgatc gagtaagaca ttaggtattc ccataattca gtgcatcaag    6180
tacataatta caatgagacc taaaaaatta ttcactctttt taagagttta tagacctgtt    6240
gaatttaaga gtccgagata gcaatcccaa tagcagggcc aaggattttt gcaacagaat    6300
ttgatgaacc agataggcac tataagatga gttcattatg gtgaggataa taaccttgaa    6360
atataaatgt gacttttttag tgatgtgtta attatttatt tatgcaagcc tgtgtatgcg    6420
catttattta tcattactag tgagcctcta tacttaccag gtttctaaca gttaacagtc    6480
ttagactcta tataagaatt tattaaaaat tctgtttatt ctgcctaaag tttcattgta    6540
ttatttttaa taacgcaacc tttttttctt tgtaataaga tggctatcac attcatttat    6600
aggttctgta attatattac ttagtttaat tagactaggc attaattttg attcataaaa    6660
tcattgactg tttaaagtag ttgatatata ataaaatatt acagttaaaa atggactttc    6720
ttgaaaacaa aaattattga atatttaaaa aaattaatga aatctttcac ctgtgttgtt    6780
agcaaaatgt aacttcattt agaaatgtgt aatgtgttag tagtcctttta ctcagccggc    6840 ccatggattc cctggagtat gaaactgctg acttgttggc acaggtgtca tcggagcctt    6900
gagagccagg tgctttgctg ccacagaagg ggagcagaag cagtctcttg tggttcactc    6960
tccttttgtc accattgtga ccactgcttc tgcagagtga catcagacac agtccagtgg    7020
atttacaact cattagtaaa gcagtatgtc agggctctgc acttaatgga aacttgttca    7080
gggttagtgg tgtggtaaga tggaacccag ctgtaagttg taatatttta ttatgtatca    7140
actactttac atagtcagtg atttatataaa tcaaaattaa aacaggatga ggagattctt    7200
gaaattagaa ccttctactt cacaaacaac agccatttct atagcttttc tttactctga    7260
caaatactaa gtatctatat aggttctctg tggaatatag cacacacata aaatggaaaa    7320
tatattaaat atgccaagtc ctagatccca tgtgtacctg ttaattaaat ttatgggaaa    7380
gaacaacttc tatgatctcc tttaacaaat gctaaggtaa ttcttctttt tgctaacatc    7440
taaaatcatc aactcaacga taaaacaggt ttggataacc caacaggtct tcattgggct    7500
aacatcctcc tcctcctcct cctccccctc ttcctcctcc tcctcctctt cagtaaatta    7560
acaataaaga cacaaaaata ggtcaactcg gaattctgta gttttgcctc tatcttccag    7620
cccttattaa gtacactcaa gagattacat acattatctc agtgaagttt ttaatctgtc    7680
tttgataatt gcacatataa gaaatgtggt tttaggggac tgcagtttag cagccaccaa    7740
gctaagagat gtgatgtcag atgtatcttt agattggtgt aaatccagac ataaaatttt    7800
```

```
aatcaataca tcacacacct agaatagaat tgatcaatta tttcacatgg ctttatatat    7860
actttaatgt tttttcttgg gtctgaaata atttttttact gcatttgttt atagacaaca   7920
ttaaacaggc catcagttag tcttcttgga agggcttgtt gctttaacaa caacaaagaa    7980
ttactttatt ttatgtgtac agtagttttt ccagcttgtt tgtttgtgca cattctgcca    8040
gtggaagcca gaagagggtg ctgaatagac tggagttgca ggtagtggag agacatctga    8100
agatgctgaa aactgaggtg agggcctctg gaagagcagc tcttaagccc atctcttctc    8160
tgagccatct cttcagccca tttattcagt ctgtttctta gcataggtct ttatgacatc    8220
cacaggaggc aggatggaac tttcctaaaa ataacaatat ccttatagtt tactttcagt    8280
attatttgaa aacaaaacaa aacaaaacaa taaaaacaga caatatagca ggccagaaaa    8340
cgtggcagta gctaaacatt gtcacagtaa cagctcagtt acagtgagtg tgattccagc    8400
tgtgcttcct gtcctgaata aggtagctaa gtactaggca gtgcctttta ctcagcccca    8460
cttttcctact ttccattttc tctctaggat accaagctgg gactttgagt tttcacctcc   8520
taaccctact tcccttcact ctctaagcac atcacagcca tctttggcat ctatgccagc    8580
attaccaccc agtacttgtt ctcatcattc atgtcatctg attttctat tggtctttct     8640
tcttatccac ctgctaaggt tgcaggaagt ggtagagaca cctgatagat ggttcttcaa    8700
ttttatactt gtcactttat atatacaaat ttcagatttt cttcatatgg tagtatctat    8760
agttctttta gaaagtgctt ttatcagtaa gtcttcatgg aatttaaata cttcatgaaa    8820
tttctagtgt aaacatgtat gtatggcaat aaaagaattg cttttccaca aacaaaaaga    8880
tataaagtcc caaataaaag caaaacattt atataatatt ttaagcatta ttttcttgat    8940
tccctttttct gtgttttaca caattatata cttctgaaat tgaattgtct tataattgat   9000
tttttttccca aacttctttc tggccatcag atccaggaat aaattattat caacacataa   9060
aagttgcata tttcctgtat cctgtgactt caagtgattt tttttttta ctttttggcat    9120
taatttcacc caacaatgtt gacttttaac tttgattgct tgatattcct tgagaaagag    9180
tactttatga tccagttttg gaagtatcag gtaatgtgta cttggatgct tgtctggcat    9240
gctaggcatt gtaattacag tagacattca ccaagtttag tactctacct taacttgaaa    9300
ttgtacacct gtcccagagg tgaagggggtt ctgaaggcag atttacacta taaacctatt   9360
catagattct aaagggcaag agtgattcag aaaactaatt tttacttgag tatgaaaatg    9420
gcttaggcta aaacttttaat tatggttcca aaagtaataa gtacttatat aaatgattat   9480
ataatttttaa tttctaaaaa cagtatgtca tgtacatttt gacagtggaa gtgttggttt   9540
aatagtgaat ctcataatca gtgtcacctt agaatgaaca taaccacttt attttaaaaa    9600
catgataatg tcacctatgg tttgtcactt atcacttcct aggggttttg ttgccctggg    9660
ttatgctgtg atcttgtgtc aacaggtgta ctgcaggcat gctaggctgt taactgagtt    9720
tggctcatat gtcctatagg gacatgctca cttatgcact gtagagataa cagtaaatat    9780
cacagtaagt ttcaatattc accaaaaaag aaatgtccgg tgaagttttc ctatttgtag    9840
gactattatg ggactaaaat tatcatatat ttaagaatat gtaatttttt attccttttta   9900
ttcctaaaaa aaaaaatga aaccaactca gtcactttaa aagatataca tttcagatca    9960
aaattttgtg gggtgtgtct ggagagtggc agatattagg attcaagatt tcaaagacat   10020
tgaaggtaga ttatgcttat cttgattgtg cctggcaatt tttgagtccc atgcttcatc   10080
tccccatgct tttagaaaag tctcacattt agcttctctg tcagttctta ggaaccagcg   10140
```

-continued

```
tgtagcggaa gaaatgtgca ctttggaatc aggcttagct ggagtcctca ttctgtgact    10200
tattaacgtg tgttcttagg cacttaatct ttctgatact caattattct cactgggata    10260
atgagttact ttcatttcaa cctggcctaa gaatataata atattcaata ttctctgagt    10320
acttactctg tatattagag ttctcctgag aataagaatc aatagtaaat ctatttaata    10380
tataagatta tttataaaga attagcttcc gtgactaaga aaactgtcaa gttcaatact    10440
tgcagggttg ttttcaaagt ggagactggg aaagctaata ttcaggtttg agttcaaaag    10500
cagtcgccag gagttcggtg tcatttgggg aggctggtct ttttttttgt cagactcatg    10560
ttttcagtgg attagggaag acagcttaca ttagagagca tgtagtggtg cacagacatc    10620
tggcttccct tgtgatttcc ggaacagaat taacacaaat aatagaacaa tccataacag    10680
gagctcaacc tgctctaacc taaatgctct catttaatgt tagtctgacc tccaagtatc    10740
ttatcaattg ccatagccat caccCctgtg aggactttct gtgtcttcag tgataagtag    10800
tgcaagatac agaatgcctc tttaataagt aaatggtaac agtcttatga acactaaggc    10860
acttaacacc tttccagtgt gtaacagact agctcgctct ttcctacatc taacattcct    10920
ctcctagaaa gtaggcacaa catgtcactg aattataatt ctcttt ccca aaatcccttg    10980 cccagtctac aagttttgtt taccatagac tttcatcctc aattgtgtgt gtgtgtgttc    11040
attgctgggt ttgaactcct gggtaaatgc agcatactaa gcaaatgctc tgaggcactg    11100
agttacactt ccaaccctca tcttaaattt taagtttatt ttaagcattc aggctactct    11160
ttttgctccg acatatttcc tttctgtttg gggcccatgt gtttgcagag ctgctatca    11220 catagtatat aaactgaatg gattagacac tcaaaattta tcgttatagt tctaaatgct    11280
acaaggctga catcaaggtg ttagttaatt gttttttccc aaggatgtga gtgagaatct    11340
attctgtgct ttctggccta gcgtttgtca gcatgctggt ggggatcctt agcattttga    11400
gatctgtaga ggtatcacct ccagaggcac ccttttcaca gatttctcct tgtatcttca    11460
gataaatgtc caaaatcaat tccttt gtaa ggaaaacagt catgttgtct ggaacctact    11520
aaatgtgttt actccacatg ttttgagggt cataggttag agggggtggg tgggtggatg    11580
agcaccttca tagaagcagg gggaggagga tgggataggg ggtttccagc agggaaacca    11640 ggaaagggg c taacatttaa aatgtaaata aataatatat ccaataaaaa agtaaataca    11700
tatatatcct taaaaatatg gagacactac agaggacact gtaagacggg ataagggaac    11760
tatctaggga gtagttcatg aatctttagt atatctttag tatatctgta ctaaaacatt    11820
aatgaagatc aaatattgag aaggtttaga taatgaaaaa tatttcataa aattttattc    11880
aacaaaatta ataaaattct tggttgaata tttagtattg tgggccatta atgatatgta    11940
aaatgaacat gttatctctg accaagtaca aatcctcaat gtttatatta cattcttgta    12000
gagttggttt ttcttttctc ctttcggtgc cttgaccaga agtaatgaat aagcaaaacg    12060
tccttgcaat cagtgtcctt agggtgccat aaacatacta tgtttgtgga attaattact    12120
aacagatcaa ttcaccaagt ttctaatttg ctcagtgcaa tgaacaggac aatgaacata    12180
ggaagataaa ttatacacta tgttgtcctt atgaatttaa tcttgtgagg aaaaataagc    12240
agagtgaaat atcttaactt ttaaattcaa aaatttaaaa tattaagtga gaattatgtg    12300
ccatgttcag tggacagtgc agagtagaca gtgcagctta aacagagctc tttatgcaat    12360
gtggtataca gtttagtgta cttggggacc tgtggttgat aaagggagga atagagaaag    12420
gtggggtagg gtaggacagt gtacacagga gactgattaa ccagactgga gagagagagg    12480
ctcttcctga ccaatatcaa tgcactaaac cttcttagaa atagaagtca ggctttgttt    12540
```

```
caaggaagct gtcagttttt attcagtgta actcagcaaa atcagagatt agcttgctca    12600
gtgatggtga taggaaaatc tttttaaata ttaagagcca ccctattatc agtgttttca    12660
tccagttgaa ctcctgcaga gttcaaaagc tggagagtct ggctcaatgt ttccttaaa     12720 gttcattttc ttaaaaccta aatggaaaca aaagatcatg acatcttgag gaaaaaagga    12780
aaacaaaacc tttaaatagt tataaaaata atttttatta atctaccatg gtttgtgtta    12840
ggagctatcc ttttaagtac ctgattgcta agatggctaa cttgatctct taaattgctt    12900
attagaaaca atgaattaat cactattatt tatatatgtt atagtcttga aaaaatcagc    12960
aattttaatt tttgacagat cttaaaaggt ttgtattaac atgcattgct atgcttaaat    13020
gaacataaaa atattaagta gagacttaaa gtaaggcctt ggagtagttt tctttcatgg    13080
caaatcctgg actaatctgg tcaacaactc cattccctgc tgaatctcaa ttttccaaag    13140
gaatacgtgg tgagaaaggg tgaggacgag cctctgtttt cctctcctgc agctctgggg    13200
agcttcagtg tttgttctta gtgatgccaa ggttttggga caatgcaaat agaaatactt    13260
cgcctcccaa attcaggaac aggatatgaa ccttatagtc cgagtcatga actgtgccta    13320
cttacatcct cctcagcact aaagggaaa aggcataaag atttgaaact tccatttcaa     13380
tttgttgcat aatagaaggt aaaaaggatt aaaatgacat taataaacaa atttcatatt    13440
taactgggag gtaggaaaat atccacagat gagaagccca aatcaaatgc cacaccactc    13500
ttctaatccc actggggatt cacagtgggt atcagtgcct taaaagtggc atcatactta    13560
aacaaacttg gggaagagga ggttaagaca atgaggaaaa tttcagactg acttatcaga    13620
ctagttgatt gcatggagaa ctatggaaac tatgtttacc acaaactgaa gtttaacctt    13680
gtcttcctgg taccaaatta cttcttctag aaaacattaa cattcttatt gtgtatacat    13740
ggaatgtgtt ttgattaaat cctcctccta tctctttccc tctcatatat cctcttcttc    13800
ctactacttt tgcctcccaa cttcatgtgc tcttatttat ttaaatttaa tacccactga    13860
agccattcag tactgcctta tatgactata tgtgcatgga gaccatctac taaacatacg    13920
tatccaccct ttcaggaatg ggcatccctg aatactgatt ctcccttccc cagcagctac    13980
ggattcccaa taacttctca gatagagcta agacttcatg agtcccttcc tagtccatgc    14040
tggggttttg actggcttaa tcctgttact attttcattt aaaaaatgat atagatgcct    14100
ctaatctctg ctgtatcatt ttatctgcca agcaaatcta tcaaatgaga aaatgatctc    14160
aaatgatgtg ggcagatgca ttttaaaatt acatttgtgt ctttgtgtgt gtgtgtgcac    14220
atatacacat gcacacacac actgctgtgt actaatgtat ggaggtcaga ggacaacttg    14280
taagtcagtc ctctctttct accatatagt ttctatgtgt tgagcttagg tcatcaaact    14340
tgacaccaac tacctcctaa gccatctgct ggtcctggaa tatatagaag tcatttttgat   14400 gtaatgaatg acaaacatct atcaaaagac aaaaagaact tctttgtaca catagtgagg    14460
agctattaaa tgatttagat attgaagatc acgagaagtt gtactttgtg ttttatgtgc    14520
catggctcat gccagatgat atctgtagga atctaccacc tgtccagaac ctcatagaag    14580
ttctttgtct ctaagaaata attatgttct ttatacattt ggggaaaacc ttggagagtc    14640
aagtaggtat gcttccaaat atttagtcac tgtcagaatg acagtcatgg ctcagtaaag    14700
gacatgctta tttccgtgat aaatgaaaag tattgaattt gggtctttgt gatgccatct    14760
gataaagcaa aatgaacaaa gaaccacaat aaaggataca aagttctaga gaagggggaga   14820 aaacactgaa ataaatcgaa taattatttt taaaaaagca gcaaggaaat gcgtatctcc    14880
```

```
catataggag atgtcatgaa tgccacttgt gcacagtcaa gtctttcagt tgcctagtca   14940
gaagccggga ggagcttatg cccatcttcc actttcacac ttccgtgagg atgcggtgag   15000
agtgcttctg acctctgtgt tccaggagat gattcaacac tgcacagagg gtcagttccc   15060
tgatagcaca gaggtttcca tctgaaagct tgcacacatg cctgtccata actcaggagc   15120
attgctacgg taaaactgca acaccaggct gtttcctgtc ttccttgttc ttttggtttc   15180
aaatatattt cttattgatg atgaaaatat cgctcagtaa tttgaaagcc attgtttcct   15240
cagaagtctc ctaaaaggaa actcgcatgt aggaaatagg cagcttcatg gggcaattag   15300
tactattttc ttggatttgg tgtaggtaca gtgatatctg tagcttcaca gaaaggcact   15360
taggctgctt tttcagagga cattggtact tgacagtaaa tgacatcctt tgtgtcttat   15420
gttacctcct aagatgagca ggattcctcc cctcccttcc cttcctctcc cttcccctcc   15480
tctcccctct gacctcccct tccaacctcct ctccctcct ctcccctccc ctcccctccc   15540
ctcccctccc ctcctttcc ctccccccctt ccctcctctt ccttcccctt tcctatttcc   15600
ttttctattt ttttcttgta gcgttgcttg ttgtctttag attttagaaa tgctcgtgtc   15660
ctctcactgc caacaaacac ttcttcattt ctatacaata tgatatcaca atgccatttt   15720
ttcccctcag aattcatagt agttccaaaa tctaagtttc tggctttgag agaccggaaa   15780
taaacaatgt ataacattca tgttgcttgt catcaaccgt taactggtcc catgagtttt   15840
ttacacactg tgatatcatt gtcaggagcc atcagaacaa ctgcgtatgt gaaaggatt    15900 agagtttgaa aatcaccact ggaaagtttc accagttcta caagcatatc tatctcactt   15960
agaaaaccct tccagcacca acgttgattt ctcaaccctt cacactgctt ttctaactta   16020
tagctttatt gaggtagaat ttacacatca aacactttac ccatttacaa tatacaaaat   16080
aatgaatttt aagcatattt ataattttgt taaatatcac aaaataaatg taggaacctt   16140
tattcataca aagaaagaaa gaaagaaaga aagaaagaaa gaaagaaaga aagaaagaaa   16200
gaaaactatt cagctttctc atgcctatct gcagatctgt ttcaagggcc ttgtgtactt   16260
gaagcagata gagccacctg ggaagagcct acactgagaa actggcttca tcagactagc   16320
ccagaagcaa ggtcattggt tttattattatttatttatttatttattagtggttttt   16380 tgtttgtttg tttgtttgat taatgattca tgtggaagaa gcaagcccac tgtagacaat   16440
gccattcatt agtaggtgac cttacaatat ataagaaagg aaatcctata agccatagag   16500
aacaaaccca taaacatact cctccttagg tcctctgctt cgattcctgt ctttaggttg   16560
ctgtttaagt tagttactgc cctgacttcc attcatgata aattgtgatg cacaagtgta   16620
agcttttctt cctcaagttg ctttttggtca gtgtcttaac acagtagcag agaaacaagc   16680
tctatatttt gcctcccact tcttgttcta ggcaactgtt agtctacttc tgcctttatc   16740
ttgttgcttc ataaaaatga aacaattcag tgttttgtga ctggtcttgt tcaatggttc   16800
aaaaagttga cactattatt acatggttca tcacttggtt tagggatata tatgttgtta   16860
agtttttact tgacagttaa tgtttttttaa ccatttgcct gttgtaaatg atactcatat   16920
gaatatcatt tgggtattag ttttttatgta gatgtatgtt tttatccttt ggggtatata   16980
cctaagagtg gaatgggtaa gtcatgctgt aaatttatgc ttaatatttt aaatatctta   17040
ctgattattt tccaaaatat atacacaaat ttatattcct ctagcagaac acagggttac   17100 aatttttccat acatttgcaa cgatttgtat gtttagtttg ttgttattac agcgattcta   17160
atgggtataa aatggaatct agctgtagtt ttgaattgca ttttcctact ttgtaatgac   17220
catttcatgt gcttactggt catttatgta atttctatttt tagataaatt tttatccagc   17280
```

```
tcatgtaatt ttaaattttg gtttatgtct attactgagt tagaagtctt ttatatatct   17340
gatattaaaa ccacttagca gatatttgac ttgcagaaat tatatagact atacactatt   17400
ttctttattg tatattttaa aggataagaa gttttattca ttttatccat tttggttatt   17460
gttgtttatg cttctggtat tatatttaat tatgtgctac tttttcaaat taattatgaa   17520
atatggcaaa ttagacaaat aagctttgat attacatgcc tattttaaa ttctaacttc    17580 acattaacaa attgcttaag catcactaga tccagtttca tatctataac atggatatgt   17640
aaggtctgtg cccagagctg gtccagtgcc acagtgctct gtacccaaat actgtccgga   17700
gagagctggt ctcccaggag tgccaacaca catgtgaaca caggtaagac caccactttt   17760
gattaaattc ctggcccaaa agggtctcgc ccagagccat caggacacag gaaccaagga   17820
acagctgggg acaggatcct tcagtttctg tctgtattct ggagcttacc ttgtgccaca   17880
gctctccata accaaattac tccaggaggg aactcccagg agtacagaca cacaggtttg   17940
aaggagggac aagccacagt cagagacagg aaggccagct aacagcagag atatcaagat   18000
ggcaagaggc aagggcaaga acataagcaa cagaaaccaa ggctacttgg catcatcaga   18060
aaccagttct cccaccacag ctatccctgg atactccaac aaaccagaaa agtaagactc   18120
tgaattaaaa tcatatctca tgatgatgat aagcgatgtt aagaaggata taaataactc   18180
tgtaaagaag tacaggggaa aacaggttaa cagctagaag ccttaaagag gaaacacaaa   18240
aattccttaa agaattacag aaaaacacaa acaggtcaag gaattgaaca aaaccttcca   18300
ggatctaaaa atggaaatag aaataataaa gaaatcacaa agggagacca gcctggagat   18360
agaaaaccta ggaaaaagat caggagttag atgcaagcat caccaacaga acacaagaga   18420
cagaaaagag aatctcaggt gcagaagata ccagagaaaa cattgacaca acagtcaaag   18480
aaaatgcaaa atataaaaat ctaacccaaa acatccagga aatccaggac acaatgagaa   18540
gaacaaacct aagaataata ggtgtagaag aaagtgaaga atcccaactt aagggccagt   18600
aaatatcttc aacaaaatta tagaaggaaa cttccctaac ctaaaggaag atacccat    18660 aagcatacaa gaagcctaca gaactccaaa tatattagat cagaaagaa attcctccca     18720 tcacataata gtcaaaacac caaatgcaca aaacaaagaa agaatattaa aagcagtaag   18780
ggaaaaaggt caagtaacat atacaggctg atctatcaga attacaccag acttctcacc   18840
agagactatg aaatctagaa gattctgggc agatgttata cagagcctaa gaaacgcaa    18900 atgccagccc aggttactat acccaacaaa actctcattt accatagatg gagaaaccaa   18960
gatattccat gacaaaaata aacttacaca atctctctcc acaaatccag tactataaag   19020
ggtaatagat ggaaaactcc aacacaagga gggaaactac accgtagaaa agcatgaaa    19080 gtaatcttct ttcaacagat ccaaaagagg atccacacaa tcataaaaat aatataaaga   19140
ataacaggaa gcaacaatca ctattcttta gtatctctta acatcaatgg actcagtttc   19200
ccaataaaaa gacatagaat aacagactgg atacatacac agaacccagc attttgctgc   19260
atacaggaaa cccacatcag agacaaagac agaaattacc tcagagtaaa gggctgaaac   19320
caattttcca agcaaatggt cccaagaaac aagctggagt agccattcta atattaaata   19380
agatcaactt tcagcaaata gttatcaaaa agaataagga aggacacccc atatgcatca   19440
aaggaaaaat caaccaagaa gatctctcca ttctgaacat ctatgctcca aatgcaaggg   19500
cacccacatt cataaaagaa actttgtact acagctcaaa gtactcattg caccccacac   19560
attaatagtg ggagacttca acaacctgct ctcagcaatg gacagatcat gggaacagaa   19620
```

```
actaaacaga gacacagtga aactaacaga agttatgaac caaatggatc taacagatat    19680
ctatagaaca tttcacccta aaacaaaaga atatacttc  ttctcagcac ctcgtggtac    19740
tgtctccaaa actgaccata taattggtca caaaacaggc ctcaacatat acaagaagag    19800
tgaaataatc ctgtgcatcc tatcagattt tcaacagcaa caaaaataac agaaaaccca    19860
catccaaatg gaatctgaat gttctagtca atgataactt ggtcaaggaa gaagtaaaga    19920
aaaaaaaatt aaagactttt tagagtgtaa tgaaaatgaa ggcacaacat acccaaactt    19980
atgggacaca gtgaaagcag tgctaagaga aaaactcagc ccccagtccc ttttaaaaga    20040
aactggagag agcatacact agcggcttga cagcacacct gaaagctcta gaacaaaaag    20100
aagcaaacac acccaagagg agtagacggc aggaaataat caaactcagg gctgaaatca    20160
accaagtaga aacaaaaaga actatacaaa gaacaaaatc aggagctggt tctttgaaaa    20220
aaaatcaaca atatagatga actcttagcc agactaacca gatgtcgcag agacagcatc    20280
caaattaaca aaatcagaaa tgaaaagtga tataaaaaac tgaaactgag gaaattaaaa    20340
aaaatcagat cctactacaa aagcctatat tcaactatac tggaaaatat ggatgaaatg    20400
gataattttc tagagagatg ctaaatacct aaattaaatc aggatcagat aaaccatcta    20460
aatagtccca taaccccctaa agaaatagaa gcagccatta aaagtttctc aacagaaaga    20520
agcctaggac cagatgggtt tagtgcagaa ttctatcaga ccttcaaaga agacctaata    20580
acaatactct tcaaactgtt ccacaaaata gaaacagaag gaacactacc caattcattc    20640
tatgaagcca cagttatact cccttggaga tggaatggtt tctgtctaat caggaaccgg    20700
tcacaatttc ataagactat aaggacttca taagagattt tttccatttt tatcatattt    20760
aatgttacaa atagatttt  ttaagactgg ctgagtgcat attacttttta gcttcagatg    20820 atatcgtgta tatttaagag gcattttgca attatagatt atttgatga cttaaaaatg    20880 tcaataccga gttgtaaata ttaaaataaa ttcctacccc cacagtgaca cacctacttc    20940
aacaaggcca tacccctagt cactgctcat ctccttaatt ggcttatttg gacaggtggc    21000
tgagccttgt atttagcaat tgtggagcag ggacttccac cctcaatctc tggcaacaca    21060
tcatttcatt attagaaatg agatgtcatc ctataaaaaa ttagagttttt cacaaagaaa    21120 tggaatgaac taagctaaac agtcgggtta atatgtgctt gtttaaaaac taaaatacta    21180
gcatttttca taataaaatc tgaagctttt catggttaag tgaacagaac agtatatcga    21240
agatactagg ttttttttttt ttttcctgtg aatgttagtg aactcttaaa aatacacacg    21300
agtctgctaa cttatagttg attagctagt ttctgttaga agtagccaaa attttggaga    21360
ccactatatt tttgaggaat accattttat aagtccattg agtatataca tggctgggca    21420
tgaatcaaga tgcataaagt cacttggata tgaggtgaag agctatcagg gataatggaa    21480
agacagaaaa ggagatcctc aatgcattgc ctcccgttgt tccaagcgaa ccaccgagac    21540
tcatgaaatg cctgactgac tataaattcc ttgcctgaac attactgaat ttacacaagt    21600
tcactgaata taatcagaat cactgaaaag aagaatggct tgaatttcat atcattattg    21660
caaagtgtct aaaacttgaa tgcctgtctt ttaatttttt aattttttt  tacttttgtt    21720 ttatatttct tagactgacc tgcagttgac agagagaact cactggtagg agacatttgg    21780
tttgatttat tggtttaatc tcaagatata aaatctttct cgaagatgac tctctggtga    21840
ttgcatagag ctaatagatt ttagttttta aaaattcttt ttagacttat aaagtatatg    21900
atgagtgttt tgcctgtatg taaatatgtg tactgcacat gcgcttggag ccctcagagg    21960
tcaaaacaag acatctgatc ccctggccct ggagtcccag atgtgagtca ccatgtcggt    22020
```

```
gctgagaatc aaaccctggt tctctgtaag agcagcaaat gctctaaacc actgatcatc   22080
cctcctgtcc ctatatttta gtttttataa tttactttga accagtttca acttgggagc   22140
ataaatatag gttcatttta ttgtaacttc caaaaagaaa tgctaactaa taataaaata   22200
caggtggtga gctgtgtgat gtgtgggtat attatatcac cgaattttat tttgccttca   22260
gtcgttgatc taaggttctc ttgttaaaac tagatgtcac tgtataacat aatatcttaa   22320
aaattctgag atagcaaaga aggtttttat aaaagcatct cacacattgt gttactttga   22380
aatgagctgg aagctcattt atggggatgg ccactatatt ttatacatga gccaaaagaa   22440
tcatagttat attttttcaa ggggataaga tgatttcaaa tttgcctcta aatgcttttt   22500
gaggcatggg tttggaggac agtaaaattc tacttactta aaaggtgatg tgtccaagaa   22560
aatcaagaag aaggaagacc aacgcatgca tacttcattc ctccttaggg aacaaaatac   22620
ccatggaagg agttaacaga gacaatgttt ggaactgaaa caaaaggatg gaccatccag   22680
agactgcctc accctgggat ccatcccata atcagccacc aaacgcagac actattgcat   22740
atgccagcaa gattttttgtg gaaaagaccc tgatatagct gtctcttgtg aggctatacc   22800
agtttctggc aaatacagaa gtggatgctc attgccatct attggatgga acacagggcc   22860
cccaatggag gaactagaga aattacccaa gagctgaagg ggtctgcaac cctataggtg   22920
aacaacaata tgaactaacc agtacccccca gagcttgtgt ctctatctgc atatgtatca   22980
gaagatggcc tagtcggcca tcaatgggaa aagaggctcc ttggtcttgc aaacttata   23040 tgcctcagta tggggaatg ccagggccaa gaagtgggag tgggtgggta gaggagcagg   23100
gcagggggag ggtataggg actttcatga tagcatttga aatgtaaatg aagaatatat   23160
ctaataaaaa ttgaaaaata acataaaatg tgatgtgtca tttaatatt ttcaaatcta   23220 ttgcgagcac aaggcttctg gtaggtggaa ttcatcttta aactgtgttc taaggaccac   23280
catccttcct gtcccatccc atcagccgtc tgagatttcc aatctcggcc agtcgtcaac   23340
acacgtgaat ctttctagct gaattgaact gtgaactagc tgctaagcac agccgttttt   23400
aaatttcaga ttgtagaacc taaattatga tatggtaaac aaaggttaaa gaggttgtca   23460 cttttgcattt attttgtacc ttgctgttat ggtattaagg gcatttgtgc ttgctgtctc   23520
tgaggaggta ggcatactac tattttatgc aggttagtcc tcttcccagt tctcatctgt   23580
agtagctaga agctgatcat ggaaagagtc cttataaagc agtgactgct gaaggtcatg   23640
agtcaggttt gcttttgttt tctggaaagg ggtttattat ttgtttacag atcacacccc   23700
caccctcagc ctagtagttt tcagttccct tactttaatc taagtttgtg tcttatttta   23760
atacaactca ctctacctac ttttgtaaag ctgaacatgg ttaaatgaat tcagaagaat   23820
gtgaagaaat ctttgatgtt agtaattcag aaaagttttg tgcctctgag taccatttcc   23880
taaccctggt aataaagcaa cagcccttt gtcctgtttg cctaacagga acttaagatg   23940
caaataaagt gctaatggtg tggaatttct ttggcaattg ctaaatagat actttaaaaa   24000
aattgtagta aactcttgct ttaagtttat ggagaataat agcccaaatc acaacatccc   24060
acaaggccat cttccttta cctcctatac ttattgccag atacttttca gtgtcacttt   24120
ccttctgtga gatgctgggc aataagtacc tagctgtaga actaactttc tttctttctt   24180
tctttctttc tttctttctt tctttctttc tttctttctt tctttcttta tttcttcctt   24240
ccttccttcc ttccttcctt ccttccttcc ttcctttctc tctctctctc tctctctctc   24300
tctttctttc ttctttctaa atttattaga tattttcttt ttccttcctt ccttccttcc   24360
```

-continued

```
ttccttcctt ccttcctcc ttccttcctt cctttctttc tttctttctt tctttctttc    24420
tttctttctt tctttctttc ttaattttt attagatatt ttcttcattt acatttaaaa    24480
tgctatcccc aaagtcccct ataccctccc cctgccctgc tctccaaccc acccactctt    24540
gcttcctggc cctggaaatc ccctgtactg gggcatatgc tcttcccaag accaagggcc    24600
tctcctccca ttgatggctg actaggccat cctctgctac atatgcaact agagacatag    24660
ctctagggg tactggttag ttcatattgt tgttccacct atagggttgc aaaccccttt    24720
agctccttgg gtactttctc tagttccttc attaggggcc ctgtgttcca tccaatagct    24780
gactgtgagc atccacttct gtatttgcca ggcactggca tagcctcaca acggagagct    24840
atatcagggt cctgtcagca aaaattctta ggcaaatgga tcgatctggt ggatatcatc    24900
ctgagtgagg taacctaatc acaaaagaac atacatgata tgcactcact gataatctgg    24960
tattagccca gaaacctagg atattcaaga tacaatttgc aaaacacgtg tagtacccctt    25020
tcttagatga tgccactaga ggcactacac cattgtggca ccattttcct catgcatcca    25080
gaccactttc ataaatattc actcttttt ccctctcaca aaatgaccag tgaatcacag    25140
tgagctgtga agatatctag ttaacctttg tcaagaagg cttttgttaa agtgtaagct    25200
ttcaagttaa agggagaaag tgacacacta aaccatagtc aatcactaat gtcttagcaa    25260
ggaatagata ataagtttac ttagtcttat ggattgacct aaatttagat tagccttaaa    25320
ggcaacttac agaacaatta aggacatagg gctggtgcta gtgatcaagc cagagatgga    25380
agtagtgtaa agaatatgga cccttataag ggagggagga gggtaatcat gaaggccacc    25440
tggaacattg tgtcctagag aggtatcaaa atgttgacat ttggcaagac atttctttgc    25500
tctctcaaat gactttgata gtgtcttagt tagggtttta ctgctgtgaa cagacaccat    25560
gaccaaggca agtcttataa aaaacaacat ttaattgggg ctggcttaca ggttcagagg    25620
ttcagttcat tatcatcaag gtgggagcat ggcagtatcc aggcagactt ggcacagcag    25680
gagctgagag ttctatgtct tcatctaaag gcgactagtg gaagactgac ttccaggcaa    25740
ctagggtgag aatcttaaac ccacacccac agtgacacac ctactccaac caggtcacac    25800
ctattccaac taggtcacac ctccaaatgg tgccacttcc tggcccaaga atatacaaac    25860
catcatagat agagtatgtt tttctgttac atgtttatct tgcttctcag atactgactt    25920
ttggtggttt agtgtgcata tttcttcttc tttttttt tttttacat cattaagaag    25980
tctcaataac gataaatctt agacatctct gagttacaaa aaggtgctga gggagaaacc    26040
agtttttgtaa accactaaat ccagatgaat ttcttcctta agcaaataca caaaacgact    26100
tgcagtaatc acacatgtct ttaatctcag cactctagag gcagaaatag gtggatctct    26160
atgagttcaa ggtcagtatg gtttacagag tgagttccag gacagctagg gttacacaga    26220
aaatactgtc tcaaataac aaaaaattta agctgagaaa tatctcattc ttttgaattt    26280
attttacaat tttctcttga tatatgattg attttttta aatataattc tccttttctt    26340
ctcagcctgt cttcctctca tattttcag gcttcctcta atacacacac acacatacat    26400
acatacatac atacatacat ttccaaaggc taatacttta atacttggtc accagttggt    26460
gaagctcttt gggaggatt aagaggtgtg gccgtgtgtg tgtgtgtgtg tgtgtgtgtg    26520
tgttagaatt tctgattttt gtcattgtga aggttatcct gcctgttgcc ttaatagtta    26580
aagcagcatg tttgagcaaa tagggctaat ctgcttattt cttccatcat aaattatata    26640
ttaaattcct aataaatatc tacagtgtaa agagaacaga tggtgatgat tcatatttcc    26700
aagcaatgat atagtgataa ttatatcagc taactggtat aagctactca atgtttatac    26760
```

```
tcacttttta attttttaaa acttttaaaa aattttattc tttaatcctt tcttacagtc   26820
cagtctttct ctccctctca ctcttcccac tgaccactcc ctgtcccta ccttcccctt    26880 gtctccaaga gaatgtcacc atcttccacc ccaaacccaa cccccactcc accagacctc   26940
cctggggcct caagtctcta gatactgctg gtcttcccat ggggccaccc tactcctcag   27000
gttcctctag ctttttcccca attcaaccac aggtttctcc agcttccata tattggttgg  27060
gtcctagtat ctgcatccaa ctctttcagg tgcttgttgg gcctttctga gggcagtcgt   27120
gctaggttcc tgtctgcaag cacaccacag catcagtaac agtgttatag ctaacacatt   27180
gctgaattgc catgggctac ttttaggaaa gactacactg taatagattt cttgtctgtt   27240
agaactaagc aatggcatca gtttagagat gttagtgttt atgtgggtat atcaactaag   27300
atatgaatta ctgcatttat gtaagttgtc ttatttaact ttcatctttt tgtatgcata   27360
cagttggtat aagaatcatg tctacattag agacccaacc aagtgaataa atctgtctgc   27420
cctcttctct tttagctgga ccacaccaat tttgaggaaa gggtacagac accacttgga   27480
gttgtcagac ataccaag ccccttctgc tgattcagct gaccacttgt ctgaaaaact     27540
agaaaggtat gatcttatca ttgactttac tggcaaaaga aagatgtttt tcatgtcttt   27600
taaagaacag aaagctggaa tattagaggt tccatttaaa agtgatgcat ttaaataaaa   27660
tcgtactctt gatgaatctt gatctactca agaattaaac aatgaaacaa tgaattaaag   27720
ataataactt tcttaagaaa tggcctcttc tacaaaaata gataatgcat agtctgagaa   27780
tttctatcta gtgttggaat tgatgctttt tttactcttt gtcaagcatt cttaacaatg   27840
aggtgcattc ttagccttgg ccttttgata caaaatatca ttagtccagg ataactctaa   27900
actcactata taaccaggat ggcctcaaaa cctcttcctt tttgcattaa cctcctaaga   27960
actaaaggca tataccacca agtctggctt ttttgaaaat attttttaagt tgaagatttt   28020 tataatgatg gtggtctgag tgagaatggc ccccataagc ttatatattg aatacttggt   28080
actgagttgg agaggctgtt tgggaaggaa tgggaagtct tgcctttaag gtttcaaaag   28140
cccatgctgt tcccaattag ctctctctct ctctctctct ctctctctct ctctctctct   28200
ctctctctct ctctcagctg ccccaggatc atgcctgcct actgctaaac tccccaccat   28260
catgaactct ccctctcaaa gtataagctc ccaataaact aattcttctg taagttgtct   28320
gagtcacagt gtcctggcac aatagtataa agtaactaa acaattata ttagtcaaaa     28380 tacataagcc agttgaatat tcttaaaata gtagtttctt ttatgattat tataagtagg   28440
agtagtttag ctttgtgata ttaaaacaaa atatatttgg aattttttgag atgagaactt  28500 atgtattttt tctttctaat tttggtttat tatattgata atttcatgca agcatatatg   28560 ttttttgtcaa gtccatcttt gattccagtc tactcaatgc ctatctgatc ctcccccccc  28620
tcaccctccc agcttccatg tgcttttttaa aaatcacagt tagagctacc atatgcggat   28680
aatataggac catctactgt gttgtgggtt gcctctccag ctgcatttct gaaaaccagc   28740
tctccattaa ttactagtag ctcctcaggt agtagtggga cttcataagc ccctctcatc   28800
catgctgaga ttctcttgac atgattgtat acaggtcttg tacatgcagt tgcagctgtt   28860
atgagttcat atgtgctgtc atgttcagca catactgtat ttctgcatgt atccaataac   28920
tttagctctt aaactcatcc tacatccact tctatgatga tccctgaaca tataggtatc   28980
ttatttatag ctgaggactc cacagtcatg tcttcatata ctgatcagtt gtagacctca   29040
aaattaattg ctatctactg caaaaagtag cttatctgat gaaggttgag gtatgcacaa   29100
```

```
atctgtaaat atagataact taggcagcag gttaatacta tgtctattta tcaggataat    29160
agtaataggt tctcccctgg gtaccaagca taactcctat cttgtgaagt gggccttcaa    29220
tccaatcaga aaaaggttaa ttacgtgagt tgacatcatt catgtctctg tgtcctactc    29280
atgggcatgt ctttctgaag ccagtcttca ttatagatgg cagtgtttat atgtaagcct    29340
gttactttt cctccagtca catgcataga attttcagca ctatgaccac cggccactat     29400
gggtgaagct tacttttgc tacctgattg attttttttt ttttttttt tacatttttt       29460
ggctcaagta tccaattact tgagcagtag ggtgtttcca tcaaactctg gaagcttacc    29520
aaaaacattg gcaatatgta aagcctgtaa tatttggggg attatgggat cccagtaacc    29580
aaaaactcta gagagataat cactgcctgg cactgggaat ttttttatta atttacttta    29640
tatcctgatc atagcttccc cttcctcctc ttcttcctcc tccctctcaa cttacccct     29700
ctgttttcta caggatcctg tctgattaga tttcccaata agattttta cttggattat      29760
tgatgttttt tcatttccag aatcatttta gtttgaaatt gtccaacaat tctcttaatt    29820
gaaggttatt atcctatctt ctaatgactt ctttacttca ttgatccctt tattcttttt    29880
aatacattca tgccttttc cagatgtttg aatatactca tactttatta ggtgctatta     29940
ttgtaggatt agtaatctgt tgaggaaaca tggtatcttg attttcatg tttatttcct     30000
ttctatgctg agacttgtac atctcaaata gttgttgagt tccctccttc tccttttcat    30060
tcacatcact gcctttcact gaagtcatct acaatggcca tgagagtact aggtctcagt    30120
agggttgaga atgccatttc catctgtggt gcttttagag ggaatgtggg tctgagtaga    30180
tggcctaaga aagggtagcc agctttcctg ctacctgtac aaagatacat agttgaggca    30240
tctggagcaa aatttatgtg agctgaatgt gtgaatgcca ttatacttca tgggaaccat    30300
tatactttat gaatttgaat cttcacatt tcaaccataa tttctcatct cggccactct      30360
ggaagaaaaa ccgtaattat cttcagctta cagataaaca catcatggct tagagataat    30420
gtaatttgcc aaccactgaa tgatgaataa ttcagtcctg gtgaatttat catagttccc    30480
ttttctgact attggttggg gccattgtga ttgtgagtga cagaagccta atcaactagg    30540
ttcatcaatt aagaagagga catttaatag ctcacaaagc ctaaagtatg tgagtgtcta    30600
gatagatgac tagcctgagg gctcagtggg tccaatatat ctgcactcaa atttctactt    30660
gtgatatttt ccctctgttg gcttattttc ttagattagt tttctcctca ggttgacctc    30720
tcagaactct atgcttatac ctgtctgctc cacagaagat aataagcctc ccttcccttc    30780
cttccccctt ccccttcccc cttctctcct tccctcctc cctccttccc tccatccttc      30840
cttccttcct tcctctctgc ttttatttc atcaccaaat ttatagaatt atttagactt      30900
agttttatgt cccctattct gatagagttt ttaaaattta tctattgtgt tttaattcaa    30960
acactgtctc agactggata cataagttct agtaagaaat aaattctaac ctatattgtc    31020
tttgatacaa ttttgtatct ctttatctta tttcttatat atttatgaaa accactcctt    31080
tacccacttg gggagtgact gaagttctca gtctgtggct gagatccatt gattgactca    31140
tctgcttcaa ttttgtgacc atgagattga atctgcagtg tgaaaaccat gagcccactc    31200
tgtgttccta actaacttat gagctttgcc agtctggaac tctttccct cattaagttt      31260
ctttactgtg ttgctggatt aataccatct acttttattg ataattgctc tagagctaca    31320
gattttcaa gtcctatgat taaaaataac agcttctttt cccctcaagt ctatatgtct      31380
tccatttcat agctgacaat tctttgctgt tctcgtttcc acttgtttat cattcattta    31440
tatatcaatg cctgaaatat ggtttctcat cagactatgt tcctcaaact gcatagatga    31500
```

```
gggataacag tgacctgtta ctgtcaaatg tgacactttt tttttgtatt tactatccta   31560
ctgttattgg tatcttcatc ttgaaaccat ttctttgatt tatggacatt ctctcctctg   31620
catttcctag atcattaaat tataagtgaa gtattgatga aaattttaa cgagacctat    31680 tgtgtggaga ttatactgct actatgtatt ttagtgcctt attttttta ttaaatttat    31740 ttacttattc cctttacaac tcaatatcag cccttcctct cctcccagta cccctgaca    31800 caagttctcc tccattactc ttctgaatgg gaagcccccc tttgggtgtc caccctcca    31860 ctctagcata tcaagtcact gtgggactag gtgactaggt atatcctctc ccacttagac   31920
tctctaaata ttacagatgg agaaactggc tctctgtttg tgaataaaga gtagaagaga   31980
accataggtt gactaggctt tatagatcag ctgccgttag catgtttctt agggaagtca   32040
tggtccatgt agtgcgactt ccaagctttt cattaatatc agttgtatgc tcttcctatc   32100
aagtgagata ggaccatatt tagttatgct aacttaatga taatgagaat agccattaaa   32160
gaaatccaag gcctttatct gatcattcag ttctggtctg tggtttatgg aatttttttt   32220
catctcagga taatttgaaa attgagatga aagtgagact gagacatatt ttattccatt   32280
acaaaaattg taaatagttt tttttttaaa taaaaagcag tggtagtact gaaataaaac   32340
tttttcaata ctatttagta cctatcctta ctataaaaca tattttatt ttgctctatt    32400 ttcaaagagt tagatactat taaatgaatt cagtagttgg atatgaagtt taatgatggt   32460
tctctcattg ttttttcttta aaactccaaa tgggttttttc ttgtgttaaa tcacaaaatg  32520
ttcccctttc attagaatgt ctgttggtat tgtcattgtt caggtctctt ttaggcaacc   32580
aggttgtatt atggctgtca cttcactgtc atttctaaga gacatatctt aagtagactt   32640
tctggccttc tggctcttac agtgcttcag cccttcttt caagagcccc acttctaaac    32700
aaagaactat agacaactga gagagaaatg tttttttcta gaggtgagct ccctaattag   32760
ttatcaaatg ccaaggagtc atccctgaat catatttata caagcagcac taaaggact    32820 caccaggttg tttgtatgta tgtatttatg tatgtaaata ttttaaaata ataatagata   32880
ttataatcaa agacatgagg ctatgaattt gagaaggaat gtggaagagg gacaggggag   32940
gggctgaagg gaagagacat aggaggggct agaacgtgaa caatgaaaga gaaatgatg    33000 caaattatag tagttaaaat taaaatatat atatttaaaa caaaaaattc acctgatatt   33060
ttgttgtttg aaagttgcat attgtgaagt atgtgacagt taaaaacaca taatatcat    33120 gaggtaacag gaaaaaagct taaaatatgt attttttgcat cttgttctga gcacaaatgc  33180
attctcagtg ttatccatca tttgctcacc cttgtcattg cttttaagaa acctagtatg   33240
gttctttaac atacaaaact tagtatttt ataaatgaaa ctggacagag tgatttcatg    33300
gaagaccatc agattatgac agatatctat tgggcagttg gtactggagc aacttccaca   33360
ggttttatca cttacatcac agttaatctc tttgacactc atgggacaga agtatgaag    33420 ggagatagag cagctcatat attgcacct gcagttcact ggtttcattt tcttattcct    33480
tgcagagaat gggacagaga acaagcttca aaaagaatc cccagcttat ccacgccctt    33540
cggcgatgct ttttctggag attcctcttc tatggaattt tgctatacct aggggtaaga   33600
atctcacgtg taaatatggt gtcatatatt attaagatat aatcatagtt ttgtgattac   33660
agaagggtga ggacaatctt gtaaccaaag ccttttgttt tctgtttagt atttgttttc   33720 attttttat atagaatttt attacaagtc caaacacaaa tgactgaaaa ttctatcaaa    33780
gataagtgaa aattcttaaa atgtagatct caattgatag ttcaaaatta gaatgggtcc   33840
```

```
aaaaatcaaa ttacttgttt caaaattatg ctcatttatg aatccagatt ataatgactt    33900
aatagtatat gaggttactg gcacctttac ttttctgtgc taaaaaagag aatgttagaa    33960
ggcaatctca taccaagaat gagactccat tcagtcagtg ataccaagga atgtttatga    34020
tattttctgc tcagatagat agatagatag atagatagag atagatagag atagatagat    34080
agatagatag aggtaatgta atgtttatat tttgaaaaca tatatatgta tatatgtata    34140
aatagatata tagatagaat tatatagagt aatgtagatt aatgtttatg atattttgaa    34200
aacacacaca catatatgga gagagagaga gagagggaga gagagagaga ctgaattgtt    34260
tacaaaagat aataaaaatt taaaatgagg tggtgaggtg cacatagaat gtattttgtc    34320
agcaccctat gtcttcatca ttgtaaagag aatagcagcc tgggaacctg ggctttgtgc    34380
tgtttaagaa ctttggatat atcccagatg tgttcagaag tggttattgt tttctgggtc    34440
atgcgagcat cactttgaag cttgatcata gcctgtaaaa agggtgacaa gtggaaagtg    34500
tgttgagtct gatgtatcaa ctcagcacaa tactgccttg gggtgttatg tttcatctgg    34560
gttgacttgc attgtatttc ttcaggtctt tatcctcaga ttgcatgggc tttggtttct    34620
cctcaaatga tgtatgaaca atatgtagcc gtgctactta ataattttta ttttatcctg    34680
tcccagaaaa agtcattaaa aatttatctt gataaaattg actataatta ctctagaatc    34740
ttttctagtg ctattatttt ctagaagaaa ttcttctggt ctttcttaat ccatatatat    34800
gtatgaacat aaatgtatag atgtatagat ttgaatttct ttttaagcaa attcatgcat    34860
attatattat cacatatttc catgtagatt catatattat attcacatat aataaataat    34920
gtgttatata ttatagatct gttatttaat ggtagttcta tatatgaaag aaaagactat    34980
aaaaaagata atataatttc ttctagtaga atatgtgtta taaaatgcat atatagacac    35040
ataaagatat agacagaaga atgagatatc gtttaaagat atctttgtgg tcattttat     35100 cagtgagcac acccaagcat ttgaagatat tttcagtcaa gatctccttg tgagtagaca    35160
ttaagaagag ggagatgcag taaatatgaa aaaatattta aaattttgaa gattaaaaat    35220
agcaaaaaaa aatcacaaag cattcacaat gtattaatta tctatggata gtgattagaa    35280
gtacttctga gacaaacgga gtgctggaat gtatctctgg acccatcaca gcctttggag    35340
ccgaagatca aatttctgca aatacccaat aaaatgggta aggaaaggtc ctgatgggag    35400
agagtagatg aatgtgcaga gtgagaaggc acgagaaaca aagtgagcag acacagtgt     35460 aatgatgttg aagggtctct tttatccctc cccatccccc atacacagtt tcactgagat    35520
cacaaagttc agtgttgtaa aactgttgaa atctagatcc cacttattta ggtaagtata    35580
atttccaaga tctattattt atttcaattt aagttttatc ttaaaatatt tatttgacaa    35640
atataaattg tcattgtaga atatacagtg tatatttcaa tatatgtata cattttttca    35700
tgatcaaata agggtaatta acatacagat cactcagtca tttaccattt ctttatggtg    35760
agaagagtaa aatactctcc tggttgtttt gagatactgt tgctaactat aatcactcta    35820
gcagaacgta ttccctcaat acttgaattt gttgctgata acagagcttt cccagcatcc    35880
tcgtccctcc tacccttact agtctttgtt atcttaactc ctcttccaac tcacagtgga    35940
aatgggacaa agttgagcca ttttaataag cttctactgt gtcaagtaac cgctgccgtt    36000
gctttactgt tgtgtgttct ttctgagcat tttcttcttc ctgttaaata aacaaacatt    36060
actgagacag atataacaat tgtacagata aagataacgg gacatacatt caaaatgtgt    36120
ttatattctt ggtcgctgta ggccatgata attgtgcat aacaattatt tagttgtttt     36180
cagtattgat agaaaaaaac actattaaaa atgccttcaa ctatgaaagg ttaagacaaa    36240
```

```
ggaaatacca ttacaaagga ccttatttct acaacagtga tgcaatttta aaatcatatt   36300
agctatagta catccccatt aactgtggac ttgttttttc tttatctgat tcagcagcca   36360
gacatagcat gctctttaat atttcagact tccagcagag aagagcaaca ggctgctgaa   36420
aacctaagta ggagaatcaa ctaaggataa tcattttttt atttattttt attttttaaac  36480 tagatgtttt ctttatttac attgctaatt ttgtcccctt ttctcatttc ccctcaaaac   36540
cccccctgtc ccattcccct ccccttgctc actaacccac ccactcccac ttccctgacc   36600
tggcattccc ctacactggg gcatcaagcc ttcacaagac caagggcctc tcctcccatt   36660
gatgtcccac aaggtcatca tctgctatgt atgcagctgg agccatgggt ccctccatgt   36720
gttttctttg gttggtggtt tagtccctgg gagctctggg ggtactggtt agttcatatt   36780
gttgttcctc ctatagggct acaaacccct tccgctcctt gggtcttttc tctggctcct   36840
ctactgggga tgctgtgctt agtctaatgg ttggctgaga gcatccacct ctatatttgt   36900
caggtactgg cagagcctct caggagacag ctaaatcaga ctcctatcag caagcacttg   36960
ttggcatcca taatagtgtc tgggtttgat aactgtatat gggatggatc cccaggtggg   37020
acagtcactg gatgacattt ccttcagttt ctggctcaaa cttgcctct gtatttccta   37080 caatgggtat tttgttcccc ctaagaagga ctgaagtatc ctcactgtgg tcttccttct   37140
tcttgagctt catgtggtct gtgaattgta tcttgggtat tgtgaacttc tgggctaata   37200
tccacttatc aatgaatgtg tgttcttttg tgattgagtt acctcactca ggatgagttc   37260
catccatttg cctaagaact tcatgaattc atcatttta atagctatgt agtactccat   37320
tgtgtaaatg tgccacattt tctgtattca ttcctctgtt gaaggatatc tgggttcttt   37380
ccagcttctg gctatcataa ataaggctgc tatgaacaca gtgatataag tgtccttatt   37440
acgtgttgga gcatcttcta ggtatatgcc caggagaggt attgctggat cctctggtag   37500
tcctatgtcc aattttctga gcaactgcca aattgatttc cagagtacca gcgtgcaatc   37560
ccactagcaa tggatgagtg ttcctctttc tccacatcct tgccagcatc tgctgtcacc   37620 tgagttttt atcttagcca ttctgattgg tgtgagatag actctcaggg ttgttttgat   37680
ttgcatttct ctgatgacta aggatattga atatttctct aggtgcttct cagccactcg   37740
atattcctta gttgagaatt ctttgtttag ctctgcaccc catttaaaaa tagcgttatt   37800
tgattctcta tagtcacttc ttgagttttt tgtatatatt ggatattagc ccactattgg   37860
atgtagggtt ggtaaagatc ttttcccaat ctgttggttg ccattttgtc ctattgacag   37920
tgtcctttgc cttacagaag ctttgaaatt ttatgaggtc ccatttgtca attcttgatc   37980
ttagagcata aactatttgt gttttgttca gaaaaaaatt tcctctgtgc ttatgtgttg   38040
gagacgctgg tattggtacg gtgacaggca ggtagataaa tggaatagaa ttgaagacac   38100
agatatgaac ccacacatct atggtcacct gatctttgac aaaggagcta aaaccatcca   38160
gtggaaaaaa agacagcatt ttcaccaaat ggtgctggtt caactggcag ttatcatgta   38220
gaagaatgcc aatcgatcca ttcttatctc cttgtacaaa gctcaagtcc aaatggacca   38280
aggatcacca cataaaagca gataaactga aactaataga aagaaagtg aggaagagcc   38340 ttgagcacat gggcacagga gaaaattcag ggtaatctaa gggaagctaa ataaagggaa   38400
tctgtaagca tgttcctgac agactgtgat caccagagag agcttgttac tgtagaagtc   38460
acaggtgtat actcacacgt atcttcgatt ccatgtttcc atcactacat gtaagtatca   38520
ttagttcagc ttaaatcgag acctttttt ttaagtccca gaaagctaac ggacatgaag   38580
```

```
aaagcctggt tctcacaatg ccacagttct tatattcccc agactgttat aaagaggat   38640 ctgtctctca tatttagaca aagacaggct tttgaatcca agcctcctgc tcctgaagca   38700
agagtatttg cggtaattct gcttatgagt aggctctgcc tagggtactt tttcttcata   38760
catcccctca gtacgaatgc tctcagcaaa gcttctagag gcctgctatc taggattcac   38820
ttctcatctc tgtcccatcc ctgcgaacac ccacagctgg ttgcttctct ggattcagct   38880
tcactcacac ctgaactctt cctaagccat ttctctagcc cctctatatg tgttattatg   38940
tcatgtttta cacttacata tctatgccac ttagaattta cttctccact gaattaagtt   39000
ccatgcatta taagttaaat tgttatatat atttgggtct tttactggaa tttctagata   39060
aatcagtata ctttctttga cctgtgaagt gtatacatgt atggtttaat atccagtagc   39120
ttaaatgttc atattatttt tattcttcaa atagtttcaa ttagaattta ttcctaaatt   39180
aaattcagaa taatttttatt tgttgtttta acaaatattt attggttaag catgctcact   39240
aagaatgtat tatatatgtc ataacacttg tgacaatata aacatatagc caataacctg   39300
gtgcaaattt attcattttt aaaatatact taaaattttt atgtgattac actaatctta   39360
caaaatggat taggtgaaac atcatctttg taatatgtag attttttttag ttcagttagt   39420 ttttttaaaa tgtgcttagt agtttctgga atcaatcaca tatcatacta atacaggtgc   39480 ttttttacttt ttatataatt catagctatc attttttctca ttaaattatc ttagctagac   39540
atttcagaat aatgttaggt ggtcatagta gtcaaggttc ttttgctttc ctgcctccca   39600
cacttgtgtt tatcaactat tcctgattct ggaagaaagt ctttcttagg ttaacaagca   39660
atgttgcgat tcagctttgt agaaaatttta accagatact gatactttttt atcaaattag   39720 ttatttcatt gttactgtga tattcacagc ttgttcagta gtatattagt attctgttag   39780
ttgatttctt ggtatcacta gcattaatat tctaaatgta acaatataca aaatgtgctt   39840
gcaacaagtg aaggtgatac tattacttag tagctgcaca agatatagca agaaactctt   39900
aaacctcaca tgctagcaaa gcaagcactc ctgaactaaa tccgcaggcc tgtaaaaatg   39960
cagtattttt ttttaagtat aaagataaag tccatataat ttagctgcaa gcctgagtct   40020
gcacttgttt ttgtatgaac ttttctctat ggtctgcata tgcactcaac acagacttac   40080
ctgtctgtct ctagaaacat ctgattattt gtcaggtaca atggaaatgg cttaagggta   40140
tgcatctaca gtgacttaga gctttgttct ggaagtgcat tcaggtgtcc cctggtcggc   40200
tgcagtgaga actgaattat tcctaccatg agtgcaagtc ttttagctag tttttacatg   40260
gtcacttacc cagatgacac atggtcttat agtgggaagg aagtatatat agactggcct   40320
ggaattcata ataatccttt tgcagccttc ctagataggg ttatactcat gtggcaggcc   40380
tctgcatagt actcctagac tcaggtcatg cttccagggg tgatgttata ggagcgaacc   40440 tgtaggtaa ccagagtttg ccaataagga gaactgtcca acaacagaa gtgcctgagg   40500 tgacacagaa taaatataca ggaataagaa tagtaaggaa gaaggcatga actcgtgagg   40560
gagtcagatg ggacatggat ggagttggaa gtgagaaagt ggtaaagtgt ttctgtgtgt   40620
gtgaagtatt catgtatgaa attctcaaaa ataaatggaa aaatgggta tttgagtttt   40680 atgattctga atttagtgtt cttattgtca taaacattag tattaagctt attttctaag   40740
gaaaacaatt aagaaacttg cgttttgatt tatgcctgat aaaattgtta aaatacgtca   40800
ttgaatatta tcttatttaa aatagttttg catttttct attggataca attctatttg   40860
gagtagtatt tcaatgtggt gaaaattagg gaatttttt tcggaaaata gtctgagcag   40920
cagaggacat gcaactcgca tgcaccaatg ctgatttttta aaagggggct gtgctttata   40980
```

```
gattaactga ggtatcagtt acagtttttc ttcacactta aaaaatgtca tgtggatcta   41040
tgaatggttc cattgtaaat attagagaac atgatacata aaagagatta ggggaaatga   41100
tagaaggaga gagtctagaa gtgctggttt tgtccttgag aactgtgagg tagtaaggtt   41160
tatgctgtgc tctacaaacc atcttgttat tgaaattttc cagtaaagaa acaagctgta   41220
tcttactgtg tgaatatatg ctcctccaga gtaatactgt cagtgtcctt atgagatgac   41280
gtgtattgtt gaaagatgga gtatgtcttg ctagttgagg caagatgaga tctaactcat   41340
tagtagcaat atgtaaaata ggcatgccat ttaaagtatt gaaagctata attactgtat   41400
taaattgtaa tcaaataatt aagcaaataa gtctagtatg ataaagtagg ttattgaaaa   41460
ctgtaatgga gttctaacat tagtaaacag aagaaaaaca tttaagctta taacttacaa   41520
cttgaaaaaa aatctgtgta tttataagag ccagaagctg gaaagaaccc agatgtccct   41580
caatagagga atggatacag aaaatgtggt acatttacac aatggagtac tactcagcta   41640
ttaaaaacaa tgagttcatg aaattcttag gcaaatggat ggaactagaa aacacacaca   41700
catggaggga cccatggctc cagccacata tgtagcagag gatgaccttg ttggcatcag   41760
tgggagaaga ggaccttggt cttgtgaagg cttgatgccc cagtgtcggg aaatgtgaag   41820
gtgggaaaga gggagtgggt gggtgggtgg gtggataggg gcacaccctc atagaagcag   41880
gagaatgggt gatgggatag ggaatctcca gagagggagt tcgttaaagg ggatagaatt   41940
tgaaatgtaa ataaataaaa tacccaataa aataaattat agataggcca tatcaccctg   42000
aatgtgcctg cttagtctct aatataattc aacatctaaa tatgttaaag atgtttagct   42060
atgtaataaa aatatgatgc atatgtaaga tgatgtacaa taagaaatat tttatatact   42120 tttaaaata agtttattt attagatgtc tcaaacaatt ggcatattat atctgggtaa   42180
gaggttagaa attcttttg atacctccct ttttatttgg cataattcaa atccatttca   42240
accctgcatg taaaggaaa gaattatatc tcattttgtg attatcttgg aaacttttcc   42300
aaaggcttga atcttctttt ctatgcagag ctttgaatta tactaatatg aagtgctgta   42360
tataaagtag agaatgagca tctacaataa aggcaatgat taatgacagt taggttgtag   42420 ttaattcct gtgaagatga aggtgagata caaaacatgg tcatattctg ggactggtgg   42480
gacaggtagt gttggcactt gggatttgga aaagccatca tagagaacaa tgaaaagcaa   42540
attaacagta aaaatttgat gtcacatcta tattaatctt cttttcaagat ttagccctaa   42600 gttctatttt actaagttat cataaaataa aaattgggag atgatgtctt tttgtaattc   42660
aaaggccatt tgtggttcaa atccatccat gtacatttag aagggttgat gaatcagttg   42720
aacggcttgg ttggtaatca gttttggatt attgaagttt atgggtttat tggaaactgg   42780
ctcaagatag agtgctctag tgcacacctt actgatgcac atacccagct ctacactggc   42840
aaagggaagg aacaggaccc aagcggctgg ctttaaataa taccagtggt gctggcatgc   42900
tcttccctcc tgaatccagc tccgctcaat ggttgtactc ttgagaagct gttccttctg   42960
atcataatac catggctcaa aatccttaaa gaagttcatt ttgaaatttc ttagtgtctt   43020
gcttttcttg gcctccattt cttcacctgc ctgcatagtg aaaacagttc gtacatgact   43080
gagagttgtg aaatcctctg ggacatattt taggaatggt ttgtgacatg tacatgttac   43140
tagttaatgt accacttcat caagtacccc tttacaatat agttgctatt catgcaggtt   43200
ttagtgaaca cctcacacaa acttgtctct aaatgacttt tgctgtaaac taataaccaa   43260
gtcttatttc agagtatgca caaagacact atcagcagtt tcataaattg tccaaccttc   43320
```

```
tctgtaaaat tattttaaat tattgtaaag atgaaatttt cataattaaa atgtgaacaa    43380
gaaatgaaat ttaatcactg ccttctcctg caggaagtca ccaaggctgt ccagcctgtc    43440
ttgctaggaa gaatcatagc atcctatgat ccagaaaaca aggtggaacg ttccattgcc    43500
atttaccttg gcataggctt atgccttctc ttcattgtca ggacactgct tcttcaccca    43560 gctattttg gccttcatcg cattggaatg cagatgagaa cagctatgtt tagcttgatt    43620
tataagaagg taatacttt tggaagatgt tatttggtct tgttttacta tttcagtgct    43680
ggatattaaa ttcagggttt cttgtatgcc aggcaagttc tttgctgagt ttgctgccct    43740
gcacagtctc aggtattcta cctgacatgt cttcagtgcc ctaaatgtga gcttgtacaa    43800
gaataggtgt gaatacttat tcctgtttta ggtgcctatg aaatatatgg caggtgcaag    43860
tattgttctg agttatctat ccttgataat gcaaagtgat tcagtcgaca gttattaaat    43920
atcttctgta aattacctat atttcagatg tcatattta ggggaagtat ttgaatagtt    43980
tagtggtttt ttttaattgt cacacaaaat agacaagtga gcagtaagct aaatcaatgt    44040
cagatttttt aatccacttt ttttcagtta aaatggcaaa tagtacaaga ctcattgaca    44100
aaatatcatc ctatgataaa attctatttt tactagcaat aatatatcac tgttaatgat    44160
aacctaagaa atacattccc accttagcca gctgccacag atggtgacag tgtcacagtg    44220
gtgacactca tccatctcca ctgtcttact ttgagtttga ttttttttgtc atccagtgaa    44280 ttctgaaact ttataacatt tttgaaatag catgtacgtt gagatcatgt gaacttaact    44340
ttgcttttct gcattcatta gctagataag aaggctttgt aggatctaaa tagattgaaa    44400
tgaacagtaa acctccctgc actccagcca cagccacctg ccaaaccaag caggcctctg    44460
accaagacaa agactctcct ctctgtggga cctagcctgg agcccgtcc tcctgccctt    44520 ttcccttctg cccggggtag agtctgcccg ccggttccca ctctgttctc agttcttctg    44580
tgacaggcat ctgaggtgtt caagactgag aacttgacgt tcctagcctc catgtggccc    44640
agggacccca gaactggctc ttctacaacc cccagtggaa ggcctgccca gtggtgccat    44700
gtgggtgtgt gcagttaaac gccctgcatc tgccttgcct agtggcccga gccctgatag    44760
gatgtgggat cccacttttt tttttattag ataattttctt tatttacatt tcaaatgtta    44820 tccccttttcc taatttcccc cctgaaaatc ccctatccta tcctctcctc cctcccctgc    44880
tccccatccc acccattccg gcttcctggc caggcattcc cctattctga agcatagaac    44940
cttcacagga ccaagggcct ctcctctcat tgatgactga ctaggccatc cacagctaca    45000
tatgcagcta gagccatgag tctctccatg tgttttcttt gattggtggt ttagtcccag    45060
ggagctctgg ggttactggt tagttcatat tgttgttcct cctagggagc tgcagacccc    45120
tttagctcct agggtccttt ctctagctcc ttcattgggg accctgtgtt ccatctaata    45180
gctaactgag catcccttc tgtattagtc aggtactggc agagcctctc aggagacagc    45240
tatatcagtt tcctgtcagc aagctcttgt tggcatctgc aatagtgtct ggggatccca    45300 cttttttaact cacatctaaa tgttgtctta aattttgaca aaactcaagt tatttcagtg    45360
gcaccaatgt gacttcattg ctctaccaag tgatcaaaga aagatatatt ggtggtatt    45420 agatattacc tttatctttg ctattttctt tctttagtaa cacattatat atatatttgg    45480
cttataaggg ctatgggtct gaaattgacc tctaacaagt aatccattat accactacag    45540
tacatactca aggtcagttg tgttataaaa tcttgatagc catactttat tgcttaaaaa    45600 acactttat gccaggcgtg gtggcacacg ccttaatcc tagcacttgg gaggcagaga    45660
caggcagatt tctgagttca aggccagcct ggtctacaaa gtgagttcca ggacagccag    45720
```

```
gactacacag agaaaccgtg tctcaaaaaa aaaaaaaaaa aaaaaaaaaa aaacaacaac    45780
aacaacaaaa aatcagtttt atgaaggcag agaagaacaa aaagaagtca gagtttaatt    45840
caatctctta tgctacaaaa tcatcaattc ataagttcca agaaacatg aataaacaaa     45900 aattttagag attatttgga atgtagaatc tataaacttg ctatcaaaga aaattgaatt    45960
tactttaata aatatttgtt aaaagtactt ctaataaaga taataactaa gcatatgtat    46020
attgcaccaa tgaattattt aaatgtgatc taatttatc tacccacaag tttctactat     46080
agttgctatt atccttcttt taaggaaccc aaatcctata agaaagaac attgaaaaaa     46140 aaggtatttc aaaactttaa aatagataag taacagcctt agaaaatggt ttccaagtaa    46200
ttaggtaaaa cagaagtatg gaaacataat attgaggcaa aggacatgtg aagtaaaatg    46260 aagggatgg ttaattggta atcaagtcct tagagatatt ggtgaagaat ttgaagctgc     46320
tgcatattta tttccctcac aacatcacct actgtgattg ctgatcaatt agtttatctt    46380
atagaccaca tttaacttcc cgatactggc ttatcaccaa agagtatgag gacatcttca    46440
tggttctcta gctggtccct acttgcactt tgtcttggct tgtcccgtag cttatatcca    46500
ttcccctatc cgtactgttt caggttcaag gcaaggacac ataggatcct tccaacaaca    46560
tctgcaattt atagtagaga aatccactcc cattaaattc tgaaaccaaa catgttatac    46620
tcaaaataat gaatactaac acaagctgaa ctttgcccat cattttgaag attaccaaga    46680
taactgaata ttaactatgt gctatggatg aagctccatg ctttagcctg tgcattgctt    46740
tatctgacac tgaaattcct tctaaacata tgtaatctac cacagtgggt tctccctctc    46800
ttcttatttc tctaataata ttttgtaatt acctatactc attccttctt catctttgct    46860
tctctaaata tatctatttt ataatttat ctctataaaa tctttcatat ttttaatcca     46920
aattttgagc ccactctaca ttctgccttc cttaactaat ttatcatatt atctatatga    46980
taaacacaca ctcacacaca tatgtgtgag tgtgtgtttg tgtatatata tatgaatttt    47040
ttctaggtta ctcccaggaa agaattgtat cttaataaat gctaattcct gatacataca    47100
gaacaatggt ttcatctat taaatactca acaaatatgt gatgagttga acatataaa      47160 atgggtgctt tgctgcaaag ccatctaaca gaaaataagt tactaaattt caccaggcaa    47220
aggattactc tatttcatga tcataattta tctaataagt taaaacatta atttatagat    47280
aaataaatgt ttttaatcag tgatcttcca tgttttcct ttgtaatatt tgaagactttt    47340 gttttgttaa cataaaaata ctgattcagt tattagtaac atactttgt tggatttaag     47400 tacttttatc ccaaagaatt agtgaaggac tttatgaaaa aattaagaca aggattcact    47460
gccttaggtt ccatctttta tttctaaact ttcaattttt ttattgtttg acgtctttaa    47520
atggttacat aattaatttt agttatctgt atcctcagtt tctctctcat tccttgcctt    47580
ccctctctgg aactcattgt agcagtactc gtctatttta atgccttttt gcgtgtggct    47640
cattaagttt aatgagagca tgggtgcaat gatatttagt ggagcaaggg acgcttacat    47700
gtgttgcaga catgagaaca gaataggaca actcctctct aacaaccatg agcctgcctc    47760
acccatccta aaatgtttta ccatgtacag ataaccccag ctctaatggg ttcatgactg    47820
taagtggtat gtcctgtagc aaaggtgtgt gtctactctt tctataggtc agctcttaaa    47880
ttcttcatgc tcccacttct gccatgttct ctgaatcatg gtggaatgat acaaccttcc    47940
catttatgcc aaatattctg ttaccactta tttgccactg gttaggtttc tgcagtcacc    48000
gggaaccatt gtagtaagaa actttacag taacagctgg gtgcaagctc taatctatgg     48060
```

```
tataaacatg agtagtgaga aggtagcttg ataacatgac catttagcag aataacagtt    48120
acttgcatac cttggtggtc aaagacctcc ccagtcagag acttaactag ggttacagaa    48180
ccaaatataa gttcccattt gtggaacagg ccatacatat aatcagcaag caggtagtca    48240
tcaccataag aattcactca ctgctctact agaggacaca ttttacaaag gtatgtgatt    48300
actatagctt atagtcccag ctgggtaagg ctgatgatgc tttccccagt gacttgcata    48360
tgctgcctct ggcactacga accagtaagc aggaagctta cacttcatct ccatgacctg    48420
tgaccatagc atacaatact taacatcaag ttctggtagg tatccaagag cactgggaaa    48480
agcctgtgtt gtttggggca cctctgagat cccccttgtc agtcactcat agggaggtat    48540
cccctaccca gcactgggac ttttgtttga ttattcatgg tatctgagag aatagcatc     48600
taaaagaaga cctctattta agcttttttaa agattacata tatttcttag aactgtagaa    48660
tagtttacta aaatggtaaa tttgaactca aatatgtata gtttttaaac aggttcaact    48720
attattaact aatttctcaa ggcatgatat atgttattgg caagacaaac actaataata    48780
atgtttacaa atctctatat taaatcatct tgataattgc aatttgggac acacttcatt    48840
actacatagg atagcatatg ttttcttgca ttattggtga cagagacaga tgatgagtaa    48900
atgagtctct gccagtgtat ttctgtatgc tgataagatt gtattattgt ggtgctggag    48960
agatggctca gcagttaata acactgacta ttcttccgaa ggtcctgagt tcaaatccca    49020
gcagccacat ggtggcttac aaccatccgt aatgagaact gacaccctct tctggtgcat    49080
gtgaagatat aataattaat aaatcttaaa aaatagattg tattattgca aatcctatcc    49140
ccaccacata gtcctctgtg gaactccatt ctgagaaagc tagttaagtt aaaactaggt    49200
agtgccattt tgaagccact caacagagaa tgcctcagcc acccaaagta gagggaagat    49260
gactgtctac cctactcctt attgaactct ccactgtgaa ctactacttg ctactcttct    49320
tgctgtctac tgtctcccca ccatgttcct ttcataagtc tttaccttaa gtagccctca    49380
accctggcct ccattttcat gtctaatgtg taatactatc ctcctctctt tctctactgt    49440
ctctctctat ttttcttact tttgtcaaca tattattaca cttgatattc taaaaatgaa    49500
aagctgagat cctcacatga ggaagatctg gtagatttgt cctttgggc ctggcttacc     49560
tgactcagtg taatatttat ttctgttaaa aaaataaaa gaaaaacaaa tccccaaaac      49620
tcaaacaaaa ccactcaaaa caacaacaca aaagattcaa ccttatattt tgcaagtgga    49680
aataaaatat cattcttatt gtcaaagaca acaaagtttc tatatgacag aaaatatcta    49740
aatgtaagca tttcaatata tttgttttc agttgtatat ttttaaagct gaaaaagtat     49800
aacagtaaca aatatgaaac aaggttgacc tctcaggtta agatacattc agtcacatct    49860
tactaatgtg ttattgatga atacatttta tatttgtttg ttgacatcac ctaacttgcc    49920
acttttctt ttagacttta aagttgtcaa gccgcgttct tgataaaata agtattggac      49980
aacttgttag tcttctttcc aacaacctga acaaatttga tgaagtatgt accattgact    50040
taatgtttta tgcattttat tagaaatcaa acaattctaa agaaagattt atcctgcatc    50100
agctaacagt gataagtagc aaagtcccac caatagctag tttggctatt tctggaaact    50160
gggaaagcta gtcctgtagc agagcaccat tctgaggtca ggtacgattg cccaactcaa    50220
acatacctca gcttgctctt aataatgttt ttcaaaactt gatccttatc agacttagct    50280
tgcttccttt tagtataata ctttaaattg ttatgtactt tgactaaaata tgatactctg    50340
agcagttctt gttctgtgct gtcttatgtc acaagtaaat tcaaggacct tgaggacaga    50400
taccatgttt tatttatctt tgcattttca atatttaata gagcaagtgt tacggctgaa    50460
```

```
ttgagtagca gagagagaga gagagagaga gagagagaga ggaaaacctt tttggagagt   50520
cccttgttct catgtgttct gtgtgagaac actagcttta ttttaaaaag gtattaataa   50580
aacctaggcg caatttcaaa gatacacaat cttaattcca ctgaataaaa acataatgca   50640
taaattgtaa tatgctaaga accatgaatt tattgattgg ataactcttc agtgttcatt   50700
ttcttccaca tgtgtctctc tgcttggttt tgattgtgga atgtaatata ccacttgatt   50760
ttctctgtgc ttttattttt cagggacttg ccttggcaca ttttatatgg attgctcctt   50820
tacaagtgac tcttctgatg gggcttctct gggacttgtt acagttctca gccttctgtg   50880
gccttggttt actgataatc ctggttattt ttcaagctat cctagggaag atgatggtga   50940
agtacaggta gtggtctttt tcaaagcttg aagaaatttg aattgggctt ctctaagccc   51000
taacaataaa actatgccat gtcacttaga agggattatt ttaattctgt aaataatttt   51060
ttctataaga aaaaggcaat tattttccct attggtctat agaatttctt tattcatgtt   51120
ctaagtaagg ttcagtacat tttatattca taaagtttag gtaaaatgga tattgtattt   51180
ctttgaactg gaaggaatgc ctaaattttg tatggaacaa actggcctct tcctctccat   51240
atagtagggc cattctacca aagcatttat tacttttatt ggtaatatga gttatatgat   51300
gtgcttattg cagagaattt gtagtttgcc tgtttgaatg tgatagaaag ttgaaaatct   51360
ggggctatac agacaggttt ctgttttagt ttgtatatgc tttcatttgc ttcacaaaat   51420
ggaggtgatc tcctcttaga gactttgtaa aggattggat tagagatatt gtccaaagtt   51480
catctaatgg cgggtatctg acacttttta aaaattttt ctcttcctgt ttttctgtga   51540
cagagcgtct ctctgtatcc ctggctgtcc tggatctcac tctgtagctg atctagaact   51600
cagaggtcta cctgcctctg cctcctgagt gctggattta aaagtgtgca ctggctatga   51660
ttttgtttgt tcccagctgt ttaataacaa aatgtttatc tatgtaataa aaatatggaa   51720
tttttcaaaa ttttgaatag ttattagtag ataatttgac ttgttttgt tattgattgt    51780 ttgatcaatt gattggttta cagagatcag agagctgcaa agatcaatga aagactcgtg   51840
atcacatcag aaattattga taatatctat tctgttaagg catattgttg ggaatcagcg   51900
atggagaaaa tgattgaaaa cttgagagag taagttgaca taattacaat actggtccaa   51960
ttttatattt aacatttaaa actgaccact caggtggatt ttcaactcaa ctcatctaaa   52020
actcaaatat atgtatgtcc tgagttttac atggtttata tgtcagtgcc tataatcatt   52080
ttggtgagca aatgttttct tttgtttttt gagactggtt ctcaatatac ccttggctag   52140
catagacctc tgtatgtaga tctagacctt aaaggcatgt gccaccacac ctgtccctgg   52200
cttatggttt tacagttgat tcagtttttt tgtagtgcat agatagttat ctcttactaa   52260
tgattctgct atactagttc acagttgttt catacccctta atttaattaa acaatgatg    52320 aagatgctgg ggggctaatt gaaaccataa atggaaatac tgaaatatat aattgtaaga   52380
ggaaagggtg atcttgtatg acactgtact tcaagtatta tgcacaaag agcgggtgac     52440 agccacattt ggacaacttc tgttattctg agcctgagga ataatgacaa aggaaatttt   52500
ccttagggct actcatataa attgcttaca agaggctaag tcagtccttg taacaaaagc   52560
catctcctga gatggaatct ttacttagca cctgtgtgta tcttatcttc tttcacctca   52620 gataacccttt tgcagatcag taaagattac ctctgaccaa aaaaaaaaaa aaaaaaaaa    52680 gcacagcaag gctgatacat cattactaag ataatttttgg gtaaaataac catgagcatt   52740
gctgtggcca tggaccgttt ttatttagtt gacttccgtg tcctaccaac tacagtcaag   52800
```

```
gaaatgtttt agacttctgg ggatgagcgg accacgaaag atactactaa tttaaagaca    52860
tgagatatat gagtatttca cagggaaaag gaaataaaga gtgctctttg caatggtgtg    52920
aatttgatta tttcatattc agggtgctgg agacctgtag acaatggtaa ctgagccaca    52980
gctgtgtgat tggaacaaca atggaaatgc ttaaatgtta agtcctttgc catgtaaata    53040
gaaatagcaa aaagagtgtt tattttccaa atactattgc tcacctgttt ttgttatgcc    53100
tttcaaggta aatctaggaa aggaattgca ttttctttct agaaacatcc ttaaagatct    53160
tggggaattg ttgagttgat aagagttgtt tctcacgtta acaggttgag tgctcccctg    53220
cactgcctgt aaacacagtc atggcagggc tggttatcac agaatccagt tttctcaggc    53280
ttcataatca gcttgcagta ggccgttcct gtggctgacg ggttttgtt tccttttgg    53340
ggttggtttt ctttttttga cattggtatt ttaccctct tttcctcaca taataaatc    53400
catctttcct attctgaatt tcaggctggt taattctaat agctagcatt tgtctggttg    53460
taacctgttt gatacatcat gaaattgtta cctgaaaaag ctggagagtt ctgacgtaaa    53520
aaggaaagca ggaattgctt taccccgcag agtaaataca atgttctagg ggagactgac    53580
tggatgttct taggattacc tcagcctaga aagctgttga actcggccaa aggctatgtt    53640
aatgttcttg aaaaaaaaat ctgccttta ttgcttttta gccattaagg tactttcaat    53700
tttttatacg aaactgatag aattttttta tgactcataa aatgttaggg attttatgtt    53760
agtgtataga tgattctgtt gcgtgtttgg gatcaattat tcttttcct atgtgacttc    53820
ttccttttct gagctgttct aaaatattgg aacagttttg acactttact accatttgta    53880
aacattcttt cctttatataa ataccaggct tatcaatgta tttttttatc tctagaagaa    53940
agggatacac attgctcttt tacatctgct atgctgtcat ctaagcttaa ttacatctct    54000
acaagggaag tattacggtt tttttagtga tagaatcaca tttaattaga tggaagagtg    54060
tcttcctta aacataagta agactagtcc atcttcagta caaatttatt gaaacactac    54120
aactcactag gctgatcaca atataggcta tacacatgac ctctatccgt gagctcaata    54180
gtatattgtt ttctttgagg acttattttt tttttttttt agttctacca cttgacaata    54240
acacttgctt ctatggatta gaggaacagt ggaagcatag tgcctgtata tcatgtgcct    54300
tcctgcacca ggctgtagat cagatactgt tccttttccga cagagccttc attttgtgtt    54360
caccattggc ctttgcccac acaagaactg gttgttttta caaatgatca caattggggtt    54420
gaggtttatg gctcctggaa cagtggcgag gttgactgca gtattgttct ccatcttcct    54480
tttgtcacta aagcatttaa cctcttcctg tatatgttaa aaaagtaaat acctcccagt    54540
tgaagtacag actagaacag actagaggac tgcaactcta gtgaggtgcg actgcagata    54600
attacatgac aatgagaggg actaggaggg aggagctact ccctgctctt tgaaggaccc    54660
cctgcaactg agtgacttgg cctctgactc cagagtggct cctgggaagc tcaggcagca    54720
gctcagcaga tgtcagcaga tgtgactgag agacaatgcc cagtcacgtg tttctcactg    54780
ctctttgata tacacacctc gccagtgcta tttaaagcca agctagaatc tcaaaactac    54840
taagaatatg atggataact acagaactgt ccctttgtt cataaagctt gtaacattgt    54900
tttcccttcc acacatcact tcaagcgtta ataagaagt tactaaagat ataaaaataa    54960
tataaaagta aatctattta gataatacaa tttaaataaa ttttaattat aattataaat    55020
ttaattatga tagcaattga agttcttaat tgttttatgt taacaagcat tctgtgtaaa    55080
taaatggtat attcttaag agtcatataa gctaattaag gtcaagagaa gttttgtaac    55140
ttgcccaaac tttggactgt atattcagat tttgtattct aagacacctg attattgaaa    55200
```

```
gaaaataacg tgtcacgtct tcttctgttt tgcacagggt ggagctgaaa atgacccgga    55260
aggcggccta tatgaggttc ttcactagct ctgccttctt cttttcaggg ttctttgtag    55320
tctttctatc tgtgcttccc tacacagtca tcaacggaat cgtcctacga aaaatattca    55380
caaccatttc attctgcatt gtcctacgta tgtcagtcac acggcagttc cccactgccg    55440
tacagatatg gtatgattct tttggaatga taagaaaaat acaggtaact tccatgatgg    55500
tatacttaca tgatttttgga aacattttag aatttgtata gtggggaaaa tctctaaaat    55560
gaatttcttg attttggatt tattaatgga ttagatttcc actcttcatt ttcatacata    55620
atttcatgag cgcttacagt gaaaatctaa tgaaataaaa tcctaggaga ttttgtaggt    55680
caaatgaatt taaaataatt atttctataa tctagaaaat cccatccaag aaatctgtga    55740
atagatcatt tctaggcagc ttgtaaatat ccaaaaacat tgaaaataaa tttcagcagg    55800
aagttaaaaa aatgttctag ctagccctgg aatgctcacc ttgtaggcca ctgtactttc    55860
ccatgaagca ttgctatgtt ccaagaactt cagcttccag cagaccagaa agttacctga    55920
tccctggcca ggtgggactt acagggttat tttgagcatt aggtaagaag tagtttattc    55980
agagcaagtt gaataaactt ctgagaaaaa aaatgtctta ttatccctta aaatgtatat    56040
ttaaatattc agtgcagaaa gtaaatcatt gtgaagaata aatgtgggat cgagggtaga    56100 ctgctttttta agaggttctc caattgttta ccttggactg atgtcacaaa tgacagaaaa    56160
catgtaattt tggcttttaa atctgtttta tttggtcttt gaaacttttg aattaattaa    56220
tagaaattag aagtagagag attatcatgt gtacctctgt ccacaggcat ccatgtgtat    56280
tcacttacgt gtattgagtg tcttctggag atttgcgatt atgtagtaat ttgggttccc    56340
acagttacag caactgccct caaatgtgta tagcctgccc agctcatcaa atcttttaca    56400
gccttttcta ttcagcgttt cacccccaag gttaaatcaa cttgagttgt gtgactagag    56460
cagtcactca aacttagaat catagtggct ctatgacaaa tcttatttcc ctgctgacat    56520 cacccctagtt gggtggaggg atgagagaag aaagacagag agaaggggag agatgtaaga    56580
ggagaaatgg gagtatctat gaacagtaac acagaaacat ctaaaaaaaa aaaagagaag    56640
gaaatgagac aaaccaatag aggaagagag gggggtacaa ggaagaaaga tcagagcaaa    56700
gattccaggt gcacagattt aagtcttatg ctctccacct ttcctaagaa ccatgtggct    56760
ggaattctct gatggaggcc tttctcagag aactgagaaa tagttctatg aagtccttct    56820
ccttcccttt atataaggag caatgattat gatgttgctc gtaaagagag tgttaaaaaa    56880
aattgttgtt cttttcactt gtactagcct tgaactggta catgaataat tgtcagggtt    56940
tcattagaaa ttcatattct ataacagt ataagaaga aacaattgca ctgatatcta    57000
atgtataaaa ctaatttcat acattaatat atttaaagaa tatattttga ctatgatgag    57060
tcctactgct tggtacttta actttaagac aattgtaacg ttaatttatt aagaaacaat    57120
ttctaattta attgttaaaa tccatacaag acactgtaat gttagagtgg aagaagatat    57180
aacaatacat ttttgctatt gtgattctac aattgaaaga ttttgtctt cattgactag    57240 gatttcctgc agaaacaaga gtataaagta ctggagtata acttaatgac cacaggcata    57300
atcatggaaa atgtaacagc attttgggag gaggtgagat ttctaaatat ggtcgatttt    57360
taaaatatgt aaacaattgt gcttttttcct tttcttgcac ctaaatttct actcaataac    57420
atataagatt caaagatat tatatctcat agggatgtaa ggagggctat cctcttttat    57480
aaggtgaaaa gtgggtaacc aggaatatta aatgcagcat aaagtgcctt tatttcttta    57540
```

-continued

```
aagtcatata attgatttca tataatgggc caggaagatg attaccttcg atactagatc    57600
taaatcctgt ctctgcaata cactttccat gtaatctaaa tcatattatg ttcaagttat    57660
taagcctcaa gtgtcttcat gtgtaaaata gacattattt ccctactgac taagatgatt    57720
tacatggtct gttcattagt gcactttgca aataatggtc tttcagtgaa gattaacttc    57780
tctaatcatg actcctaagt cttccctgcc tatcactcag aattgatgag ccactgagtt    57840
cccatgagca gcttccagca gtttactcac tctgtatgtg gtgtaggtga cctcatccag    57900
cctcaacatc agtgagctga tgacatgcaa gtgcaaatct ctaggcctaa tttcaggctt    57960
gcatgctcct catcaacttc acagtcatca ctcctcaagc tttactgccc tcgtgctcca    58020
gcatgttctc catctccttt cctggccaca ctgagaggca agctaggata ggatgcatta    58080
catgccaaac tttcactaga taaatatttc tttttaccgt gttcaacttc cattcttcct    58140
ccttactcct aattgaatcc tcaatgttga acttagaact actgtttatg aaaggtgaag    58200
atagacccat acatttgaaa tctagatgaa atacaacgtt acttccttt ttcccttact    58260
attttaacct ttgcttttgt ggttctctct tgtttcaaga catcatcatt ccttttaata    58320
ctattgtttg ggtctgagtt ttcatattct ggagccttag tgatattggc ataatattaa    58380
aaaagggagt tgattctgta gaaagcaagg caagaacaat tgtgaggtgc aagtggatca    58440
taagaagtag cagacaatga attctcaggc aggttacctt taggaaagag gatcgttgga    58500
tggtgtggac ctaaaaatag attcacttaa aactaggcac acaagtttcc caggcttctt    58560
catgaccact atttgatgat atatattttg ctttggagac agtacctccg agcttccatt    58620
gggcaataga gaggcaagca attttttaaaa gaggatttct ctccacccca tacatactct    58680
tgtacagaaa aattatttg aatccactag caactttgtc acttgtattt gtagccaatg    58740
ataaatgttt ggagcaagtc ttagaggatt ggaagtgagg attgccttgt aaatctacct    58800
tgtgagctac ttgtttttga cttttgctg agccaaagtc tacagtttta aagaggagg    58860
attgaaaaat tggtcttata tattatattg aagattaatt aatgtttatt tactaagtct    58920
gtaggaaaaa gggtatatgt gtatacttcc ttatagtctt ggtgtacaca cacacactca    58980
tacacacaca ctcacacata cacacacaca cacacacaca cacatacttt agccaataat    59040
atgagactga ggcaatgata agtaaaagtc tgataaagag aaattttgtt ctcattacac    59100
ataactattt ctcaaacaca ttcaaccata ctctccagaa accatgtgct ttatagttat    59160
atattataaa ttaattaata ctatgtatgt attttaatgg atcctgtacc atgtatttct    59220
taaactgatt gcatataaag ttttctatgg aaaatctgaa agcattatta tcttcaatgt    59280
gtatgaatag ggatttgggg aattactgga gaaagtacaa caaagcaatg gtgacagaaa    59340
acattccagt gatgagaaca atgtcagttt cagtcatctc tgccttgtgg gaaatcctgt    59400
gctgaaaaac atcaatttga atatagagaa aggagagatg ttggctatta ctggatctac    59460
tggatcagga aaggtactgt ctcttaaat tgttaatttt ctgagaaatt tgtacacaaa    59520
tactgtaatt atgtaatttc tatccccctt tccagtatct tactccttcc atgtacccct    59580
cctcacttcc attaaaattc aagacctttt tgtttatgat tattatatat aatgttcttg    59640
atctatttg tgtttatat atacacgtgt ttagaactga tcactcaaga ttggataacc    59700
tatcagcgag ctaatttta aagaaaactg attctccctc ataacaattt tgcctgtaaa    59760
ttttcatcta ggggatggag ccttgtgaga taacctcata tgcattgtca tgtcaactgg    59820
taatgtcatc ctgtaggact tgtttagtta acagtgtttt gaatatttca taggtgtagc    59880
atctcattgt ctaggagata ctatctagca gtagacatgc ctgttttctg gctatgtttt    59940
```

```
agccacatct tccacaatta gccctgagcc ttaaatacag agtttgcatt gtagatgtat    60000
caacatggtc agttcttctt tgactagctc tagatctctg caatgctttg catccagtgc    60060
aaaaaaaaaa gatgtgtcta caaaaagtgg tgagaactat gcttacctgt ggctatgaag    60120
agaagtattt agaacccagt tagaaattat attagtttac aaaatggcag tagtaagagc    60180
tatgacctct ccagctatgg gtagtagtta ggtctacatt acaagattac taggtatgaa    60240
ttgaatactc ttaatgattt ggtcttaggt ctaatcaggc agctgttagg tatccctagg    60300
ataccactgt tgtaccattg atgttgtatt ttgccaagac atcaggtttt tttttgttt    60360 gcttgttttt taatctattt atttcatatc attaagaatt taatttacta ttcatttctc    60420 cttttgtgt actttgaagt atatgtaata tttcagagaa aatcacatat gtatggaata    60480
tctggtgtaa tatatatata tataaaata aatatatata tatatatata tatatatgta    60540
atatgtagga atgtttgagt ataatgtata taagttgctt cagtaatgat ttccttcagg    60600
tttttcacat aattttatac ttttttgtat ataatttagc cttgtcatac atatagatgg    60660
ctttcaagaa aaccatcctt ttaaccgttc tttacttcag atctatttc aaaactggta    60720 caaaaaaaac cctgctttag atttcaccta tttctctata tatttgacat ctctctatat    60780
gtggattttt actgaataga cccaggcttg cttttatat attattaaaa tatgtcaagt    60840
aagtgttaaa atgttaaaaa ttttaattta ttcagtggct atgttactcc ccacccagta    60900
ccaagaacaa tcaattatga tttggagaga tatctgacaa aatctaattg gctagaagtg    60960
aaaagcgctc agggattgtc acggtttcag atatgttctg tcatgtagat aatgatagat    61020
acttggtttt tggtagttac ctagataaat cattaaggac caaagaaatg aaatgtactt    61080
gagccaatgc tttgagcagc agagtacttg ctgtggggat ccataaaata gatccttgtt    61140
gcaatcagat tgttgtttta gagtaccttt cagtaataca aatatatatt tattaatctc    61200
taaaattcta tttcaaaata taagcaatg ggagaggaag ggtgggaaga aaaaagaggt    61260
gggagaaaaa taaggacaag gcagtgttgt tataaaataa aaatgaaaat taaggatcac    61320
aggagcctag catagatgtc tcctgagaag cttcatctag cagtggatgg aaccagatgc    61380
aaagacccac agccaaacat caggctgagc tcaggaagcc ttgtggaagg gttgggggta    61440
ggattgaaca agccagaggg ctcaaacaca ccacaaaaga cctacagagt caactaagct    61500
gggccgatgg gtgctcccag agatcaaagc aaacaaagag caggcaggag ttgttcctag    61560
gctcgctaca cgtttataga agatgtgcag cttggtcttc atgtgagtcc cctagtaact    61620
ggaccagggc tctctgattc tgttgcctgc agttggatcc cctacccct agcaggaatg    61680 ctttgttggg gcctcactgg gagaggatgc aaaaatttaa tcctactgag acttgatgta    61740
ccagaccagg ctggtaccca agtgggctt ctctttctct gaggagaagg ggaggtggta    61800 atggggtag ggatttgtga gaattcgact gggagagggg gctgaagcca ggatgtaaag    61860
tgaattaata aaccaattaa ttaatgaaaa caaaaagcat tctaaaaggt aatttgtttc    61920
tattttatac tagtatctta aacagggatt ttattttaaa gagttttata tgagattttg    61980
gaaatagcac aaattttcta atcactgtac attttgctta ttttctctc caattgtttt    62040 cttatctgtg acatagacat gttgtttgt tttattttat ttatttaaag actgaatgac    62100
ctttattgct cattttttaat taattatttt atttatctac atctatgctc ccagaaatct    62160
tcaccctatt caccctcccc tttgcctctg agagggtatc taaggctggg catctctctt    62220
ctctgggaca tcaaatctct acaggattag gtgcatcttc tcacactggg gccagacaga    62280
```

```
tggcataggc atcttaaata aagtagctat aattttatat tctcttccta cagaaatgct   62340
tgctcctcag agtgttattt ctttcctcat tttctgatat ggaaatagag acagttttca   62400
cgattaaatg aaaatggtag cacaggaatc tgcataacta atgctataaa agacacagat   62460
gaccagaaac acactgtctg ctgaggaggg ggtattacta gcattacaca gaattttaaa   62520
aatgaattgt tcatgtactt aagatcaata catgaaagag gtataaaaat agctttggaa   62580
gcacagttgt tgaacttgtc agtagttaac catcaggcaa ttctatgaaa ccttaatgaa   62640
taagtaatta aaatctggga ctgttcttgc ctctcacaga aaattgctgt gaaggcagag   62700
aaagatctgg gttcccttct gacaacttac tcagagagac tgctgttttg taagaataag   62760
aaggaaaaac gattatttga ttgaaaaaat gtgaagctat aatataagat ttaaaatatt   62820
aatatttaaa gttaatttta tacctctcaa tttgatagtt tattatttaa gacttaaata   62880
taacctaata atcttatatg ttatacccct atatatttac agagattttt gtataggtat   62940
ctttggagta gtatggctat attttgaagt tctgtagtcc ttggttatag aaaaatttac   63000
aagatatgta gttaagtgag aaaagcaaaa caaaattttt gtatagtaat gctacaatgt   63060
actcaaggat actaaactat attattattt tccataaagt ctatattttg ttctactgga   63120
tacatttata atatctatat atgcttcata tttcacttat tcttaacagt ttcttcattc   63180
ataaggagct tggataaaaa aatcaatatt tttccttctc ctgctacctg ttttctttc    63240 taccaaatgg tacattagga gcccttctg tgtaagcacg gggacctaag cttgaattcc    63300
aagctcacat gttaggtgga tccataaccc cacaatgaga ggctcagaca gttggatcaa   63360
aggagctcac aggcagccag tgaagctgag actgtgagct tcagtttatt gagacacttg   63420
gtttgcctca agcaatggaa agagacatag aagatactag tatcctgctc tggcctctac   63480
atgtacacag aagggtacag gtgtccacat gttcacattg tagctctctc tctctctctc   63540
tctctctctc tctctctctc tctctctctc tctctctctc tcccccactc tgtgtgtata   63600
cacaaacttg acatccatca tttctttttt tattgtagtt ttttagaaa acatttatta    63660 ggtttttat tggatatttt ctttatttac atttcaactg ttatcctctt ccttgtttc     63720 ccctgtgaaa actcccctat cccatctccc ctctccctgc tcactcaccc acccactcct   63780
gcttctctgt cctggcattc ccatacatgg agcatcgatc ctttacagga ccaagggcct   63840
ctcctctcat tgatgtccca caaagccatc ctctgctata tatgtggcta gagccttgag   63900
taccgccttg tatactctgg ttggtggttt agaccctggg agatctgggg gtactggttg   63960
gttcattttg ttgtttccct tcagtttctt gggtcctttc tctagctcct ccattgagga   64020
ccctgtgctc agtcccatat gttttttataa tttcttaaag atgaaagcaa attttcatac   64080
tagtaaaatg aaagtacttt ctaagactga atctgtgtta gtttattata atgaacacac   64140
tcatgtagtt agagcatagg ggcagcccat agcccaagag ctttcagcaa gtgctcactg   64200
tcaccagtct cttactacaa actgatcaca gcaatttaag tagggctcg ctcttctttg    64260 tgaaccttag tcctatgttg cccagatctc tttcatcccc tttgtatttt ttatgcctag   64320
aaaagtccct gtatcatgaa gtactaaaac atctttaatc aaatgagtta cactctttaa   64380
acattgggag acttgtgatt ggaataattg gacgcaagaa agggataagt aatttgatca   64440
aacaatttag ctgttgtttt tatttgtaga catcactcct gatgttgatt ttgggagaac   64500
tggaagcttc agagggaatt attaagcaca gtggaagagt ttcattctgc tctcaatttt   64560
cttggattat gccgggtact atcaaagaaa atatcatctt tggtgtttcc tatgatgagt   64620
acagatataa gagtgttgtc aaagcttgcc aactacagca ggtaagcata tttatgaaaa   64680
```

```
atgctgattg tgttagctac ttgtgtcagt gttgtgataa aattgcttga ctactcacct    64740
tgaaaagggt tttattttaa attcttttca gggatgatac cgtccatctt ggcaaaggag    64800
gggcaggaat gggaagatgg cgagacatgt tatatccata gtcaggaagc agacagccag    64860
caggaagtgg ggcttcaagg cctaattcta gtagcttact ttctccagta aagctccaag    64920
ttgtaaacac tgtcctaccc cagtgtaccc ccaactggaa ataatgtttt caaacacatg    64980
agcccattgt aggtatttca cgttcacacc actacatgga ttatgctcat tcagtcttca    65040
gactaaccaa attacacagt tagttctcta ttgagttaat gtaaacatgt caaggacccc    65100
ctaggattaa gctggagtgg gtgggtcagt gaataaaacc atgctcctac tttaagttta    65160
caaaattata aatagatgca gtttattttt aaagtgtgtt tgggtgttgt aaaaataaaa    65220
attccttatg catggggtgt ggtacttcat gagtgcaatc ctaatactca agagactgaa    65280 gcaaaaggt catgaagttg aagccagtct tagctgtcta atgagttcta ggccagtctg    65340
gatcacatgg taggatcatg ctaaaaacta acaaaccaaa agtctgtatg aattcaatag    65400
gagtattttg tgtacacttt gagaccacag tgaaaagaga agctatccta gaaacttgtg    65460
ctaaccttga agaagatagc catactttcc caaaagtcct tcttctacaa catgggggtt    65520
gatgtgttct gggcttgtta ccagatctgt ttttagaaga gttttttctgg gcaagaattg    65580 gagggagtaa taagtcttac ttggcttatt ttggggggtgg tgggggtgag atagggtggt    65640
actttcttgc tagatttaga ttttgctttg cttgagtatg tatttttccca tataaatgat    65700 ttcacagatg atattttgag taatcaaagt cgatctacaa aatgtacata atccaaatat    65760
agcatttata cattactatt aataaattta gagctgtgga tcatccatgc aacaagtatt    65820
tacaacattc tggacacagg tagatcattg gaatgcttag atgaagaaaa ttgtattttat    65880 tgttaaagct tcatagtagg atggtatata ttaataatag aggattatat ggtttgtata    65940
gtatatatca ataaaatagt gagagaagga gaagcaaaat atattgttct ttcatttgga    66000
tgcaaggaca tattacaatt attttatagt gtatgattta ttgtgttta gaatagttac    66060 agtggtacag tgatgaccac ccttttagaa cccctgaaaa gaaactccat attcattaat    66120
agtcaaatcc tatttttta aaatatttt tattattaca tattttcatc aattacattt    66180
agaatgctat cccaaaagtc ccccatacc tccccccca cttccctacc cacccattcc    66240 cacttttttgg ccctggcatt ccctgtact ggggcatata aagtttgtgt gtccaatggg    66300
cctctctttc cagtgatggc cgattaggcc atcttttgat acatatgcag ctagagtcaa    66360
gagctccgga gtactggtta gttcataatg ttgttgcacc tacaggggttg cagatctctt    66420 tagctccttg gttactttct ctagctcctg cattgggggc cctgtgatcc atccaatagc    66480
tgactgtgag catccacttc tgtgtttgcc aggccccgc ctagtctcac aagagacagc    66540
tatatcaggg tcctttcagc aaaatcttgc tagtgtatgc aatgatgtca tcgtttggag    66600
gctaattatg ggatggatct ctgggtatgg cagtctctag atggtccatc cttttgtctc    66660
agctccaaac tttgactctg taactctatg caaccactga tctatctcca taaattctcc    66720
tggtcctttt cttttttcaca ttttttacataa aggaaattta ttgagaattt catacatata    66780
tctagtgtat gtttatctta atccatctct ctctatcttt cctttaactt ctctcatact    66840
cccttcaacc acttcacccca cccacatctg tgctctgcct taaccttcag agttcagtct    66900
gtgatcctag tatatggcct tgtacccatg ctatgctggc agctctaagg aaattttaat    66960
gtaaagcaat taatgtaaag caattagttt tcatcgactt agacttgctg tgcttatac    67020
```

```
agtgtcctga agagtgatag aaacagacca ataatgaatt tagttaaaaa tgggggaaaa    67080
aagagaatat tttaggagta aaagaagaa  acagagagac tccatcaggg tctacccaaa    67140
aatagcagcc tccacatgca gaaaagggta ataatattcc tgatggtgtg attctttgta    67200
gaattctgag gttcacaggg aaagcgagcg gcccaagagt tctttattag gaacattgga    67260
actatgaaaa aagagagcca gactggactt aagaagtagg gaaatggggt ctggttgttt    67320
agagtaactg atagttgccc agtgaaacat tcggtataag atccttccag taaacactaa    67380 gttattttg  cttcttttga aatatagaat aatatcacta cagagaaaag caggaaaata    67440
ctttgagagc cagttgttct tagaaagtga attctgtaga gacaaagttg ttaaggacaa    67500
gaagagcctc caaaccaaag aataatgaaa agacattgat atgatatcaa tattgacaaa    67560
actggtcata gcgaagatga taacaatggc atttaaatt  tttggctacg tgacatagtt    67620
aacaaaattt gggtatctat ggaagaaatg aaaatgacag cagagcctgg aggtttggaa    67680
tgtggatgca ctggctttct gcttagtgtc ggtgagagct ggaagtcact ccactttagt    67740
gtatcttcag accccccaaaa ctatatgtgt cattcctta  tgtccgactg ttttggtttg    67800
atttccagtg ctataatttt gaccaaaaac atcttcaggg agaaaaggga taatgtggct    67860
tacacttcct ggtcacagtt gatcattggt gaactcagag taaggaacta aaggtgggaa    67920
cttgaagcag aaaccaaaaa gaatgctata ttctcatctg ttctttgtct tgctagcagg    67980
cttcacctta  cctagctttc tcttacaaag tagaatacct gccaggaagt ggcaccaccc    68040
aaaggttgtc tgggccctcc cacatcaatt agccatcaag acaacttccc acagatatga    68100
atagtccagt tgcactggaa aaatttctat ttccaggtga ctctgtccaa tttcaataaa    68160
aactgtctac tttaggagag tcaaggtgaa tagcaaatga aagcttaacc atctctcata    68220
taaaggattt atatgataaa tttgggggaa acaaacttaa ggttctaatt tctatatgct    68280
atgacagttg ttgggttaaa gtcagtggtg aaatttgagc ctacttggat aattcaggaa    68340
gcccctctct aagagaagac ttcttgaaga gcaggtcaaa aagaaaggta acattatgta    68400 taaagaaaa  tgaataggtg tgaaaccacc tattgcaggg attataagca tcttgataga    68460
gccacggtgc aattaaagag aatgaatgag caggaatgga tttagggaac cagacctggg    68520
aggtttatcc tagagaactg ttagcaagag tgctgtgaga gctttgaagt ctgtccctgt    68580
cattctggga tgatggagag cacaattaag gtgggtacca catgaagctt agcacagcat    68640
aaatagcata gactttgaaa tcgtacaaag ctgagtcata aggttattta acttgtgcca    68700
atactcggct tttctgctct gcaataggaa gctaatatcg cctattctat agcttttgta    68760
aagtgctcta gtacatagaa agttcaccat aagtaaagca ccagttatta ttattactgt    68820
catcatcatt ggcaatagtg ctctgttcac ggttgtgact agaagaaggg agactaatag    68880
gaaactattt cagttacaca gattatggtc atgatgtaca agagacaaca gttatataaa    68940
agaattgtgg gaatatagga agttatttat gtaattttta ttcaatggaa aggacatcag    69000
tgaaaaaaat ggttattcat ggagaataag gtatttctgc aaataatgtc tttaaaagtg    69060
tataaatggg ttcaagatta agaaatctga gatctttaaa acaacagtca gaaaaatgga    69120
catgtatagg tcatggcctc aagaaggaca cagagagtga acaaagtaga gggtcgcaga    69180
tgtggctgac aaggaacaat ggaggggact aggaagggct taataaatag ttatgaaata    69240
gttatacact ctagattttc gttttaacg  tattgcatac atagatcttc aattacttct    69300
agaccatttc ctgttgttat gctttcaaag attatttcac ttttactgct ctccaaagct    69360
tcccattaac tgtgtgacag tgtctgccta gcctcctcta gtggagaatg aactcagggt    69420
```

```
cttgccgaac ctctgtcatc atatgcctag ttagtctcca aaccctcagg gtttctgttt    69480
tcatgcattc cattgtgtgt tatctaggct ctgtctttta gttttagttt tgagactgtt    69540
ctgtcactct cactcacacc ctctatcttg ctctcgttga aattaaaggt ctccttttcc    69600
tcagctgttg ctacttggac taccctcagc tttccttagc tgcctgtggt tctttgccca    69660
gggctgagac tcctgaactt ttccccttct gcattaaaaa gcccattggt gtcattgttg    69720
ttgattgtcc ctttaatttg caataccctt cttttttctta gttaaataaa atgtgaagta    69780
aaactatttt tttaatttta aagaatccct aagtctttgt tccttttgtg ccactgcttt    69840
ttgccaccaa gttagaacct tttagttaac atttgaaagg cttttttctt aaatcccttt    69900
gctctttaaa atggcaaatg tagtattaca atgagctatg tatatgctgt ggtattatct    69960
tttgaactac agagtaaagt tctgaacaca acaactctaa aaatgttaat ttaatttagt    70020
ctatttagtg tactgataga atagtccatt tttactggat gactgttttg gaatggtttg    70080
aggtaacatg atggttggga gaattttgct cagcaaaggt tctgtgagtg ttgtggtctc    70140
agaatctgag cagattggtt cttgaatgag cacacttttt ggaagcttgg gatgattgtg    70200
cttgtctgac tacaaagaaa agcatcagga gtctcccctg tgtccagtga ctgaaacttc    70260
catgtttgtt tctgttatat aaacacacat ttggtcaggt acataaggaa cttcaacaca    70320
ctaaaatacc ttgttttctt agataaataa aatgttaagt aaaacgtctt tttttaaatt    70380
ttaaagaatc cctaagtctt tttccttttt tatgccactt tttaccatat atacatatac    70440
atacgcatac acacgtgcat atgcacatac atacatacat acatcacac gtatgtatgt     70500 ataatgacaa tttaagaatg caggaattttt gatcacagga acacagtata cctacagagc    70560
tcagtggctc aagagctggc accaacacaa gaacccctca gcatgatctg tggacggtcc    70620
catttgcgaa acccagacat tcatgactct gttttgcattc tgactgctga agttgatctg    70680
tttctcagtg tgctgcatca aggcttggaa tcagagatgg ggatgggata tcctcttcct    70740
catgcttgtg attttgttca actccgagat cttcaaagtc ccctgtgtgt cgtgatgctc    70800
agtgtcacag gagtatgtga gtgtggaagg gcaaagcatg cacaacatat ttcacatagt    70860
tttctgattt cagtctgttg ttggaaatta ttcactagat gaggcagctc aagggggaag    70920
ggcatggtgg ttctgttgat agaatgattt ttagcatgaa gtctcaaata aatatgttat    70980
gggttttttt ttgtttgttt ttttttttac ttttaagctc tcctttggga aaaatctcca    71040
tgctttgctt tttaaaaatg aattttagag tctagatttt aagacaacag gcttttaggt    71100
gaattgagag tcacttgcaa acactgttct gcgtccttgt gtccattggc tctcttcatt    71160
ttcctctgcg ggccattagg gtttccttga cacatttctt ttcagggccc agcactagag    71220
actgttctag ctttgagaga agaactagtg tgatgtagct ctagtagaat aacatgtctt    71280
atgaaattag agtcctattt cagtgttgag agagagcaag ggcttacact gttctctcat    71340
ctaccttctc tgcctcacac agccccagtg acaagagaat tctggacagg ccagtgtttg    71400
agcaataaat gatttgatgg tctttattct gtgactcatt ttcttataaa agtacctggg    71460
tttggagaag taattaaagt ttataatact ttatggtggg gcgtaaggat gggcaatgtg    71520
caaaggaggt caggggctta ggatatgtaa tcagtttcca caaaattatt gtgatgcttt    71580
tgaaaccaca aaatgatcct catcaagtaa gtatctgtca tgacagccat tacacacgca    71640
ctgcagcaaa aattactatg tgagctgaag aaggaggaat cgtgcatgtc tttctctttc    71700
atagctgctt agtggttttt gtatttaact tgctagagaa aatactgaga agaaaattgt    71760
```

```
caagaattca gtaaaagatt aaaaaaaaga agaagaacca tcttgggaga gaaattggca   71820
agaagttatt aaaaagttgg gagggaaata agctgagaaa tgagggtgtt ccaaaaaata   71880
aattccacca tagagattcc acatgactaa ctgaatttga atttgacctc tggctctcca   71940
tgttctgcat gactaaccta tgagaaggtg agacttaacc tttgaatagt caacttacca   72000
agttggataa ttcacagctt tacagttaga agtaatgaga agataagtgc cataggactc   72060
agcattgtac tagctcagac ataatgtata tctaaagaag atatttgaaa cacattgaac   72120
tatgtcccct tcaaccagaa taaatcacat tgactatacc gtaccatgga ctacctataa   72180
tttactgatt atatgtgatt aggaaacact agatattatt tactataaca tgaagccaag   72240
aatacttata gaattactga accagaacta aatgggaatg ccatgatatt ttatagtctg   72300
aactggtatt tcactgcatt tgagccttgg aacttaaaaa atatgtacta gctaatattt   72360
agggaaagag tatctatggc agcattgtgc taagcacgcg catgaactgg cccatggagt   72420
tgtctcttct gatttatttta gtgatagctt caccaagagt ttgcagtaga gtgaaaatat   72480
gctgacttca aaatgcaggc taggctttag gccctaagcg catgaagttc ccgtgctaat   72540
tatcaggtta acacatcaga gttcttaagt cacaaaaacc aaaatagcac caggatagcc   72600
actcctagtg agatttgaag tcaacagagc agtagcttat gaacataatt ataactgtct   72660
gaacagacta cctcatgagt agactgtgaa actatgacat gtaagcctga ccttcatatt   72720
taaaacaaaa acaataggga aacttacaaa gataaaaata attttataca aatccttatt   72780
atgtgtttcc agtttctacc tttttttaagg tataggaaac ccagattcag agttctccat   72840
atttagatgg tgaataatat tatttaaacc aagaaaaaat ataattttag atgcaggatg   72900
gtgctccgaa gaccctagct aaacttcaca ttcgtggaaa atttgacatt ttaccagact   72960
tgtaactcta tagatgttca caaaagctta cccagagaag gaatcctggt gtttgctaaa   73020
ttgaatgtga agtcttctct agataggtga aatgttctag cattgacagc tattagaagt   73080
aactccatga tgataggata agtgcttta tttatattgc ttattcttgg tttagattga   73140
tgaattaaaa agaaattgat atcagctggg tatgatggca catgccttaa tcccagcatg   73200
tgggagatag aggcagacgt gtctctgagt ttgaggtcag cctggtttac agagcgagtt   73260
ccaggacagc cagggctaca acacagatgg agcctgtaga aagaaagaaa gaaagaaaga   73320
aagaaagaaa agaaagaaag aaagaaagaa aggaaggaag gaaggaagga aagaaaggaa   73380
ggaaggaaag aaaggaagga aaggaaggaa gaaggaagaa aaggaaggaa aggaaggaa   73440
aaagaaaaga aaaggaagga aagaaggaa ggaaagaaag gaaggaaaga aaggaaggaa   73500
agaaaggaag gaaagaaagg aaagaaagag agaaagagag aaagagagag agagagagag   73560
aaaggaagga agaaaaaaag gaaggaagga aggaagaagg agggaaaagg aaaggaaggg   73620
aaaggaaaga gaaagtgtgc gtgtgtgtga gggagagaga gagggagaga gagagagaaa   73680
gaaagaaagg aaggaagaag gaaggaaaag gaaaggaaag gaagggaaag gaaagagaaa   73740
gtgtgcttgt gtgtgaggga gagagagaga gggagagaga gagagaaaga aaggaagaaa   73800
gaaagaaaga aagaaagaaa caaaggaagg aagaaggaag gaaaggaag ggaaaggaaa   73860
gagaaagtgt gcgcgtgtgt gagggagaga gagagggaga gaaagaagag agagggagag   73920
agaagaaaaa ggagagaaga agaagaggag gaggaggagg aggaggagga gaaggagaag   73980
gagaagaaga agaagaagaa gaagaagaag aagaagaaga agaagaagaa gaagaagaag   74040
aagaagaaag ttgttaatct cagcaacttt tcactgagct cccactataa gcacaatggt   74100
gcaataagca cagtagatgt tgcctgcagg tataactagt aacttgtcta tagtgagatt   74160
```

```
tttgttacaa aaatttatag caggatggca tatattcatt cagtaaatat ttttgaatat    74220
atgcatcaag ctaatgatta taccaaactc tgggaattac actggtaaga aaggcacaat    74280
gcttgctcta aaagaggttt ttttttttt cctcatagaa aagaacaatt aaagattagc    74340
ataggttaat gtatcgtatg tttcttaggg ctctttata cattaggaag ttaacaatgt    74400
tctcctaaaa gatgatggaa gtttccccgc aaggaagtga catctaagtg agagctgaat    74460
gaagaagcag aagaacattt taggaaggga acagaatgta caagggtgca gaaccaaaag    74520
aagatactgt acccggcaac gtggggagcc ttgtgcatat agtagagtaa gcatgggcat    74580
ctgtaaagga aaggctgtgt gaagagggc gaactgggga acggaaaggt agtcacattc    74640
tcagaaccca ttctgctata ctcaggaact cagactttaa agcttaggag attcaccaaa    74700
ggctttaaag taggaggtaa tgccacacaa ttaccttttt caaagatgtt ttcagttata    74760
atgtatagtt atcatgctct caattaaatg actagcaaag ctgctggcag atagataatt    74820
tcggttatct atctgagaga cagagacaga aggattctcc aagtcagggc ccaccttgtc    74880
tgtgtagtga gttccaggca agctggagct acacagtgag actgttaaaa caaacaaaca    74940
aacaaacaaa caaacacaaa tttaaaaact attcactgag cataaaatat aagatgtaat    75000
agtgactata gtcaccatgc tacagggtag atctctagaa cctattcatc ttgtctgaga    75060
cattctgtct tatgaatact tctctatgat ggtgctattt gctgagcaag ttgacacaat    75120
aaaagcattg tgcttcatta tggaaatctg gaagggatgt agaattgtga tgtatacatt    75180
ctatcaaaat gtatagaaac taagaagggc aaaaagtagg taaggtatat aagtagaata    75240
tttgtttaaa atatctaaaa caactaaaca tgtaatactc gagctaattg ataattaaga    75300
gaataagcac aactgagtgg caataggagg ctccgcggag gggatctccc aaaggctcag    75360
tgcagaagag cagagatgac ttacagcaca acaaggccaa tccatagagc aggctgttag    75420
tctgagctca gtacatgaag ggcaccttca tttggagaat taagagaatg aaaataagat    75480
attacatatg aaaatataag gtcagtgtag tgggaaatta aagaattcca tattcgttgg    75540
aaagttttta ctacgtttcc ttgtggcatc attgctttag aacaaaggac acacttagac    75600
aaggatcttt gttctcagct tacatttac tcaaggaga tagactttc acaggaaggc    75660
agctcttgag agacaagaga ttagttggga acttcaaagg tagtgggtt tgaagctctt    75720
ctaagaatct gagttataag agacttcata ataggaacca gaaaataatt tggggaacat    75780
agtctagata acacaagatg ttctattgaa gtatggtatt ctttcccca ggcattagag    75840
ttgtcctagc attagggata ggtatagtta gaggagaaaa taaggaattg taccacttaa    75900
atatccatac tgccaatgcc ataggagtta tttagagagt ttccttgcat ctgagctcgt    75960
gctatccaga agtctatgac taaatgagtc tgaatgaggc ataataggat tacagacact    76020
gaatagcatt tgaaaggatt tttggctggc tggctggctg gttggttggt tggtttcatt    76080
tagtaaaagc cagagaaatc cagttcccat atcattctct agctgtaggg gagttcagga    76140
atcccagcac ttttctattt ctggacactc tttccctgca cacataaaat cactgcactc    76200
tacagttcct ctcttaagaa tgcttgagct atccattctg aatataaacc cagatctata    76260
acacaaggaa gtacacaata gcaatagcta tatttatat catacataca cacatgaaaa    76320
ctgattataa aacagtttag tttgtgttat gatttatac acacacacac acacacacac    76380
acacacacac acacacacat atatatatat atatatat atatatat atatatat    76440
gctctcttct gtatgaggat gtgtgcatat catggtaaat gtgtagaggt cagatggcaa    76500
```

```
cattgggtac tgagctttac tgtctaccat gtttgaggca gagttgttcc ttttgttgct    76560
atatacacta ggctagttgg cttgtgagct actggatctc aggcagttct cctgctctac    76620
ttttcatctt ccagtacagg cataatggga ttacagacac tcagggcgtc tagttttaat    76680
gtggatcctg gggatccaaa ctcaaattgt tgggcctgtg aggcaggtgc tttatcccac    76740
tgcaccatct ttccaggcca gagcctttag tgttgatggc aactactata acatcaatat    76800 ttatatttt ctttgttata ataaagatga tgttaagtgt ttttttttc tgctataaac    76860 ttggttacta ttcactggtg aaggtaaatc tttttatctt taaatcgatg aaaaatctta    76920
caccaccatc cttttagca gagcttagtc ttttgaaaat gtttcttcat gcagctattt    76980
gtaataaagt ttgacttatg tcaacaacct atcttattta ttagacataa gccaatttaa    77040
atgagctcct tagtgtctgc attctgttat gaggcttaca tctgtggatc tctgtcagag    77100
tctactaggt atctgcttac cacactcaaa tgtacaataa gctatgtaga aatgatcact    77160 agattttct ctttttccag tgcttcttg gctgcccatt ttcccatcct gacttcttcc    77220
tacctgtttt tcctacctt ctcttccatt ggctatcttc tgtatgcaca aaacaaagca    77280
gtgttttgtg ctttttaagc cttattaaca atggcattaa ctatccagtg attcaccgtt    77340
agagatatgc tttattgagc agcattcccc tgaagttaat gttcccttaa ccctggcttc    77400
tcactgtgcc caccctcttc ttcccacaag cgtctgtatt gtcaaggttg ttctaaaaat    77460
gataagccag ccatataaaa gtttatggta ttttcctatc ttcaaagcta caggaagctc    77520
aaataaactc agcaaatatt gctcaattac acaagactat taaatgtaac acccccaccct   77580 tctaaaaagc acctcctctt ctatatcttt cccttttctt tcttagtata acagcctaga    77640
tcattatggc tctattgtgt gatcaggtca gagcaaatga ggttcatatt aacaagtttc    77700
cttaataact tctggcttgt ttgatatagt tgaaggatac caagatgata aattctaaat    77760
ttctaagaga agtcagtggt aaatgtgaat aaatggaaca taccacaata agtatgttct    77820
ctagtcctta atgataaagt aagttaatct ttattgcaca cttattatag tattactttg    77880
accctctcca gtgtgcttat ctcagcgttt tcaagtgttt tacaacctca aacacacaca    77940
ttgtgttgtg tgcacagtct gctttgaagt tgacatttgc cttctgacg aggctgtaat    78000 aaaggaagtc aaccacctga gagaacaagt gtcagatgag gatttcaggc cctggcgagc    78060
accgctgttc agggttaagt gcagaaaccc aggttccttc cagatgcctt tgagtcacca    78120
caggtgcagc aattttaaac aaataaagtt tctgtgaatt agctcaagag cctcaccctta   78180 gtttggcaga tatttgatgt tatttgtaga taaactacac cgaaaaaata aataaaatat    78240
caaaaaatta aaataaatta aaattgggaa tagagaataa tttgaaagaa aagttaataa    78300
tgttctcctt ctataagagt agtctttgat tacataagtt tatatttcag gataagacag    78360
ttttctttta ttaaacaaaa ttcttctgga cacttaataa gcatgtgcaa gggcctctat    78420
ttcatccata gcaccaattt aaaaaaaaaa aaaacctaaa cgaaaatcca acagctaatt    78480
ttatagaata ttttatagct aattttatcg tcaaatatta tctaataccc ttgtctagga    78540
cccttattcc aatagatgca tttcttcaag gagttttatg gataaatgcc cctcaccccc    78600
caaaaaaaat ttcagagaa ttttcagtat taacaaagaa aagtagcccc tgtagctgtg    78660
tgccaggctt cctctaaaag ccacgtgtgc tcgtgcagca ttctaaagag ctcacaacac    78720
accctaatgg atggtcatgt acccatgctc atactgggca acactagttg aactaagggg    78780
attattgata aaaataaaaa gacaaggttt gagtaagaat ggggtaaggt gtagaagggg    78840
gcgttagagg gaggaaactg tgggatttat atgatcaaag tgcattgtat aaatgtgtgg    78900
```

```
ggttttcaaa aagaatatat gtatatacat atatttcaaa aagaatatct atgcattatc   78960
tatgccatta acaaaaacca ggaaaaaatg gaagggatgg atgaggaggg tttgcaggga   79020
gggagggaat ggataaatgt aattatgtta tagtctcaga cataaaaata aagattaaaa   79080
acaaatcctc atgataggca cgagtgatat aacagttttt aaattgtgat ttttacaggt   79140
ggggaaaatc tatgaagtct gaaaccaaca cccttaagat aaatatatta ccagatttga   79200
gtatccttag tagtcagcaa aggtcaatgt ttaacgatgc atgcaaaaca gagtgctttg   79260
ttttaaatca aacagaatgt taagtactca taaatttgca gacggatgag gcataaactg   79320
agtaatcaaa ccaagtgctc agattaaagg aggatattgg cgtgctgatg tattaggctg   79380
taatgagtgc aatctcagta gatccccgct gcctgtccct catttcactc tcagcagcat   79440
gaaatcttca ctcacggagt gaaagttacc catatttctc ttcacgagtg gattcagtcc   79500
ataaacaaca gttcaaacct tggctcagta ggcagatcta ctttcatacc attgaaagtc   79560
aattcctaga ataatatgt tatagaagag aacatgtatg tctcagtgtt cttattttgt   79620
tcaatgttaa aagcctggat agcatcacca aaactgtgcc acaaaactct aagattcagc   79680
aaatagaata atgaaatatg tattttttcca atccatttaa tacaagttac acccatatat   79740
gcagttcagc tttaaaattc acatacagta taatttgcac acattattct ctaacttatt   79800
cagttcccgt tatcttttta agatataaca atacctatat acatgtttat acactaattt   79860
agggatgagt gagtgtgtac atgtggcaga cggctcagat ggaggtctgc agtgtcagtc   79920
cttcatcctt gacggccatt aatgagtgtt tgctgggagg agaggtcctt ggtcctgtga   79980
aggctccata gatgcctcag tgtaggggaa ttcaaggtgg ggggaggtgg gagtgggtgg   80040 gtgggggag ggatactatc atagaagggg gggtggtata gggggtgtac gtgggggggg   80100
aacgggaaag gggataacat ttggaatgta aataaagaaa aatatccaat aaaaaaacct   80160
tcctatcagt gactttaatc ttttttggtca ttctgactcc taaatcaaaa tttctattat   80220
tttgtctcta ttctatttag atgaatatgt aagagattat aaatatactt tcatgtttat   80280
taactatctt gatttcctaa catttaaact tgaacacttt ttgtaagata taatgatgga   80340
taaaatatgt attatataga tcactgctat aggaaacaat tgaatgaaga gtccagtttt   80400
gttttgaagt ccttaactga gtttgtcttg agactacctc tacattcatg aatgtttccg   80460
gcaggattac taaaatagat ttctattttg aaaacataag aactattagc taattttga   80520 cataaaaatc accaagctgc tttgccaaat tctcccttgg actaaattgg tataatattc   80580
tcccatacca accatcaatc ctactttagg atcagagttg cagtgggctc ttcagactgc   80640
ccatctatcc tatgtgtttc cttttccaca gtatctcccc caattaaact cttggacatt   80700
tgatatcatg ttggaatctg gttggagaat tttgactgat agctgcatat attacattat   80760
catcttctgt agtgatagtt tttcttataa ttttatatag tcaattttat ctaaatgcca   80820
ttttatgttt tgacatttct gacttctctt aaagatgttc gttagagcaa aaaataaga   80880 cattctgtcc taatagtttt acattttcat ttatcaagaa tatgggttat tagaattata   80940
tggtgtgcag ttttatgttg acattttaca ctcttaatta aaatataatg gctgctttc   81000 ccgctcccct tccttccctc cattccttct catgtccctt ctctccaaac ccttccatttt  81060 cacctctctt tcaaattggt gtcctcttta ttgttgttac atgcatatgc ataaatatgt   81120
aaatactcat atcttagaat tagccaaggg tggtttaact agatggaggg catgctcaat   81180
agtgagattt ttctatttag gaaagtaatg tgatatatct taatcataga aactttaat   81240
```

```
atcactcttc ttcatcctga tcaaagtggt cagaatacag atttctagat ttctttgaac    81300
aaatctactc tactttgaag aaatttagtc cactgctgtt tctgttgaaa aagaaattga    81360
ctttgcatgt tagctctatg atcaaattgt agacaaacat ttaagataac tagctcttcc    81420
ttacagaaaa gtcatctaaa gatataaatg ggaaacaact attcagttca caataatggc    81480
aaaccttaaa gtatttagtg attgttatag ctctcatggg acatttacag aatatgaaga    81540
aaatgataaa tcttattgaa gtattgaatt caacatctga atcaggatta aaaaacatTT    81600
tgatttagtg ttgcaaacta gaattctatg taagtgcaag gtatttaaaa gttgcaaata    81660
aattctaata aggttatctt aaactaaact taatataaaa tcttagaagt aatttattga    81720
caaattattt tggtggaatt tttgcttcat catatgtaga cttgatatca tggtatttgt    81780
acttcttata tttgaaatgt tagtgaggaa gaattactgc attaaaattg ttcaagtcag    81840
cacttgagac tatgttagct catcttttaa tgatatatta tttcaatagt tgacatggct    81900
actatgtcaa aaactaagaa agccaactct ttcatgaggt aggattatat tttatcagat    81960
attaaatgat atataatttt atttaaaatc aaggacccaa aagtccagaa aatattaata    82020
tagaaataaa aaaatggatc agaaaaataa gagaacccag aactaggaac catgacagat    82080
gatagaggca tcagtaaacc attcatttga tgattattgt tgccttgtaa caaatgaaag    82140
atagggtaga caaatagaaa actgtgccat aagggttttg aacattttat tttgaaaata    82200
gtattcaaga taacacatat agctagctgg tggggagtag atacatttat ttcacaaaat    82260
ctttttgcac atgataagtg atatgcacag tgaaaaaaag agaacgaatg ggagtttttt    82320
atatgcagcc tataaagttg caaaaactac atacaaatat tagacacttc aaagaagaaa    82380
atgcaacaca gcaaatattt aaaatctttg tgattaagaa aaatgtaaat gaaaagagaa    82440
aattagcaaa aattatcata atcatactag tacaacttag taaattgtaa tttaactctt    82500
tagttgcttt gtaaagcaat ctggtggtaa cttttgaaag tagaacatat gcatttgata    82560
tagtcatcct actcatgaga atatatcttc cagctacaga tcacaaaagc atatatgtat    82620
tcagtgatat taatagtagg ctttgtaggg aggaagtggg gagcaattgc tagggaagaa    82680
ttgcatgcct caccatttta atgtagtctg gactacaaag agaaaccaat gacttcaaat    82740
gaaccacctg gaagcagctt gcatggatca gctctcttgt agtattctgt tctcacagtg    82800
ttgtaagtac tgaaacattt attttttctga gtgcctcacc ttatagtgtg tcactcagcc    82860
aagagtatgg ggattacaaa cactgtttgt tctagtggaa atctcacatc tgtcattacg    82920
tcatcatctt caaaacagga gggagtgttt tagagacgtg atggtagtga acctgaatcc    82980
ccttcctttt tcctttcttt ttaaaaaagc aataaggtaa cagaggaaat aaatataaaa    83040
ttgtatttac tcttgtgaaa taaaatcacc aacaatctgt gctagctagt ttttatgcca    83100
caggtagagt tttatgacat gagctagaat aatttgggaa cagagaagtt caattgagaa    83160
aatgcctcac cagattggcc tgtggacaag cctatgggaa atttTcttgg ttgaggattg    83220
tgggaggtcc cagttcatga tggttggtgc cacctctagg ccagtggtcc tgggtgctat    83280
aagaaagcag gctaaggagc cacatggagc aaatcagtaa gtagcactcc tccatggcct    83340
gtgtttcact ccctgcttcc agattcctgc ctgagttcct gcactggctt ccctcagtga    83400
tggacataaa agttgcaaaa tgaaataaac cctttcttcc ccaagttgct tttggtcctc    83460
tgttatcaca gtaacaaaca aacaactaac aaagacccca tgtctgcaat ggtgtatgtg    83520
ggaagtcact gatttatccc aagtcttTgg tcacgctgtc aggaatgctt gttagacggg    83580
gttccttgtt aaaagtgaat agcatggcaa tctaaggagg tgatagaaaa catgagaggg    83640
```

```
ggctgggagg agagaatatt aaaggaaatt ggtacctaac ttgatcacat tttaactact   83700
caagtgaagc tcttcatgga aggcctcgaa cattctctct gtggtgtgtg ctttattcct   83760
atcgtctaaa taattaacat gccatgtata ctgttgtata atacgttgta aaattgtttt   83820
ttaagaagtt agattgttac ttaattctcg ctccaggatt agagcttatc ttctaaatta   83880
ggtttacact gtctggagtc ctggactatt tcttacaaac ccaggtcgtc ttttactgtg   83940
ccttcatagt tgttactaca gaaaagatca ttattgggca aggaatggca tatgtgacag   84000
gagaggagta gtaagtggac aaggacagaa aaataatgga agtggtgagg atgtttgtgt   84060
tgttgtttgg gaagatgaat gaaagaatgc ggaaataaac tgacatgtcc cgttgttagc   84120
cactgaagaa tgcagaaata aactgacatg tcccgttgtt agccactgaa gaatgcggaa   84180
ataaactgac atgtcccatt gttagccact gaagaatgag gaaataaact gacatgtcct   84240
gttgttagcc actgaagaat gcagaaataa actgacatgt cctgttgtta gccactgaag   84300
aatgcagaaa taaactgaca tgtcctgttg ttagccactg aagaatgcag aaataaactg   84360
acatgtcctg ttgttagcca ctgaagaatg tggaaataaa ctgacatgtc ctgttgttag   84420
ccactgaagt tgcctgcatg tttctgtggg tgtggagagt tttgttttag cttttcttat   84480
taacaggctt attcagtctt ttgacatttt ttaaaagtga ttttaagttg aaagtatatt   84540
tgaatggcac ttgagtttat atgatgggct tatgggtagt ctttgaatat aaacattccc   84600
caaataaata gttgcatctg aagaaaaatg ttctttttcaa ttttggattg tgcatgctaa   84660 atttatttc tggtgttatg ctttggataa taggacatca ccaagtttgc agaacaagac   84720
aacacagttc ttggagaagg tggagtcaca ctgagtggag gtcagcgtgc aaggatttct   84780
ttagcaaggt aaatatttaa ctgttggtct tgtgagcact tgctgtaaat actatgggtt   84840
tttaattata catacacatt tctcttctgc ttcctgttct gtctctggaa ttgatgcttt   84900
ttctttaaga actatagaca ttataatatt caaatttggt aaagatggtg gttttttttt   84960
ttcaaaatgt atacttttca aaatgtatac tcttatttat atttgtccaa acttgttgtt   85020
atggtgcatg gattgttatg aagagaaaag tatagaattc taaagaaaaa aagaaaagga   85080
aattacaagt ttctattaat ccccccttt tccctgtccc cagatgcctc tgatttgaat   85140
ttctgtttat tcttctaagt ttagatatac acattttcaa ttttaatttt ttagaacata   85200
atctatgata gtataacaaa aataggaagg taaatgatgt cactaaggtt tctcattgt   85260 ttacagacaa aggacaaggt ctccctattt agaaattagg atctttctgt gtttgtttct   85320
gtatactagg atgaaagtgt gtgccaccac acccggtaag ctttatactg aatacatgct   85380
ttcatttgtg atgctgattg tcctcatggt catgtttaat tattgtcaga acgaaagtat   85440
tttatttaaa ttgtagcttc cgtttaaaga caattggtgg tatgggattt caaatgctct   85500 ctaatttat tgaaacaaaa ttcttactac attaccaaag ctgttaatga gaaattacat   85560
tggctcagtg gtatcttggt atcttggcca tttatcttcc atctcctgga aaagtaaaca   85620
ctaagtatca caactgatcc ttgataccat tccttctccc cctcccttg tctgtgtgcc   85680 tgcctgtctg tctgtctctg aatgtatgtt tatgatctca atccccatac aagactagaa   85740
gcagaaattg ttttctttat tttatggaag aaatcacaag ataattgagg tagtcagaca   85800
ttaacttgcc aaaggccaca aggaaatgat acagtcacta tttaatcaag gtcatcttga   85860
ctccttacat taaactatgc ttcggtctgg aaaatacact gcgaaatcag atcaatagat   85920
agaatttcca gacaatggct tcaaaatgat tggaagctaa ttcccttatc tgtgtggcaa   85980
```

-continued

```
aagtcatatc ttaagcattc catttgagtt ttaagtaaaa tatggtatgt gacttcagta    86040
tagtattaac atttactagt ttaagattta gtcatatttg ctatgtacaa tatatggcac    86100
tactcaaaac agttgtctac tatttttata gttgcacatg ttattctcat ttacatatgc    86160
aataaatatg tcatccactt ttatatgaag aatatacaca ttttaatctt gagaaactgg    86220
ccacacatgt gaatgagagt ttttaccttg gttttgcact aataatttac caatatattc    86280
agagtaaatt ttacagaaaa tcactttta ttcccactta ctgtttaagg taaaggagtc    86340
atatccagtg atggcttctt gttggcagag tcttgagaca gcacacacaa aaaaatcata    86400
tgtcaagaaa aaaaggaat gtgtgtgtgt tctctgttat tcctttcctc atgaagccac     86460
cattatccaa tcatgaaacc ccaccttgat aatcttactt aatcctcatc attttgcaaa    86520
atgaccacca acagctttgc tgttggacta agtttccatc ttcttcctgc ctctgatgga    86580
tatgaaatct atattagttt cagaatggac aaatatattt gattatatta cagagaaata    86640
aataaaatct aaatgttgat aaagacagga gagttcattt ttatggagtc cattagctct    86700
tctgtttcct tccagacaat ttatagcata aagggcttgt ttgtttgttt gtttattttt    86760
attctttaat ccttttttac agttcagaat tcatcccct cccagtctgc ccccgactgc     86820
tccccatccc atacctcctc cctaccccta acctccatcg ccaagaggat gtccccaccc    86880
tgagcataaa agagcattat gacttaatct ggaattttt ttgctatttc tattttattc     86940
attgttttc ttatttgtga tgattaagta cattttaaaa acaaaagtat caataaatag     87000
tttctacagc atgtcctctg taactgggat agaggtagca ttattagtaa tcacacttga    87060
aaaagtaag atgtataag aaattatttc cttttttgtta gttggaaaa tatacccttta    87120
tatttttcct attgtaagtc aactcaaatt gttttagtt tcaatttcaa gtgaaataag     87180
agctggggag agatagctca ttggtgagga gcgctggctg tcttccaaa ggctccaggc     87240
ttgagtcaca gtactaatct gcttcacaat catctgtaat tggtaaccca gcacacctga    87300
catttccttt tggtctccat aggcactgaa cacacatggt acacatacat gtaggtaaaa    87360
accgtcaaac acacagtaca gaagttacta acagtactcc ctgtgctctg tgctgtgaca    87420
cgtgtgcttt cagtacatgg ttttgatgac cattgtataa cacaagttct gtgtttaaaa    87480
tatctattct caatgacgta aaagatcttg agggatccta actttctttc cattttgttt    87540
atagagcagt atataaagat gctgatttgt acctattaga ttcccctttt ggatatctag    87600
atgtttttac tgaagaacaa gtatttgaaa ggtatgttct atgactgagt tacttataat    87660
gctcatgtta aaagataata aatgtctgtt tcaccaaagg ctgcatatta gcatattagc    87720
tccagagtaa tatccactat ttctattgct caaaacatca ggatctagca cagtgcttat    87780
tcagtcctgg catcccctta atggtcaagg gtgaagttgc ttctgccaca ccctttttctg    87840
atgatcacat ctgaagccaa tttcttgatt gctatcctgt tctaacagtt gatatttaag    87900
aatcgtttat attttgctat cttgaaaagt cttccagtat tttaagtagt ttacttttaa    87960
aattccacct accattctgt attagtattt ttattttatg ttgttttaga aagaaaataa    88020
tgtttattgg taaatgccca tactgtacct ctgtcttagt cctctttaga tgcccctctt    88080
tggtcacaga gaacatagat atttccttaa agtttttatt agagcccaaa tgggtgtaaa    88140
atctctaaga ggtaacatta gttataccat ttgatttcaa atgttaaaat aattttatgg    88200
gcaacaaagt agcttattag aatagacatt atagcactct agaaacaaat gagttttgt     88260
tttaaggata gaatgtagtg tgtgtgttaa gatggtttga ttatttattg atttatttca    88320
aacttttact ttaggacatt gtgctaaagg gttgaaatat tctagagccc tgcttattgt    88380
```

```
gtcttaaaat atgtggaata acatgtttca ctaatggact ttactgtact tacacatgaa  88440
gccagcaggt ctcagtcctg aagctacttt tattcagagg tggaatacta tggcatgttt  88500
gttttgacat tttccgttta cgtttctgtt gcatggtgtt tattagcatg gtttatccgg  88560
ccacaatccc aagaacatcg tgatctctga atgaagggcc aagtcccaac aatgccatct  88620
ctagcccaca gatcccagtc ctcattgttg ctcataagct tccgatcaaa tctatagtga  88680
agaagtcctt atatgacaat gtattttcat agttcccttc atcttctctt gcttattcta  88740
atctaatgca aacggctgta gaaggtccta gtacatttct gcctcccgca aagcttttg   88800 catctccttc actacagctg tgcattaaca ttgtcttctg agtctctaaa gttgttttgt  88860
aattcccatt gcatcaagtt ctctgtgtcc attacagtct gaatgctgac cactttaagc  88920
atataacact ctgtaagaca aacattttct tcttttattc tttctttttt ctctttcttt  88980
ttttttcttt ttttcttttt tttagatgca agctggctct cttttccctg atgattctca  89040
atattattta ttcttcaact tgaggttaat aatcagagag agcctaaaca ttgtattta   89100 tttactaaag ctacatcatt aaggctttga taattgttaa ttcatttatt tattcacttt  89160
acaaaactcc tctcctccca gtatcaccct cacaaatttg ccccccccc cccatgagtc    89220 ttctcagaga agaggatgtc cccttggccg ttggatacct gccagccatg ggacatcaag  89280
tcacagcaca agcctatcct ttcccaatga ggcctgacta agcagctcag ctggaggaag  89340
gtaattccag tggcaggcaa tagattcaga gacagccccg ctgcagttgt tagggaccc   89400 acatgaaggc caaacagcac aactgctaca tatggtttag tctctgcagg ctctctggtt  89460
ggtgcttcag tctttctgag ctcccatggg cccaggttag tatactctgt aggtctttgt  89520
ggtgtcctta acccctctac ctccctcagt cctatcccct actcttacaa aagactcccc  89580
caaatctgct taatgcttgg ctgtggatct ctgcatctgt ttccatcacc tgctggatga  89640
agcctctaaa gagacacatt tgctagggtt ctatgtgcaa acataatatc attaatagtg  89700
ttgggagttg gctctctccc atgggatagg tatcaaattg gaccagacac tggtgaactt  89760
ccttcaatct ctatattttt tagtattttt tttatatttt tattatctgt aatcattttt  89820
ttaaagtgca gtcgttatcc ccctcctgtt ctgccctctg acagttcttc atctcattcc  89880
tcctccccta tatccaagat gatgtctcta caccccaca catgcccaca ccgcaccaga   89940
cctccccatt ccctggggcc tctcaagggt taggtgcatg catcttctct cattgatgcc  90000
agaataggcc atcctcagat gtaaatatgt ttcccaacta gtgtatgctg cctggtgggt  90060
ggctcagtgt ctgagagatt tggggaagtt caggtttgtt gagacagcta gtctttctat  90120
tggatcaccc tcttcgtcag attcttccag cctttcccta gttcaaccac aggggtcccc  90180
aacttctgat cattggatct gcttctgtct cagtcatctc tttgttgggc ctctcagagg  90240
gcagccatgc taggctcctg tttataagta catcatagca tcagtaatag catcagacct  90300
tggagactca cgctgagatg gctcccagtt tggaccagtc agtggacctc ctttccctca  90360
ttcttttctc cattttttgtc cctgcagttc ttttagacag gaataattct aggtctgagt  90420
tttggattgt acaatggcaa ccccatccct ccatgccctg tctttctact ggaggtggac  90480
tctataagtg ctctctcaac actgttgggt attttaccta aggtccctt gagtcctgaa    90540 agtctctcac ttctcaggtc tctggtatat tctagaaggt ccccccacat cccacctcct  90600
gagttgcctg ttttcattca ttctgcttgc cctcagtgct tcactcctgt ttcctaccct  90660
gctaatacct gaacatgtta tgaaattctt aggcaaatgg atgtcctcat tcttaatagc  90720
```

```
tgcctagtat tcattgtgta aatgtaccac attttctgta tctattcttc tgttgtggga   90780
catctgggtt gtttacagct tctggatatc aaaaataagg ctactataaa cacagtggac   90840
ttgtagcatg gtgggacatc ttttggtat atgcctagga acagtatagc tggctcttca    90900
tttacaatta tttctaattt tctgaggaac ctccagattt atttccaaag ttgttgtacc   90960
agctagcaat cccaccagca atagaggagt gttcctctta ttccacattt tgccaaaat    91020
gtgctgtgac ctgaggtttt gatcttaacc attctgattg gtgtaaaggt ggaatctcga   91080
ggtcatttta tttgcatttc cctgatcaaa aaggactttg aacatttctt taattgccat   91140
tcaaaatttc tctgccgtga attctctgtt tagttctata ccccattttt tttattggaa   91200
gttttttgt ggaagttagc ttctttagtt ctttatatat tttggatatt agtcaactat    91260
gagatgtggg attagtggag attttttccc caatctgtag gttgccaatt tgtcctattg   91320
acaatgtcca ttgccttaca gaagctttac agtttcatga agtcccattt atcaattctt   91380
gatcttagag cctgagtcat tggagttttg tataggaaat ccccacccac accccctaat   91440
ccccaaattt ctccccaacc tccatggcca tgagttcaag gctctttccc attttctctt   91500
tctgttagat ttatcttatc tggctttttt tgttaaggtt cttgatccac ttggacttga   91560
gctttgtgca aggtgacaaa tataaatcta ttttaattca tttacaaact gactcccagt   91620
tagatcagca ccatttattg acggttcttt tttacctttg tatattttt gcttctttgt    91680
caaagatcaa gtatccataa gtatgtgctt ttactgttgg gtcttcaatt caattccatt   91740
aatcaactga tctgtctctg taccaaaacc attcaggttt gttttttgtt ttttgttttg   91800
ttttgttttg tttttatcac tattgctgta tagtatagct tgaggtcagg gtgatgattt   91860
cctcagaagt tcttttattg ttatgaattg ttttttgcttt cctgtttttt tggtttcttt   91920
ccagatgaaa ttgagaattg ttcttttccat gtctttgaag aattgtgttg gaattttaat  91980
gggtattgca ttgaatctgt agactccttt tgtaggatgg ccatttttac tatgttaatc   92040
ctaccaatcc atgagcatgg aagatctttc cattttctga tgatttctttt cttgagagac  92100
ttgaagttct tgtcatgcag atctttcact tgtttggtta gtttccccaa gatattctct   92160
ctctctcttt cttccttcct tccttccttc cttccttcct tccttccttc ctttctttct   92220
tccttcttt ccttctctat ttcttctt gtttctttct ctcattctct cttttttct       92280
ttttctttt ttttctttct tttctttttt ttttctttt ttttttttt tttggtgttt      92340
ccctatttc attctcagcc ctgtttatcc ttagtataaa ggaaggctac tgatttgttt    92400
gagtaaattt tacattcagt cactttgctg aagatgtttg tcagctgtag aagttctctg   92460
gtaggatttt ggggtcactt atgtatacta tcatatcatc tccaaatagt gataccttga   92520
cttttctttt gccagtttgt atccccttca tctccttttg ttgtcttatt gctctggcta   92580
gaaccttgaa aactatattg aataggtatg gggagagtga gcatccttgt cttgttcctt   92640
attttagtgg gattgcttca agtgtctctc catttaattt gatattttct gttggtttgc   92700
tgtatattgc ttttattatg tttagatatg ggccctgaat tcatgatctc tccaatactt   92760
ttaacatgaa ggcatgttat attttgtcaa atactttttc agcatctaat gggatgatca   92820
tgtgattttt ttcttgagt tgttgatat agttgattat attaatgtat tttcttatat     92880
tgaaccaacc ttgcagccct ggaatgaagc ctacttcatt gtggtgaatg accgttttaa   92940
tgtgtgctta gattcagttt gctttatgag tactttctga agttcttttg ttgttgttgt   93000
tgggtctgtg tatagtttag ataacagagt aattatgtca tcatagagtg aattaggtag   93060
cattccttct gtttctattt tatggaatag tttgaggagt gttggctctt ctttgaaagt   93120
```

```
ctgtgtgatg ccttcttagc agaaaggttg ccacaaaatt ttacatgagt ctttctatgt   93180
ggtccagagc acaaagtacc tttgtctgaa ttacttgttc aaatcttcca ggagccactg   93240
tactgttttt gtttgttcag ttgttgtttt cctttatata taataatttt agcttcactt   93300
gtttgggggg agctcctttg tatctgtaga acctgcatag tgccagaaat atgaactagc   93360
actgtagcca tatgcatttc agaagtctgt ttccagcagg actctagttt aagacaaaga   93420
gaaaattcca ttaaatgaaa ttccccccct ccccaatgct attttatga tgctctgact   93480 atagttgcca atgtttactg tcataaactt acctaaaatt atattattta acttaagag    93540 aatttaatgg ttcttatttt tttatatttt aatggataaa aggaacagat tttccctgta   93600
gtatccactg caatacttaa ctttttttt ccttttccat tttttattag gtatttagct    93660
catttacatt tccaatgcta taccaaaagt ccccatacc cacccacccc cactcccta     93720 cccacccact cccccttttt ggccctggtg ttccctgta ctggggcata taaagtttgc    93780
gtgtccaatg ggcctctctt tccagtgatg gccgactagg ccatcttttg atacatatgc   93840
agctagagtc aagagctccg gggtactggt tagttcataa tgttgttcca cctatagggt   93900
tgcagatccc tttagctcct tgggtacttt ctctagctcc tccattggga gccctgtgat   93960
ccatccatta gctgactgtg agcatccact tctgtgtttg ctaggccccg gcatagtctc   94020
acaagagaca gctacatctg ggtccttcg ataaaatctt gctagtgtat gcaatggtgt    94080
cagcgtttgg atgctgatta tggggtggat ccctggatat ggcagtctct acatggtcca   94140
tcctttcatc tcagctccaa actttgtctc tgtaactcct tccaagggtg ttttgttccc   94200
acttctaagg aggagcatag tgtccacact tcagtcttca ttttcttga gtttcatgtg    94260 tttaggaaat tgtatcttat atcttgggta tcctaggttt tgggctaata tccacttatc   94320
ggtgagtaca tattgtgtga gttcctttgt gaatgtgtta cctcactcag gatgatgccc   94380
tccaggtcca tccatttgcc taggaatttc ataaattcat ttttttttca attttttatt   94440
aggtatttag ctcatttaca tttccaatgc tataccaaaa gtcccccata tccacccacc   94500
cccactcccc tgcccaccca ctcccccttt ttggccctgg tgttccctg tactggggca    94560 tataaagttt gcaagtccaa tgggcctctc tttccactga tggccgccta ggccatcttt   94620
tgatatatat gcagctagag tcaagagctc cggggtactg gttagttcat aatgttgttc   94680
cacctatagg gttgcagatc cctttagctc cttggctact ttctctagct cctccattgg   94740
gagccctatg atccatccat tagctgacag tgagcatcca cttctgtgtt tgctaggccc   94800
cggcatagtc tcacaagaga cagctacatc tgggtccttt cgataaaatc ttgctagtgt   94860
atgcaatggt gtcagcgttt ggatgctgat tatgggtgg atccctggat atggcagtct    94920
ctacatggtc catcctttca tctcagctcc aaagtttgtc tctgtaactc cttccatgga   94980
tgttttgttc ccaaatctaa ggaggggcat agtgtccaca cttcagtctt cattcttcat   95040
gagtttcatg tgtttagcaa attatatctt atatcttggg tatcctaggt ttggggctaa   95100
tatccactta tcagtgagta catattgtgt gagttccttt gtgaatgtgt tacctcactc   95160
aggatgatgc cctccaggtc catccatttg gctaggaatt tcataaattc attctttta    95220 atagctgagt agtactccat tgtgtagatg taccacattt tctgtatcca ttcctctgtt   95280
gaggggcatc taggttcttt ccagcttctg gctattataa ataaggctgc tatgaacata   95340
gtggagcatg tgtccttctt accagttggg gcatcttctg gatatatgcc caggagcgga   95400
attgctggat cctccggtag tactatgtcc aattttctga ggaaccgcca gactgatttc   95460
```

```
cagagtggtt gtacaagcct gcaatcccac caacaatgga ggagtgttcc tctttctcca    95520
catccacgcc agcatctgct gtcacctgaa ttttttgatct tagccattct gactagtgtg   95580
aggtggaatc tcagggttgt tttgatttgc atttccctga tgattaagga tgttgaacat    95640
ttttttcaggt gcttctctgc cattcggtat ttttcaggtg agaattcttt gttcagttct   95700
gagccccatt ttttaatggg gttatttgat tttctgaagt ccaccttctt gagttcttta    95760
tatatgttgg atattagtcc cctatctgat ttaggatagg taaagatcct ttcccaatct    95820
gttggtggtc tttttgtctt attgacggtg tcttttgcct tgcagaaact ttggagtttc    95880
attaggtccc atttgtcaat tctcgatctt acagcacaag ccattgctgt tctgttcagg    95940
aatttttccc ctgtgcccat atcttcaagg ctttttccca ctttctcctc tataagtttc    96000
agtgtctctg gttttatgtg aagttccttg atccacttag atttgacctt agtacaagga    96060
gataggaatg gatcaattcg cattcttcta catgataaca accagttgtg ccagcaccaa    96120
ttgttgaaaa tgctgtcttt cttccactgg atggttttag ctcccttgtc gaagatcaag    96180
tgaccatagg tgtgtgggtt catttctggg tcttcaattc tattccattg gtctacttgt    96240
ctgtctctat accagtacca tgcagttttt atcacaattg ctctgtagta aagctttagg    96300
tcaggcatgg tgattccacc agaggttctt ttatccttga caagacttttt tgctatccta   96360
ggttttttgt tattccagat gaatttgcaa attgctcctt ctaattcgtt gaagaattga    96420
gttgaattt tgatggggat tgcattgaat ctgtagattg cttttggcaa gatagccatt     96480
tttgcaatgt tgatcctgcc aatccatgag catgggagat cttttccatct tctgagatct   96540
gtaggaaaat gttattggag gacagtcaac tttattaggt atttctcagt tgtaatgttt    96600
tatcttaaag aaaacagatt agtcaacata aaatataaga gaaaattcat taaaaactaa    96660
aaatagaaaa tctctaacat cttagaagtt atatggacat ataaacttta ggaacatata    96720
ataattcttt tatttctag aaaatataat caagaccaaa gagaaaatga tttggttaaa     96780
atcagatact tgattattta aaattgtatt tgatttatg tctgctagta tttactttac     96840
agtaagatat gctatttcat actgcaattc atgaggcacc taagagttat gatggagtgg    96900
ttatttgtat aagtgtatta aataaagcaa taaaatgcta tgatagattt tatgcaatga    96960
aactttatgc tgaagttaaa tatacatcac tatttatgaa gtaatatctt atatcttttt    97020
tatatttcca aagctgtgtt tgtaaattga tggccaacaa aactaggatt ttggttacat    97080
ctaaaatgga acacttaagg aaagctgaca aaatactaat tttgcatcag ggcagtagct    97140
attttttatgg gacatttttct gagctacaaa gtctacgtcc agacttcagt tcgaaactca   97200
tggggtatga tacttttgac cagtttactg aggaagaag aagttcaatt ctaactgaga    97260
ccttacgcag gttctcagta gacgattcct ctgccccgtg gagcaaaccc aaacagtcgt    97320
ttagacagac tggagaggtg ggagaaaaaa ggaagaactc tattctaaat tcattcagct    97380
ctgtaaggaa aatttccatt gtgcaaaaga ctccattatg tatcgatgga gagtctgatg    97440
atctccaaga aaagagactg tccctagttc cggattctga acaggggag gctgctctgc    97500
cgcgcagcaa catgatcgcc accggcccca catttccagg cagaagaaga cagtctgttt    97560
tggatctgat gacgttcaca cccaactcag gctccagcaa tcttcagagg accagaactt    97620
ctattcgaaa aatctcctta gtccctcaga taagcttaaa tgaagtggat gtatattcaa    97680
ggagattatc gcaagatagc acactgaaca tcactgaaga aattaacgaa gaagatttaa    97740
aggtatatac ccgtcaagtc ttaagataca tctcatccta accccataat tggagtaaat    97800
tttgtcacat actatgtatt tcatggcatc ccattgtggt ctatgggcta aggatacaaa    97860
```

```
gtccattacc tgtgtaagca acttgaaaca taaaactatt tctggttatc attgaaatat   97920
catccccacc ccacaaatgt gtggtaagcc aaaacagggc ctcagtgttg agtttttcta   97980
ctagactcat gaaatgatat tcacttttat aacttaataa ttgtctcctt tagtgttttt   98040
ctaggaaaag gcggaataga gtattatata acaaatact tgcatttatg tagacaccaa    98100
aaagtgtttt taaggcatgg ccttgataag gattacacac acctggcttc ttgacaagat   98160
aaattcacat tcctgcctgc atttagttag catatatttt ctaacctttc agatttgtgt   98220
tgtgtttttt aaagggtttc tctaaggaag atatgtgcag ctcggcatat attagtgaca   98280
gtagtcagat taaagttctt aactctatgt gttaaggagc aaaacgacct ctcttaaaat   98340
agaaagcagt ggaaaacaag agggcgattg ttaccagtg gatgtacctt agatgaagtt    98400
aaagcagagt cctagtggat gatatattta atggtgactg tctttaatat aaagttaact   98460
tttgggcagt tgcaattcat ttagtatctc tgggcctgag ttcactctgt tgtgaaataa   98520
aggaataagt aattctcaaa aatatatgct cgatatttct ataatctaaa actgatttgc   98580
taaaagataa ttcatctata tgatttaata tccatctaaa taaaattacc aaattgaagt   98640
atatacattt tggtttgtgt gcattttaaa gaatgctttc tttacctgat tttgttacta   98700
agttatcaat tatttcacct tccaggcaac acactttttg tctccttcac tgtgacatca   98760
ttgtccctat taacaaagaa ataaaataaa gttctgagaa attcagtatc ttcatacatt   98820
caaacatcct acgatgttac catttggtct tgattttaaa taaagggcag tttagttcaa   98880
caatctaatt tttaatcagt aaaccttatt ccaggttaat aggcttcctt ctttgtgagt   98940
ctaatggcac ttaatgaact tcatggattt tatgagggca tcgtttccct ttagaatata   99000
tagactctct ttttctcaca tttttataat gtagcttcca aaagacaaag gcttttagag   99060
gctgtatttg gaattggatt ttgtaactta agttgtagct agaaaagcaa ccatgtaatg   99120
cctaaggact atacaaatat aagccagctt ctaaaataga agactcaagt agctagcaaa   99180
ttctacattg cccttgtctc tggctcactg aatcaagctc aatcatgaag agtttgggag   99240
cttcactcat ttgacaaaag gtgtgggctg taaagcattt acatgctaag gtttgggaag   99300
tctcactgtg tttggtactt tataaactat attgcttgag cagacatcct attctctgtg   99360
gccatcatca cccgtggcat ttttagtggc tttttatttt taaagatcct tggctgtaaa   99420
tggtactgtt cccttatttc cctgaattca taataaaagc tcagtggcag catggagtag   99480
gattgtctca gaatcacact tcttttctca ggagtgtttt cttgatgatg tgatcaagat   99540
accccggtg acaacatgga acacatacct acgatatttc actctccata aaggcttact   99600
gctagtgctg atttggtgcg tactggtttt tctggttgag gtaagtatgt ttgtttggaa   99660
attgtcactg tgagtttaaa tttaggataa aaaagctgta tgtattcata tgagcatgta   99720
cacatgtgta tgtgcatgtg tacaacggta gtttcctgta aagttcatcg cttctgaaaa   99780
ccaagaggag ctgacgaggc agctatgtgg ttaagggcac tggttgcttt cccagacaac   99840
ctagccaaat tcccagaccc cacatggtgg tttacagcat ctgtaactga agtctcagga   99900
acctggtact cttttctggc ctctgtgtgt acaacatgtg tgtagtacac agatgtgtgc   99960
aggcaaaaca ttcatacaca gaaaataag ttaaactttt ttaaaatcca cagttagaat   100020
tactattgat atttttagtac ttcagacata aggaaatatg cataaataca aatgctatat   100080
atgatgaatt gtcataaaat aaaatttatt gggaatattt tttataatca gcatattttg   100140
attcataagt attgtaaaga gattactata acaaaatcaa taacataact atgtcatctc   100200
```

```
aagtaacatt ttttgttgtt tttgtgacaa ggggtcctaa aatccacaca tctaacaagt   100260
aaaataatag tttgttattt ataatcctca catcatttat tacacctcca tacatttagt   100320
ttttaacaga ttcagaagcc caacctacaa agagtgaata tgagttgaag ttaagtactg   100380
aaaagaattc tagatgtcca tctagatgat ctaatgaggc aggcagtgac tcatgtggta   100440
atgatcctta cttgcctgct gtacctttgt ctcaggcagt gttcatcgag ggaagctttc   100500
acaatgatgt aattacttca ttgtgtgctg acctgctgca caagaatgca gtattagtca   100560
ctctattatt tttcctgttg ccatgataaa gcacctaaaa gttaaggaaa ggagatatat   100620
atgtgctttc tgtttgaggg aacatattcc acagaggctg ggaaggcatg atagcagaag   100680
tagcaggttg gtaggtcata ttgcaagcac actttggaag caaatagtga aaaagtgggg   100740
ccaggctgta aacctgaagg cctgctcaag aaccgaagga ttccatagcc ttcctaaaca   100800
gcacagtagc ttgagaccaa gtattcaaac acaggagtct ttagcacatt ttacatccaa   100860
atcatcaaca gtcacctgag gggaaaaaaa agacattttg ggaaggaag tcaggggaca   100920 ggggcagggt tcatagtgga caaaattcaa tgatgcactt gtcagaaaac aatctaatgg   100980
tgtgcttttc tttcttttcg tcttccttcc ttccttcctt ccttccctcc ttccttcctt   101040
ccttccttcc ttccttcttt tcattttgt cagtatctta taggcattgt ccagttaaat   101100
agctctcaaa tgctagatta aagaaagca atgatatgca cattttaca actaaacaac   101160 atatttgcta atgtttatgt tgttttcctt caatcaaaat ttacatagac tttgtttaag   101220
tctaaacttt ttttctttgt gtcagtgcca atgtgtagat ttcttttggc tactggaatg   101280
tttcttggta cattccatca tggaacaggt gccaatccac agtggcagtt tagtttttaa   101340
agcactgttt aagtcctaag tgacaagaaa ttcccaaatg catatcctcc tccattaaag   101400
tgatttagat aattttaagt cttaataagg actgtatttc catttagatt tatgacttta   101460
tagcatctct tctgtgtgtg atcccttttg taataggaaa taaactttgt ggcccacgct   101520
gtcttttctt attccttcac agctacttaa attagtggtg ggggaaataa tatttctcag   101580
tcatgtgtta ttttgaaaaa gtgtatattt tgtattttcc ctcaaaagca atgttgtctc   101640
taagttctta acactgaaca aatagactaa tatttctatt gtgctgctct ttctagtgcc   101700
ccttcttggc agtgtattat ggacaagaga gggaaaatgt aaacactgga ttaatggatg   101760
tttacaataa cctgatggtg tgtagagtgc agcatctcaa gatcctgttt gctccttggt   101820
cttgtggtct ttaagactgt gtcaaaggcc tgctgtgtct gtttgttaat aaggagttgt   101880
tttacatcag taataaaatg gagattatag tgaacttcta taaaactacc tttgctagtc   101940
agtgttagag tcccttagc acatcatctt tattgtgaat gtggatttta gggttatatt   102000
tgtcccacaa aatatgtgaa aatctgcaaa ttatggtgta ttacattcca tgtgatatgg   102060
caccgtgtgt tacctcccca ccttaggaat aaaaatgatt attacttatt tgttgctgc   102120 ttcagcgtaa tcctccaaga gtacccttct ttgaaaaatt acatgaactt tatatagtct   102180
tgaatcattt tgaagtgaaa taatagtgtg tattccatta tctctttaat tcccaaatat   102240
ttttcctaaa ggcttcctac caagtatttg aaaaaatttt tatctactgt agtcagtaaa   102300
tatagcttgg attggtcaat ctatgtgata gacaagaaac tactttgtta ggatctaggc   102360
ctccattggt aactacgtat ttctcttatt gcttctattc agagtgtgtt ggcagtgctg   102420
gtgctgctga ttttctctt cttggatcaa aggagatgta atggagaagt ggctcagaac   102480
atgtgcccca tctagggtct agagtcattt gattagtctg aagattgagg aagacttttc   102540
tataagaata aagacatttt aaaagcttag attattacca ggtttctagt tttgcattaa   102600
```

```
cttgagtctt aagacatcag aagttttcct ttcttactga gacagtacac agagactatg  102660
tgtacattga gaaaacatga caattaaaat aataccatta gatcttcatc atagaagtta  102720
ataagataaa ctaaaataaa atatattatt taaacagaca acccttacct ttcctgtatg  102780
attcaataaa tagtgtttgt ggaaaaatga atgtgcaaaa tgagagagtg gaattccata  102840
agcttaatgt gctcttaacc aatagcaatt gctgaagtga cttcagaggt gtaaagccaa  102900
gacactaaga gtgtgtgcac ttcgatgttg gtcatattga atttagaaat gggtgtggaa  102960
ggcttagata aagacgctag aaaaaaatca actgtggatt gttccattgc aggtggctgc  103020
ttctttattt gtgttatggt tgcttaaaaa gtgagtatgc cacactttat gtggattgtg  103080
ttttgtttat atttagaggt tataaactat tttaatatat actatgttca ttacacccctt  103140 ccatattcct gctgattatg agggagaaa ccatgtttca ataattcttc aatttctgag  103200
gagactgggt cccagaacaa agataccaaa ttctgcactc gtgctccatg tgtaaaactg  103260 tttttttacac atacaataca atagtatttt gcatatagcc taggcatatc accacatata  103320
ctttaaaaca tttctagatt tatatgatgc ccagtataat gtaattttca tgtaagtagt  103380
tatatccttt agagaaatga tgataagaaa aataagtatg tgcgtgttca ctaaagatgc  103440
aattttaaga ataattttct cagtaaactg atggctgaat ccatagatac acaggagata  103500
cataaggttt gctatatttg ttcaagttga aagctgttca gtgcctttat ctcttcattt  103560
ctaaaatata tgttgttttc agttttcatg aaatgcaata aaatatatga agcaacagtt  103620
catatttaat agtttctact aattattttg ttcaaataag aatcaattac atctatttca  103680
attatgagaa accttaacac cttttggcaa tacaaaattt ataaaactaa gggtatagtc  103740
tcttttaaag tcagcatttc atgtttcctt atacttattt ttattagtga ttcacttggc  103800
aagtttggtt gtcaaataat ccttttcttt tgttttacag caaccctgtt aacagtggaa  103860
acaatggtac taaaatttcc aatagctcct atgttgtgat catcaccagt accagtttct  103920
attatatttt ttacatttac gtgggagtgg ctgacacttt gcttgccctg agcctcttca  103980
gaggtttgcc gctggtgcat acgttaatca cagcatcaaa aattttgcac aggaaaatgt  104040
tacactccat tcttcacgcc cctatgtcga ccatcagcaa gctgaaagca ggtacttgtg  104100
actaggtata aagtggagct gcccgcttgc catctgtgtg gctcatcggc ctgcctgcct  104160
tcagtagcag catgagcggg aacacaggca tctgcccctc atccaactac cttgtttggc  104220
atttctaaga tactgcaggc aagcataccc atgctcccca gcatttctgt atcagcctag  104280
tagagtaaat tatcttgtta caatgtgatt tgcgttcagt ggactcactt gaagcaacct  104340
cttttggata acttgacctt ctcacatact tatcttgatg ggaaaaaaaa taactgtttc  104400
ttgtgcctct tcaagagtgg tcatatgaat gcattagatg actttggggg gaggggata  104460 gtttttaatt attatgagac aattatagta catgatcctt gtataatgca tttgacaccg  104520
atttaattac agtcacagaa agtaagataa tttgaaaaat agaaccaaac atttcaaaac  104580
ctatggtaag aagggtcttt gaaaatgtgg tgcattgatt cgcctctgag ttagcttact  104640
ttaaagacca tgaagataat aagcctccta agttctcctt cactggagag cctgctgtgt  104700
gacactaagc cagggaagtc ctggcgcata caaataatta agtatcatt catgtcaggc  104760 atagaaattc aactaaatgt agagaaagct acagtattga gaccttttta ctgtaatctg  104820
tctaaaaatc tcaaatgtgc atcagatttt tttaggtgac aaaattaagt gttgatgtat  104880
gaaaaagatt atatttatcc tggagcccct atgcctcggc aaagggttgc ctcatttgca  104940
```

```
tatgatcctg gtcatcctct tttagtctaa gaatcttaaa actaaggaaa tgggcaattc   105000
actctttaag agaggcgttc tctcacattt ctggcagaat tgaacatgga cacgtggaaa   105060
ggacacagac atttgaggct taggcttagt ttggccacac accattggta gtaatggctg   105120
tcagcagcct acgtgaaatg aatattagca tatttctgcc attcttttct gtgaggttgt   105180
tgctctcaaa ggaagtgaac catcctcttt ctcccaaaat ccactcacag cgccctctcc   105240
gccctctctg ttttccctct cagtgatcac catacattct tctttcctca tttgtcttcc   105300
caaaatgtca tctgtgtctc aggttagttc ctaaccactt tatgctgtgt tcctccttat   105360
tcaacctcct ggacctaagc agcaagatga cctcaagaga tttccaatca gcctgcactc   105420
attatttggt agctgtggta catatagttt gcttttaatt aaaaaaagtt attagattca   105480
tggtttatga ttctcatctg atactgaatt attctgctat actttgcaac aacttggaat   105540
ttcccttgga tgagctcttc agaattgtgc attgaccatg cttttccttg acagtaattt   105600
tctcaggctt ttttttttcct gttactttct cccactttgt catactcaaa ttgcgatcat   105660
acagacacat aataaaggtc ctcagcaaaa tgcggttata atacacagat gctcctggtt   105720
gaaataaaat ttgaaatata aatatcacta tgagtatact attttgccca agcatacttt   105780
cagttttaaa tagttattac aaatgtcatg gaatatacat tatttctctg acttatttat   105840
ggaaggatat ccataatggg tatccatata atatattcat aaaatatcct aaattaatat   105900
gttttctaat gtatcacatg tctgcataag acttttttact tttgtctgtg ggtcatataa   105960
aatagacatg gaattatcta tcctattgac ttcaaaaatc tcctatctgg gaaagagat    106020 aagttatatg tacacacaca agcagctgtg atatacagca cgtatgtagt ctctgcaact   106080
caggcataca gacaaggaca ggaagagatt ttttttccaga tgcagtaaat accctactct   106140
cttgcagaca ggctatttga attgaaccag gaaagaggta cagatttgac aagaggagac   106200
agggctttta gatagaaagg aacaacacat aggcaaagta ggaaaaggta gactaaagaa   106260
gacatactta ccagaagcag tgggtttgaa tagcaggatc taggttagtt aaggacaaat   106320
tatgggaaac tattaaatat taaagaattt tggactttaa tccagtaggt aatagtgaac   106380
gagtgataag gttcactatt acattgttgc catagtgttg tgttacactt tatctgttgg   106440
cttagctcct tttttagaag atgaattcct gcactacaag gagaatgact taatcacctc   106500
cctgtagcca gcattaccaa agcatgtagt agacatggaa ttttttagttc attgacacaa   106560 caatcaagac tcaaatgggg tgaatctgga atttagaata caggttgaag cttatattcc   106620
cagtgaagaa gatagacaaa ataaaaaagg aagtctggtg tgtactgaga gagacagctg   106680
tgggttttgg atcagcatat ctaaatggca gaaaactcca cagggagggt gtatgtgccc   106740
tgtttggtgg agttaacat aaaaaattga tgaaagcacc gccattaaga cacccttgaaa   106800 ccgagagcag cagaagtgag gcccaagggg tacgatgacc agacattcct acccttaatt   106860
atagtaagaa cttgattaaa gacactgctt ggagctgagt cgtaggggac tatgtgtttt   106920
ataaaagttc aaaagtagga ggcaataact taaataaata catagaattc tcaacaaagc   106980
taatatttgt aagttcttga atttctgact agatgataat tcttatttta aatgattttg   107040
ctgtgctgtg aatttaggat aaaatatatt ggtgtccttc taaagtgat taatatttga   107100 gaatatttat ttgtatcaca ggtgggattc ttaacagatt ctccaaagat atagcaattt   107160
tggatgactt tctgcctctt accattttg acttcattca ggtttgtaaa gaataactat    107220
tatcaagttt ttctatttgc cataaagttt tgtgaataat ttcaaaagga agcaagtgaa   107280
tttgttgcta attttccaca tactagttga agtcctggct agtgaataag ttttatgaag   107340
```

```
aacagcaatg tttaatagtc ataaatttag tgaattcagt aactagctat gtctatctat  107400
ttcaggcatg ccctggatat gatactatcc tcttgaattg gtttgaaagg tacaaaagac  107460
agttttccgc ccaatcattg accataaaat ttgactcata gaacatttct taagtccaac  107520
actgaaatga aaatgaagtt cctggagagg ctacactcta atccagccat acccatgaac  107580
acttaaacac aaatttagct aagcagtttc cccacaaaag tataacttaa tggaaggatg  107640
aaaaatggat tgttgaaaaa atgtgaagga aagaaatat ttagagcctc tgaggctctc  107700
ccttagtgac tgctgtgaca gacctccagg gtagccatgc tatggagatg actgaaagtc  107760
acttaataac aaaagaaggc cattgagtgg agaccaaagt gaccatgaaa gcatcacatt  107820
aggactccaa tgtcaaagga cttacaggag ttgtaagctg atactcttgc ctgttgaatc  107880
aggcagtttt ctgagctccc tgttggcttc ctgaagcttc agagagcaaa tgcacttgga  107940
gaagtagttg taacacaaca tggtccttgt tggaatgaca cagtctcata gcttgtccct  108000
tcccttctct ttaaaatagt actgcatctc tgaaaaacttg gaaaaaatgt ggaactattg  108060
cccctgtatg tatacacaca agccacatca gcagatgcag agaaagcagc tgttggttca  108120
cctcctctga aatgattgac ataattaaat acacttactg tactaagtga actgtgtttt  108180
ggatttcctt cattgctgtg tttaaagata taactttacg gtagcagcac ctactggaat  108240
tttttttaacc caagttttga tttatgtact caaaagtgtt agtttatgtg tgttctttta  108300
gcatgagaca tttgtttccc agtctcagaa aataaaccaa aggtccgtaa taaaagtata  108360
ctaaatacta tatactaata taatataatg caatataata tagtatggtc aaaaactgga  108420
atgtggatat ctatctgaat ctgcctacaa aagtcttaaa aatggtgctt gagtgatata  108480
tatatttatg gtctcctaag tatctcttgt tatttagttt atctcagaaa tctgggagag  108540
ctaatttca aatatttatc ttacaaatta aaggttattt gacatttgtg atggctttca  108600
agtccttta tgtatcttaa acactttat ttcaggttct agagctgcta aagcttcatg  108660
aggtagcaaa tctctcagag ctttcttttg agctgagatc taccctgccc atttcccttc  108720
aggacaccag ccagaaagcc catggaaact agtggagaat tagcgtatga aagttacact  108780
aagttggttt taaagttagc acatgtttga tgtcatgtgg accatttatt tggtaaactg  108840
tagtgaggtt gcaaacagta ttctaatttt ctggggtgta atacagtaag atgtctgcat  108900
tgcatggcag aattcatttt gatagtgtgg ctagaaaaat acttaatttc aaattaaatc  108960
catctactat aaacctttg agttactgga gtatctccag ttattacagt aggcataggt  109020
gaggtgagat ataaataaca cttattaaat aatactcctt tcaatattac atatgaaaaa  109080
ttagagtcag aaaagtgaac ttgtcaacat gactaaacct aggtttaaaa cagatatttg  109140
taatttaaaa tgttctgtta agaatgtttc attttaaacg actccaacaa aatcacaaaa  109200
gataatattt atactaaaat tattttgaaa ttttaatttt tcaatggaca ggatgaagaa  109260
aatcataatc atttcacatt tacttcttat aaaatttaga gtgtgtgata aataaaaata  109320
tcccaagaac agaaagcacc gtgtaaagct tcagcagctg aactatcaca tcagcaaact  109380
aaacaatttg aacattgttt ctctgcagcc ggcagactgc cttcgagctg gcaccttatt  109440
catggatgca tgtttcctca ctgagaatag tgcagtctaa gaacgtgtgt agacacagct  109500
cagcaatgcc cctgtccact taacaaagtg aaaatgtctc tcactaccat gttctctttg  109560
acccccgcagt tggtgttcat tgtgattgga gctataatag tcgtctcggc attacaaccc  109620
tacatcttcc tagcaacggt gccagggcta gtagtcttta ttttactgag ggcctacttc  109680
```

```
cttcatacag cacagcagct caaacaactg gaatctgaag gtacagcatg gaatgcattg 109740
caggggttcc tggaagtggg tgaggggac cacatttact aaccactata ctgctttaaa 109800
tctctaatta tataacagtg gtgtgtgtgt gtctgtgtgt gtgtctgtgt gtgtgtctgt 109860
gtctgtgtct gagtagtagt agtagtagta tgtgtgtggg catacttgct cgtgcaggca 109920
tgtgtgggaa ccaaaggcta cctttgtcaa ttgcttctct tcttttttcc cttatcatct 109980 tcttctact tcctccttct ctgttccctc cctccctccc ttccctctcc ctctctcccc 110040 cctccccca ccatccctct tttcttcctt cctcccttc ttccttccct tctctctctc 110100
tcatgagttt ctcacagaac ctggcatttg ctggttcagc tggactggct ggccagggag 110160 gcccgggac ccatgtgtct tcatctctag cattacagac attcagtaca ggcccaaagt 110220
ttttcatgtg tgcttggaat ctgacctcag gttcttatgt ttgtgtagca gacatattac 110280
cgactgaact ctcccggccc aacaatgaaa cttataaagt acgtgaggat tgactttgtt 110340
aactactatg gctttgtttt ggctttcaaa caagtgtata cccttaccat tgtgtatgca 110400
tagacatgca tacgttctta tactgctcaa agtcaaaacc agcaatgcta tttttcctca 110460
gagtttctcc cagatttcaa gtgagactgg atggaattct tccatttggc ttatcgtctt 110520
caggcctttc cttattggcc tggcttggtt aatctttgct ccatctcctt aggaagcatc 110580
tctttcagaa ggaaccttgg tgtgaggcaa ttattttttt aatattttt attaggtatt 110640 ttcctcattt acacttccaa tgctatccca aaacccccca taccccccca ctcccctacc 110700
cacccactcc cacttcttgg ccctggcgtt cccctgtact ggggcatata agtttgcaa 110760 gtccaatggg cctctctttg cagtgatggc agactaggcc atcttttgat acatatgcat 110820
ctagagtcaa gagctccggg gtactggtta gttcataatg ttgtttcacc tatagggttg 110880
cagatccctt tagctccttg ggtactttct ctagctcctc cattgggggc cctgtggtcc 110940
atccaatagc tgactgtgag catccacttc tgtgtttgtt aggcccggc atagtctcac 111000 tagagacagc tatatcaggg tcctatcagc acaatcttgc tagtgtgtgc aatggtgtca 111060
gcatttggaa gctgattatg ggatggatac ctggatatgg cagtctctag atggtcgatc 111120
ctttcatcac agctccaaac tttgtctctg taactccttc catgggtgtt ttgttctcaa 111180
ttctaagaag gggcaaagtg tccacacttt ggtcttcgtt cttcttgagt ttcatgcgtt 111240
tagcaaattg tatcttatat cttggatatc ctaagtttct aagccaatat ccacttatca 111300
gtgagtacat attgtgtgag ttccttttta ttttaagag agtaaactta atgtgtgttt 111360
ctgctttgaa acttaggagc taaatcaatt cacagaaatt ctacactgag agacttagag 111420
attgagtctc aaaagacaaa acccatttc tcagcagtta ctaatttagg attagccaag 111480
aatattgact actcttagac aaggaaatgt gagttaacaa ggaaagtggt tctgtccact 111540
acctacctat ctaccatggt cagcaggtaa aagggcaggg ccatgcactt taaaagtaaa 111600
ttccggtttc agtgagaagc ccacaccata gatgcttatc gtgaagttac tctggagttc 111660
atctttgtca gaaacatggt agtatgaaat tctgttctgt attgcaagct gtacattatc 111720
tcctatggga tgatttacag gcaggagtcc aattttcacc caccttgtga caagcttaaa 111780
aggactctgg acacttcgag ccttccgacg ccagactta tttgaaactc tgttccacaa 111840
agctctgaat ttgcacactg ccaactggtt tatgtatctg gcaaccttgc gctggttcca 111900
aatgagaata gacatgatat ttgtcctctt cttcattgtt gttaccttca tctccatttt 111960
aacaacaggt aatctgaact tattttttg tcagtgatta aaatgccata tgtttatatt 112020
aaaatattta gatgattta agtagacttg tagagcttac aagtaatttc tttgcatttc 112080
```

-continued

```
tgttgttttg tttctaaata atttatttaa aggtttatat ggtattgtta ctagtttcac   112140
tatttaagaa taatgagaca ctgagtcaga tagcaaatat gtgactaaca agaaaaatgt   112200
ctttttcatg ccaatgttgg aaatctatat ggggaaagaa aaacatattt gtatacacat   112260
gcacacatgt acacacactt atcatttcac acttcctgta aaatttcttc acttaacaac   112320
tacttattgg taaaattctt gtctaatatg aatttgaata aataaaaatt agcatagaag   112380
taaaataact gacataaaag tgcattattt ttcaaatata aatgttctga aatttaggat   112440
cttcaaggaa aaataagtc acaataagaa aaattaaaat ctatacagat aaatgagtat   112500
tttaaggtgc tggatttctg agtcaaaatg ctatgttact tatatataca ccattttatt   112560
atatataaaa tattgtatat tatttatagc aaaatttcag agcgaatgac acatcaatgc   112620
cagatttgca acattatttg attataagaa cagaattgct caactccaat gaagcagcct   112680
ttgacaagtt atcaaattgt gtcatgcagc ctcagggtgg gtatcacact tgattacctg   112740
aaggaaccag cacaggcact ggagagtcag gcataagtat gactcatgta gatactggtt   112800
tctgttctct tcattctgtg gatgatgcat ttctttctca ctctgtctct ctgtatctct   112860
ctgtctttct ctgtctctct atgtcatatc tatatctata tacacacata tataatatta   112920
tataatatat ttgtatataa taaatgtata ttatgtatat atttcatgta taatacatat   112980
ataatatata cacatataac atatatatat atatatatat atatatatat atatatatat   113040
atatatatat gagagagaga gatctgtgta tgtgtctccc tctctcttcc tccctgccct   113100
ctctcagaat aatagttatc ttcatttaac aggaccataa cacatgagct tcatgtgcca   113160
tcttcattct tcttcttgaa ttaatggtat ggatcctgtg tccaattatt aaatcctaga   113220
gaaggcaaaa aacatattcc ttctggcttt gggcccactg cagattgaca actgctatga   113280
ggatggttaa cttacccata tattgctttc ttcatgcatg gctatgaaat gaatctatat   113340
gtaggtatat ttgtggatac acatatagtc attttgacac cttaaaataa tttttggaag   113400
gtataatatt gattatttgt atataaggta attcagaggg gatcaaagat gactaaatta   113460
catggattaa gacttcacaa ttaactcaag ccaatgtatc acatgctgta tcagactgta   113520
tattatgact aagtcctggg ttactaaggc cagtactcaa aatcttcact agtcaacaca   113580
gtagaacctc caactgtgat gagcagcaca gcccaggaac ccagccataa ccaaccaact   113640
ctattggtct taattttatt gatgatatta acttacatta atttcagcc attaattaac   113700 ttccctaatt ccctaatcgt gtgggcagat gcacactaat aacactttca taatattgtg   113760
tgatattttg tgtaatacag tgtagtcttg tttgtaataa atggccagtg attattaaat   113820
aatactactt ggtattaaaa tattaccta ctttttttta accctcagaa taagaaatgt   113880
ataagggacc tatataaaat gaactattaa caattttcaa tatattattt gatattaaca   113940
cagcataaca tgtgttatct atggtgtacc taagaaggag aaaatgtcaa catgaaattt   114000
ttcagctatt aataggatga cttgttcatc ttgatgttta actttatagt aatttaatgg   114060
tagattaagc attatcattt gggatatgat atcctaactt taaaataatt tatgaacact   114120
tatcttaaaa atatttgtag tcataatcct catttttaa aatttaaatt agttgcccctt   114180 tctaatccta aatgaaattt actctaaaat aacatattaa cactgttctt ttcaagcaga   114240
ttgggcattt ttcttcttgc ttttaatgta atgtgcaaac ttctccctta aatggctggc   114300
attagttttc tgactgcctg gtgacaagtg aagactcctt tcttagaaac agcttttgat   114360
gagcagagac catgacccctt acagaggtgc tcagcacatg tgctagtgct actcggatgg   114420
```

```
atgtggccct cctttgagtt ctgtacagga tctcatttcc tatttatttt tatctatcta   114480
tctacctatc tatctatcta tctatctatc tatctatcta tctatctatc tattcactca   114540
tttatggtgt ggtattcaat cagtatttgt ttatattgtt acatacagag taagagtaga   114600
caattactca ctaccaacat taccttcaag acctaagcat catttaaaag tgcagcagtt   114660
cccaatattc agtcactatt tgattttaaa ttctggatga aagcttactc aatgaaggca   114720
ttattgttca aaggagtcac taaaactgca ttaaattgaa acataaattt attggcaagc   114780
gatgagagag agatgaatac aataattcac agaagagaga aataacatat actttgttca   114840
aaacccttt ccatgtctag gtgaaggaga aggaacagct ggtattattc taactttagc   114900
tatgaatatc atgagtactt tgcagtgggc tgtgaactca agcattgata cagatagctt   114960
ggtaagttac tatttttaat tttatgaaaa gttgagagaa caaaacaaaa agagtaggca   115020
ctaacatatg aaatatatat atatatatta ctcagtttaa gaaataaaat attcaggtta   115080
ctttaaggac attctgtatt ccacattaag ctgtggcatg atttatcttt cgtcctcatg   115140
gattatcatt attatgtgtc tttgccctgg agttttccaa agcaaatctt agaagtggaa   115200
gacattgctg aggttagaat ctccccaaac ttggcttcac taacgccaaa ttactccagt   115260
ctgttgtgcc actatatact tccagcaaga gagcatgtga atgtttccag cagtatttct   115320
tattcaggct tttacaattt tgccagcttg atgaatgtga agtaactact aaaatttctg   115380
gataacttag taagtctcta ttgttgacca cttggatttt tattgttgtt tatttctgtt   115440
aaatgcttgt ttctgttatt tgcaacctga tgaggtttga tgtgcttgtt tgttttcct   115500
tatgttatag gtgttcttaa gtcctggatc agtcatcagt tctatacatt tcaatggccc   115560
ttgagccagt ggcttactc acagtatacc ttaatgaatg gaaacattga atttgataga   115620
gagtagttta ttttccttta cctttatggc ttgtgcattt ggtgtcttgt ttatgaaatc   115680
cttctgtata ttaggtttcc acattcaaca gcctgacatt tttcataatc ctcttgtctt   115740
attttgaaaa tgtctggtca tagtgtttgt cattgctctg ttcctttgtg cttaacggat   115800
gctgtcttgc atttgaggac tttgtgtgtt caaagaccat atttggtgta ttcttccata   115860
gagtgagagc ctgaagtgat atttgtgtgc taaaatgata caaaggacta ctaattcaca   115920
agggccaggg caagaaatga aaagaggttc cataaacttc cctatttata ttttaataaa   115980
agccatatta tcagttagac tttagaattg gcctgagaat gtcataactg atttcttttt   116040
acatatttga ttacagttat ttgtgtcagt aaggaatgtc cataccacag catgagtgtg   116100
gagggttcaa agggaaactg gtggggctca cctccctctt ttcaccatgt gggtcctagg   116160
ggctgaactc aagtcatcgg gcttagcagc agttgccatc acatgctgat ctgtcattgc   116220
ggacctgtca ctgaagctta aggctttgga catacattca tccattcctt atgtcatttc   116280
taagaggtct agaatccata caactccctt tacttccatt tcagacacc cattcatgtg   116340
attgcaaaat ttctatagtt ataatatata aatacataca gtatatttt ttcataaata   116400
tgtcacaagg gaaaaaccta aaatctttta aagcctcttc ttgtttgttc attttcatca   116460
ttccatgagg cagcttagta attccttgaa atacagtttt cttaggtttt atttagttag   116520
accagtccct agtctcttct ccacacttct tggttttgtg ttggaattag ctgaagaaga   116580
ttatataaat gctgtttcta tttacttaaa ttttttaaaac tatgacttca taattcaaaa   116640
cccttgtgca cattatatat ttctttacat aaaaattctc ttcttgtaca tgtacaattc   116700
cctttgcaac cttaatttc tggcttaatc acatagccaa acttttgaca ttgcaacaca   116760
atgttgtcac ctacagagtt cacactcaag atatgtacag ttaagctcct aaacttagtc   116820
```

```
acacacattc aacctaagat tttcagtaag tagtaagttt ttgatttgtg ttgggcttct   116880
ttcatagctc tgtttgtgca gctggatgtg gcctgtgaac tgtggattgg acagtcctgt   116940
tagaatagcc tttgcacagg ctgacaaaac cgttgctaaa tacatttcta cttcatgtat   117000
ctagtgtcca tgaaagacac ttaaagtatt tctccaggtt ttcccatggc tatgctagac   117060
tttgttgtct gacattgtat ctttcatggt gtgtgaaagg acccttttaca gacctattgt   117120
gtttgtgaca tggtctatga aatgtatcaa tatttgcagt tgattacgtt ttcaaaagta   117180
atgctctttt gtttaatatc aaagagcgta tgttagtttg catctctttg ccaagcaatg   117240
ctggcgggcc ttcctgggtg ttggtggtcc cttcctgcta ttacctccca tcgtgctggt   117300
ctcacctgca ctgctgcgaa aactacccgg tagtgctctt cttttccacct cttgcttggg   117360
aatctgaagg gagaatgtct gatcagtggc cagtagtgct cttctttcca cctcttcctt   117420
gggaatctga agggagaatg tctggtcagt gctttcagat ttcacaccca cctgatgtaa   117480
ccccaaggtt ttacaacact aagcaaaaac tcagtgtgat gtaattttat cttactgtgc   117540
tttaaactgc atcaagagtg atctgagttt aaaatggaac aaatacaatg ttttctttac   117600
tatattataa agctaagtac aaggctattc aggaaaaact tcagagttgg aataattact   117660
tcatttccca tctgtcccaa tttaaaaatt aatacagtca atttgactat gaagttatga   117720
atatagcagt ataactttgt ttttattttc tacctgttac ataccacat atctctagct   117780
ttctttatct ctcagctatt aaatccaata tcacaacaac acaagttatg ttgtgtttat   117840
tatcacatat ctggaatgct gatactcaga actatccagc aaccttttca ttatgttttc   117900
ataataaaat ttactcccaa gctctttcct ttatttctac atcctttttag acattataat   117960
aattctattc tttaaactct tagccaaaga cctttctata tatctcacag aaatacatac   118020
atataaccag aaataattcc cttacatctc tctactatct cttttctcttt tgtcttttta   118080
aaattttttt aattaatttt ttacactcca tattccattc cccacccccc catccactct   118140
cccactgctc cacatcacac acttcctccc cactccccca tccccactc ctccacccccc   118200
acctgatctc taaactccct ggggcctcca gtctcttaag ggttaggtgc atcatctctg   118260
aatgaacaca gatctggaag tcctctgctg tatgtgtgtt gggtgcctca tatcagctgg   118320
tgtatgctgc ctgtttggtg gtccagtgtt tgagagatct caaggttaat tgagactgct   118380
gctcctccta caggatcacc cttctcagct tcttcagcc ttccctaatt caacaacagg   118440
ggtcagctgc ttccattggt tgaatgcaaa tatctgcatc tctttcagct gcttgttggg   118500
tctttcagag ggcagtcatg atagatccct ttttgtgagc actccatggc ctcagtaata   118560
gtgtcaggaa tgccttttga gctggatccc actttgggcc tgttgctgga ccttcttttc   118620
ctcaggtttc ctctccattc caatccctgc aattctttca gacaggaaca attatgggtc   118680
agagatgtga ctgtgggatg acaaccccat ccctcacttg atgtcctgtc ttactgctgg   118740
agctgagggc cagcaggaag agtggaaaca gggcaacctc aggaaatagg aggttggggg   118800
ggggggggacg acgaccctcc agaatgcacc agaggcctgg gaggtaagag actctcagga   118860
atcaaaggga gggaccttag atgaaatgcc caacagtagg gagagggaac ttatagagct   118920
ctttcttaat gtagcatact actagaaaat cttgcagtag acatgacatc ttagagtatg   118980
agtacaggtt tattgaatct ctagtcatat gtactctctt tacccatgtc cttgcttcta   119040
tctagaggca agtcctgtgt agttgcctgc cctttatgag acttttcacc agtgaatact   119100
ttcatttggt ctccagtttc tgccctaatt atttgacctg tttacagcaa aacttctaaa   119160
```

```
gagattgcct ttctctgtta tatcttctgt tctttacaca gtttcttcca tattcatcac 119220
ccatgtgagt cacaataaac atcatgtaca aagcaatgtc cttgtcttct gaagttgttg 119280
agcactattt cacatggatg aatccttata ctatttcatt tttctgctac ctcctgggcc 119340
ttcatctcat gtatccttta aatcatcatt tgtattactt cttcttccca catgcattct 119400
ctatagctat tggtatctaa ccccatggtt caaaagttgt ctcttgatga attatagatt 119460
catatattta gtgtacatct ctctattcct ctctatacat gtccagctac catcttgata 119520
cctccatgaa tctataaaat attctgctag attgttttct agtagatttg acatgcaagc 119580
atatgagttc ctgtacatca cctcagagtg cacatatgat cttaagtggc catcgaaatg 119640
atacaaagtt tatactccct gaaaggccaa ataaataaat gagagccaac aaaggtataa 119700
aaggtgatat tttaaacttg gcagtattaa accatctggt gtctaagagg ttgctcacac 119760
ataatttctt catttgataa ctcatatcct tccagaactt tctaccacag aaggaacaga 119820
aagtgagcag tcttaaatatg tgaatgccat tgccttcgtt tttcaagaag accagcaaat 119880
aagcatccct gtttccacta gattattgaa ctgaactgta tgtccctagt aaaagaagg 119940 aagttgcaaa gttaagaaca atgagcttat aagacttcca tttagatcac tattagtgaa 120000
gttccagaaa gttcttgcat ggttggtgca atctgagaag agttttctgt cagcacaaag 120060
tcactctgtg tctcctttgt gctctcatca cctgtgttta ttttgggttc cactgaggat 120120
caggtgacta attgtagaat gagcaacatg aaatgtggga ggacaaaaaa gaatttctcc 120180
ttccttcatg actgccgtca ccaaatgtcc ttgtattgaa agcagttcct gttgtaccaa 120240
tctgacggat gagttaattc atcctctttg tcttttgcct ccttttaatg gtagcttgat 120300
tgtggtttgt tgttgttctt acaagtcttt gtggtgtatt tttcaagaca ttatgcattc 120360
aaccgcaaag agccttgcat ttcttctgg ctcagacact aaaaagttga gtgcctttag 120420
acaagtcatt tttcctcatt tccaaggcct tattttcctc ctctgtaaaa ttaaatggtt 120480
tggttaggaa ttttttcagat tgctggcatg tttgacattc tctctctgct gaacccttcc 120540
atataaaaat ataaactctt aacctacatg tagatattat ttcagttctt aggaaatcca 120600
cacaccaacc ctatcctgaa tgctgacatt cattgaatac tagcctgtag ttactacagc 120660
tgactcagta tgttactaca gccaacaaag aaaagtaac taatagaatg atattttga 120720 accttgaatt aagacaagaa atttaacagc cccctcagga attgctggag tgtacaaaat 120780
tgtgtgataa acttggaaaa ttgactaggg ctttggtcct gccactttat cttcctggtt 120840
taggttttgt cctatgtaca atgaaaggat ggattagatc atgggctctc tcagtctggc 120900
tacagatgaa taaagctgct ttttcaggtt cacagaggcc agggaaatta gttcttctgc 120960
tggggcaagt atcagggcct gttttctgta ttttgaaatg tgcccaggtg attcaatgt 121020 gtatggaggc ctttaaatca ctggattaag tggtcctgca gattcctttt tgctttgaat 121080
gtctgtgagt cacgttacaa ggattagcaa attttttcta ttaaggttga atgaaaata 121140 gtttcagctt tgtaagctta tgggctcatg acagcaactc aactcaacct ttgtatgaca 121200
aagcagccat agacgttcat gagtggtgtg tgtgtttcat ttcactttgg caattattat 121260
tttcagttta tttgaatttt gagtggtttg ggtttgagag atagggagaa aatatgaaat 121320
tgagaggata gagagatagt aagtagaatc tggaagaaac tggggaaga ggaagaata 121380 tagtcaaaat acgtaaaaaa aatataaatg aacctaaaat aacaaatcaa atatcctat 121440 caagaattca gtattttcct ctaagcatct atattttgaa atattctaac ttctccaaag 121500
cattctgtca gtcagcttca ttttctgtat gtaacatgaa tacttaggta agcatcattg 121560
```

```
acagcacaaa acatggtttg ctagtggtcc ttccatttac tagtaactat accctgtagg   121620
ctaagcatga gtagaaatat ggccactatg tcatattcct ccactccatc tgcttatata   121680
ttgtattcac caactaatgc tatgcaagag gcctggtttg gtctgtggta catacaccag   121740
tgacactcca ttgaaaggat tgattttttct ctttcccagc aaatatcaat tgcaaatagt   121800
ttattagtta agggtgagac atgtccaatt cccctttccc ttctcagccc tgagagtttt   121860
gtctgctttg aacatgtggc aaccttgtga atgctatcac tgtctctgtg agttcacttg   121920
tgtacaatcc tgttgtatct ggatgacact atttccttga aatcatctac caccacttgc   121980
tatctcccct tcctataaat ctctcagttt tgagaggagt ggttctctca ttctctgcac   122040
attgtccagt catggattgt tttgttcatt agtttctgct gtaaggaaag gcttctctga   122100
tggtggctga gtgaggcact aatctatggg tacaacatta ggtcattaag agacatgttc   122160
ctgttatatt ctttaggctg aataatagaa gtaggctttc ccctacagcc catgacctac   122220
ctaataaggt ttttgcccac tttagatgtg tcaagtatcc tatctcatgg aataggtctt   122280
aactccaatt atctaattgt tggttagtct ataatacttg tgcctctatt gcacttctat   122340 tatagttttct ggatttgtag ctagatgata ttaatgattt gtaattactt tatgtgtgtg   122400
gggggtttgc ctgcatctga tcaccatatg tatatctgat gtccatggag gacaggagac   122460
agtgttagat cctctggaac tggagttata gacagttgtt agctacttta tgaatgttga   122520
gaaccaaaac caagtcccct agaagaatag cctgtgctct taaccactga actatctctc   122580
aatcctcccc cataatgaca tttttgtctg ggattgatga acattttggg catgggaaac   122640
aatgtcacta ttgccatgac tttggagtgc ttggtcattc attgaagcat aattttgtta   122700
ttctgccttc taaagaacta agtaaaatta gcaaatattt ttatgagaca tttctggatt   122760
cctgaaaatg ctgtaatgac ttctgtgatt agctagaaaa gatgaacagg aaaatttaga   122820
gtcgttttca tgataaccga gttgcctcct ttataaatta acattgaaag gaagctattg   122880
aactacattt tgttcttgcc atcatcattg tcatcttggt gcttagatta gtacatttag   122940
gcattactgt aaggataata acagttttaa ggattacctc ttcctcaata tatttagggg   123000
aaggctttgg ctcttaatac aattaatgta ccagaaatta caagcacacg aatcgcaagc   123060
aaacatttca ctttatcttg gctacattcc aatttgaaag aataagaacc tatgctatgt   123120 taagtttttct tgtccataaa taaaaaacag attcagtgtt ttagcacctg gctcacctgg   123180
ctctcctttt gtcctttgcc tttaaagtat gagaacatgg tgttaattcc ttacctgact   123240
tcattgtaat ttaactctag ccacacagag attttttccta tccatggggc tgactaacct   123300
tcctgggtag ggctgcccat actccttcct tcctaaatct tctaagcaca gcagacagca   123360
gcttgagact ggggagtatg tcagtctaca gctataatga taattaccaa tgctgagtga   123420
ctgtctagcg ctaagacacc aaggttttta cataccatgt ggaaatatat agtagacaat   123480
cctttaagaa aggattaagt gagttttgca agtttttatga aaacagatag gggtaatctc   123540 tgcagggta atctctgctg tagtatgtgg aagaataacc tgtcatatgt gctttcctga   123600
tggagagatg cttccaaggt gccgcccacc ctttgagggt ctccagggtt gtgatgggca   123660
gctcctatga tgaacacact atgctcaagg ctgacccggt ggtgtttctt aacactctca   123720
cctgctttaa ggatcaatta aagtggcaga gaaagttcat tgaggaaatt tgagaactct   123780
gtgccatttg cagcaagaaa aacaatttga agcaagaagt ttaaggtcca cagctcagag   123840
caacccaact ccaggtctct gagccccacc cccaccccca gcgctagcag gaagtggaat   123900
```

```
ttgatgtgca gccagcctat gatgtcctta tgaaatgaga aactacaaga actttgactc  123960
caatagctac aacaaaatct atacccaact catccatgag tgcatcacgc taaagaagaa  124020
ggatgaattc ttgatctgct tcacagacat ccatcaaaac ttcctgaggt atcgtgcacc  124080
caggctatgg actctcctct gtctggtcaa gcactggtat caactgtgta aggagaagct  124140
gagggagcca ctgtccccac agtatcccct ggagctgctc acagtctatg cctgggaatg  124200
caggctccaa gacagctctg gactacatac agcccagtgc ttctgaactg tcttagaact  124260
gatcactaac tatccatgtc tttgaatcta ctggacatgg tgttatgatt ttaaacatga  124320
gatctctgac tacttgcgca gagagatcca aaacgacagg cctctgatcc tggatccagc  124380
agactcaaca aggaatgtgg ctgggtcaga cttacaggcc tggcaccttc tggcaagaaa  124440
ggctctgatc tggatgcgtt cgagactttc tttatgaact gtgatgtgtc ctttgtgaat  124500
ggctgggaag tgccaccaga gagaaaagaa tgtgtcttcc agtgagtact gcagtacttg  124560
cccaggaggc tccagagtca gggcatgcac tcactcctct gctgcaagac cttgatctag  124620
agaggacagg aaggtgctca aggcttcagt gaggggcatc cagcctgtga tcagactcca  124680
ggcttctgat tcctgcctgc ccatggacag ccttcctcac agcctgattc atctgccttg  124740
tcctccaaca gtgttctctg ggagtaagac tctgaaggaa agagaagaac tcaagcttga  124800
cttccatcta tctacccatt gggaggttct acctccccca aaatttctga tcatcagcaa  124860
taaaccacag gaagccatga gtgggtgtgt gtactctgag ggatgtatcc tcatcccaca  124920
aagaaactgt tcagcattgc acgtagccct ggagccctgg agccctggag ccctggagcc  124980
ctggagccct ggagccctgg agccctggag ccctggagcc ctggagccct ggagccctgg  125040
agccctggag ccctggagcc ctggaaattt gacaagtgtt catcaagctg cactatttct  125100
tcaacatgca ggctggggtt acagcagtgc aggaaaataa aattgcaagc actttaaaat  125160
gtatgacttt aaaacttagg tgggtgtgtt aggatgagac ctgaagcact gatttaaagc  125220
aaaatgcatt gaaaaaaaag aataaatggg ataataagtt cagagttact tggggaacca  125280
gccctgccta tggcctaggc atttattaat aatattaagc ctctccgttt ttattcaggt  125340
actggcacat gggtgaaaaa gcccatggct atataaaact agtgttctat gttataacct  125400
ctgactaatc cagttagcaa tatacagttt tagactaaga aaatgagata taaattccca  125460
gtcttgaaga cataccttat catcctcaca gcattgccat tatcactgca tagtagaaa   125520 aacaatggct ttattagtta gtgaaaaagg tttacatgtc tttgtatggt taagcactag  125580
atgttctgaa gattccgttc ttcgagtaca agaaatactg tggacattta caatagtgag  125640
taggatcatc accaggggac ataatcttca ggtcttgact tggatcgacc tttccacagg  125700
cccttgagtc agtctggttt ctgtcactgc aacaaaatac ctggtgtaaa ccccatgaag  125760
aaatgaaatg tttctttggg cttacacagt ccccgaagtg tcagtccatg gttacctgcc  125820
ttgacttcag tcctttgctg aggcagaaca tcatggcaac aggaatatgt gttagagaag  125880
gcagcttacc tcatggcagc caggaagtgg ggttagggat ttaggattgg ggacaaactc  125940
tcaggggcca actttcagta gttatccata cctcccaatg tttctactat actctaaaag  126000
ccccatcatc ttgaaccaaa gcctttatct tggagtgaca tttacaatcc aacttataac  126060
tactaggttt tagggacaag ggtaggttca agagagatat atgttggatc atcattcagg  126120
cactgagggg gtcattagca tgactagcat ggcaggggct gtctctatcc ttctccattt  126180
aggaatctgc tacctgcaag tcctgttttcc gggaaggatg ggctcctgat tttctgactt  126240
gatattacct ctatagttaa tttggtatgt acaatttgaa ttctattttt gtaagaagga  126300
```

```
cctaccaaat tgcttgagct ttccacaaag ctgagatccg tttttataga ggatatgaaa    126360
ttttgacagg gaaatcaagc gtacaatgaa taggacttca actttcctgt agttagtttt    126420
ttattattgt tgcttttgct gtacggaggg aagaactctg gctaattgag accctcttag    126480
ttttgtagtg gagctgagct ctttcgcagg ctcctttgtg agttctcttt ccatgactca    126540
ccgaagttcc tgtcttgtct acaagaatca tctgggagac ttggtcttgt tctgtcttct    126600 cttttgcag aaccttcttg gtttcttcca tgcttcttag gatacaggac aggacacctt    126660
cttgcacctt gcccatattc atgcttcata tcgtgagtcg aggagggtga ctgttctcgg    126720
acatcctaag ttaatcaatg acaaattttt tttctaaaac tcctaagtct tcagtgttcc    126780
agacagtgga ttttcatttt tataagcaac agtcttgctt tcttgcccaa gctgacatct    126840
gagcctgaac tcaaatgacc acttcttaga agacatgaat acctacagtt gtatgtctct    126900
ttgggacttg gcctttgaag cataaaagtc attgttcata tgactacaaa atgctgaact    126960
gttactatgt cttgactttt aaagactgt ttgtgagact tgaaagaatg ctgtggttcg    127020
ggggtgactc ctccttctag aggcaatcaa catgctgaca gcccctggt tcaagaaatt    127080 ggttagtgac tagtctattc cataatggca tttcagtagt tgctacttta tctgactgtc    127140
agaaaacgtc ctcagatatt gaattgaact acactttgct catattgtta taacgagtgt    127200
tggttaggga tattttcacc agggtgagaa tagttagact tgaggttcat tttaagcatt    127260
gatattgtaa gaaacaactt ataaactttt attttaaca ctcaataagt atgtgctgtc    127320
tagcacatag aatgttaaat gttctggatt tgtctttaat ggtgactatc actgatcaag    127380
ttaggctaca gtgcttcagt caaagaaatg tgtattactt ttcaaatgac caaaatcccc    127440
catctctctc tctctctctc tacatataca tatatatgta tatatatata tatatatata    127500
tatactccat catatattca tttactaatt gttcaaatag ataatatctg ttgtcatcat    127560
attttaaaat tatcacaaca aagttaatca gattattaaa atcagagtat taaaataaaa    127620
ttaaagcagc attcttttgt tgttgaaaat ttgccaagtt cctgtatttc tgtgtgcact    127680
aaatatgtac tttattaaat gtcatattgg aatatttata aaccagattg ttgcattaac    127740 ttttttccaag gaaaggtgaa caaatgtatt ttcactccca accagacact gaagaagggc    127800
aaaagtaaga atttcatcca agtctaactt ggtgaacaat gagtttattg agagtacaat    127860
aagcatggat gacggatcac ttacagactg tgagcgaaca taaaacactt tcacactaca    127920
atgttcaact ctagcatgga tgatgacctt gtggaagctg ctccaacgtg ccctacttcc    127980
tctcttaggg tctcccaaga tcacttcagc tgaaagggaa gagaaacaga aggggactga    128040
tggttggagt cccagaggag ggtcccgaac tctactctcc tcccttctag tatggagcat    128100
cactatagac ctagctgtca gtgaatatta tcctgtctat tttgccacat ggctaccagg    128160
cccaagcata tctccactct aagatgagga agaacaagc cactcttcca caattccatg    128220
gaattgagaa tataaccttt atataaagtc acctttgct aatgatgcaa attgatttca    128280
aagtaatatt tattagaagt gtaaactttt tcactttcta tctgtgcaat aacttaaaca    128340
ttgtggattc actaaaaatt gatatatgcc ttcagttcca gtactcagaa ggtagagaca    128400
gacagatctc tatacattca agggcagcct ggtctacaga atgagttcca gaaaagctag    128460
agctacacac acacaaaga aaacccttgt tttgaaaaaa caccccccccc cccaacgaaa    128520 aagaaggaga aaaaagaaa ttgactaagc atcaggtgtc tacaaataac ttagttgaca    128580
tacaggatta tagatgttaa agaaagtgga gaggcagtac tgtctgcagt gctacaatct    128640
```

```
tacaacataa tatgtagtac tgtcatagtg gggaaaagag ttctctttga catcatctat    128700
gcccttgaga atactttggt tatttgtgtg tggactgcgt aactgagatt taagcaatca    128760
caaaaataaa caggtctcta cagaacccaa ttatatgtgt cttagttgtt tcgctggcta    128820
aacatttaat tatatctaat tatttcctgt tacttcactg aaaaccctgt caaataacct    128880
agtgacagtt ttcttgcatc ataatttaaa ggttatcttt ttaggcaacg tcaaactaat    128940
tatggccact gtctagagtt ttcaaacaaa caaacatact gttattttca tttcagatgc    129000
gatctgtgag cagagtgttt aagtttattg atatacaaac agaagaaagt atgtacacac    129060
agataattaa agaactacct agagaaggat catctgacgt tttagtcatt aagaatgagc    129120
atgtgaagaa aagtgatatc tggccctctg gaggcgaaat ggttgtcaaa gaccttactg    129180
tgaaatacat ggatgatgga aatgccgtat tagagaacaa ttcttttcca ataagtcctg    129240
gacagagggt gagatttcag cattacttgc tttgttagtg ggtcccaact accagagcaa    129300
tatgttcgta aaaaccattt gtaacataat tatataatca gtatccctta tacatagttg    129360
aaggtgtgac tgtgcaaagt ttttatgttt catatgaaat ttgaattaca gactctacac    129420
aacaggttat tgtaaatgtg attgtatttg aatgtgacta tacttgcaaa tatgtaagat    129480
tttccaactg cagatgcctt taaatacaca cagacaccaa aaatacaacc atcactatga    129540
acagtagcac caaattggtt gattggcaca gtataaatta atccatccct taattaactt    129600
agatgaaact ttaaacttga gtgattttct tgcaggcaat gggtagttat atcttagttc    129660
tttgggccac tctgtcagtc catgtttctc aagtggtgca tttagaccat gagcatctag    129720
agtggtaggc acacattcag gcattataac ttgttctgct ttttgttcct tgcttttgct    129780
ctttatccct attttttacct tgaatccttt tctttctgtt gctgttcctt agtatttatg    129840
attccaagac tttctcattt cctaacatag cgattctact tttgtggttt ttatgagttt    129900
ctctagaggt cacaatatat attcacaatg aatccaggtc catttttaaaa gaataatgtt    129960 atcacataag aggcatcagc accctgtagt cccaattgct ctctcatgtg tgtcatattc    130020
ttcctatggg tcatttttgtg tattcacaga taatatgtgc aaatagatgt tattaaaatg    130080
actttaagta agcttccctg ttagatccag taagagtaag aaaagcattt tagttttctaa   130140 aatgcttcct ttattcattt agcttcaagt ttgcaactcc ttgtagatct gagttgtgtc    130200
ttttctctga gtaagttctc ttaacatatc tttcaagata agcccattga cagcacatag    130260
cttctgtgtt ggtttgataa tttcttactt tgccataagt tttaaaagat aactgcacaa    130320
ggttcacgat cctagtttgg cagagttttg ctttttctct tcttttctac tcgtttcctg    130380
actttgtggt gtccataaag ttataagtca ttcttatctc aaattgtttt gttttgtttt    130440
tttgagacag ggtttctctg tgtagccctg gctatcctgg aactcactct gtagatcggg    130500
ctggcctcaa actcagaaat ccgcctgcct gtgcctccca aatgctggga ttaaaggtgt    130560
gtgccacttt aggggaaatt ttcctgaaca taatgccata acttatgctc tgagatcagg    130620
aatcaacaaa ttggacctta taaaattgca aagattctgt aaagcaaggg acactgtcaa    130680
taggacaaaa tggcaaccaa catatttgga aaagatcttt atcaatccta catgatagaa    130740
ggctaatagt caatatatat aaagaactca ggaaattaga ctttagataa tcaaatagct    130800
gatttaaaat ggtgtaaaga gcttaaaaaa aaagaaaga aagaaggtg tgtgccacga    130860 ctgcctggcc ctcaatattt aataaataat atatttttta ctgggctttc ttcaagagga    130920 tttcttaaa aaatttttg tactttaag atgatatgct gtggtatggg tttttagctt    130980
taagcaacat tctggttatt tttctctgtg tatggattga gtatatgaca ctaatttttg    131040
```

```
agggaaccct cttagtaact attatttgaa atatcccect ctatctttct cagcatcctt   131100
ttcttctctt tttctttctt cttcatttct gtcttctttc tctttctggt atctacatta   131160
tatacaagtt acacctttcc taattgtgcc atgattcttg gatatgctgg gggaggggt    131220
tgtttgttgt gcagaggcat gttggtgttg gctgctttta gtaacatatc ctcaagctca   131280
gggttctttc ctcacacatg tctaaactat tgttgaactc ctcaaggcat cctccatctt   131340
tgttgtacat ggttttgttt tgtttgctta cctgcttgat tttttttttt ttgctatact   131400
tgtagaagtc ttttgatttt gctttagaat gacgcctttc tgtttactaa ggatccatct   131460
gttactatat gccaattttt tcatgatgaa atccttatca cattagtcat agttgttttg   131520
cattcccaac gtatgaatta gagtgtcatt gtcacatctg gctttgttct atcctagtat   131580
tgcttattat ttcctctttt ccctttcaac atgtctcatt gtttttcttt gagagggaac   131640
atagatgacg tgcttgggaa agggaccgtg ataataggct gttagtaata gactggctat   131700
gctgtgttgg actgtagagt tctgtagctg catagttatg ttagagaaat tacattttcg   131760
gctgtgagct tttaaatggc accagcttag ttactttagg tagtacagac tggttagagt   131820
gagttagcac taaatattac tgtttcctaa agtcagttag tctgggcttt tggaaaaaaa   131880
atctctaagt tacaaatgat aaaatagtct cactcaagat gggccttaaa tgggagaccg   131940
tgctctggcc taacagaatg atcactgtct tgtggggtcc ttgaaagcta gggaaacttc   132000
ctctagtctt cctgtgaggt cactggaggc tgacaggaat tgtttccctc tccatggtcc   132060
acaatgagcc caggtcatct tctcagtgta gtgcttgtac ttgctccctc cagctgtctg   132120
cttgctggtt tctgctggtc tctgtgactg tatctgcttg cctttctctc tggctctagg   132180
ggcagagtca ttcgttctat ggttttacct ttctgacaga aaatgtgttg cttacctttt   132240
tacttaagat ggagtgactt ttcagttagt ggtagcacat acctttaatc ccagcacttg   132300
agattcctgt gaattcaagg ccagcctggt tcacagagta agttccagaa caaccaaggc   132360
tacacaaaag accctgtctt taaaaaacaa aaacaaacaa caacacaacc caaaaagaat   132420
agcaatgttc tctacaaatg aagacatcta aataggtgct ggatttgtta aaagtgcacc   132480
ccattctgcc tttatagaat ctggcgtgag gctgctgact catttaacaa tctgagtggc   132540
ccatgtgtct tattaacaat aaacagatgt gtcgacatat gagaggctca gttataatca   132600
cccatgaatc tgatgtttca tttgattgtc tgtcttggtt tctggggacc acaaggaaac   132660
aagataatta tagtgcactt ccctctgcca ttaaagtgca gagaaggtgc tttaagggga   132720
ctgtgcccca actgcgctac tcttgacaca atggaattcc tgctcctacc tagttttggca  132780
ctgaatagct ctccagattg tagtctgatt tatgttgatc taaattttgc agagctgagg   132840
tgcattgagg ttaataaaaa cgttgactca tacttaggac acatctttaa agcttgtttg   132900
caggaagtac tcttagaaat aagaagataa ttagtatgtg acaattactc aaccagacaa   132960
ccttgttagg gtacaaatca attaagttcc ttgctgttga aaaactggtc agacttaata   133020
catgccagca ctttgatgtg aggaaactag agcaatagac aaagggtttc aagctaaaga   133080
aagtatttat tcattgcctc tcaggccagt attatgccag cataagaact gagttttctg   133140
aaaatgtatt tccttctgga ggaaatgcag tgaactcatt taccctact aggtccattc    133200
aaggtccttt ctgccaacta tcctgtaatg aacttagcac tcttccatcg gtccactgtc   133260
actttctttt ttcctcctgt acatcacctg cactgaccga ttctgatttc ttatttaact   133320
tatttaacat tgcagtattg gaaaaatcct aacatggtga atgtgtattt gtatggcatg   133380
```

```
gtctagcaca gagatgggag catgcagtgt gaaattcctc cagattttaa aattaatgct    133440
ttatctagtc attgaacaaa attattgtat tatttattta taaggtacaa taatatgtat    133500
gctcattcat ttgctctcct atctgactgt ctttcagtcc acctcaatat ttcttgagta    133560
cctttttaaa gccaagtaca catgggtcct tttattcctc cattcttcca gccatctcac    133620
tttcccatcc tttcaccctc caatctgact atcagctaat ccaagtattt attatttaag    133680
tacaccatta ttccagatgg agaaactgaa aaaacaatca aaacggataa actatgcaac    133740
ctttgttgaa tttatattct ttatgtaaat acaaagctac aagaaggaga aaataaatca    133800
ttacaaaatt cttcttcata acatttgttt attttcccaa caacaatgat ttatataaat    133860
taccttgtag agctcttttg agggttagga aggcaattat tcttgtcact gtcctttacc    133920
agcttatcac aaaggcctac attattgcca agtaatttac tcagtaaatt attattattt    133980
ccattggttg tggcccatgc caccattgga gtttataagt tattactagt ctacaatgaa    134040
ataagtatag agtctgtaaa tatttagaaa ttcatttttt aatttattta aagtactgat    134100
ttgcagttca ttaaaaacag atggttttc accaaccaca tatatgtaaa gaacactttt    134160
caaaaagacc attttctcct taaagaggtc aaacaatagg aaataaaggg gcagtgtgaa    134220
cagcatgaaa caaatttaag tgttgcatat atactgcagc ttattctgtg atcagttagt    134280
cattgcaagg aactgagctt atatcataac aaagaatgtg agctttgagg gctacctgga    134340
caactgatct ctgtaatggg aagtagcctt aatctgatgc tgtgctcttg cagctgtggt    134400
ctttgcataa tgagaacagt ttaatatcct ttttgcttct tagagtttcc ttcttgccag    134460
aagagtcata tgttagttag catttgattc aaacattgct gagaagctga gtgatcttgg    134520
ctctcgactc aacctgaatt ctgtgagaat gtatacttta ctgaacatgc ctgtatctta    134580
tcatcaggcc tgaacttgac actgctcatt ccttaagggc agaatccatc tgcctcttca    134640
atgccggggc ccaatccctg gaccttgtac atgctagaca actgtacatg ctccaccaat    134700
gaggaaataa gttagtcca gggacagtaa gtagtgttag gcctattttg agtaaacttc    134760
aagtttgtat ccatattcaa aagtacatcg ggcagcaggt ccctgcttct ggtttgagct    134820
gacgtgcatc aagatagact gttttttactc ttccttgact ttaaatggac actttctccc    134880 ttttctcat tagtaaaagt cagtggtcaa tgaagcccac atcaggaata cagttctgta    134940
tggccagttt ctgatttcag ttgcagatta tgatgagttc cagatcagtt ccagatagtg    135000
atgagaattc ggagtgtgta aacaggctta cgtggctcca tgagaagaga acccattcca    135060
ctgctttctg tccaaggagc agtgctgatt ggataatagg tgctatcctt ggtgcaagag    135120
taatgccatc actttctcct tctaggtggg gctcttagga agaactggat caggaaaaag    135180
tactttgctt tcagcatttt tacgaatgtt gaacattaaa ggtgatatag agattgatgg    135240
tgtctcatgg aattcagtga ccttacaaga atggaggaaa gctttcggag tgataacaca    135300
ggtgagcaca aaaatgtaaa aagcaatacg aattaacatt tttatcatta tttgacatac    135360
ttaagaaatt catatcactc tgcaaaatat atttggtggg tcctaccatc tcgtctactg    135420
tgcaagagaa ctgtagcata tggaatgaga gtacctccca atgtctggaa ttctgcgtgg    135480
tgtatatttc ttaaagtgtt ttgatagtgt tctcccaaag cacaatctgt aacagcagcc    135540
tgggtagttc cttgtgcagg cttcctagtc ttgcttaagt acttgatctc cgagggagtg    135600
atagcagcct gtagataaat gctttgcaag atgtggaaga tgcttctgag atcataagct    135660
ctcggaagca ggacatagtg gaattgaaag ttgaagtgca gtgatgtttt cccttttggag    135720 tctgagtagg aagaagtatg tcaggtcaat ctagattctt ataaagggca gtgttgatt    135780
```

```
caggcagtac agcatctcga acatcgccat ttagtgctat tctgtctgtg ttactgcaca   135840
tgctgatttc ttgtgtagag gagaaacggc aatggttgcg ggcaacatga cccaaatgtg   135900
aaccaagaga tgctgaagcc agaagaattg cagtatttct gctgctgttg gcccttttct   135960
ctgagacttt tcctccttt gtgctactag acactaaatc caacccacta agatggctct    136020
ttgaagcact tctgtatttt taacacaaaa ttaacattcc gggactatca ccaggtagac   136080
caactacaaa gctagaccaa gaaaatgctt gtacttcttg ataaatgatc ttcacagaac   136140
atttgctcct ttcaagtggt gagacaatag atactgtaac caccaaactg atgctttcaa   136200 tttgttcta tggtgtgcca ttttttcaa atgcttcatc ttggctgaag ttgtggaaac     136260
actgtgtgtt caaaacaca aaagggattg tcagatggcc taaagaaaaa gaaacgctag    136320
gagtacaagg ttcctgaggt gagagcacta gtcgagtaaa aatgctaagg ccagtggaag   136380
ggtgtggttg tctgagaagc actgctgttg gacttgccca ggtcctgtgc tgccagttga   136440
actaaagcag ggtaggcttt gccttggttg ctcttgttcg aacacattgg cctacaagaa   136500
gcgtcaacct ctaaaacttc tatcctcttg ctcatcatcg tagctgctac acaatagaag   136560
ggctccgtct tcctcactag ctctgcttag gagcttactt atgccaggca cagagtacac   136620
tgcagtgggc cagagctgga aaatctcccc tgcctttctg cctaaatgac tcttcagact   136680
tgactcaatt catgtctgct cttttatgga ttcaaggctt acatttaaaa aaaaaaaaa    136740 gaaaaaagga aaaaaaaag tgtgttcagg gcatccttca gaaatactga agggtctctg    136800
gaacatcagc cagcatggtt aacatgtctc agtgacaatt tttgaatgtc atgtgaaacc   136860
taaggaagga aggagagaga gagagagaga gagagagaga gagagagaga gagagagaga   136920
gagagagaga gcaaaccaag tccttatatg cttgatgtct aaactacggg ttactttgct   136980
tttcctatct tttcttggaa cgtgaggatt gcagcatgct tctcctttcc ttagaaagat   137040
aaaagaagga gaaagtgaa tatccacaga aaactaacta gtttggtctg cttttttcatc   137100 ttttcttttc tcctctgtct cctttaacaa ggatgtactt cagaaggtcc cacactgagc   137160
tagtgtaatg ttaaaggttc actggccact ggttctcaga tacatgaaac aggtattttg   137220
aaaagtaccc tcttatacag agatccaaaa gcatttgctg ggcagtcaca aaaggtcctg   137280
ttggtttgga cggttcttaa caatttttc cctcctttta tagtttagta actacatagc    137340
aatctcagaa tacgtgcagc ccagaattca gactatcatg tgcattccaa aacagagcct   137400
ctttcatttg ttctgagtca agcagagcag gcagtgaagc cgatagatgg catctgattt   137460
actttggcaa ttagagcacc aagaagaaag caccactaa tgctgcgcct ggctaggcag    137520
ataattaata aaaagcaact atttaaagc ttcagttaca attttggaag gctgtaagtt    137580
cttctgagta aaggactaga agttttcct tttgttgatt actattgtat gtggtatgtg    137640
tctgagagga ggggagaatg ggtggggtat tcatcacgtc atggctcact tggagaggtc   137700
agcacacaac tttcaggaac aagttctccc cttccagcat ggcatttaga cactggattc   137760
aggtcatcag ggctgtgtgg caagcgtgag ttatccactg agccatctca ctggctcctt   137820
ttcttaatga attgaaaata ctcaccatcc acccatcatt ctcaccacag acagaggtga   137880
ggcatctttt gttttgaaag agatcagaca gcatgtatag atataaacag tgaaattggt   137940
ggtgacagct taaaattcac tatataaaat aattacatct tgtgcttaca attataatat   138000
cacagtcatt ttatttatat caatgtaga gatactactt gccattaata tgccagaaa    138060 gttccagtcc aacctgtaaa cttctaatga gaaactcaaa acgatgttca tagtcgtgtg   138120
```

```
acagaaatta aaaacagaaa cagtaaagcc aaagtgagtg gctgagagtt agtaatgaaa   138180
ccatagctgc ctgtaagctg tgggctaaca agggagtata taggcagaga gaactgtcca   138240
gattaagcta gctgtcactc ctgccagtac atctgtgtct ttcctgtcct gctgttttgt   138300
ctcccttctt ttcttgtttt ctctctgatt gcagaaaaca tgtaactgtt tactggttag   138360
acattatgaa ttgaggggtt ttctttcttt gtttgttttg ggggtatttt tttaacacaa   138420
atactttgct tgactgccca aacccagatg ggatctcaaa ccttgcttat gtatttctgc   138480
gtgtagttct aatatgtctc attttcaaat tatccacata tctcccttaa ttatgcaaga   138540
tttaaacaga gtgaccagaa aatggaagca gagtttataa aagaaggata gaaatacata   138600
gtaaaatact tttcttctga gttttctccg ttgtaagaca tctaacataa caccttggat   138660
gagaagaatt caaagacag tgttctatgc tgaatcatta aatgttgctg tctctcacat    138720
gtgtggttct ttcagcattt ggaccctaat ctgtataatc ttaggacagc tatataattt   138780
ctctgtcata gtttccttgt ttgtaaaatg agtatagtaa taataacaat tatttgtact   138840
ttggggaaa ttgaacgaga aatacttaaa cttttacttc ccacatggct tgataattat    138900
cctctgttat ggtagttatt attttaatt cagtgggggt ggggagtcat gtctcctctg    138960
tctttctact ggactggggg tatgttctat gaataagtat gaataagtat gaataaatga   139020
gcttgcacaa tttcacaaag aaagttgtaa tgaatacatg ccatagagtg tcataaagtt   139080
tataggttta gaatgattgg gtacatggag ttctaggcag gaagactgtg aacaatcaaa   139140
aggataggtc agtgtgaagg gaaagggaga agggtcagag ggaaccacag cttagagggt   139200
attagacgtc atggcatggt ccagtaggaa ggggctaatt ctcctgggct gaggaaggga   139260
atggagaacg tttggtggca cattgctata tacatgatga actagcaaat gattatactg   139320
tgatgtggtt aattagaact tactgaggta gacagttgga cagagtgtag aattcaaggg   139380
agggcagaaa aataactgtc atgtccaatt ttcaaattag tataacacaa tttagctatt   139440
tcagagacta aactttgaaa cctttgatta tatgctttgg ttagaaaaca ttttatgta    139500
tctttggaaa tgtttatact aaaactttgt agtataaaaa ctgttaggaa gctgggcagt   139560
ggcagcgcat gcctcggcag aggcagtcag atctctgaat tcgaggccag cctggtttac   139620
agagtgagtt ctaggacagc cagggctgca catagaaacc ttgtctcaaa aaaaaaaaa    139680
aacaacaaag aaaaaacaac ctgtaatgaa gcactctgga tttctagaaa actaaacttt   139740
aactatcctg tatgcagtct tttatattta aatcaatagc atatacactg gtagtatagc   139800
aatctatatt tgttacaaac tgttaatagt tcttagtaga aatatgtcat tcataatttt   139860
atagttgggc cacatttcaa gggaactatt catgatgtac acatacatac ataagcaggg   139920
gtagtcattt ctcctattaa tctatttat attaagtgca atcaccacat aagctggatt    139980
acttttttt catttgacat ctagtactat aaagcatatt agctgttgca acgatatatg    140040
gtcagctgtg ggaagtccat gtaggcttag ccacttccac agagttgagg agtggaggca   140100
gcagctgcag ggaggagatg ggacatgtgg ggaacaatga tgatctcttt gttctgctta   140160
gagtctcaag aactgctcat tatagcatac atgacattaa ataaatatca aatatttgct   140220
tgccctaact gacttattag tgagtagttt cttttaaggg cgacagggga tccctgggat   140280
gtgacagctt caggtgcatt ttttaattgg tgcacagcag atctgagagt gccatgctgg   140340
ccaaatcatt ccacttctca gggccttcat tttgaatatg taaaccagag agagagggtt   140400
taggttgacc tccaaagacc tttaggttag acagaggagt ttgaggatga ttaaacagct   140460
taggaaacaa gtaagacctc tgctggcacc gtgaaggcaa gggactgcca gattctcttt   140520
```

```
gaattaaagg aatggaatgt ctgattgatg gtatacaatt gaattctagc tgaaccggtt   140580
tctttagttg attttctctt aaaattggat atgttgtcca ttaccttta ccagacatga    140640 aattatgaag gaaagcctgc aagatttctg agttgtgata aatctaccac acctacagct   140700
tctagattcc tgcagcttc tttccttcat aattttgaat gtgtatctgc ttaaaataaa    140760
ttagttaaaa catcataaat ttagtaaact agtatacatt atagatttta tgactaaaag   140820
ttaaataatt tctgaagcac ccgtaggaat cttcacaggt gtattgggtt gttagtgtta   140880
cacttaaaga actgtgatag ctgtgagcat ttgggtcaca tttagagatc tctctctgtc   140940
tctgtctctc tctgtctctc tgtctctcac acacacacac acacacacac acggagaggg   141000
ggagggagga gagaaaaaga ggaggagggg agggaaggat gagagagaga actttattag   141060
ccagaaaaat agccttatag aagttaactt tcaaatctga ggaaaaacag catttactct   141120
gattgttatt attttctact tttacttctt cacgtctgct cactcatttg ggacttttgc   141180
tgagcttatt caaaatttgc atctaaaaaa gaaagtaaag acatggcctt cgacactcat   141240
agatatccac ggacttagta attttctttg atacacacta ccgagattgg gctccatctt   141300
catatgtaac aaagaataac tctgaaactc taatcctctt ttttctattt cctgtgtgtt   141360
ggaattaagg gcacatacta cagtgccaag tttatatgct tctgggataa gacccaaggc   141420
ctcttgcaaa ttaagtaagc atttttttgcc aactgagcca catccccacc aactaaactt  141480
ggtgttattt aaggaatgaa agtataagaa ataattgggg agcttgtttg gtctgaggat   141540
aaggaacagt gcccctagga aatgaagctt gatttgaaac ctgaaggata tagattgttg   141600
tgtgaagatc agggaggata agatttccag ctgagaagaa aacttaggtg actaagctaa   141660
gaaagtgtgt gcttagaata gaatggagtg gaaaggagcc ctgagatctt gggaccatcg   141720
taaggatatt gtacccttag tgaaggggaa agtcattgac attttttcatg aattacttgg  141780 gtatattgta agagaagcaa aagtataaag aagaagatca attttaggaag ctcctgcagt  141840 gacacaaaaa ggactagtga tagtttggca tgttcagtgg gaacagaaat tgagaaagaa   141900
attgatttga catatagttt gaggataata taaatgacca atgactcatt tttaagataa   141960
gctgaggaat aagatgaatt atgagtgact ctcagttcct gatgtgcact gagatggaga   142020
tgcagaaagg acaaaagtag ggtggcattt ctctgctta caaagcatgg ggatgaaaga   142080
gactgggttc ctatgagcaa ctgtctgttt taaagataaa acatcttgtc cattcctttc   142140
attcttccgg gataatgaaa ttattctgtt tgtcccaagt aaatatttct attgtatatt   142200
tcaactaaat atataactct ttcaaagtta cagagatgca accaaaacaa taagaggaaa   142260
gaaaattatt ttagacattg acatcaaaaa tttttgcca gtcttgtata tataaagagt   142320
actaaatatt atttttaaaa tattattacc tgagatctct taagacagtg gttttctctt   142380
aagcacatgg tccacctaag tggaagtgtt actgcaagtg gagcatcttg acaatggtca   142440
tacagtgcta tttgcacacc agagcatctg cctcttccct agcacacatg ccctgaaca   142500 aacggttgat ctatgatcac atgggtttct gagttgtcct ttcagcttct ctttgttcat   142560
agaagtaaga agatgtgtaa agggatgtta gtagaagaag agtctcaatt cttcccagag   142620
cacagtggcc tcaatttcct tatctcaagg gcattgaaat aaaaaaatc caaaagagt    142680 tttaaatgtt gccctatttt tctttaaaat gatgtaaagc aaatgtagaa aagtatgact   142740
agctaatggg taccatagat gataggcagt tttacacatc taccagtgtg tgtatgtgtg   142800
aatacagaaa tgcatgtata ctcaccttgt agcacagtgc tctagtggat gctcatttgt   142860
```

```
tccttttcttt acttgaaatt ggtttgaata aagagaaaaa cattaaaaga tgtataggtt    142920
atttatactt tctaattatc tttaccattg cagaaagtat ttatcttttc tggaacattc    142980
agacaaaacc tggatcccaa tggaaaatgg aaagatgaag aaatatggaa agttgcagat    143040
gaggtaagga tgacaaataa agtagtttta aagaagtaga tcatacacac aagtgtggtt    143100
gccatagatg ataggcagtt ttacacatct actggtgtgt gcatgtgtga acacagaaat    143160
gcatgtatac tcaccttgta gcacagtgct ctcatttact ggcacatcct tgtcagaacc    143220
tttgactcat cccccttttca ggagtgtcgc tcctttccat atactctatt cgtggtgctt    143280
tactaaagtt ctatagaccc ttgctcctag acgacgtatg tttctctcac tattttgaag    143340
actgagaagt ccaaggttaa ggagccagca gacagtattt actatctgct aaggccctac    143400
ttgctgtcac tcccgaggtg ttttctgca cctcactcag tataagtggt cagtgagcgc    143460
tgtggagcct cttttcatta tagtgttaat tccatctatg gggtactcag agcccatgac    143520
ctaatcactt cctaaacatt ttattttatg tctcagtagc actgccttgg acagtcaggt    143580
gttaacatga gtttctgaag acatgcggac ctagaactcc ctccttttcct ccctccaag    143640 ttatgtcttg ttcttatgaa aatagattac tccacttaaa caaatgccaa agtcttaaca    143700
cattttggtg tcagtgtaca actggaaatc acaaagtctc aattcagcca ccatgagact    143760
tgggacttta ggttttttcat gttggcattc caccattccc tgcactttgc ccattgttgt    143820
tcccttgatg ttcgctcttc ggcctccccc agaacagatc ttgccaggag ctttgaagcc    143880
tctgagtgct aaatgctaac cccttgagta accaaccctta accttctcct aataaaatga    143940
actgagatta accgtttttc attatcaggg tttccttatt acccagcaaa cacaaggttt    144000
ttaaagaaaa cattaactaa attgctagtg atatactgta agatccttga tgtacttta    144060 cagagtgacc tgtcagaata cagtgtgctg ggagagagct tgggaaagaa ggaattagcc    144120
tttgtaaagc ttaccaggta ttgccaagtc tccataaaat ttgcaggaaa ctgagatcat    144180
aaaatcatct aaaatgttag gagataggtt tagaagactt tagattccag aataatacag    144240
gtagttatgt gattagattt tgtctaccag tccatctttta gatgtacgtt ttcattggat    144300
tctcttttta aatttatgtt cataaagatg ctgctcctga gctaaccgta atgtcccatg    144360
gtttgagtaa gagtgacaaa ttttttgctg aagagtccac aaagaaacat aaacaccaac    144420
ccctagctta cagcagcagg caggagattt aggttaaagg caggaatcct aggctttaat    144480
cctgtatggt tgatgatcca atatagtcaa ataggaacac gttgaggtgt gtcagcctac    144540
taaggcacta ggacaaaagt ctaaccttcc tgccctggtt catggcagct tgctgcccta    144600
ttcagctctg gggatctttc tttttttttt taatttttttt atttaaaaca attttttaaa    144660 tatttttat tacatatttt cctcaattac atttccaaag ctatcccaaa agtccccat    144720 accctccccc cccacttccc tacccaccca ttcccatttt tttggccctg gcgttcccct    144780 gtactgggc atatacagtt tgcgtgtcca atgggcctct cttccagtg atggccaact    144840 aggccatctt ttgataccta tgcagctaga gtcaagagct tcggggtact ggttagttca    144900
taatgttgtt ccacctatag ggttgcagat ccctttagct ccttgggtac tttctctagc    144960
tcctccattg ggagccctgt ggtccatcca atagctgact gtgagcatcc acttctgtgt    145020
ttgctaggcc ccggcatagt ctcacaagag acagctacat ctgggtcctt tcgataaaat    145080
cttgctagtg tatgcaatgg ctttctaaag gctgcatctt tagcctactt ctcacccctc    145140
cctgtgctgc tgctgacag ggttcctgtt gtacactgac tgcttaaagg acctttatga    145200
tttggtcttt gctgctctac tttcagcccc agccccatg tgtcctgtga gtccactact    145260
```

```
gtgaatttta attttcttta gagcacagtg tgctgctctc tgttctatgg tacgggttgg  145320
ggcagttgtt tctgcttttt accttctggt ttctggacct gggaaaccct tgcagagcac  145380
tactcctgct ccttctcacc attcaagcct tccttcacac atcactttgt tctgaactcc  145440
atcctgaccc tcctgctttg ggaaaagaga cttttcctagg tatagctatg cctcggctcc  145500
tcaaaatttc ctacactgaa tcaaaattca cctcttggct actccatatc tcctatgatt  145560
atggaatcat gccctgctct ctgttgttcc tgcagtagtt ggatccctgg gtggtttttg  145620
ataagtactg actgaatgat ctgagcaagt aaagaattct tttaactcat gtaaaatatg  145680
ttgtgaaaat atcctcatgc ttaatgccca atagacatta ctaccttcat ctcagtaaag  145740
gtcttgcaag atggctggcg gattctgaaa agaactgcag ccctgacttg gggccctctg  145800
ctgttttagc cctactaagc tatgtgatct tggccccttg actctggctc ttagatgtgg  145860
ggactttgtt tgtttgtttg tgtttcctta ttagaataat ttttaaattt atcatcttta  145920
catcctaata gtcaagggaa ctgttgtaga gacaatttaa atagcagaaa cagggaccct  145980
gtaagtggga catttccctg agaagtttgc agaatggaaa cacaaggagc tgagggtatc  146040 cattttttaca ttgcccacta gtgcttacag gcaaagcata atccacctttt tttactgaaa  146100 aaaaaaaact gtcatagaaa acaaaaatcc tacaaatact tctgagtagt ttggtataga  146160
gtactgattt atctaaacat atttgaatac ttttaacttt gttatttgat ggatggtcat  146220
agagttaaag atttacagag tacagtatat aatttctgag ctaaaactag cactaattca  146280
ttcattctta agttctaatg cttaaagact catagtacat attaaatgaa tgactgaaag  146340
gaagatgaat gaatgaatga atggattaat aaatatatga atgaatgaat gaatgaatga  146400
atgatgaatt gttgaggctg agagtgttcc taactgaaaa acacatattt gctttcaaga  146460
aatgtatggt ctaacaggga aaaaatacac aattctaata caggatgcct ggctgtcctg  146520
tgggtaggca aggatattta agagagtaat cagactgagc agaaggacaa accctgagaa  146580
tgttaagctg tataaagaat taaaagttga tgctgctgga cacagtagta ggtgtgtgtg  146640 tggggggcgga ggaggtcagg atgtcctgtg ggccacatga gaacaattat attttatttt  146700
tccagtaaaa gaacttctgt aggatttaaa acagagaaat gatccaagtt caaacctgca  146760
ttttagggag agctcttaaa tatttctgtg acatgttgac aatttgactc attgatactt  146820
gcagtatgat gtttaagaaa tgacagaagg ccagacgagg atcagtgtgc cagaactgac  146880
aaaaagaacg gtttcagaaa ccctggggga acttctaggc tggagagagg cattgaaagc  146940
cattagctta aacatacaca ttgatgccat gtacataacc aaaatctgga cacaggaggg  147000 gagggggacat tggtgttgaa acctgatatg gatgggacaa agctgtatag tatagtatcc  147060
cctgtgatac accaggcagt cttccttgtc ttctgtgcct acattcccta ctatctcagg  147120 aacctttttaa acattaacga gtttacacaa agggtagttt taacaagcca catgtttgaa  147180
cttccataat gagcacataa gagtctggca ttaacaatga tatgagccac ttctgaactc  147240
atctccaaaa tcatgaatct ttcttaaggc cttatctaac tctgcacatg ttagagtgat  147300
atgggtatat atcttacctg tacatacaaa attccagatt catgaagcac aagaaacaat  147360
cctgtctgta tttatttaac tcttatacac ctagtggttc ttagcaaaga agacacaatg  147420
tacatgtatt gaataaggaa aaaccaccaa gacatctata attatgcctt aattttgaca  147480 gactacttttt tgatcttttt attaaacccc ctttaaaatt gcagtttaaa aatataagcc  147540
attaattcta aaataatctt catattctac cctaacaata agagccttta aattttagtc  147600
```

```
gtgttccatt tttaactaag taacttctta ctttatgaga aagttatcag tttctcagat   147660
tttataagtg aaggagataa gtattatgat ggcatgattt ttttaaagcc tcctcagcta   147720
attttcatga tatttctcat cctgtattac agatagaaga tgaacatgtc atgctatgtt   147780 ttctacccctt tctgctcttg aatcctttgc catcagttat aatggagtga ataactgtgt   147840
tctctatctg ttatctttaa agcccatatt gaattgtatt gcaattgcat ctatccatct   147900
atctatatct gtatctgtac ctatccatct atataatgtg acaggaatag gtataattgt   147960
ttatcactgc tagggaacat gacacttaca aggtgaacac tgaatgattt tgtaatcaag   148020
tgtggggctg aaagaaatcc tccagtctgt ttagagctac cgatattatt gccagatttt   148080
ggttactcaa actaagtagg agttgggagt tgagggtgat gtgaaattta ttctgtgcaa   148140
actcatgtct gcttttagaa tgcaagcctc ttaagtgatt ttagttatgc cccttctaag   148200
cacagtgttt ttcttttattt tctacaggtt ggactcaagt ctgtaataga gcagtttcct   148260
ggacagctca actttacccct tgtggatggg ggttatgtgc taagccatgg ccataagcaa   148320
ttaatgtgct tggcccgatc agttctcagt aaggccaaga tcatactgct tgatgagccc   148380
agtgcccatc tagaccccat gtaagttcca aaaatcttta gataatcatg caatagaagt   148440
agagtccttg aagttacctc atattggtac aaattcccat tcagctacca cacctacaag   148500 taggggggtac aaaataattt tccaggggaa aaatcactat ttaacatgag cacaagtact   148560
tttttttttt tcaacaagag ctttgttttt cctcctgact ggagtctgga atttataaac   148620
ccttcaacct cattaacaca taataaatac ttagttaggt atgcacacac ttatggcttc   148680
cctctgtatc ctatttatat cataaataca ttaacagcac aaaataaata actgatgctg   148740
aatctacata aaatgtagtc tcatttttat gaaattttct tctaagcatt tgctttatta   148800
gtgtatgaaa ttatattaaa tacttagaat ggcttaaaag ctgattgtag ctcattctgt   148860
atcatcatta tcctaaaagt attttttaagt aaagaattaa gtccatagaa tactatacgt   148920
attgtcaaag ataaaggcag aaaattcaca ctctataatg tcttatgtgg tattttcttg   148980
ctttgctaga acataccaag tcattcgacg agttctaaaa caagccttcg ctggttgcac   149040
agtcatcctc tgtgaacaca ggatagaagc gatgttggat tgccagcgat ttttggtaag   149100
tcatttacac ttgattgata tctcattctc catttattta aataatcctg cacagctgga   149160
tttgcacacc ctttcttcac acttatgtca cacatttacc acctaccctc agtctctttc   149220
cctggacttg agctatgaag tggtgaggaa atttagcaca cttctctggt atcatatcac   149280
taaacgacac tgtagataag gtaactatgc tttcagatct tttgtggcga acaagtcaca   149340
aaatgtacaa ttgaaaaaaa aaatgtctgt ttcttacagt aactcagctt cccatgggga   149400
agataagggt gggccttacc attagtggtt caatgtagta ggagagaagc ctgttccatc   149460
atccccatta ctactggaac tcagggtagt gtccctgtca gacaccttct cattctcccc   149520
ccgcccccaa aaaaagtca ctgttcctgt ttagacatgg gaagttccaa ggatcatgta   149580 aaattttttac tttcccaagg cttttgaata ttctggaggt aaatgctttt ttactgaagc   149640
acttttgatc ctattgttat tgcccagtta caagtgccta gagagtagat gcatctcttg   149700
ttctgtggtg gtcaagtaca gggactaggt aaggggctct actctctgac ctcaagcttg   149760
caaacagttt aacatgcact gaaggcgtta ttctctgtca ttcctggcca atttgaaacc   149820
tttcggcctc aaccccaggt atgaggaagc tcaaagttaa tggttatata tagctcggtt   149880
taagagtgcg tgggtcattg attattttgc tttgcaaagc tccttcagtt cctcaactgt   149940
tctctgaagg atggcaacag ctagtattac attaattttt caaatcccta tcgctacttt   150000
```

```
cccggatgtg aaagctaaga gaaaagtaca agctctgaat cctgtgcttt ctttggactt 150060
ttgttcttct ttgggcctgg ctcagtttat gtgtcagcac tggcctgctc ttcactcaga 150120
ggtctcacta atgccctctc ccttaggtca tagaagagag caatgtctgg cagtacgact 150180
cccttcaggc acttctgagt gagaagagta tcttccagca ggccattagc tcctcggaaa 150240
agatgaggtt cttccagggc cgccactcca gcaagcacaa gcctcggacg caaattactg 150300
ctctgaaaga ggagacagaa gaagaagttc aagaaacccg tctctagtgc tgggatgctg 150360
aggaagcaac tcagtgcact gagtccattc ccagaaccca tgcagaatga aaaagccag 150420 gcatttccca tgcttctaac cccagtgctg ggacacaga gacaggtgga tccctggggc 150480
tctgtggcaa gtgatcctag cccacaaaga gagttccagg ctgggcacct gagggacaat 150540
acctgtggat atactcttgc ttccacatgc aagtacatat acacatgcat gcacattagt 150600
ggacatacac acagaaaagc aaagaagaag gaaagaggga agaaaatagt gcaaataatt 150660
gcaaaacgat catgtatgga gtctgctcat ggacttagag gaggtgaact ctactacctg 150720
tgcctttgaa agaagggtga agcctgcgac ttgctcttta agagactgtt ttggaagaga 150780
gttcaaaaac gttcatatgg gtatgggtaa ctgactttcc agcagtagtc aaattgtttg 150840
aacttcagat agttgataat gaccacttgt gtattgcaag gcagattttt ctgaaaacat 150900
ttgcccccta atagtagctg aaaaagcagc tataaatgcc aaccaggtta gtcattcggc 150960
ttattgttca gtacagctgg ttaatttgca ttattgaaga actgaaatta tagtgcttag 151020
atataggaca aagtaaagag aactaaaaac agtgtcttat ataactcaaa gcccaactta 151080 cttttcctcta agatatgtat tgccttctat acattgtctg ccccattcca agcaaatgtt 151140
agaatattat acaaaatact gggtggtatt gattgaaaga tgcccgacat ctggtgatct 151200
agtaacccat caggattaag gatatccagg tcttggaaat taaggttaag accatctagc 151260
cttactaccg tacagctaaa cattcttatt accagaataa gacctaggaa aagaactgtt 151320
tcagtcccat aaagtggcct ggataatttc cttgatatgg aaatcgacac acttatgttc 151380
ccagaaagca acagatcttt aagacttctg aagtgaagga aggttgtgtt agtgcaaact 151440
agtgcagccc agtgccaggt ccaggagtta acatgtagac aggccatgga ctgtgtgggt 151500
agatgctcat ggaaatgtgc agtagtatgt tcatgtgctc tcagctagct gtgtgtactt 151560
caaactgtct ccacagagtt gttggggaga cactctgaaa aagaattaat tgtgaattag 151620
ttttatatac tttgttttat aatttgtgat gcaaatgaaa atttctctgg gaaatattta 151680
ttttagtaat aatgtttcaa actcatatat aacaatgctg tattttaaga atgattacat 151740
aatgacttat atttgtataa aataattttt atatttgaaa tgttaacttt ttatagcact 151800
agctatttta aaacagggga gtgaggagga cagggatgat aaggatcatt caacttcatg 151860
ttgtgaagac gagctgatgt aaatcttgta cccatctgtg tggttctcag acaacacatg 151920
ctctctttta atgcagcttt gaagaagatg gtaccaaagg ttaagacggc ccctgatgg 151980 gcacatcaac ttctgaactg caaactaagc tttagaggaa tgtattatat ttattactgt 152040
aatagaatat catgtgtcaa taaaatcctt ttatttgtgt ga                152082
```

<210> SEQ ID NO 148
<211> LENGTH: 6305
<212> TYPE: DNA
<213> ORGANISM: Mus musculus

<400> SEQUENCE: 148

```
aattggaagc aaatgacatc acctcaggtc tgagtaaaag ggacgagcca aaagcattga    60
cctggtcctg gatatccaga tgtcgagtcc aacctgaatt tagccgaaca cagacctcat   120
tgcctcacgg agacatcatg cagaagtcgc ctttggagaa agccagcttt atctccaaac   180
tcttcttcag ctggaccaca ccaatttga ggaaagggta cagacaccac ttggagttgt    240
cagacatata ccaagcccct tctgctgatt cagctgacca cttgtctgaa aaactagaaa   300
gagaatggga cagagaacaa gcttcaaaaa agaatcccca gcttatccac gcccttcggc   360
gatgcttttt ctggagattc ctcttctatg gaattttgct atacctaggg gaagtcacca   420
aggctgtcca gcctgtcttg ctaggaagaa tcatagcatc ctatgatcca gaaaacaagg   480
tggaacgttc cattgccatt taccttggca taggcttatg ccttctcttc attgtcagga   540
cactgcttct tcacccagct attttggcc ttcatcgcat tggaatgcag atgagaacag    600
ctatgtttag cttgatttat aagaagactt taaagttgtc aagccgcgtt cttgataaaa   660
taagtattgg acaacttgtt agtcttcttt ccaacaacct gaacaaattt gatgaaggac   720
ttgccttggc acattttata tggattgctc ctttacaagt gactcttctg atggggcttc   780
tctgggactt gttacagttc tcagccttct gtggccttgg tttactgata atcctggtta   840
tttttcaagc tatcctaggg aagatgatgg tgaagtacag agatcagaga gctgcaaaga   900
tcaatgaaag actcgtgatc acatcagaaa ttattgataa tatctattct gttaaggcat   960
attgttggga atcagcgatg gagaaaatga ttgaaaactt gagagaggtg gagctgaaaa  1020
tgacccggaa ggcggcctat atgaggttct tcactagctc tgccttcttc ttttcagggt  1080
tctttgtagt ctttctatct gtgcttccct acacagtcat caacggaatc gtcctacgaa  1140
aaatattcac aaccatttca ttctgcattg tcctacgtat gtcagtcaca cggcagttcc  1200
ccactgccgt acagatatgg tatgattctt ttggaatgat aagaaaaata caggatttcc  1260
tgcagaaaca agagtataaa gtactggagt ataacttaat gaccacaggc ataatcatgg  1320
aaaatgtaac agcattttgg gaggagggat ttggggaatt actggagaaa gtacaacaaa  1380
gcaatggtga cagaaaacat tccagtgatg agaacaatgt cagtttcagt catctctgcc  1440
ttgtgggaaa tcctgtgctg aaaaacatca atttgaatat agagaaagga gagatgttgg  1500
ctattactgg atctactgga tcaggaaaga catcactcct gatgttgatt ttgggagaac  1560
tggaagcttc agagggaatt attaagcaca gtggaagagt ttcattctgc tctcaatttt  1620
cttggattat gccgggtact atcaaagaaa atatcatctt tggtgtttcc tatgatgagt  1680
acagatataa gagtgttgtc aaagcttgcc aactacagca ggacatcacc aagtttgcag  1740
aacaagacaa cacagttctt ggagaaggtg gagtcacact gagtggaggt cagcgtgcaa  1800
ggatttcttt agcaagagca gtatataag atgctgattt gtacctatta gattcccctt   1860
ttggatatct agatgttttt actgaagaac aagtatttga agctgtgtt tgtaaattga    1920 tggccaacaa aactaggatt ttggttacat ctaaaatgga acacttaagg aaagctgaca  1980
aaatactaat tttgcatcag ggcagtagct atttttatgg acattttct gagctacaaa   2040 gtctacgtcc agacttcagt tcgaaactca tggggtatga ctttttgac cagtttactg   2100 aggaaagaag aagttcaatt ctaactgaga ccttacgcag gttctcagta gacgattcct  2160
ctgccccgtg gagcaaaccc aaacagtcgt ttagacagac tggagaggtg ggagaaaaaa  2220
ggaagaactc tattctaaat tcattcagct ctgtaaggaa aatttccatt gtgcaaagga  2280
ctccattatg tatcgatgga gagtctgatg atctccaaga aaagagactg tccctagttc  2340
cggattctga acaggggag gctgctctgc cgcgcagcaa catgatcgcc accggcccca   2400
```

```
catttccagg cagaagaaga cagtctgttt tggatctgat gacgttcaca cccaactcag   2460
gctccagcaa tcttcagagg accagaactt ctattcgaaa aatctcctta gtccctcaga   2520
taagcttaaa tgaagtggat gtatattcaa ggagattatc gcaagatagc acactgaaca   2580
tcactgaaga aattaacgaa gaagatttaa aggagtgttt tcttgatgat gtgatcaaga   2640
tacccccggt gacaacatgg aacacatacc tacgatattt tactctccat aaaggcttac   2700
tgctagtgct gatttggtgc gtactggttt ttctggttga ggtggctgct tctttatttg   2760
tgttatggtt gcttaaaaac aaccctgtta acagtggaaa caatggtact aaaatttcca   2820
atagctccta tgttgtgatc atcaccagta ccagtttcta ttatatttt tacatttacg   2880 tgggagtggc tgacactttg cttgccctga gcctcttcag aggtttgccg ctggtgcata   2940
cgttaatcac agcatcaaaa attttgcaca ggaaaatgtt acactccatt cttcacgccc   3000
ctatgtcgac catcagcaag ctgaaagcag gtgggattct taacagattc tccaaagata   3060
tagcaatttt ggatgacttt ctgcctctta ccattttga cttcattcag ttggtgttca   3120
ttgtgattgg agctataata gtcgtctcgg cattacaacc ctacatcttc ctagcaacgg   3180
tgccagggct agtagtcttt attttactga gggcctactt ccttcataca gcacagcagc   3240
tcaaacaact ggaatctgaa ggcaggagtc caattttcac ccaccttgtg acaagcttaa   3300
aaggactctg gacacttcga gccttccgac gccagactta ctttgaaact ctgttccaca   3360
aagctctgaa tttgcacact gccaactggt ttatgtatct ggcaaccttg cgctggttcc   3420
aaatgagaat agacatgata tttgtcctct tcttcattgt tgttaccttc atctccattt   3480
taacaacagg tgaaggagaa ggaacagctg gtattattct aactttagct atgaatatca   3540
tgagtacttt gcagtgggct gtgaactcaa gcattgatac agatagcttg atgcgatctg   3600
tgagcagagt gtttaagttt attgatatac aaacagaaga agtatgtac acacagataa   3660 ttaaagaact acctagagaa ggatcatctg acgttttagt cattaagaat gagcatgtga   3720
agaaaagtga tatctggccc tctggaggcg aaatggttgt caaagacctt actgtgaaat   3780
acatggatga tggaaatgcc gtattagaga acatttcttt ttcaataagt cctggacaga   3840
gggtggggct cttaggaaga actggatcag gaaaaagtac tttgctttca gcattttac   3900 gaatgttgaa cattaaaggt gatatagaga ttgatggtgt ctcatggaat tcagtgacct   3960
tacaagaatg gaggaaagct ttcggagtga taacacagaa agtatttatc ttttctggaa   4020
cattcagaca aaacctggat cccaatggaa aatggaaaga tgaagaaata tggaaagttg   4080
cagatgaggt tggactcaag tctgtaatag agcagttcc tggacagctc aactttaccc   4140
ttgtggatgg gggttatgtg ctaagccatg gccataagca attaatgtgc ttggcccgat   4200
cagttctcag taaggccaag atcatactgc ttgatgagcc cagtgcccat ctagacccca   4260
taacatacca agtcattcga cgagttctaa acaagccttt cgctggttgc acagtcatcc   4320
tctgtgaaca caggatagaa gcgatgttgg attgccagcg attttggtc atagaagaga   4380 gcaatgtctg gcagtacgac tcccttcagg cacttctgag tgagaagagt atcttccagc   4440
aggccattag ctcctcggaa aagatgaggt tcttccaggg ccgccactcc agcaagcaca   4500
agcctcggac gcaaattact gctctgaaag aggagacaga agaagaagtt caagaaaccc   4560
gtctctagtg ctgggatgct gaggaagcaa ctcagtgcac tgagtccatt cccagaaccc   4620
atgcagaatg aaaaaagcca ggcatttccc atgcttctaa ccccagtgct ggggacacag   4680
agacaggtgg atccctgggg ctctgtggca agtgatccta gcccacaaag agagttccag   4740
```

-continued

```
gctgggcacc tgagggacaa tacctgtgga tatactcttg cttccacatg caagtacata      4800
tacacatgca tgcacattag tggacataca cacagaaaag caaagaagaa ggaaagaggg      4860
aagaaaatag tgcaaataat tgcaaaacga tcatgtatgg agtctgctca tggacttaga      4920
ggaggtgaac tctactacct gtgcctttga agaagggtg aagcctgcga cttgctcttt      4980
aagagactgt tttggaagag agttcaaaaa cgttcatatg ggtatgggta actgactttc      5040
cagcagtagt caaattgttt gaacttcaga tagttgataa tgaccacttg tgtattgcaa      5100
ggcagatttt tctgaaaaca tttgcccct aatagtagct gaaaaagcag ctataaatgc       5160
caaccaggtt agtcattcgg cttattgttc agtacagctg gttaatttgc attattgaag      5220
aactgaaatt atagtgctta gatataggac aaagtaaaga gaactaaaaa cagtgtctta      5280
tataactcaa agcccaactt actttcctct aagatatgta ttgccttcta tacattgtct      5340
gccccattcc aagcaaatgt tagaatatta tacaaaatac tgggtggtat tgattgaaag      5400
atgcccgaca tctggtgatc tagtaaccca tcaggattaa ggatatccag gtcttggaaa      5460
ttaaggttaa gaccatctag ccttactacc gtacagctaa acattcttat taccagaata      5520
agacctagga aaagaactgt ttcagtccca taaagtggcc tggataattt ccttgatatg      5580
gaaatcgaca cacttatgtt cccagaaagc aacagatctt taagacttct gaagtgaagg      5640
aaggttgtgt tagtgcaaac tagtgcagcc cagtgccagg tccaggagtt aacatgtaga      5700
caggccatgg actgtgtggg tagatgctca tggaaatgtg cagtagtatg ttcatgtgct      5760
ctcagctagc tgtgtgtact tcaaactgtc tccacagagt tgttggggag acactctgaa      5820
aaagaattaa ttgtgaatta gttttatata ctttgtttta taatttgtga tgcaaatgaa      5880
aatttctctg ggaaatattt attttagtaa taatgtttca aactcatata taacaatgct      5940
gtattttaag aatgattaca taatgactta tatttgtata aaataatttt tatatttgaa      6000
atgttaactt tttatagcac tagctatttt aaaacagggg agtgaggagg acagggatga      6060
taaggatcat tcaacttcat gttgtgaaga cgagctgatg taaatcttgt acccatctgt      6120
gtggttctca gacaacacat gctctctttt aatgcagctt tgaagaagat ggtaccaaag      6180
gttaagacgg ccccctgatg ggcacatcaa cttctgaact gcaaactaag ctttagagga      6240
atgtattata tttattactg taatagaata tcatgtgtca ataaaatcct tttatttgtg      6300
tgaaa                                                                  6305
```

<210> SEQ ID NO 149
<211> LENGTH: 1476
<212> TYPE: PRT
<213> ORGANISM: Mus musculus

<400> SEQUENCE: 149

```
Met Gln Lys Ser Pro Leu Glu Lys Ala Ser Phe Ile Ser Lys Leu Phe
1               5                   10                  15

Phe Ser Trp Thr Thr Pro Ile Leu Arg Lys Gly Tyr Arg His His Leu
            20                  25                  30

Glu Leu Ser Asp Ile Tyr Gln Ala Pro Ser Ala Asp Ser Ala Asp His
        35                  40                  45

Leu Ser Glu Lys Leu Glu Arg Glu Trp Asp Arg Glu Gln Ala Ser Lys
    50                  55                  60

Lys Asn Pro Gln Leu Ile His Ala Leu Arg Arg Cys Phe Phe Trp Arg
65                  70                  75                  80

Phe Leu Phe Tyr Gly Ile Leu Leu Tyr Leu Gly Glu Val Thr Lys Ala
                85                  90                  95
```

```
Val Gln Pro Val Leu Leu Gly Arg Ile Ile Ala Ser Tyr Asp Pro Glu
            100                 105                 110

Asn Lys Val Glu Arg Ser Ile Ala Ile Tyr Leu Gly Ile Gly Leu Cys
            115                 120                 125

Leu Leu Phe Ile Val Arg Thr Leu Leu His Pro Ala Ile Phe Gly
130                 135                 140

Leu His Arg Ile Gly Met Gln Met Arg Thr Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Ser Asn Asn Leu Asn Lys Phe Asp
                180                 185                 190

Glu Gly Leu Ala Leu Ala His Phe Ile Trp Ile Ala Pro Leu Gln Val
            195                 200                 205

Thr Leu Leu Met Gly Leu Leu Trp Asp Leu Leu Gln Phe Ser Ala Phe
            210                 215                 220

Cys Gly Leu Gly Leu Leu Ile Ile Leu Val Ile Phe Gln Ala Ile Leu
225                 230                 235                 240

Gly Lys Met Met Val Lys Tyr Arg Asp Gln Arg Ala Ala Lys Ile Asn
                245                 250                 255

Glu Arg Leu Val Ile Thr Ser Glu Ile Ile Asp Asn Ile Tyr Ser Val
            260                 265                 270

Lys Ala Tyr Cys Trp Glu Ser Ala Met Glu Lys Met Ile Glu Asn Leu
                275                 280                 285

Arg Glu Val Glu Leu Lys Met Thr Arg Lys Ala Ala Tyr Met Arg Phe
            290                 295                 300

Phe Thr Ser Ser Ala Phe Phe Phe Ser Gly Phe Phe Val Val Phe Leu
305                 310                 315                 320

Ser Val Leu Pro Tyr Thr Val Ile Asn Gly Ile Val Leu Arg Lys Ile
                325                 330                 335

Phe Thr Thr Ile Ser Phe Cys Ile Val Leu Arg Met Ser Val Thr Arg
                340                 345                 350

Gln Phe Pro Thr Ala Val Gln Ile Trp Tyr Asp Ser Phe Gly Met Ile
            355                 360                 365

Arg Lys Ile Gln Asp Phe Leu Gln Lys Gln Glu Tyr Lys Val Leu Glu
            370                 375                 380

Tyr Asn Leu Met Thr Thr Gly Ile Ile Met Glu Asn Val Thr Ala Phe
385                 390                 395                 400

Trp Glu Glu Gly Phe Gly Glu Leu Leu Glu Lys Val Gln Gln Ser Asn
                405                 410                 415

Gly Asp Arg Lys His Ser Ser Asp Glu Asn Asn Val Ser Phe Ser His
            420                 425                 430

Leu Cys Leu Val Gly Asn Pro Val Leu Lys Asn Ile Asn Leu Asn Ile
            435                 440                 445

Glu Lys Gly Glu Met Leu Ala Ile Thr Gly Ser Thr Gly Ser Gly Lys
            450                 455                 460

Thr Ser Leu Leu Met Leu Ile Leu Gly Glu Leu Glu Ala Ser Glu Gly
465                 470                 475                 480

Ile Ile Lys His Ser Gly Arg Val Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510
```

```
Asp Glu Tyr Arg Tyr Lys Ser Val Lys Ala Cys Gln Leu Gln Gln
            515                 520                 525

Asp Ile Thr Lys Phe Ala Glu Gln Asp Asn Thr Val Leu Gly Glu Gly
            530                 535                 540

Gly Val Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Phe Thr Glu Glu Gln Val Phe Glu Ser Cys Val Cys
            580                 585                 590

Lys Leu Met Ala Asn Lys Thr Arg Ile Leu Val Thr Ser Lys Met Glu
            595                 600                 605

His Leu Arg Lys Ala Asp Lys Ile Leu Ile Leu His Gln Gly Ser Ser
            610                 615                 620

Tyr Phe Tyr Gly Thr Phe Ser Glu Leu Gln Ser Leu Arg Pro Asp Phe
625                 630                 635                 640

Ser Ser Lys Leu Met Gly Tyr Asp Thr Phe Asp Gln Phe Thr Glu Glu
                645                 650                 655

Arg Arg Ser Ser Ile Leu Thr Glu Thr Leu Arg Arg Phe Ser Val Asp
            660                 665                 670

Asp Ser Ser Ala Pro Trp Ser Lys Pro Lys Gln Ser Phe Arg Gln Thr
            675                 680                 685

Gly Glu Val Gly Glu Lys Arg Lys Asn Ser Ile Leu Asn Ser Phe Ser
690                 695                 700

Ser Val Arg Lys Ile Ser Ile Val Gln Lys Thr Pro Leu Cys Ile Asp
705                 710                 715                 720

Gly Glu Ser Asp Asp Leu Gln Glu Lys Arg Leu Ser Leu Val Pro Asp
                725                 730                 735

Ser Glu Gln Gly Glu Ala Ala Leu Pro Arg Ser Asn Met Ile Ala Thr
            740                 745                 750

Gly Pro Thr Phe Pro Gly Arg Arg Arg Gln Ser Val Leu Asp Leu Met
            755                 760                 765

Thr Phe Thr Pro Asn Ser Gly Ser Ser Asn Leu Gln Arg Thr Arg Thr
770                 775                 780

Ser Ile Arg Lys Ile Ser Leu Val Pro Gln Ile Ser Leu Asn Glu Val
785                 790                 795                 800

Asp Val Tyr Ser Arg Arg Leu Ser Gln Asp Ser Thr Leu Asn Ile Thr
                805                 810                 815

Glu Glu Ile Asn Glu Glu Asp Leu Lys Glu Cys Phe Leu Asp Asp Val
            820                 825                 830

Ile Lys Ile Pro Pro Val Thr Thr Trp Asn Thr Tyr Leu Arg Tyr Phe
            835                 840                 845

Thr Leu His Lys Gly Leu Leu Leu Val Leu Ile Trp Cys Val Leu Val
850                 855                 860

Phe Leu Val Glu Val Ala Ala Ser Leu Phe Val Leu Trp Leu Leu Lys
865                 870                 875                 880

Asn Asn Pro Val Asn Ser Gly Asn Asn Gly Thr Lys Ile Ser Asn Ser
                885                 890                 895

Ser Tyr Val Val Ile Ile Thr Ser Thr Ser Phe Tyr Tyr Ile Phe Tyr
            900                 905                 910

Ile Tyr Val Gly Val Ala Asp Thr Leu Leu Ala Leu Ser Leu Phe Arg
            915                 920                 925

Gly Leu Pro Leu Val His Thr Leu Ile Thr Ala Ser Lys Ile Leu His
```

```
                930            935            940
Arg Lys Met Leu His Ser Ile Leu His Ala Pro Met Ser Thr Ile Ser
945                 950            955                 960
Lys Leu Lys Ala Gly Gly Ile Leu Asn Arg Phe Ser Lys Asp Ile Ala
           965            970                 975
Ile Leu Asp Asp Phe Leu Pro Leu Thr Ile Phe Asp Phe Ile Gln Leu
                980            985            990
Val Phe Ile Val Ile Gly Ala Ile Ile Val Val Ser Ala Leu Gln Pro
           995            1000           1005
Tyr Ile Phe Leu Ala Thr Val Pro Gly Leu Val Val Phe Ile Leu
    1010           1015           1020
Leu Arg Ala Tyr Phe Leu His Thr Ala Gln Gln Leu Lys Gln Leu
    1025           1030           1035
Glu Ser Glu Gly Arg Ser Pro Ile Phe Thr His Leu Val Thr Ser
    1040           1045           1050
Leu Lys Gly Leu Trp Thr Leu Arg Ala Phe Arg Arg Gln Thr Tyr
    1055           1060           1065
Phe Glu Thr Leu Phe His Lys Ala Leu Asn Leu His Thr Ala Asn
    1070           1075           1080
Trp Phe Met Tyr Leu Ala Thr Leu Arg Trp Phe Gln Met Arg Ile
    1085           1090           1095
Asp Met Ile Phe Val Leu Phe Phe Ile Val Val Thr Phe Ile Ser
    1100           1105           1110
Ile Leu Thr Thr Gly Glu Gly Glu Gly Thr Ala Gly Ile Ile Leu
    1115           1120           1125
Thr Leu Ala Met Asn Ile Met Ser Thr Leu Gln Trp Ala Val Asn
    1130           1135           1140
Ser Ser Ile Asp Thr Asp Ser Leu Met Arg Ser Val Ser Arg Val
    1145           1150           1155
Phe Lys Phe Ile Asp Ile Gln Thr Glu Glu Ser Met Tyr Thr Gln
    1160           1165           1170
Ile Ile Lys Glu Leu Pro Arg Glu Gly Ser Ser Asp Val Leu Val
    1175           1180           1185
Ile Lys Asn Glu His Val Lys Lys Ser Asp Ile Trp Pro Ser Gly
    1190           1195           1200
Gly Glu Met Val Val Lys Asp Leu Thr Val Lys Tyr Met Asp Asp
    1205           1210           1215
Gly Asn Ala Val Leu Glu Asn Ile Ser Phe Ser Ile Ser Pro Gly
    1220           1225           1230
Gln Arg Val Gly Leu Leu Gly Arg Thr Gly Ser Gly Lys Ser Thr
    1235           1240           1245
Leu Leu Ser Ala Phe Leu Arg Met Leu Asn Ile Lys Gly Asp Ile
    1250           1255           1260
Glu Ile Asp Gly Val Ser Trp Asn Ser Val Thr Leu Gln Glu Trp
    1265           1270           1275
Arg Lys Ala Phe Gly Val Ile Thr Gln Lys Val Phe Ile Phe Ser
    1280           1285           1290
Gly Thr Phe Arg Gln Asn Leu Asp Pro Asn Gly Lys Trp Lys Asp
    1295           1300           1305
Glu Glu Ile Trp Lys Val Ala Asp Glu Val Gly Leu Lys Ser Val
    1310           1315           1320
Ile Glu Gln Phe Pro Gly Gln Leu Asn Phe Thr Leu Val Asp Gly
    1325           1330           1335
```

```
Gly Tyr Val Leu Ser His Gly His Lys Gln Leu Met Cys Leu Ala
    1340            1345            1350

Arg Ser Val Leu Ser Lys Ala Lys Ile Ile Leu Leu Asp Glu Pro
    1355            1360            1365

Ser Ala His Leu Asp Pro Ile Thr Tyr Gln Val Ile Arg Arg Val
    1370            1375            1380

Leu Lys Gln Ala Phe Ala Gly Cys Thr Val Ile Leu Cys Glu His
    1385            1390            1395

Arg Ile Glu Ala Met Leu Asp Cys Gln Arg Phe Leu Val Ile Glu
    1400            1405            1410

Glu Ser Asn Val Trp Gln Tyr Asp Ser Leu Gln Ala Leu Leu Ser
    1415            1420            1425

Glu Lys Ser Ile Phe Gln Gln Ala Ile Ser Ser Ser Glu Lys Met
    1430            1435            1440

Arg Phe Phe Gln Gly Arg His Ser Ser Lys His Lys Pro Arg Thr
    1445            1450            1455

Gln Ile Thr Ala Leu Lys Glu Glu Thr Glu Glu Glu Val Gln Glu
    1460            1465            1470

Thr Arg Leu
    1475

<210> SEQ ID NO 150
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 150
cctttcaggg tgtcttactc accat                                         25

<210> SEQ ID NO 151
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 151
cctcttacct cagttacaat ttata                                         25
```

ANTISENSE COMPOUNDS TARGETING GENES ASSOCIATED WITH CYSTIC FIBROSIS

CROSS REFERENCE TO RELATED APPLICATIONS

This application is a continuation-in-part of U.S. application Ser. No. 15/045,999, filed Feb. 17, 2016 (now U.S. Pat. No. 9,840,709, which is a non-provisional application of U.S. Provisional Application 62/118,794, filed Feb. 20, 2015, the disclosures of which each of which are incorporated by reference in their entirety.

SEQUENCE LISTING

The sequence listing submitted herewith is incorporated by reference in its entirety.

FIELD OF THE DISCLOSURE

The present disclosure relates generally to compounds comprising oligonucleotides complementary to a cystic fibrosis transmembrane conductance regulator (CFTR) RNA transcript. Certain such compounds are useful for hybridizing to a CFTR transcript, including but not limited to a CFTR RNA transcript in a cell. In certain embodiments, such hybridization results in modulation of splicing of the CFTR transcript. In certain embodiments, such compounds are used to treat one or more symptoms associated with Cystic Fibrosis.

BACKGROUND OF THE DISCLOSURE

Cystic fibrosis (CF), also known as mucoviscidosis, is a genetic disorder that affects mostly the lungs, but also the pancreas, liver, kidneys, and intestine. Long-term issues include difficulty breathing and coughing up mucus as a result of frequent lung infections. Other signs and symptoms include sinus infections, poor growth, fatty stool, clubbing of the fingers and toes, and infertility in males among others. Different people may have different degrees of symptoms.

CF is inherited in an autosomal recessive manner. It is caused by the presence of mutations in both copies of the gene for the cystic fibrosis transmembrane conductance regulator (CFTR) protein. Those with a single working copy are carriers and otherwise mostly normal. CFTR is involved in production of sweat, digestive fluids, and mucus. When CFTR is not functional, secretions, which are usually thin, instead become thick. The condition is diagnosed by a sweat test and genetic testing. Screening of infants at birth takes place in some areas of the world.

There is no cure for cystic fibrosis. Lung infections are treated with antibiotics which may be given intravenously, inhaled, or by mouth. Sometimes the antibiotic azithromycin is used long term. Inhaled hypertonic saline and salbutamol may also be useful. Lung transplantation may be an option if lung function continues to worsen. Pancreatic enzyme replacement and fat-soluble vitamin supplementation are important, especially in the young. The average life expectancy is between 42 and 50 years in the developed world. While CF is a multi-organ disease, lung problems are the dominant cause of morbidity and mortality. Other CF symptoms include pancreatic insufficiency, intestinal obstruction, elevated electrolyte levels in sweat (the basis of the most common diagnostic test), and male infertility. CF is most common among people of Northern European ancestry and affects about one out of every 2,500 to 4,000 newborns. About one in 25 people are carriers. While treatments for Cystic Fibrosis are available, more effective therapies are needed.

SUMMARY OF THE DISCLOSURE

The present disclosure relates to general compounds and methods to treat cystic fibrosis in subjects using antisense oligonucleotides (ASOs) that induce specific pre-mRNA splicing events in CFTR gene transcripts that result in mRNAs that code for proteins that fully or partially restore the function of CFTR (i.e., resulting in increased levels of correctly localized CFTR protein at the plasma membrane and with increased function).

In one aspect, the disclosure provides a compound comprising a modified oligonucleotide having 8 to 30 linked nucleosides having a nucleobase sequence comprising a complementary region, wherein the complementary region comprises at least 8 contiguous nucleobases complementary to an equal-length portion of a target region of a cystic fibrosis transmembrane conductance regulator (CFTR) transcript. In certain embodiments, the target region of the CFTR transcript comprises at least a portion of intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of the CFTR transcript. In other embodiments, the nucleobase sequence of the antisense oligonucleotide comprises any one of SEQ ID NOs: 1 to 144, or SEQ ID NO:150.

In another aspect, the disclosure provides a pharmaceutical composition comprising at least one compound as described herein and a pharmaceutically acceptable carrier or diluent.

In yet another aspect, the disclosure provides a method of modulating splicing or expression of a CFTR transcript in a cell comprising contacting the cell with at least one compound as described herein.

The yet another aspect, the disclosure provides a method of treating cystic fibrosis, comprising administering at least one compound as described herein to an animal in need thereof.

The present disclosure provides the following non-limiting numbered embodiments:

Embodiment 1. A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a cystic fibrosis transmembrane conductance regulator (CFTR) transcript.

Embodiment 2. The compound of embodiment 1, wherein the target region of the CFTR transcript comprises at least a portion of intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of the CFTR transcript.

Embodiment 3. The compound of embodiment 1, wherein the target region of the CFTR transcript comprises at least a portion of exon 2 of the CFTR transcript.

Embodiment 4. The compound of embodiment 1, wherein the target region of the CFTR transcript comprises at least a portion of exon 4 of the CFTR transcript.

Embodiment 5. The compound of embodiment 1, wherein the target region of the CFTR transcript comprises at least a portion of exon 5 of the CFTR transcript.

Embodiment 6. The compound of embodiment 1, wherein the target region of the CFTR transcript comprises at least a portion of exon 7 of the CFTR transcript.

Embodiment 7. The compound of embodiment 1, wherein the target region of the CFTR transcript comprises at least a portion of exon 9 of the CFTR transcript.

Embodiment 8. The compound of embodiment 1, wherein the target region of the CFTR transcript comprises at least a portion of exon 10 of the CFTR transcript.

Embodiment 9. The compound of embodiment 1, wherein the target region of the CFTR transcript comprises at least a portion of exon 11 of the CFTR transcript.

Embodiment 10. The compound of embodiment 1, wherein the target region of the CFTR transcript comprises at least a portion of exon 13 of the CFTR transcript.

Embodiment 11. The compound of embodiment 1, wherein the target region of the CFTR transcript comprises at least a portion of exon 15 of the CFTR transcript.

Embodiment 12. The compound of embodiment 1, wherein the target region of the CFTR transcript comprises at least a portion of exon 16 of the CFTR transcript.

Embodiment 13. The compound of embodiment 1, wherein the target region of the CFTR transcript comprises at least a portion of exon 20 of the CFTR transcript.

Embodiment 14. The compound of embodiment 1, wherein the target region of the CFTR transcript comprises at least a portion of exon 22 of the CFTR transcript.

Embodiment 15. The compound of embodiment 1, wherein the target region of the CFTR transcript comprises at least a portion of exon 23 of the CFTR transcript.

Embodiment 16. The compound of embodiment 1, wherein the target region of the CFTR transcript comprises at least a portion of exon 24 of the CFTR transcript.

Embodiment 17. The compound of any of embodiments 1 to 16, wherein the complementary region of the modified oligonucleotide is at least 80%, at least 85%, at least 90%, at least 95% or at least 100% complementary to the target region.

Embodiment 18. The compound of any of embodiments 1 to 17, wherein the complementary region of the modified oligonucleotide comprises at least 10 contiguous nucleobases.

Embodiment 19. The compound of any of embodiments 1 to 17, wherein the complementary region of the modified oligonucleotide comprises at least 12 contiguous nucleobases.

Embodiment 20. The compound of any of embodiments 1 to 17, wherein the complementary region of the modified oligonucleotide comprises at least 14 contiguous nucleobases.

Embodiment 21. The compound of any of embodiments 1 to 17, wherein the complementary region of the modified oligonucleotide comprises at least 15 contiguous nucleobases.

Embodiment 22. The compound of any of embodiments 1 to 17, wherein the complementary region of the modified oligonucleotide comprises at least 16 contiguous nucleobases.

Embodiment 23. The compound of any of embodiments 1 to 17, wherein the complementary region of the modified oligonucleotide comprises at least 17 contiguous nucleobases.

Embodiment 24. The compound of any of embodiments 1 to 17, wherein the complementary region of the modified oligonucleotide comprises at least 18 contiguous nucleobases.

Embodiment 25. The compound of any of embodiments 1 to 17, wherein the complementary region of the modified oligonucleotide comprises at least 19 contiguous nucleobases.

Embodiment 26. The compound of any of embodiments 1 to 17, wherein the complementary region of the modified oligonucleotide comprises at least 20 contiguous nucleobases.

Embodiment 27. The compound of any of embodiments 1 to 26, wherein the nucleobase sequence of the oligonucleotide is at least 80% complementary to an equal-length region of the CFTR transcript, as measured over the entire length of the oligonucleotide.

Embodiment 28. The compound of any of embodiments 1 to 26, wherein the nucleobase sequence of the oligonucleotide is at least 90% complementary to an equal-length region of the CFTR transcript, as measured over the entire length of the oligonucleotide.

Embodiment 29. The compound of any of embodiments 1 to 26, wherein the nucleobase sequence of the oligonucleotide is 100% complementary to an equal-length region of the CFTR transcript, as measured over the entire length of the oligonucleotide.

Embodiment 30. The compound of any of embodiments 1-29, wherein the nucleobase sequence of the antisense oligonucleotide comprises any one of SEQ ID NOs: 1 to 144, and SEQ ID NO:150.

Embodiment 31. The compound of any of embodiments 1-30, wherein the modified oligonucleotide comprises at least one modified nucleoside.

Embodiment 32. The compound of embodiment 31, wherein at least one modified nucleoside comprises a modified sugar moiety.

Embodiment 33. The compound of embodiment 32, wherein at least one modified sugar moiety is a 2'-substituted sugar moiety.

Embodiment 34. The compound of embodiment 33, wherein the 2'-substitutent of at least one 2'-substituted sugar moiety is selected from among: 2'-OMe, 2'-F, and 2'-MOE.

Embodiment 35. The compound of any of embodiments 31-34, wherein the 2'-substiuent of at least one 2'-substituted sugar moiety is a 2'-MOE.

Embodiment 36. The compound of any of embodiments 1-47, wherein at least one modified sugar moiety is a bicyclic sugar moiety.

Embodiment 37. The compound of embodiment 36, wherein at least one bicyclic sugar moiety is LNA or cEt.

Embodiment 38. The compound of any of embodiments 1-37, wherein at least one sugar moiety is a sugar surrogate.

Embodiment 39. The compound of embodiment 38, wherein at least one sugar surrogate is a morpholino.

Embodiment 40. The compound of embodiment 38, wherein at least one sugar surrogate is a modified morpholino.

Embodiment 41. The compound of any of embodiments 1-40, wherein the modified oligonucleotide comprises at least 5 modified nucleosides, each independently comprising a modified sugar moiety.

Embodiment 42. The compound of embodiment 41, wherein the modified oligonucleotide comprises at least 10 modified nucleosides, each independently comprising a modified sugar moiety.

Embodiment 43. The compound of embodiment 41, wherein the modified oligonucleotide comprises at least 15 modified nucleosides, each independently comprising a modified sugar moiety.

Embodiment 44. The compound of embodiment 41, wherein each nucleoside of the modified oligonucleotide is a modified nucleoside, each independently comprising a modified sugar moiety Embodiment 45. The compound of any of embodiments 1-44, wherein the modified oligonucleotide comprises at least two modified nucleosides comprising modified sugar moieties that are the same as one another.

Embodiment 46. The compound of any of embodiments 1-44, wherein the modified oligonucleotide comprises at least two modified nucleosides comprising modified sugar moieties that are different from one another.

Embodiment 47. The compound of any of embodiments 1-46, wherein the modified oligonucleotide comprises a modified region of at least 5 contiguous modified nucleosides.

Embodiment 48. The compound of any of embodiments 1 to 47, wherein the modified oligonucleotide comprises a modified region of at least 10 contiguous modified nucleosides.

Embodiment 49. The compound of any of embodiments 1 to 48, wherein the modified oligonucleotide comprises a modified region of at least 15 contiguous modified nucleosides.

Embodiment 50. The compound of any of embodiments 1 to 48, wherein the modified oligonucleotide comprises a modified region of at least 20 contiguous modified nucleosides.

Embodiment 51. The compound of any of embodiments 45 to 50, wherein each modified nucleoside of the modified region has a modified sugar moiety independently selected from among: 2'-F, 2'-OMe, 2'-MOE, cEt, LNA, morpholino, and modified morpholino.

Embodiment 52. The compound of any of embodiments 45 to 51 wherein the modified nucleosides of the modified region each comprise the same modification as one another.

Embodiment 53. The compound of embodiment 52, wherein the modified nucleosides of the modified region each comprise the same 2'-substituted sugar moiety.

Embodiment 54. The compound of embodiment 52, wherein the 2'-substituted sugar moiety of the modified nucleosides of the region of modified nucleosides is selected from 2'-F, 2'-OMe, and 2'-MOE.

Embodiment 55. The compound of embodiment 54, wherein the 2'-substituted sugar moiety of the modified nucleosides of the region of modified nucleosides is 2'-MOE.

Embodiment 56. The compound of embodiment 52, wherein the modified nucleosides of the region of modified nucleosides each comprise the same bicyclic sugar moiety.

Embodiment 57. The compound of embodiment 56, wherein the bicyclic sugar moiety of the modified nucleosides of the region of modified nucleosides is selected from LNA and cEt.

Embodiment 58. The compound of embodiment 50, wherein the modified nucleosides of the region of modified nucleosides each comprises a sugar surrogate.

Embodiment 59. The compound of embodiment 58, wherein the sugar surrogate of the modified nucleosides of the region of modified nucleosides is a morpholino.

Embodiment 60. The compound of embodiment 59, wherein the sugar surrogate of the modified nucleosides of the region of modified nucleosides is a modified morpholino.

Embodiment 61. The compound of any of embodiments 1 to 60, wherein the modified nucleotide comprises no more than 4 contiguous naturally occurring nucleosides.

Embodiment 62. The compound of any of embodiments 1 to 61, wherein each nucleoside of the modified oligonucleotide is a modified nucleoside.

Embodiment 63. The compound of embodiment 62, wherein each modified nucleoside comprises a modified sugar moiety.

Embodiment 64. The compound of embodiment 63, wherein the modified nucleosides of the modified oligonucleotide comprise the same modification as one another.

Embodiment 65. The compound of embodiment 64, wherein the modified nucleosides of the modified oligonucleotide each comprise the same 2'-substituted sugar moiety.

Embodiment 66. The compound of embodiment 65, wherein the 2'-substituted sugar moiety of the modified oligonucleotide is selected from 2'-F, 2'-OMe, and 2'-MOE.

Embodiment 67. The compound of embodiment 65, wherein the 2'-substituted sugar moiety of the modified oligonucleotide is 2'-MOE.

Embodiment 68. The compound of embodiment 64, wherein the modified nucleosides of the modified oligonucleotide each comprise the same bicyclic sugar moiety.

Embodiment 69. The compound of embodiment 68, wherein the bicyclic sugar moiety of the modified oligonucleotide is selected from LNA and cEt.

Embodiment 70. The compound of embodiment 64, wherein the modified nucleosides of the modified oligonucleotide each comprises a sugar surrogate.

Embodiment 71. The compound of embodiment 70, wherein the sugar surrogate of the modified oligonucleotide is a morpholino.

Embodiment 72. The compound of embodiment 70, wherein the sugar surrogate of the modified oligonucleotide is a modified morpholino.

Embodiment 73. The compound of any of embodiments 1 to 72, wherein the modified oligonucleotide comprises at least one modified internucleoside linkage.

Embodiment 74. The compound of embodiment 73, wherein each internucleoside linkage is a modified internucleoside linkage.

Embodiment 75. The compound of embodiment 73 or 74, comprising at least one phosphorothioate internucleoside linkage.

Embodiment 76. The compound of embodiment 73, wherein each internucleoside linkage is a modified internucleoside linkage and wherein each internucleoside linkage comprises the same modification.

Embodiment 77. The compound of embodiment 76, wherein each internucleoside linkage is a phosphorothioate internucleoside linkage.

Embodiment 78. The compound of any of embodiments 1 to 77, comprising at least one conjugate.

Embodiment 79. The compound of any of embodiments 1 to 78, consisting of the modified oligonucleotide.

Embodiment 80. The compound of any of embodiments 1 to 79, wherein the compound modulates splicing of the CFTR transcript.

Embodiment 81. The compound of any of embodiments 1 to 80, having a nucleobase sequence comprising any of the sequences as set forth in SEQ ID Nos: 1 to 144, and SEQ ID NO:150.

Embodiment 82. The compound of any of embodiments 1 to 81, having a nucleobase sequence comprising any of the sequences as set forth in SEQ ID Nos: 64, 65, 66, 71, 76, 78, 79, 81, 82, 84, 91, 92, 93, 94, 102, 111, 116, 117, 120, 122, 127, 128 or 129.

Embodiment 83. The compound of any of embodiments 1 to 81, having a nucleobase sequence comprising any of the sequences as set forth in SEQ ID Nos: 1, 4, 8, 9, 10, 12, 13, 17, 18, 19, 20, 22, 23, 24, 26, 27, 36, 37, 38, 42, 43, 44, 47, 48, 49, 50, 53, 55, 57, 59 or 60.

Embodiment 84. The compound of any of embodiment 82, having a nucleobase sequence comprising SEQ ID NO. 91, 97, 99, 100, 103, 104, 110, 114, 126, 127, 128, 129, or 150.

Embodiment 85. A pharmaceutical composition comprising a compound according to any of embodiments 1-84 and a pharmaceutically acceptable carrier or diluent.

Embodiment 86. The pharmaceutical composition of embodiment 85, wherein the pharmaceutically acceptable carrier or diluent is sterile saline.

Embodiment 87. A method of modulating splicing of a CFTR transcript in a cell comprising contacting the cell with a compound according to any of embodiments 1-86.

Embodiment 88. The method of embodiment 87, wherein the cell is in vitro.

Embodiment 89. The method of embodiment 87, wherein the cell is in an animal.

Embodiment 90. The method of any of embodiments 87 to 89, wherein the amount of CFTR mRNA without exon 11 is increased.

Embodiment 91. The method of any of embodiments 87 to 89, wherein the amount of CFTR mRNA without exon 16 is increased.

Embodiment 92. The method of any of embodiments 87 to 89, wherein the amount of CFTR mRNA with exon 23 or exon 24 is increased.

Embodiment 93. The method of any of embodiments 87 to 92, wherein the CFTR transcript is transcribed from a CFTR gene.

Embodiment 94. A method of modulating the expression of CFTR in a cell, comprising contacting the cell with a compound according to any of embodiments 1-86.

Embodiment 95. The method of embodiment 94, wherein the cell is in vitro.

Embodiment 96. The method of embodiment 94, wherein the cell is in an animal.

Embodiment 97. A method comprising administering the compound according to any of embodiments 1-84 or the pharmaceutical composition of embodiments 85 or 86 to an animal.

Embodiment 98. The method of embodiment 97, wherein the administering step comprises delivering to the animal by inhalation, parenteral injection or infusion, oral, subcutaneous or intramuscular injection, buccal, transdermal, transmucosal and topical.

Embodiment 99. The method of embodiment 98, wherein the administration is by inhalation.

Embodiment 100. The method of any of embodiments 97-99, wherein the animal has one or more symptoms associated with cystic fibrosis.

Embodiment 101. The method of any of embodiments 97-99, wherein the administration results in amelioration of at least one symptom of cystic fibrosis.

Embodiment 102. The method of any of embodiments 97-101, wherein the animal is a mouse.

Embodiment 103. The method of any of embodiments 97-101, wherein the animal is a human.

Embodiment 104. A method of treating cystic fibrosis, comprising administering the compound according to any of embodiments 1-84 or the pharmaceutical composition of embodiments 85 or 86 to an animal in need thereof.

Embodiment 105. Use of the compound according to any of embodiments 1-84 or the pharmaceutical composition of embodiments 85 or 86 for the preparation of a medicament for use in the treatment of cystic fibrosis.

Embodiment 106. Use of the compound according to any of embodiments 1-84 or the pharmaceutical composition of embodiments 85 or 86 for the preparation of a medicament for use in the amelioration of one or more symptoms associated with cystic fibrosis.

Embodiment 107. A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a CFTR transcript.

Embodiment 108. The compound of embodiment 107, wherein the CFTR transcript comprises the nucleobase sequence of SEQ ID No. 130.

Embodiment 109. The compound of embodiment 107 or 108, wherein the complementary region of the modified oligonucleotide is 100% complementary to the target region.

Embodiment 110. The compound of any of embodiments 107-109, wherein the complementary region of the modified oligonucleotide comprises at least 10 contiguous nucleobases.

Embodiment 111. The compound of any of embodiments 107-109, wherein the complementary region of the modified oligonucleotide comprises at least 12 contiguous nucleobases.

Embodiment 112. The compound of any of embodiments 107-109, wherein the complementary region of the modified oligonucleotide comprises at least 14 contiguous nucleobases.

Embodiment 113. The compound of any of embodiments 107-109, wherein the complementary region of the modified oligonucleotide comprises at least 15 contiguous nucleobases.

Embodiment 114. The compound of any of embodiments 107-109, wherein the complementary region of the modified oligonucleotide comprises at least 16 contiguous nucleobases.

Embodiment 115. The compound of any of embodiments 107-109, wherein the complementary region of the modified oligonucleotide comprises at least 17 contiguous nucleobases.

Embodiment 116. The compound of any of embodiments 107-109, wherein the complementary region of the modified oligonucleotide comprises at least 18 contiguous nucleobases.

Embodiment 117. The compound of any of embodiments 107-116, wherein the nucleobase sequence of the modified oligonucleotide is at least 80% complementary to an equal-length region of the CFTR transcript, as measured over the entire length of the oligonucleotide.

Embodiment 118. The compound of any of embodiments 107-116, wherein the nucleobase sequence of the modified oligonucleotide is at least 90% complementary to an equal-length region of the CFTR transcript, as measured over the entire length of the oligonucleotide.

Embodiment 119. The compound of any of embodiments 107-116, wherein the nucleobase sequence of the modified oligonucleotide is 100% complementary to an equal-length region of the CFTR transcript, as measured over the entire length of the oligonucleotide.

Embodiment 120. The compound of any of embodiments 107-119, wherein the target region is within intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of human CFTR.

Embodiment 121. The compound of embodiment 120, wherein the target region is within exon 11 of human CFTR.

Embodiment 122. The compound of embodiment 120, wherein the target region is within exon 23 or exon 24 of human CFTR.

Embodiment 123. The compound of any of embodiments 107-119, wherein the target region is within intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of mouse CFTR.

Embodiment 124. The compound of any of embodiments 107-119, wherein the modified oligonucleotide has a nucleobase sequence comprising any of the sequences as set forth in SEQ ID NOs: 1-144, and SEQ ID NO:150.

Embodiment 125. The compound of any of embodiments 107-119, wherein the modified oligonucleotide has a nucleobase sequence consisting of the nucleobase sequence of any one of SEQ ID NOs: 1-144, and SEQ ID NO:150.

Embodiment 126. The compound of any of embodiments 107-119, wherein the modified oligonucleotide has a nucleobase sequence comprising the nucleobase sequence of SEQ ID NO. 64, 65, 66, 71, 76, 78, 79, 81, 82, 84, 91, 92, 93, 94, 97, 99, 100, 102, 103, 104, 111, 114, 116, 117, 120, 122, 127, 128, 129, or 150.

Embodiment 127. The compound of embodiment 125, wherein the modified oligonucleotide has a nucleobase sequence consisting of the nucleobase sequence of SEQ ID NO. 64, 65, 66, 71, 76, 78, 79, 81, 82, 84, 91, 92, 93, 94, 97, 99, 100, 102, 103, 104, 111, 114, 116, 117, 120, 122, 127, 128, 129, or 150.

Embodiment 128. The compound of any of embodiments 107-119, wherein the modified oligonucleotide has a nucleobase sequence comprising the nucleobase sequence of SEQ ID NO. 91, 97, 99, 100, 103, 104, 110, 114, 126, 127, 128, 129, or 150.

Embodiment 129. The compound of embodiment 125, wherein the modified oligonucleotide has a nucleobase sequence consisting of the nucleobase sequence of SEQ ID NO. 91, 97, 99, 100, 103, 104, 110, 114, 126, 127, 128, 129, or 150.

Embodiment 130. The compound of any of embodiments 107-129, wherein the modified oligonucleotide comprises at least one modified nucleoside.

Embodiment 131. The compound of any of embodiments 107-130, wherein each nucleoside of the modified oligonucleotide is a modified nucleoside selected from among: 2'-OMe, 2'-F, and 2'-MOE or a sugar surrogate.

Embodiment 132. The compound of embodiment 132, wherein the modified nucleoside is 2'-MOE.

Embodiment 133. The compound of embodiment 132, wherein the modified nucleoside is a morpholino.

Embodiment 134. The compound of embodiment 131, wherein at least one modified nucleoside comprises a modified sugar moiety.

Embodiment 135. The compound of embodiment 134, wherein at least one modified sugar moiety is a 2'-substituted sugar moiety.

Embodiment 136. The compound of embodiment 135, wherein the 2'-substitutent of at least one 2'-substituted sugar moiety is selected from among: 2'-OMe, 2'-F, and 2'-MOE.

Embodiment 137. The compound of any of embodiments 135-136, wherein the 2'-substiuent of at least one 2'-substituted sugar moiety is a 2'-MOE.

Embodiment 138. The compound of any of embodiments 107-137, wherein at least one modified sugar moiety is a bicyclic sugar moiety.

Embodiment 139. The compound of embodiment 138, wherein at least one bicyclic sugar moiety is LNA or cEt.

Embodiment 140. The compound of any of embodiments 107-139, wherein at least one sugar moiety is a sugar surrogate.

Embodiment 141. The compound of embodiment 140, wherein at least one sugar surrogate is a morpholino.

Embodiment 142. The compound of embodiment 141, wherein at least one sugar surrogate is a modified morpholino.

Embodiment 143. The compound of any of embodiments 107-142, wherein the modified oligonucleotide comprises at least 5 modified nucleosides, each independently comprising a modified sugar moiety.

Embodiment 144. The compound of any of embodiments 107-143, wherein the modified oligonucleotide comprises at least 10 modified nucleosides, each independently comprising a modified sugar moiety.

Embodiment 145. The compound of any of embodiments 107-143, wherein the modified oligonucleotide comprises at least 15 modified nucleosides, each independently comprising a modified sugar moiety.

Embodiment 146. The compound of any of embodiments 107-143, wherein each nucleoside of the modified oligonucleotide is a modified nucleoside, each independently comprising a modified sugar moiety.

Embodiment 147. The compound of any of embodiments 107-146, wherein the modified oligonucleotide comprises at least two modified nucleosides comprising modified sugar moieties that are the same as one another.

Embodiment 148. The compound of any of embodiments 107-146, wherein the modified oligonucleotide comprises at least two modified nucleosides comprising modified sugar moieties that are different from one another.

Embodiment 149. The compound of any of embodiments 107-148, wherein the modified oligonucleotide comprises a modified region of at least 5 contiguous modified nucleosides.

Embodiment 150. The compound of any of embodiments 107-148, wherein the modified oligonucleotide comprises a modified region of at least 10 contiguous modified nucleosides.

Embodiment 151. The compound of any of embodiments 107-148, wherein the modified oligonucleotide comprises a modified region of at least 15 contiguous modified nucleosides.

Embodiment 152. The compound of any of embodiments 107-148, wherein the modified oligonucleotide comprises a modified region of at least 16 contiguous modified nucleosides.

Embodiment 153. The compound of any of embodiments 107-148, wherein the modified oligonucleotide comprises a modified region of at least 17 contiguous modified nucleosides.

Embodiment 154. The compound of any of embodiments 107-148, wherein the modified oligonucleotide comprises a modified region of at least 18 contiguous modified nucleosides.

Embodiment 155. The compound of any of embodiments 107-148, wherein the modified oligonucleotide comprises a modified region of at least 20 contiguous modified nucleosides.

Embodiment 156. The compound of any of embodiments 149-155, wherein each modified nucleoside of the modified region has a modified sugar moiety independently selected from among: 2'-F, 2'-OMe, 2'-MOE, cEt, LNA, morpholino, and modified morpholino.

Embodiment 157. The compound of any of embodiments 149-156, wherein the modified nucleosides of the modified region each comprise the same modification as one another.

Embodiment 158. The compound of embodiment 157, wherein the modified nucleosides of the modified region each comprise the same 2'-substituted sugar moiety.

Embodiment 159. The compound of embodiment 157, wherein the 2'-substituted sugar moiety of the modified nucleosides of the region of modified nucleosides is selected from 2'-F, 2'-OMe, and 2'-MOE.

Embodiment 160. The compound of embodiment 157, wherein the 2'-substituted sugar moiety of the modified nucleosides of the region of modified nucleosides is 2'-MOE.

Embodiment 161. The compound of embodiment 157, wherein the modified nucleosides of the region of modified nucleosides each comprise the same bicyclic sugar moiety.

Embodiment 162. The compound of embodiment 161, wherein the bicyclic sugar moiety of the modified nucleosides of the region of modified nucleosides is selected from LNA and cEt.

Embodiment 163. The compound of embodiment 157, wherein the modified nucleosides of the region of modified nucleosides each comprises a sugar surrogate.

Embodiment 164. The compound of embodiment 163, wherein the sugar surrogate of the modified nucleosides of the region of modified nucleosides is a morpholino.

Embodiment 165. The compound of embodiment 163, wherein the sugar surrogate of the modified nucleosides of the region of modified nucleosides is a modified morpholino.

Embodiment 166. The compound of any of embodiments 107-165, wherein the modified nucleotide comprises no more than 4 contiguous naturally occurring nucleosides.

Embodiment 167. The compound of any of embodiments 107-165, wherein each nucleoside of the modified oligonucleotide is a modified nucleoside.

Embodiment 168. The compound of embodiment 167, wherein each modified nucleoside comprises a modified sugar moiety.

Embodiment 169. The compound of embodiment 168, wherein the modified nucleosides of the modified oligonucleotide comprise the same modification as one another.

Embodiment 170. The compound of embodiment 169, wherein the modified nucleosides of the modified oligonucleotide each comprise the same 2'-substituted sugar moiety.

Embodiment 171. The compound of embodiment 170, wherein the 2'-substituted sugar moiety of the modified oligonucleotide is selected from 2'-F, 2'-OMe, and 2'-MOE.

Embodiment 172. The compound of embodiment 170, wherein the 2'-substituted sugar moiety of the modified oligonucleotide is 2'-MOE.

Embodiment 173. The compound of embodiment 171, wherein the modified nucleosides of the modified oligonucleotide each comprise the same bicyclic sugar moiety.

Embodiment 174. The compound of embodiment 173, wherein the bicyclic sugar moiety of the modified oligonucleotide is selected from LNA and cEt.

Embodiment 175. The compound of embodiment 169, wherein the modified nucleosides of the modified oligonucleotide each comprises a sugar surrogate.

Embodiment 176. The compound of embodiment 175, wherein the sugar surrogate of the modified oligonucleotide is a morpholino.

Embodiment 177. The compound of embodiment 175, wherein the sugar surrogate of the modified oligonucleotide is a modified morpholino.

Embodiment 178. The compound of any of embodiments 107-177, wherein the modified oligonucleotide comprises at least one modified internucleoside linkage.

Embodiment 179. The compound of embodiment 178, wherein each internucleoside linkage is a modified internucleoside linkage.

Embodiment 180. The compound of embodiment 178 or 179, comprising at least one phosphorothioate internucleoside linkage.

Embodiment 181. The compound of embodiment 179, wherein each internucleoside linkage is a modified internucleoside linkage and wherein each internucleoside linkage comprises the same modification.

Embodiment 182. The compound of embodiment 181, wherein each internucleoside linkage is a phosphorothioate internucleoside linkage.

Embodiment 183. The compound of any of embodiments 107-182, comprising at least one conjugate.

Embodiment 184. The compound of any of embodiments 107-183, consisting of the modified oligonucleotide.

Embodiment 185. The compound of any of embodiments 107-184, wherein the compound modulates splicing of the CFTR transcript.

Embodiment 186. A pharmaceutical composition comprising a compound according to any of embodiments 107-186 and a pharmaceutically acceptable carrier or diluent.

Embodiment 187. The pharmaceutical composition of embodiment 186, wherein the pharmaceutically acceptable carrier or diluent is sterile saline.

Embodiment 188. A method of modulating splicing of a CFTR transcript in a cell comprising contacting the cell with a compound according to any of embodiments 107-187.

Embodiment 189. The method of embodiment 188, wherein the cell is in vitro.

Embodiment 190. The method of embodiment 188, wherein the cell is in an animal.

Embodiment 191. The method of any of embodiments 188-190, wherein the amount of CFTR mRNA without exon 4 is increased.

Embodiment 192. The method of any of embodiments 188-190, wherein the amount of CFTR mRNA without exon 16 is increased.

Embodiment 193. The method of any of embodiments 188-190, wherein the amount of CFTR mRNA with exon 23 or exon 24 is increased.

Embodiment 194. The method of any of embodiments 188-193, wherein the CFTR transcript is transcribed from a CFTR gene.

Embodiment 195. A method of modulating the expression of CFTR in a cell, comprising contacting the cell with a compound according to any of embodiments 107-185.

Embodiment 196. The method of embodiment 195, wherein the cell is in vitro.

Embodiment 197. The method of embodiment 195, wherein the cell is in an animal.

Embodiment 198. A method comprising administering the compound of any of embodiments 107-185 to an animal.

Embodiment 199. The method of embodiment 198, wherein the administering step comprises delivering to the animal by inhalation, parenteral injection or infusion, oral, subcutaneous or intramuscular injection, buccal, transdermal, transmucosal and topical.

Embodiment 200. The method of embodiment 198, wherein the administration is inhalation.

Embodiment 201. The method of any of embodiments 198-200, wherein the animal has one or more symptoms associated with cystic fibrosis.

Embodiment 202. The method of any of embodiments 198-200, wherein the administration results in amelioration of at least one symptom of cystic fibrosis.

Embodiment 203. The method of any of embodiments 198-202, wherein the animal is a mouse.

Embodiment 204. The method of any of embodiments 198-202, wherein the animal is a human.

Embodiment 205. A method of preventing or slowing one or more symptoms associated with cystic fibrosis, comprising administering the compound according to any of embodiments 107-185 to an animal in need thereof.

Embodiment 206. The method of embodiment 205, wherein the animal is a human.

Embodiment 207. Use of the compound according to any of embodiments 107-185 for the preparation of a medicament for use in the treatment of cystic fibrosis.

Embodiment 208. Use of the compound according to any of embodiments 107-185 for the preparation of a medicament for use in the amelioration of one or more symptoms associated with cystic fibrosis.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

A better understanding of the disclosure may be obtained in light of the following drawings which are set forth for illustrative purposes, and should not be construed as limiting the scope of the disclosure in any way.

FIG. 4 shows the genomic DNA of exon 2 in human CFTR and surrounding introns (the sequence of FIG. 4 is given the sequence identifier SEQ ID NO: 131).

FIG. 5 shows the genomic DNA of exon 4 in human CFTR and surrounding introns (the sequence of FIG. 5 is given the sequence identifier SEQ ID NO: 132).

FIG. 6 shows the genomic DNA of exon 5 in human CFTR and surrounding introns (the sequence of FIG. 6 is given the sequence identifier SEQ ID NO: 133).

FIG. 7 shows the genomic DNA of exon 7 in human CFTR and surrounding introns (the sequence of FIG. 7 is given the sequence identifier SEQ ID NO: 134).

FIG. 8 shows the genomic DNA of exon 9 in human CFTR and surrounding introns (the sequence of FIG. 8 is given the sequence identifier SEQ ID NO: 135).

FIG. 9 shows the genomic DNA of exon 10 in human CFTR and surrounding introns (the sequence of FIG. 9 is given the sequence identifier SEQ ID NO: 136).

FIG. 10 shows the genomic DNA of exon 11 in human CFTR and surrounding introns (the sequence of FIG. 10 is given the sequence identifier SEQ ID NO: 137).

FIG. 11 shows the genomic DNA of exon 13 in human CFTR and surrounding introns (the sequence of FIG. 11 is given the sequence identifier SEQ ID NO: 138).

FIG. 12 shows the genomic DNA of exon 15 in human CFTR and surrounding introns (the sequence of FIG. 12 is given the sequence identifier SEQ ID NO: 139).

FIG. 13 shows the genomic DNA of exon 16 in human CFTR and surrounding introns (the sequence of FIG. 13 is given the sequence identifier SEQ ID NO: 140).

FIG. 14 shows the genomic DNA of exon 20 in human CFTR and surrounding introns (the sequence of FIG. 14 is given the sequence identifier SEQ ID NO: 141).

FIG. 15 shows the genomic DNA of exon 22 in human CFTR and surrounding introns (the sequence of FIG. 15 is given the sequence identifier SEQ ID NO: 142).

FIG. 16 shows the genomic DNA of exon 23 in human CFTR and surrounding introns (the sequence of FIG. 16 is given the sequence identifier SEQ ID NO: 143).

FIG. 17 shows the genomic DNA of exon 24 in human CFTR and surrounding introns (the sequence of FIG. 17 is given the sequence identifier SEQ ID NO: 144).

FIG. 19A shows a radioactive RT-PCR of CFTR RNA isolated from hippocampus that demonstrates that ASO 5-1 induces CFTR exon 5 skipping in vivo. Splice isoforms are labeled and exon 5 skipping quantification is shown at the bottom.

FIG. 23B shows ASO-+10kb rescues CFTR function similar to Corr951 in patient HBE cells. Representative Ieq traces of treatment (Corr951 or ASO-+10 kb) compared to control (ASO-C, top, or DMSO, bottom).

Figure 1A:
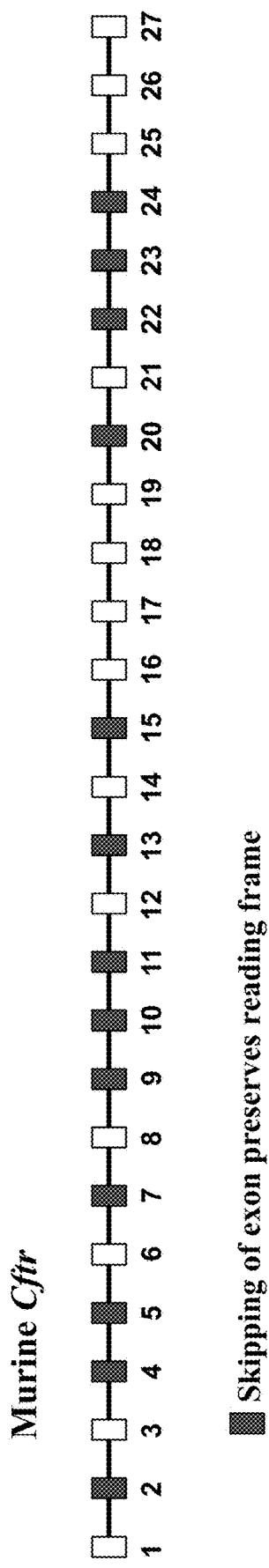
FIG. 1A shows a map of the murine/mouse CFTR gene. Boxes represent exons and lines represent introns. The exons that can be skipped or spliced out of the mature mRNA and still maintain the open reading frame of the mRNA are shaded. The CFTR mRNAs lacking any one of these exons will code for a full-length CFTR protein with an internal deletion of the specific targeted exon sequence.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present disclosure.

DETAILED DESCRIPTION OF THE DISCLOSURE

The present disclosure relates to general compounds and methods to treat cystic fibrosis in subjects using antisense oligonucleotides (ASOs) that induce specific pre-mRNA splicing events in CFTR gene transcripts that result in mRNAs that code for proteins that fully or partially restore the function of CFTR (i.e., resulting in increased levels of correctly localized CFTR protein at the plasma membrane and with increased function). For example, some ASOs can base-pair with the target RNA and correct aberrant splicing caused by mutations, and other ASOs can induce skipping of exons with mutations that cause open reading frame-shifts. In such instances, skipping of the mutated exon using ASOs can restore the reading frame and generate an mRNA that codes for a CFTR isoform with partial function.

The CFTR gene encodes a member of the ATP-binding cassette (ABC) transporter superfamily. ABC proteins transport various molecules across extra- and intra-cellular membranes. ABC genes are divided into seven distinct subfamilies (ABC1, MDR/TAP, MRP, ALD, OABP, GCN20, White). The CFTR protein is a member of the MRP subfamily that is involved in multi-drug resistance. The encoded protein functions as a chloride channel and controls the regulation of other transport pathways. Mutations in the CFTR gene are associated with the autosomal recessive disorders cystic fibrosis and congenital bilateral aplasia of the vas deferens. Alternatively spliced transcript variants have been described, many of which result from mutations in this gene.

Human (*Homo sapiens*) cystic fibrosis transmembrane conductance regulator is located on chromosome 7: 117,465,784-117,715,971 (forward strand; SEQ ID NO: 130). The gene is 6132 bp mRNA (Gene ID: 1080; Official Symbol: CFTR; Official Full Name: cystic fibrosis transmembrane conductance regulator) and is assigned NCBI Reference Sequence: NM_000492.3 (SEQ ID NO: 145); ACCESSION: NM_000492; Ensembl: ENSG00000001626; HPRD: 03883; MIM: 602421; and Vega: OTTHUMG00000023076. CFTR is also known as: CF; MRP7; ABC35; ABCC7; CFTR/MRP; TNR-CFTR; dJ76005.1. Human CFTR protein is assigned NCBI Reference Sequence: NP_000483.3 (1480 aa; SEQ ID NO: 146).

The mouse (*Mus musculus*) cystic fibrosis transmembrane conductance regulator is located on chromosome 6: 18170687-18322768 (SEQ ID NO: 147). The mouse CFTR gene is 6305 bp (Gene ID: 12638; Official Symbol: Cftr; Official Full Name: cystic fibrosis transmembrane conductance regulator), and is also known as: Abcc7; AW495489; ATP-binding cassette sub-family C member 7; ATP-binding cassette transporter sub-family C member 7; ATP-binding cassette, subfamily c, member 7; cAMP-dependent chloride channel; channel conductance-controlling ATPase; cystic fibrosis transmembrane conductance regulator homolog cystic fibrosis transmembrane conductance regulator homolog; ATP-binding cassette, subfamily c, member 7. The mouse CFTR gene has been assigned NCBI Reference Sequence: NM_021050.2 (SEQ ID NO: 148), and Ensembl: ENSMUSG00000041301. The mouse CFTR protein is assigned NCBI Reference Sequence: NP_066388.1 (1476 aa; SEQ ID NO: 149).

Antisense compounds, (e.g. antisense oligonucleotides (ASOs)) have been used to modulate target nucleic acids. Antisense compounds comprising a variety of chemical modifications and motifs have been reported. In certain instances, such compounds are useful as research tools, diagnostic reagents, and as therapeutic agents. In certain instances, antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Pre-mRNA splicing involves the precise and accurate removal of introns from the pre-messenger RNA and the ligation of exons together after intron removal to generate the mature mRNA which serves as the template for protein translation. Pre-mRNA splicing is a two-step reaction carried out by a spliceosome complex comprising protein and small RNA components which recognize conserved sequence elements within the introns and exons of the RNA. Recognition of these sequence elements, including the 5' splice site, 3' splice site and branch point sequence, is the primary mechanism directing the correct removal of introns.

Splicing requires direct base-pairing between small nuclear RNA (snRNA) components of the spliceosome and the splice site nucleotides of the mRNA. This interaction can be easily disrupted by gene mutations or by artificial blocking using short oligonucleotides complementary to the RNA. Such so called antisense oligonucleotides (ASOs), when designed to be complementary to a splice sites, will compete for base-pairing with the snRNAs, thereby blocking an essential step in splicing at the site. In this way, antisense oligonucleotides can potently block unwanted splicing or redirect splicing to alternative splice sites, and can result in mRNAs that code for proteins that fully or partially restore the function to target transcripts.

For example, ASOs can target the 2789+5 G>A mutation in intron 16 of the CFTR gene that causes cystic fibrosis. This mutation has been observed in 521 patients with cystic fibrosis. Because aberrant splicing of exon 16 due to the mutation is the cause of cystic fibrosis in patients with this mutation, improving splicing using antisense oligonucleotides to interfere with the deleterious effects of the mutation, can have a therapeutic benefit to the patients. In a non-limiting example, an antisense oligonucleotide that targets the 2789+5 G>A mutation of the CFTR gene that causes cystic fibrosis can be SEQ ID NO: 97.

In another non-limiting example, antisense oligonucleotides can target the 3849+10 kbC->T mutation in intron 19 of the CFTR gene. This mutation has been observed in 496 patients, and in 1,100 patients in CFTR2 database. The 3849+10 kbC>T mutation creates a cryptic splice site that results in an aberrant mRNA that does not produce CFTR protein and antisense oligonucleotides targeted to the region of intron 19 surrounding and encompassing this mutation can potentially block splicing to this cryptic splice site. In a non-limiting example, an antisense oligonucleotide that targets the 3849+10 kbC>T mutation of the CFTR gene that causes cystic fibrosis can be SEQ ID NO:150.

In yet another non-limiting example, antisense oligonucleotides can target the 3272-26 A->G mutation of the CFTR gene that causes cystic fibrosis. This mutation is found in 186 patients. The 3272-26 A>G mutation creates a cryptic splice site that results in an aberrant mRNA that does not produce CFTR protein. Antisense oligonucleotides targeted to the region of surrounding and encompassing this mutation can potentially block splicing to this cryptic splice site. In a non-limiting example, an antisense oligonucleotide that targets the 3272-26 A->G mutation of the CFTR gene that causes cystic fibrosis can be SEQ ID NO: 114.

In another non-limiting example, antisense oligonucleotides can target exon skipping in exons that have nonsense mutations. For example, skipping of exon 4, exon 23 or exon 24 all can result in an mRNA transcript that is in-frame so that translation will continue to the natural stop-codon (i.e., mutations such as CFTR 621+1 G>T and CFTR 406 G>T). Exons 4, 23, and 24 have a number of different patient nonsense mutations that cause cystic fibrosis and any of these can be treated by ASOs that induce exon skipping of the exons that house nonsense mutations to correct the reading frame and allow translation through to the natural termination codon.

In yet other non-limiting examples, 70-90% of all Cystic fibrosis (CF) patients have a mutation in exon 11 (deltaF508) which can be targeted by ASO 11-6 (SEQ ID NO.: 91). Five percent of CF patients have a splice site mutation in intron 16 which can be targeted and corrected by ASO 16-8 (SEQ ID NO.: 102); 2.5% of CF patients have a nonsense mutation in exon 23 which can be targeted for skipping and frameshift correction using ASO 23-4 (SEQ ID NO.: 126); 2.5% of CF patients have a nonsense mutation in exon 24 which can be targeted for skipping and frame-shift correction using ASO 24-1, 24-2, 24-3 (SEQ ID NO.: 127, 128, 129; respectively); CF mutation databases indicate that nonsense and splicing mutations in and around exon 4 are common and can be targeted for gene expression correction either by splicing redirection or frame-shift correction using ASO 4-1 (SEQ ID NO.: 65); and CF causing nonsense mutations in exons 2, 5, 7, 9, 10, 13, 20 and 22 are also commonly annotated in the Human Gene Mutation Database and can be targeted by ASOs 2-4, 5-1, 7-4, 9-1, 11-6, 13-1, 15-1, 20-2, 22-1 (SEQ ID NO.: 64, 71, 76, 78, 91, 92, 94, 111, 116; respectively).

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "antisense compound" or "antisense oligonucleotide (ASO)" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one sub stituent group that differs from that of a naturally occurring sugar moiety. Substituted sugar moieties include, but are not limited to, furanosyls comprising substituents at the 2'-position, the 3'-position, the 5'-position and/or the 4'-position.

As used herein, "2'-substituted sugar moiety" means a furanosyl comprising a substituent at the 2'-position other than —H or —OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring).

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments, the 4 to 7 membered ring is a furanosyl. In certain such embodiments, the bridge connects the 2'-carbon and the 4'-carbon of the furanosyl.

As used herein, the term "sugar surrogate" means a structure that does not comprise a furanosyl and that is capable of replacing the naturally occurring sugar moiety of a nucleoside, such that the resulting nucleoside is capable of: (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group.

As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein, the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)-0-2'bridge.

As used herein, "locked nucleic acid nucleoside" or "LNA" means a nucleoside comprising a bicyclic sugar moiety comprising a 4'-CH$_2$-0-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more substructures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to, pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre -mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification,"

even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, 20 or 25 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment. Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett,* 1990, 259, 327-330; Svinarchuk et al., *Biochimie,* 1993, 75, 49-54), a phospholipid, e.g., di-hexadecyl-rac-glycerol or triethyl-ammonium 1,2-di-0-hexadecyl-rac-glycero-3-H-phosphonate (Manoharan et al., *Tetrahedron Lett.,* 1995, 36:3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36:3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *Pharmacol. Exp. Ther.,* 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_2$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Pharmaceutical Compositions

In certain embodiments, the present invention provides pharmaceutical compositions comprising one or more antisense compound. The pharmaceutical composition may comprise a cocktail of antisense compounds, wherein the cocktail comprises 2, 3, 4, 5, 6, 7, 8, 9, 10 or more antisense compounds. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations.

Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof.

Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide (DMSO) are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™ the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human. In certain embodiments, the animal is a mouse.

In certain embodiments, the present invention provides methods of administering a pharmaceutical composition comprising an oligomeric compound of the present invention to an animal. Suitable administration routes include, but are not limited to, oral, rectal, transmucosal, transdermal, intestinal, enteral, topical, suppository, through inhalation, intrathecal, intracerebroventricular, intraperitoneal, intranasal, intratumoral, and parenteral (e.g., intravenous, intramuscular, intramedullary, and subcutaneous). In certain embodiments, a pharmaceutical composition is prepared for transmucosal administration. In certain of such embodiments penetrants appropriate to the barrier to be permeated are used in the formulation. Such penetrants are generally known in the art. In certain embodiments, pharmaceutical compositions are administered to achieve local rather than systemic exposures. For example, pharmaceutical compositions may be aerosolized and inhaled directly in the area of desired effect (e.g., into the lungs).

In certain embodiments, a pharmaceutical composition is administered to an animal having at least one symptom associated with Cystic Fibrosis. In certain embodiments, such administration results in amelioration of at least one symptom. In certain embodiments, administration of a pharmaceutical composition to an animal results in an increase in functional CFTR protein in a cell. In certain embodiments, the administration of certain antisense oligonucleotides (ASOs) delays the onset of Cystic Fibrosis. In certain embodiments, the administration of certain antisense oligonucleotides prevents the onset of Cystic Fibrosis. In certain embodiments, the administration of certain antisense oligonucleotides rescues cellular phenotype.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence

EXAMPLES

The Examples that follow are illustrative of specific embodiments of the invention, and various uses thereof. They are set forth for explanatory purposes only, and are not to be taken as limiting the invention.

Methods

Antisense Oligonucleotides (ASOs). ASOs with phosphorodiamidate morpholino (PMO) chemistries were generated by GeneTools LLC and were dissolved in 0.9% saline.

Cell culture and transfection. T84 cells are a human colonic adenocarcinoma cell line and the mouse primary cell line, 208EE, was established from an adult C57BL/6 mouse kidney. ASOs (15 µM final concentration) were transfected into cells using Endo-Porter (GeneTools). RNA was collected 48 hours post-transfection.

RNA isolation and analysis. RNA was isolated from tissue and cells in culture using TRIZOL™ reagent (Life Technologies, Carlsbad, Calif.) according to the manufacturer's protocol. For human tissue, RNA was isolated and treated with 4 µg of DNase-I (RNase-free) (Life Technologies) followed by reverse transcription with GoScript™ reverse transcription system (Promega, Madison, Wis.). Radiolabeled and cold PCR was carried out using primers specific for human or mouse CFTR region encompassing the ASO target exon. PCR products were separated by polyacrylamide or agarose gel electrophoresis and bands on gels were quantitated by densitometry analysis using Image J software.

Example 1

Figure 1B:
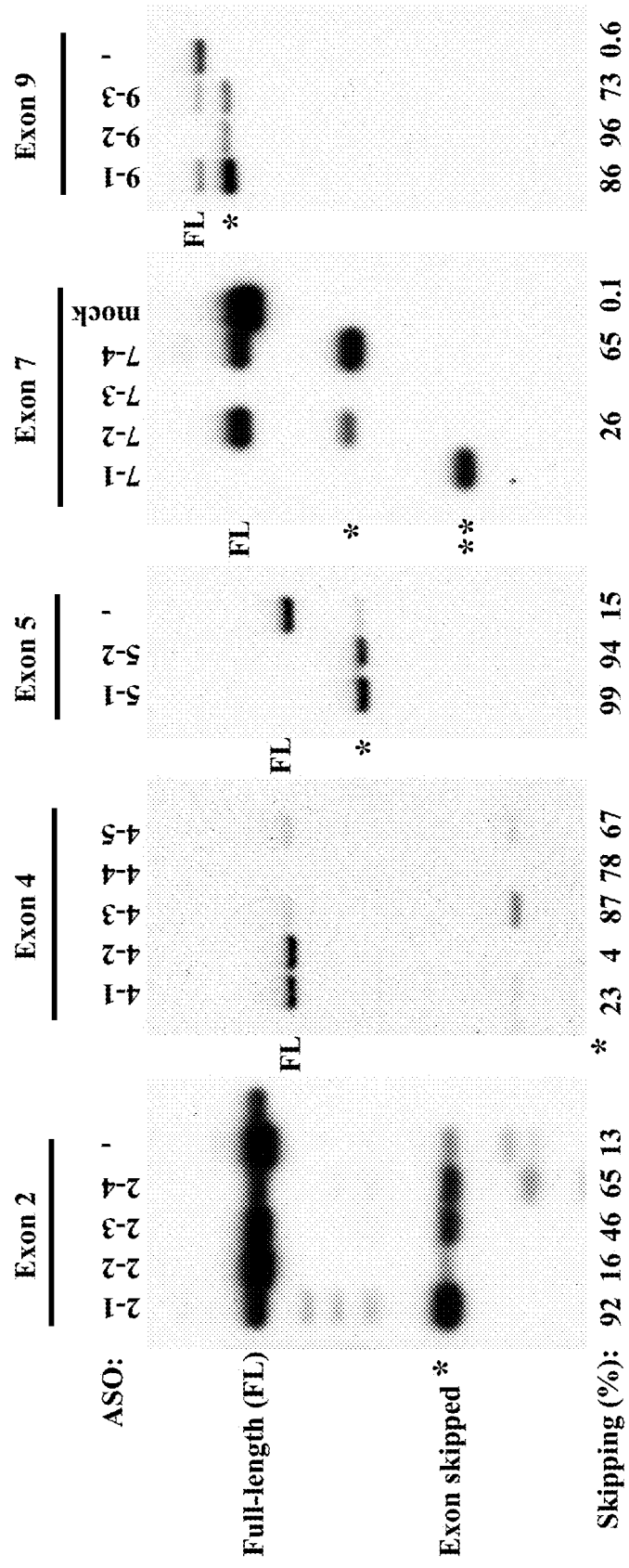
FIG. 1B shows antisense oligonucleotides induce skipping of targeted exons 2, 4, 5, 7 and 9 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (−). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 1C:
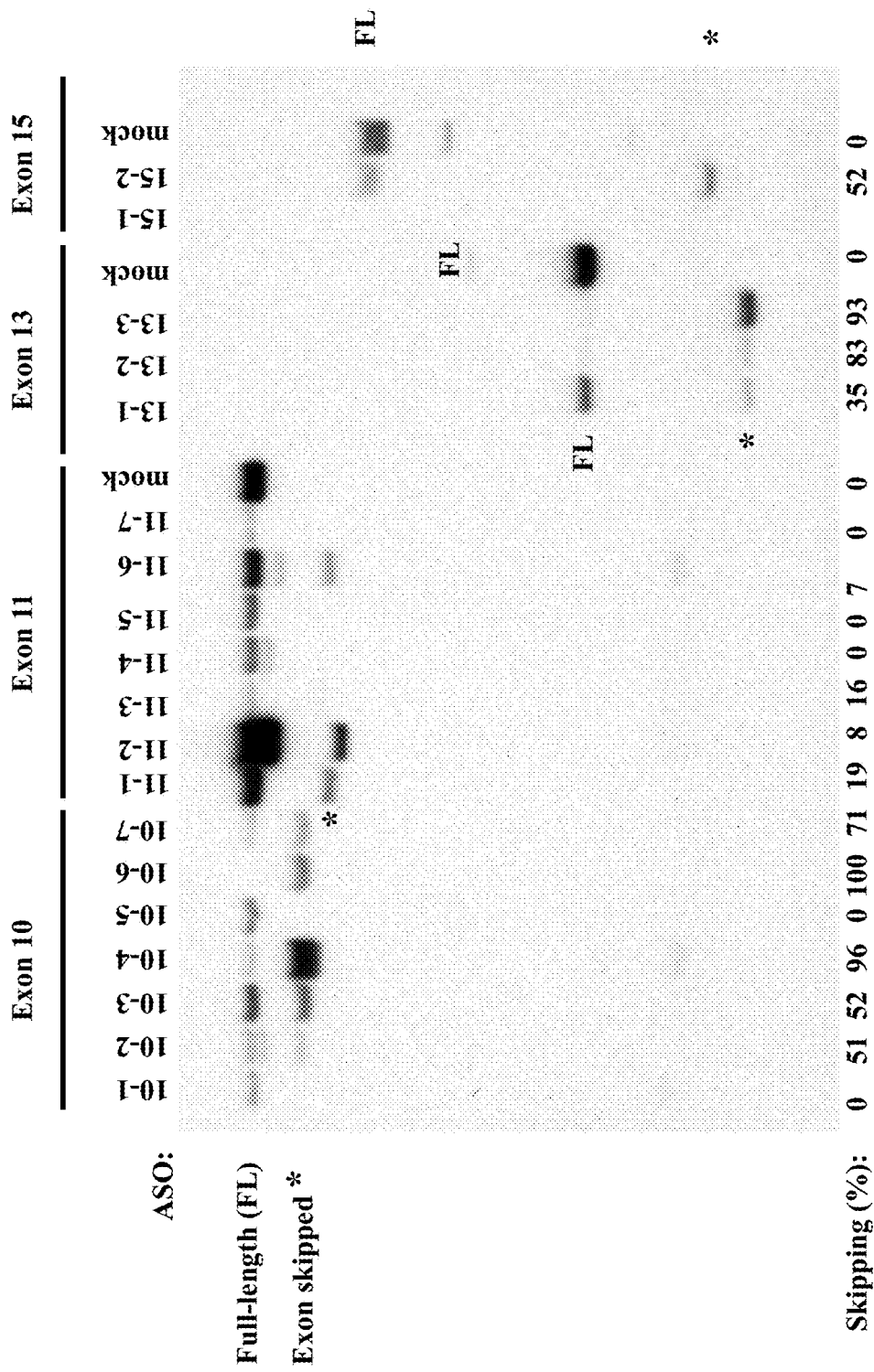
FIG. 1C shows antisense oligonucleotides induce skipping of targeted exons 10, 11, 13 and 15 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (−). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 1D:
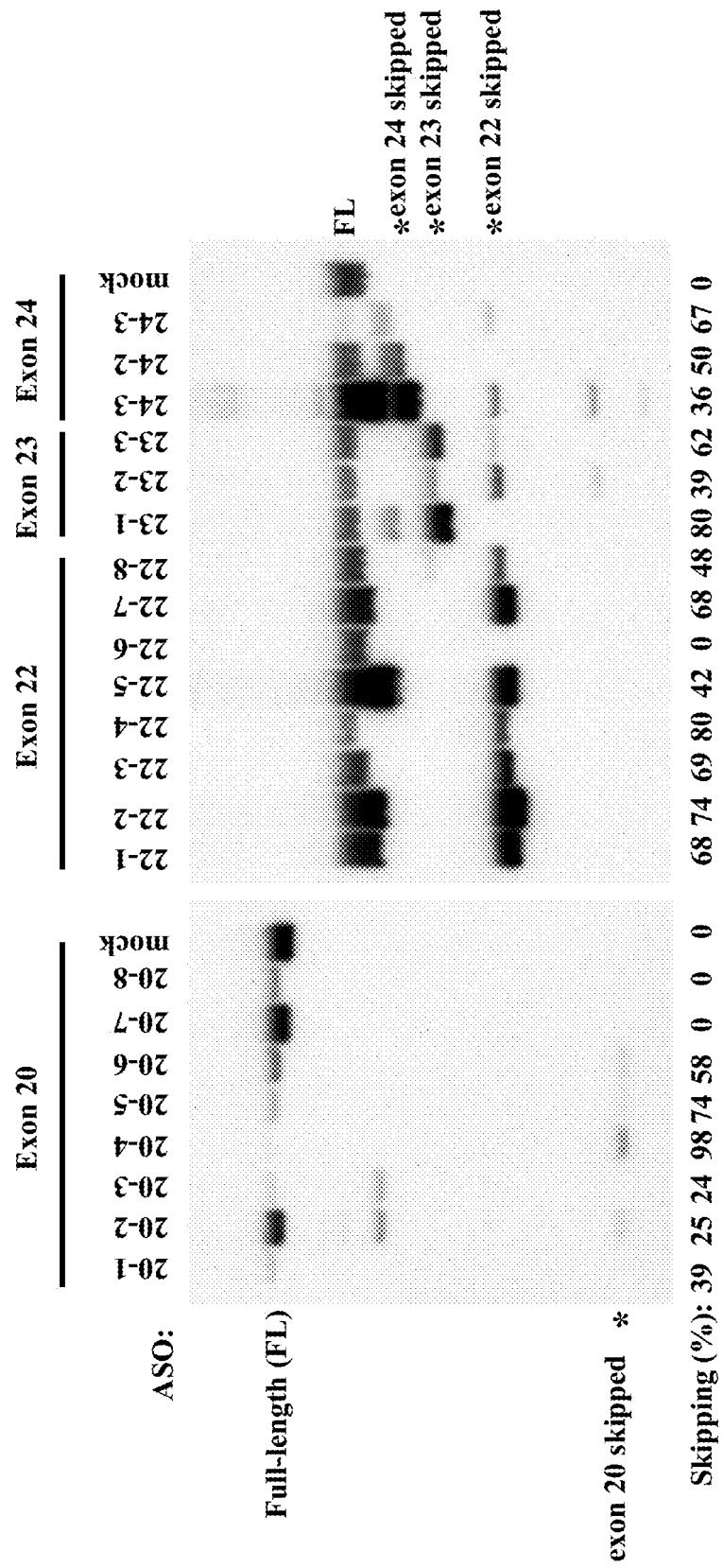
FIG. 1D shows antisense oligonucleotides induce skipping of targeted exons 20, 22, 23 and 24 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (−). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 2A:
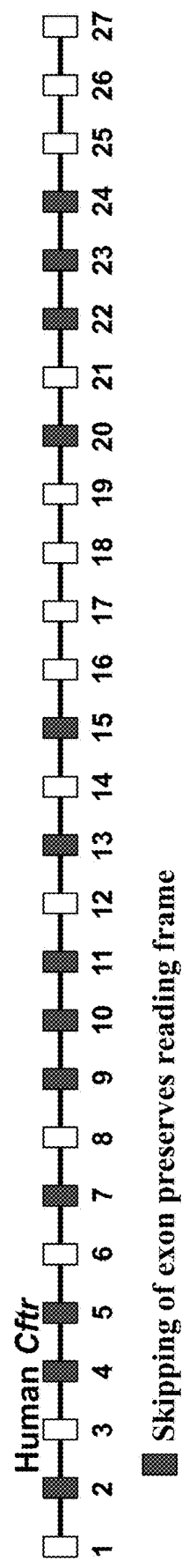
FIG. 2A shows a map of the human CFTR gene. Boxes represent exons and lines represent introns. The exons that can be skipped or spliced out of the mature mRNA and still maintain the open reading frame of the mRNA are shaded. The CFTR mRNAs lacking any one of these exons will code for a full-length CFTR protein with an internal deletion of the specific targeted exon sequence.
Figure 2B:
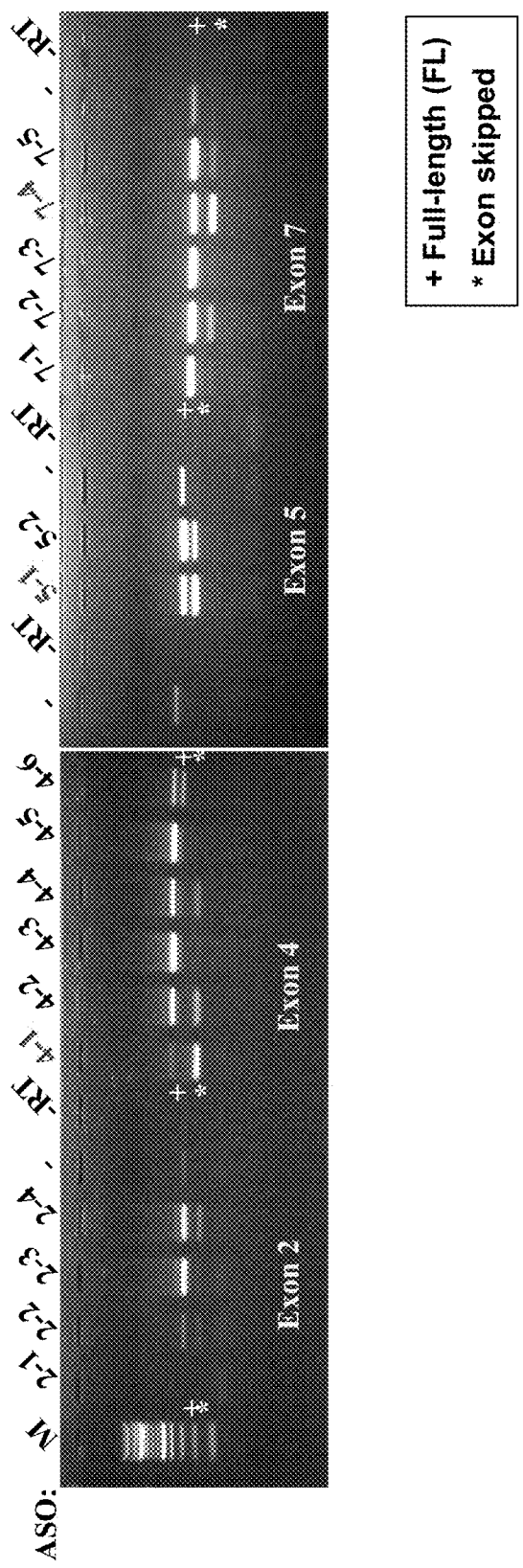
FIG. 2B show antisense oligonucleotides induce skipping of targeted exons 2, 4, 5 and 7 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (−) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 2C:
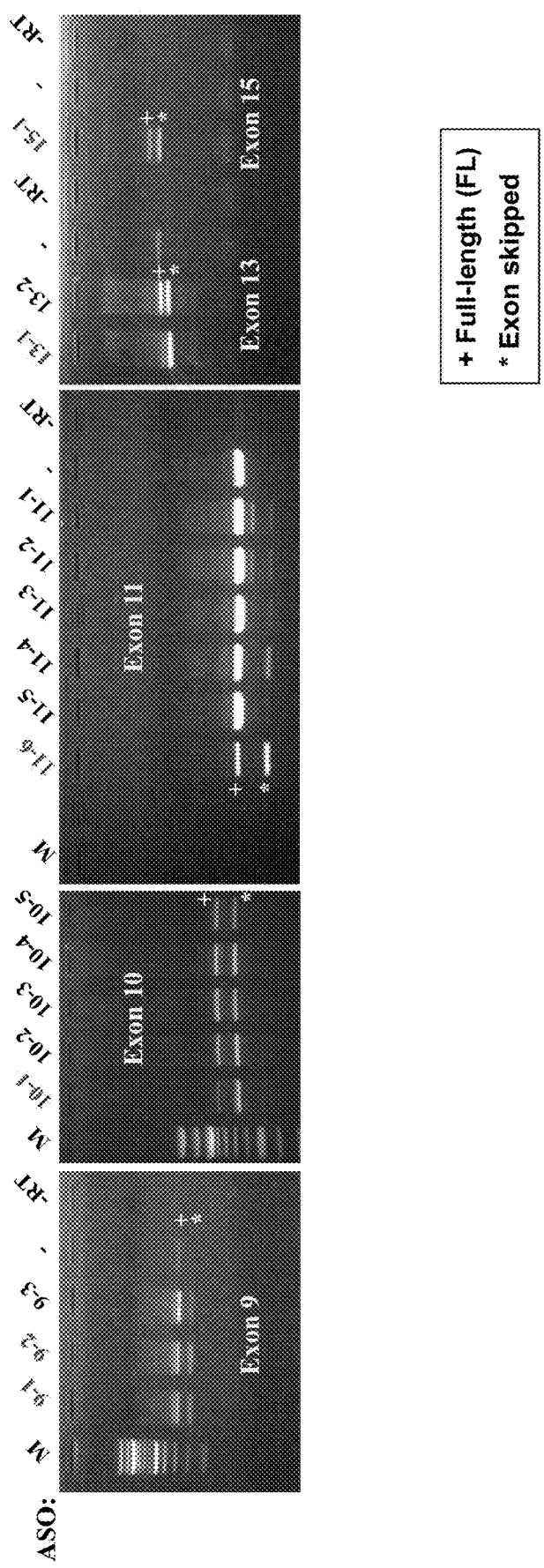
FIG. 2C show antisense oligonucleotides induce skipping of targeted exons 9, 10, 11, 13 and 15 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (−) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 2D:
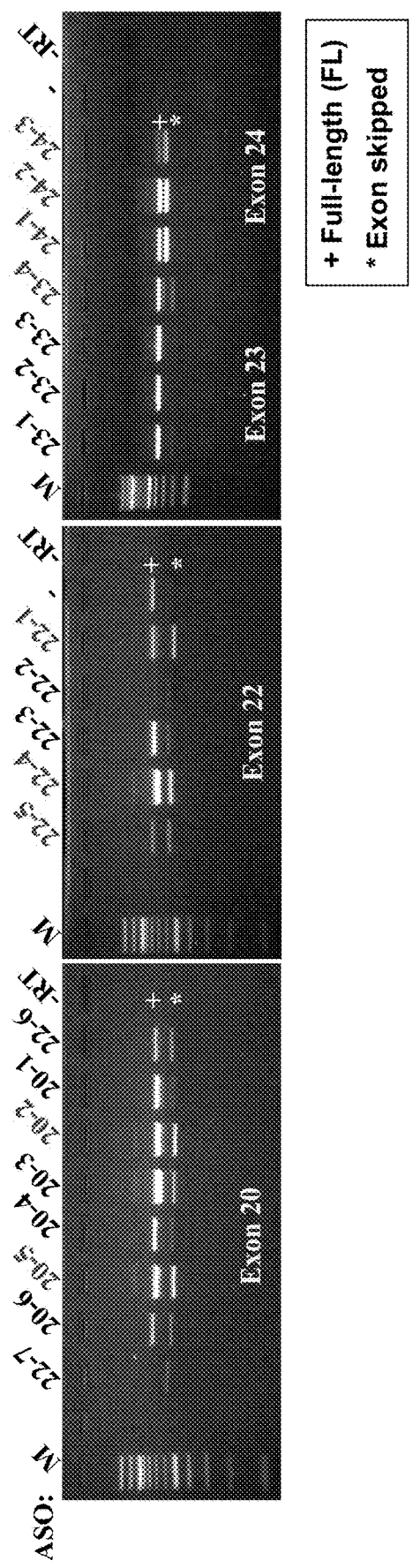
FIG. 2D show antisense oligonucleotides induce skipping of targeted exons 20, 22, 23 and 24 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (−) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 3A:
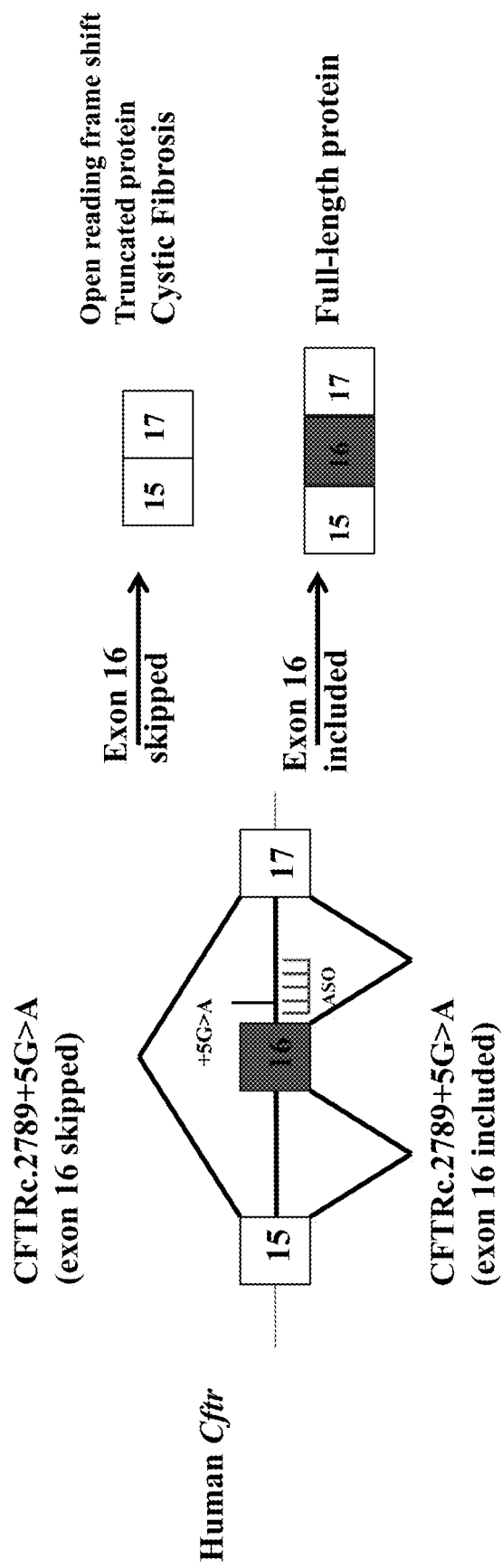
FIG. 3A shows a schematic of the splicing pattern of human CFTR c.2789+5 G>A without and with ASO targeting. Boxes are exons and lines are introns. Diagonal lines indicate splicing pathway FIG. 3B demonstrates that antisense oligonucleotides correct splicing of human CFTR exon 16 with c.2789+5 G>A mutation. Polyacrylamide gel images of reverse-transcription/polymerase chain reaction (RT-PCR) products were separated by electrophoresis. RT-PCR was performed on RNA isolated from human lymphoblast cell line GM11859, whose donor is homozygous for G-to-A substitution at nucleotide 2789+5 in intron 16 which results in an mRNA splicing defect (2789+5 G>A). Cells were treated with the indicated ASO. The products were amplified with primers specific to exons flanking the specific ASO-targeted exon in order to resolve the full-length (FL) and exon-skipped products. ASO 16-8 was effective at correcting exon 16 splicing of CFTRc.2789+5 G>A.
Figure 3B:
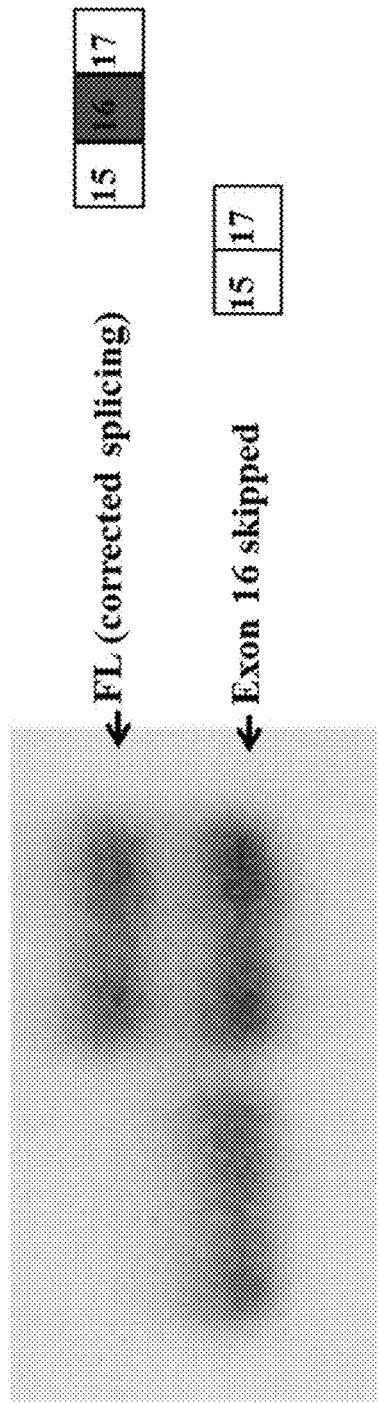

Antisense Oligonucleotides Induce Skipping of Targeted Exons in Murine CFTR Gene-derived Pre-mRNA Various ASOs (see Table 1; SEQ ID NOs: 1-60) were tested in the mouse primary cell line, 208EE (which was established from an adult C57BL/6 mouse kidney). ASOs (15 µM final concentration) were transfected into cells using Endo-Porter (GeneTools). FIGS. 1B, 1C and 1D demonstrate that ASOs induce skipping of targeted exons in murine CFTR.

TABLE 1

Antisense oligonucleotides targeting mouse CFTR induce exon skipping.

| Name | Target Exon | Sequence | % skipped * | SEQ ID NO. |
|---|---|---|---|---|
| 2-1 | 2 | GGTCCAGCTAAAAGAGAAGAGGGCA | 92 | SEQ ID NO. 1 |
| 2-2 | 2 | CTTTCCTCAAAATTGGTGTGGTCCA | 16 | SEQ ID NO. 2 |
| 2-3 | 2 | TATGTCTGACAACTCCAAGTGGTGT | 46 | SEQ ID NO. 3 |
| 2-4 | 2 | CTAGTTTTTCAGACAAGTGGTCAGC | 65 | SEQ ID NO. 4 |
| 4-1 | 4 | TTCCTAGCAAGACAGGCTGGACAGC | nd | SEQ ID NO. 5 |
| 4-2 | 4 | ATAGGATGCTATGATTCTTCCTAGC | 23 | SEQ ID NO. 6 |
| 4-3 | 4 | ATAAGCCTATGCCAAGGTAAATGGC | 4 | SEQ ID NO. 7 |
| 4-4 | 4 | TGTCCTGACAATGAAGAGAAGGCAT | 87 | SEQ ID NO. 8 |
| 4-5 | 4 | AATGCGATGAAGGCCAAAAATAGCT | 78 | SEQ ID NO. 9 |
| 4-6 | 4 | TAGCTGTTCTCATCTGCATTCCAAT | 67 | SEQ ID NO. 10 |
| 4-7 | 4 | CATCTTCCAAAAAGTATTACCTTCT | nd | SEQ ID NO. 11 |
| 5-1 | 5 | TTGTTCAGGTTGTTGGAAAGAAGAC | 99 | SEQ ID NO. 12 |
| 5-2 | 5 | ATCAAGAACGCGGCTTGACAACTTT | 94 | SEQ ID NO. 13 |
| 7-1 | 7 | CACGAGTCTTTCATTGATCTTTGCA | 20 | SEQ ID NO. 14 |
| 7-2 | 7 | CTGATTCCCAACAATATGCCTTAAC | 26 | SEQ ID NO. 15 |
| 7-3 | 7 | CAATCATTTCTCCATCGCTGATTC | 42 | SEQ ID NO. 16 |
| 7-4 | 7 | ATTATGTCAACTTACTCTCTCAAGT | 65 | SEQ ID NO. 17 |
| 9-1 | 9 | GCCTGTGGTCATTAAGTTATACTCC | 86 | SEQ ID NO. 18 |
| 9-2 | 9 | CTCCTCCCAAAATGCTGTTACATTT | 96 | SEQ ID NO. 19 |
| 9-3 | 9 | TATTTAGAAATCTCACCTCCTCCCA | 73 | SEQ ID NO. 20 |

TABLE 1-continued

Antisense oligonucleotides targeting mouse CFTR induce exon skipping.

| Name | Target Exon | Sequence | % skipped * | SEQ ID NO. |
|---|---|---|---|---|
| 10-1 | 10 | CTTTCTCCAGTAATTCCCCAAATCC | 0 | SEQ ID NO. 21 |
| 10-2 | 10 | GTCACCATTGCTTTGTTGTACTTTC | 51 | SEQ ID NO. 22 |
| 10-3 | 10 | CTGAAACTGACATTGTTCTCATCAC | 52 | SEQ ID NO. 23 |
| 10-4 | 10 | AGGATTTCCCACAAGGCAGAGATGA | 96 | SEQ ID NO. 24 |
| 10-5 | 10 | ATAGCCAACATCTCTCCTTTCTCTA | 0 | SEQ ID NO. 25 |
| 10-6 | 10 | CTTTCCTGATCCAGTAGATCCAGTA | 100 | SEQ ID NO. 26 |
| 10-7 | 10 | TTAAAGAGACAGTACCTTTCCTGAT | 71 | SEQ ID NO. 27 |
| 11-1 | 11 | TCCAGTTCTCCCAAAATCAACATCA | 19 | SEQ ID NO. 28 |
| 11-2 | 11 | TGTGCTTAATAATTCCCTCTGAAGC | 8 | SEQ ID NO. 29 |
| 11-3 | 11 | ATTGAGAGCAGAATGAAACTCTTCC | 16 | SEQ ID NO. 30 |
| 11-4 | 11 | GATATTTTCTTTGATAGTACCCGGC | 0 | SEQ ID NO. 31 |
| 11-5 | 11 | ACACTCTTATATCTGTACTCATCAT | 0 | SEQ ID NO. 32 |
| 11-6 | 11 | CTGCTGTAGTTGGCAAGCTTTGACA | 7 | SEQ ID NO. 33 |
| 11-7 | 11 | CATAAATATGCTTACCTGCTGTAGT | 0 | SEQ ID NO. 34 |
| 13-1 | 13 | GGGAATCTAATAGGTACAAATCAGC | 35 | SEQ ID NO. 35 |
| 13-2 | 13 | CAAATCAGCATCTTTATATACTGCT | 83 | SEQ ID NO. 36 |
| 13-3 | 13 | ACTCAGTCATAGAACATACCTTTCA | 93 | SEQ ID NO. 37 |
| 15-1 | 15 | AACAAACATACTTACCTCAACCAGA | 52 | SEQ ID NO. 38 |
| 20-1 | 20 | CCTGCCTGTAAATCATCCCATAGGA | 39 | SEQ ID NO. 39 |
| 20-2 | 20 | CAAGGTGGGTGAAAATTGGACTCCT | 25 | SEQ ID NO. 40 |
| 20-3 | 20 | CGAAGTGTCCAGAGTCCTTTTAAGC | 24 | SEQ ID NO. 41 |
| 20-4 | 20 | CAGAGTTTCAAAGTAAGTCTGGCGT | 98 | SEQ ID NO. 42 |
| 20-5 | 20 | TTGGCAGTGTGCAAATTCAGAGCTT | 74 | SEQ ID NO. 43 |
| 20-6 | 20 | CTATTCTCATTTGGAACCAGCGCAA | 58 | SEQ ID NO. 44 |
| 20-7 | 20 | AGAGGACAAATATCATGTCTATTCT | 0 | SEQ ID NO. 45 |
| 20-8 | 20 | ATGGAGATGAAGGTAACAACAATGA | 0 | SEQ ID NO. 46 |
| 22-1 | 22 | AACTTAAACACTCTGCTCACAGATC | 68 | SEQ ID NO. 47 |
| 22-2 | 22 | CTAAAACGTCAGATGATCCTTCTCT | 74 | SEQ ID NO. 48 |
| 22-3 | 22 | TATCACTTTCTTCACATGCTCATT | 69 | SEQ ID NO. 49 |
| 22-4 | 22 | ACCATTTCGCCTCCAGAGGGCCAGA | 80 | SEQ ID NO. 50 |
| 22-5 | 22 | CATCCATGTATTTCACAGTAAGGTC | 42 | SEQ ID NO. 51 |
| 22-6 | 22 | ATGTTCTCTAATACGGCATTTCCAT | 0 | SEQ ID NO. 52 |
| 22-7 | 22 | CCTCTGTCCAGGACTTATTGAAAAA | 68 | SEQ ID NO. 53 |
| 22-8 | 22 | GTAATGCTGAAATCTCACCCTCTGT | 48 | SEQ ID NO. 54 |
| 23-1 | 23 | AATTCCATGAGACACCATCAATCTC | 80 | SEQ ID NO. 55 |
| 23-2 | 23 | GTACTTTTCCTGATCCAGTTCTTC | 39 | SEQ ID NO. 56 |
| 23-3 | 23 | CATTTTGTGCTCACCTGTGTTATC | 62 | SEQ ID NO. 57 |

TABLE 1-continued

Antisense oligonucleotides targeting mouse CFTR induce exon skipping.

| Name | Target Exon | Sequence | % skipped * | SEQ ID NO. |
|---|---|---|---|---|
| 24-1 | 24 | CATCTTTCCATTTTCCATTGGGATC | 36 | SEQ ID NO. 58 |
| 24-2 | 24 | CTCATCTGCAACTTTCCATATTTCT | 50 | SEQ ID NO. 59 |
| 24-3 | 24 | TATTTGTCATCCTTACCTCATCTGC | 67 | SEQ ID NO. 60 |

* percent of the mRNA transcripts that skip out the targeted exon

Example 2

Antisense Oligonucleotides Induce Skipping of Targeted Exons in Human CFTR Gene-derived Pre-mRNA Various ASOs (see Table 2; SEQ ID NOs: 61-129) were tested in the human colonic adenocarcinoma cell line primary cell line, T84. ASOs (15 μM final concentration) were transfected into cells using Endo-Porter (GeneTools). FIGS. 2B, 2C, 2D and FIG. 3 demonstrate that ASOs induce skipping of targeted exons in human CFTR.

TABLE 2

Antisense oligonucleotides targeting human CFTR induce exon skipping

| Name | Target Exon | Sequence | % skipped * | SEQ ID NO. |
|---|---|---|---|---|
| 2-1 | 2 | ATCCTTTCCTCAAAATTGGTCTGGT | 0 | SEQ ID NO. 61 |
| 2-2 | 2 | GTATATGTCTGACAATTCCAGGCGC | 35 | SEQ ID NO. 62 |
| 2-3 | 2 | CAGATAGATTGTCAGCAGAATCAAC | 18 | SEQ ID NO. 63 |
| 2-4 | 2 | GTACATGAACATACCTTTCCAATTT | 37 | SEQ ID NO. 64 |
| 4-1 | 4 | GAGGCTGTACTGCTTTGGTGACTTC | 77 | SEQ ID NO. 65 |
| 4-2 | 4 | GAAGCTATGATTCTTCCCAGTAAGA | 54 | SEQ ID NO. 66 |
| 4-3 | 4 | GTGTAGGAGCAGTGTCCTCACAATA | 0 | SEQ ID NO. 67 |
| 4-4 | 4 | AATGTGATGAAGGCCAAAAATGGCT | 39 | SEQ ID NO. 68 |
| 4-5 | 4 | GCTATTCTCATCTGCATTCCAATGT | 0 | SEQ ID NO. 69 |
| 4-6 | 4 | CCTGTGCAAGGAAGTATTACCTTCT | 0 | SEQ ID NO. 70 |
| 5-1 | 5 | CTAGAACACGGCTTGACAGCTTTAA | 58 | SEQ ID NO. 71 |
| 5-2 | 5 | TGGAAAGGAGACTAACAAGTTGTCC | 42 | SEQ ID NO. 72 |
| 7-1 | 7 | ACTGATCTTCCCAGCTCTCTGATCT | 15 | SEQ ID NO. 73 |
| 7-2 | 7 | ATTTCTGAGGTAATCACAAGTCTTT | 37 | SEQ ID NO. 74 |
| 7-3 | 7 | AGTATGCCTTAACAGATTGGATATT | 28 | SEQ ID NO. 75 |
| 7-4 | 7 | ATTTTTTCCATTGCTTCTTCCCAGC | 44 | SEQ ID NO. 76 |
| 7-5 | 7 | ATTGGAACAACTTACTGTCTTAAGT | 38 | SEQ ID NO. 77 |
| 9-1 | 9 | TCCATCACTACTTCTGTAGTCGTTA | 56 | SEQ ID NO. 78 |
| 9-2 | 9 | CTCCTCCCAGAAGGCTGTTACATTC | 53 | SEQ ID NO. 79 |
| 9-3 | 9 | TTAAAAATTCTGACCTCCTCCCAGA | 33 | SEQ ID NO. 80 |

TABLE 2-continued

Antisense oligonucleotides targeting human CFTR induce exon skipping

| Name | Target Exon | Sequence | % skipped * | SEQ ID NO. |
|---|---|---|---|---|
| 10-1 | 10 | GGCTGTCATCACCATTAGAAGTTTT | 64 | SEQ ID NO. 81 |
| 10-2 | 10 | AATTACTGAAGAAGAGGCTGTCATC | 56 | SEQ ID NO. 82 |
| 10-3 | 10 | TAATATCTTTCAGGACAGGAGTACC | 49 | SEQ ID NO. 83 |
| 10-4 | 10 | GATCCAGCAACCGCCAACAACTGTC | 52 | SEQ ID NO. 84 |
| 10-5 | 10 | AGAACAAAAGAACTACCTTGCCTGC | 47 | SEQ ID NO. 85 |
| 11-1 | 11 | CTCCCATAATCACCATTAGAAGTGA | 2 | SEQ ID NO. 86 |
| 11-2 | 11 | ATTTTACCCTCTGAAGGCTCCAGTT | 2 | SEQ ID NO. 87 |
| 11-3 | 11 | ACAGAATGAAATTCTTCCACTGTGC | 2 | SEQ ID NO. 88 |
| 11-4 | 11 | GTGCCAGGCATAATCCAGGAAAACT | 14 | SEQ ID NO. 89 |
| 11-5 | 11 | ATGCTTTGATGACGCTTCTGTATCT | 2 | SEQ ID NO. 90 |
| 11-6 | 11 | TTTTCACATAGTTTCTTACCTCTTC | 72 | SEQ ID NO. 91 |
| 13-1 | 13 | TCTAGGTATCCAAAAGGAGAGTCTA | 90 | SEQ ID NO. 92 |
| 13-2 | 13 | GGTATTCAAAGAACATACCTTTCAA | 66 | SEQ ID NO. 93 |
| 15-1 | 15 | ACAATAGAACATTCTTACCTCTGCC | 93 | SEQ ID NO. 94 |
| 16-1 | 16 | TCGTTATTTGGCAGCCAAAGTTACT | n/a | SEQ ID NO. 95 |
| 16-2 | 16 | GAGCCACAGCACAACCAAAGAAGCA | n/a | SEQ ID NO. 96 |
| 16-3 | 16 | TCCAAGGAGCCACAGCAC | n/a | SEQ ID NO. 97 |
| 16-4 | 16 | TTCCAAGGAGCCACAGCA | n/a | SEQ ID NO. 98 |
| 16-5 | 16 | TTCCAAGGAGCCACAGCACAACCAA | n/a | SEQ ID NO. 99 |
| 16-6 | 16 | AACAGAAATAAAACACAATCTACAC | n/a | SEQ ID NO. 100 |
| 16-7 | 16 | TTTCCAAGGAGCCACAGCACAACCA | 0 | SEQ ID NO. 101 |
| 16-8 | 16 | ACAATCTACACAATAGGACATGGAA | 56 | SEQ ID NO. 102 |
| 16-9 | 16 | CACAATCTACACAATAGGACATGGA | n/a | SEQ ID NO. 103 |
| 16-10 | 16 | ACACAATCTACACAATAGGACATGG | n/a | SEQ ID NO. 104 |
| 16-11 | 16 | GACTTTTTTTCTAACATCTTCACCT | n/a | SEQ ID NO. 105 |
| 16-12 | 16 | ATGGAACAACACACAGTTGATTTTT | n/a | SEQ ID NO. 106 |
| 16-13 | 16 | ATCGAACAAGACACAGTTGATTTTT | n/a | SEQ ID NO. 107 |
| 16-14 | 16 | GAGTGGAACAAGACACAGTTGATTT | n/a | SEQ ID NO. 108 |
| 16-15 | 16 | CACAATCTACACAATAAGACATGGA | n/a | SEQ ID NO. 109 |
| 20-1 | 20 | CAAGATGAGTGAAAATTGGACTCCT | 2 | SEQ ID NO. 110 |
| 20-2 | 20 | CGAAGGCACGAAGTGTCCATAGTCC | 29 | SEQ ID NO. 111 |
| 20-3 | 20 | AACAGAGTTTCAAAGTAAGGCTGCC | 8 | SEQ ID NO. 112 |
| 20-4 | 20 | AGTTGGCAGTATGTAAATTCAGAGC | 6 | SEQ ID NO. 113 |
| 20-5 | 20 | TTCTATTCTCATTTGGAACCAGCGC | 45 | SEQ ID NO. 114 |
| 20-6 | 20 | GGTAACAGCAATGAAGAAGATGACA | 35 | SEQ ID NO. 115 |
| 22-1 | 22 | ATGTCAATGAACTTAAAGACTCGGC | 59 | SEQ ID NO. 116 |
| 22-2 | 22 | GGCCAGATGTCATCTTTCTTCACGT | 65 | SEQ ID NO. 117 |

TABLE 2-continued

Antisense oligonucleotides targeting human CFTR induce exon skipping

| Name | Target Exon | Sequence | % skipped * | SEQ ID NO. |
|---|---|---|---|---|
| 22-3 | 22 | ATCTTTGACAGTCATTTGGCCCCCT | 7 | SEQ ID NO. 118 |
| 22-4 | 22 | CCACCTTCTGTGTATTTTGCTGTGA | 45 | SEQ ID NO. 119 |
| 22-5 | 22 | TCTCTAATATGGCATTTCCACCTTC | 67 | SEQ ID NO. 120 |
| 22-6 | 22 | CCAGGACTTATTGAGAAGGAAATGT | 37 | SEQ ID NO. 121 |
| 22-7 | 22 | AAGCAGTGTTCAAATCTCACCCTCT | 63 | SEQ ID NO. 122 |
| 23-1 | 23 | ATCCAGTTCTTCCCAAGAGGCCCAC | 0 | SEQ ID NO. 123 |
| 23-2 | 23 | AGCTGATAACAAAGTACTCTTCCCT | 0 | SEQ ID NO. 124 |
| 23-3 | 23 | AAGTTATTGAATCCCAAGACACACC | 0 | SEQ ID NO. 125 |
| 23-4 | 23 | CTAAGTCCTTTTGCTCACCTGTGGT | 24 | SEQ ID NO. 126 |
| 24-1 | 24 | GATCACTCCACTGTTCATAGGGATC | 58 | SEQ ID NO. 127 |
| 24-2 | 24 | CTCATCTGCAACTTTCCATATTTCT | 53 | SEQ ID NO. 128 |
| 24-3 | 24 | ATTTCAGTTAGCAGCCTTACCTCAT | 66 | SEQ ID NO. 129 |

* percent of the mRNA transcripts that skip out the targeted exon

Example 3

HCAI-CFTR Deletions in Fischer Rat Thyroid Cells

Figure 18A:
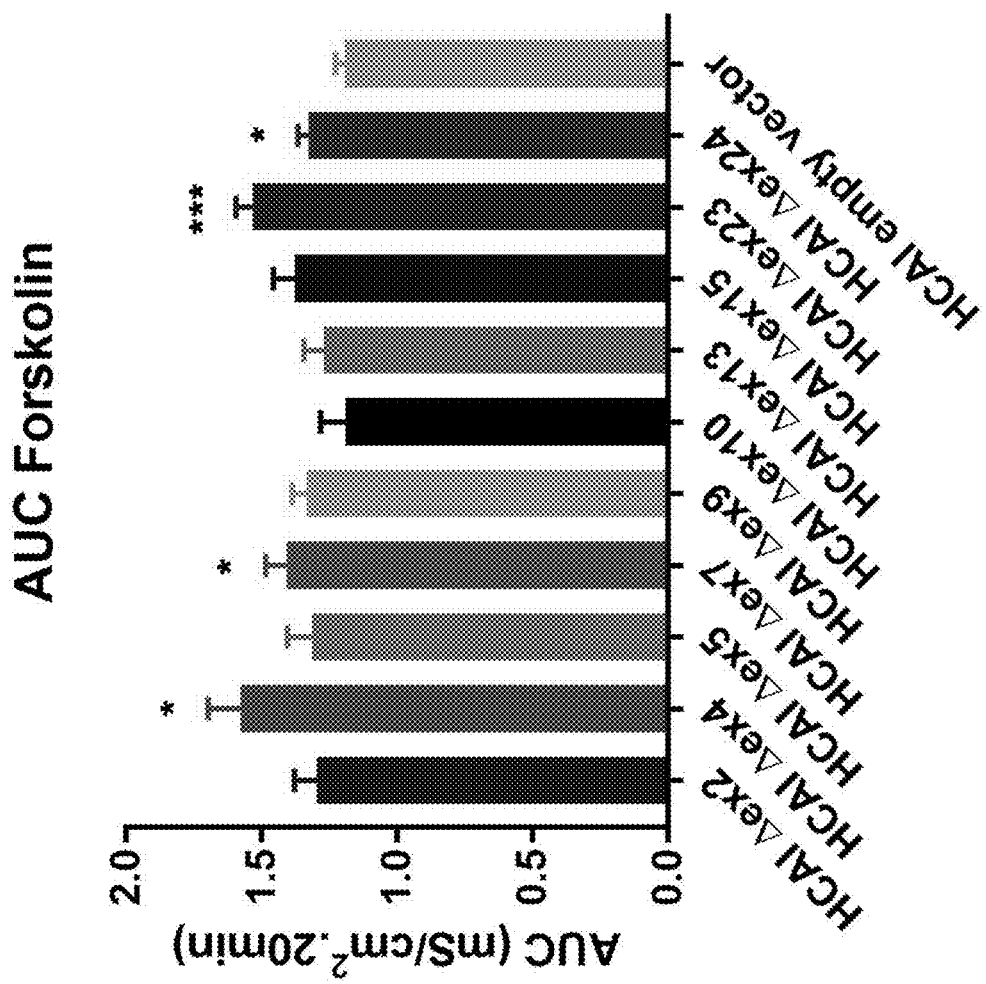
FIG. 18A shows a comparison of the AUC forskolin-stimulated HCAI-CFTR exon deletion channel activity in Fischer Rat Thyroid (FRT) cells to HCAI empty vector. Error bars represent SEM (*r0.05, ***r0.001, n=4, two-tailed t-test compared to HCAI empty vector).
Figure 18B:
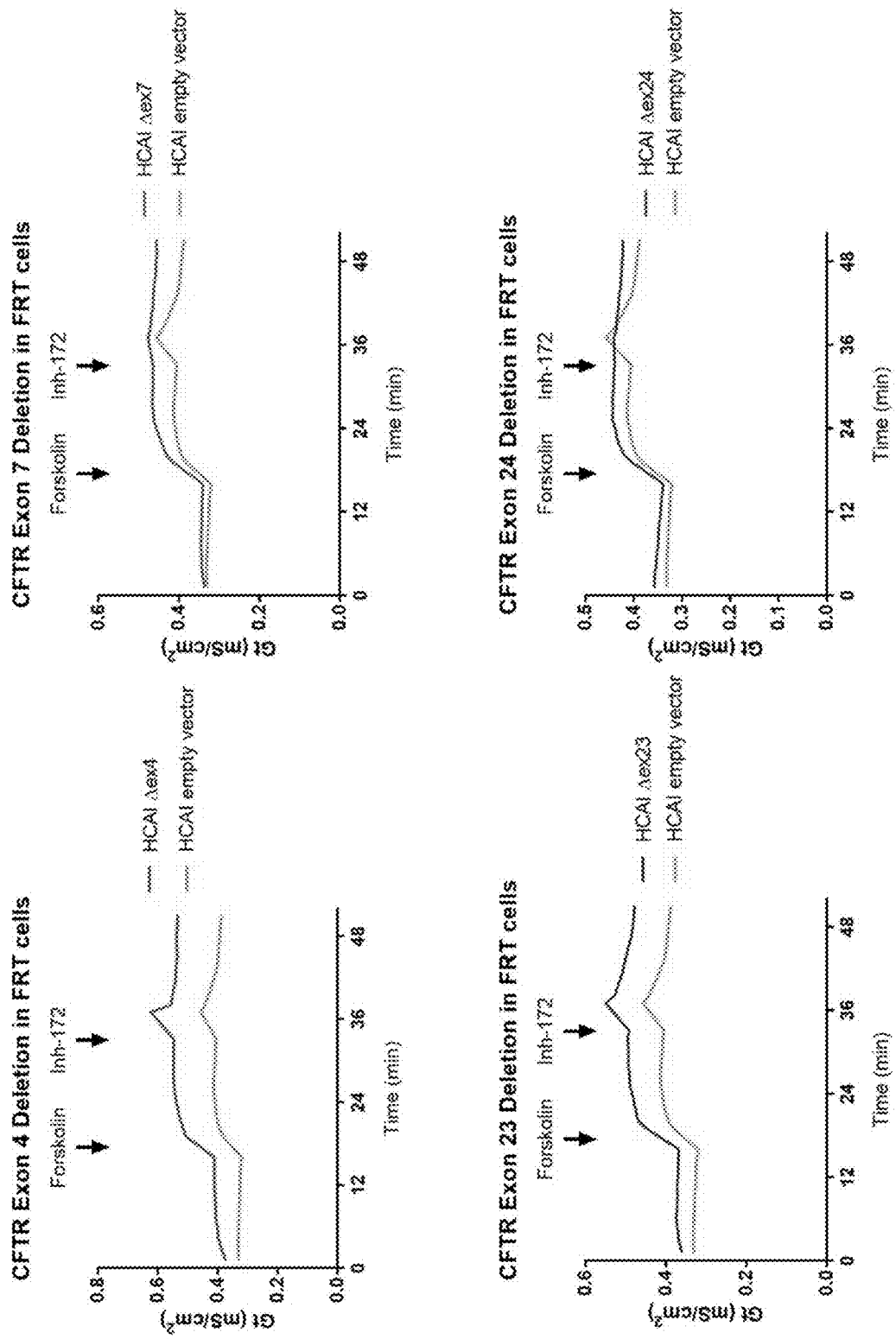
FIG. 18B shows representative Gt traces of CFTR exon 4, exon 7, exon 23, and exon 24 deletion constructs in Fischer Rat Thyroid (FRT) cells in comparison to HCAI empty vector.

Fischer Rat Thyroid (FRT) cells, which lack functional CFTR, were stably transfected with nucleic acids encoding human CFTR with deletions of exon 2, 4, 5, 7, 9, 10, 13, 15, 23, or 24 (HCAIΔex2, HCAIΔex4, HCAIΔex5, HCAIΔex7, HCAIΔex9, HCAIΔex10, HCAIΔex13, HCAIΔex15 HCAIΔex23, or HCAIΔex24). FRT cells stably the HCAI-CFTR exon deletions were seeded onto HTS Transwell®-24 well permeable filter plates (0.4 µM pore size, Polyester, Corning) and differentiated for 2 weeks. Transepithelial conductance was assessed in Gt assays that were performed 14 days after cell seeding. The data were recorded with 24-channel transepithelial current clamp (TECC)_Robot system (Design, Belgium). HCAI-CFTR activity was measured by the change in Gt upon stimulation with forskolin (10 µM). CFTRInh-172 (10 µM) was used to confirm CFTR dependence. A comparison of the AUC forskolin-stimulated HCAI-CFTR exon deletion channel activity to HCAI empty vector is shown in FIG. 18A (error bars represent SEM; *p<0.05, ***r0.001, n=4, two-tailed t-test compared to HCAI empty vector). Representative Gt traces of CFTR exon 4, exon 7, exon 23, and exon 24 deletion constructs in comparison to HCAI empty vector are shown in FIG. 18B.

Example 4

Figure 19B:
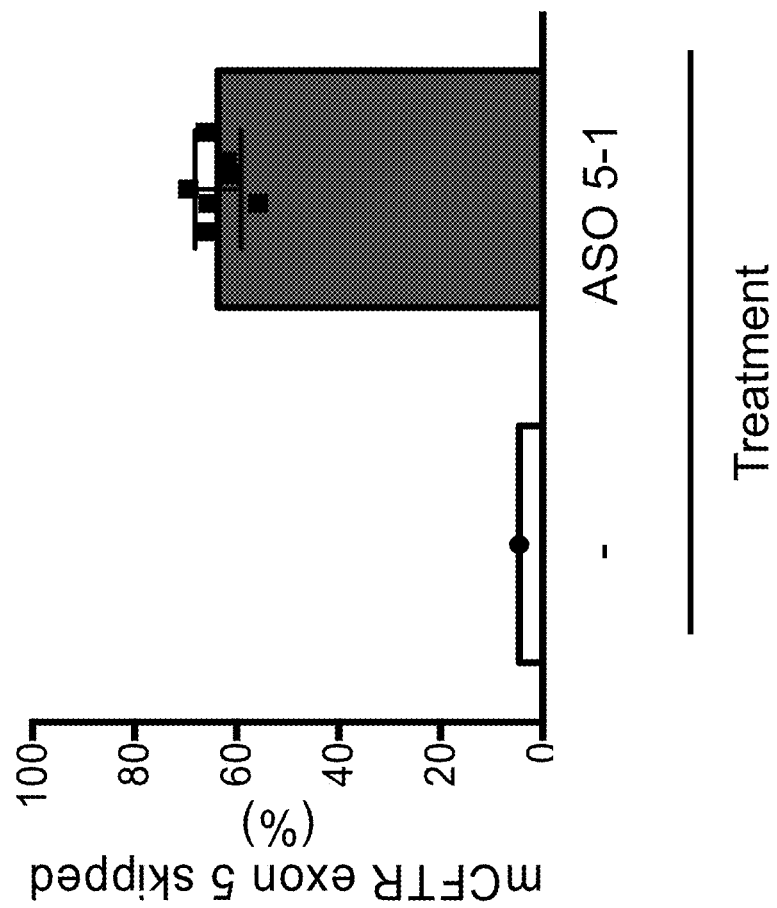
FIG. 19B shows a quantitation of the RT-PCR analysis of the RNA exon 5 skipping induced by ASO treatment. Approximately 60% of mouse CFTR gene exon 5 is skipped when mice are treated with ASO 5-1 by ICV injection.

Antisense Oligonucleotides Induce Exon Skipping of Exons with Nonsense Mutations in CFTR in vivo and Restore the CFTR Reading Frame ASO 5-1 (SEQ ID NO:12) was tested in mice and shown to induces CFTR exon 5 skipping. Intracerebroventricular (ICV) injection of mCFex5-1 was performed in wild-type mice (C57BI/6) on post-natal day 2, and mice were euthanized on post-natal day 12. RNA was collected from the hippocampus. Radioactive RT-PCR of CFTR RNA isolated from hippocampus is shown in FIG. 19A (splice isoforms are labeled and exon 5 skipping quantification is shown at the bottom). A quantitation of the RT-PCR analysis of the RNA exon 5 skipping induced by ASO 5-1 treatment is shown in FIG. 19B.

Example 5

Antisense Oligonucleotides to Correct CFTR 2789+5 G>A Splicing Mutation

Figure 20A:
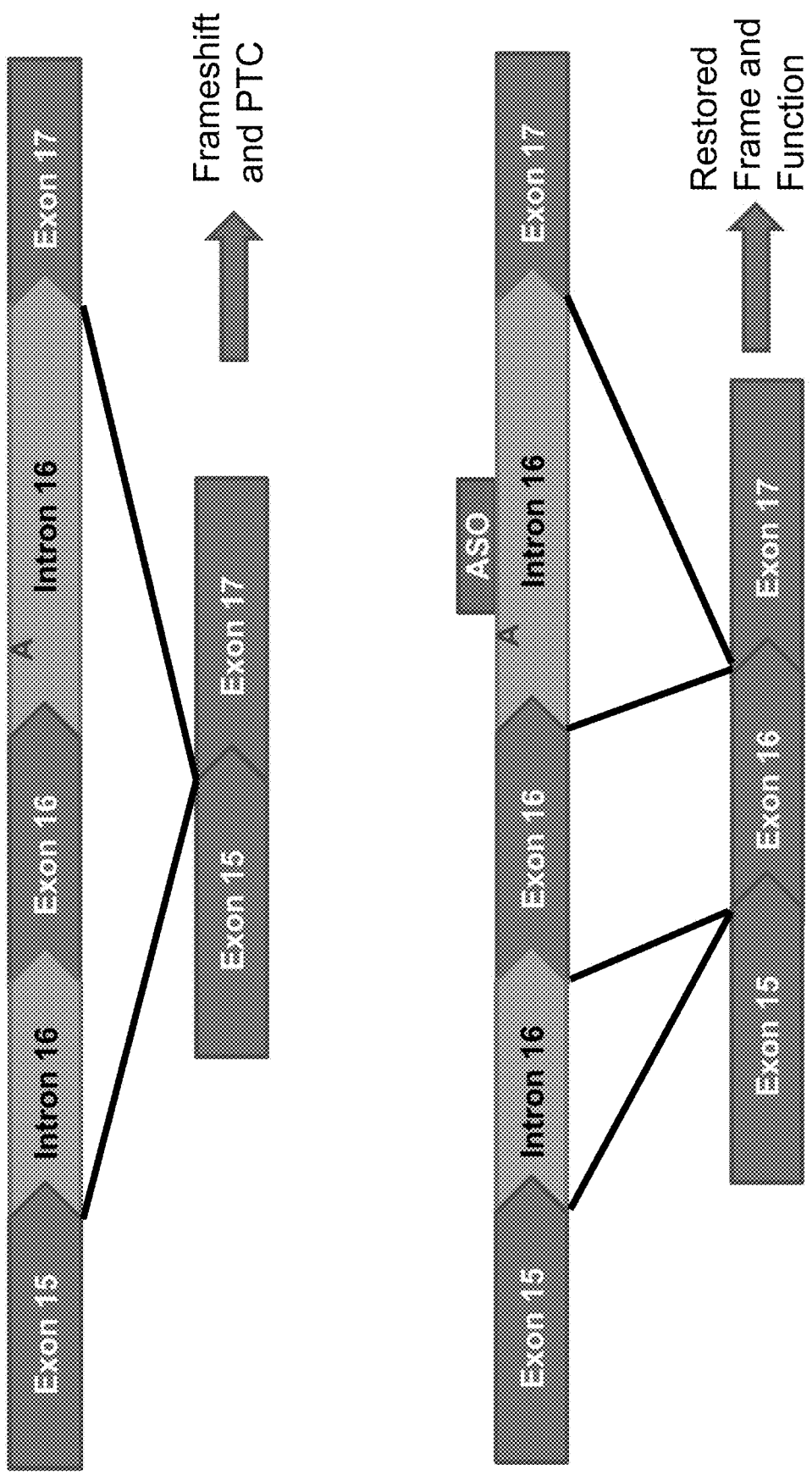
FIG. 20A shows a schematic for antisense oligonucleotides to correct CFTR 2789+5 G>A splicing mutation.
Figure 20B:
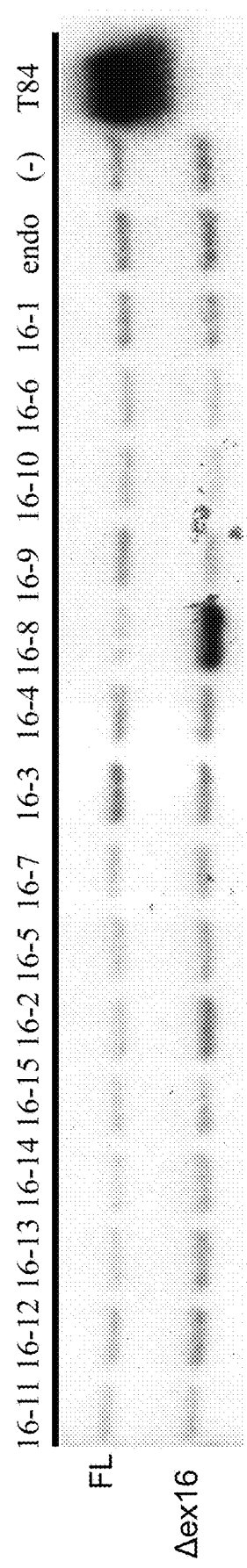
FIG. 20B shows a radioactive RT-PCR of CFTR RNA isolated from 2789+5 patient lymphoblast cells transfected with ASOs (15 µM) for 48 hours. The results demonstrate correction of CFTR splicing in 2789+5 patient lymphoblast cells using ASOs. The CFTR spliced isoforms are labelled. T84 cells were analyzed as a positive control for wild-type CFTR splicing.
Figure 20C:
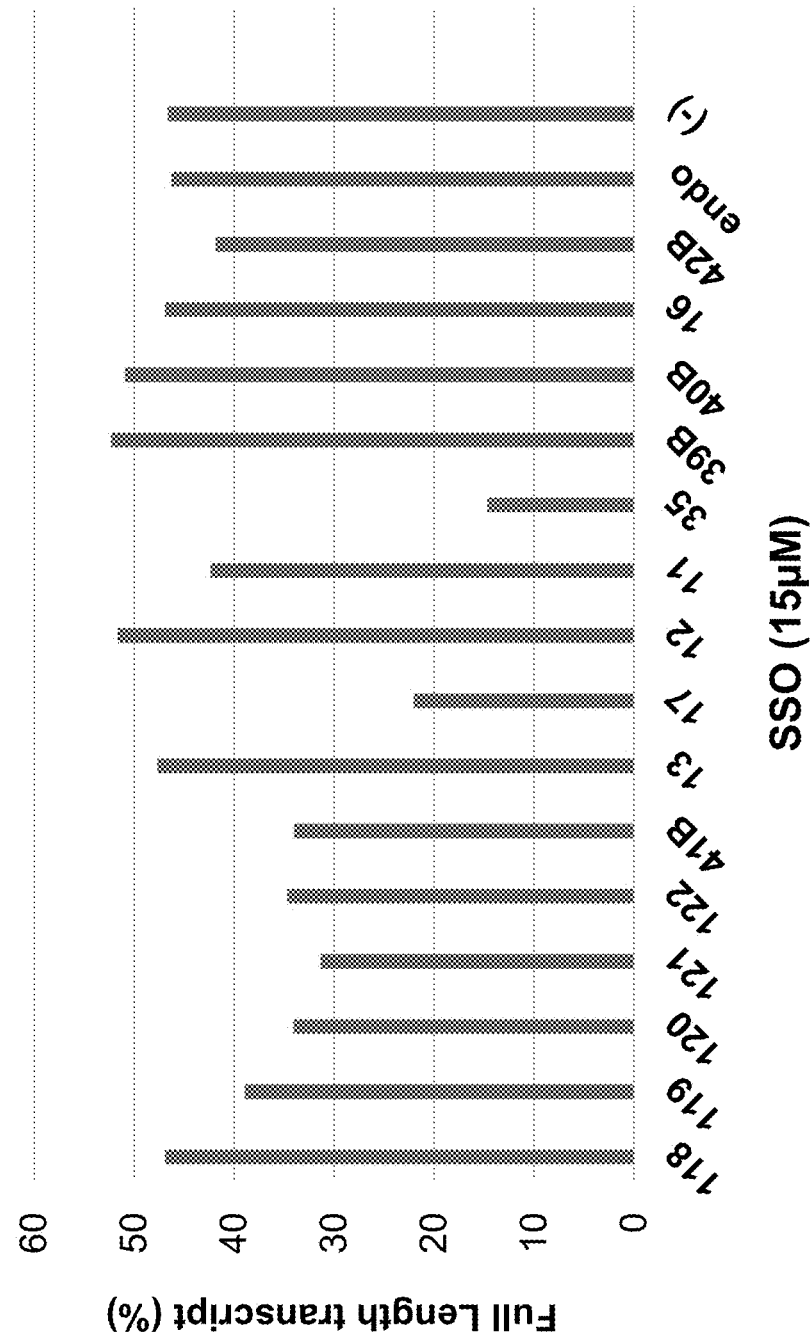
FIG. 20C shows a quantitation of the RT-PCR analysis of the RNA splice correction induced by ASO treatment in patient lymphoblast cells.

Antisense oligonucleotides were designed that increase correct splicing in 2789+5 G>A in patient lymphoblast cells lines. The lymphoblast cell line 11859, which is homozygous for the 2789+5 G>A mutation, was transfected with ASOs that were designed to correct the splicing in CFTR 2789+5 G>A (ASO concentration of 15 µM; and cells were treated for 48 hours). Correction of CFTR splicing in 2789+5 the lymphoblasts using ASOs is shown in FIG. 20B (CFTR spliced isoforms are labeled; T84 cells were analyzed as a positive control for wild-type CFTR splicing). A quantitation of the RT-PCR analysis of the RNA splice correction induced by ASO treatment in patient lymphoblast cells is shown in FIG. 20C. A summary of the 2789+5 ASOs targets, sequences, and correction activity in patient lymphoblast cells is shown in Table 3.

TABLE 3

ASO sequences tested in the 2789 +5 lymphoblast cell line.

| Name | Target Region | Sequence (SEQ ID NO.) | % Full Length |
|---|---|---|---|
| 16-11 | Intron 15 | GACTTTTTTTCTAACATCTTCACCT (SEQ ID NO.: 105) | 47 |
| 16-12 | Intron 15 | ATGGAACAACACACAGTTGATTTTT (SEQ ID NO.: 106) | 39 |

TABLE 3-continued

ASO sequences tested in the 2789 +5 lymphoblast cell line.

| Name | Target Region | Sequence (SEQ ID NO.) | % Full Length |
|---|---|---|---|
| 16-13 | Intron 15 | ATCGAACAAGACACAGTTGATTTTT (SEQ ID NO.: 107) | 34 |
| 16-14 | Intron 15 | GAGTGGAACAAGACACAGTTGATTT (SEQ ID NO.: 108) | 31 |
| 16-9 | Exon 16 | CACAATCTACACAATAAGACATGGA (SEQ ID NO.: 109) | 35 |
| 16-2 | Exon 16 | GAGCCACAGCACAACCAAAGAAGCA (SEQ ID NO.: 96) | 34 |
| 16-5 | Exon 16 | TTCCAAGGAGCCACAGCACAACCAA (SEQ ID NO.: 99) | 48 |
| 16-7 | Exon 16 | TTTCCAAGGAGCCACAGCACAACCA (SEQ ID NO.: 101) | 22 |
| 16-3 | Exon 16 | TCCAAGGAGCCACAGCAC (SEQ ID NO.: 97) | 52 |
| 16-4 | Exon 16 | TTCCAAGGAGCCACAGCA (SEQ ID NO.: 98) | 42 |
| 16-8 | Intron 16 | ACAATCTACACAATAGGACATGGAA (SEQ ID NO.: 102) | 15 |
| 16-9 | Intron 16 | CACAATCTACACAATAGGACATGGA (SEQ ID NO.: 103) | 52 |
| 16-10 | Intron 16 | ACACAATCTACACAATAGGACATGG (SEQ ID NO.: 104) | 51 |
| 16-6 | Intron 16 | AACAGAAATAAAACACAATCTACAC (SEQ ID NO.: 100) | 47 |
| 16-1 | Intron 16 | TCGTTATTTGGCAGCCAAAGTTACT (SEQ ID NO.: 95) | 42 |

| Name | Target Exon | Sequence (SEQ ID NO.) | % Full-Length |
|---|---|---|---|
| 20-1 | 20 | CAAGATGAGTGAAAATTGGACTCCT (SEQ ID NO.: 110) | 60 |
| 20-2 | 20 | CGAAGGCACGAAGTGTCCATAGTCC (SEQ ID NO.: 111) | 3 |
| 20-3 | 20 | AACAGAGTTTCAAAGTAAGGCTGCC (SEQ ID NO.: 112) | 50 |
| 20-4 | 20 | AGTTGGCAGTATGTAAATTCAGAGC (SEQ ID NO.: 113) | nd |
| 20-5 | 20 | TTCTATTCTCATTTGGAACCAGCGC (SEQ ID NO.: 114) | 56 |
| 20-6 | 20 | GGTAACAGCAATGAAGAAGATGACA (SEQ ID NO.: 115) | 12 |

Example 6

Antisense Oligonucleotides to Correct CFTR 3272-26 A>G Splicing Mutation

Figure 21A:
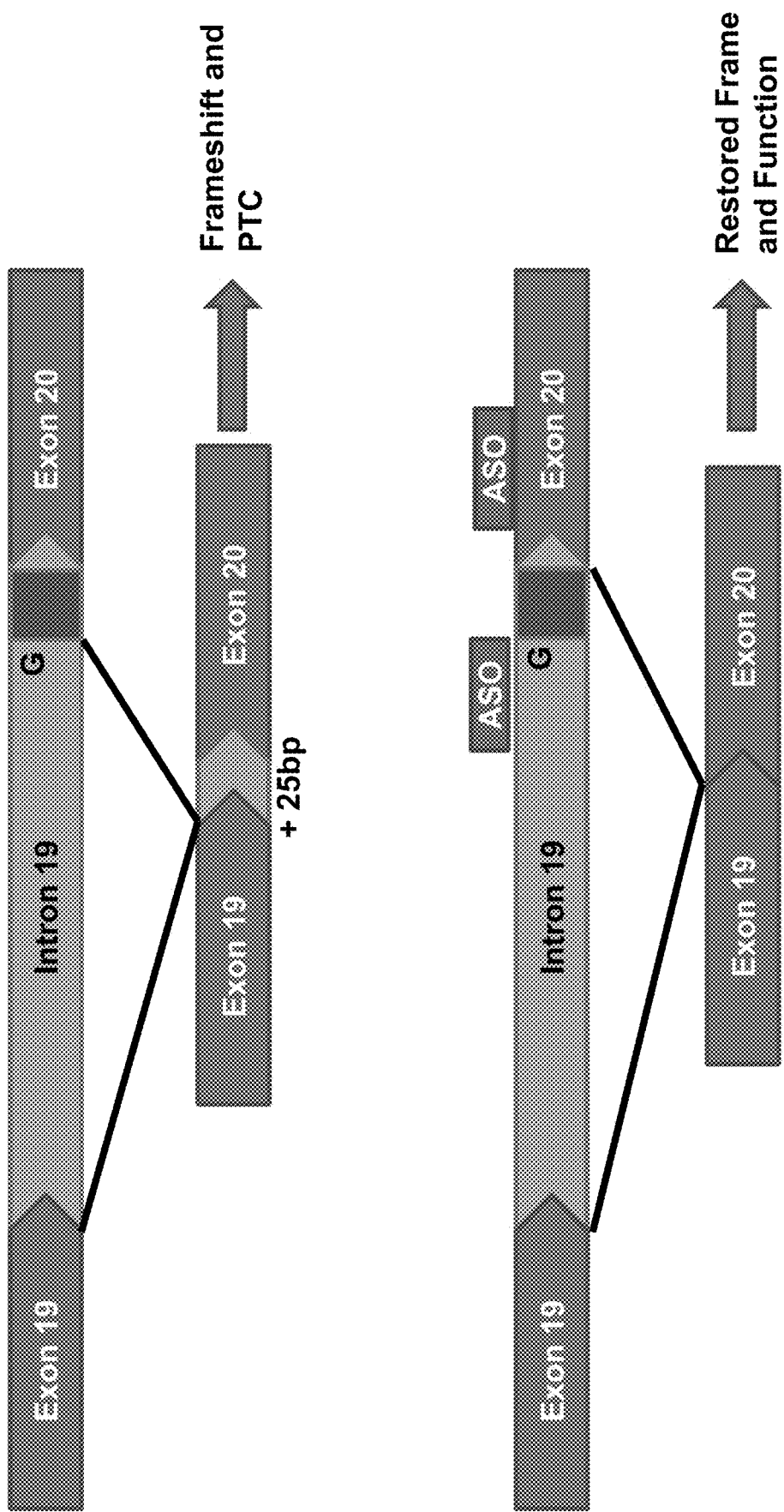
FIG. 21A shows a schematic for antisense oligonucleotides to correct CFTR 3272-26A>G splicing mutation.
Figure 21B:
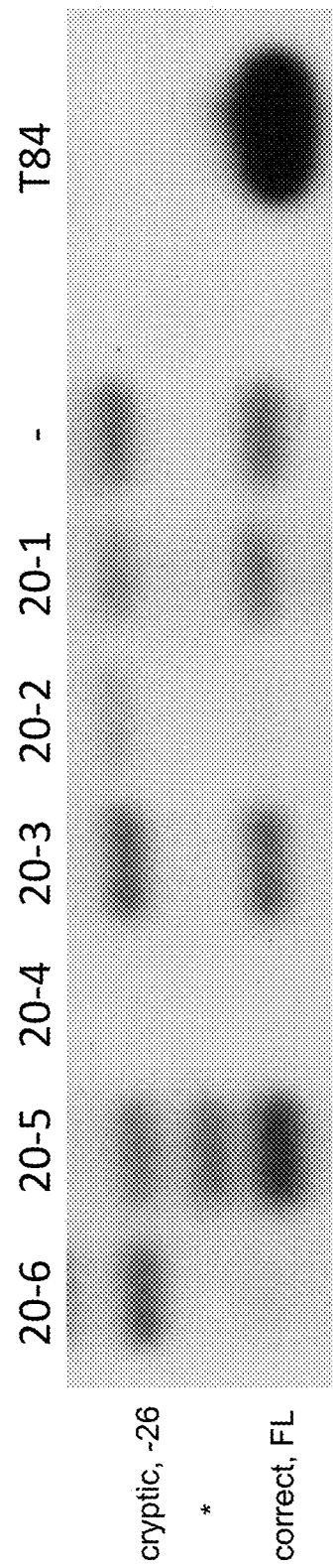
FIG. 21B shows a radioactive RT-PCR of CFTR RNA isolated from 3272-26 A>G patient lymphoblast cells transfected with ASOs (15 µM) for 48 hours. The results demonstrate correction of CFTR splicing in 3272-26A>G patient lymphoblast cells using ASOs. The CFTR spliced isoforms are labelled. T84 cells were analyzed as a positive control for wild-type CFTR splicing.

Antisense oligonucleotides were designed that increase correct splicing in 3272-26 A>G mutation in patient lymphoblast cell lines. The lymphoblast cell line 18801 (18801 is from a male donor with one allele carrying the 3272-26 A>G mutation, and no mutation was identified in the second allele) was transfected with ASOs that were designed to correct splicing in CFTR 3272-26 A>G (ASOs were transfected with Endo-Porter, the ASO concentration was 15 µM, and cells were treated for 48 hours). Correction of CFTR splicing in CFTR 3272-26 A>G in the lymphoblast cells using ASOs is shown in FIG. 21B (CFTR spliced isoforms are labeled; T84 cells were analyzed as a positive control for wild-type CFTR splicing). A summary of the CFTR 3272-26 A>G ASOs targets, sequences, and correction activity in patient lymphoblast cells is shown in Table 4.

Example 7

Antisense oligonucleotides to correct CFTR 3849+10 kb C>T splicing mutation.

Figure 22A:
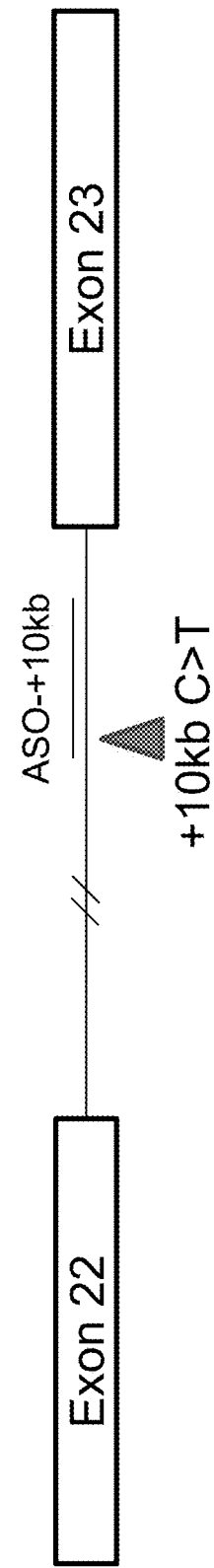
FIG. 22A shows a diagram of ASOs used for the correction of CFTR splicing in 3849+10 kb patient lymphoblast cells using ASOs. The +10 C>T mutation is labeled.
Figure 22B:
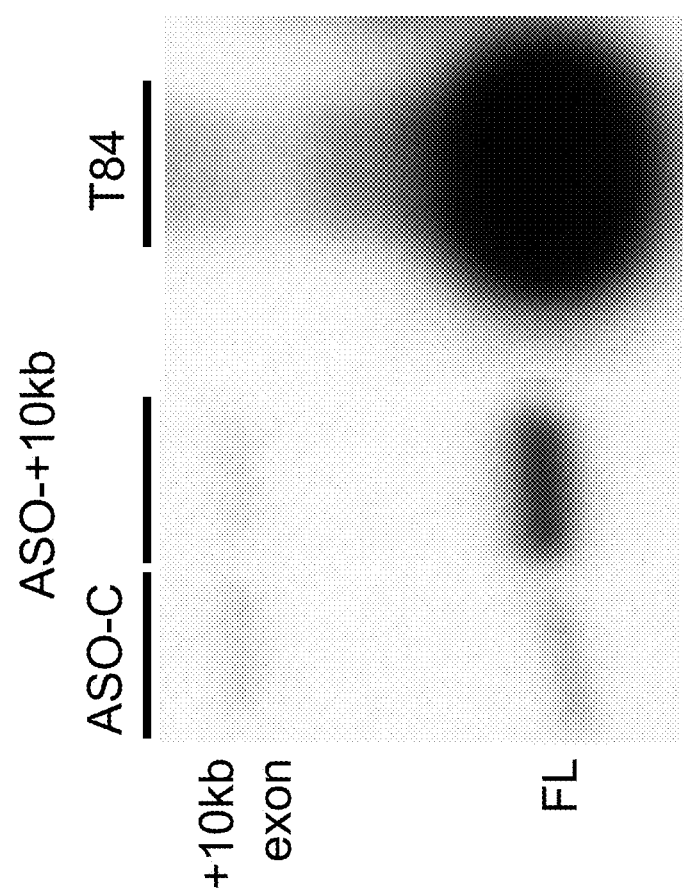
FIG. 22B shows the results of a RT-PCR assay of CFTR RNA isolated from 3849+10 kb patient lymphoblast cells transfected with ASOs (15 µM) for 48 hours. Results indicate a correction of CFTR splicing in 3849+10 kb patient lymphoblast cells using the ASOs. CFTR spliced isoforms are labeled. T84 cells were analyzed as a positive control for wild-type CFTR splicing (FL=Full-Length).
Figure 22C:
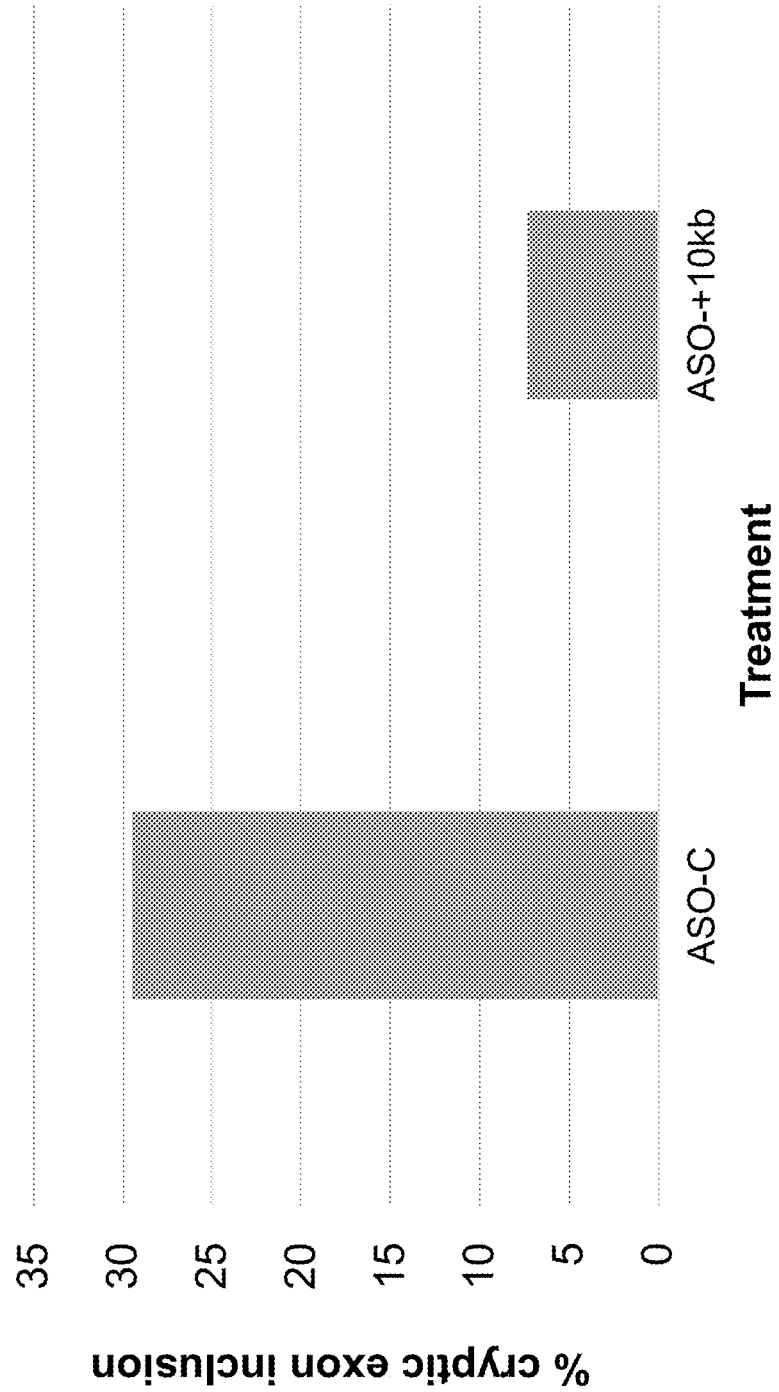
FIG. 22C shows a quantitation of the RT-PCR analysis of the RNA splice correction induced by ASO treatment in patient lymphoblast cells. The results indicate about a four-fold reduction of inclusion of the cryptic exon, resulting in approximately 93% of the CFTR transcripts being full-length.

Antisense oligonucleotides were designed to repair the 3849+10 kb C>T splice mutation and restore CFTR function. The C>T mutation creates a cryptic 5' splice site that results in the inclusion of an 84 bp insert from intron 22, and the mutated allele produces both wild-type and aberrantly spliced transcripts. The lymphoblast cell line 18860 (18860 is homozygous for 3849+10 kb CFTR mutation) was transfected with ASOs that were designed to correct splicing in 3849+10 kb C>T (ASOs were transfected with Endo-Porter, the ASO concentration was 15 µM, and cells were treated for 48 hours). Correction of CFTR splicing in 3849+10 kb C>T in the lymphoblast cells using ASOs is shown in FIG. 22B and 22C (CFTR spliced isoforms are labeled; T84 cells were analyzed as a positive control for wild-type CFTR splicing). A summary of the CFTR 3849+10 kb C>T ASO target, sequence, and correction activity in patient lymphoblast cells is shown in Table 5.

| Name | Target Exon | Sequence (SEQ ID NO.) | % Full-Lenght |
|---|---|---|---|
| ASO-+10 kb | Intron 22 | CCTTTCAGGGTGTCTTACTCACCAT (SEQ ID NO.: 150) | 93 |

Example 8

Analyzing CFTR Function in Patient Epithelial Cells Treated with ASOs

Primary patient human bronchial epithelial (HBE) cells (cells are compound heterozygotes with the 3849+10 kbC>T and ΔF508 mutation) were seeded on HTS Transwell®-24 well permeable filter plates (0.4 uM pore size, Polyester, Corning) and switched to air/liquid interphase after 3 days. Ieq measurements were carried out 99 days after seeding. Cells were treated basolaterally with C18 (Corr951/VX-661, 6 µM) or DMSO (0.1%), and apically transfected with ASO-+10 kb (SEQ ID NO:150 at 20 µM or 80 µM) or ASO-C (20 µM or 80 µM; 5' CCTCTTACCTCAGTTA-CAATTTATA 3'-SEQ ID NO:151) 4 days before Ieq measurements were taken. C18 is a corrector compound that improves F508del-CFTR folding and function. Cells were transfected using EGTA (4 mM) and Endo-Porter (Gene-Tools) for 10 hours, then EGTA was taken off and the cells were transfected again using Endo-Porter in the absence of EGTA. The data were recorded with 24-channel transepithelial current clamp (TECC) Robot system (Design, Belgium). Sodium current was inhibited by benzamil (6 µM) and CFTR activity was measured by the change in Ieq upon stimulation with forskolin (10 µM) and VX-770/KALYDECO™/Ivacaftor (1 µM), which is a CFTR potentiator that improves the transport of chloride through the CFTR channel. Inhibition with bumetanide/BUMEX™/BURINEX™ (20 µM) was used to confirm CFTR dependence.

Figure 23A:
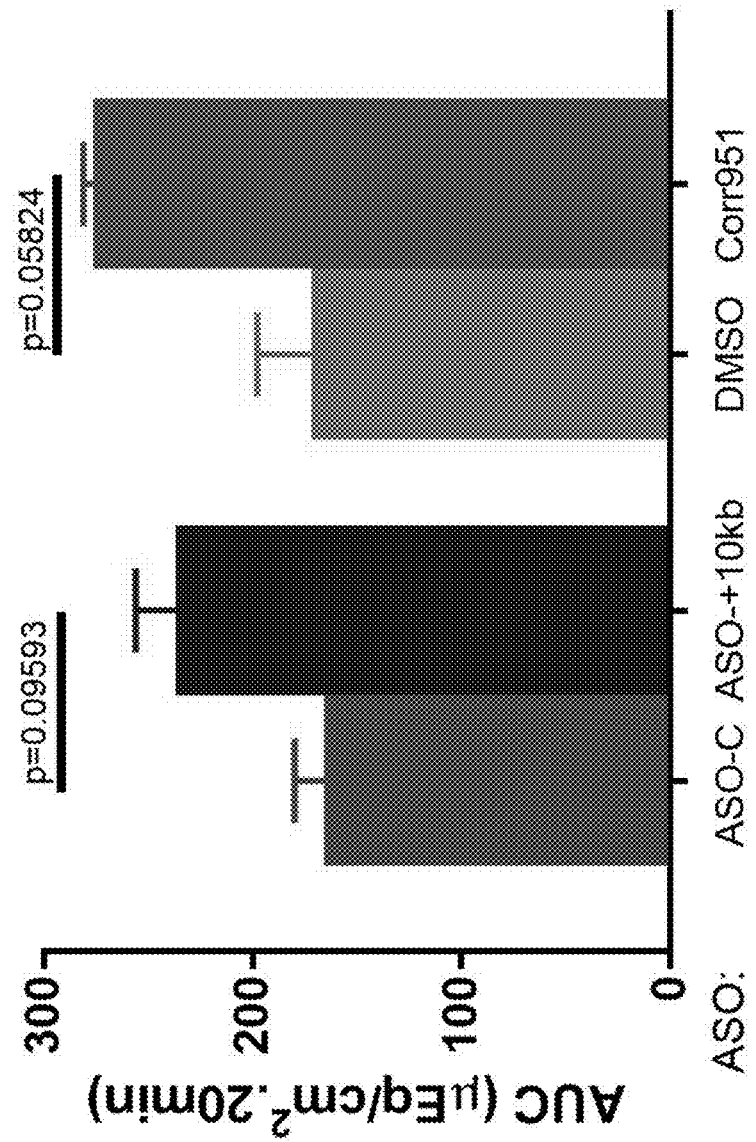
FIG. 23A shows that ASO-+10 kb rescues CFTR function similar to Corr951(VX-770) in patient HBE cells. The graph depicts the area under the curve (AUC) of time from forskolin+VX-770-stimulation of CFTR channels following indicated treatment. Error bars represent SEM (two-tailed t-test, n=2).

The results demonstrate that ASO-+10 kb (SEQ ID NO:150) rescues CFTR function similar to Corr951/VX-661 (CFTR corrector 106951 (1-(benzo[d][1,3]dioxol-5-yl)-N-(5-(((S)-(2-chlorophenyl)((R)-3-hydroxypyrrolidin-1-yl)methyl)thiazol-2-yl)cyclopropanecarboxamide)) in patient HBE cells. As shown in FIG. 23, ASO-+10kb rescues CFTR function similar to Corr951 in patient HBE cells. FIG. 23A is a graph showing the area under the curve (AUC) of time from forskolin+VX-770-stimulation of CFTR channels following indicated treatment (error bars represent SEM; two-tailed t-test, n=2). FIG. 23B depicts representative Ieq traces of treatment (Corr951 or ASO-+10kb) compared to control (ASO-C, top, or DMSO, bottom).

Figure 24A:
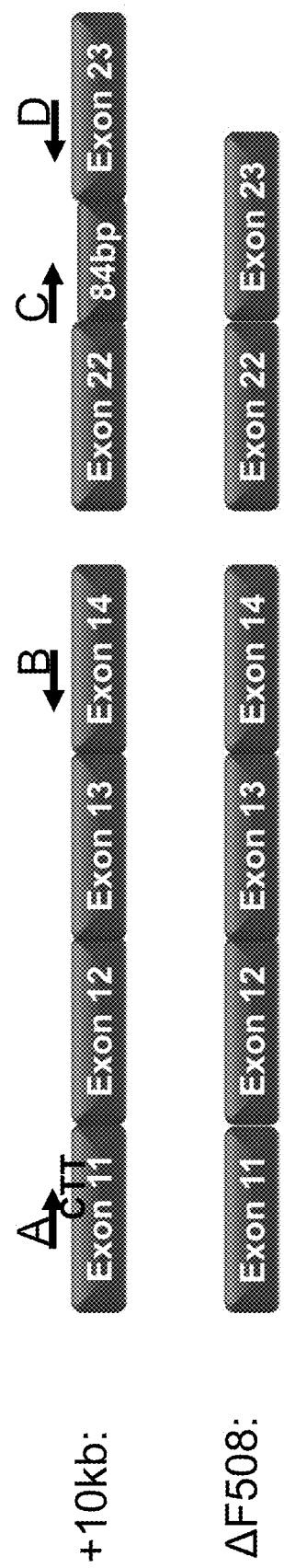
FIG. 24A shows a diagram of primer sets used to analyze splice correction by ASO-10+kb. Primer set A-B is designed to amplify ASO corrected WT isoform splicing specific to the splice mutant allele. Primer set C-D is designed to analyze the amount of uncorrected mutant splicing FIG. 24B show a quantification of total mRNA transcribed from the CFTR 3849+10 kB allele indicates an increase with ASO-+10 kb treatment (A-B primer set shown in FIG. 24A).
Figure 24B:
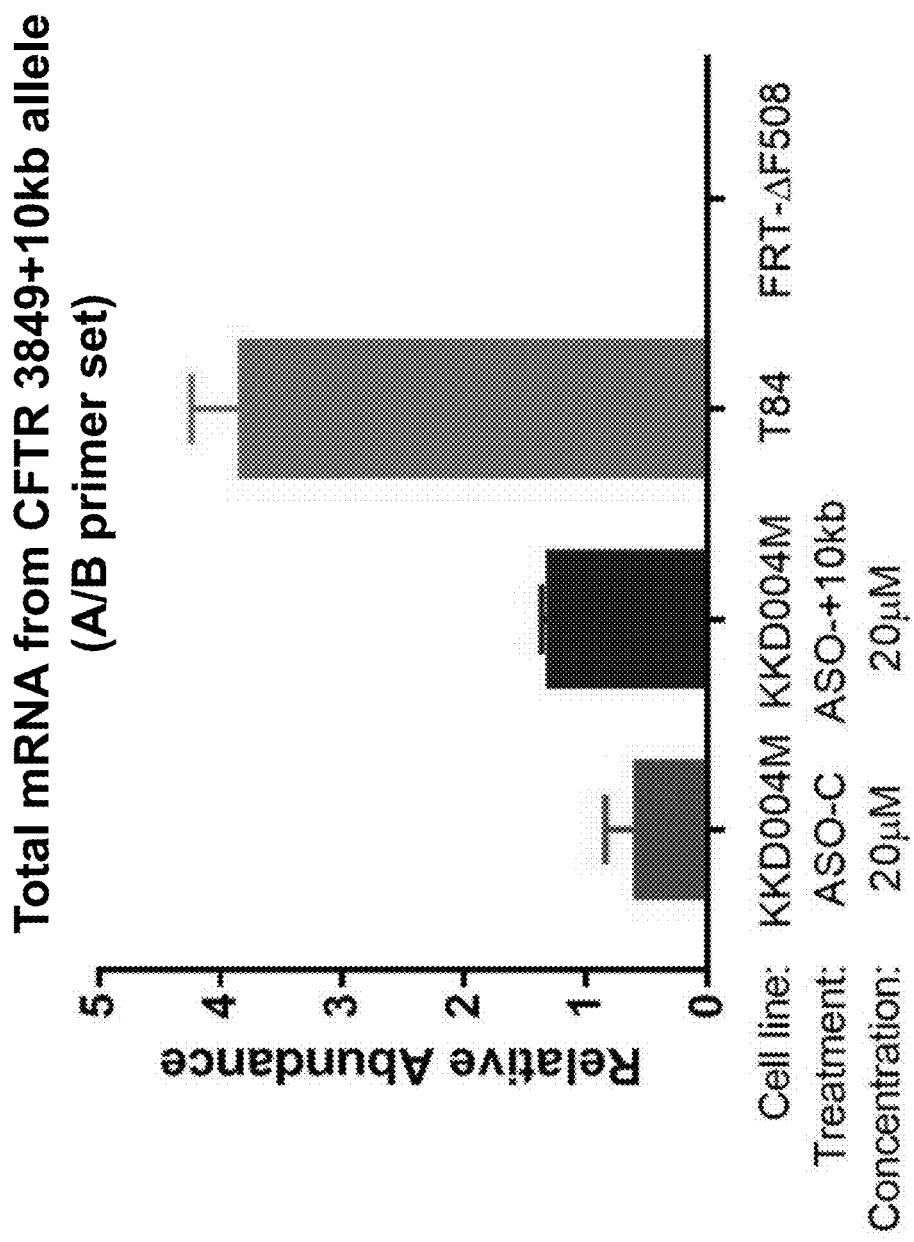
FIG. 24C shows a quantification of mutant, cryptically spliced mRNA isoform shows decrease of aberrant mRNA with ASO-+10 kb treatment (C-D primer set shown in FIG. 24A).
Figure 24C:
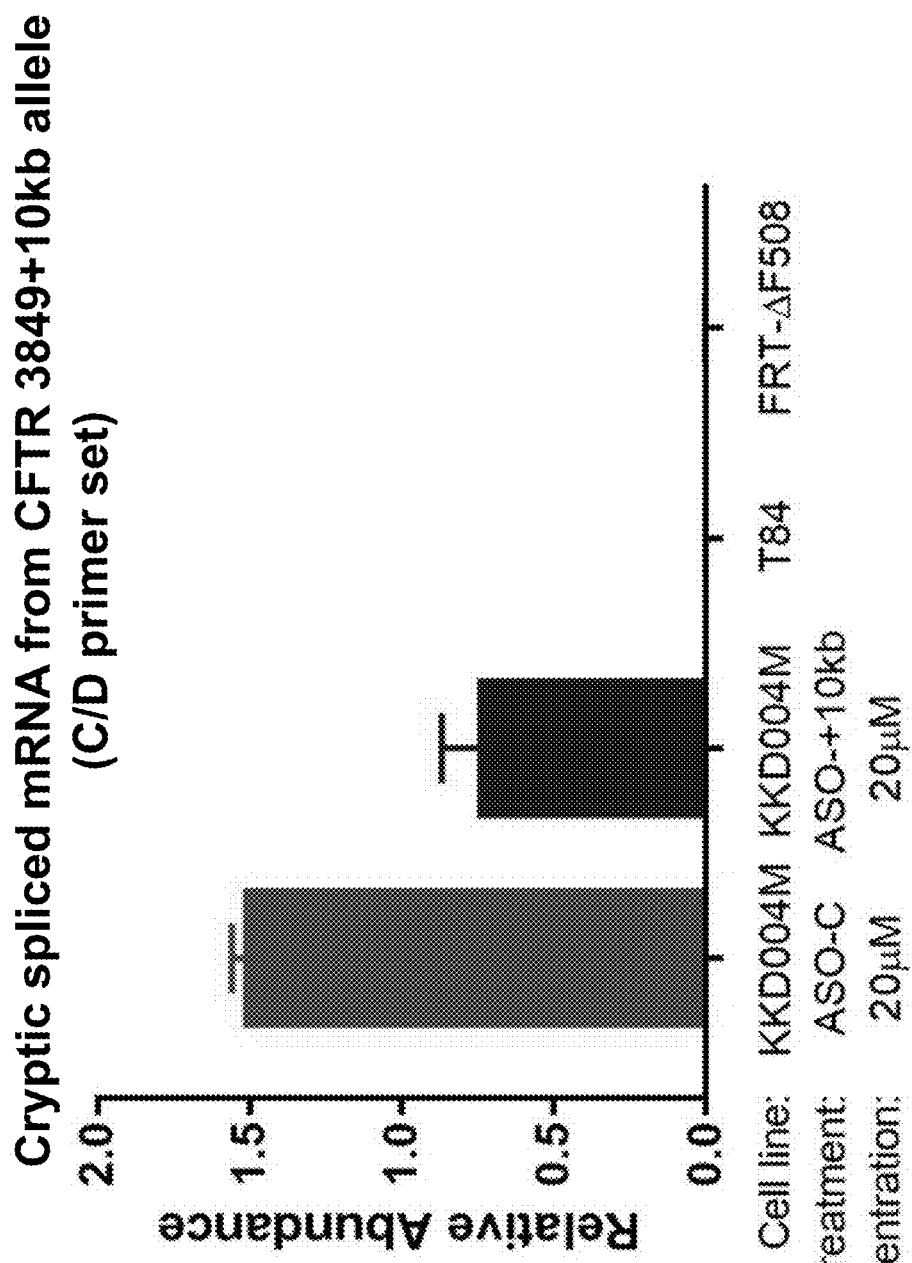

Additionally, the results show that ASO-+10 kb (SEQ ID NO:150) increases WT splicing in 3849+10 kb patient HBE cells. Primary patient HBE cells are heterozygous for the 3849+10 kbC>T mutation were transfected with ASO-+10 kb (20 uM). Total mRNA was isolated, reverse transcribed, and analyzed for splice correction using SYBER™ Green quantitative PCR. FIG. 24A depicts the primer sets used to analyze splice correction by ASO-10+kb (primer set A-B is designed to amplify ASO corrected WT isoform splicing specific to the splice mutant allele, and primer set C-D is designed to analyze the amount of uncorrected mutant splicing). FIG. 24B shows a quantification of total mRNA transcribed from the CFTR 3849+10 kB allele, and indicates an increase with ASO-+10 kb treatment (A-B primer set). FIG. 24C shows a quantification of mutant, cryptically spliced mRNA isoform, and shows decrease of aberrant mRNA with ASO-+10 kb treatment (C-D primer set).

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A compound comprising a modified oligonucleotide of 22 to 30 linked nucleosides and having a nucleobase sequence comprising at least 22 contiguous nucleosides of the sequence of SEQ ID NO:150 wherein the modified oligonucleotide comprises a complementary region, wherein the complementary region comprises at least 22 contiguous nucleobases complementary to an equal-length portion of a target region of a cystic fibrosis transmembrane conductance regulator (CFTR) transcript.

2. The compound of claim 1, wherein the complementary region of the modified oligonucleotide is at least 80% complementary to the target region.

3. The compound of claim 1, wherein the complementary region of the modified oligonucleotide comprises at least 10 to at least 25 contiguous nucleobases.

4. The compound of claim 1, wherein the nucleobase sequence of the oligonucleotide is at least 80% complementary to an equal-length region of the CFTR transcript, as measured over the entire length of the oligonucleotide.

5. The compound of claim 1, wherein the nucleobase sequence of the modified oligonucleotide comprises SEQ ID NO: 150.

6. The compound of claim 1, wherein the modified oligonucleotide comprises at least one modified nucleoside selected from a modified sugar moiety, a 2'-substituted sugar moiety, a 2'OME, a 2'F, a 2'-MOE, a bicyclic sugar moiety, a LNA, a cEt, a sugar surrogate, a morpholino, or a modified morpholino.

7. The compound of claim 1, wherein the modified oligonucleotide comprises at least 5 to at least 25 modified nucleosides, each independently comprising a modified sugar moiety.

8. The compound of claim 7, wherein each nucleoside of the modified oligonucleotide is a modified nucleoside, each independently comprising a modified sugar moiety.

9. The compound of claim 1, wherein the modified oligonucleotide comprises at least two modified nucleosides comprising modified sugar moieties that are the same as one another or that are different from one another.

10. The compound of claim 1, wherein the modified oligonucleotide comprises a modified region of at least 5 to at least 20 contiguous modified nucleosides.

11. The compound of claim 10, wherein each modified nucleoside of the modified region has a modified sugar moiety independently selected from: 2'-F, 2'-OMe, 2'-MOE, cEt, LNA, morpholino, and modified morpholino.

12. The compound of claim 10, wherein the modified nucleosides of the modified region each comprise the same modification as one another.

13. The compound of claim 12, wherein the modified nucleosides of the modified region each comprise the same 2'-substituted sugar moiety selected from: 2'-F, 2'-OMe, and 2'-MOE.

14. The compound of claim 12, wherein the modified nucleosides of the region of modified nucleosides each comprise the same bicyclic sugar moiety selected from: LNA and cEt.

15. The compound of claim 14, wherein the modified nucleosides of the region of modified nucleosides each comprises a sugar surrogate, and wherein the sugar surrogate of the modified nucleosides of the region of modified nucleosides is a morpholino.

16. The compound of claim 1, wherein the modified nucleotide comprises no more than 4 contiguous naturally occurring nucleosides.

17. The compound of claim 1, wherein the modified oligonucleotide comprises at least one modified internucleoside linkage.

18. The compound of claim 17, comprising at least one phosphorothioate internucleoside linkage.

19. The compound of claim 17, wherein each internucleoside linkage is a modified internucleoside linkage and wherein each internucleoside linkage comprises the same modification.

20. The compound of claim 19, wherein each internucleoside linkage is a phosphorothioate internucleoside linkage.

21. The compound of claim 1, comprising at least one conjugate.

22. The compound of claim 1, wherein the compound modulates splicing or expression of the CFTR transcript.

23. A pharmaceutical composition comprising at least one compound according to claim 1 and a pharmaceutically acceptable carrier or diluent.

24. A method of modulating splicing or expression of a CFTR transcript in a cell comprising contacting the cell with at least one compound according to claim 1.

25. The method of claim 24, wherein the cell is in vitro or in vivo.

26. A method comprising administering at least one compound according to claim 1 or the pharmaceutical composition of claim 23 to an animal.

27. The method of claim 26, wherein the administering step comprises delivering to the animal by inhalation, parenteral injection or infusion, oral, subcutaneous or intramuscular injection, buccal, transdermal, transmucosal and topical.

28. The method of claim 26, wherein the animal is a human or a mouse.

29. A method of treating cystic fibrosis, comprising administering at least one compound according to claim 1 to an animal in need thereof.

30. A method of treating cystic fibrosis, comprising administering the pharmaceutical composition of claim 23 to an animal in need thereof.

* * * * *